United States Patent
Blake et al.

(10) Patent No.: US 11,964,988 B2
(45) Date of Patent: Apr. 23, 2024

(54) FUSED HETEROCYCLIC COMPOUNDS AS RET KINASE INHIBITORS

(71) Applicant: ARRAY BIOPHARMA INC., Boulder, CO (US)

(72) Inventors: James F. Blake, Indianapolis, IN (US); Donghua Dai, Indianapolis, IN (US); Julia Haas, Indianapolis, IN (US); Yutong Jiang, Indianapolis, IN (US); Dean Kahn, Indianapolis, IN (US); Gabrielle R. Kolakowski, Indianapolis, IN (US); Elizabeth A. McFaddin, Indianapolis, IN (US); Megan L McKenney, Indianapolis, IN (US); Andrew T. Metcalf, Indianapolis, IN (US); David A. Moreno, Indianapolis, IN (US); Brett Prigaro, Indianapolis, IN (US); Ginelle A. Ramann, Indianapolis, IN (US); Li Ren, Indianapolis, IN (US); Shane M. Walls, Indianapolis, IN (US); Hailong Zhang, Indianapolis, IN (US)

(73) Assignee: ARRAY BIOPHARMA INC., Boulder, CO (US)

( * ) Notice: Subject to any disclaimer, the term of this patent is extended or adjusted under 35 U.S.C. 154(b) by 513 days.

(21) Appl. No.: 17/274,990

(22) PCT Filed: Sep. 6, 2019

(86) PCT No.: PCT/US2019/049859
§ 371 (c)(1),
(2) Date: Mar. 10, 2021

(87) PCT Pub. No.: WO2020/055672
PCT Pub. Date: Mar. 19, 2020

(65) Prior Publication Data
US 2022/0112214 A1    Apr. 14, 2022

Related U.S. Application Data

(60) Provisional application No. 62/729,337, filed on Sep. 10, 2018.

(51) Int. Cl.
| | |
|---|---|
| *C07D 498/22* | (2006.01) |
| *A61K 31/519* | (2006.01) |
| *A61K 31/55* | (2006.01) |
| *A61K 31/554* | (2006.01) |
| *A61K 45/06* | (2006.01) |
| *A61P 35/00* | (2006.01) |
| *C07D 487/14* | (2006.01) |
| *C07D 498/14* | (2006.01) |
| *C07D 513/22* | (2006.01) |

(52) U.S. Cl.
CPC .......... *C07D 498/22* (2013.01); *A61K 31/519* (2013.01); *A61K 31/55* (2013.01); *A61K 31/554* (2013.01); *A61K 45/06* (2013.01); *A61P 35/00* (2018.01); *C07D 487/14* (2013.01); *C07D 498/14* (2013.01); *C07D 513/22* (2013.01)

(58) Field of Classification Search
CPC .. C07D 498/22; C07D 487/14; C07D 498/14; C07D 513/22; A61K 31/519; A61K 31/55; A61K 31/554; A61K 45/06
See application file for complete search history.

(56) References Cited

U.S. PATENT DOCUMENTS

| | | | |
|---|---|---|---|
| 5,430,021 | A | 7/1995 | Rudnic et al. |
| 5,844,092 | A | 12/1998 | Presta et al. |

(Continued)

FOREIGN PATENT DOCUMENTS

| | | |
|---|---|---|
| CN | 101052629 | 10/2007 |
| CN | 105255927 | 1/2016 |

(Continued)

OTHER PUBLICATIONS

Ahmed et al., "Nine novel germline gene variants in the RET proto-oncogene identified in twelve unrelated cases.", The Journal of Molecular Diagnostics, 7(2), 283-288, 2005.

(Continued)

*Primary Examiner* — Matthew P Coughlin
*Assistant Examiner* — Ashli Ariana Chicks
(74) *Attorney, Agent, or Firm* — Meunier Carlin & Curfman LLC

(57) ABSTRACT

Provided herein are compounds of the Formula (I): (I) and tautomers, stereoisomers and pharmaceutically acceptable salts and solvates thereof, wherein $R^x$, $R^y$, W, X, Y, Z, Ring A and (AA) have the meanings given in the specification, which are inhibitors of RET kinase and are useful in the treatment and prevention of diseases which can be treated with a RET kinase inhibitor, including RET-associated diseases and disorders.

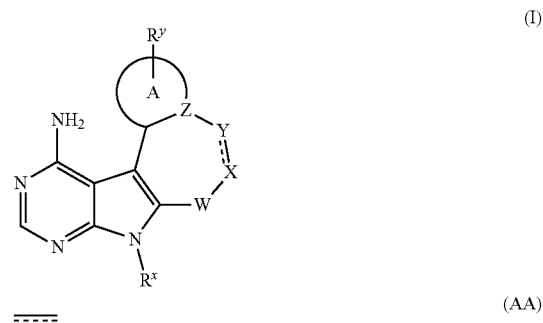

18 Claims, No Drawings
Specification includes a Sequence Listing.

(56) References Cited

U.S. PATENT DOCUMENTS

| | | |
|---|---|---|
| 5,877,016 A | 3/1999 | Presta et al. |
| 5,910,574 A | 6/1999 | Presta et al. |
| 6,025,166 A | 2/2000 | Presta et al. |
| 6,027,927 A | 2/2000 | Presta et al. |
| 6,153,189 A | 11/2000 | Presta et al. |
| 6,531,152 B1 | 3/2003 | Lerner et al. |
| 6,534,085 B1 | 3/2003 | Zeligs |
| 6,861,509 B1 | 3/2005 | Sanicola-Nadel et al. |
| 7,384,632 B2 | 6/2008 | Devaux et al. |
| 7,465,726 B2 | 12/2008 | Ahmed et al. |
| 7,504,509 B2 | 3/2009 | Ibrahim et al. |
| 7,514,446 B2 | 4/2009 | Davis-Ward et al. |
| 7,615,383 B2 | 11/2009 | Devaux et al. |
| 7,795,273 B2 | 9/2010 | Imbach et al. |
| 7,863,288 B2 | 1/2011 | Ibrahim et al. |
| 7,863,289 B2 | 1/2011 | Spevak et al. |
| 8,026,247 B2 | 9/2011 | Bold et al. |
| 8,067,434 B2 | 11/2011 | Ibrahim et al. |
| 8,106,069 B2 | 1/2012 | Salom et al. |
| 8,114,989 B2 | 2/2012 | Wang et al. |
| 8,129,374 B2 | 3/2012 | Bhagwat et al. |
| 8,198,298 B2 | 6/2012 | Salom et al. |
| 8,299,057 B2 | 10/2012 | Lombardi Borgia et al. |
| 8,338,417 B2 | 12/2012 | Li et al. |
| 8,354,526 B2 | 1/2013 | Ding et al. |
| 8,399,442 B2 | 3/2013 | Berdini et al. |
| 8,450,322 B2 | 5/2013 | Andrews et al. |
| 8,461,161 B2 | 6/2013 | Burns et al. |
| 8,501,756 B2 | 8/2013 | Artman, III et al. |
| 8,513,263 B2 | 8/2013 | Haas et al. |
| 8,524,709 B2 | 9/2013 | Liang et al. |
| 8,552,002 B2 | 10/2013 | Ding et al. |
| 8,568,998 B2 | 10/2013 | Mani et al. |
| 8,629,135 B2 | 1/2014 | Gujral et al. |
| 8,637,256 B2 | 1/2014 | Ernst |
| 8,637,516 B2 | 1/2014 | Fan et al. |
| 8,642,035 B2 | 2/2014 | Luehrsen |
| 8,673,347 B2 | 3/2014 | Traversa et al. |
| 8,686,005 B2 | 4/2014 | Gregor |
| 8,691,221 B2 | 4/2014 | Pavone et al. |
| 8,741,849 B2 | 6/2014 | Panitch et al. |
| 8,754,209 B2 | 6/2014 | Sim et al. |
| 8,791,123 B2 | 7/2014 | Allen et al. |
| 8,815,901 B2 | 7/2014 | Furet et al. |
| 8,815,906 B2 | 8/2014 | Gregor et al. |
| 8,895,744 B2 | 11/2014 | Gambacorti Passerini et al. |
| 8,912,194 B2 | 12/2014 | Ciomei et al. |
| 8,912,204 B2 | 12/2014 | Ibrahim et al. |
| 8,933,084 B2 | 1/2015 | Andrews et al. |
| 8,933,230 B2 | 1/2015 | Yun et al. |
| 8,937,071 B2 | 1/2015 | Eidam et al. |
| 8,946,226 B2 | 2/2015 | Ciomei et al. |
| 9,006,256 B2 | 4/2015 | Matsui |
| 9,035,063 B2 | 5/2015 | Eidam et al. |
| 9,102,671 B2 | 8/2015 | Molteni et al. |
| 9,149,464 B2 | 10/2015 | Bakale et al. |
| 9,150,517 B2 | 10/2015 | Bakale et al. |
| 9,186,318 B2 | 11/2015 | Yun et al. |
| 9,216,172 B2 | 12/2015 | Kohno et al. |
| 9,242,977 B2 | 1/2016 | Takeuchi et al. |
| 9,260,437 B2 | 2/2016 | Ibrahim et al. |
| 9,273,051 B2 | 3/2016 | Chen et al. |
| 9,297,011 B2 | 3/2016 | Chen et al. |
| 9,321,772 B2 | 4/2016 | Dar et al. |
| 9,487,491 B2 | 11/2016 | Shimada et al. |
| 9,493,455 B2 | 11/2016 | Cheve et al. |
| 9,505,784 B2 | 11/2016 | Choi et al. |
| 9,522,910 B2 | 12/2016 | Chilov et al. |
| 9,550,772 B2 | 1/2017 | Cheve et al. |
| 9,604,980 B2 | 3/2017 | Menichincheri et al. |
| 9,669,028 B2 | 6/2017 | Vankayalapati et al. |
| 9,682,083 B2 | 6/2017 | Angiolini et al. |
| 9,738,660 B2 | 8/2017 | Yang et al. |
| 9,758,508 B2 | 9/2017 | Hong et al. |
| 9,789,100 B2 | 10/2017 | Eidam |
| 9,801,880 B2 | 10/2017 | Micklem |
| 10,023,570 B2 | 7/2018 | Andrews et al. |
| 10,138,243 B2 | 11/2018 | Andrews et al. |
| 10,174,027 B2 | 1/2019 | Andrews et al. |
| 10,174,028 B2 | 1/2019 | Andrews et al. |
| 2004/0185547 A1 | 9/2004 | Mohammai et al. |
| 2005/0209195 A1 | 9/2005 | Menta et al. |
| 2005/0222171 A1 | 10/2005 | Bold et al. |
| 2006/0183900 A1 | 8/2006 | Huang et al. |
| 2007/0117800 A1 | 5/2007 | Arnold et al. |
| 2007/0149523 A1 | 6/2007 | Ehlert et al. |
| 2007/0184117 A1 | 8/2007 | Gregory et al. |
| 2007/0265274 A1 | 11/2007 | Fagin et al. |
| 2008/0199426 A1 | 8/2008 | Sukhatme et al. |
| 2008/0234267 A1 | 9/2008 | Lackey |
| 2008/0234276 A1 | 9/2008 | Boyle et al. |
| 2008/0234284 A1 | 9/2008 | Imbach et al. |
| 2008/0262021 A1 | 10/2008 | Capraro et al. |
| 2008/0275054 A1 | 11/2008 | Holzer et al. |
| 2008/0287427 A1 | 11/2008 | Bold et al. |
| 2008/0312192 A1 | 12/2008 | Bold et al. |
| 2008/0319005 A1 | 12/2008 | Bold et al. |
| 2009/0012045 A1 | 1/2009 | Hitoshi et al. |
| 2009/0027556 A1 | 1/2009 | Bleau et al. |
| 2009/0048249 A1 | 2/2009 | Chiu et al. |
| 2009/0069360 A1 | 3/2009 | Batt et al. |
| 2009/0099167 A1 | 4/2009 | Bold et al. |
| 2009/0130229 A1 | 5/2009 | Lanzi |
| 2009/0143399 A1 | 6/2009 | Hurley et al. |
| 2009/0152083 A1 | 6/2009 | Cheng et al. |
| 2009/0209496 A1 | 8/2009 | Chaplin et al. |
| 2009/0215761 A1 | 8/2009 | Whitten et al. |
| 2009/0227556 A1 | 9/2009 | Obaishi |
| 2009/0312321 A1 | 12/2009 | Ren et al. |
| 2010/0004239 A1 | 1/2010 | Tang et al. |
| 2010/0048540 A1 | 2/2010 | Boyle et al. |
| 2010/0069395 A1 | 3/2010 | Imbach et al. |
| 2010/0075916 A1 | 3/2010 | Gant et al. |
| 2010/0081675 A1 | 4/2010 | Hsieh et al. |
| 2010/0152219 A1 | 6/2010 | Block et al. |
| 2010/0173954 A1 | 7/2010 | Wilhelm et al. |
| 2010/0209488 A1 | 8/2010 | Wrasidlo et al. |
| 2010/0280012 A1 | 11/2010 | Lee |
| 2010/0297115 A1 | 11/2010 | Blaustein |
| 2010/0324065 A1 | 12/2010 | Ibrahim et al. |
| 2011/0046370 A1 | 2/2011 | Sim et al. |
| 2011/0053934 A1 | 3/2011 | Angell et al. |
| 2011/0118245 A1 | 5/2011 | Abraham et al. |
| 2011/0133637 A1 | 6/2011 | Ota |
| 2011/0189167 A1 | 8/2011 | Flynn et al. |
| 2011/0195072 A1 | 8/2011 | Boulay et al. |
| 2011/0212053 A1 | 9/2011 | Qian et al. |
| 2011/0269739 A1 | 11/2011 | Kim et al. |
| 2011/0281841 A1 | 11/2011 | Lee et al. |
| 2011/0301157 A1 | 12/2011 | Bold et al. |
| 2012/0065233 A1 | 3/2012 | Gregor |
| 2012/0070410 A1 | 3/2012 | Apuy et al. |
| 2012/0157451 A1 | 6/2012 | Gradl et al. |
| 2012/0157452 A1 | 6/2012 | Gradl et al. |
| 2012/0225057 A1 | 9/2012 | Flynn et al. |
| 2012/0271048 A1 | 10/2012 | Sim et al. |
| 2012/0277247 A1 | 11/2012 | Menet et al. |
| 2012/0277274 A1 | 11/2012 | Kocherlakota et al. |
| 2012/0277424 A1 | 11/2012 | Sim et al. |
| 2012/0283261 A1 | 11/2012 | Bearss et al. |
| 2012/0302567 A1 | 11/2012 | Jung et al. |
| 2013/0012703 A1 | 1/2013 | Sim et al. |
| 2013/0029925 A1 | 1/2013 | Vandier et al. |
| 2013/0053370 A1 | 2/2013 | Son et al. |
| 2013/0079343 A1 | 3/2013 | Sim et al. |
| 2013/0303518 A1 | 11/2013 | Tang et al. |
| 2014/0121239 A1 | 5/2014 | Aftab |
| 2014/0137274 A1 | 5/2014 | Ishikawa |
| 2014/0213580 A1 | 7/2014 | Cao et al. |
| 2014/0272951 A1 | 9/2014 | Chakravarti et al. |
| 2014/0371219 A1 | 12/2014 | Bae et al. |
| 2015/0018336 A1 | 1/2015 | Chen et al. |
| 2015/0051222 A1 | 2/2015 | Barbugian et al. |
| 2015/0057335 A1 | 2/2015 | Kohno et al. |

| | | | | | | |
|---|---|---|---|---|---|---|
| 2015/0065468 A1 | 3/2015 | Holladay et al. | | WO | 2009007748 | 1/2009 |
| 2015/0099721 A1 | 4/2015 | Acquaviva et al. | | WO | 2009012283 | 1/2009 |
| 2015/0099762 A1 | 4/2015 | Eidam et al. | | WO | 2009013126 | 1/2009 |
| 2015/0166564 A1 | 6/2015 | Allen et al. | | WO | 2009014637 | 1/2009 |
| 2015/0177246 A1 | 6/2015 | Shibata et al. | | WO | 2009017838 | 2/2009 |
| 2015/0238477 A1 | 8/2015 | Aftab | | WO | 2009023978 | 2/2009 |
| 2015/0272958 A1 | 10/2015 | Kodama et al. | | WO | 2009042646 | 4/2009 |
| 2015/0283132 A1 | 10/2015 | Lim et al. | | WO | 2009053442 | 4/2009 |
| 2015/0306086 A1 | 10/2015 | Wilcoxen | | WO | 2009071480 | 6/2009 |
| 2016/0000783 A1 | 1/2016 | Takeuchi et al. | | WO | 2009088990 | 7/2009 |
| 2016/0009709 A1 | 1/2016 | Cheve et al. | | WO | 2009092049 | 7/2009 |
| 2016/0046636 A1 | 2/2016 | Gray et al. | | WO | 2009118411 | 10/2009 |
| 2016/0137654 A1 | 5/2016 | Arrigo et al. | | WO | 2009143018 | 11/2009 |
| 2016/0176865 A1 | 6/2016 | Ibrahim et al. | | WO | 2009143024 | 11/2009 |
| 2016/0318929 A1 | 11/2016 | Hudkins et al. | | WO | 2009152083 | 12/2009 |
| 2017/0014413 A1 | 1/2017 | Downing et al. | | WO | 2010006086 | 1/2010 |
| 2017/0044106 A1 | 2/2017 | Aftab et al. | | WO | 2010031816 | 3/2010 |
| 2017/0096425 A1 | 4/2017 | Andrews et al. | | WO | 2010033941 | 3/2010 |
| 2017/0114032 A1 | 4/2017 | Cheng et al. | | WO | 2010048314 | 4/2010 |
| 2017/0121312 A1 | 5/2017 | Brubaker et al. | | WO | 2010058006 | 5/2010 |
| 2017/0226100 A1 | 8/2017 | Jiaang et al. | | WO | 2010111527 | 9/2010 |
| 2017/0281632 A1 | 10/2017 | Cox et al. | | WO | 2010121576 | 10/2010 |
| 2017/0283404 A1 | 10/2017 | Cheung et al. | | WO | 2010145998 | 12/2010 |
| 2017/0298074 A1 | 10/2017 | Cheung et al. | | WO | 2011006074 | 1/2011 |
| 2017/0349953 A1 | 12/2017 | Lovejoy et al. | | WO | 2011022439 | 2/2011 |
| 2018/0009817 A1 | 1/2018 | Miyazaki et al. | | WO | 2011045344 | 4/2011 |
| 2018/0009818 A1 | 1/2018 | Miyazaki et al. | | WO | 2011055215 | 5/2011 |
| 2018/0022732 A1 | 1/2018 | Brubaker et al. | | WO | 2011092120 | 8/2011 |
| 2018/0133200 A1 | 5/2018 | Andrews et al. | | WO | 2011133637 | 10/2011 |
| 2018/0133207 A1 | 5/2018 | Andrews et al. | | WO | 2011143459 | 11/2011 |
| 2018/0133213 A1 | 5/2018 | Andrews et al. | | WO | 2011146336 | 11/2011 |
| 2018/0134702 A1 | 5/2018 | Andrews et al. | | WO | 2012034091 | 3/2012 |
| 2018/0134703 A1 | 5/2018 | Andrews et al. | | WO | 2012034095 | 3/2012 |
| 2018/0148445 A1 | 5/2018 | Andrews et al. | | WO | 2012047017 | 4/2012 |
| 2018/0179203 A1 | 6/2018 | Andrews et al. | | WO | 2012053606 | 4/2012 |
| 2018/0186790 A1 | 7/2018 | Andrews et al. | | WO | 2012101029 | 8/2012 |
| 2018/0186791 A1 | 7/2018 | Andrews et al. | | WO | 2012101032 | 8/2012 |
| 2019/0127373 A1 | 5/2019 | Andrews et al. | | WO | 2012109075 | 8/2012 |
| 2019/0127374 A1 | 5/2019 | Andrews et al. | | WO | 2012113774 | 8/2012 |
| 2019/0127375 A1 | 5/2019 | Andrews et al. | | WO | 2012116217 | 8/2012 |
| 2019/0352403 A1 | 11/2019 | Schwab et al. | | WO | 2012139930 | 10/2012 |
| 2020/0055838 A1 | 2/2020 | Youhong et al. | | WO | 2012143248 | 10/2012 |
| 2020/0055860 A1 | 2/2020 | Andrews et al. | | WO | 2012152763 | 11/2012 |
| 2020/0339578 A1 | 10/2020 | Walls et al. | | WO | 2012158413 | 11/2012 |
| 2020/0339589 A1 | 10/2020 | Blake et al. | | WO | 2012171337 | 12/2012 |
| 2020/0399279 A1 | 12/2020 | Blake et al. | | WO | 2013014039 | 1/2013 |
| | | | | WO | 2013016720 | 1/2013 |
| FOREIGN PATENT DOCUMENTS | | | | WO | 2013036232 | 3/2013 |
| | | | | WO | 2013042137 | 3/2013 |
| JP | 2015109806 | 6/2015 | | WO | 2013050446 | 4/2013 |
| WO | 87/05297 | 9/1987 | | WO | 2013050448 | 4/2013 |
| WO | 97/044356 | 11/1997 | | WO | 2013074518 | 5/2013 |
| WO | 2001016169 | 3/2001 | | WO | 2013102059 | 7/2013 |
| WO | 2001062273 | 8/2001 | | WO | 2013174876 | 11/2013 |
| WO | 2003020698 | 3/2003 | | WO | 2013183578 | 12/2013 |
| WO | 2005044835 | 5/2005 | | WO | 2014011900 | 1/2014 |
| WO | 2005051366 | 6/2005 | | WO | 2014019908 | 2/2014 |
| WO | 2005062795 | 7/2005 | | WO | 2014075035 | 5/2014 |
| WO | 2005070431 | 8/2005 | | WO | 2014078322 | 5/2014 |
| WO | 2006089298 | 8/2006 | | WO | 2014078323 | 5/2014 |
| WO | 2006123113 | 11/2006 | | WO | 2014078325 | 5/2014 |
| WO | 2006130613 | 12/2006 | | WO | 2014078328 | 5/2014 |
| WO | 2006131952 | 12/2006 | | WO | 2014078331 | 5/2014 |
| WO | 2007002325 | 1/2007 | | WO | 2014078372 | 5/2014 |
| WO | 2007002433 | 1/2007 | | WO | 2014078378 | 5/2014 |
| WO | 2007022999 | 3/2007 | | WO | 2014078408 | 5/2014 |
| WO | 2007054357 | 5/2007 | | WO | 2014078417 | 5/2014 |
| WO | 2007057397 | 5/2007 | | WO | 2014078454 | 5/2014 |
| WO | 2007057399 | 5/2007 | | WO | 2014083567 | 6/2014 |
| WO | 2007087245 | 8/2007 | | WO | 2014086284 | 6/2014 |
| WO | 2007109045 | 9/2007 | | WO | 2014141187 | 9/2014 |
| WO | 2007110344 | 10/2007 | | WO | 2014160521 | 10/2014 |
| WO | 2007136103 | 11/2007 | | WO | 2014160524 | 10/2014 |
| WO | 2008031551 | 3/2008 | | WO | 2014184069 | 11/2014 |
| WO | 2008079903 | 7/2008 | | WO | WO-2014184069 A1 * | 11/2014 ........... A61K 31/496 |
| WO | 2008079906 | 7/2008 | | WO | 2014194127 | 12/2014 |
| WO | 2008079909 | 7/2008 | | WO | 2015017528 | 2/2015 |
| WO | 2008080001 | 7/2008 | | WO | 2015017533 | 2/2015 |
| WO | 2008080015 | 7/2008 | | WO | 2015057873 | 4/2015 |

| | | |
|---|---|---|
| WO | 2015058129 | 4/2015 |
| WO | 2015061572 | 4/2015 |
| WO | 2015079251 | 6/2015 |
| WO | 2015108992 | 7/2015 |
| WO | 2015112806 | 7/2015 |
| WO | 2015124697 | 8/2015 |
| WO | 2015161274 | 10/2015 |
| WO | 2015161277 | 10/2015 |
| WO | 2015175788 | 11/2015 |
| WO | 2015191666 | 12/2015 |
| WO | 2015191667 | 12/2015 |
| WO | 2016011141 | 1/2016 |
| WO | 2016011144 | 1/2016 |
| WO | 2016011147 | 1/2016 |
| WO | 2016022569 | 2/2016 |
| WO | 2016027754 | 2/2016 |
| WO | 2016037578 | 3/2016 |
| WO | 2016038519 | 3/2016 |
| WO | 2016038552 | 3/2016 |
| WO | 2016075224 | 5/2016 |
| WO | 2016077841 | 5/2016 |
| WO | 2016081450 | 5/2016 |
| WO | 2016090285 | 6/2016 |
| WO | 2016096709 | 6/2016 |
| WO | 2016127074 | 8/2016 |
| WO | 2016137060 | 9/2016 |
| WO | 2016140974 | 9/2016 |
| WO | 2016141169 | 9/2016 |
| WO | 2016149261 | 9/2016 |
| WO | 2016168992 | 10/2016 |
| WO | 2017009644 | 1/2017 |
| WO | 2017011776 | 1/2017 |
| WO | 2017013160 | 1/2017 |
| WO | 2017026718 | 2/2017 |
| WO | 2017027883 | 2/2017 |
| WO | 2017043550 | 3/2017 |
| WO | 2017049462 | 3/2017 |
| WO | 2017079140 | 5/2017 |
| WO | 2017097697 | 6/2017 |
| WO | 2017122815 | 7/2017 |
| WO | 2017145050 | 8/2017 |
| WO | 2017146116 | 8/2017 |
| WO | 2017178844 | 10/2017 |
| WO | 2017178845 | 10/2017 |
| WO | 2017197051 | 11/2017 |
| WO | 2018071447 | 4/2018 |
| WO | 2018136661 | 7/2018 |
| WO | 2019/075108 | 4/2019 |
| WO | 2019143977 | 7/2019 |
| WO | 2019143991 | 7/2019 |
| WO | 2019143994 | 7/2019 |

OTHER PUBLICATIONS

Albaugh et al., "Discovery of GNF-5837, a Selective TRK Inhibitor with Efficacy in Rodent Cancer Tumor Models," ACS Med Chem. Lett., Jan. 1, 2012;3(2):140-145.

Amit Met al., "Upregulation of cRET induces perineurial invasion of pancreatic adenocarcinoma." Oncogene Jun. 8, 2017; 36:3232-3239.

Andreucci et al., "Targeting the receptor tyrosine kinase RET in combination with aromatase inhibitors in ER positive breast cancer xenografts," Oncotarget, Dec. 6, 2016, 7(49):80543-80553.

Antonescu et al., "Molecular characterization of inflammatory myofibroblastic tumors with frequent ALK and ROS1 gene fusions and rare novel RET rearrangement," Am J Surg Pathol, Jul. 2015;39(7):957-967.

Anunobi et al., "Extracellular DNA promotes colorectal tumor cell survival after cytotoxic chemotherapy", J Surg. Res. Mar. 28, 2018.

Arighi et al., "RET tyrosine kinase signaling in development and cancer," Cytokine Growth Factor Rev, Aug.-Oct. 2005;16(4-5):441-467.

Arriola et al., "Comparison of plasma ctDNA and tissue/cytology-based techniques for the detection of EGFR mutation status in advanced NSCLC: Spanish data subset from ASSESS", Clin. Transl. Oneal., 20: 1261-1267, Apr. 5, 2018.

Aslibekyan et al., "Association of Methylation Signals With Incident Coronary Heart Disease in an Epigenome-Wide Assessment of Circulating Tumor Necrosis Factor $\alpha$", JAMA Cardiol., 463-472, Apr. 4, 2018.

Attie et al., "Diversity of RET proto-oncogene mutations in familial and sporadic Hirschsprung disease", Human Molecular Genetics 4(8): 1381-1386, 1995.

Ballerini et al., "RET fusion genes are associated with chronic myelomonocytic leukemia and enhance monocytic differentiation," Leukemia, Nov. 2012;26(11):2384-2389.

Bartsch et al., "A RET double mutation in the germline of a kindred with FMTC.", Exp Clin Endocrinol Diabetes 108(2): 128-132, 2000.

Bastien et al., "Detection and characterization of a novel RET translocation in lung adenocarcinoma." Journal of Molecular Diagnostics, 18(6):1027, Abstract No. SI20, 2016 Annual Meeting of the Association for Molecular Pathology, Charlotte, NC, 2016.

Behrens et al., "Go 6976 is a potent inhibitor of neurotrophin-receptor intrinsic tyrosine kinase," J Neurochem. Mar. 1999;72(3):919-924.

Bhinge et al., "EGFR mediates activation of RET in lung adenocarcinoma with neuroendocrine differentiation characterized by ASCLI expression," Oncotarget, Apr. 18, 2017, 8(16):27155-27165.

Boeckx et al. "Effect of primary tumor location on second-or later-line treatment outcomes in patients with RAS wild-type metastatic colorectal cancer and all treatment lines in patients with RAS mutations in four randomized panitumumab studies." Clinical colorectal cancer 17.3 (2018): 170-178.

Borecka et al., "Identification of pancreatic cancer susceptibility genes in the Czech Republic." European Journal of Cancer, (Jul. 2016) vol. 61, No. 1, pp. S26, Abstract No. 162, Meeting Info: 24th Biennial Congress of the European Association for Cancer Research, EACR 2016. Manchester, United Kingdom.

Borre, P. Vanden et al., "Pediatric, adolescent and young adult (PAYA) thyroid carcinoma harbors frequent and diverse targetable genomic alterations including kinase fusions." Annals of Oncology, 2016, vol. 27, Supp. Supplement 6. Abstract No. 427PD; European Society for Medical Oncology Congress, ESMP 2016. Copenhagen, Denmark. Oct. 7, 2016-Oct. 11, 2016.

Borrello et al., "RET inhibition: implications in cancer therapy," Expert Opin. Ther. Targets, Apr. 2013, 17(4):403-419.

Bosic et al., "Targeted molecular profiling reveals genetic heterogeneity of poromas and porocarcinomas", Pathology. 50(3): 327-332, 2018.

Boulay et al., "The Ret receptor tyrosine kinase pathway functionally interacts with the ERalpha pathway in breast cancer," Cancer Res., May 15, 2008;68(10):3743-3751.

Brodeur, "Neuroblastoma: biological insights into a clinical enigma," Nat Rev Cancer., Mar. 2003, 3(3):203-216.

Caira et al, "Crystalline Polymorphism of Organic compounds," Topics in Current Chemistry, Jan. 1998, 198: 163-208.

Calero et al., "Sunitinib suppress neuroblastoma growth through degradation of MYCN and inhibition of angiogenesis," PLoS One. Apr. 23, 2014;9(4):e95628.

Camilleri, "Peripheral mechanisms in irritable bowel syndrome," N Engl J Med, Oct. 25, 2012, 367(17):1626-1635.

Camoratto et al., "CEP-751 inhibits TRK receptor tyrosine kinase activity in vitro exhibits anti-tumor activity," Int J Cancer. Aug. 7, 1997;72(4):673-679.

Camos et al., "Gene expression profiling of acute myeloid leukemia with translocation t(8;16)(pll;pl3) and MYST3-CREBBP rearrangement reveals a distinctive signature with a specific pattern of HOX gene expression," Cancer Res., Jul. 15, 2006;66(14):6947-6954.

Cancer Genome Atlas Network, "Comprehensive molecular characterization of human colon and rectal cancer," Nature, Jul. 18, 2012;487(7407):330-337.

Cao et al., "The utilization of next-generation sequencing to detect somatic mutations and predict clinical prognosis of Chinese non-small cell lung cancer patients.", Onco. Targets. Ther., (11): 2637-2646, 2018.

Carlomagno et al., "Identification of tyrosine 806 as a molecular determinant of RET kinase sensitivity to ZD6474," Endocr. Rel. Cancer, Mar. 2009;l6(1):233-241.

Carpinelli et al., "PHA-739358, a potent inhibitor of Aurora kinases with a selective target inhibition profile relevant to cancer," Mol Cancer Ther., Dec. 2007;6(12 Pt 1):3158-68.

Cecchirini et al., "Somatic in frame deletions not involving juxtamembranous cysteine residues strongly activate the RET proto-oncogene," Oncogene, May 29, 1997;14(21):2609-2612.

Ceolin et al., "Effect of 3'UTR RET Variants on RET mRNA Secondary Structure and Disease Presentation in Medullary Thyroid Carcinoma," PLoS One, Feb. 1, 2016;11(2):e0147840. doi: 10.1371i'journal.pone.0147840. eCollection 2016.

Chai et al., "An integrated analysis of cancer genes in thyroid cancer", Oncology Reports, 35(2): 962-970. doi: 10.3892/or.2015.4466, 2015.

Chang et al., "EGF Induced RET Inhibitor Resistance in CCDC6-RET Lung Cancer Cells," Yonsei Med J, Jan. 2017, 58(1):9-18.

Chaudhuri et al., "Early Detection of Molecular Residual Disease in Localized Lung Cancer by Circulating Tumor DNA Profiling.", Cancer Discov; 7(12); 1394-403, 2017.

Chen et al., "Studies on a pedigree of multiple endocrine neoplasia type 2A caused by RET proto-oncogeneC634R mutation with G691S, R982C polymorphisms with review of literature", Medical Journal of Chinese People's Liberation Army, 2013, vol. 38, No. 4, 308-31. English Abstract.

Choi et al., "(R)-2-Phenylpyrrolidine Substituted Imidazopyridazines: A New Class of Potent and Selective Pan-TRK Inhibitors," ACS Med Chem Lett., Mar. 16, 2015;6(5):562-567.

Ciampi et al., European Thyroid Journal, vol. 7, Supp. 1, pp. 63. Abstract No. OP-09-66. Meeting Info: 41st Annual Meeting of the European Thyroid Association, ETA 2018. Sep. 15, 2018-Sep. 18, 2018. doi: 10.1159/000491542.

Cohen, Joshua D., et al. "Detection and localization of surgically resectable cancers with a multi-analyte blood test." Science 359.6378 (2018): 926-930.

Comino-Mendez et al., "Predicting Relapse with Circulating Tumor DNA Analysis in Lung Cancer.", Cancer Discov; 7(12); 1368-70, 2017.

Corsello et al., "A case of MEN2A associated to Leu56Met RET mutation." Endocrine Reviews, (Jun. 2014) vol. 35, No. 3, Suppl. S, pp. SUN-0322, Meeting Info.: 96th Annual Meeting and Expo of the Endocrine-Society, Chicago, IL, USA, Jun. 21-24, 2014.

Cranston et al., "RET is constitutively activated by novel tandem mutations that alter the active site resulting in multiple endocrine neoplasia type 2B," Cancer Res., Oct. 15, 2006;66(20): 10179-10187.

Croucher et al., "TrkB inhibition by GNF-4256 slows growth and enhances chemotherapeutic efficacy in neuroblastoma xenografts," Cancer Chemother Pharmcol., Jan. 2015;75(1):131-141.

Dabir et al., "RET mutation and expression in small-cell lung cancer.", Journal of Thoracic Oncology, 9(9), 1316-1323, 2014.

Das, Shubhajit, Pralok K. Samanta, and Swapan K. Pati. "Watson—Crick base pairing, electronic and photophysical properties of triazole modified adenine analogues: a computational study." New Journal of Chemistry 39.12 (2015): 9249-9256.

Davila et al., "Comprehensive genomic profiling of a rare thyroid follicular dendritic cell sarcoma," Rare Tumors, 2017, 9(2):6834.

Dawson et al., "Altered expression of RET proto-oncogene product in prostatic intraepithelial neoplasia and prostate cancer," J Natl Cancer Inst, Apr. 1, 1998;90(7):519-523.

De Almeida et al., "Expanded analysis of variants of unknown significance of RET gene." Endocrine Reviews, 2016, vol. 37, No. 2, Supp. Supplement 1. Abstract No. SUN-068; 93th Annual Meeting and Expo of the Endocrine Society, ENDO 2016. Boston, MA, US. Apr. 1, 2016-Apr. 4, 2016.

De Groot et al., "RET as a diagnostic and therapeutic target in sporadic and hereditary endocrine tumors," Endocrine Rev, Aug. 2006 27(5):535-560.

Demeure et al., "Whole-genome Sequencing of an Aggressive BRAF Wild-type Papillary Thyroid Cancer Identified EML4-ALK Translocation as a Therapeutic Target," World J. Surg., Jun. 2014, 38(6):1296-305.

Diner er al., "Preparation of 3-substituted-1-isopropyl-1H-pyrazolo[3,4-d]pyrimidin-4-amines as RET kinase inhibitors," J. Med. Chem., May 24, 2012, 55(10):4872-4876.

Ding et al., "Artemin, a member of the glial cell line-derived neurotrophic factor family of ligands, is HER2-regulated and mediates acquired trastuzumab resistance by promoting cancer stem cell-like behavior in mammary carcinoma cells," J Biol Chem, Jun. 6, 2014, 289(23):16057-71.

Dogan et al., "Genomic profiling of the two closely related "cousins" acinic cell carcinoma and mammary analog secretory carcinoma of salivary glands reveals novel NCOA-4-RET fusion in mammary analog secretory carcinomas." Laboratory Investigation, (Feb. 2017) vol. 97, Supp. 1, pp. 323A. Abstract No. 1298, Meeting Info: 106th Annual Meeting of the United States and Canadian Academy of Pathology, USCAP 2017. San Antonio, TX, United States.

Drilon et al. "A phase I/Ib study of RXDX-105, an oral RET and BRAF inhibitor, in patients with advanced solid tumors." S143, 2016.

Drilon et al., "Phase II study of cabozantinib for patients with advanced RET-rearranged lung cancers," Journal of Clinical Oncology, May 20, 2015, 51st Annual Meeting, 33(15S):8007-8007 [Abstract Only], 6 pages.

Dvorakova et al., "New multiple somatic mutations in the RET proto-oncogene associated with a sporadic medullary thyroid carcinoma.", Thyroid, 16(3), 311-316, 2006.

Elisei et al., "Ret Oncogene and Thyroid Carcinoma", Journal of Genetic Syndromes & Gene Therapy, 5(1), 1, 2014.

Esseghir et al., "A role for glial cell derived neurotrophic factor induced expression by inflammatory cytokines and RET/GFR alpha 1 receptor up-regulation in breast cancer," Cancer Res, Dec. 15, 2007;67(24):11732-11741.

Fang et al., "Detection of a novel RET gene fusion in a non-small cell lung cancer patient using AMP chemistrv." Journal of Thoracic Oncology, Feb. 1, 2016,11(2):S21-S22.

Fitze et al., "Association between c135G/A genotype and RET proto-oncogene germline mutations and phenotype of Hirschsprung's disease.", Lancet, 393(9313): 1200-1205, 2002.

Flavin et al., "RET protein expression in papillary renal cell carcinoma," Urol. Oncol., Nov.-Dec. 2012 30(6):900-905.

Fugazzola et al., "Molecular and biochemical analysis of RET/PTC4, a novel oncogenic rearrangement between RET and ELE1 genes, in a post-Chemoby1 papillary thyroid cancer," Oncogene, Sep. 1996, 13(5): 1093-7.

Futami et al., "A novel somatic point mutation of the RET Proto-oncogene in tumor tissues of small cell lung cancer patients," Jpn. J. Cancer Res., Dec. 1995, 86(12):1127-1130.

Gao et al., "Driver Fusions and Their Implications in the Development and Treatment of Human Cancers.", Cell Reports, 23(1), 227-238, 2018.

Gao et al., "Neurotrophic Factor Artemin Promotes Invasiveness and Neurotrophic Function of Pancreatic Adenocarcinoma In Vivo and In Vitro," Pancreas, Jan. 2015, 44(1):134-143.

Gattei et al., "Expression of the RET receptor tyrosine kinase and GDNFR-alpha in normal and leukemic human hematopoietic cells and stromal cells of the bone marrow microenvironment," Blood, Apr. 15, 1997;89(8):2925-2937.

Gattei, et al., "Differential expression of the RET gene in human acute myeloid leukemia," Ann. Hematol, Nov. 1998, 77(5):207-210.

Gattelli et al., "Ret inhibition decreases growth and metastatic potential of estrogen receptor positive breast cancer cells," EMBO Mol. Med., Sep. 2013;5(9):1335-1350.

Gautschi et al., "Targeting RET in Patients With RET-Rearranged Lung Cancers: Results From the Global, Multicenter RET Registry.", Journal of Clinical Oncology, 35(13) 1403-1410, 2017.

Gazizova et al., "Mutation analysis of the RET proto-oncogene in 35 Russian families with Men 2A, Men 2B and Fmtc: Four novel mutations for Men 2A." Endocrine Reviews, (Jun. 2014) vol. 35, No. 3, Suppl. S, pp. SAT-0304, Meeting Info.: 96th Annual Meeting and Expo of the Endocrine-Society, Chicago, IL, USA, Jun. 21-24, 2014.

Gil et al., "Paracrine regulation of pancreatic cancer cell invasion by peripheral nerves," J. Natl. Cancer Inst., Jan. 20, 2010;102(2):107-118.

Gozgit et al., "RET fusions identified in colorectal cancer PDX models are sensitive to the potent RET inhibitor ponatinib," AACR Annnal Meeting, Apr. 7, 2014, Presentation Abstract, [Abstract Only], 1 page.

Greco et al., "Molecular pathology of differentiated thyroid cancer," J. Nucl. Med. Mol. Imaging, Oct. 2009, 53:440-454.

Greene & Wuts, eds., "Protecting Groups in Organic Synthesis", 2nd ed. New York; John Wiley & Sons, Inc., 1991, Chapter One, 20 pages.

Grey et al., "The RET E616Q Variant is a Gain of Function Mutation Present in a Family with Features of Multiple Endocrine Neoplasia 2A," Endocrine Pathology, Mar. 2017, 28(1):41-48.

Grieco et al., "PTC is a novel rearranged form of the ret proto-oncogene and is frequently detected in vivo in human thyroid papillary carcinomas," Cell, Feb. 23, 1990, 60(4):557-563.

Grubbs et al., "RET fusion as a novel driver of medullary thyroid carcinoma," J. Clin. Endocrinol. Metab., Mar. 2015;l00(3):788-793.

Gudernova et al., "One reporter for in-cell activity profiling of majority of protein kinase oncogenes", eLife, 6:e21536. doi: 10.7554/eLife.21536, 2017.

Guerin et al., "Looking beyond the thyroid: advances in the understanding of pheochromocytoma and hyperparathyroidism phenotypes in MEN2 and of non-MEN2 familial forms.", Endocr Relat Cancer, 25(2):T15-T28. doi: 10.1530/ERC-17-0266, 2017.

Guilmette et al., "Novel gene fusions in secretory carcinoma of the salivary glands: enlarging theETV6 family", Hum Pathol., 83, 50-58, 2019.

Gura et al., Systems for identifying new drugs are often faulty, Science, 278:1041-1042, 1997.

Hackam, Daniel G., and Donald A. Redelmeier. "Translation of research evidence from animals to humans." Jama 296.14 (2006): 1731-1732.

Halkova et al., "A novel RET/PTC variant detected in a pediatric patient with papillary thyroid cancer without ionization history," Human Pathology, Dec. 2015, 46(12):1962-1969.

Hezam et al., "Artemin promotes oncogenicity, metastasis and drug resistance in cancer cells," Rev Neurosci, Jan. 26, 2018, 29(1):93-98.

Hirshfield et al., "Abstract P3-07-02: are we missing actionable targets in breast cancer? Novel insights into recurrent Ret alterations." Cancer Research, (Feb. 2017) vol. 77, No. 4, Supp. 1. Abstract No. P3-07-02. Meeting Info: 39th Annual CTRC-AACR San Antonio Breast Cancer Symposium. San Antonio, TX, United States. Dec. 6, 2016-Dec. 10, 2016.

Hoffman et al., "Activation of colonic mucosal 5-HT(4) receptors accelerates propulsive motility and inhibits visceral hypersensitivity," Gastroenterology, Apr. 2012;142(4):844-854.

Hofstra et al., "No mutations found by RET mutation scanning in sporadic and hereditary neuroblastoma," Hum Genet., Mar. 1996, 97(3):362-364.

Huang, Kuan-lin, et al. "Pathogenic germline variants in 10,389 adult cancers." Cell 173.2 (2018): 355-370.

Huang et al., "Preclinical Modeling of KIF5B-RET Fusion Lung Adenocarcinoma," Mol. Cancer Ther., Oct. 2016, 15(10):2521-2529.

Ibrahimpasic et al., "Genomic Alterations in Fatal Forms of Non-Anaplastic Thyroid Cancer: Identification of MED12 and RBMIO as Novel Thyroid Cancer Genes Associated with Tumor Virulence," Clin. Cancer Res., Oct. 2017, 23(19):5970-5980.

International Preliminary Report on Patentability in International Application No. PCT/US2016/042576, dated Jan. 25, 2018, 7 pages.

International Preliminary Report on Patentability in International Application No. PCT/US2018/014279, dated Jul. 23, 2019, 7 pages.

International Preliminary Report on Patentability in International Application No. PCT/US2019/014272, dated Jul. 21, 2020, 13 pages last uploaded.

International Preliminary Report on Patentability in International Application No. PCT/US2019/014277, dated Jul. 21, 2020, 11 pages.

International Preliminary Report on Patentability in International Application No. PCT/US2019/014248, dated Jul. 21, 2020, 11 pages.

International Search Report and Written Opinion in International Application No. PCT/US2016/042576, dated Sep. 27, 2016, 12 pages.

International Search Report and Written Opinion in International Application No. PCT/US2018/014279, dated May 3, 2018, 10 pages.

International Search Report and Written Opinion in International Application No. PCT/US2018/055255, dated Dec. 17, 2018, 8 pages.

International Search Report and Written Opinion in International Application No. PCT/US2018/055279, dated Apr. 1, 2019, 20 pages.

International Search Report and Written Opinion in International Application No. PCT/US2019/014272, dated May 24, 2019, 19 pages.

International Search Report and Written Opinion in International Application No. PCT/US2019/014277, dated May 24, 2019, 17 pages.

International Search Report and Written Opinion in International Application No. PCT/US2019/014248, dated May 24, 2019, 21 pages.

International Search Report and Written Opinion in International Application No. PCT/US2019/049859, dated Jan. 28, 2020, 9 pages.

Isbell et al., "Circulating tumor DNA: A promising biomarker to guide postoperative treatment and surveillance of non-small cell lung cancer.", J Thorac. Cardiovasc. Surg., 155(6), 2628-2631, 2018.

Ito et al., "Expression of glial cell line-derived neurotrophic factor family members and their receptors in pancreatic cancers," Surgery, Oct. 2005, 138(4):788-794.

Iwahashi et al., "Expression of glial cell line-derived neurotrophic factor correlates with perineural invasion of bile duct carcinoma," Cancer, Jan. 1, 2002, 94(1):167-174.

Iyama et al., "Identification of Three Novel Fusion Oncogenes, SQSTMI/NTRK.3, AFAP1L2/RET, and PPFIBP2/RET, in Thyroid Cancers of Young Patients in Fukushima ," Thyroid, Jun. 2017, 27(6):811-818.

Iyer et al., "AZ64 inhibits TrkB and enhances the efficacy of chemotherapy and local radiation in neuroblastoma xenografts," Cancer Chemother Pharmacol., Sep. 2012;70(3):477-486.

Jhiang et al., "RET mutation screening in MEN2 patients and discovery of a novel mutation in a sporadic medullary thyroid carcinoma." Thyroid, 6(2): 115-21, 1996.

Johnson et al., Relationships between drug activity in NCI preclinical in vitro and in vivo models and early clinical trials, British Journal of Cancer, 84(10):1424-1431,2001.

Jordan, V. Craig. "Tamoxifen: a most unlikely pioneering medicine." Nature reviews Drug discovery 2.3 (2003): 205-213.

Joung et al., "Diffuse sclerosing variant of papillary thyroid carcinoma: major genetic alterations and prognostic implications," Histopathology, Jul. 2016, 69(1):45-53.

Jovanovic et al., "Novel RET mutations in macedonian patients with medullary thyroid carcinoma: genotype-phenotype correlations," Pril (Makedon Akad Nauk Umet Odd Med Nauki), 2015;36(1):93-107.

Ju et al., "A transforming KIF5B and RET gene fusion in lung adenocarcinoma revealed from whole-genome and transcriptome sequencing," Genome Res., Mar. 2012;22(3):436-445.

Kaczmarek-Ryś et al., "Modifying impact of RET gene haplotypes on medullary thyroid carcinoma clinical course." Endocrine-related cancer., 25(4): 421-36, 2018.

Kaneta et al., Abstract B173: Preclinical characterization and antitumor efficacy ofDS-5010, a highly potent and selective RET inhibitor, Mol Cancer Ther Jan. 1, 2018 (17) (1 Supplement) BI 73; DOI:10.1158/1535-7163.TARG-I7-BI73.

Karachialiou et al., "Real-time liquid biopsies become a reality in cancer treatment," Ann. Transl. Med, Mar. 2015, 3(3):36.

Karrasch et al., "How to Assess the Clinical Relevance of Novel RET Missense Variants in the Absence of Functional Studies?" Eur. Thyroid J., Mar. 2016;5(1):73-77.

Kato et al., "Repair by Src kinase of function-impaired RET with multiple endocrine neoplasia type 2A mutation with substitutions of tyrosines in the COOR-terminal kinase domain for phenylalanine," Cancer Res., Apr. 15, 2002, 62(8):2414-2422.

Kato et al., "RET Aberrations in Diverse Cancers: Next-Generation Sequencing of 4,871 Patients," Clin. Cancer Res., Apr. 15, 2017, 23(8):1988-1997.

Keszthelyi et al., "Revisiting concepts of visceral nociception in irritable bowel syndrome," Eur. J. Pain, Nov. 2012.16(10):1444-1454.

Kheiroddin et al., "RET Gene Analysis in Patients with Medullary Thyroid Carcinoma," Clin. Lab., Jan. 2016, 62(5):871-876.

Kim et al., "A new germline ALA641Thr variant in the transmembrane domain of the RET gene associated with medullary thyroid cancer," Acta Endocrinologica-Bucharest, Apr. 2015, 11(2):189-194.

Kim et al., "Fibroblast growth factor receptor 3 (FGFR3) aberrations in muscle-invasive urothelial carcinoma.", BMC Urol 18(1): 68, 2018.

Kim et al., "Mammaglobin-A is a target for breast cancer vaccination," Oncoimmunology. Feb. 26, 2016;5(2):e1069940. eCollection Feb. 2016.

Kloosterman et al., "A systematic analysis of oncogenic gene fusions in primary colon cancer," Cancer Res., Jul. 15, 2017, 77(14):3814-3822.

Klugbauer et al., "A novel type of RET rearrangement (PTC8) in childhood papillary thyroid carcinomas and characterization of the involved gene (RFG8)," Cancer Res., Dec. 15, 2000;60(24):7028-32.

Kohlmann et al., "Next-Generation Sequencing Technology Reveals a Characteristic Pattern of Molecular Mutations in 72.8% of Chronic Myelomonocytic Leukemia by Detecting Frequent Alterations in TET2, CBL, RAS, and RUNX1," J. Clin. Oncol. Aug. 20, 2010, 28(24):3858-3865.

Kohno et al., "KIF5B-RET fusions in lung adenocarcinoma," Nature Med., Feb. 12, 2012;18(3):375-377.

Kooistra et al., "KLIFS: A structural kinase ligand interaction database," Nucleic Acids Res., Jan. 2016, 44(DI)D365-D371.

Kraft et al, "Abstract 4882: genomic mechanisms of disease progression in pediatric medullary thyroid cancer (MTC)." Cancer Research, 2017, vol. 77, No. 13, Supp. Supplement 1. American Association for Cancer Research Annual Meeting 2017. Washington, DC, United States. Apr. 1, 2017-Apr. 5, 2017.

Krampitz et al., "RET gene mutations (genotype and phenotype) of multiple endocrine neoplasia type 2 and familial medullary thyroid carcinoma," Cancer, Jul. 2014 l; 120(13):1920-1931.

Kubler et al. "Self-adjuvanted mRNA vaccination in advanced prostate cancer patients: a first-in-man phase I/IIa study," J Immunother Cancer. Jun. 16, 2015, 3:26, 14 pages.

Latteyer et al., "A 6-Base Pair in Frame Germline Deletion in Exon 7 OfRET Leads to Increased RET Phosphorylation, ERK Activation, and MEN2A," J. Clin Endocrinol. Metab., Mar. 2016;101(3):1016-1022.

Le Rolle et al., "Identification and characterization of RET fusions in advanced colorectal cancer," Oncotarget, Oct. 6, 2015;6(30) 28929-28937.

Lecht et al., "Angiostatic effects of K252a, a Trk inhibitor, in murine brain capillary endothelial cells," Mol Cell Biochem. Jun. 2010;339(1-2):201-213.

Lee et al., "A practical guide to pharmaceutical polymorph screening & selection," Asian J of Pharma Sci, Mar. 2014, 9(4): 163-175.

Lee et al., "Identification of a novel partner gene, KIAA1217, fused to RET: Functional characterization and inhibitor sensitivity of two isoforms in lung adenocarcinoma," Oncotarget, May 2, 2016, 7(24):36101-36114.

Lee, S-H., et al. "Vandetanib in pretreated patients with advanced non-small cell lung cancer-harboring RET rearrangement: a phase II clinical trial." Annals of Oncology 28.2 (2017): 292-297.

Lee et al., "Whole-exome sequencing identified mutational profiles of high-grade colon adenomas," Oncotarget, Jan. 2017, 8(4): 6579-6588.

Li et al., "Trk inhibitor attenuates the BDNF/frkB-induced protection of neuroblastoma cells from etoposide in vitro and in vivo," Cancer Biol Ther., 2015;16(3):477-483.

Lipson et al., "Identification of new ALK and RET gene fusions from colorectal and lung cancer biopsies," Nature Med., Feb. 12, 2012;18(3):382-384.

Liu et al., "Oncogenic RET receptors display different autophosphorylation sites and substrate binding specificities," J Biol. Chem., J Biol Chem. Mar. 8, 1996;271(10):5309-5312.

Lopez-Delisle, Lucille, et al. "Activated ALK signals through the ERK-ETV5-RET pathway to drive neuroblastoma oncogenesis." Oncogene 37.11 (2018): 1417-1429.

Louis et al., "The 2016 World Health Organization Classification of Tumors of the Central Nervous System: a summary," Acta Neuropathol, Jun. 2016, 131(6):803-820.

Lu et al., "Circulating free DNA in the era of precision oncology: Pre- and post-analytical concerns.", Chronic Dis. Transl. Med 2(4): 223-230, 2016.

Lu et al., "Targeted next generation sequencing identifies somatic mutations and gene fusions in papillary thyroid carcinoma," Oncotarget, Jul. 2017, 8(28):45784-45792.

Luo, Wenxin, et al. "Characteristics of genomic alterations of lung adenocarcinoma in young never-smokers." International journal of cancer 143.7 (2018): 1696-1705.

Luo et al., "RET is a potential tumor suppressor gene in colorectal cancer," Oncogene, Apr. 18, 2013;32(16):2037-2047.

Makki et al., "Serum biomarkers of papillary thyroid cancer.", J Otolaryngol Head Neck Surg., 42(1): 16, 2013.

Mamedova et al., "Abstract #6: Construction of Baculovirial Vectors For RET Kinase Domain Mutants," Summer Undergraduate Research Programs (SURF) Student Abstracts, University of Oklahoma Health Sciences Center, 2016, p. 28.

Matsubara et al., "Identification of CCDC6-RET fusion in the human lung adenocarcinoma cell line, LC-2/ad," Journal of Thoracic Oncology, Dec. 2012;7(12):1872-1876.

McCarthy et al., "Tropomyosin receptor kinase inhibitors: a patent update 2009-2013," Expert. Opin. Ther. Pat., Jul. 2014;24(7):731-744.

Mendiola et al., "Preparation, Use, and Safety of O-Mesitylenesulfonylhydroxylamine," Org. Process Res. Dev., Jan. 2009, 13(2):263-267.

Moati et al., "Role of circulating tumor DNA in the management of patients with colorectal cancer", Clin. Res. Hepatol. Gastroenterol., 42, 396-402, Apr. 4, 2018.

Montagnoli et al., "Anti-proliferative effects of GW441756, a novel inhibitor of NGF receptor tyrosine kinase a (TRKA), in human sarcoma," Italian Journal of Anatomy and Embryology, Nov. 11, 2010, 115(½):117.

Moon et al., "Clinical indications for, and the future of, circulating tumor cell", Adv. Drug Deliv. Rev. Apr. 4, 2018.

Morandi et al., "GDNF-RET signaling in ER-positive breast cancers is a key determinant of response and resistance to aromatase inhibitors," Cancer Res., Jun. 15, 2013;73(12):3783-3795.

Morano et al., "Abstract B049: Characterizing andtargeting RET fusions-positive metastaticcolorectal cancer (mCRC)", Molecular Cancer Therapeutics, vol. 17, No. 1, Molecular Targets and Cancer Therapeutics, 2017.

Morgensztem et al., "Circulating cell-free tumor DNA (cfDNA) testing in small cell lung cancer." Journal of Thoracic Oncology, (Jan. 2017) vol. 12, No. 1, Supp. 1, pp. S717-S718, Abstract No. PI.07-035, Meeting Info: 17th World Conference of the International Association for the Study of Lung Cancer, IASLC 2016. Vienna, Austria. Dec. 4, 2016.

Mulligan et al., "Investigation of the genes for RET and its ligand complex, GDNF/GFR alpha-I, in small cell lung carcinoma," Genes Chromosomes Cancer, Apr. 1998, 21(4):326-332.

Mulligan, "RET revisited: expanding the oncogenic portfolio," Nature Reviews Cancer, Mar. 2014, 14(3):173-186.

Nakao et al., "Novel tandem germline RET proto-oncogene mutations in a patient with multiple endocrine neoplasia type 2B: Report of a case and a literature review of tandem RET mutations with in silico analysis", Head and Neck, 35: E363-E368, 2013.

Nakaoku, Takashi, et al. "A secondary RET mutation in the activation loop conferring resistance to vandetanib." Nature communications 9.1 (2018): 1-9.

Narayanan et al., "Discovery and preclinical characterization of novel small molecule TRK and ROS1 tyrosine kinase inhibitors for the treatment of cancer and inflammation," PLoS One. Dec. 26, 2013;8(12):e83380.

Narita et al., "Functional RET G691S polymorphism in cutaneous malignant melanoma," Oncogene, Aug. 27, 2009;28(34):3058-3068.

Nelson-Taylor et al., "Resistance to RET-Inhibition in RET-Rearranged NSCLC Is Mediated By Reactivation of RAS/MAPK Signaling," Mol. Cancer Ther., Aug. 2017, 16(8):1623-1633.

Nunes, Adriana B., et al. "A Novel Val 648 Ile Substitution in RET Protooncogene Observed in a Cys 634 Arg Multiple Endocrine Neoplasia Type 2A Kindred Presenting with an Adrenocorticotropin-Producing Pheochromocytoma." The Journal of Clinical Endocrinology & Metabolism 87.12 (2002): 5658-5661.

Oliveira, Duarte Mendes, et al. "Next-generation sequencing analysis of receptor-type tyrosine kinase genes in surgically resected colon cancer: identification of gain-of-function mutations in the RET proto-oncogene." Journal of Experimental & Clinical Cancer Research 37.1 (2018): 1-12.

Ott et al., "An immunogenic personal neoantigen vaccine for patients with melanoma," Nature. Jul. 13, 2017, 547(7662):217-221.

Oussalah et al., "Plasma mSEPT9: A Novel Circulating Cell-free DNA-Based Epigenetic Biomarker to Diagnose Hepatocellular Carcinoma", EBioMedicine, 138-147, 2018.

Pearce et al., Failure modes in anticancer drug discovery and development, Cancer Drug Design and Discovery Edited by Stephen Neidle, Chapter 18, pp. 424-435 (2008).

Petersen et al. "The RET and TRKA pathways collaborate to regulate neuroblastoma differentiation," Oncogene, Jan. 8, 2004;23(1):213-225.

Pirker et al., "Alectinib in RET-rearranged non-small cell lung cancer-Another progress in precision medicine?" Transl. Lung Cancer Res., Dec. 2015;4(6):797-800.

Plaza-Menacho, Iván. "Structure and function of RET in multiple endocrine neoplasia type 2." Endocrine-related cancer 25.2 (2018): T79-T90.

Plaza-Menacho et al., "Targeting the receptor tyrosine kinase RET sensitizes breast cancer cells to tamoxifen treatment and reveals a role for RET in endocrine resistance," Oncogene, Aug. 19, 2010;29(33):4648-4657.

Plenker et al., "Drugging the catalytically inactive state of RET kinase in RET-rearranged tumors," Sci Transl Med, Jun. 14, 2017, 9(394). 11 pages.

Plosker, "Sipuleucel-T: in metastatic castration-resistant prostate cancer," Drugs. Jan. 1, 2011;71(1):101-108.

Postow et al., "Immune Checkpoint Blockade in Cancer Therapy," Journal of Clinical Oncology, Jun. 10, 2015;33(17):1974-1982.

Qi et al., "RET germline mutations identified by exome sequencing in a Chinese multiple endocrine neoplasia type 2A/familial medullary thyroid carcinoma family.", PLoS One 6(5):e20353, doi: 10.1371/journal.pone.0020353, 2011.

Qi, et al., "RET mutation p.S891A in a Chinese family with familial medullary thyroid carcinoma and associated cutaneous amyloidosis binding OSMR variant p.G513D," Oncotarget, Oct. 20, 2015;6(32):33993-4003.

Quintela-Fandino, Miguel, et al. "Selective activity over a constitutively active RET-variant of the oral multikinase inhibitor dovitinib: Results of the CNIO-BR002 phase I-trial." Molecular oncology 8.8 (2014): 1719-1728.

Raue et al., "Long-Term Survivorship in Multiple Endocrine Neoplasia Type 2B Diagnosed Before and in the New Millennium.", J Clin Endocrinol Metab, 103(1): 235-243. doi: 10.1210/jc.2017-01884, 2018.

Rausch et al., "mRNA vaccine CV9103 and CV9104 for the treatment of prostate cancer," Human Vaccin immunother, 2014;10(11):3146-3152.

Reeser et al., "Validation of a Targeted RNA Sequencing Assay for Kinase Fusion Detection in Solid Tumors," J Mol. Diagn., Sep. 2017, 19(5):682-696.

Reithdorf et al., "The current status and clinical value of circulating tumor cells and circulating cell-free tumor DNA in bladder cancer.", Transl. Andro., Urol. 6(6): 1090-1110, 2017.

Reungwetwattana et al., "Targeted therapies in development for non-small cell lung cancer," J Carcinog., Dec. 31, 2013;12:22.

Roblin et al., "Topical TrkA Kinase Inhibitor CT327 is an Effective, Novel Therapy for the Treatment of Pruritus due to Psoriasis: Results from Experimental Studies, and Efficacy and Safety of CT327 in a Phase 2b Clinical Trial in Patients with Psoriasis," Acta Denn Venereal, May 2015;95(5):542-548.

Romei et al., "Next generation sequencing revealed RET or RAS mutations in medullary thyroid cancer that were negative at sanger sequencing", European Thyroid Journal, vol. 7, Supp. 1, pp. 63. Abstract No. PI-07-69, 2018.

Romei et al., "RET mutation heterogeneity in primary advanced medullary thyroid cancers and their metastases.", Oncotarget, 9(11): 9875-9884. doi: 10.18632/oncotarget.23986, 2018.

Romei and Elisei, "RET/PTC Translocations and Clinico-Pathological Features in Human Papillary Thyroid Carcinoma," Front Endocrinol (Lausanne), Apr. 11, 2012, 3:54.

Romei et al., The mutation profile of medullary thyroi carcinoma can be different in primary and metastatic tissues. European Thyroid Journal (Aug. 2016) vol. 5, Supp. Supplement 1, pp. 75; 39th Annual Meeting of the European Thyroid Association, ETA 2016. Copenhagen, Denmark. Sep. 3, 2016-Sep. 6, 2016.

Rosenzweig et al., "A case of advanced infantile myofibromatosis harboring a novel MYHIO-RET fusion," Pediatr Blood Cancer, Jul. 2017;64(7). doi: 10.1002/pbc.26377. Epub Dec. 28, 2016.

Roskoski et al., "Role of RET protein-tyrosine kinase inhibitors in the treatment RET-driven thyroid and lung cancers.", Pharmacol. Res., 128, 1-17, 2018.

Roy, Madhuchhanda, Herbert Chen, and Rebecca S. Sippel. "Current understanding and management of medullary thyroid cancer." The Oncologist 18.10 (2013): 1093.

Sabari et al., "Targeting RET-rearranged lung cancers with multikinase inhibitors," Oncoscience, Mar. 2017, 4(3-4):23-24.

Sahin et al., "Personalized RNA mutanome vaccines mobilize poly-specific therapeutic immunity against cancer," Nature, Jul. 13, 2017, 547(7662):222-226.

Saito et al., "Gene aberrations for precision medicine against lung adenocarcinoma," Cancer Science, Jun. 2016;107(6):713-720.

Santoro et al., "Development of thyroid papillary carcinomas secondary to tissue-specific expression of the RET/PTCI oncogene in transgenic mice," Oncogene, Apr. 18, 1996, 12(8):1821-1826.

Santoro et al., "Minireview: RET: normal and abnormal functions.", Endocrinology, 145(12), 5448-5451, doi: 10.1210/en.2004-0922, 2004.

Scollo et al., "A novel RET gene mutation in a patient with apparently sporadic pheochromocytoma," Endocr. J., 2016;63(1):87-91.

Severskaya et al., "Germline Polymorphisms of RET and GFRA1 Genes in Patients with Medullary Thyroid Carcinoma", Genomics Transcriptomics Proteomics, 40(3) 375-384, 2006.

Silva et al., "Identification and characterization of two novel germline RET variants associated with medullary thyroid carcinoma," Endrocrine, Jun. 2015, 49(2):366-372.

Simone, Oncology: Introduction, Cecil Textbook of Medicine, 20th Edition, vol. 1, pp. 1004-1010, 1995.

Sjoblom et al., "The consensus coding sequences of human breast and colorectal cancers," Science, Oct. 13, 2006;314(5797):268-274.

Skalova et al., "Molecular Profiling of Mammary Analog Secretory Carcinoma Revealed a Subset of Tumors Harboring a Novel ETV6-RET Translocation: Report of 10 Cases," Am. J Surg. Pathol., Feb. 2018, 42(2):234-246.

Soca-Chafre et al., "Targeted next generation sequencing identified a high frequency genetic mutated profile in wood smoke exposure-related lung adenocarcinoma patients.", Oncotarget 9(55):30499-30512, doi: 10.18632/oncotarget.25369, 2018.

Solassaol et al., "Comparison of five cell-free DNA isolation methods to detect the EGFR T790M mutation in plasma samples of patients with lung cancer", Clin. Chem. Lab Med., vol. 56, issue 9,e243-e246, 2018.

Song et al., "Case report: Whole exome sequencing of circulating cell-free tumor DNA in a follicular thyroid carcinoma patient with lung and bone metastases", J Circ. Biomark., vol. 7, 1-6, Mar. 25, 2018.

Song et al., "Potent antitumor activity of cabozantinib, a c-MET and VEGFR2 inhibitor, in a colorectal cancer patient-derived tumor explant model," "International Journal of Cancer, Apr. 15, 2015;136(8):1967-1975".

Sromek et al., "Analysis of Newly Identified and Rare Synonymous Genetic Variants in the RET Gene in Patients with Medullary Thyroid Carcinoma in Polish Population," Endocr Pathol., Sep. 2017, 28(3):198-206.

Su et al., "RET/PTC Rearrangements Are Associated with Elevated Postoperative TSH Levels and Multifocal Lesions in Papillary Thyroid Cancer without Concomitant Thyroid Benign Disease," PLoS One, Nov. 1, 2016, II(II):e0165596.

Takeuchi et al., "RET, ROS1 and ALK fusions in lung cancer," Nature Med., Feb. 12, 2012;18(3):378-381.

Tan et al., "The prognostic value of circulating cell-free DNA in breast cancer: A meta-analysis.", Medicine 97(13):e0197, 2018.

Tang, Zhenya, et al. "Coexistent genetic alterations involving ALK, RET, ROS1 or MET in 15 cases of lung adenocarcinoma." Modern Pathology 31.2 (2018): 307-312.

Taraviras et al., "Signalling by the RET receptor tyrosine kinase and its role in the development of the mammalian enteric nervous system," Development, Jun. 1999;126(12):2785-2797.

Thress et al., "Identification and preclinical characterization of AZ-23, a novel, selective, and orally bioavailable inhibitor of the Trk kinase pathway," Mol. Cancer Ther., Jul. 2009;8(7):1818-1827.

Tjaden et al., "The developmental etiology and pathogenesis of Hirschsprung disease," Transl. Res., Jul. 2013 162(1):1-15.

Uchino et al., "Somatic mutations in RET exons 12 and 15 in sporadic medullary thyroid carcinomas: different spectrum of mutations in sporadic type from hereditary type.", Cancer Science, 90(11), 1231-1237, doi: 10.1111/j.1349-7006.1999.tb00701.x, 1999.

Urbini et al., "Whole Exome Sequencing Uncovers Germline Variants of Cancer-Related Genes in Sporadic Pheochromocytoma.", Int J Genomics, 6582014. doi: 10. I 155/2018/6582014, 2018.

VandenBoom et al., "Genomic Fusions in Pigmented Spindle Cell Nevus of Reed.", Am. J Surg. Pathol. 42(8): 1042-1051, 2018.

Van Linden et al., "KLIFS: A knowledge based structural database to navigate kinase-ligand interaction space," J Med Chem., Jan. 23, 2014, 57(2):249-277.

Velcheti et al., "FRMD4A/RET: A Novel RET Oncogenic Fusion Variant in Non-Small Cell Lung Carcinoma," J Thorac Oncol., Feb. 2017, 12(2):e15-e16.

Volkmar et al., "A field guide for cancer diagnostics using cell-free DNA: From principles to practice and clinical applications.", Genes Chromosomes Cancer 57(3): 123-139, 2018.

Wang et al., "Genomic Profiling of Driver Gene Mutations in 498 Chinese NSCLC Patients", Journal of Thoracic Oncology, (Nov. 2017) vol. 12, No. 11, Supp. Supplement 2, pp. S2105. Abstract No. P2.02-018.

Wang et al., "Identification of 4-aminopyrazolylpyrimidines as potent inhibitors of Trk kinases," J Med Chem. Aug. 14, 2008;51(15):4672-4684.

Wang, Chengyan, et al. "Synthesis and structure-activity relationship study of pyrazolo [3, 4-d] pyrimidines as tyrosine kinase RET inhibitors." Bioorganic & medicinal chemistry letters 27.11 (2017): 2544-2548.

Wang et al., "Trk kinase inhibitors as new treatments for cancer and pain," Expert Opin. Ther. Pat., Mar. 19, 2009; (3):305-319.

Wells et al. "Targeting the RET pathway in thyroid cancer," Clin Cancer Res., Dec. 1, 2009;15(23):7119-7123.

Wells et al., "Revised American Thyroid Association guidelines for the management of medullary thyroid carcinoma," Thyroid, Jun. 2015;25(6):567-610.

Weng et al., "[A comparison of clinical characteristics between 2 pedigrees of multiple endocrine neoplasia type 2A with different RET mutations].", Zhonghua Nei Ke Za Zhi, 57(2):134-137, 2018. Abstract Only.

Wood et al., "The genomic landscapes of human breast and colorectal cancers," Science, Nov. 16, 2007, 318(5853):1108-1113.

Yao et al., "[DelD631: a novel mutation of the RET proto-oncogene in multiple endocrine neoplasia type 2A (MEN2A)].", Zhonghua Yi Xue Za Zhi. 87(28): 1962-1965, 2007. English Abstract.

Yeganeh et al., "RET proto oncogene mutation detection and medullary thyroid carcinoma prevention.", Asian Pac J Cancer Prev, 16(6), 2107-17, 2015.

Yi et al., "A Novel RET D898Y Germline Mutation in a Patient with Pheochromocytoma", Case Rep. Endocrinol. 2018:8657314, 2018. doi: 10. I 155/2018/8657914, 6 pages, 2018.

Yoon et al., "A Pyrazolo[3,4-d]pyrimidin-4-amine Derivative Containing an Isoxazole Moiety Is a Selective and Potent Inhibitor of RET Gatekeeper Mutants," J. Med. Chem., Jan. 14, 2016, 59(1):358-373.

Yu et al. "Multiple Biomarker Testing Tissue Consumption and Completion Rates With Single-gene Tests and Investigational Use of Oncomine Dx Target Test for Advanced NoneSmall-cell Lung Cancer: A Single-center Analysis", Clin Lung Cancer, 20-29, 2019.

Zage et al.,"The selective Trk inhibitor AZ623 inhibits brain-derived neurotrophic factor-mediated neuroblastoma cell proliferation and signaling and is synergistic with topotecan," Cancer, Mar. 15, 2011;117(6):1321-1391. doi: 10.1002/cncr.25674. Epub Oct. 19, 2010.

Zamay et al., "Current and Prospective Protein Biomarkers of Lung Cancer.", Cancers (Basel). 9(11): 155, 2017.

Zeng et al. "The relationship between overexpression of glial cell-derived neurotrophic factor and its RET receptor with progression and prognosis of human pancreatic cancer," J. Int. Med. Res., Jul.-Aug. 2008;36(4):656-664.

Zhang et al., "Identification of a novel KIF13A-RET fusion in lung adenocarcinoma by next-generation sequencing", Lung Cancer, 118, 27-29. doi: 10.1016/j.lungcan.2017.08.019, 2018.

Zhang et al., "Morphological and molecular features of gastric glomus tumors." Laboratory Investigation, (Feb. 2017) vol. 97, Supp. 1, pp. 209A. Abstract No. 840, Meeting Info: 106th Annual Meeting of the United States and Canadian Academy of Pathology, USCAP 2017. San Antonio, TX, United States.

Zhao et al., "Mutation profiling and treatment choosing of Chinese RET positive advanced lung cancer patients", Journal of Clinical Oncology vol. 36, No. 15, Supp. [S], MA e21139, 2018. Abstract Only.

Chawla, Mohit, et al. "Structural and energetic impact of non-natural 7-Deaza-8-azaadenine and its 7-substituted derivatives on H-bonding potential with uracil in RNA molecules." The Journal of Physical Chemistry B 119.41 (2015): 12982-12989.

Klein, Michael, et al. "Synthesis of 3-(1, 2, 3-triazol-1-yl)-and 3-(1, 2, 3-triazol-4-yl)-substituted pyrazolo [3, 4-d] pyrimidin-4-amines via click chemistry: potential inhibitors of the Plasmodium falciparum PfPK7 protein kinase." Organic & biomolecular chemistry 7.17 (2009): 3421-3429.

STN Registry [online]. CAS No. 2167046-22-0. "1H-Pyrazolo[3,4-d]pyrimidin-4-amine, 3-(5-thiazolyl)." Dec. 31, 2017 [Search date Jul. 21, 2021].

STN Registry [online]. CAS No. 2167335-08-0. "1H-Pyrazolo[3,4-d]pyrimidin-4-amine, 3-(1-methyl-1H-imidazol-2-yl)" Jan. 1, 2018 [Search date Jul. 21, 2021].

STN Registry [online]. CAS No. 2167728-20-1. 1H-Pyrazolo[3,4-d]pyrimidin-4-amine, 3-(1-methyl-1H-imidazol-5-yl). Jan. 1, 2018 [Search date Jul. 21, 2021].

STN Registry [online]. CAS No. 2168093-44-3. "1H-Pyrazolo[3,4-d]pyrimidin-4-amine, 3-(2-thiazolyl)." Jan. 2, 2018 [Search date Jul. 21, 2021].

STN Registry [online]. CAS No. 2169511-28-6. "1h-Pyrazolo[3,4-d]pyrimidin-4-amine, 3-(4-methyl-2-oxazolyl)." Jan. 4, 2018. [Search date Jul. 21, 2021].

Yoon, Hojong, et al. "Identification of a novel 5-amino-3-(5-cyclopropylisoxazol-3-yl)-1-isopropyl-1H-pyrazole-4-carboxamide as a specific RET kinase inhibitor." European journal of medicinal chemistry 125 (2017): 1145-1155.

CAS Registry Database [Online], "1-methyl-3-[1-(2-pyridinyl)-1H-1,2,3-triazol-4-yl]-1H-Pyrazolo[3,4-d]pyrimidin-4-amine ", Chemical Abstracts Service, Columbus, OH, USA. STN entry date Oct. 29, 2015 (Oct. 29, 2015), Retrieved from STN, CAS RN: 1816992-73-0.

CAS Registry Database [Online], "1-Methyl-3-(1-phenyl-1H-1,2,3-triazol-4-yl)-1H-pyrazolo[3,4-d]pyrimidin-4-amine", Chemical Abstracts Service, Columbus, OH, USA. STN entry date Oct. 29, 2015 (Oct. 29, 2015), Retrieved from STN, CAS RN: 1816992-69-4.

CAS Registry Database [Online], "1-Methyl-3-(1-pentyl-1H-1,2,3-triazol-4-yl)-1H-pyrazolo[3,4-d]pyrimidin-4-amine", Chemical Abstracts Service, Columbus, OH, USA. STN entry date Oct. 29, 2015 (Oct. 29, 2015), Retrieved from STN, CAS RN: 1816992-65-0.

* cited by examiner

FUSED HETEROCYCLIC COMPOUNDS AS RET KINASE INHIBITORS

CROSS REFERENCE TO RELATED APPLICATIONS

This application is a national stage application filed under 35 U.S.C. § 371 of PCT/US2019/049859 filed on Sep. 6, 2019, which claims the benefit of U.S. Provisional Patent Application Ser. No. 62/729,337 filed Sep. 10, 2018, which is incorporated by reference herein in its entirety.

BACKGROUND

The present disclosure relates to novel compounds which exhibit Rearranged during Transfection (RET) kinase inhibition, pharmaceutical compositions comprising the compounds, processes for making the compounds, and the use of the compounds in therapy. More particularly, it relates to fused heterocyclic compounds useful in the treatment and prevention of diseases which can be treated with a RET kinase inhibitor, including RET-associated diseases and disorders.

RET is a single-pass transmembrane receptor belonging to the tyrosine kinase superfamily that is required for normal development, maturation and maintenance of several tissues and cell types (Mulligan, L. M., *Nature Reviews Cancer*, 2014, 14, 173-186). The extracellular portion of the RET kinase contains four calcium-dependent cadherin-like repeats involved in ligand binding and a juxtamembrane cysteine-rich region necessary for the correct folding of the RET extracellular domain, while the cytoplasmic portion of the receptor includes two tyrosine kinase subdomains.

RET signaling is mediated by the binding of a group of soluble proteins of the glial cell line-derived neurotrophic factor (GDNF) family ligands (GFLs), which also includes neurturin (NTRN), artemin (ARTN) and persephin (PSPN) (Arighi et al., *Cytokine Growth Factor Rev.*, 2005, 16, 441-67). Unlike other receptor tyrosine kinases, RET does not directly bind to GFLs and requires an additional co-receptor: that is, one of four GDNF family receptor-α (GFRα) family members, which are tethered to the cell surface by a glycosylphosphatidylinositol linkage. GFLs and GFRα family members form binary complexes that in turn bind to RET and recruit it into cholesterol-rich membrane subdomains, which are known as lipid rafts, where RET signaling occurs.

Upon binding of the ligand-co-receptor complex, RET dimerization and autophosphorylation on intracellular tyrosine residues recruits adaptor and signaling proteins to stimulate multiple downstream pathways. Adaptor protein binding to these docking sites leads to activation of Ras-MAPK and PI3K-Akt/mTOR signaling pathways or to recruitment of the CBL family of ubiquitin ligases that functions in RET downregulation of the RET-mediated functions.

Aberrant RET expression and/or activity have been demonstrated in different cancers and in gastrointestinal disorders such as irritable bowel syndrome (IBS).

SUMMARY OF THE INVENTION

It has now been found that certain fused heterocyclic compounds are inhibitors of RET kinase, and are useful for treating diseases such as proliferative diseases such as cancers.

Accordingly, provided herein is a compound of the Formula I:

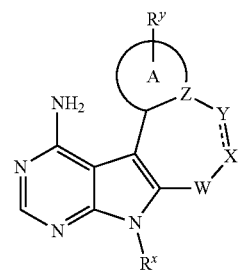

(I)

and tautomers, stereoisomers, and pharmaceutically acceptable salts and solvates thereof, wherein $R^x$, $R^y$, W, X, Y, Z, Ring A and ------- are as defined herein.

Also provided herein is a pharmaceutical composition comprising a compound of Formula I or a pharmaceutically acceptable salt or solvate thereof, in admixture with a pharmaceutically acceptable diluent or carrier.

Also provided herein is a method of inhibiting cell proliferation, in vitro or in vivo, the method comprising contacting a cell with an effective amount of a compound of Formula I or a pharmaceutically acceptable salt or solvate thereof, or a pharmaceutical composition thereof as defined herein.

Also provided herein is a method of treating a RET-associated disease or disorder in a patient in need of such treatment, the method comprising administering to the patient a therapeutically effective amount of a compound of Formula I or a pharmaceutically acceptable salt or solvate thereof, or a pharmaceutical composition thereof as defined herein.

Also provided herein is a method of treating cancer and/or inhibiting metastasis associated with a particular cancer in a patient in need of such treatment, the method comprising administering to the patient a therapeutically effective amount of a compound of Formula I or a pharmaceutically acceptable salt or solvate thereof or a pharmaceutical composition thereof as defined herein.

Also provided herein is a method of treating irritable bowel syndrome (IBS) and/or pain associated with IBS in a patient in need of such treatment, the method comprising administering to the patient a therapeutically effective amount of a compound of Formula I or a pharmaceutically acceptable salt or solvate thereof or a pharmaceutical composition thereof as defined herein.

Also provided is a method of providing supportive care to a cancer patient, including preventing or minimizing gastrointestinal disorders, such as diarrhea, associated with treatment, including chemotherapeutic treatment, the method comprising administering to the patient a therapeutically effective amount of a compound of Formula I or a pharmaceutically acceptable salt or solvate thereof or a pharmaceutical composition thereof as defined herein.

Also provided herein is a compound of Formula I or a pharmaceutically acceptable salt or solvate thereof, or a pharmaceutical composition thereof as defined herein for use in therapy.

Also provided herein is a compound of Formula I or a pharmaceutically acceptable salt or solvate thereof or a pharmaceutical composition thereof as defined herein for use in the treatment of cancer and/or inhibiting metastasis associated with a particular cancer.

Also provided herein is a compound of Formula I or a pharmaceutically acceptable salt or solvate thereof or a pharmaceutical composition thereof as defined herein for use in the treatment of irritable bowel syndrome (IBS) or pain associated with IBS.

Also provided is a compound of Formula I or a pharmaceutically acceptable salt or solvate thereof or a pharmaceutical composition thereof as defined herein for use providing supportive care to a cancer patient, including preventing or minimizing gastrointestinal disorders, such as diarrhea, associated with treatment, including chemotherapeutic treatment.

Also provided herein is a compound of Formula I or a pharmaceutically acceptable salt or solvate thereof for use in the inhibition of RET kinase activity.

Also provided herein is a compound of Formula I or a pharmaceutically acceptable salt or solvate thereof or a pharmaceutical composition thereof as defined herein, for use in the treatment of a RET-associated disease or disorder.

Also provided herein is the use of a compound of Formula I or a pharmaceutically acceptable salt or solvate thereof, as defined herein in the manufacture of a medicament for the treatment of cancer and/or inhibiting metastasis associated with a particular cancer.

Also provided herein is the use of a compound of Formula I or a pharmaceutically acceptable salt or solvate thereof, as defined herein in the manufacture of a medicament for the treatment of irritable bowel syndrome (IBS) or pain associated with IBS.

Also provided herein is the use of a compound of Formula I or a pharmaceutically acceptable salt or solvate thereof, as defined herein in the manufacture of a medicament for providing supportive care to a cancer patient, including preventing or minimizing gastrointestinal disorders, such as diarrhea, associated with treatment, including chemotherapeutic treatment.

Also provided herein is a use of a compound of Formula I or a pharmaceutically acceptable salt or solvate thereof, as defined herein in the manufacture of a medicament for the inhibition of RET kinase activity.

Also provided herein is the use of a compound of Formula I or a pharmaceutically acceptable salt or solvate thereof, as defined herein, in the manufacture of a medicament for the treatment of a RET-associated disease or disorder.

Also provided herein is a method for treating cancer in a patient in need thereof, the method comprising (a) determining if the cancer is associated with a dysregulation of a RET gene, a RET kinase, or expression or activity or level of any of the same (e.g., a RET-associated cancer); and (b) if the cancer is determined to be associated with a dysregulation of a RET gene, a RET kinase, or expression or activity or level of any of the same (e.g., a RET-associated cancer), administering to the patient a therapeutically effective amount of a compound of Formula I or a pharmaceutically acceptable salt or solvate thereof, or a pharmaceutical composition thereof.

Also provided herein is a pharmaceutical combination for treating cancer (e.g., a RET-associated cancer, such as a RET-associated cancer having one or more RET inhibitor resistance mutations) in a patient in need thereof, which comprises (a) a compound of Formula I or a pharmaceutically acceptable salt or solvate thereof, (b) an additional therapeutic agent, and (c) optionally at least one pharmaceutically acceptable carrier, wherein the compound of Formula I or the pharmaceutically acceptable salt or solvate thereof and the additional therapeutic are formulated as separate compositions or dosages for simultaneous, separate or sequential use for the treatment of cancer, wherein the amounts of the compound of Formula I or a pharmaceutically acceptable salt or solvate thereof and of the additional therapeutic agent are together effective in treating the cancer. Also provided herein is a pharmaceutical composition comprising such a combination. Also provided herein is the use of such a combination for the preparation of a medicament for the treatment of cancer. Also provided herein is a commercial package or product comprising such a combination as a combined preparation for simultaneous, separate or sequential use; and to a method of treatment of cancer a patient in need thereof.

Also provided herein is a method for reversing or preventing acquired resistance to an anticancer drug, comprising administering a therapeutically effective amount of a compound of Formula I or a pharmaceutically acceptable salt or solvate thereof, to a patient at risk for developing or having acquired resistance to an anticancer drug. In some embodiments, the patient is administered a dose of the anticancer drug (e.g., at substantially the same time as a dose of a compound of Formula I or a pharmaceutically acceptable salt or solvate thereof is administered to the patient).

Also provided herein is a method of delaying and/or preventing development of cancer resistant to an anticancer drug in an individual, comprising administering to the individual an effective amount of a compound of Formula I or a pharmaceutically acceptable salt or solvate thereof, before, during, or after administration of an effective amount of the anticancer drug.

Also provided herein is a method of treating an individual with cancer who has an increased likelihood of developing resistance to an anticancer drug, comprising administering to the individual (a) an effective amount of a compound of Formula I before, during, or after administration of (b) an effective amount of the anticancer drug.

Also provided are methods of treating an individual with a RET-associated cancer that has one or more RET inhibitor resistance mutations that increase resistance of the cancer to a first RET inhibitor (e.g., one or more amino acid substitutions in the kinase domain (e.g., amino acid positions 700 to 1012 in a wildtype RET protein), a gatekeeper amino acid (e.g., amino acid position 804 in a wildtype RET protein), the P-loop (e.g., amino acid positions 730-737 in a wildtype RET protein), the X-DFG residue (e.g., amino acid position 891 in a wildtype RET protein), ATP cleft solvent front amino acids (e.g., amino acid positions 806-811 in a wildtype RET protein), the activation loop (e.g., amino acid positions 891-916 in a wildtype RET protein), the C-helix and loop preceeding the C-helix (e.g., amino acid positions 768-788 in a wildtype RET protein), and/or the ATP binding site (e.g., amino acid positions 730-733, 738, 756, 758, 804, 805, 807, 811, 881, and 892 in a wildtype RET protein) (e.g., a substitution at amino acid position 804, e.g., V804M, V804L, or V804E, or a substitution at amino acid position 810, e.g., G810S, G810R, G810C, G810A, G810V, and G810D, and/or one or more RET inhibitor resistance mutations listed in Tables 3 and 4), that include administering a compound of Formula I or a pharmaceutically acceptable salt or solvate thereof, before, during, or after administration of another anticancer drug (e.g., a second RET kinase inhibitor). See also J. Kooistra, G. K. Kanev, O. P. J. Van Linden, R. Leurs, I. J. P. De Esch, and C. De Graaf, "KLIFS: A structural kinase-ligand interaction database," *Nucleic Acids Res.*, vol. 44, no. D1, pp. D365-D371, 2016; and O. P. J. Van Linden, A. J. Kooistra, R. Leurs, I. J. P. De Esch, and C. De Graaf, "KLIFS: A knowledge-based structural database to navigate kinase-ligand interaction space," *J. Med. Chem.*, vol. 57, no. 2, pp. 249-277, 2014, both of which are incorporated by reference in their entirety herein. In some embodiments, a wildtype RET protein is the exemplary wildtype RET protein described herein.

Also provided are methods of treating an individual with a RET-associated cancer that include administering a compound of Formula I or a pharmaceutically acceptable salt or solvate thereof, before, during, or after administration of another anticancer drug (e.g., a first RET kinase inhibitor or another kinase inhibitor).

Also provided herein is a method for treating irritable bowel syndrome (IBS) in a patient in need thereof, the method comprising (a) determining if the IBS is associated with a dysregulation of a RET gene, a RET kinase, or expression or activity or level of any of the same; and (b) if the IBS is determined to be associated with a dysregulation of a RET gene, a RET kinase, or expression or activity or level of any of the same, administering to the patient a therapeutically effective amount of a compound of Formula I or a pharmaceutically acceptable salt or solvate thereof, or a pharmaceutical composition thereof.

Also provided herein is a pharmaceutical combination for treating irritable bowel syndrome (IBS) in a patient in need thereof, which comprises administering (a) a compound of General Formula I or a pharmaceutically acceptable salt or solvate thereof, (b) an additional therapeutic agent, and (c) optionally at least one pharmaceutically acceptable carrier, for simultaneous, separate or sequential use for the treatment of IBS, wherein the amounts of the compound of Formula I or a pharmaceutically acceptable salt or solvate thereof and of the additional therapeutic agent are together effective in treating the IBS. Also provided herein is a pharmaceutical composition comprising such a combination. Also provided herein is the use of such a combination for the preparation of a medicament for the treatment of the IBS. Also provided herein is a commercial package or product comprising such a combination as a combined preparation for simultaneous, separate or sequential use; and to a method of treatment of the IBS a patient in need thereof.

Also provided herein is a process for preparing a compound of Formula I or a pharmaceutically acceptable salt or solvate thereof.

Also provided herein is a compound of Formula I or a pharmaceutically acceptable salt or solvate thereof obtained by a process of preparing the compound as defined herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and FIGURES, and from the claims.

DETAILED DESCRIPTION OF THE INVENTION

Provided herein is a compound of Formula I:

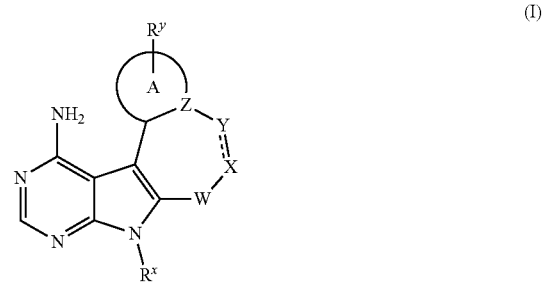

and tautomers, stereoisomers, and pharmaceutically acceptable salts and solvates thereof, wherein:

W is $CR^3R^4$,

------- represents a single or double bond, wherein when ------- is a double bond, then X is $CR^5$ and Y is $CR^6$, and when ------- is a single bond, then X is O, $CR^7R^8$ or $NR^9$ and Y is $C(=O)$, $SO_2$, $CR^{10}R^{11}$ or O, and Z is C or N;

$R^3$ is hydrogen;
$R^4$ is hydrogen;
$R^5$ is hydrogen;
$R^6$ is hydrogen;
$R^7$ is hydrogen or C1-C6 alkyl;
$R^8$ is hydrogen;
$R^9$ is hydrogen, C1-C6 alkyl, hydroxyC1-C6 alkyl-, (C1-C6 alkyl)$SO_2$—, (C1-C6 alkoxy)C1-C6 alkyl, C3-C6 cycloalkyl, (C3-C6 cycloalkyl)C1-C6 alkyl-, hetCyc$^1$, (hetCyc$^1$)C1-C6 alkyl-, Ar$^1$, (Ar$^1$)C1-C6 alkyl-, hetAr$^1$, (hetAr$^1$)C1-C6 alkyl-, (C1-C6 alkyl)C(=O)—, (fluoroC1-C6 alkyl)C(=O)—, $H_2NC(=O)$—, Ar$^1CH_2C(=O)$— or (C3-C6 cycloalkyl)C(=O)—;
$R^{10}$ is hydrogen, hydroxy, C1-C6 alkoxy, or $R^aR^bN$— wherein $R^a$ and $R^b$ are independently H or C1-C6 alkyl;
$R^{11}$ is hydrogen, C1-C6 alkyl, or fluoroC1-C6 alkyl;
hetCyc$^1$ is a 5-6 membered saturated heterocyclic ring having 1-2 ring heteroatoms independently selected from N and $SO_2$, wherein said heterocyclic ring is optionally substituted with C1-C6 alkyl or (Ar$^2$)C1-C6 alkyl-;
Ar$^1$ is phenyl optionally substituted with one or more substituents independently selected from halogen and C1-C6 alkoxy;
hetAr$^1$ is a 5-6 membered heteroaryl ring having 1-2 ring nitrogen atoms, wherein said heteroaryl ring is optionally substituted with C1-C6 alkyl;
Ar$^2$ is phenyl optionally substituted with one or more substituents independently selected from halogen and C1-C6 alkoxy;
Ring A, including the atoms at the points of attachment to the ring containing Z, Y, X, and W, is (i) a monocyclic aryl ring when Z is C, wherein said ring is optionally substituted with halogen, C3-C6 cycloalkyl, C1-C6 alkoxy, $R^cNHC(=O)$—, $R^cC(=O)NH$—, or $R^cNHC(=O)NH$—, (ii) a 5-membered monocyclic heteroaryl ring having 2 ring heteroatoms independently selected from N and O when Z is C, or when Z is N, a 5-membered heteroaryl ring having two ring nitrogen atoms, one of which is Z, wherein said rings are optionally substituted with C1-C6 alkyl or C3-C6 cycloalkyl, or (iii) when Z is N, a bicyclic heteroaryl ring having one ring nitrogen atom that results when Z is N, wherein said ring is optionally substituted with $R^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—;

$R^c$ is C3-C6 cycloalkyl or (C3-C6 cycloalkyl)CH$_2$—;

$R^d$ is C1-C6 alkyl, C1-C6 alkoxy, Cyc$^1$, Cyc$^1$CH$_2$—, phenyl or hetAr$^2$;

Cyc$^1$ is C3-C6 cycloalkyl optionally substituted with C1-C6 alkyl;

hetAr$^2$ is (i) pyrazolyl optionally substituted with 1-2 substituents independently selected from C1-C6 alkyl, fluoroC1-C6 alkyl, (di-C1-C6 alkyl)NC(=O)CH$_2$—, (hetCyc$^2$)CH$_2$CH$_2$—, phenyl, and (C1-C6 alkoxy)C1-C6 alkyl, or (ii) pyridyl;

hetCyc$^2$ is a 6-membered saturated heterocyclic ring having 2 ring heteroatoms independently selected from N and O;

$R^x$ is hydrogen, C1-C6 alkyl, fluoroC1-C6 alkyl, Cyc$^2$, Cyc$^3$, hetCyc$^3$, Ar$^3$ or hetAr$^3$;

Cyc$^2$ is a 3-6 membered saturated carbocyclic ring optionally substituted with 1-2 substituents independently selected from halogen, C1-C6 alkyl, hydroxy, hydroxyC1-C6 alkyl, and (C1-C6 alkoxy)C(=O)—;

Cyc$^3$ is cyclopentenyl;

hetCyc$^3$ is a 5-membered saturated heterocyclic ring having a ring heteroatom selected from N and O and optionally substituted with (C1-C6 alkyl)C(=O)—;

Ar$^3$ is phenyl optionally substituted with (C1-C6 alkoxy)C(=O)—;

hetAr$^3$ is a 5-6 membered heteroaryl ring having 1-2 ring nitrogen atoms and optionally substituted with C1-C6 alkyl or C1-C6 alkoxy; and $R^y$ is hydrogen or halogen.

For complex chemical names employed herein, a substituent group is typically named before the group to which it attaches. For example, methoxyethyl comprises an ethyl backbone with a methoxy substituent.

The term "halogen" means —F (sometimes referred to herein as "fluoro" or "fluoros"), —Cl, —Br and —I.

The term "C1-C6 alkyl" as used herein refers to saturated linear or branched-chain monovalent hydrocarbon radicals of one to six carbon atoms. Examples include, but are not limited to, methyl, ethyl, 1-propyl, isopropyl, 1-butyl, isobutyl, sec-butyl, tert-butyl, 2-methyl-2-propyl, pentyl, neopentyl, and hexyl.

The term "fluoroC1-C6 alkyl" as used herein refers to a C1-C6 alkyl radical as defined herein, wherein one to three hydrogen atoms is replaced with one to three fluoro atoms, respectively. Examples include, but are not limited to, fluoromethyl, difluoromethyl, trifluoromethyl, 2-fluoroethyl, 2,2-difluoroethyl, and 2,2,2-trifluoroethyl.

The term "C1-C6 alkoxy" as used herein refers to saturated linear or branched-chain monovalent alkoxy radicals of one to six carbon atoms, wherein the radical is on the oxygen atom. Examples include methoxy, ethoxy, propoxy, isopropoxy, butoxy and tert-butoxy.

The term "(C1-C6 alkoxy)C1-C6 alkyl" as used herein refers to saturated linear or branched-chain monovalent radicals of one to six carbon atoms, wherein one of the carbon atoms is substituted with a C1-C6 alkoxy group as defined herein. Examples include methoxymethyl (CH$_3$OCH$_2$—) and methoxyethyl (CH$_3$OCH$_2$CH$_2$—).

The term "hydroxyC1-C6 alkyl", as used herein refers to saturated linear or branched-chain monovalent alkyl radicals of one to six or two to six carbon atoms, respectively, wherein one of the carbon atoms is substituted with a hydroxy group.

The term "C3-C6 cycloalkyl" as used herein refers to cyclopropyl, cyclobutyl, cyclopentyl or cyclohexyl.

The term "(hetCyc$^1$)C1-C6 alkyl-" as used herein refers to saturated linear or branched-chain monovalent alkyl radicals of one to six carbon atoms, wherein one of the carbon atoms is substituted with a hetCyc$^1$ group, wherein hetCyc$^1$ is as defined herein.

The term "(Ar$^1$)C1-C6 alkyl-" as used herein refers to saturated linear or branched-chain monovalent alkyl radicals of one to six carbon atoms, wherein one of the carbon atoms is substituted with an Ar$^1$ group, wherein Ar$^1$ is as defined herein.

The term "(hetAr$^1$)C1-C6 alkyl-" as used herein refers to saturated linear or branched-chain monovalent alkyl radicals of one to six carbon atoms, wherein one of the carbon atoms is substituted with a hetAr$^1$ group, wherein hetAr$^1$ is as defined herein.

The term "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified.

The term "tautomer" as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the invention, and the naming of the compounds does not exclude any tautomer. An example of a tautomeric forms includes the following example:

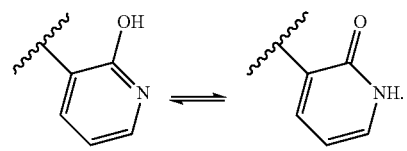 [SMILES: *c1cccnc1O ; *c1ccc[nH]c1=O]

It will be appreciated that certain compounds provided herein may contain one or more centers of asymmetry and may therefore be prepared and isolated in a mixture of isomers such as a racemic mixture, or in an enantiomerically pure form.

Where a dashed line ( ---- ) appears in a structure, the dashed line represents a bond that is optionally present, indicating, together with the single bond to which it is adjacent, either a single or double bond. Accordingly, when ------ is a single bond, the general structure of Formula I may be represented as:

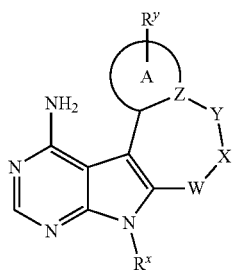

and when ------ is a double bond, the general structure of Formula I may be represented as:

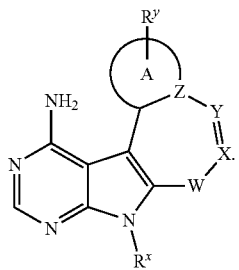

It is to be understood that the ring in compounds of Formula I comprising atoms W, X, Y and Z does not contain two adjacent oxygen atoms or two adjacent S atoms.

In one embodiment of Formula I, $R^x$ is hydrogen.

In one embodiment of Formula I, $R^x$ is C1-C6 alkyl. In one embodiment, $R^x$ is isopropyl.

In one embodiment of Formula I, $R^x$ is fluoroC1-C6 alkyl. In one embodiment, $R^x$ is 1,3-difluoropropan-2-yl or 1,1,1-trifluoropropan-2-yl.

In one embodiment of Formula I, $R^x$ is $Cyc^2$. In one embodiment, $R^x$ is cyclopropyl, cyclobutyl, cyclopentyl optionally substituted with 1-2 substituents independently selected from halogen, C1-C6 alkyl, hydroxy, hydroxyC1-C6 alkyl, and (C1-C6 alkoxy)C(=O)—. Non-limiting examples when $R^x$ is $Cyc^2$ include the structures:

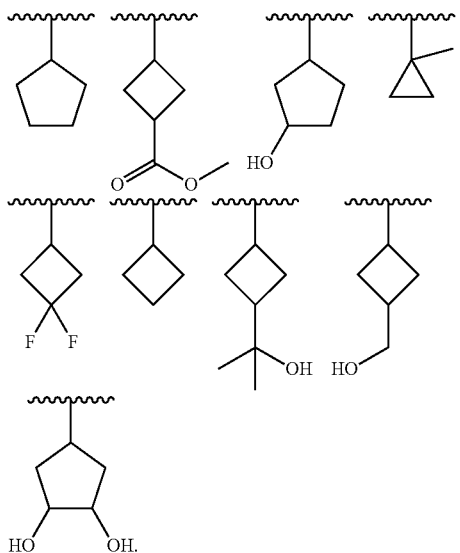

In one embodiment of Formula I, $R^x$ is $Cyc^3$. In one embodiment, $R^x$ is cyclopentenyl.

In one embodiment of Formula I, $R^x$ is $hetCyc^3$. Non-limiting examples include the structures:

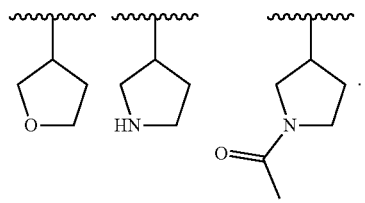

In one embodiment of Formula I, $R^x$ is $Ar^3$. Non-limiting examples include phenyl and (4-methoxycarbonyl)phenyl.

In one embodiment of Formula I, $R^x$ is $hetAr^3$. Non-limiting examples include pyridin-2-yl, pyridin-3-yl, 6-methoxypyridin-3-yl and 1-methylpyrazol-4-yl.

In one embodiment of Formula I, $R^y$ is hydrogen.

In one embodiment of Formula I, $R^y$ is halogen. In one embodiment of Formula I, $R^y$ is chloro.

In one embodiment of Formula I, Z is carbon and Ring A, including the atoms at the points of attachment to the ring containing Z, Y, X, and W, is a monocyclic aryl ring optionally substituted with halogen, C3-C6 cycloalkyl, C1-C6 alkoxy, $R^cNHC(=O)$—, $R^cC(=O)NH$—, or $R^cNHC(=O)NH$— wherein $R^c$ and $R^d$ are as defined for Formula I. Accordingly, when Ring A is a monocyclic aryl ring, and Z is carbon, Ring A may be represented by formula (i):

wherein the bond labeled "a" indicates the point of attachment to Y. Non-limiting examples when Z is C, Ring A is a monocyclic aryl ring and $R^y$ is hydrogen or halogen include the structures:

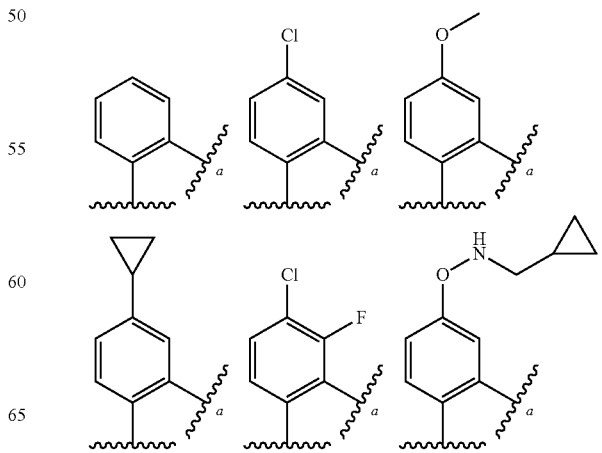

-continued

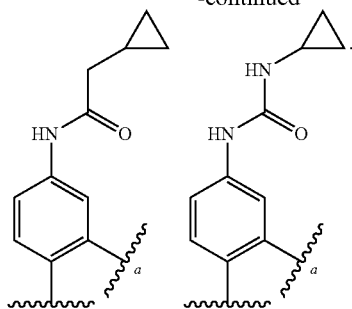

In one embodiment, Ring A is a 5-membered monocyclic heteroaryl ring having 2 ring heteroatoms independently selected from N and O when Z is C, or when Z is N, a 5-membered heteroaryl ring having two ring nitrogen atoms, one of which is Z, wherein said rings are optionally substituted with C1-C6 alkyl or C3-C6 cycloalkyl.

In one embodiment, Z is N and Ring A is a 5-membered heteroaryl ring having two ring nitrogen atoms, one of which is Z, wherein said heteroaryl ring is optionally substituted with C1-C6 alkyl or C3-C6 cycloalkyl. In one embodiment when Z is N, Ring A can be represented by the formula (ii):

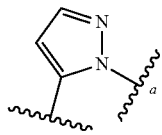

(ii)

wherein the bond labeled "a" indicates the point of attachment to Y, wherein said ring is optionally substituted with C1-C6 alkyl or C3-C6 cycloalkyl. Non-limiting examples include the structures:

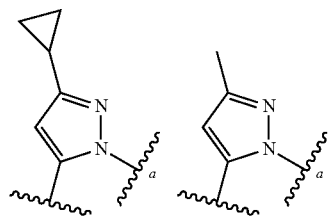

wherein the bond labeled "a" indicates the point of attachment to Y.

In one embodiment, Z is C and Ring A is a 5-membered monocyclic heteroaryl ring having 2 ring heteroatoms independently selected from N and O, wherein said ring is optionally substituted with C1-C6 alkyl or C3-C6 cycloalkyl, and $R^y$ is hydrogen or halogen. In one embodiment, Z is C, Ring A is a 5-membered monocyclic heteroaryl ring having 2 ring heteroatoms independently selected from N and O, wherein said ring is optionally substituted with C1-C6 alkyl or C3-C6 cycloalkyl, and $R^y$ is hydrogen. In one embodiment when Z is C, Ring A can be represented by formulas (iii-1), (iii-2) and (iii-3):

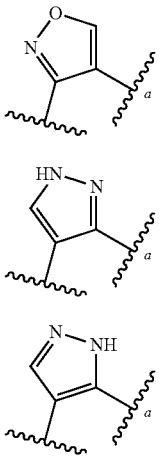

(iii-1)

(iii-2)

(iii-3)

wherein the bond labeled "a" indicates the point of attachment to Y, wherein each of said formulas (iii-1), (iii-2) and (iii-3) is optionally substituted C1-C6 alkyl or C3-C6 cycloalkyl. Non-limiting examples include the structures:

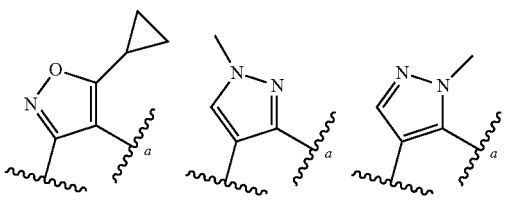

wherein the bond labeled "a" indicates the point of attachment to Y.

In one embodiment, Z is N, $R^y$ is hydrogen or halogen, and Ring A is a bicyclic heteroaryl ring having one ring nitrogen heteroatom that results when Z is N, wherein said bicyclic heteroaryl ring is optionally substituted with $R^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—. In one embodiment, Z is N and Ring A is a 5,6-bicyclic heteroaryl ring having one ring nitrogen heteroatom that results when Z is N, wherein said bicyclic heteroaryl ring is optionally substituted with $R^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—. In one embodiment when Z is N and Ring A is a bicyclic heteroaryl ring, Ring A can be represented by formula (iv):

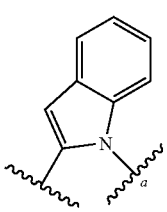

(iv)

wherein the bond labeled "a" indicates the point of attachment to Y and formula (iv) is optionally substituted with $R^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—. Non-limiting examples when Z is N, Ring A is a bicyclic heteroaryl ring, and R$^y$ is hydrogen or halogen include the structures:
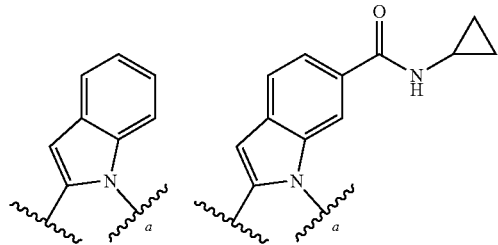
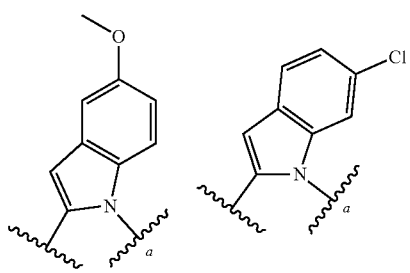
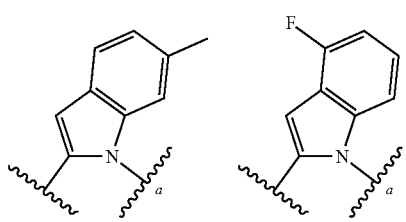
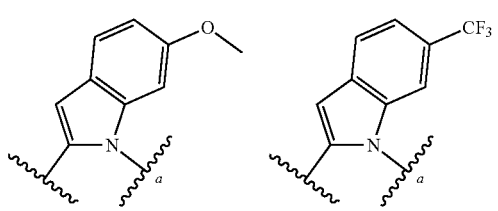
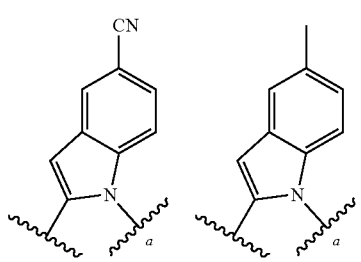
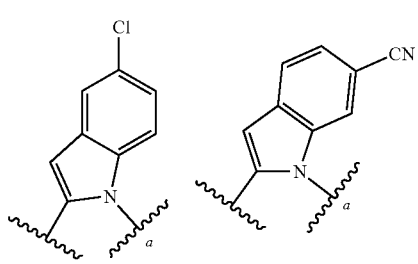
-continued
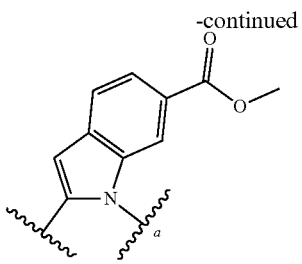
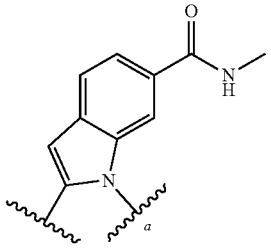
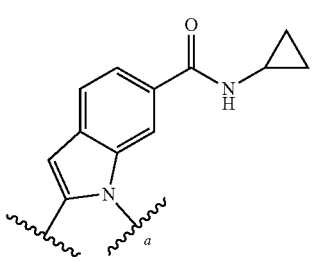
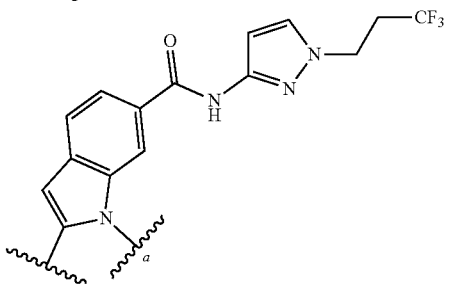
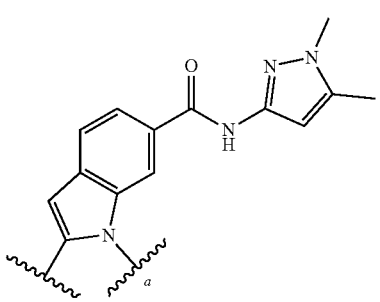
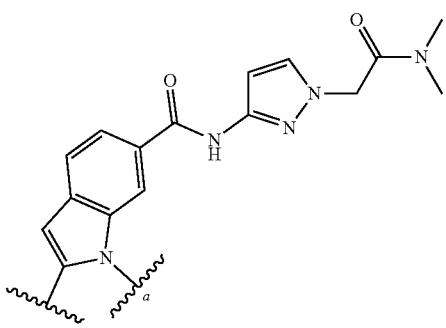

15
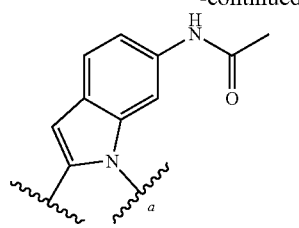
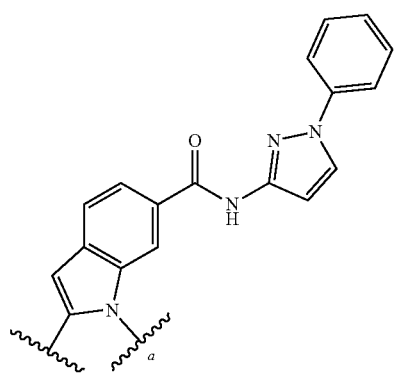
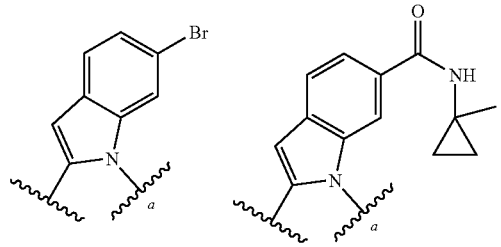
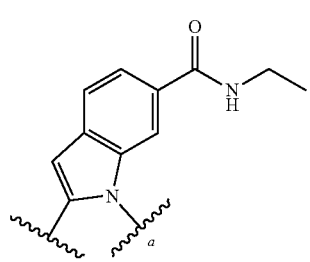
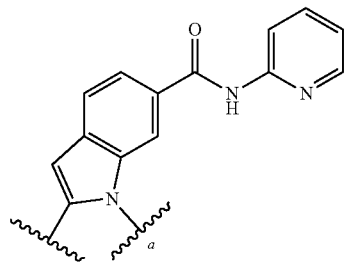
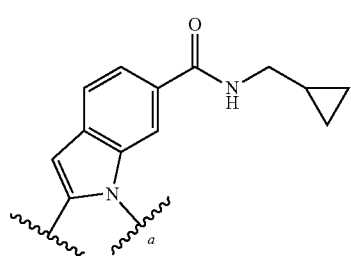
16
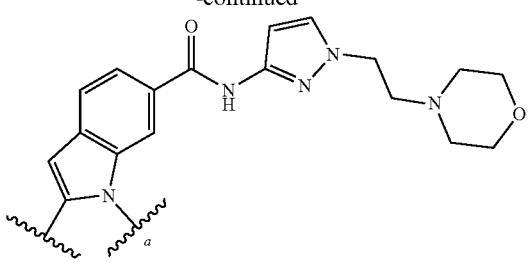
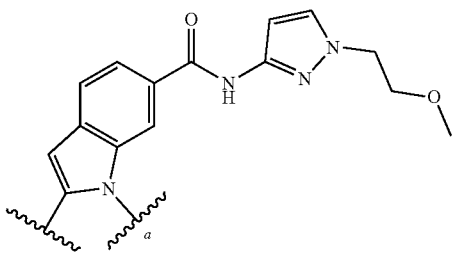
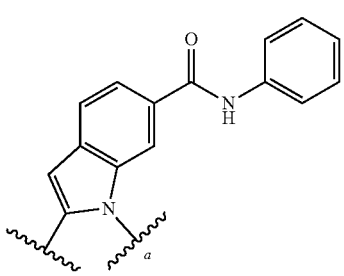
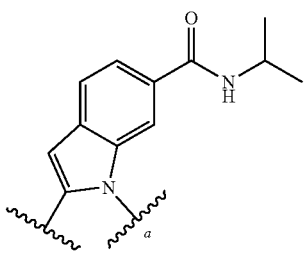
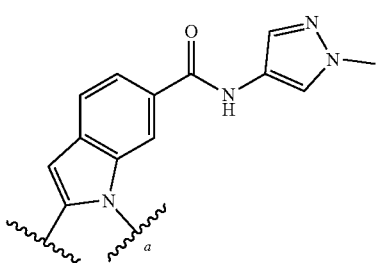
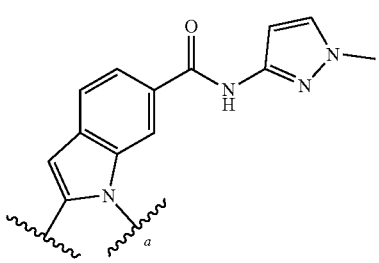

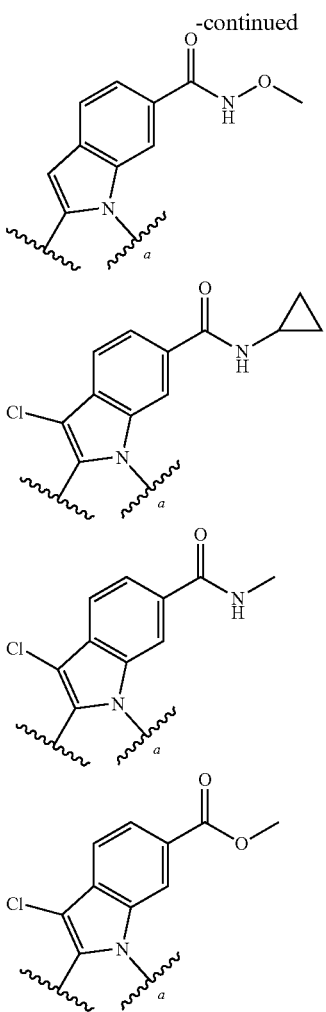

wherein the bond labeled "a" indicates the point of attachment to Y.

In one embodiment of Formula I, W is $CR^3R^4$, X is $CR^7R^8$, Y is C(=O), Z is N, and ------- is a single bond, wherein Formula I can be represented by Formula I-A:

I-A

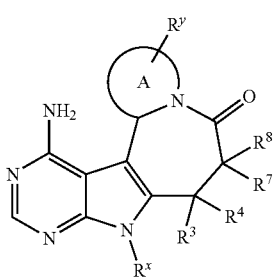

wherein $R^x$, $R^y$, $R^3$, $R^4$, $R^7$ and $R^8$ are as defined for Formula I and Ring A is (ii) a 5-membered heteroaryl ring having two ring nitrogen atoms, one of which is Z, wherein said ring is optionally substituted with C1-C6 alkyl or C3-C6 cycloalkyl, or (iii) a bicyclic heteroaryl ring having one ring nitrogen atom that results when Z is N, wherein said ring is optionally substituted with $R^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—

In one embodiment, Ring A is a bicyclic heteroaryl ring having one ring nitrogen atom that results when Z is N, wherein said ring is optionally substituted with $R^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—. In one embodiment, Ring A is a 5,6-bicyclic heteroaryl ring having one ring nitrogen atom that results when Z is N, wherein said ring is optionally substituted with $R^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—. In one embodiment, Ring A is a 5,6-bicyclic heteroaryl ring optionally substituted with $R^d$NHC(=O)—. In one embodiment, Ring A is a 5,6-bicyclic heteroaryl ring optionally substituted with $R^d$NHC(=O)— wherein $R^d$ is C3-C6 cycloalkyl. In one embodiment of Formula I-A, Ring A is selected from the structures:

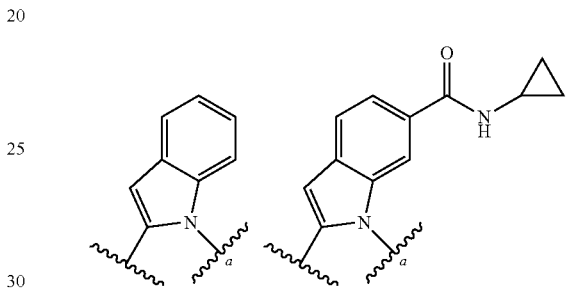

wherein the bond labeled "a" indicates the point of attachment to Y.

In one embodiment of Formula I-A, $R^7$ and $R^8$ are hydrogen.

In one embodiment of Formula I-A, $R^x$ is C1-C6 alkyl.
In one embodiment of Formula I-A, $R^y$ is hydrogen.
In one embodiment of Formula I, W is $CR^3R^4$, X is $NR^9$, Y is C(=O), Z is N, and ------- is a single bond, wherein Formula I can be represented by Formula I-B:

I-B

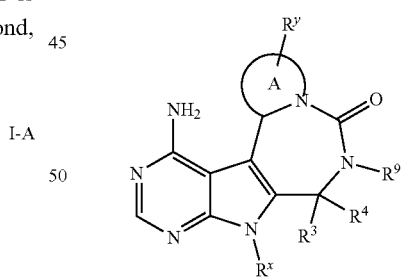

wherein $R^x$, $R^y$, $R^3$, $R^4$, and $R^9$ are as defined for Formula I and Ring A is (ii) a 5-membered heteroaryl ring having two ring nitrogen atoms, one of which is Z, wherein said ring is optionally substituted with C1-C6 alkyl or C3-C6 cycloalkyl, or (iii) a bicyclic heteroaryl ring having one ring nitrogen atom that results when Z is N, wherein said ring is optionally substituted with $R^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—.

In one embodiment of Formula I-B, Ring A is a 5-membered heteroaryl ring having two ring nitrogen atoms, one of which is Z, wherein said ring is optionally substituted with C1-C6 alkyl or C3-C6 cycloalkyl. In one embodiment, Ring A is a pyrazolyl ring optionally substituted with C1-C6 alkyl or C3-C6 cycloalkyl. In one embodiment of Formula I-B, Ring A is selected from the structures:

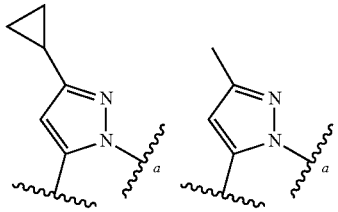

wherein the bond labeled "a" indicates the point of attachment to Y.

In one embodiment of Formula I-B, Ring A is a bicyclic heteroaryl ring having one ring nitrogen atom that results when Z is N, wherein said ring is optionally substituted with $R^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—. In one embodiment of Formula I-B, Ring A is a 5,6-bicyclic heteroaryl ring having one ring nitrogen atom that results when Z is N, wherein said ring is optionally substituted with $R^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—. In one embodiment of Formula I-B, Ring A is selected from the structures:

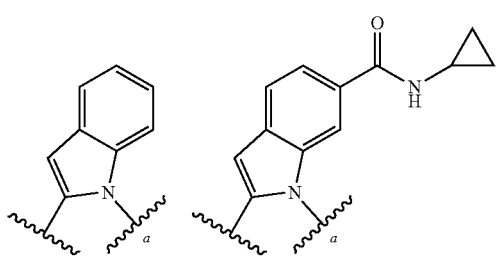

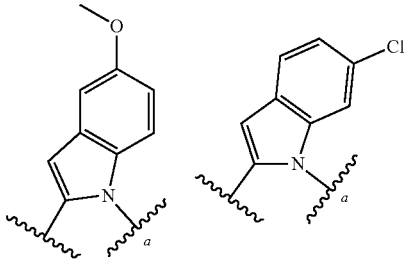

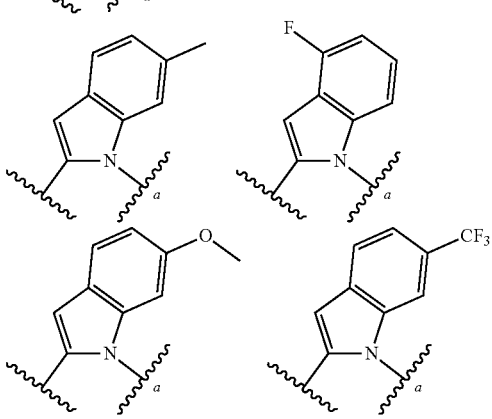

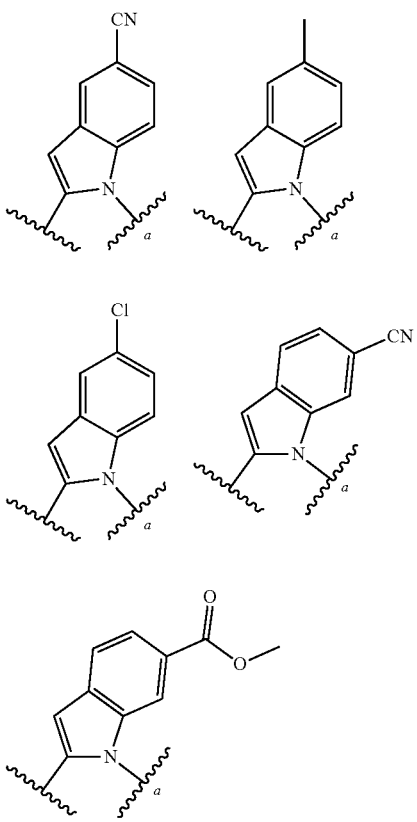

-continued

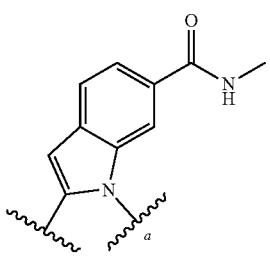

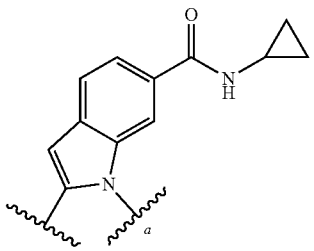

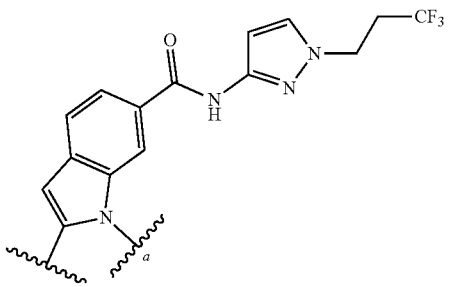

21
-continued
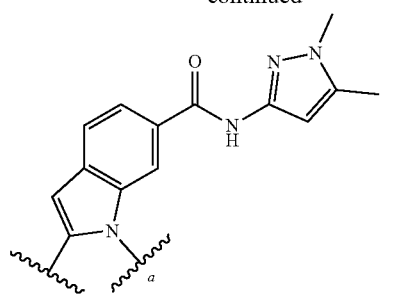
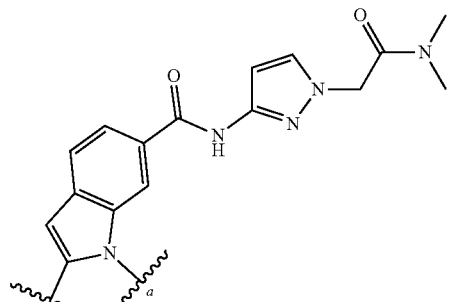
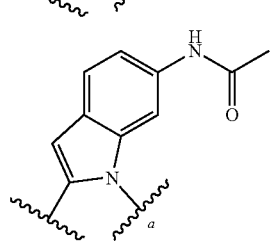
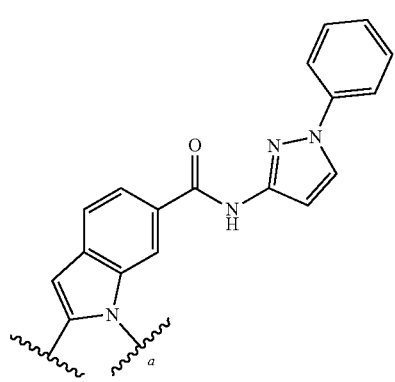
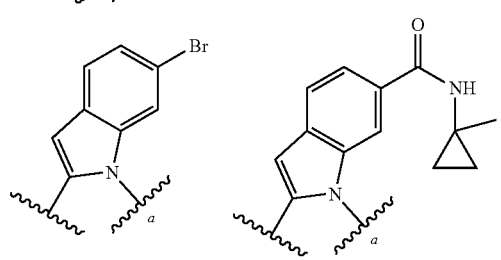
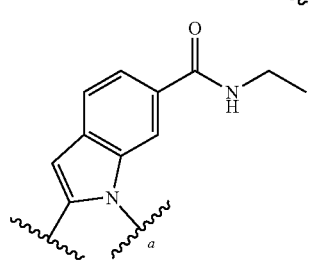
22
-continued
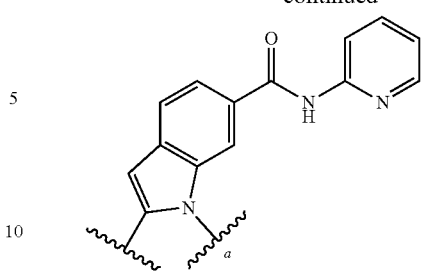
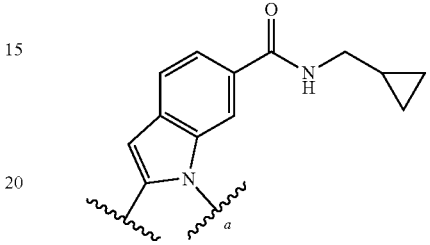
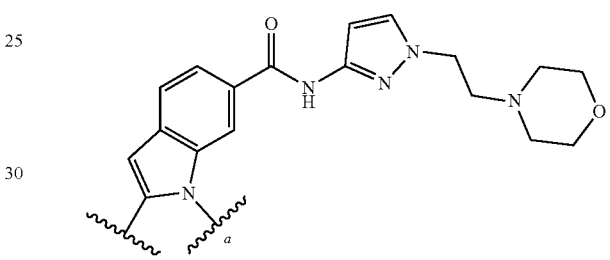
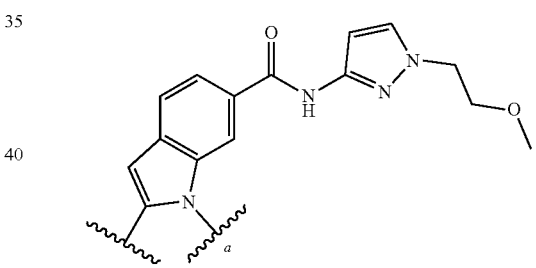
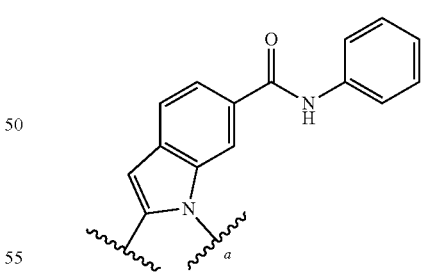
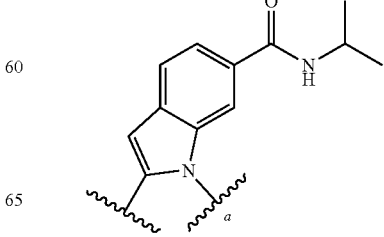

-continued

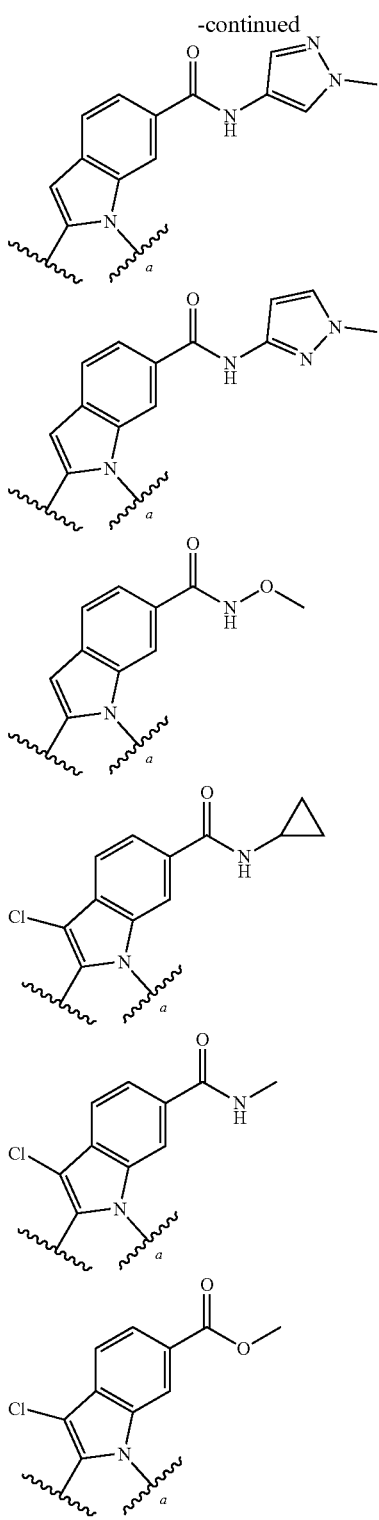

wherein the bond labeled "a" indicates the point of attachment to Y.

In one embodiment of Formula I-B, $R^9$ is hydrogen.

In one embodiment of Formula I-B, $R^x$ is C1-C6 alkyl.

In one embodiment of Formula I-B, $R^y$ is hydrogen.

In one embodiment of Formula I-B, $R^y$ is halogen. In one embodiment of Formula I-B, $R^y$ is chloro.

In one embodiment, W is $CR^3R^4$, X is $NR^9$, Y is C(=O), Z is C, and ------ is a single bond, wherein Formula I can be represented by Formula I-C:

I-C

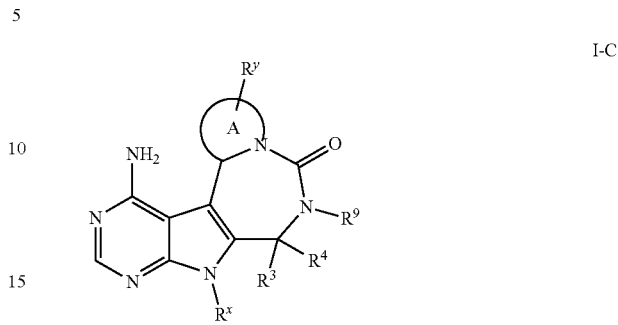

wherein $R^x$, $R^y$, $R^3$, $R^4$, and $R^9$ is as defined for Formula I, and Ring A is (i) a monocyclic aryl ring, wherein said ring is optionally substituted with halogen, C3-C6 cycloalkyl, C1-C6 alkoxy, $R^cNHC(=O)—$, $R^cC(=O)NH—$, or $R^cNHC(=O)NH—$ wherein $R^c$ is as defined for Formula I or (ii) a 5-membered monocyclic heteroaryl ring having 2 ring heteroatoms independently selected from N and O, wherein said ring is optionally substituted with C1-C6 alkyl or C3-C6 cycloalkyl.

In one embodiment of Formula I-C, Ring A is a monocyclic aryl ring, wherein said ring is optionally substituted with halogen, C3-C6 cycloalkyl, C1-C6 alkoxy, $R^cNHC(=O)—$, $R^cC(=O)NH—$, or $R^cNHC(=O)NH—$ wherein $R^c$ is as defined for Formula I. In one embodiment of Formula I-C, Ring A is selected from the structures:

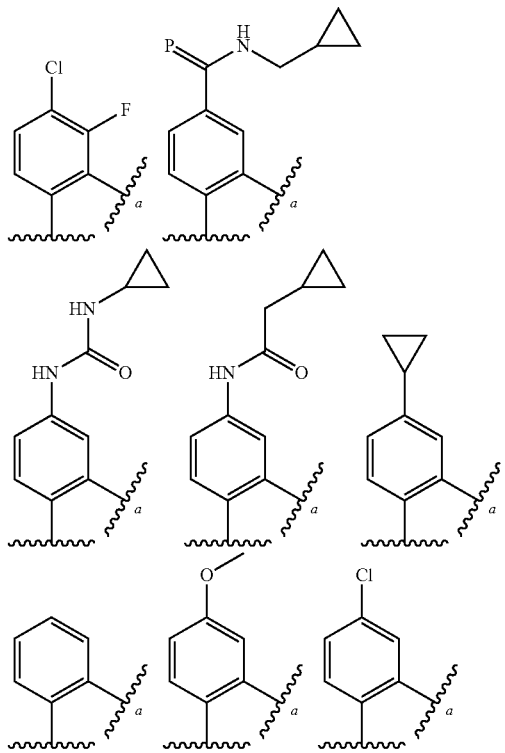

wherein the bond labeled "a" indicates the point of attachment to Y.

In one embodiment of Formula I-C, Ring A is a 5-membered monocyclic heteroaryl ring having 2 ring heteroatoms independently selected from N and O, wherein said ring is optionally substituted with C1-C6 alkyl or C3-C6 cycloalkyl. In one embodiment of Formula I-C, Ring A is an isoxazolyl ring or a pyrazolyl ring optionally substituted with C1-C6 alkyl or C3-C6 cycloalkyl. In one embodiment of Formula I-C, Ring A is selected from the structures:

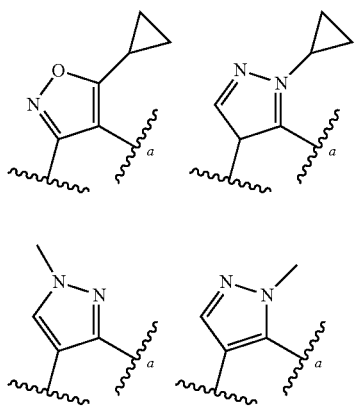

wherein the bond labeled "a" indicates the point of attachment to Y. In one embodiment of Formula I-C, Ring A is 5-membered heteroaryl ring having 2 ring heteroatoms independently selected from N and O, wherein said ring is optionally substituted with C1-C6 alkyl or C3-C6 cycloalkyl, with the exception that Ring A does not include the structures:

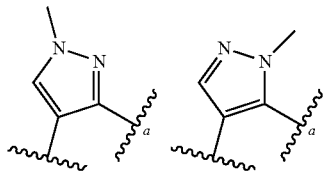

wherein the bond labeled "a" indicates the point of attachment to Y.

In one embodiment of Formula I-C, $R^x$ is hydrogen, C1-C6 alkyl, or $Cyc^2$.

In one embodiment of Formula I-C, $R^x$ is C1-C6 alkyl.

In one embodiment of Formula I-C, $R^9$ is hydrogen, C1-C6 alkyl, (C1-C6 alkoxy)C1-C6 alkyl, (C3-C6 cycloalkyl)C1-C6 alkyl-, hetCyc$^1$, (hetCyc$^1$)C1-C6 alkyl-, hetAr$^1$, (hetAr$^1$)C1-C6 alkyl-, or (Ar$^1$)C1-C6 alkyl-.

In one embodiment of Formula I-C, $R^y$ is hydrogen.

In one embodiment of Formula I-C, $R^y$ is halogen. In one embodiment of Formula I-C, $R^y$ is chloro.

In one embodiment, W is $CR^3R^4$, X is O, Y is C(=O), Z is C, and ------- is a single bond, wherein Formula I can be represented by Formula I-D

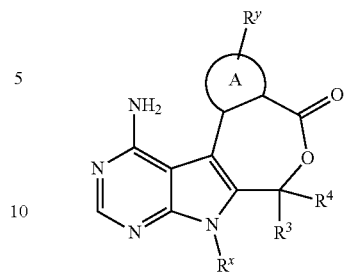

I-D wherein $R^x$, $R^y$, $R^3$, and $R^4$ are as defined for Formula I and Ring A is (i) a monocyclic aryl ring, wherein said ring is optionally substituted with halogen, C3-C6 cycloalkyl, C1-C6 alkoxy, $R^c$NHC(=O)—, $R^c$C(=O)NH—, or $R^c$NHC(=O)NH— wherein $R^c$ is as defined for Formula I or (ii) a 5-membered monocyclic heteroaryl ring having 2 ring heteroatoms independently selected from N and O, wherein said ring is optionally substituted with C1-C6 alkyl or C3-C6 cycloalkyl.

In one embodiment of Formula I-D, Ring A is a 5-membered heteroaryl ring having 2 ring heteroatoms independently selected from N and O, wherein said ring is optionally substituted with C1-C6 alkyl or C3-C6 cycloalkyl. In one embodiment of Formula I-D, Ring A is a 5-membered heteroaryl ring having 2 ring heteroatoms independently selected from N and O, wherein said ring is optionally substituted with C3-C6 cycloalkyl. In one embodiment of Formula I-D, Ring A is an isoxazolyl ring, wherein said ring is optionally substituted with C1-C6 alkyl or C3-C6 cycloalkyl. In one embodiment, Ring A is an isoxazolyl ring optionally substituted with C3-C6 cycloalkyl. In one embodiment of Formula I-D, Ring A is:

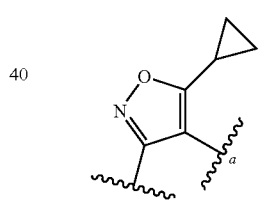

wherein the bond labeled "a" indicates the point of attachment to Y.

In one embodiment of Formula I-D, $R^x$ is C1-C6 alkyl.

In one embodiment of Formula I-D, $R^y$ is hydrogen.

In one embodiment, W is $CR^3R^4$, X is $NR^9$, Y is $SO_2$, Z is C, and ------- is a single bond, wherein Formula I can be represented by Formula I-E:

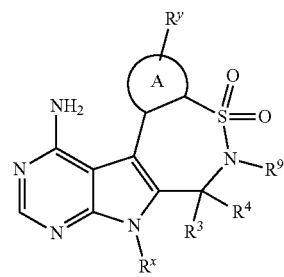

I-E wherein R^x, R^y, R^3, R^4, and R^9 are as defined for Formula I, and Ring A is (i) a monocyclic aryl ring, wherein said ring is optionally substituted with halogen, C3-C6 cycloalkyl, C1-C6 alkoxy, R^cNHC(=O)—, R^cC(=O)NH—, or R^cNHC(=O)NH— wherein R^c is as defined for Formula I or (ii) a 5-membered monocyclic heteroaryl ring having 2 ring heteroatoms independently selected from N and O, wherein said ring is optionally substituted with C1-C6 alkyl or C3-C6 cycloalkyl.

In one embodiment of Formula I-E, Ring A is a 5-membered heteroaryl ring having 2 ring heteroatoms independently selected from N and O, wherein said ring is optionally substituted with C1-C6 alkyl or C3-C6 cycloalkyl. In one embodiment of Formula I-E, Ring A is a 5-membered heteroaryl ring having 2 ring heteroatoms independently selected from N and O, wherein said ring is optionally substituted with C3-C6 cycloalkyl. In one embodiment of Formula I-E, Ring A is an isoxazolyl ring, wherein said ring is optionally substituted with C1-C6 alkyl or C3-C6 cycloalkyl. In one embodiment, Ring A is an isoxazolyl ring optionally substituted with C3-C6 cycloalkyl. In one embodiment of Formula I-E, Ring A is:

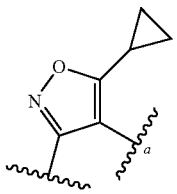 [SMILES: *c1noc(C2CC2)c1*]

wherein the bond labeled "a" indicates the point of attachment to Y.

In one embodiment of Formula I-E, R^x is C1-C6 alkyl.
In one embodiment of Formula I-E, R^9 is hydrogen or C1-C6 alkyl.
In one embodiment of Formula I-E, R^9 is hydrogen.
In one embodiment of Formula I-E, R^9 is C1-C6 alkyl.
In one embodiment of Formula I-E, R^y is hydrogen.
In one embodiment, W is CR^3R^4, X is CR^7R^8, Y is SO_2, Z is C, and ------ is a single bond, wherein the compound has the structure of Formula I-F:

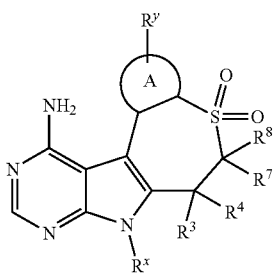

I-F wherein R^x, R^y, R^3, R^4, R^7, and R^8 are as defined for Formula I and Ring A is (i) a monocyclic aryl ring, wherein said ring is optionally substituted with halogen, C3-C6 cycloalkyl, C1-C6 alkoxy, R^cNHC(=O)—, R^cC(=O)NH—, or R^cNHC(=O)NH— wherein R^c is as defined for Formula I or (ii) a 5-membered monocyclic heteroaryl ring having 2 ring heteroatoms independently selected from N and O, wherein said ring is optionally substituted with C1-C6 alkyl or C3-C6 cycloalkyl.

In one embodiment of Formula I-F, Ring A is a 5-membered heteroaryl ring having 2 ring heteroatoms independently selected from N and O, wherein said ring is optionally substituted with C1-C6 alkyl or C3-C6 cycloalkyl. In one embodiment of Formula I-F, Ring A is a 5-membered heteroaryl ring having 2 ring heteroatoms independently selected from N and O, wherein said ring is optionally substituted with C3-C6 cycloalkyl. In one embodiment of Formula I-F, Ring A is an isoxazolyl ring, wherein said ring is optionally substituted with C1-C6 alkyl or C3-C6 cycloalkyl. In one embodiment, Ring A is an isoxazolyl ring optionally substituted with C3-C6 cycloalkyl. In one embodiment of Formula I-F, Ring A is:

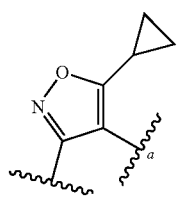 [SMILES: *c1noc(C2CC2)c1*]

wherein the bond labeled "a" indicates the point of attachment to Y.

In one embodiment of Formula I-F, R^x is C1-C6 alkyl.
In one embodiment of Formula I-F, R^7 and R^8 are hydrogen.
In one embodiment of Formula I-F, R^y is hydrogen.
In one embodiment, W is CR^3R^4, X is CR^7R^8, Y is C(=O), Z is C, and ------ is a single bond, wherein the compound has the structure of Formula I-G:

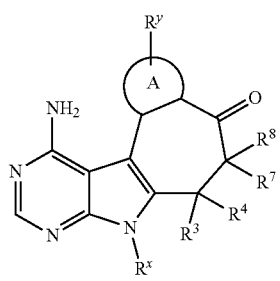

I-G wherein R^x, R^y, R^3, R^4, R^7, and R^8 are as defined for Formula I and Ring A is (i) a monocyclic aryl ring, wherein said ring is optionally substituted with halogen, C3-C6 cycloalkyl, C1-C6 alkoxy, R^cNHC(=O)—, R^cC(=O)NH—, or R^cNHC(=O)NH— wherein R^c is as defined for Formula I or (ii) a 5-membered monocyclic heteroaryl ring having 2 ring heteroatoms independently selected from N and O, wherein said ring is optionally substituted with C1-C6 alkyl or C3-C6 cycloalkyl.

In one embodiment of Formula I-G, Ring A is a 5-membered heteroaryl ring having 2 ring heteroatoms independently selected from N and O, wherein said ring is optionally substituted with C1-C6 alkyl or C3-C6 cycloalkyl. In one embodiment of Formula I-G, Ring A is a 5-membered heteroaryl ring having 2 ring heteroatoms independently selected from N and O, wherein said ring is optionally substituted with C3-C6 cycloalkyl. In one embodiment of Formula I-G, Ring A is an isoxazolyl ring, wherein said ring is optionally substituted with C1-C6 alkyl or C3-C6 cycloalkyl. In one embodiment, Ring A is an isoxazolyl ring optionally substituted with C3-C6 cycloalkyl. In one embodiment of Formula I-G, Ring A is:

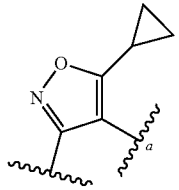 [SMILES: *c1noc(C2CC2)c1*]

wherein the bond labeled "a" indicates the point of attachment to Y.

In one embodiment of Formula I-G, $R^x$ is hydrogen, C1-C6 alkyl, fluoroC1-C6 alkyl, $Cyc^2$, or $hetCyc^3$.

In one embodiment of Formula I-G, $R^7$ and $R^8$ are hydrogen.

In one embodiment of Formula I-G, $R^y$ is hydrogen.

In one embodiment, W is $CR^3R^4$, X is $CR^7R^8$, Y is $CR^{10}R^{11}$, Z is C, and ------ is a single bond, wherein the compound may be represented by the structure of Formula I-H:

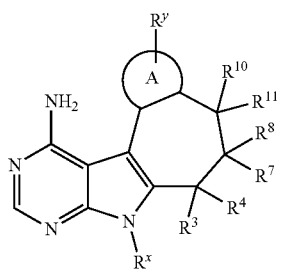

I-H wherein $R^x$, $R^y$, $R^3$, $R^4$, $R^7$, $R^8$, $R^{10}$, and $R^{11}$ are as defined for Formula I and Ring A is (i) a monocyclic aryl ring, wherein said ring is optionally substituted with halogen, C3-C6 cycloalkyl, C1-C6 alkoxy, $R^cNHC(=O)$—, $R^cC(=O)NH$—, or $R^cNHC(=O)NH$— wherein $R^c$ is as defined for Formula I or (ii) a 5-membered monocyclic heteroaryl ring having 2 ring heteroatoms independently selected from N and O, wherein said ring is optionally substituted with C1-C6 alkyl or C3-C6 cycloalkyl.

In one embodiment of Formula I-H, Ring A is a 5-membered heteroaryl ring having 2 ring heteroatoms independently selected from N and O, wherein said ring is optionally substituted with C1-C6 alkyl or C3-C6 cycloalkyl. In one embodiment of Formula I-H, Ring A is a 5-membered heteroaryl ring having 2 ring heteroatoms independently selected from N and O, wherein said ring is optionally substituted with C3-C6 cycloalkyl. In one embodiment of Formula I-H, Ring A is an isoxazolyl ring, wherein said ring is optionally substituted with C1-C6 alkyl or C3-C6 cycloalkyl. In one embodiment, Ring A is an isoxazolyl ring optionally substituted with C3-C6 cycloalkyl. In one embodiment of Formula I-H, Ring A is:

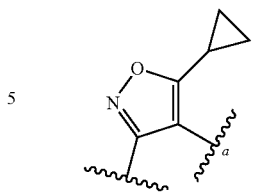

wherein the bond labeled "a" indicates the point of attachment to Y.

In one embodiment of Formula I-H, $R^x$ is hydrogen, C1-C6 alkyl, fluoroC1-C6 alkyl, $Cyc^2$, $Cyc^3$, $hetCyc^3$, $Ar^3$ or $hetAr^3$.

In one embodiment of Formula I-H, $R^7$ and $R^8$ are hydrogen.

In one embodiment of Formula I-H, $R^y$ is hydrogen.

In one embodiment, W is $CR^3R^4$, X is $NR^9$, Y is $CR^{10}R^{11}$, Z is C, and ------ is a single bond, wherein the compound may be represented by the structure of Formula I-I:

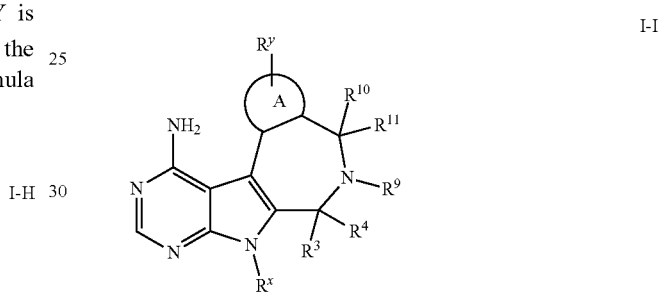

I-I wherein $R^x$, $R^y$, $R^3$, $R^4$, $R^9$, $R^{10}$, and $R^{11}$ are as defined for Formula I and Ring A is (i) a monocyclic aryl ring, wherein said ring is optionally substituted with halogen, C3-C6 cycloalkyl, C1-C6 alkoxy, $R^cNHC(=O)$—, $R^cC(=O)NH$—, or $R^cNHC(=O)NH$— wherein $R^c$ is as defined for Formula I or (ii) a 5-membered monocyclic heteroaryl ring having 2 ring heteroatoms independently selected from N and O, wherein said ring is optionally substituted with C1-C6 alkyl or C3-C6 cycloalkyl.

In one embodiment of Formula I-I, Ring A is a 5-membered heteroaryl ring having 2 ring heteroatoms independently selected from N and O, wherein said ring is optionally substituted with C1-C6 alkyl or C3-C6 cycloalkyl. In one embodiment of Formula I-I, Ring A is a 5-membered heteroaryl ring having 2 ring heteroatoms independently selected from N and O, wherein said ring is optionally substituted with C3-C6 cycloalkyl. In one embodiment of Formula I-I, Ring A is an isoxazolyl ring, wherein said ring is optionally substituted with C1-C6 alkyl or C3-C6 cycloalkyl. In one embodiment, Ring A is an isoxazolyl ring optionally substituted with C3-C6 cycloalkyl. In one embodiment of Formula I-I, Ring A is:

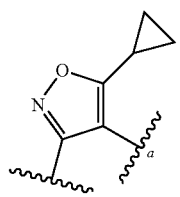 [SMILES: *c1noc(C2CC2)c1*]

wherein the bond labeled "a" indicates the point of attachment to Y.

In one embodiment of Formula I-I, $R^x$ is C1-C6 alkyl.

In one embodiment of Formula I-I, $R^9$ is hydrogen, C1-C6 alkyl, hydroxyC1-C6 alkyl-, C3-C6 cycloalkyl, $Ar^1$, $hetAr^1$, (C1-C6 alkyl)C(=O)—, (fluoroC1-C6 alkyl)C(=O)—, $H_2NC(=O)$—, $Ar^1CH_2C(=O)$—, (C3-C6 cycloalkyl)C(=O)— or (C1-C6 alkyl)$SO_2$—, wherein $Ar^1$ and $hetAr^1$ are as defined for Formula I.

In one embodiment of Formula I-I, $R^{10}$ and $R^{11}$ are hydrogen.

In one embodiment of Formula I-I, $R^y$ is hydrogen.

In one embodiment, W is $CR^3R^4$, X is O, Y is $CR^{10}R^{11}$, Z is C, and ------ is a single bond, wherein the compound may be represented by the structure of Formula I-J:

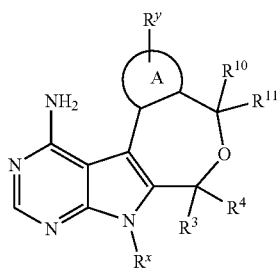

I-J wherein $R^x$, $R^y$, $R^3$, $R^4$, $R^{10}$, and $R^{11}$ are as defined for Formula I, and Ring A is (i) a monocyclic aryl ring, wherein said ring is optionally substituted with halogen, C3-C6 cycloalkyl, C1-C6 alkoxy, $R^cNHC(=O)$—, $R^cC(=O)NH$—, or $R^cNHC(=O)NH$— wherein $R^c$ is as defined for Formula I or (ii) a 5-membered monocyclic heteroaryl ring having 2 ring heteroatoms independently selected from N and O, wherein said ring is optionally substituted with C1-C6 alkyl or C3-C6 cycloalkyl.

In one embodiment of Formula I-J, Ring A is a 5-membered heteroaryl ring having 2 ring heteroatoms independently selected from N and O, wherein said ring is optionally substituted with C1-C6 alkyl or C3-C6 cycloalkyl. In one embodiment of Formula I-J, Ring A is a 5-membered heteroaryl ring having 2 ring heteroatoms independently selected from N and O, wherein said ring is optionally substituted with C3-C6 cycloalkyl. In one embodiment of Formula I-J, Ring A is an isoxazolyl ring, wherein said ring is optionally substituted with C1-C6 alkyl or C3-C6 cycloalkyl. In one embodiment, Ring A is an isoxazolyl ring optionally substituted with C3-C6 cycloalkyl. In one embodiment of Formula I-J, Ring A is:

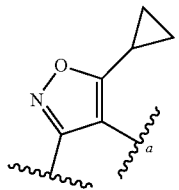

wherein the bond labeled "a" indicates the point of attachment to Y.

In one embodiment of Formula I-J, $R^x$ is C1-C6 alkyl.
In one embodiment of Formula I-J, $R^{10}$ and $R^{11}$ are hydrogen.

In one embodiment of Formula I-J, $R^y$ is hydrogen.

In one embodiment, ------ is a double bond, W is $CR^3R^4$, X is $CR^5$, Y is $CR^6$, $R^5$ and $R^6$ are hydrogen, and Z is C, wherein the compound may be represented by the structure of Formula I-K:

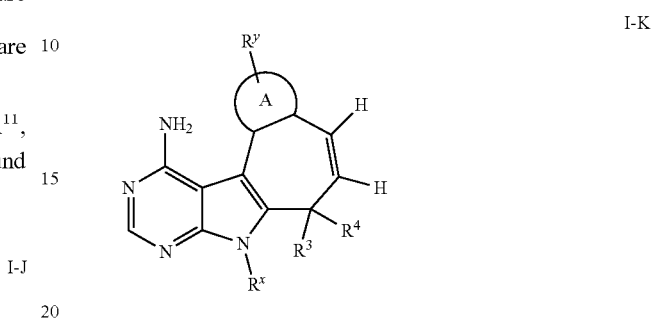

I-K wherein $R^x$, $R^y$, $R^3$, $R^4$ are as defined for Formula I and Ring A is (i) a monocyclic aryl ring, wherein said ring is optionally substituted with halogen, C3-C6 cycloalkyl, C1-C6 alkoxy, $R^cNHC(=O)$—, $R^cC(=O)NH$—, or $R^cNHC(=O)NH$— wherein $R^c$ is as defined for Formula I or (ii) a 5-membered monocyclic heteroaryl ring having 2 ring heteroatoms independently selected from N and O, wherein said ring is optionally substituted with C1-C6 alkyl or C3-C6 cycloalkyl.

In one embodiment of Formula I-K, Ring A is a 5-membered heteroaryl ring having 2 ring heteroatoms independently selected from N and O, wherein said ring is optionally substituted with C1-C6 alkyl or C3-C6 cycloalkyl. In one embodiment of Formula I-K, Ring A is a 5-membered heteroaryl ring having 2 ring heteroatoms independently selected from N and O, wherein said ring is optionally substituted with C3-C6 cycloalkyl. In one embodiment of Formula I-K, Ring A is an isoxazolyl ring, wherein said ring is optionally substituted with C1-C6 alkyl or C3-C6 cycloalkyl. In one embodiment, Ring A is an isoxazolyl ring optionally substituted with C3-C6 cycloalkyl. In one embodiment of Formula I-K, Ring A is:

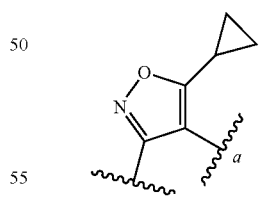

wherein the bond labeled "a" indicates the point of attachment to Y.

In one embodiment of Formula I-K, $R^x$ is C1-C6 alkyl.

In one embodiment of Formula I-K, $R^y$ is hydrogen.

In one embodiment, W is $CR^3R^4$, X is $CR^7R^8$, Y is $CR^{10}R^{11}$, Z is N, and ------ is a single bond, wherein the compound may be represented by the structure of Formula I-L:

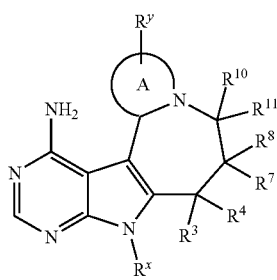

I-L wherein $R^x$, $R^y$, $R^3$, $R^4$, $R^7$, $R^8$, $R^{10}$, and $R^{11}$ are as defined for Formula I and Ring A is (ii) a 5-membered heteroaryl ring having two ring nitrogen atoms, one of which is Z, wherein said ring is optionally substituted with C1-C6 alkyl or C3-C6 cycloalkyl, or (iii) a bicyclic heteroaryl ring having one ring nitrogen atom that results when Z is N, wherein said ring is optionally substituted with $R^d$NHC (=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—.

In one embodiment of Formula I-L, Ring A is a bicyclic heteroaryl ring having one ring nitrogen atom that results when Z is N, wherein said ring is optionally substituted with $R^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—.

In one embodiment of Formula I-L, Ring A is a bicyclic heteroaryl ring having one ring nitrogen atom that results when Z is N, wherein said ring is optionally substituted with $R^d$NHC(=O)—, (C1-C6 alkoxy)C(=O)—, halogen, or (C1-C6 alkyl)C(=O)NH—.

In one embodiment of Formula I-L, $R^7$ and $R^8$ are hydrogen.

In one embodiment of Formula I-L, $R^{10}$ and $R^{11}$ are hydrogen.

In one embodiment of Formula I-L, $R^x$ is C1-C6 alkyl.

In one embodiment of Formula I-L, $R^y$ is hydrogen.

In one embodiment of Formula I-L, $R^y$ is halogen.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Non-limiting examples of pharmaceutically acceptable salts of compounds of Formula I include trifluoroacetic acid and hydrochloride salts.

It will further be appreciated that the compounds of Formula I or their salts may be isolated in the form of solvates, and accordingly that any such solvate is included within the scope of the present invention. For example, compounds of Formula I and salts thereof can exist in unsolvated as well as solvated forms with pharmaceutically acceptable solvents such as water, ethanol, and the like.

In one embodiment, the compounds of Formula I include the compounds of Examples 1-151 and stereoisomers and pharmaceutically acceptable salts and solvates thereof. In one embodiment, the compounds of Examples 1-151 are in the free base form. In one embodiment, the compounds of Examples 1-151 are in the salt form. In one embodiment, the compounds of Examples 1-151 are trifluoroacetate salts. In one embodiment, the compounds of Examples 1-151 are in the form of hydrochloride salts.

The term "pharmaceutically acceptable" indicates that the compound, or salt or composition thereof is compatible chemically and/or toxicologically with the other ingredients comprising a formulation and/or the patient being treated therewith.

Compounds provided herein may also contain unnatural proportions of atomic isotopes at one or more of the atoms that constitute such compounds. That is, an atom, in particular when mentioned in relation to a compound according to Formula I, comprises all isotopes and isotopic mixtures of that atom, either naturally occurring or synthetically produced, either with natural abundance or in an isotopically enriched form. For example, when hydrogen is mentioned, it is understood to refer to $^1H$, $^2H$, $^3H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}O$, $^{16}O$, $^{17}O$, $^{18}O$ or mixtures thereof; and when fluoro is mentioned, it is understood to refer to $^{18}F$, $^{19}F$ or mixtures thereof. The compounds provided herein therefore also comprise compounds with one or more isotopes of one or more atoms, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds provided herein, whether radioactive or not, are intended to be encompassed within the scope of the present invention.

For illustrative purposes, Schemes 1-25 show general methods for preparing the compounds provided herein as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

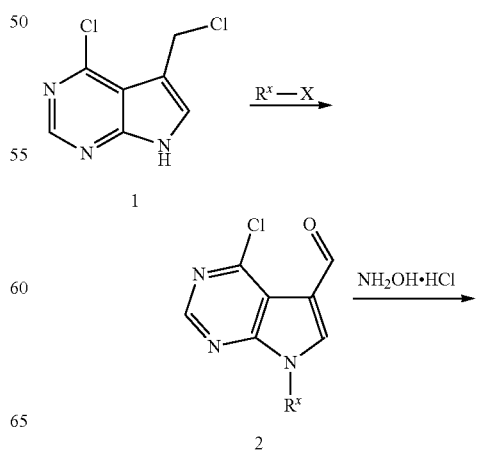

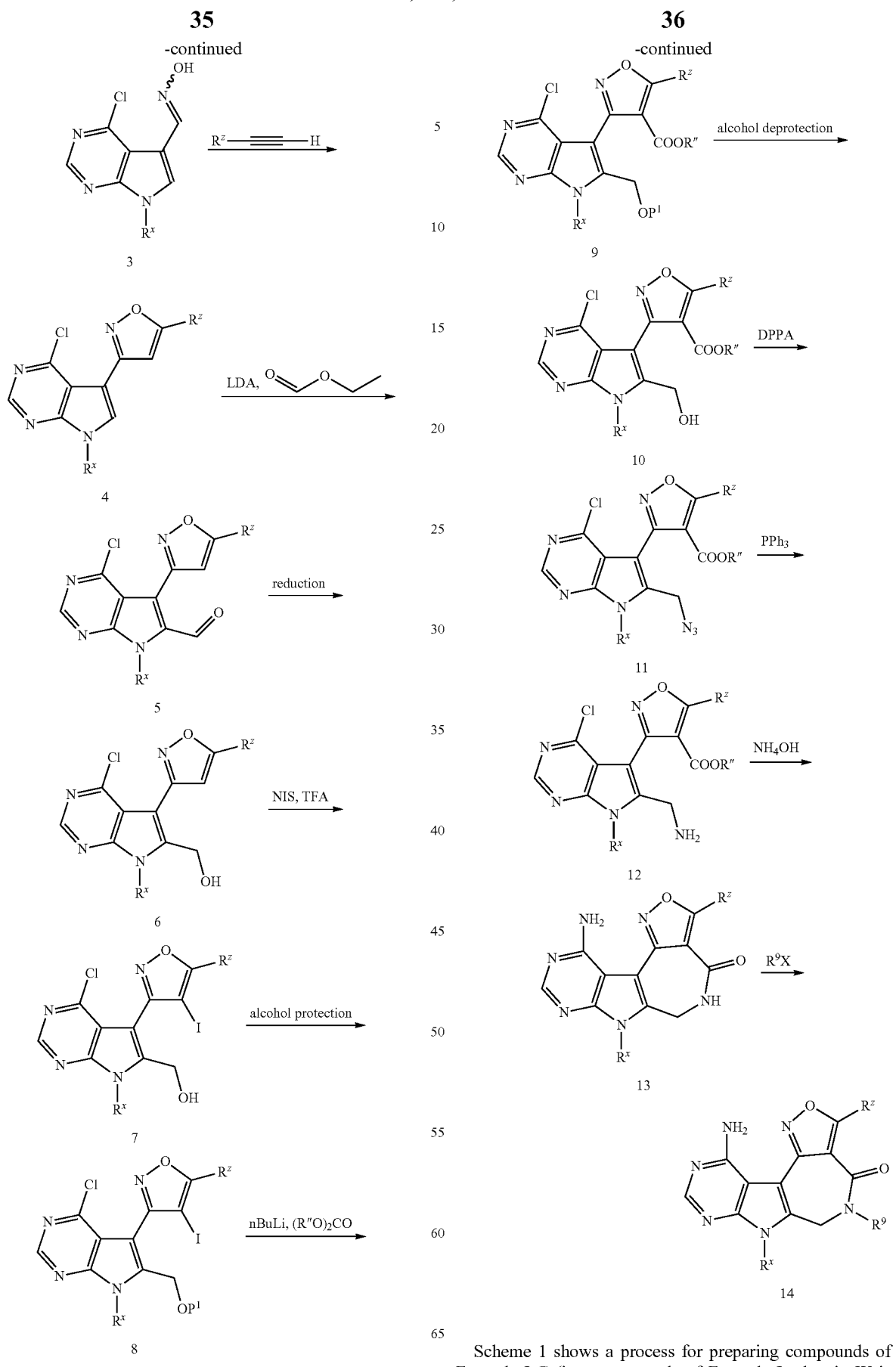
Scheme 1 shows a process for preparing compounds of Formula I-C (i.e., compounds of Formula I wherein W is CR³R⁴, X is NR⁹, Y is C(═O), Z is C, and ------- is a single bond, R⁹ is hydrogen, C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, (hetCyc¹)C1-C6 alkyl-, (Ar¹)C1-C6 alkyl-, or (hetAr¹)C1-C6 alkyl-, Rˣ is C1-C6 alkyl, fluoroC1-C6 alkyl, Cyc², or Cyc³, and Ring A is

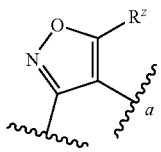

wherein the bond labeled "a" indicates the point of attachment to Y and Rᶻ is C1-C6 alkyl or C3-C6 cycloalkyl.

Compound 1, which is commercially available, may be reacted with a reagent having the formula Rˣ—X wherein Rˣ is C1-C6 alkyl, fluoroC1-C6 alkyl, Cyc², or Cyc³, and X is a leaving group such as a halogen, to provide compound 2. Compound 2 may be reacted with hydroxylamine hydrochloride to provide oxime compound 3. The oxime moiety of compound 3 may undergo cycloaddition to form an isoxazole ring upon treatment with a compound having the formula HC≡C—Rᶻ wherein Rᶻ is C1-C6 alkyl or C3-C6 cycloalkyl to provide compound 4. Compound 4 may be treated with LDA and ethyl formate to provide the carbaldehyde-substituted compound 5. The carbaldehyde group of compound 5 may be reduced upon treatment of compound 5 with a reducing agent such as sodium borohydride to provide compound 6. The isoxazole ring of compound 6 may be iodinated upon treatment with N-iodosuccinimide in the presence of a catalytic amount of TFA to provide compound 7. The alcohol group of compound 7 may be protected with a suitable hydroxy protecting group P¹ such as a t-butyldimethyl silyl group to provide compound 8. The iodo group of compound 8 may be replaced with a carboxylate group upon treatment, for example, with a reagent of formula (R"O)₂CO where R" is C1-C6 alkyl in the presence of an organometallic reagent such as n-butyl lithium to provide compound 9. The hydroxy protecting group P¹ may be removed under standard conditions, for example in the presence of TBAF (tetrabutylammonium fluoride), to provide compound 10. The alcohol group of compound 10 may be displaced by an azide group upon treatment with diphenylphosphoryl azide to provide compound 11. The azide group of compound 11 may be reduced upon treatment with triphenylphosphine to provide compound 12. Reaction of compound 12 with ammonium hydroxide results in the displacement of the chloro group with an amino group as well as an intramolecular cyclization to provide compound 13, which is a compound of Formula I-C wherein R⁹ is hydrogen. Compound 13 may be reacted with a reagent having the formula R⁹—X wherein R⁹ is C1-C6 alkyl, hydroxyC1-C6 alkyl- wherein the hydroxy group is protected with a suitable hydroxy protecting group (e.g., t-butyldimethyl silyl), (C1-C6 alkoxy)C1-C6 alkyl-, C3-C6 cycloalkyl, (C3-C6 cycloalkyl)C1-C6 alkyl-, (hetCyc¹)C1-C6 alkyl-, (Ar¹)C1-C6 alkyl-, or (hetAr¹)C1-C6 alkyl- and X is a leaving group such as a halogen, to provide compound 14 which is a compound of Formula I-C, following removal of protecting groups where applicable, wherein R⁹ is C1-C6 alkyl, hydroxyC1-C6 alkyl-, (C1-C6 alkoxy)C1-C6 alkyl-, C3-C6 cycloalkyl, (C3-C6 cycloalkyl)C1-C6 alkyl-, (hetCyc¹)C1-C6 alkyl-, (Ar¹)C1-C6 alkyl- or (hetAr¹)C1-C6 alkyl-.

Scheme 2

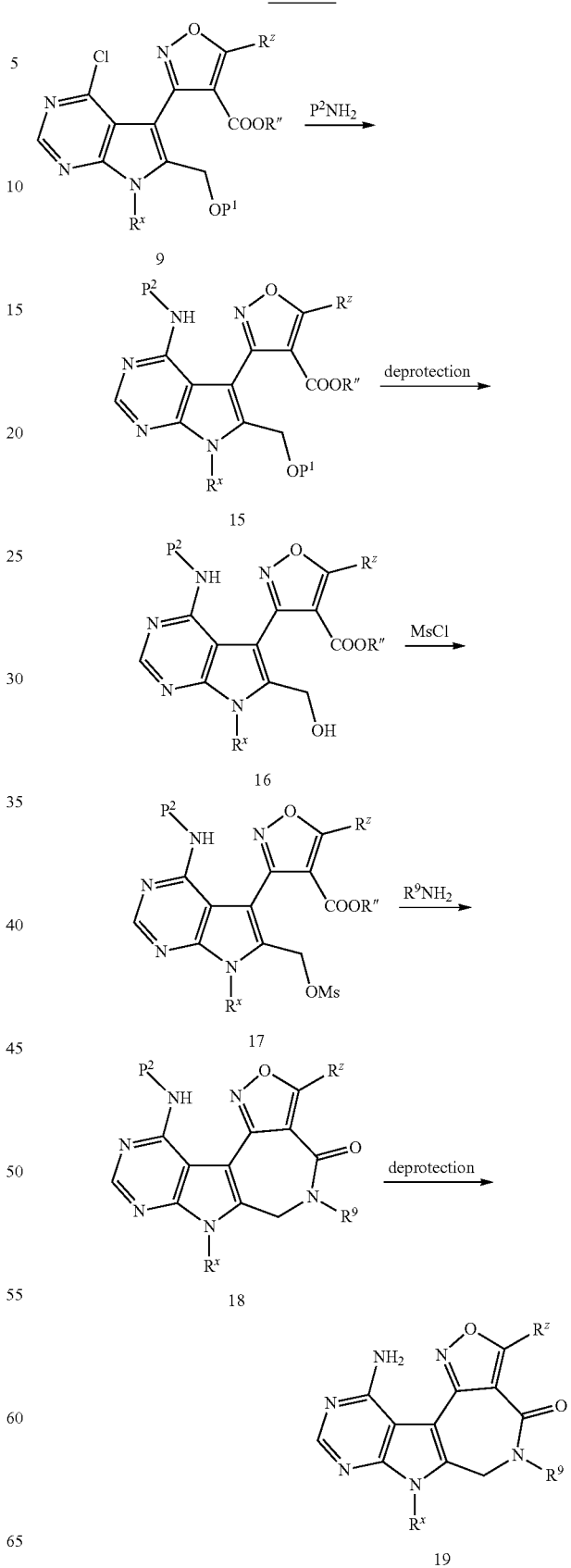

Scheme 2 shows a process for preparing compounds of Formula I-C (i.e., a compound of Formula I wherein W is CR³R⁴, X is NR⁹, Y is C(=O), Z is C, and ------- is a single bond), wherein R⁹ is C1-C6 alkyl, hydroxyC1-C6 alkyl, (C1-C6 alkoxy)C1-C6 alkyl, C3-C6 cycloalkyl, (C3-C6 cycloalkyl)C1-C6 alkyl-, (hetCyc¹)C1-C6 alkyl-, (Ar¹)C1-C6 alkyl-, or (hetAr¹)C1-C6 alkyl-, R$^x$ is as defined for Formula I, and Ring A is

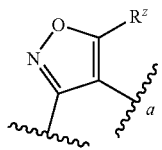

wherein the bond labeled "a" indicates the point of attachment to Y and R$^z$ is C1-C6 alkyl or C3-C6 cycloalkyl.

Compound 9 (wherein R$^x$, P¹ and R$^z$ are as defined in Scheme 1), which may be prepared according to Scheme 1, may be reacted with an amine reagent having the formula P²NH₂ wherein P² is a suitable amino protecting group such as DMB (2,4-dimethoxybenzyl) to provide compound 15. The hydroxy protecting group P¹ of compound 15 may be removed under suitable reaction conditions such as treatment with TBAF to provide compound 16. The alcohol group of compound 16 may be converted to a mesylate leaving group upon treatment with methanesulfonyl chloride to provide compound 17. Compound 17 may be undergo mesylate displacement and cyclization upon treatment with a reagent having the formula R⁹NH₂ wherein R⁹ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, (hetCyc¹)C1-C6 alkyl-, (Ar¹)C1-C6 alkyl-, or (hetAr¹)C1-C6 alkyl- to provide compound 18. The amino protecting group P² may be removed under standard conditions, for example in the presence of TFA, to provide compound 19, which is a compound of Formula I-C wherein R⁹ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, (hetCyc¹)C1-C6 alkyl-, (Ar¹)C1-C6 alkyl-, or (hetAr¹)C1-C6 alkyl-.

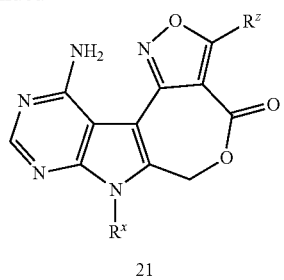

21

Scheme 3 shows a process for preparing a compound of Formula I-D (i.e., a compound of Formula I wherein W is CR³R⁴, X is O, Y is C(=O), Z is C, and ------- is a single bond) wherein R$^x$ is C1-C6 alkyl, fluoroC1-C6 alkyl, Cyc², or Cyc³, and Ring A is

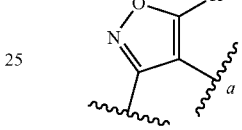

wherein the bond labeled "a" indicates the point of attachment to Y and R$^z$ is C1-C6 alkyl or C3-C6 cycloalkyl.

Compound 15, (wherein R$^x$, R$^z$, R", P¹ and P² are as defined in Scheme 2) which may be prepared according to Scheme 2, may undergo an intramolecular cyclization upon treatment with TBAF to provide compound 20. The amino protecting group P² may be removed under standard conditions, for example in the presence of TFA, to provide compound 21, which is a compound of Formula I-D.

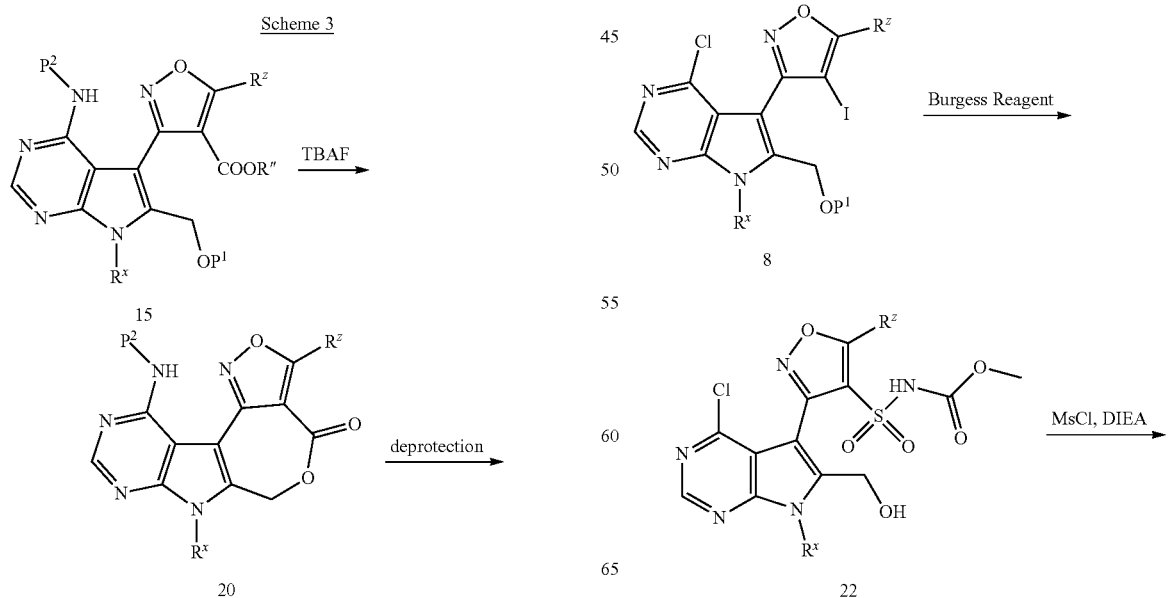

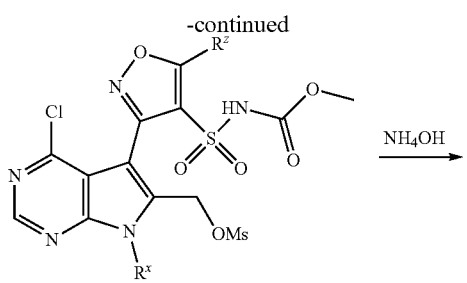

22a

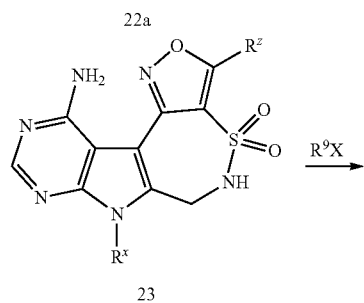

23

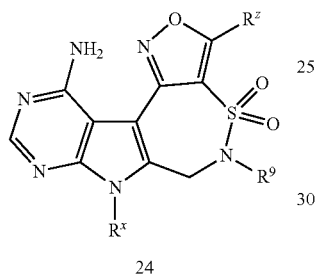

24

Scheme 4 shows a process for preparing a compound of Formula I-E (i.e., a compound of Formula I wherein W is $CR^3R^4$, X is $NR^9$, Y is $SO_2$, Z is C, and ------- is a single bond) wherein $R^9$ is hydrogen, C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, (hetCyc$^1$)C1-C6 alkyl-, (Ar$^1$) C1-C6 alkyl-, or (hetAr$^1$)C1-C6 alkyl-, $R^x$ is C1-C6 alkyl, fluoroC1-C6 alkyl, Cyc$^2$, or Cyc$^3$, and Ring A is

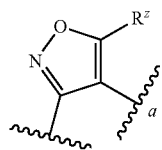

wherein the bond labeled "a" indicates the point of attachment to Y and $R^z$ is C1-C6 alkyl or C3-C6 cycloalkyl.

Compound 8 (wherein $R^x$, $R^z$ and $P^1$ are as defined in Scheme 1), which may be prepared according to Scheme 1, may be reacted with Burgess Reagent (methyl N-(triethylammoniumsulfonyl)carbamate) to provide compound 22. The alcohol group of compound 22 may be converted to a mesylate leaving group upon treatment with methanesulfonyl chloride to provide compound 22a. Compound 22a may undergo mesylate displacement and intramolecular cyclization upon treatment with ammonium hydroxide to provide compound 23, which is a compound of Formula I-E wherein $R^9$ is hydrogen. Compound 23 may be reacted with a reagent having the formula $R^9$—X wherein $R^9$ is C1-C6 alkyl, hydroxyC1-C6 alkyl- wherein the hydroxy group is protected with a suitable hydroxy protecting group (e.g., tert-butyldimethylsilyl), (C1-C6 alkoxy)C1-C6 alkyl-, C3-C6 cycloalkyl, (C3-C6 cycloalkyl)C1-C6 alkyl-, (hetCyc$^1$)C1-C6 alkyl-, (Ar$^1$)C1-C6 alkyl-, or (hetAr$^1$)C1-C6 alkyl- and X is a leaving group such as a halogen, to provide compound 24 which is a compound of Formula I-E, following removal of protecting groups where applicable, wherein $R^9$ is C1-C6 alkyl, hydroxyC1-C6 alkyl-, (C1-C6 alkoxy)C1-C6 alkyl-, C3-C6 cycloalkyl, (C3-C6 cycloalkyl)C1-C6 alkyl-, (hetCyc$^1$)C1-C6 alkyl-, (Ar$^1$)C1-C6 alkyl- or (hetAr$^1$)C1-C6 alkyl-.

Scheme 5

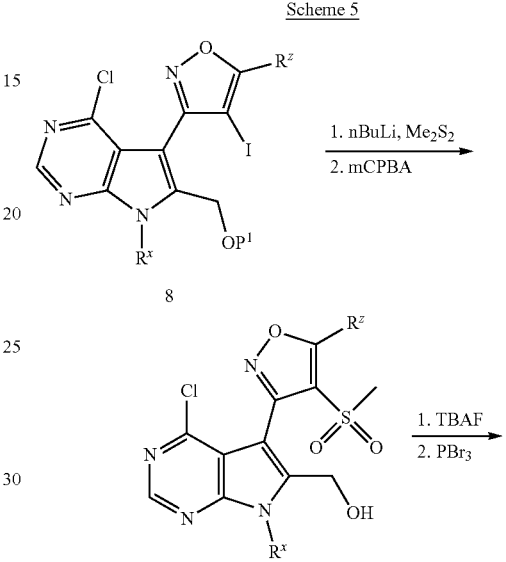

8

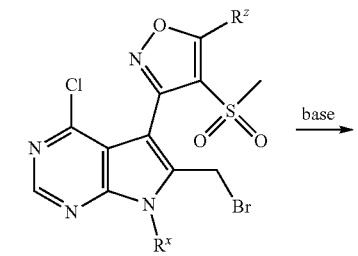

25

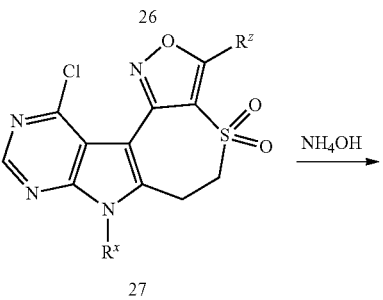

26

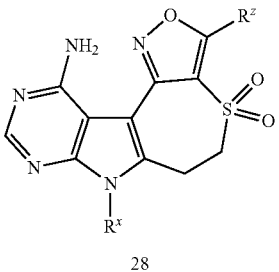

27

28

Scheme 5 shows a process for preparing a compound of Formula I-F (i.e., a compound of Formula I wherein W is CR³R⁴, X is CR⁷R⁸, Y is SO₂, Z is C, and ------- is a single bond), wherein R⁷ and R⁸ are hydrogen, R$^x$ is C1-C6 alkyl, fluoroC1-C6 alkyl, Cyc², or Cyc³, and Ring A is

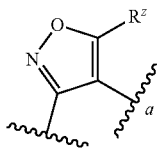

wherein the bond labeled "a" indicates the point of attachment to Y and R$^z$ is C1-C6 alkyl or C3-C6 cycloalkyl.

Compound 8 (wherein R$^x$, R$^z$ and P¹ are as defined in Scheme 1), which may be prepared according to Scheme 1, may be reacted with dimethyl disulfide in the presence of an organometallic reagent (e.g., n-butyl lithium). Oxidation of the intermediate sulfide to a sulfone upon treatment with mCPBA (meta-chloroperoxybenzoic acid) can provide compound 25. The hydroxy protecting group P¹ of compound 25 may be removed under standard conditions to provide the intermediate alcohol (not shown), which may be converted to the bromide upon treatment with PBr₃ to provide compound 26. Compound 26 may undergo an intramolecular cyclization upon treatment with a strong non-nucleophilic base such as LHMDS (lithium hexamethyldisilazide) to provide compound 27. The chloro group of compound 27 may be displaced by an amino group upon treatment of compound 27 with ammonium hydroxide to provide compound 28, which is a compound of Formula I-F.

Scheme 6

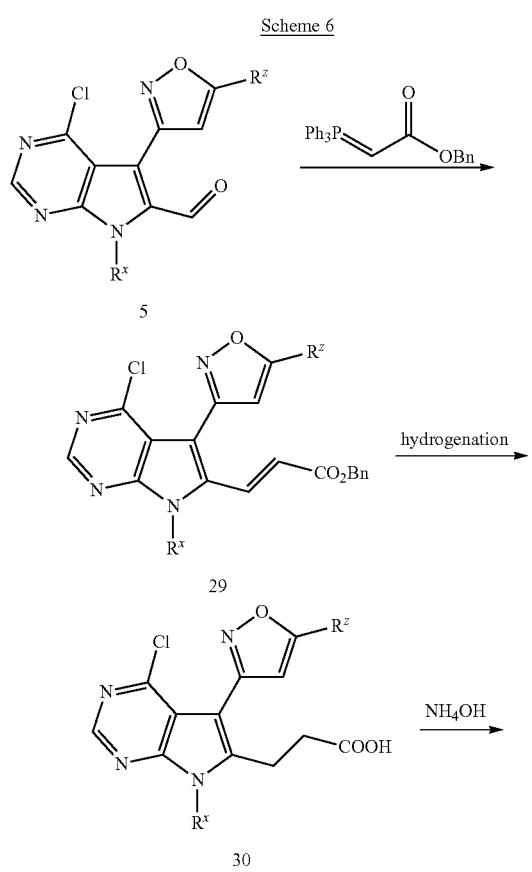

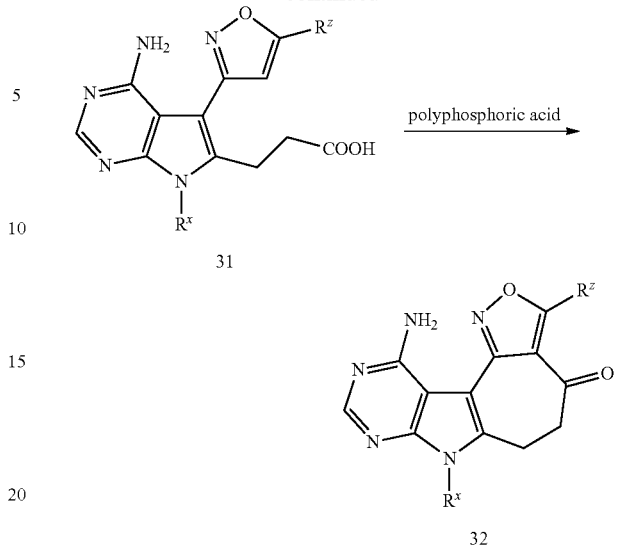

Scheme 6 shows a process for preparing a compound of Formula I-G (i.e., a compound of Formula I wherein W is CR³R⁴, X is CR⁷R⁸, Y is C(=O), Z is C, and ------- is a single bond), wherein R⁷ and R⁸ are hydrogen, R$^x$ is C1-C6 alkyl, fluoroC1-C6 alkyl, Cyc², or Cyc³, and Ring A is wherein the bond labeled "a" indicates the point of attachment to Y and R$^z$ is C1-C6 alkyl or C3-C6 cycloalkyl.

Compound 5 (wherein R$^x$ and R$^z$ are as defined for Scheme 1), which may be prepared according to Scheme 1, may be converted to compound 29 upon treatment with benzyl (triphenylphosphoranylidene)acetate. The double bond of compound 29 may be reduced under standard hydrogenation conditions (e.g., palladium catalyzed hydrogenation conditions) to provide compound 30 with concomitant cleavage of the benzyl group. The chloro group of compound 30 may be displaced by an amino group upon treatment of compound 30 with ammonium hydroxide to provide compound 31. Compound 31 may be cyclized upon treatment with polyphosphoric acid to provide compound 32, which is a compound of Formula I-G.

Scheme 7

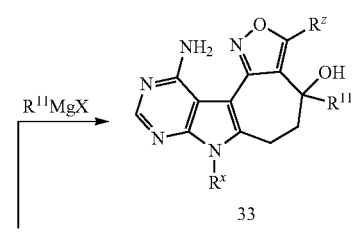

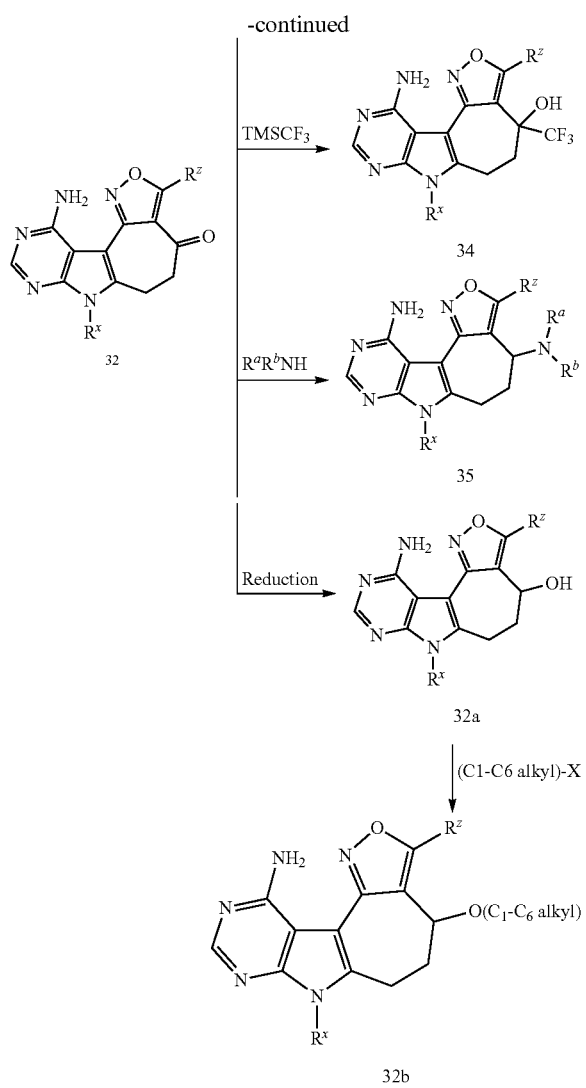

Alternatively, compound 32 may be reacted with TMSCF₃ (trifluoromethyltrimethylsilane) to provide compound 34, which is a compound of Formula I-H wherein $R^{10}$ is hydroxy and $R^{11}$ is $CF_3$.

Alternatively, compound 32 may be reacted with a reagent having the formula $R^aR^bNH$ wherein $R^a$ is hydrogen and $R^b$ is H or C1-C6 alkyl in the presence of a reductant (e.g., sodium triacetoxyborohydride) to provide a compound of Formula I-H wherein $R^{10}$ is $R^aR^bN$— where $R^a$ is hydrogen and $R^b$ is H or C1-C6 alkyl, and $R^{11}$ is hydrogen.

Alternatively, compound 32 may be treated under standard hydrogenation conditions for reducing a ketone to an alcohol (e.g., using sodium borohydride) to provide compound 32a, which is a compound of Formula I-H wherein $R^{10}$ is OH and $R^{11}$ is hydrogen. Compound 32a may be reacted with a reagent having the formula (C1-C6 alkyl)-X wherein X is a halogen to provide compound 32b, which is a compound of Formula I-H wherein $R^{10}$ is C1-C6 alkoxy and $R^{11}$ is hydrogen.

Scheme 7 shows processes for preparing compounds of Formula I-H (i.e., a compound of Formula I wherein W is $CR^3R^4$, X is $CR^7R^8$, Y is $CR^{10}R^{11}$, Z is C, and ------ is a single bond), wherein $R^7$ and $R^8$ are hydrogen, $R^x$ is as defined for Formula I, $R^{10}$ and $R^{11}$ are as defined below for Scheme 7, and Ring A is

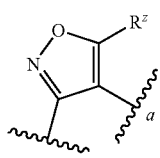

wherein the bond labeled "a" indicates the point of attachment to Y and $R^z$ is C1-C6 alkyl or C3-C6 cycloalkyl.

Compound 32 (wherein $R^x$ and $R^z$ are as defined in Scheme 6), which may be prepared according to Scheme 6, may be reacted with a Grignard reagent having the formula $R^{11}MgX$ wherein $R^{11}$ is C1-C6 alkyl and X is Br, I or Cl to provide compound 33, which is a compound of Formula I-H wherein $R^{10}$ is hydroxy and $R^{11}$ is C1-C6 alkyl.

Scheme 8

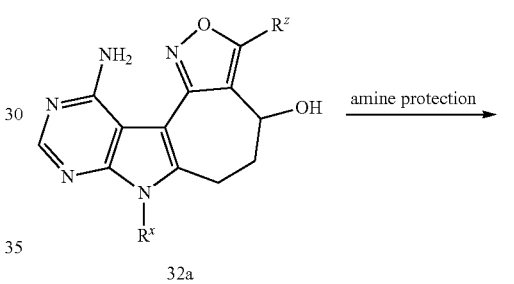

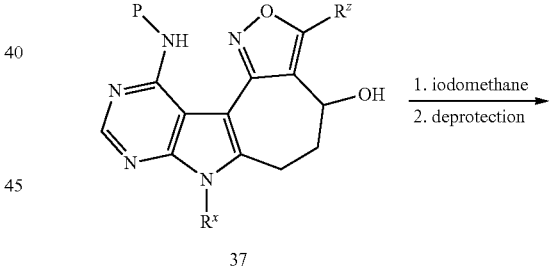

Scheme 8 shows a process for preparing compounds of Formula I-K (i.e., compounds of Formula I wherein W is $CR^3R^4$, X is $CR^5$, Y is $CR^6$, Z is C, and ------ is a double bond), wherein $R^5$ and $R^6$ are hydrogen, $R^x$ is C1-C6 alkyl, fluoroC1-C6 alkyl, $Cyc^2$, or $Cyc^3$, and Ring A is

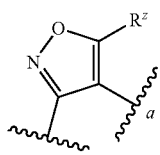

wherein the bond labeled "a" indicates the point of attachment to Y and $R^z$ is C1-C6 alkyl or C3-C6 cycloalkyl.

Compound 32a (wherein $R^x$ and $R^z$ are as defined in Scheme 6), which may be prepared according to Scheme 7, may be protected with an amino protecting group (e.g., dimethylformamide dimethyl acetal) to provide compound 37 where P is an amino protecting group. Treatment of compound 37 with iodomethane in the presence of a base (e.g., diisopropylethylamine), followed by removal of the amino protecting group under standard conditions provides compound 38, which is a compound of Formula I-K.

Scheme 9

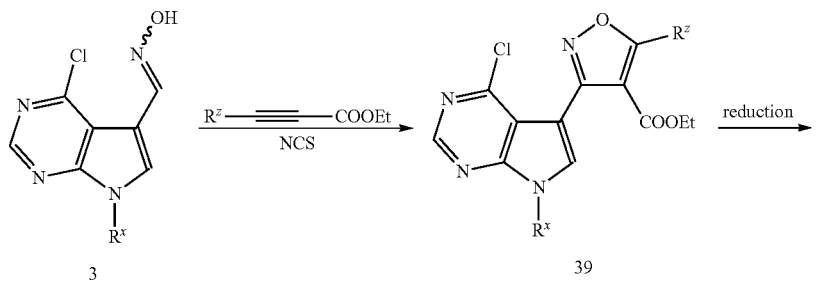

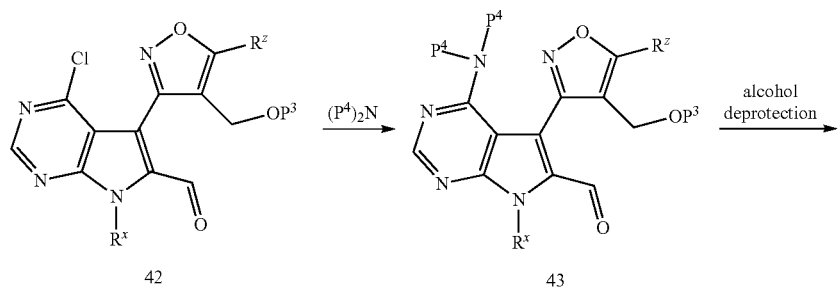

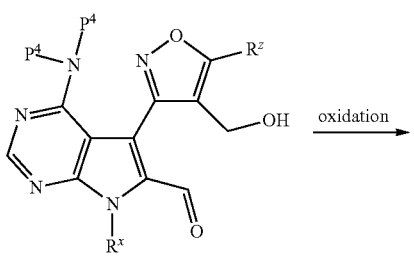

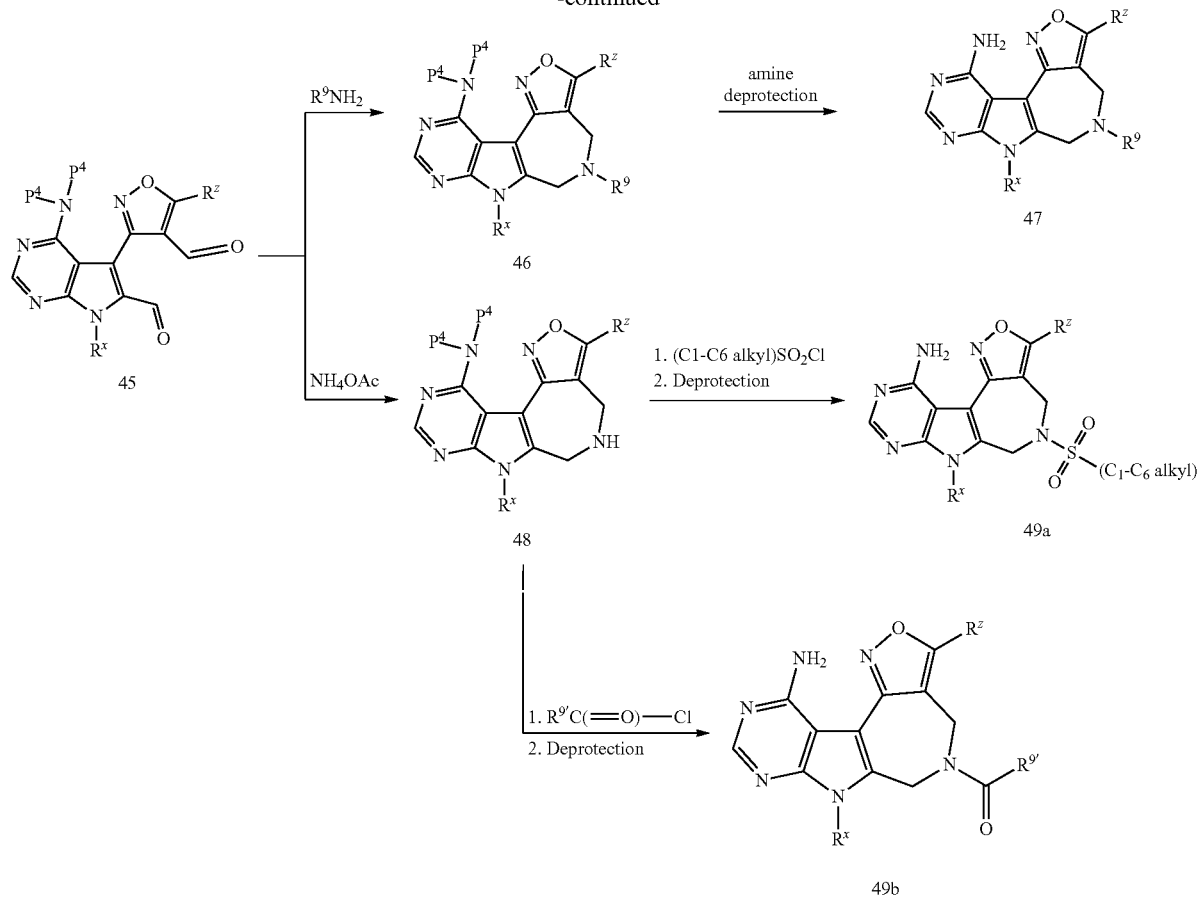

Scheme 9 shows a process for preparing compounds of Formula I-I (i.e., compounds of Formula I wherein W is $CR^3R^4$, X is $NR^9$, Y is $CR^{10}R^{11}$, Z is C, and ------- is a single bond), wherein $R^{10}$ and $R^{11}$ are hydrogen, $R^x$ is C1-C6 alkyl, fluoroC1-C6 alkyl, $Cyc^2$, or $Cyc^3$, $R^9$ is as defined below for Scheme 9, and Ring A is

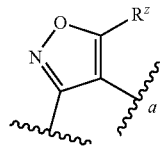

wherein the bond labeled "a" indicates the point of attachment to Y and $R^z$ is C1-C6 alkyl or C3-C6 cycloalkyl.

Compound 3 (wherein $R^x$ is as defined for Scheme 1), which may be prepared according to Scheme 1, may undergo cycloaddition to form an isoxazole ring upon treatment with a compound having the formula $R^zC≡C$—COOEt wherein $R^z$ is C1-C6 alkyl or C3-C6 cycloalkyl to provide compound 39. Compound 39 may be treated with a suitable ester-reducing agent such as DIBAL-H to provide compound 40. The alcohol group of compound 40 may be protected with a suitable hydroxy protecting group $P^3$, for example, a tert-butyldimethylsilyl protecting group upon treatment with TBSCl, to provide compound 41. Compound 41 may be treated with LDA and ethyl formate to provide the carbaldehyde-substituted compound 42. Compound 42 may be reacted with an amine of the formula $(P^4)_2N$ where $P^4$ is a suitable amino protecting group (e.g., a benzyl protecting group such as 4-methoxybenzyl) to provide compound 43. The hydroxy protecting group $P^3$ of compounds 43 may be removed under standard conditions to provide compound 44. The alcohol group of compound 44 may be oxidized to a carbaldehyde under suitable oxidation conditions (e.g., by treatment with Dess-Martin periodinane), to provide compound 45. Compound 45 may be treated with a reagent having the formula $R^9NH_2$ where $R^9$ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, $hetCyc^1$, ($hetCyc^1$)C1-C6 alkyl-, $Ar^1$, ($Ar^1$)C1-C6 alkyl-, $hetAr^1$ or ($hetAr^1$)C1-C6 alkyl-, in the presence of a reducing agent (e.g., sodium triacetoxyborohydride) to provide compound 46. Removal of the amino protecting groups $P^4$ of compound 46 provides compound 47, which is a compound of Formula I-I wherein $R^9$ is C1-C6 alkyl, hydroxyC1-C6 alkyl-, (C1-C6 alkoxy)C1-C6 alkyl, C3-C6 cycloalkyl, (C3-C6 cycloalkyl) C1-C6 alkyl-, $hetCyc^1$, ($hetCyc^1$)C1-C6 alkyl-, $Ar^1$, ($Ar^1$) C1-C6 alkyl-, $hetAr^1$ or ($hetAr^1$)C1-C6 alkyl-.

Alternatively, compound 45 may be cyclized upon treatment with ammonium acetate in the presence of a reducing agent (e.g., sodium triacetoxyborohydride) to provide compound 48. Compound 48 may be treated with (C1-C6 alkyl)$SO_2Cl$, which after removal of the amino protecting groups $P^4$ provides compound 49a, which is a compound of Formula I-I wherein $R^9$ is (C1-C6 alkyl)$SO_2$—.

51

Alternatively, compound 48 may be treated with a reagent having the formula R9'C(=O)Cl, wherein R9' is C1-C6 alkyl or fluoroC1-C6 alkyl, to provide compound 49b, which is a compound of Formula I-I wherein R9 is C1-C6 alkyl or fluoroC1-C6 alkyl.

Scheme 10

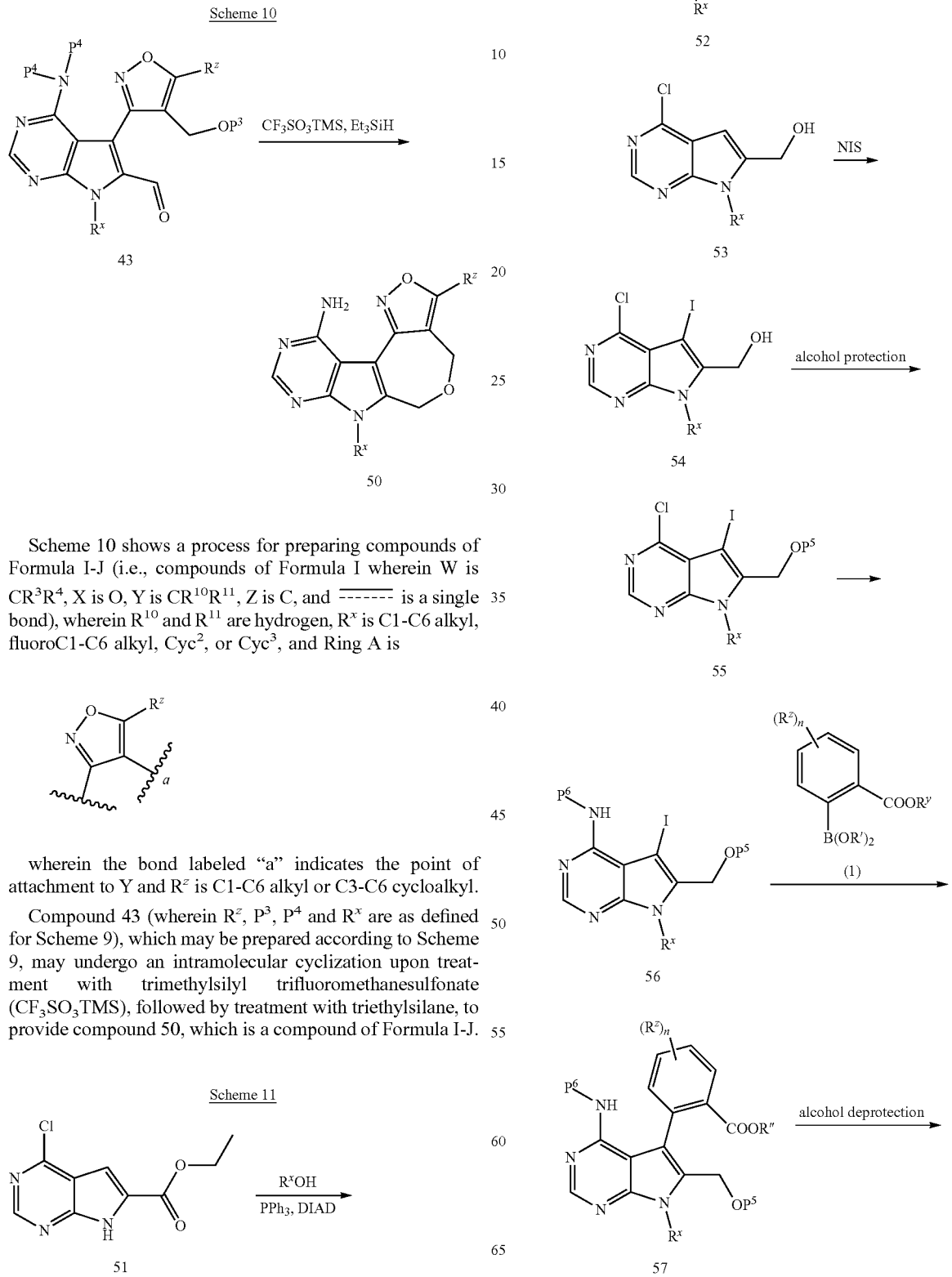

Scheme 10 shows a process for preparing compounds of Formula I-J (i.e., compounds of Formula I wherein W is CR3R4, X is O, Y is CR10R11, Z is C, and ------ is a single bond), wherein R10 and R11 are hydrogen, Rx is C1-C6 alkyl, fluoroC1-C6 alkyl, Cyc2, or Cyc3, and Ring A is

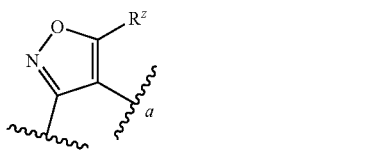

wherein the bond labeled "a" indicates the point of attachment to Y and Rz is C1-C6 alkyl or C3-C6 cycloalkyl.

Compound 43 (wherein Rz, P3, P4 and Rx are as defined for Scheme 9), which may be prepared according to Scheme 9, may undergo an intramolecular cyclization upon treatment with trimethylsilyl trifluoromethanesulfonate (CF3SO3TMS), followed by treatment with triethylsilane, to provide compound 50, which is a compound of Formula I-J.

Scheme 11

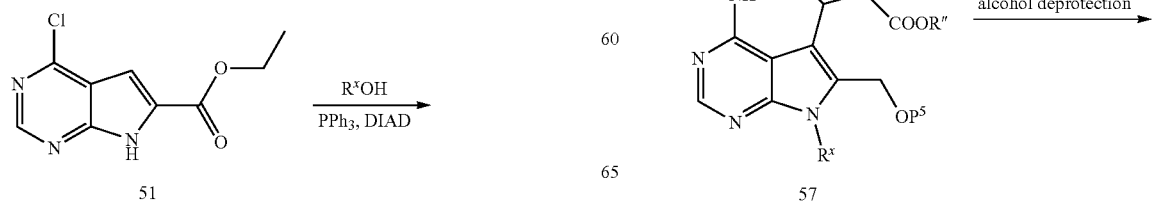

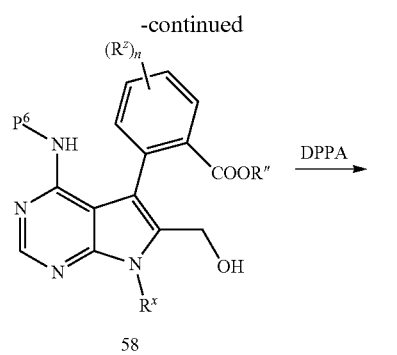

Scheme 11 shows a process for preparing compounds of Formula I-C (i.e. compounds of Formula I wherein W is CR³R⁴, X is NR⁹, Y is C(=O), Z is C, and ------- is a single bond), wherein Ring A is a 6-membered aryl ring optionally substituted with one or more substituents independently selected from halogen, C3-C6 cycloalkyl, C1-C6 alkoxy, R$^c$NHC(=O), R$^c$C(=O)NH—, or R$^c$NHC(=O) NH—, wherein R$^c$ is C3-C6 cycloalkyl or (C3-C6 cycloalkyl)CH$_2$—, R⁹ is hydrogen, C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, (hetCyc¹)C1-C6 alkyl-, (Ar¹) C1-C6 alkyl-, or (hetAr¹)C1-C6 alkyl-, and R$^x$ is C1-C6 alkyl, fluoroC1-C6 alkyl, Cyc², or Cyc³. Compound 51, which is commercially available, may be reacted with an alcohol having the formula R$^x$OH, wherein R$^x$ is C1-C6 alkyl, fluoroC1-C6 alkyl, Cyc², or Cyc³, under standard Mitsunobu reaction conditions, to provide compound 52. The ester group of compound 52 may be reduced under standard conditions (e.g., by treating with a reducing agent such as DIBAL-H) to provide compound 53. Compound 53 may be iodinated upon treatment with N-iodosuccinimide to provide compound 54. Compound 54 may be treated with a suitable alcohol protecting reagent to provide compound 55 where P⁵ is a hydroxy protecting group (e.g., t-butyldimethylsilyl). Compound 55 may be treated with a suitably protected amine to provide compound 56 where P⁶ is an amino protecting group (e.g., a benzyl group, e.g., 2,4-dimethoxybenzyl). Compound 56 may be treated with a boronic ester reagent (1) wherein n is 0, 1, 2, 3 or 4, each R$^z$ is independently selected from halogen, C3-C6 cycloalkyl, C1-C6 alkoxy, R$^c$NHC(=O)—, R$^c$C(=O)NH—, or R$^c$NHC(=O)NH—, wherein R$^c$ is C3-C6 cycloalkyl or (C3-C6 cycloalkyl)CH$_2$—, R" is C1-C6 alkyl, and each R' is independently H or (1-6C)alkyl, or each R' together with the atoms to which they are connected form a 5-6 membered ring optionally substituted with 1-4 substituents selected from (C1-C3 alkyl), using appropriate palladium-catalyzed cross-coupling reaction conditions, e.g., Suzuki coupling reaction conditions, to provide compound 57. The hydroxy protecting group of compound 57 may be removed under standard conditions to provide compound 58. The alcohol group of compound 58 may be displaced by an azide group upon treatment with diphenylphosphoryl azide to provide compound 59. The azide group of compound 59 may be reduced upon treatment with triphenylphosphine to provide compound 60. Compound 60 may undergo an intramolecular cyclization upon heating at elevated temperatures to provide compound 61a, which is a of Formula I-C wherein R⁹ is hydrogen. Compound 61a may be reacted with a reagent having the formula R⁹—X wherein R⁹ is C1-C6 alkyl, hydroxyC1-C6 alkyl- wherein the hydroxy group is protected with a suitable hydroxy protecting group (e.g., tert-butyldimethylsilyl), (C1-C6 alkoxy)C1-C6 alkyl-, C3-C6 cycloalkyl, (C3-C6 cycloalkyl)C1-C6 alkyl-, (hetCyc¹)C1-C6 alkyl-, (Ar¹)C1-C6 alkyl-, or (hetAr¹)C1-C6 alkyl- and X is a leaving group such as a halogen, to provide compound 61b which is a compound of Formula I-C, following removal of protecting groups where applicable, wherein R⁹ is C1-C6 alkyl, hydroxyC1-C6 alkyl-, (C1-C6 alkoxy)C1-C6 alkyl-, C3-C6 cycloalkyl, (C3-C6 cycloalkyl) C1-C6 alkyl-, (hetCyc¹)C1-C6 alkyl-, (Ar¹)C1-C6 alkyl- or (hetAr¹)C1-C6 alkyl-.
Scheme 12
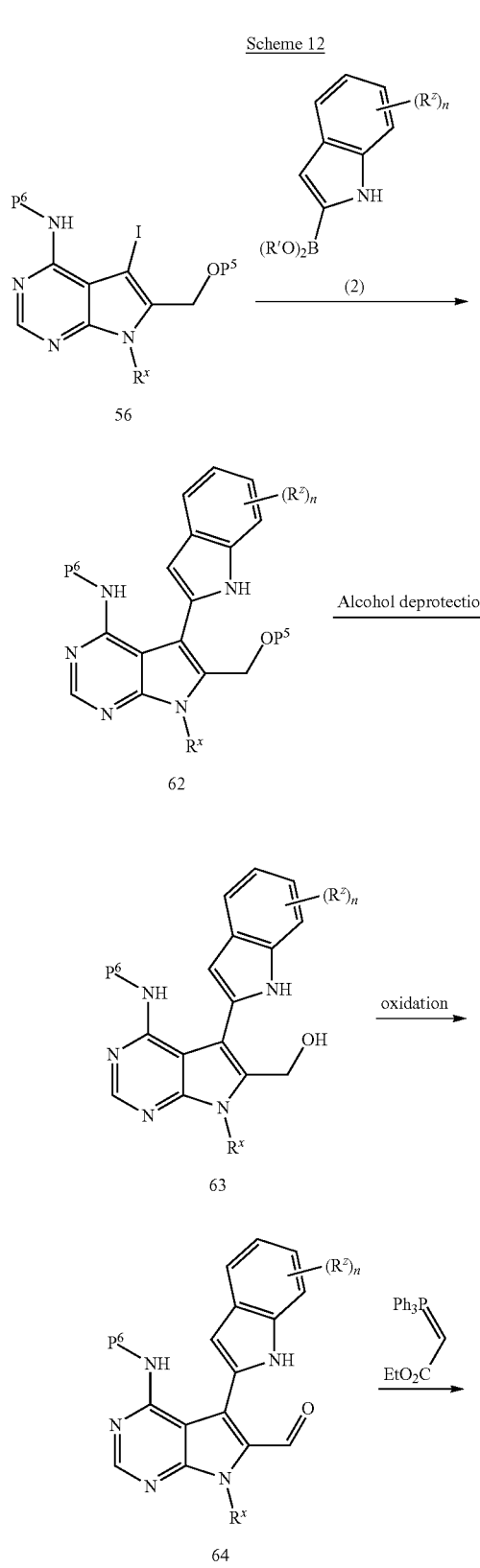
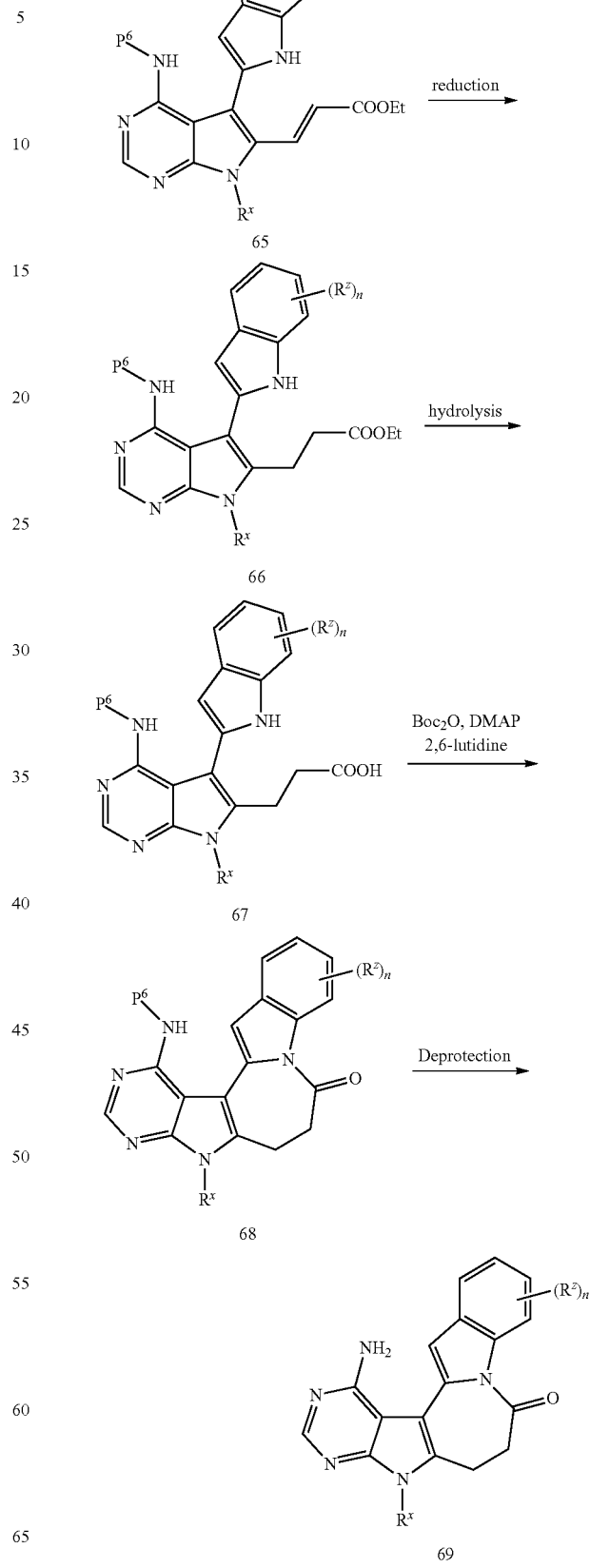

Scheme 12 shows a process for preparing compounds of Formula I-A (i.e., compounds of Formula I wherein W is CR³R⁴, X is CR⁷R⁸, Y is C(=O), Z is N, and ------- is a single bond) wherein R⁷ and R⁸ are hydrogen, R$^x$ is C1-C6 alkyl, fluoroC1-C6 alkyl, Cyc², or Cyc³, and Ring A is

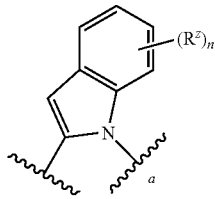

wherein the bond labeled "a" indicates the point of attachment to Y, n is 0, 1, 2, 3 or 4, and each R$^z$ is independently selected from R$^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH— wherein R$^d$ is C1-C6 alkyl, C1-C6 alkoxy, Cyc¹, Cyc¹CH₂—, phenyl or hetAr².

Compound 56 (wherein R$^x$, P⁵ and P⁶ are as defined in Scheme 10), which may be prepared according to Scheme 10, may be reacted with a compound of formula (2) wherein n is 0, 1, 2, 3 or 4, each R$^z$ is independently selected from R$^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH— wherein R$^d$ is C1-C6 alkyl, C1-C6 alkoxy, Cyc¹, Cyc¹CH₂—, phenyl or hetAr², and each R' is independently H or (1-6C)alkyl, or each R' together with the atoms to which they are connected form a 5-6 membered ring optionally substituted with 1-4 substituents selected from (C1-C3 alkyl) using appropriate palladium-catalyzed cross-coupling reaction conditions, e.g., Suzuki coupling reaction conditions, to provide compound 62. The hydroxy protecting group P⁵ may be removed under standard conditions to provide compound 63. The hydroxy group of compound 63 may be oxidized to a carbaldehyde under suitable oxidation conditions (e.g., by treatment with Dess-Martin periodinane), to provide compound 64. Compound 64 may undergo a Wittig olefination upon treatment with ethyl 2-(triphenyl-λ⁵-phosphanylidene)acetate to provide compound 65. The double bond of compound 65 may be reduced under standard conditions (e.g., copper-catalyzed hydrogenation reaction conditions) to provide compound 66. Compound 66 may be converted to compound 67 under standard ester hydrolysis conditions. Compound 67 may undergo an intramolecular cyclization upon treatment with di-tert-butyl dicarbonate (BoC₂O) to provide compound 68. Removal of the amino protecting group P⁶ provides compound 69, which is a compound of Formula I-A.

Scheme 13

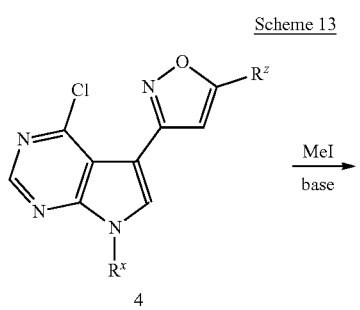

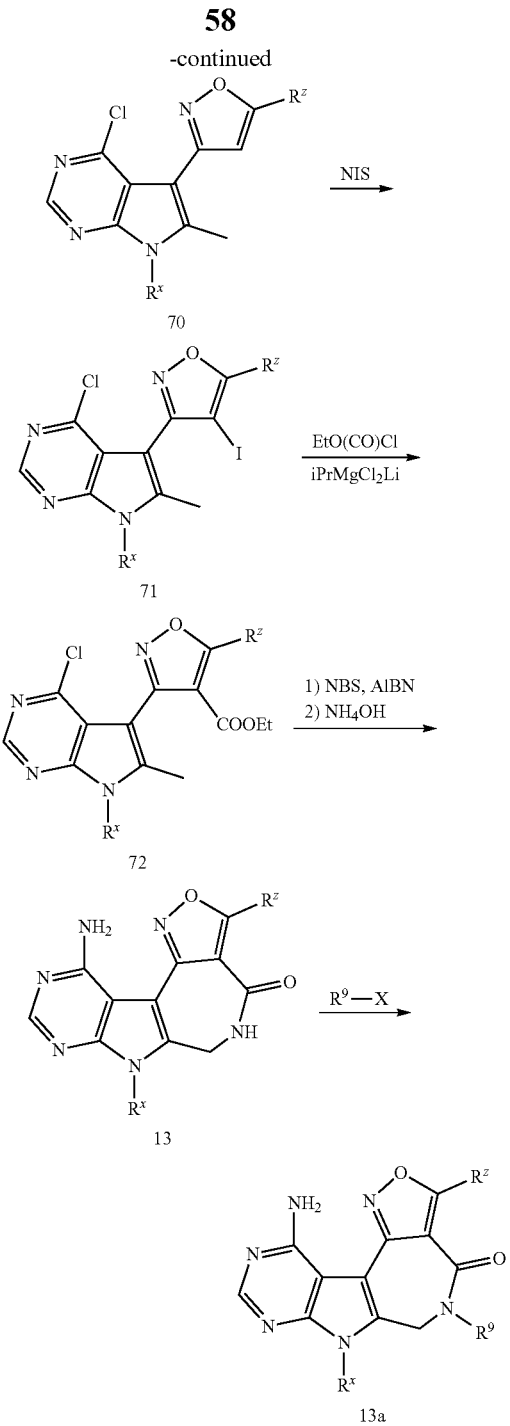

Scheme 13 shows a process for preparing compounds of Formula I-C (i.e., a compound of Formula I wherein W is CR³R⁴, X is NR⁹, Y is C(=O), Z is C, and ------- is a single bond), wherein R⁹ is hydrogen, C1-C6 alkyl, hydroxyC1-C6 alkyl-, (C1-C6 alkyl)SO₂—, (C1-C6 alkoxy)C1-C6 alkyl, C3-C6 cycloalkyl, (C3-C6 cycloalkyl)C1-C6 alkyl-, hetCyc¹, (hetCyc¹)C1-C6 alkyl-, Ar¹, (Ar¹)C1-C6 alkyl-, hetAr¹, (hetAr¹)C1-C6 alkyl-, (C1-C6 alkyl)C(=O)—, (fluoroC1-C6 alkyl)C(=O)—, H₂NC(=O)—, Ar¹CH₂C(=O)— or (C3-C6 cycloalkyl)C(=O)—, R$^x$ is C1-C6 alkyl, fluoroC1-C6 alkyl, Cyc², or Cyc³, and Ring A is

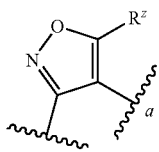

wherein the bond labeled "a" indicates the point of attachment to Y and $R^z$ is C1-C6 alkyl or C3-C6 cycloalkyl.

Compound 4 (wherein $R^x$, $R^z$, and $R^9$ are as defined in Scheme 1), which may be prepared according to Scheme 1, may be methylated upon treatment with methyl iodide in the presence of a strong base such as n-butyl lithium to provide compound 70. Compound 70 may be iodinated upon treatment with N-iodosuccinimide in the presence of a catalytic amount of TFA to provide compound 71. Compound 71 may be converted to compound 72 upon treatment with ethyl chloroformate and isopropylmagnesium(II) lithium chloride. Compound 72 may be treated with N-bromosuccinimide in the presence of AIBN to provide a brominated intermediate (not shown); subsequent treatment with ammonium hydroxide results in an intramolecular cyclization to provide 13, which is a compound Formula I-C wherein $R^9$ is hydrogen. Compound 13 may be reacted with a reagent having the formula $R^9$—X wherein $R^9$ is C1-C6 alkyl, hydroxyC1-C6 alkyl- wherein the hydroxy group is protected with a suitable hydroxy protecting group (e.g., tert-butyldimethylsilyl), (C1-C6 alkyl)SO$_2$—, (C1-C6 alkoxy)C1-C6 alkyl, C3-C6 cycloalkyl, (C3-C6 cycloalkyl)C1-C6 alkyl-, hetCyc$^1$, (hetCyc$^1$)C1-C6 alkyl-, Ar$^1$, (Ar$^1$)C1-C6 alkyl-, hetAr$^1$, (hetAr$^1$)C1-C6 alkyl-, (C1-C6 alkyl)C(=O)—, (fluoroC1-C6 alkyl)C(=O)—, H$_2$NC(=O)—, Ar$^1$CH$_2$C(=O)— or (C3-C6 cycloalkyl)C(=O)— and X is a leaving group such as a halogen, to provide compound 14 which is a compound of Formula I-C wherein $R^9$ is C1-C6 alkyl, hydroxyC1-C6 alkyl-, (C1-C6 alkyl)SO$_2$—, (C1-C6 alkoxy)C1-C6 alkyl, C3-C6 cycloalkyl, (C3-C6 cycloalkyl)C1-C6 alkyl-, hetCyc$^1$, (hetCyc$^1$)C1-C6 alkyl-, Ar$^1$, (Ar$^1$)C1-C6 alkyl-, hetAr$^1$, (hetAr$^1$)C1-C6 alkyl-, (C1-C6 alkyl)C(=O)—, (fluoroC1-C6 alkyl)C(=O)—, H$_2$NC(=O)—, Ar$^1$CH$_2$C(=O)— or (C3-C6 cycloalkyl)C(=O)—, after removal of protecting groups where applicable.

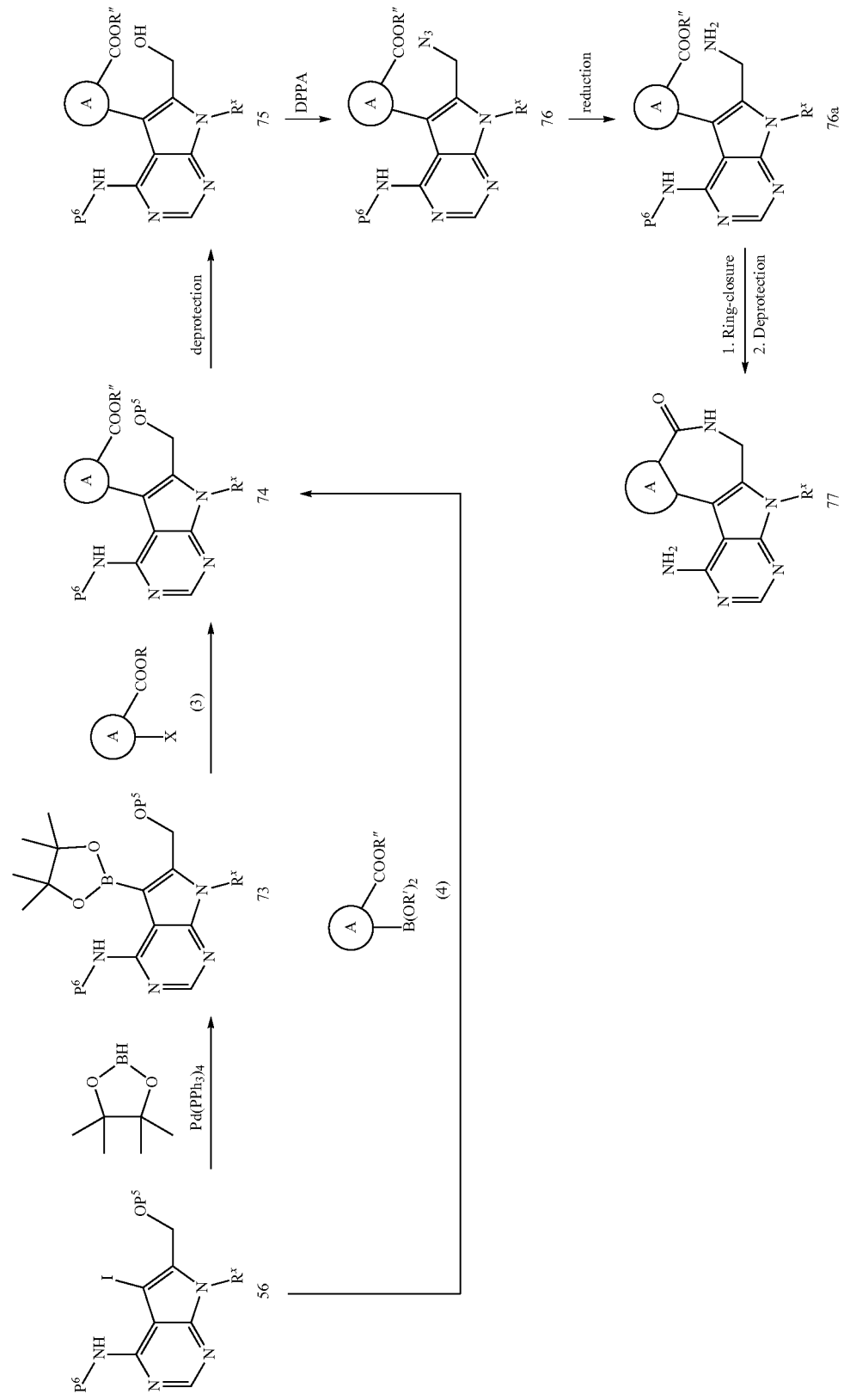

Scheme 14 shows processes for preparing compounds of Formula I-C (i.e., compounds of Formula I wherein W is $CR^3R^4$, X is $NR^9$, Y is $C(=O)$, Z is C, and ------- is a single bond), wherein $R^9$ is hydrogen, $R^x$ is C1-C6 alkyl, fluoroC1-C6 alkyl, $Cyc^2$, or $Cyc^3$, and Ring A are as defined for Formula I.

Compound 56 (wherein $R^x$, $P^5$ and $P^6$ are as defined in Scheme 11), which may be prepared according to Scheme 11, may be reacted with 4,4,5,5-tetramethyl-1,3,2-dioxaborolane in the presence of triphenylphosphine to provide compound 73. Compound 73 may be coupled to a reagent having formula (3) wherein Ring A is as defined for Formula I, X is a leaving group such as halogen, and R is C1-C6 alkyl, using appropriate palladium-catalyzed cross-coupling reaction conditions, e.g., Suzuki coupling reaction conditions, to provide compound 74. Alternatively, compound 74 may be prepared by coupling compound 56 with a boronic acid or boronic ester reagent (4) wherein Ring A is as defined for Formula I, R is C1-C6 alkyl, and each R' is independently H or (1-6C)alkyl, or each R' together with the atoms to which they are connected form a 5-6 membered ring optionally substituted with 1-4 substituents selected from (C1-C3 alkyl), using appropriate palladium-catalyzed cross-coupling reaction conditions, e.g., Suzuki coupling reaction conditions. The hydroxy protecting group of compound 74 may be removed under standard conditions to provide compound 75. The alcohol group of compound 75 may be displaced by an azide group upon treatment with diphenylphosphoryl azide to provide compound 76. The azide group of compound 76 may be reduced upon treatment with triphenylphosphine to provide compound 76a. Reaction of with ammonium hydroxide results an intramolecular cyclization of compound 76a, which after removal of the amino protecting group provides compound 77, which is a compound of Formula I-C wherein $R^9$ is hydrogen.

Scheme 15

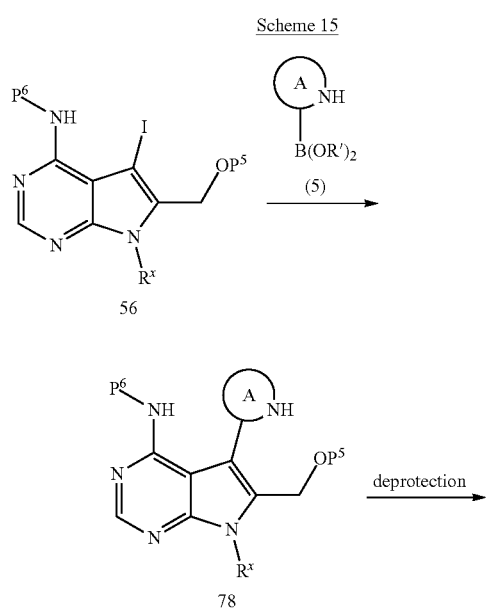

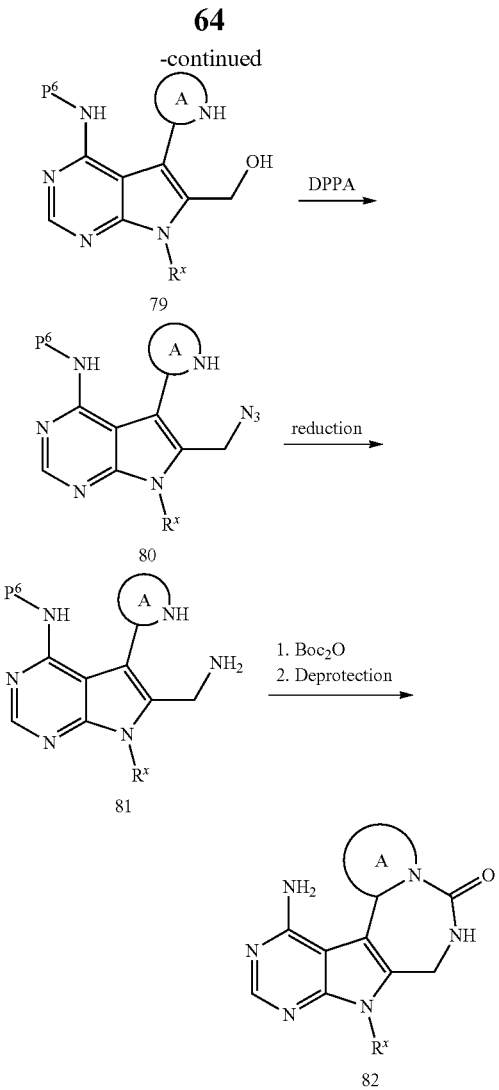

Scheme 15 shows a process for preparing compounds of Formula I-B (i.e., compounds of Formula I wherein W is $CR^3R^4$, X is $NR^9$, Y is $C(=O)$, Z is N, and ------- is a single bond) wherein $R^9$ is hydrogen, $R^x$ is C1-C6 alkyl, fluoroC1-C6 alkyl, $Cyc^2$, or $Cyc^3$, and Ring A is a monocyclic heteroaryl ring or a bicyclic heteroaryl ring as defined for Formula I.

Compound 56 (wherein $R^x$, $P^5$ and $P^6$ are as defined for Scheme 11), which may be prepared according to Scheme 11, may be treated with a boronic ester reagent (5) wherein Ring A is a monocyclic heteroaryl ring or a bicyclic heteroaryl ring as defined for Formula I, and each R' is independently H or (1-6C)alkyl, or each R' together with the atoms to which they are connected form a 5-6 membered ring optionally substituted with 1-4 substituents selected from (C1-C3 alkyl), using appropriate palladium-catalyzed cross-coupling reaction conditions, e.g., Suzuki coupling reaction conditions, to provide compound 78. The hydroxy protecting group $P^5$ of compound 78 may be removed under standard conditions to provide compound 79. The alcohol group of compound 79 may be displaced by an azide group upon treatment with diphenylphosphoryl azide to provide compound 80. The azide group of compound 80 may be reduced upon treatment with triphenylphosphine to provide compound 81. Ring closure may be effected upon treatment of compound 89 with di-tert-butyl dicarbonate in the presence of DMAP, after which removal of the amino protecting group P⁶ provides compound 82, which is a compound of Formula I-B wherein R⁹ is hydrogen.

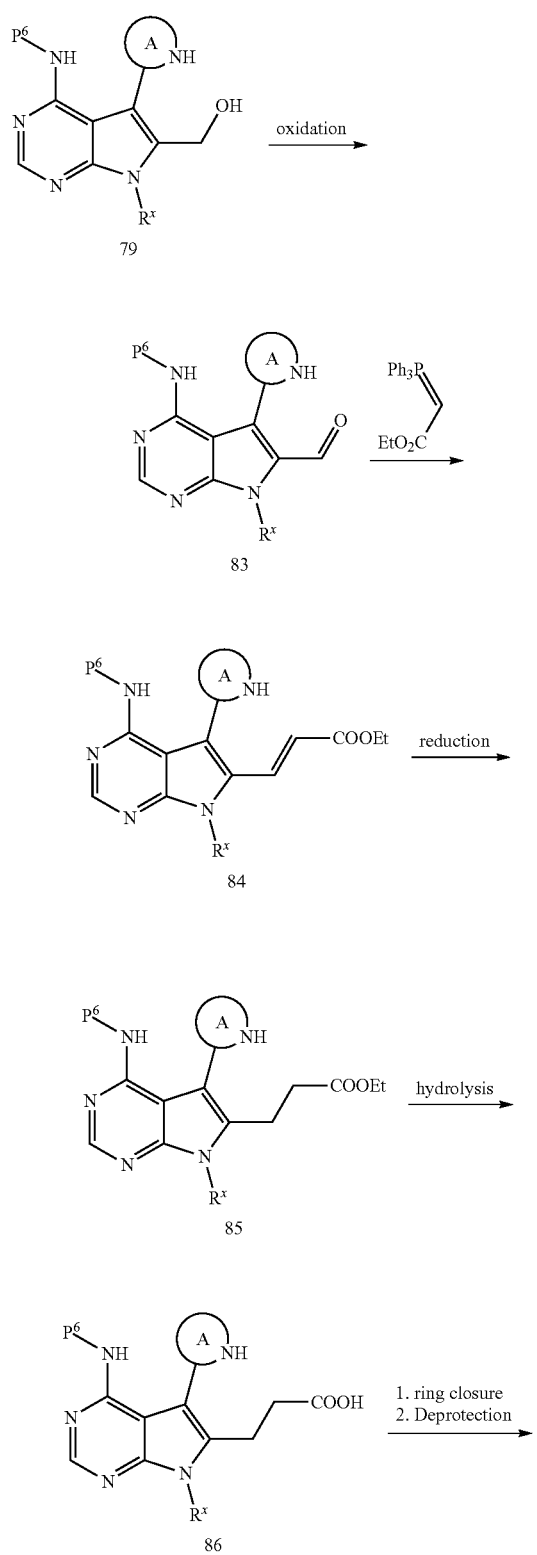

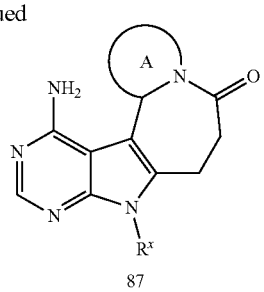

Scheme 16 shows a process for preparing compounds of Formula I-A (i.e., compounds of Formula I wherein W is $CR^3R^4$, X is $CR^7R^8$, Y is C(=O), Z is N, and ------- is a single bond) wherein $R^7$ and $R^8$ are hydrogen, $R^x$ is C1-C6 alkyl, fluoroC1-C6 alkyl, $Cyc^2$, or $Cyc^3$, and Ring A is a monocyclic heteroaryl ring or a bicyclic heteroaryl ring as defined for Formula I.

Compound 79 (wherein Ring A, $R^x$ and $P^6$ are as defined in Scheme 15), which may be prepared according to Scheme 15, may be oxidized to a carbaldehyde under suitable oxidation conditions (e.g., by treatment with Dess-Martin periodinane), to provide compound 83. Compound 83 may undergo a Wittig olefination upon treatment with ethyl 2-(triphenyl-λ⁵-phosphanylidene)acetate to provide compound 84. The double bond of compound 84 may be reduced under standard conditions (e.g., using copper-catalyzed hydrogenation reaction conditions) to provide compound 85. Compound 85 may be converted to compound 86 under standard ester hydrolysis conditions. Compound 86 may undergo an intramolecular cyclization upon treatment with di-tert-butyl dicarbonate to provide compound 87, which is a compound of Formula I-A, after removal of the amino protecting group.

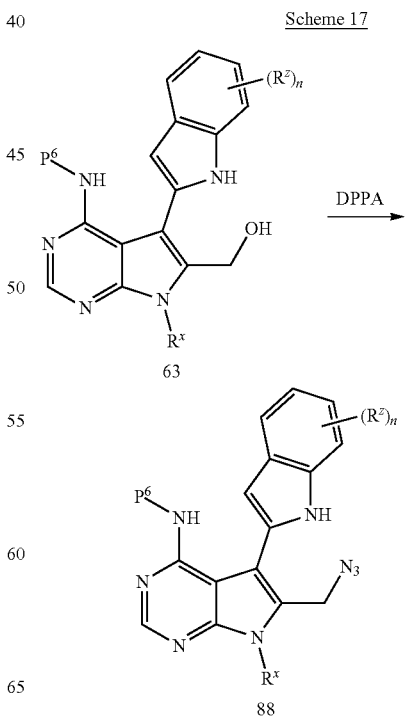

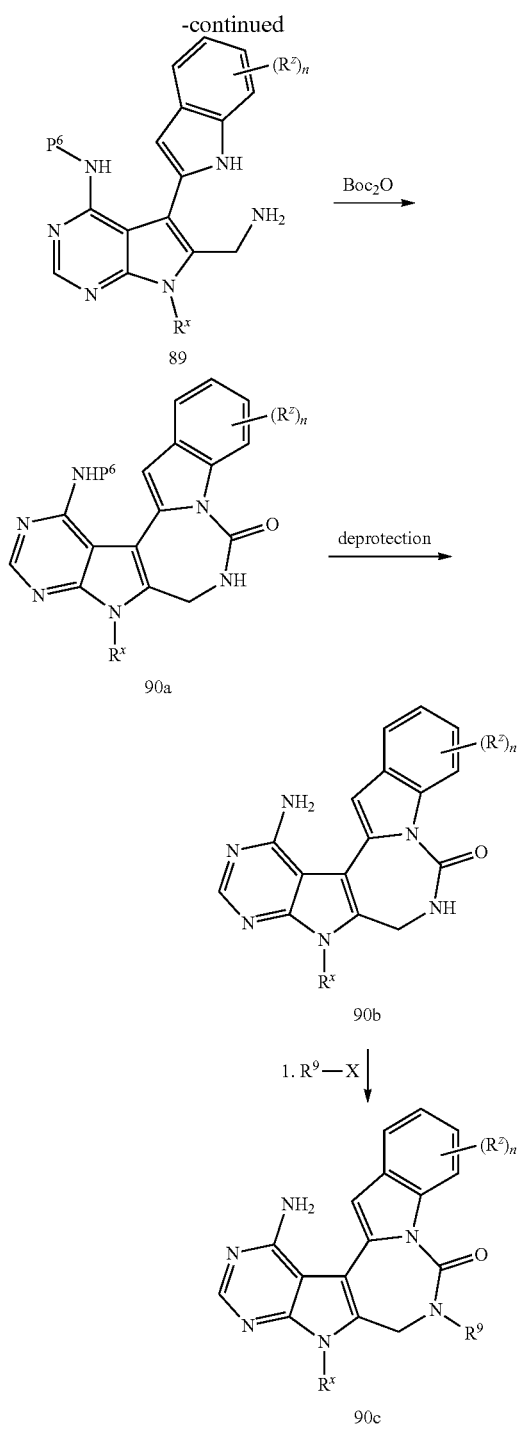

Scheme 17 shows a process for preparing compounds of Formula I-B (i.e., compounds of Formula I wherein W is $CR^3R^4$, X is $NR^9$, Y is C(=O), Z is N, and ------ is a single bond) wherein $R^9$ is hydrogen, C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, hetCyc$^1$, (hetCyc$^1$)C1-C6 alkyl-, (Ar$^1$)C1-C6 alkyl-, or (hetAr$^1$)C1-C6 alkyl-, $R^x$ is C1-C6 alkyl, fluoroC1-C6 alkyl, Cyc$^2$, or Cyc$^3$, and Ring A is

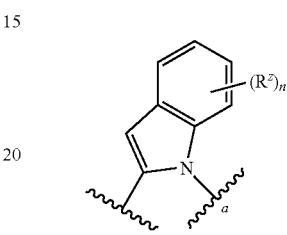

wherein the bond labeled "a" indicates the point of attachment to Y, n is 0, 1, 2, 3 or 4, and each $R^z$ is independently selected from $R^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—.

Compound 63 (wherein $R^x$, $P^6$, $R^z$ and n are as defined for Scheme 12), which may be prepared according to Scheme 12, may be treated with diphenylphosphoryl azide to provide compound 88. The azide group of compound 88 may be reduced upon treatment with triphenylphosphine to provide compound 89. Ring closure may be effected upon treatment of compound 89 with di-tert-butyl dicarbonate in the presence of DMAP to afford 90a, after which removal of the amino protecting group under standard conditions provides compound 90b, which is a compound of Formula I-B wherein $R^9$ is hydrogen. Compound 90a may be treated with a reagent of formula $R^x$—X, wherein X is a leaving atom (e.g., halo) or leaving group (e.g., mesylate); and X is C1-C6 alkyl, to provide compound 90c, which is a compound of Formula I-B wherein $R^9$ is C1-C6 alkyl, after removal of the amino protecting group.

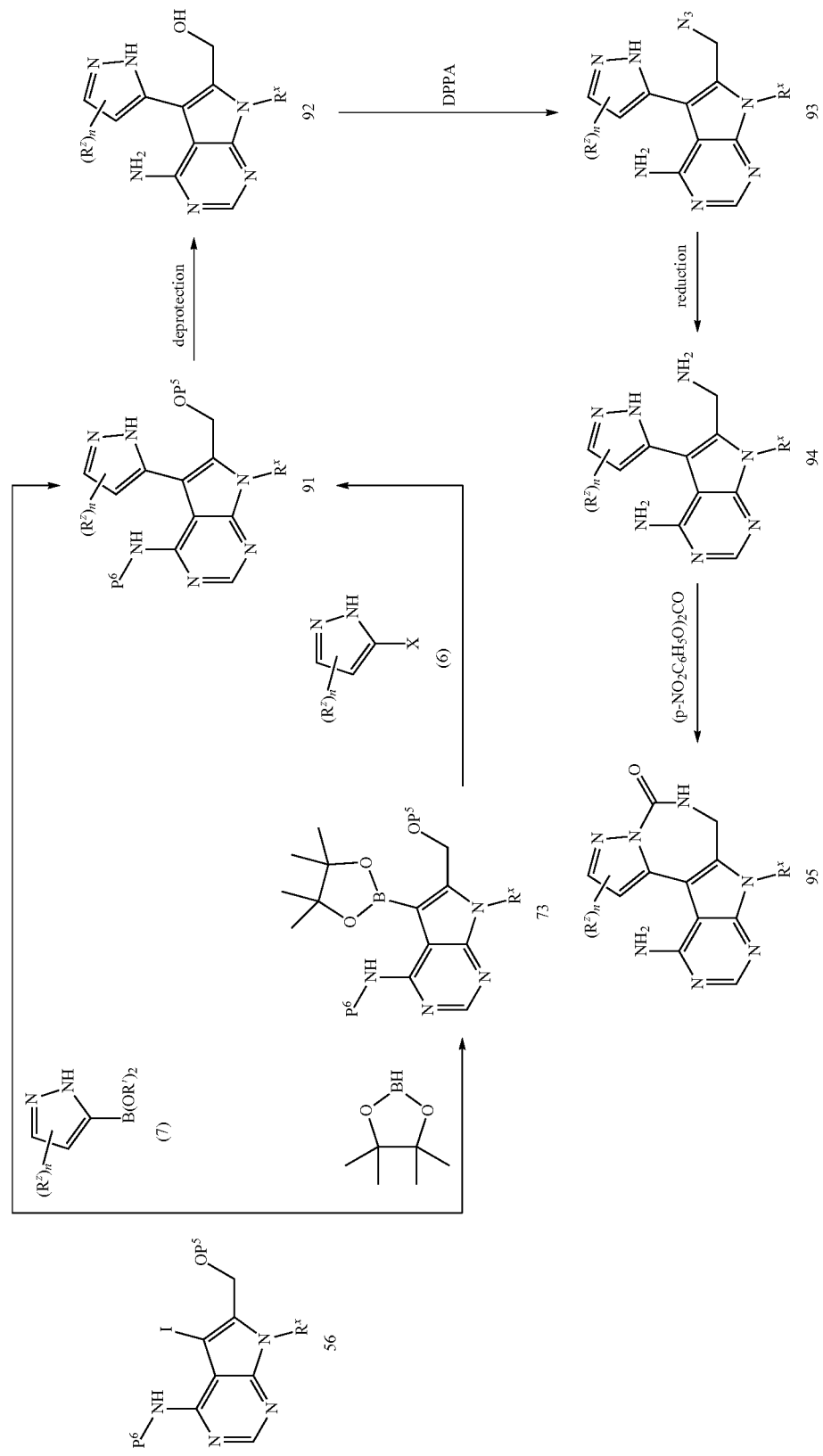

Scheme 18 shows processes for preparing compounds of Formula I-B (i.e., compounds of Formula I wherein W is $CR^3R^4$, X is $NR^9$, Y is $C(=O)$, Z is N, and ------- is a single bond), wherein $R^9$ is hydrogen, $R^x$ is C1-C6 alkyl, fluoroC1-C6 alkyl, $Cyc^2$, or $Cyc^3$, and Ring A is

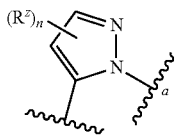

wherein the bond labeled "a" indicates the point of attachment to Y, each $R^z$ is independently selected from C1-C6 alkyl and C3-C6 cycloalkyl, n is 0, 1 or 2, and ring A is further optionally substituted with one occurrence of halo.

Compound 56 (wherein $R^x$, $P^5$, and $P^6$ are as defined for Scheme 12), which may be prepared according to Scheme 12, may be reacted with 4,4,5,5-tetramethyl-1,3,2-dioxaborolane in the presence of triphenylphosphine to provide compound 73. Compound 73 may be coupled with a reagent having formula (6) wherein each $R^z$ is independently selected from halogen, C3-C6 cycloalkyl and C1-C6 alkoxy, and n is 0, 1 or 2, using appropriate palladium-catalyzed cross-coupling reaction conditions, e.g., Suzuki coupling reaction conditions, to provide compound 91. Alternatively, compound 91 may be prepared by coupling compound 56 with a boronic ester reagent (7) wherein each $R^z$ is independently selected from halogen, C1-C6 alkyl, C3-C6 cycloalkyl and C1-C6 alkoxy, n is 0, 1 or 2, and each $R^1$ is independently H or (1-6C)alkyl, or each $R^1$ together with the atoms to which they are connected form a 5-6 membered ring optionally substituted with 1-4 substituents selected from (C1-C3 alkyl), using appropriate palladium-catalyzed cross-coupling reaction conditions, e.g., Suzuki coupling reaction conditions. Compound 91 may be converted to compound 92 using appropriate conditions to remove both the amino protecting group $P^6$ and the hydroxy protecting group $P^5$. The alcohol group of compound 92 may be displaced by an azide group upon treatment with diphenylphosphoryl azide to provide compound 93. The azide group of compound 93 may be reduced upon treatment with triphenylphosphine to provide compound 94. Ring closure may be effected upon treatment of compound 94 with bis(4-nitrophenyl) carbonate to provide compound 96, which is a compound of Formula I-B wherein $R^9$ is hydrogen.

Scheme 19

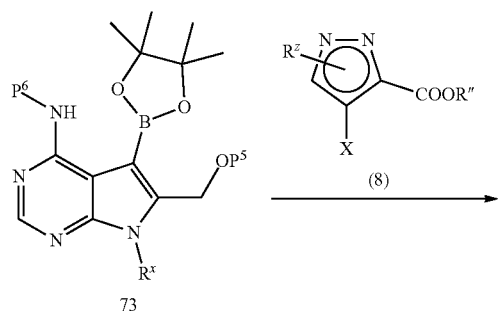

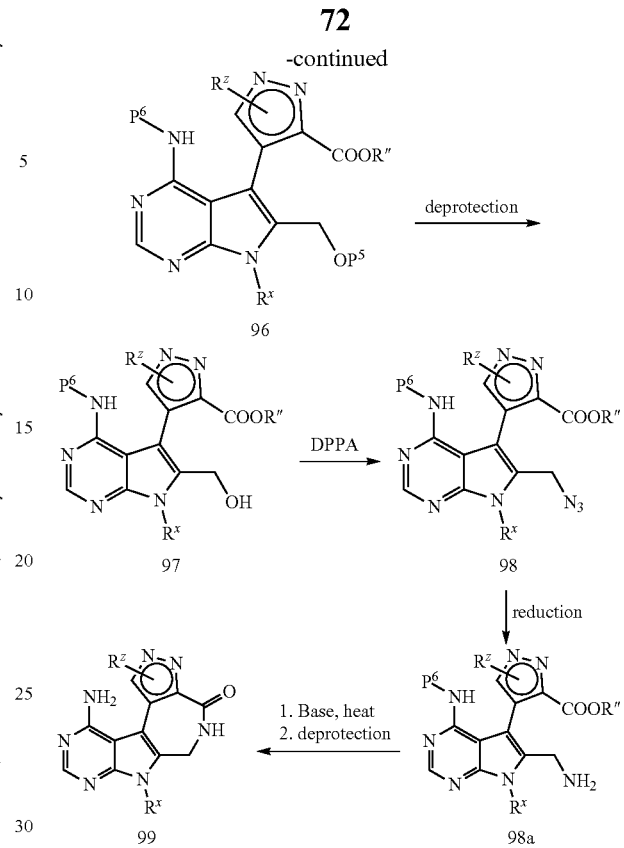

Scheme 19 shows a process for preparing compounds of Formula I-C (i.e., compounds of Formula I wherein W is $CR^3R^4$, X is $NR^9$, Y is $C(=O)$, Z is C, and ------- is a single bond), wherein $R^9$ is hydrogen, $R^x$ is C1-C6 alkyl, fluoroC1-C6 alkyl, $Cyc^2$, or $Cyc^3$, and Ring A is

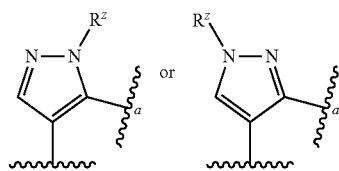

wherein the bond labeled "a" indicates the point of attachment to Y, and $R^z$ is C1-C6 alkyl or C3-C6 cycloalkyl.

Compound 73 (wherein $R^x$, $P^5$ and $P^6$ are as defined for Scheme 18), which may be prepared according to Scheme 18, may be coupled with a reagent having the formula (8) wherein $R^z$ is on one of the ring nitrogen atoms and is selected from C1-C6 alkyl and C3-C6 cycloalkyl and R" is C1-C6 alkyl, using appropriate palladium-catalyzed cross-coupling reaction conditions, e.g., Suzuki coupling reaction conditions, to provide compound 96. The hydroxy protecting group of compound 96 may be removed under standard conditions to provide compound 97. The alcohol group of compound 97 may be displaced by an azide group upon treatment with diphenylphosphoryl azide to provide compound 98. The azide group of compound 98 may be reduced upon treatment with triphenylphosphine to provide compound 98a. Compound 98a can undergo an intramolecular cyclization upon treatment with a base at elevated temperatures, after which removal of the amino protecting group under standard conditions provides compound 99, which is a compound of Formula I-C wherein $R^9$ is hydrogen.

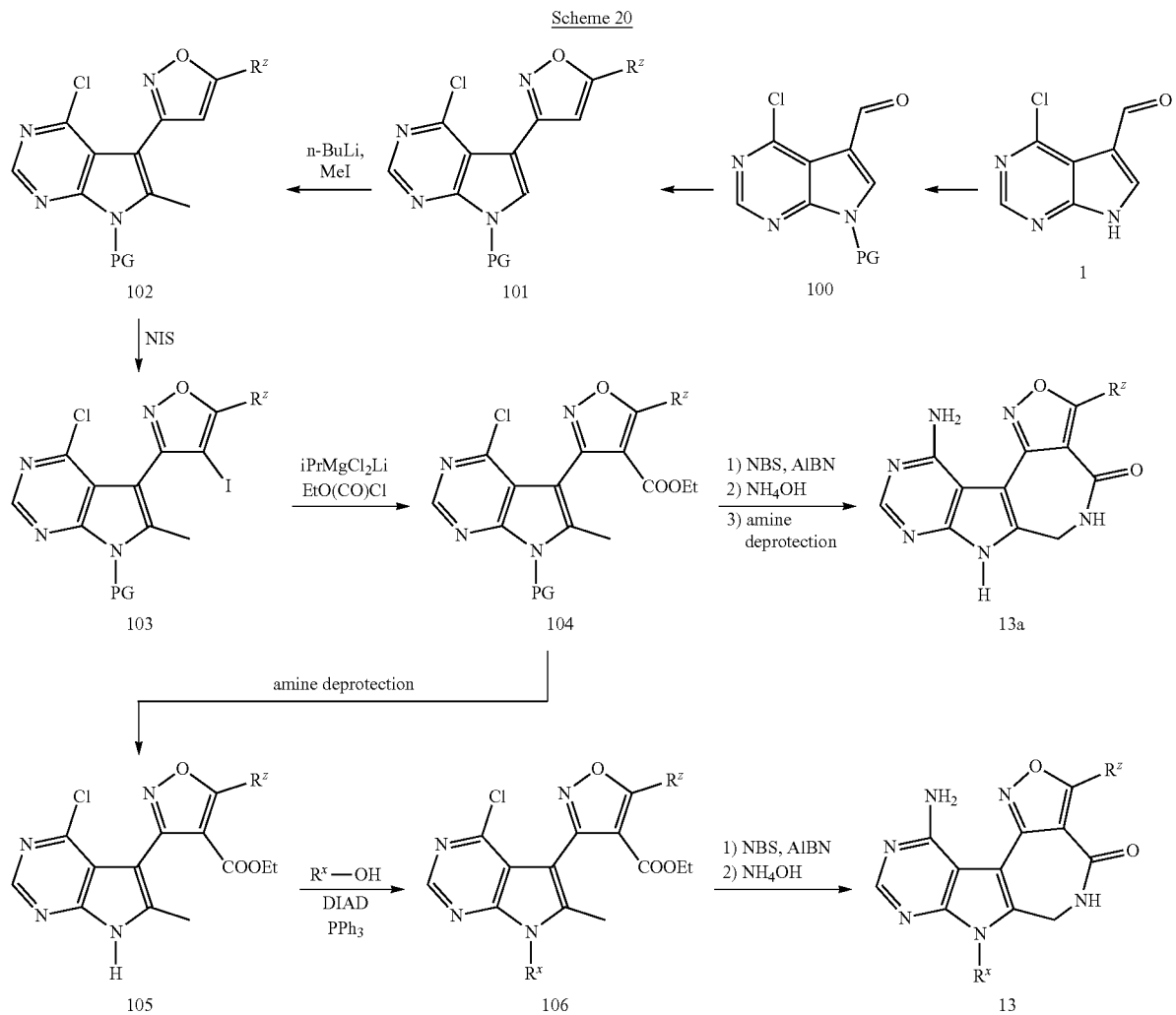

Scheme 20 shows a process for preparing compounds of Formula I-C (i.e., compounds of Formula I wherein W is $CR^3R^4$, X is $NR^9$, Y is C(=O), Z is C, and ------ is a single bond), wherein $R^9$ is hydrogen, $R^x$ is C1-C6 alkyl, fluoroC1-C6 alkyl, $Cyc^2$, or $Cyc^3$, and Ring A is

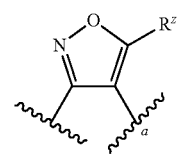

wherein the bond labeled "a" indicates the point of attachment to Y and $R^z$ is C1-C6 alkyl or C3-C6 cycloalkyl.

The ring nitrogen atom of Compound 1, which is commercially available, may be protected by reacting compound 1 with a suitable reagent to provide compound 100 wherein PG is an amino protecting group (e.g., SEM). Compound 100 may be reacted in a similar manner described for the conversion of compound 2 to compound 4 in Scheme 1 to provide compound 101 wherein $R^z$ is C1-C6 alkyl or C3-C6 cycloalkyl. Compound 101 may be methylated upon treatment with methyl iodide in the presence of a strong base such as n-butyl lithium to provide compound 102. Compound 102 may be iodinated upon treatment with N-iodosuccinimide in the presence of a catalytic amount of TFA to provide compound 103. Compound 103 may be converted to compound 104 upon treatment with ethyl chloroformate and isopropylmagnesium(II) lithium chloride. Compound 104 may be treated with N-bromosuccinimide in the presence of AIBN to provide the corresponding methyl bromide intermediate (not shown), followed by treatment with ammonium hydroxide which results in an intramolecular cyclization. Removal of the amino protecting group PG provides compound 13a, which is a compound Formula I-C wherein $R^9$ is hydrogen.

Alternatively, the amino protecting group PG of compound 104 may be removed under standard conditions to provide compound 105. Compound 105 may be reacted with a reagent having the formula $R^x$—OH wherein $R^x$ is C1-C6 alkyl, fluoroC1-C6 alkyl, $Cyc^2$, or $Cyc^3$, using Mitsunobu reaction conditions to provide compound 106. Compound 106 may be cyclized upon treatment with N-bromosuccinimide in the presence of AIBN to provide compound 13.
Scheme 21
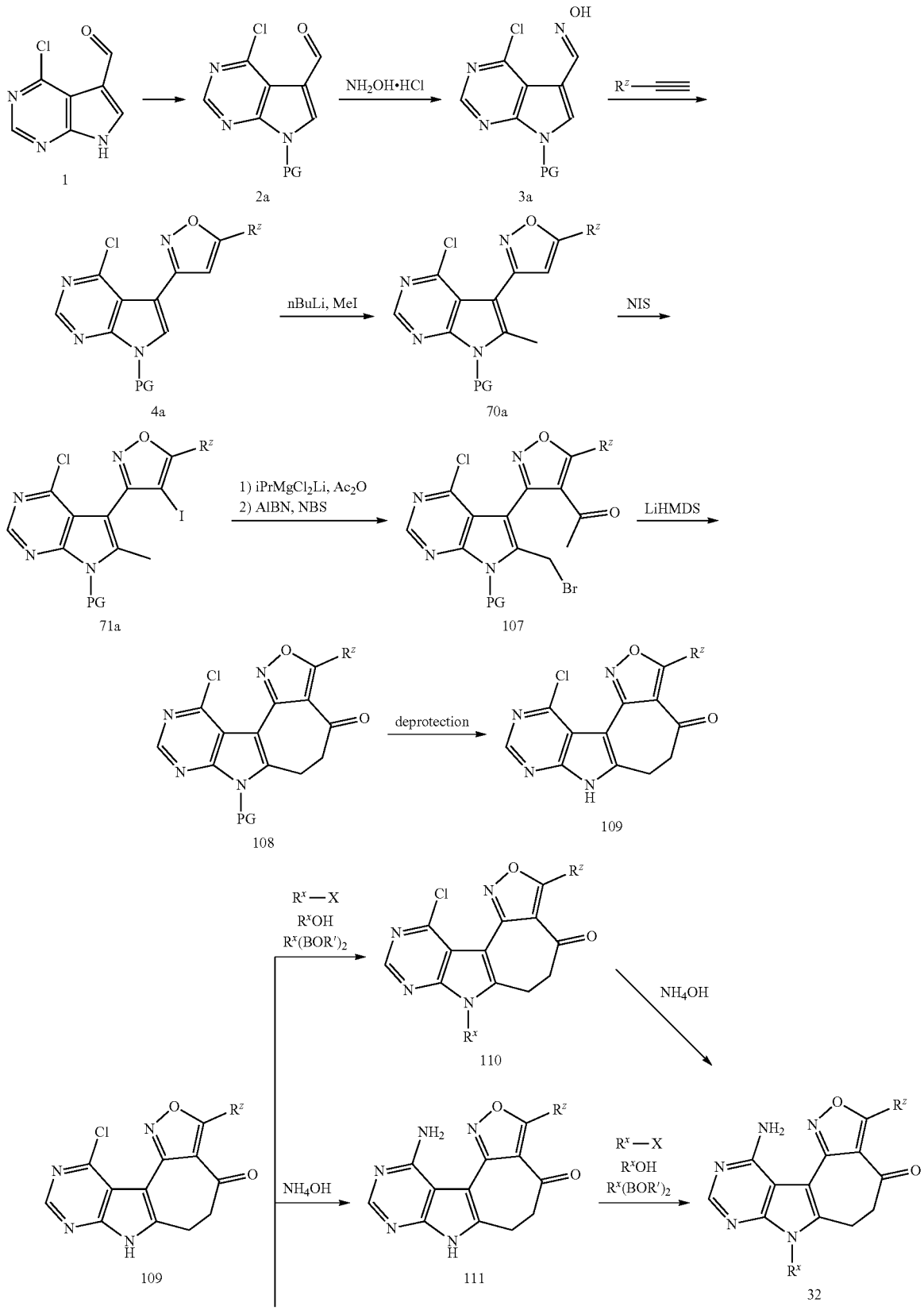

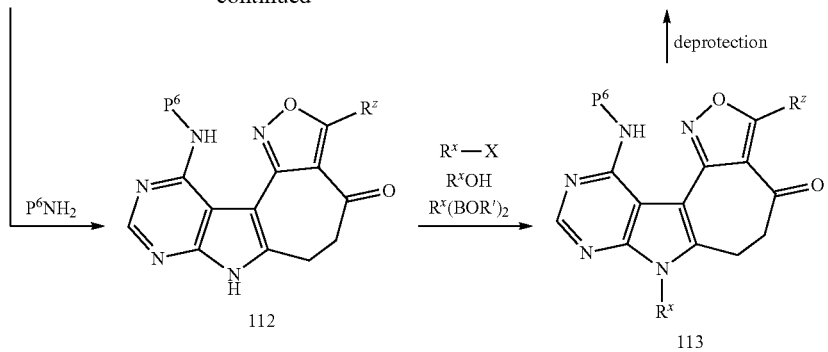

Scheme 21 shows a process for preparing a compound of Formula I-G (i.e., a compound of Formula I wherein W is CR³R⁴, X is CR⁷R⁸, Y is C(=O), Z is C, and ------- is a single bond), wherein R⁷ and R⁸ are hydrogen, R$^x$ is hydrogen, C1-C6 alkyl, fluoroC1-C6 alkyl, Cyc², Cyc³, hetCyc³, Ar³ or hetAr³, and Ring A is

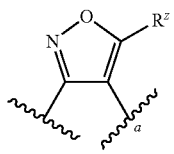

wherein the bond labeled "a" indicates the point of attachment to Y, and R$^z$ is C1-C6 alkyl or C3-C6 cycloalkyl.

Compound 1, which is commercially available, may be reacted with a reagent having the formula PG-X wherein PG is a suitable amino protecting group (e.g., SEM), and X is a leaving group (e.g., halo, e.g., Cl) to provide compound 2a. Compound 2a may be reacted with hydroxylamine hydrochloride to provide oxime compound 3a. The oxime moiety of compound 3a may undergo cycloaddition to form an isoxazole ring upon treatment with a compound having the formula HC≡C—R$^z$ wherein R$^z$ is C1-C6 alkyl or C3-C6 cycloalkyl to provide compound 4a. Compound 4a may be treated with n-butyl lithium and methyl iodide to provide the methyl-substituted compound 70a. The isoxazole ring of compound 70a may be iodinated upon treatment with N-iodosuccinimide in the presence of a catalytic amount of TFA to provide compound 71a. The iodo group in compound 71a may undergo metal halogen exchange with an organometallic reagent (e.g., iPrMgCl₂Li) followed by trapping with acetic anhydride to provide an acetyl substituted intermediate (not shown), whereupon treatment of this intermediate with N-bromosuccinimide and AIBN under radical bromination conditions can afford compound 107. Treatment of compound 107 with a strong non-nucleophilic base such as LHMDS (lithium hexamethyldisilazide) allows an intramolecular cyclization, thereby affording compound 108. Removal of the protecting group on 108 provides compound 109. Compound 109 may be treated with a reagent of formula R$^x$—X wherein X is a leaving group such as halogen, a reagent of formula R$^x$—OH, or a reagent with formula R$^x$B(OR')₂ wherein each R' is independently H or (1-6C)alkyl, or each R¹ together with the atoms to which they are connected form a 5-6 membered ring optionally substituted with 1-4 substituents selected from (C1-C3 alkyl) to provide compound 110, wherein in each of R$^x$—X and R$^x$B(OR')₂, R$^x$ is C1-C6 alkyl, fluoroC1-C6 alkyl, Cyc², Cyc³, hetCyc³, Ar³ or hetAr³; and in R$^x$—OH, R$^x$ is C1-C6 alkyl, fluoroC1-C6 alkyl, Cyc², Cyc³, or hetCyc³. As non-limiting examples of the foregoing, compound 109 may be reacted with R$^x$—X under transition-metal (e.g., palladium or copper) catalyzed cross-coupling conditions or under nucleophilic substitution conditions (e.g., base and/or heat); compound 109 may be reacted with R$^x$B(OR')₂ under transition-metal (e.g., copper) catalyzed cross-coupling conditions; and compound 109 may be reacted with R$^x$—OH under Mitsunobu conditions. The chloro group in 110 may be displaced with ammonium hydroxide to provide compound 32, which is a compound of Formula I-G, wherein R$^x$ is C1-C6 alkyl, fluoroC1-C6 alkyl, Cyc², Cyc³, hetCyc³, Ar³ or hetAr³, and R$^z$ is C1-C6 alkyl or C3-C6 cycloalkyl.

Alternatively, compound 109 may be reacted with ammonium hydroxide to provide compound 111, which is a compound of Formula I-G wherein R$^x$ is hydrogen, and R$^z$ is C1-C6 alkyl or C3-C6 cycloalkyl. Compound 111 may be treated with a reagent of formula R$^x$—X wherein X is a leaving group such as halogen, a reagent of formula R$^x$—OH, or a reagent with formula R$^x$B(OR')₂ wherein each R¹ is independently H or (1-6C)alkyl, or each R¹ together with the atoms to which they are connected form a 5-6 membered ring optionally substituted with 1-4 substituents selected from (C1-C3 alkyl) to provide compound 32, which is a compound of Formula I-G, wherein R$^x$ is C1-C6 alkyl, fluoroC1-C6 alkyl, Cyc², Cyc³, hetCyc³, Ar3 or hetAr3, and R$^z$ is C1-C6 alkyl or C3-C6 cycloalkyl. In each of R$^x$—X and R$^x$B(OR')₂, R$^x$ is C1-C6 alkyl, fluoroC1-C6 alkyl, Cyc², Cyc³, hetCyc³, Ar³ or hetAr³; and in R$^x$—OH, R$^x$ is C1-C6 alkyl, fluoroC1-C6 alkyl, Cyc², Cyc³, or hetCyc³. As non-limiting examples of the foregoing, compound 111 may be reacted with R$^x$—X under transition-metal (e.g., palladium or copper) catalyzed cross-coupling conditions or nucleophilic substitution conditions (e.g., base and/or heat); compound 111 may be reacted with R$^x$B(OR')₂ under transition-metal (e.g., copper) catalyzed cross-coupling conditions; and compound 111 may be reacted with R$^x$—OH under Mitsunobu conditions.

As another alternative, compound 109 may be reacted with a reagent of formula P⁶—NH₂ wherein P⁶ is a suitable amino protecting group (e.g., a benzyl group, e.g., 2,4-dimethoxybenzyl, DMB) to provide compound 112. Compound 112 may be treated with a reagent of formula R$^x$—X wherein X is a leaving group such as halogen, a reagent of formula R$^x$—OH, or a reagent with formula R$^x$B(OR')₂ wherein each R¹ is independently H or (1-6C)alkyl, or each R¹ together with the atoms to which they are connected form a 5-6 membered ring optionally substituted with 1-4 substituents selected from (C1-C3 alkyl) to provide compound 113, wherein in each of $R^x$—X, and $R^xB(OR')_2$, $R^x$ is C1-C6 alkyl, fluoroC1-C6 alkyl, $Cyc^2$, $Cyc^3$, $hetCyc^3$, $Ar^3$ or $hetAr^3$; and in $R^x$—OH, $R^x$ is C1-C6 alkyl, fluoroC1-C6 alkyl, $Cyc^2$, $Cyc^3$, or $hetCyc^3$. As non-limiting examples of the foregoing, compound 112 may be reacted with $R^x$—X under transition-metal (e.g., palladium or copper) catalyzed cross-coupling conditions or nucleophilic substitution conditions (e.g., base and/or heat); compound 112 may be reacted with $R^xB(OR')_2$ under transition-metal (e.g., copper) catalyzed cross-coupling conditions; and compound 112 may be reacted with $R^x$—OH under Mitsunobu conditions. Removal of the amino protecting group on compound 113 affords compound 32, which is a compound of Formula I-G, wherein $R^x$ is C1-C6 alkyl, fluoroC1-C6 alkyl, $Cyc^2$, $Cyc^3$, $hetCyc^3$, $Ar^3$ or $hetAr^3$, and $R^z$ is C1-C6 alkyl or C3-C6 cycloalkyl.

Scheme 22

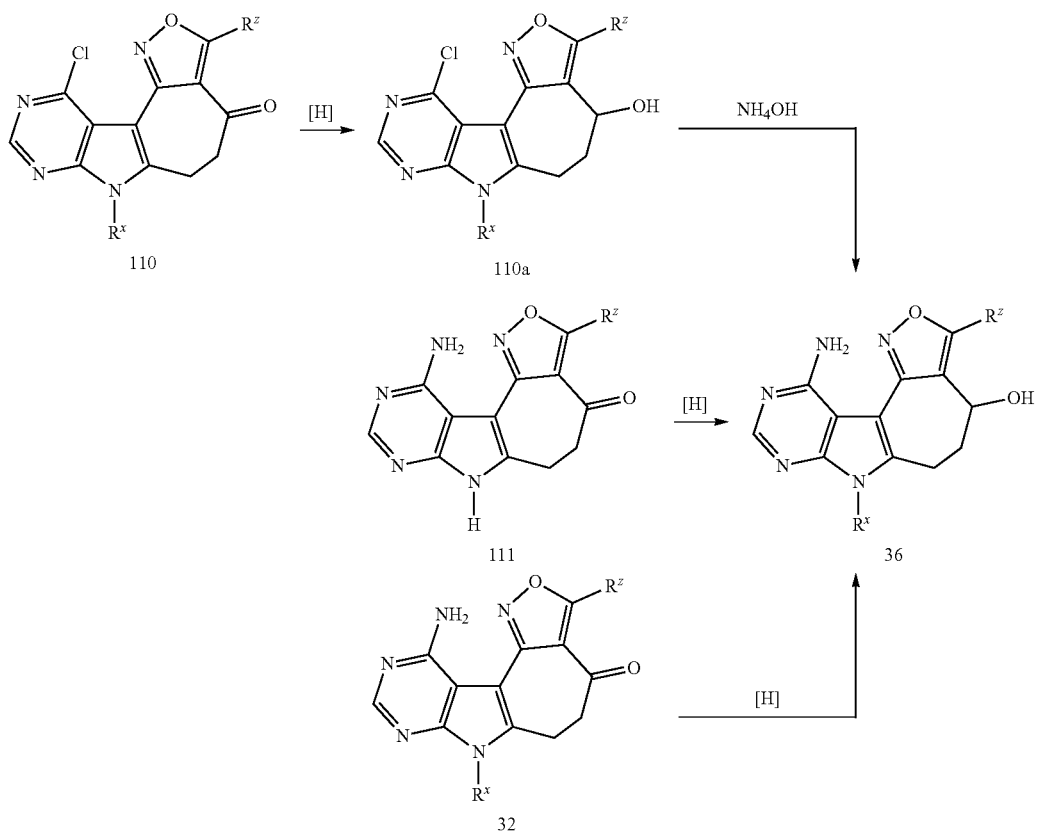

Scheme 22 shows a process for preparing a compound of Formula I-H (i.e., a compound of Formula I wherein W is $CR^3R^4$, X is $CR^7R^8$, Y is $CR^{10}R^{11}$, Z is C, and ------- is a single bond), wherein $R^7$ and $R^8$ are hydrogen, $R^x$ is hydrogen, C1-C6 alkyl, fluoroC1-C6 alkyl, $Cyc^2$, $Cyc^3$, $hetCyc^3$, $Ar^3$ or $hetAr^3$, $R^{10}$ and $R^{11}$ are as defined below for Scheme 22, and Ring A is

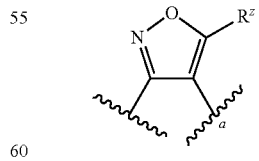

wherein the bond labeled "a" indicates the point of attachment to Y, and $R^z$ is C1-C6 alkyl or C3-C6 cycloalkyl.

Ketone-containing compound 110 (wherein $R^x$ and $R^z$ are as defined for Scheme 21), which may be prepared according Scheme 21, may be reduced under standard conditions to provide compound 110a, which may be reacted with ammonium hydroxide to afford compound 36, which is a compound of Formula I-H, wherein $R^x$ is C1-C6 alkyl, fluoroC1-C6 alkyl, $Cyc^2$, $Cyc^3$, $hetCyc^3$, $Ar^3$ or $hetAr^3$, $R^z$ is C1-C6 alkyl or C3-C6 cycloalkyl, $R^{10}$ is hydroxyl, and $R^{11}$ is hydrogen.

Alternatively, compound 32 (wherein $R^x$ and $R^z$ are as defined for Scheme 21), which may be prepared according to Scheme 21, may be subjected under ketone reduction conditions (e.g., with sodium borohydride) to provide compound 36 which is a compound of Formula I-H, wherein $R^x$ is C1-C6 alkyl, fluoroC1-C6 alkyl, $Cyc^2$, $Cyc^3$, $hetCyc^3$, $Ar^3$ or $hetAr^3$, $R^z$ is C1-C6 alkyl or C3-C6 cycloalkyl, $R^{10}$ is hydroxyl, and $R^{11}$ is hydrogen.

Alternatively, compound 111 (wherein $R^z$ is as defined for Scheme 21), which may be prepared according to Scheme 21, may be subjected under ketone reduction conditions (e.g., with sodium borohydride) to provide compound 36 which is a compound of Formula I-H, wherein $R^x$ is hydrogen, $R^{10}$ is hydroxyl, and $R^{11}$ is hydrogen.

Scheme 23

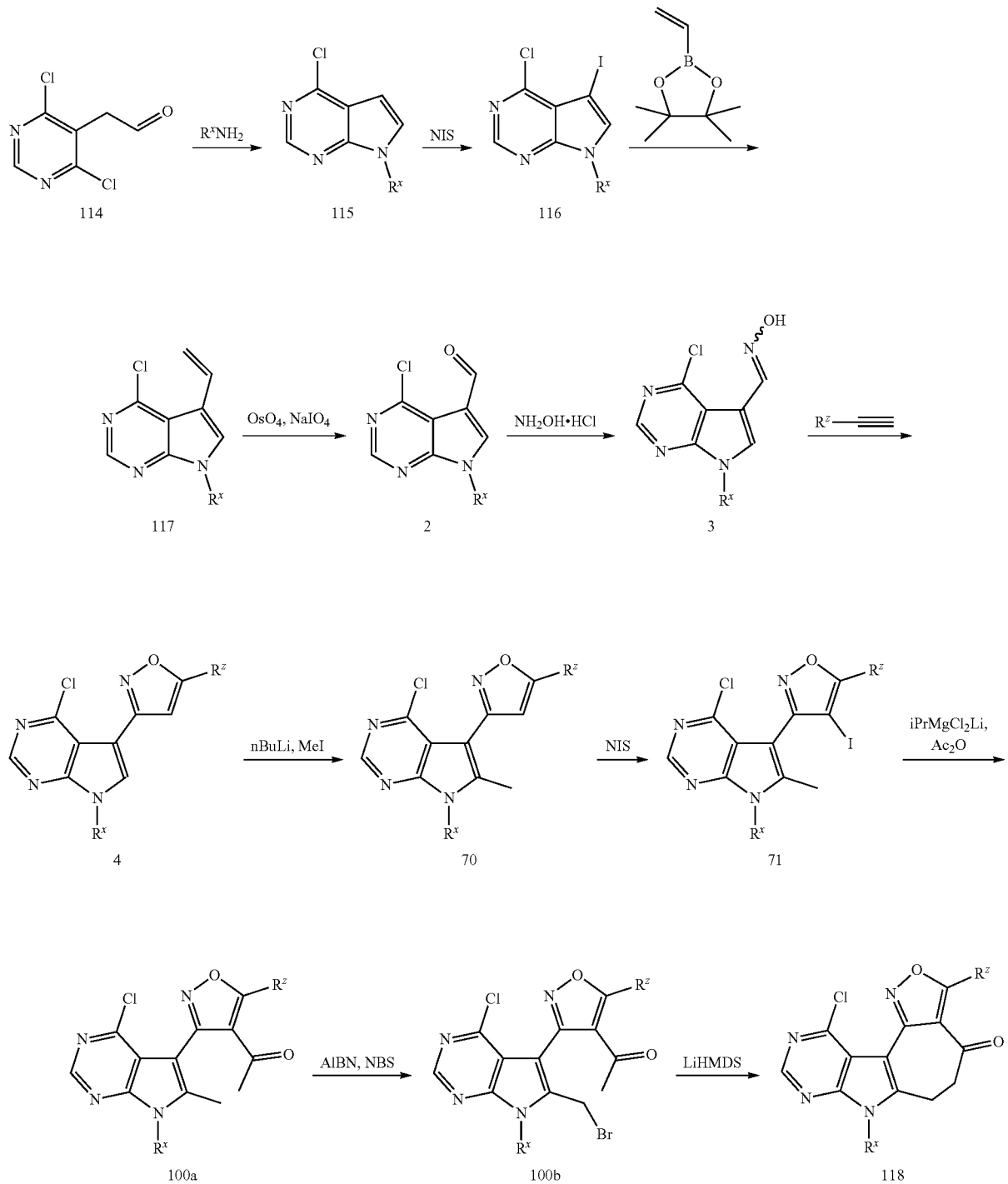

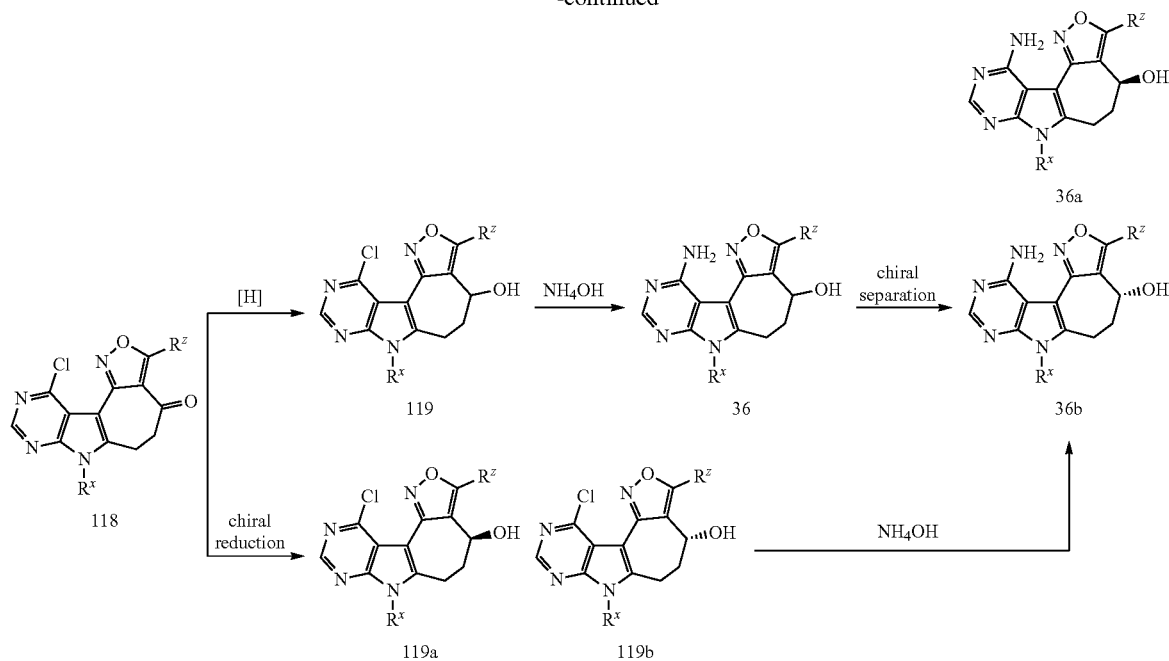

Scheme 23 shows a process for preparing a compound of Formula I-H (i.e., a compound of Formula I wherein W is $CR^3R^4$, X is $CR^7R^8$, Y is $CR^{10}R^{11}$, Z is C, and ------- is a single bond), wherein $R^7$ and $R^8$ are hydrogen, $R^x$ is C1-C6 alkyl, fluoroC1-C6 alkyl, $Cyc^2$, $Cyc^3$, $hetCyc^3$, $Ar^3$ or $hetAr^3$, $R^{10}$ and $R^{11}$ are as defined below for Scheme 23, and Ring A is

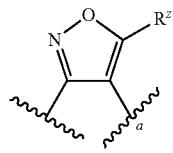

wherein the bond labeled "a" indicates the point of attachment to Y, and $R^z$ is C1-C6 alkyl or C3-C6 cycloalkyl.

Compound 114 may be treated with a reagent of formula $R^xNH_2$ wherein $R^x$ is C1-C6 alkyl, fluoroC1-C6 alkyl, $Cyc^2$, $Cyc^3$, $hetCyc^3$, $Ar^3$ or $hetAr^3$ to provide compound 115. Iodination of compound 115 (e.g., with N-iodosuccinimide, NIS) can afford compound 116, whereupon treatment of 116 with 4,4,5,5-tetramethyl-2-vinyl-1,3,2-dioxaborolane e.g., under palladium catalyzed cross-coupling (e.g., Suzuki coupling) conditions can provide compound 117. Oxidative cleavage of the olefin moiety in 117 allows the formation of aldehyde compound 2 which can react with hydroxylamine hydrochloride to provide oxime compound 3. Compound 3 may undergo cycloaddition with a reagent of formula

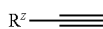

wherein $R^z$ is C1-C6 alkyl or C3-C6 cycloalkyl to provide compound 4. Exposure of compound 4 to the presence of a strong base (e.g., n-butyl lithium) and iodomethane can lead to compound 70 which can be iodinated at the isoxazole (e.g., with NIS) to afford compound 71. Compound 71 can undergo metal-halogen exchange with an organometallic reagent (e.g., $iPrMgCl_2Li$, $Ac_2O$) wherein trapping with acetic anhydride can provide compound 100a. Compound 100a may be treated with N-bromosuccinimide (NBS) and AIBN to afford bromination product 100b. Treatment of 100b with a strong non-nucleophilic base e.g., LHMDS (lithium hexamethyldisilazide) can provide compound 118. The ketone moiety in compound 118 may be reduced under standard conditions (e.g., with sodium borohydride) to provide compound 119, whereupon treatment with ammonium hydroxide can displace the chloro group to afford compound 36 which is a compound of Formula I-H wherein $R^x$ is C1-C6 alkyl, fluoroC1-C6 alkyl, $Cyc^2$, $Cyc^3$, $hetCyc^3$, $Ar^3$ or $hetAr^3$; $R^z$ is C1-C6 alkyl or C3-C6 cycloalkyl; $R^{10}$ is OH; and $R^{11}$ is hydrogen. Compound 36 may be subjected to chiral resolution to provide enantiomerically enriched compounds 36a and 36b both of which are compounds of Formula I-H wherein $R^x$, $R^z$, $R^{10}$, and $R^{11}$ are as defined for compound 36. Alternatively, compound 118 can be subjected to chiral reduction conditions to afford compound 119a or 119b selectively. The chloro group in compound 119a or 119b can be displaced with ammonium hydroxide to provide compound 36a and 36b, wherein $R^x$ is C1-C6 alkyl, fluoroC1-C6 alkyl, $Cyc^2$, $Cyc^3$, $hetCyc^3$, $Ar^3$ or $hetAr^3$; $R^z$ is C1-C6 alkyl or C3-C6 cycloalkyl; $R^{10}$ is OH; and $R^{11}$ is hydrogen.

Scheme 24

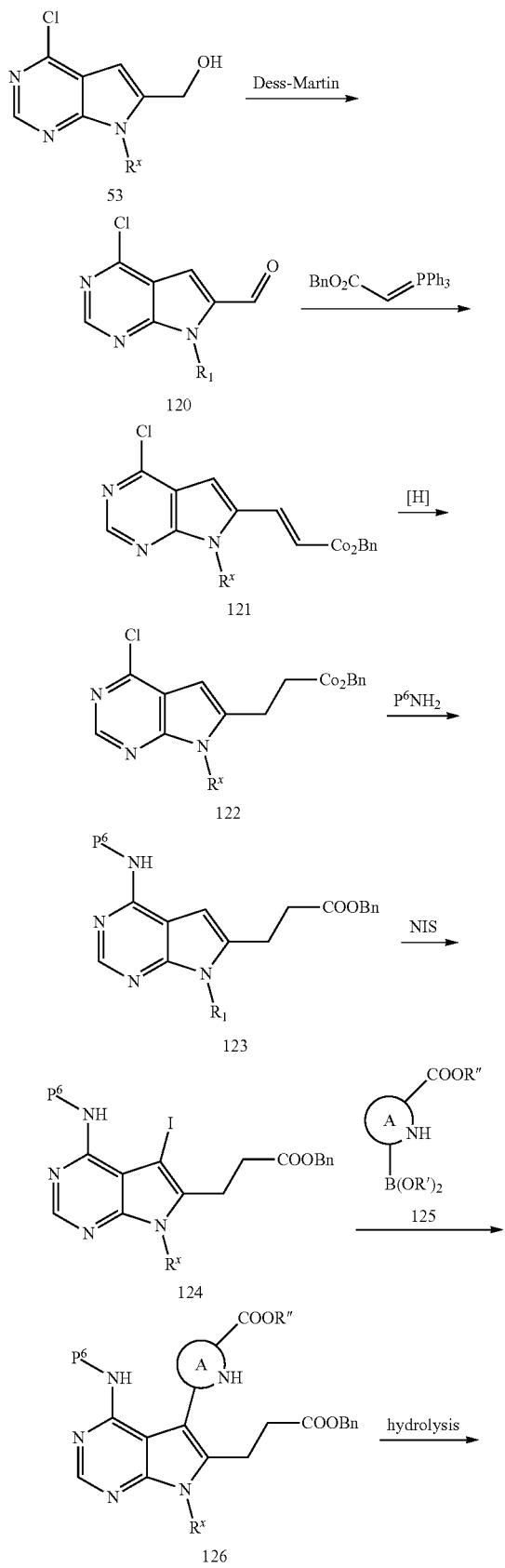

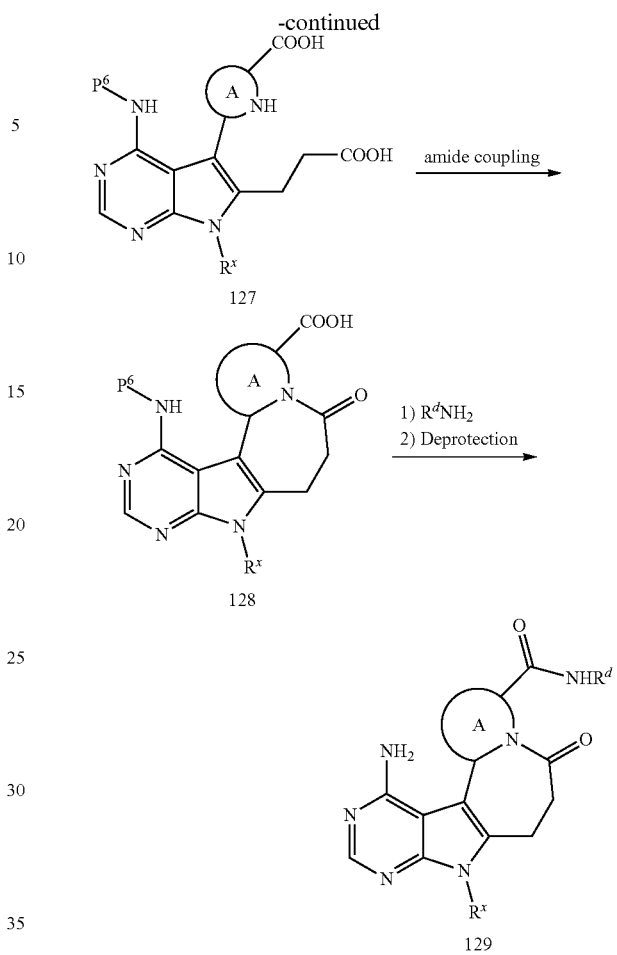

Scheme 24 shows a process for preparing a compound of Formula I-A (i.e., compounds of Formula I wherein W is $CR^3R^4$, X is $CR^7R^8$, Y is C(=O), Z is N, and ------- is a single bond) wherein $R^7$ and $R^8$ are hydrogen, $R^x$ is C1-C6 alkyl, fluoroC1-C6 alkyl, $Cyc^2$, or $Cyc^3$, and Ring A is as defined for Formula I, wherein ring A is substituted with $R^dNHC(=O)$—; and $R^d$ is C1-C6 alkyl, C1-C6 alkoxy, $Cyc^1$, $Cyc^1CH_2$—, phenyl or $hetAr^2$.

Compound 53 (wherein $R^x$ is as defined in Scheme 11) which may be prepared according to Scheme 11 may be subjected under alcohol oxidation conditions (e.g., in the presence of Dess-Martin periodinane) to afford aldehyde 120. Compound 120 can be subjected under Wittig olefination conditions (e.g., with benzyl 2-(triphenyl-λ5-phosphanylidene)acetate) to provide compound 121, whereupon reduction of the olefin in 121 can afford compound 122. The chloro group in 122 can be displaced with a nucleophile of formula $P^6$—$NH_2$ wherein $P^6$ is an amino protecting group (e.g., benzyl, e.g., 2,4-dimethoxybenzyl, DMB) to provide compound 123. Iodination of compound 123 (e.g., with N-iodosuccinimide) can lead to compound 124. Compound 124 can be coupled with boronic acid or boronic ester 125 under appropriate palladium-catalyzed cross coupling conditions (e.g., Suzuki coupling) to provide compound 126. In compound 125, each R' is independently H or (1-6C)alkyl, or each R' together with the atoms to which they are connected form a 5-6 membered ring optionally substituted with 1-4 substituents selected from (C1-C3 alkyl); and R" is C1-C6 alkyl. Hydrolysis of the ester groups in 126 provides dicarboxylic acid compound 127 whereupon treatment of 127 under standard amide coupling conditions allows intramolecular cyclization to provide compound 128. Compound 128 may be coupled with a reagent of formula $R^d$—$NH_2$ wherein $R^d$ is C1-C6 alkyl, C1-C6 alkoxy, $Cyc^1$, $Cyc^1CH_2$—, phenyl or $hetAr^2$ under standard amide coupling conditions. Subsequent removal of the amino protecting group (e.g., with TFA) provides compound 129 which is a compound of Formula I-A, wherein $R^x$ is C1-C6 alkyl, fluoroC1-C6 alkyl, $Cyc^2$, or $Cyc^3$; ring A is substituted with $R^dNHC(=O)$, and $R^d$ is C1-C6 alkyl, C1-C6 alkoxy, $Cyc^1$, $Cyc^1CH_2$—, phenyl or $hetAr^2$.

Scheme 25

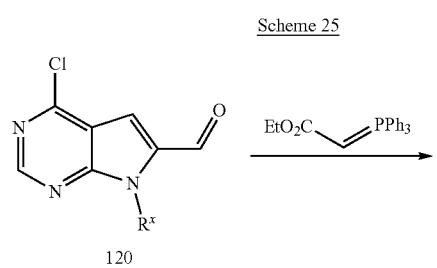
120

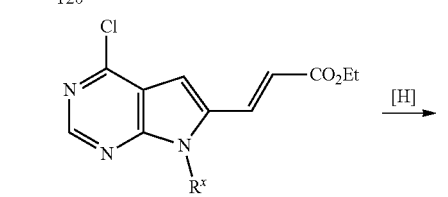
130

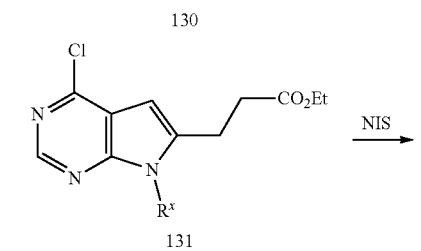
131

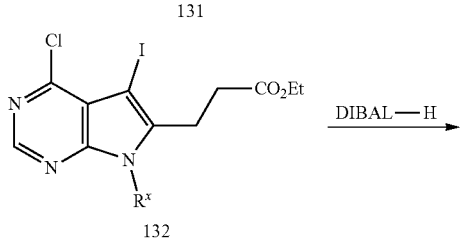
132

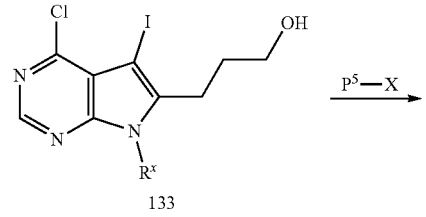
133

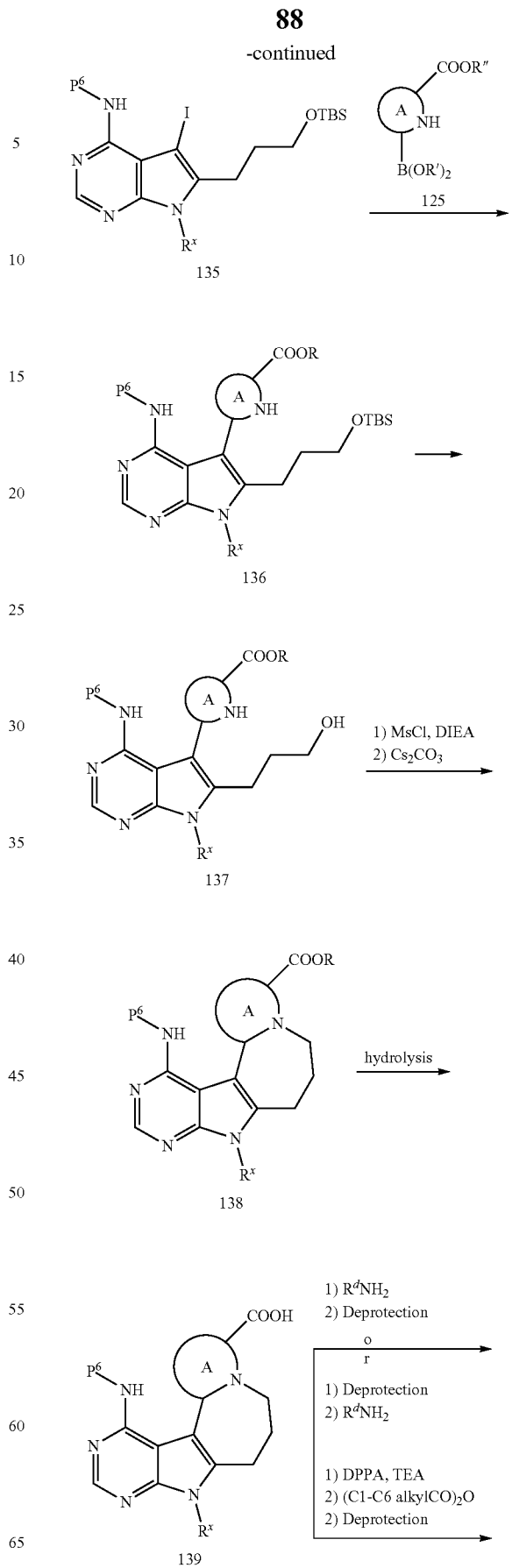

-continued

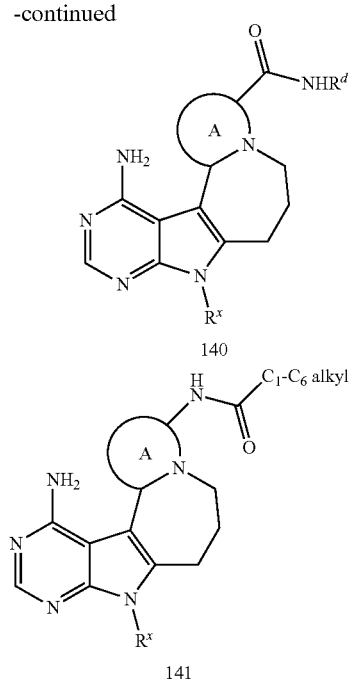

140

141

Scheme 25 shows a process for preparing a compound of Formula I-L (i.e., compounds of Formula I wherein W is $CR^3R^4$, X is $CR^7R^8$, Y is $CR^{10}R^{11}$, Z is N, and ------- is a single bond) wherein $R^7$ and $R^8$ are hydrogen, $R^{10}$ and $R^{11}$ are hydrogen, $R^x$ is C1-C6 alkyl, fluoroC1-C6 alkyl, $Cyc^2$, or $Cyc^3$, and Ring A is as defined for Formula I, wherein ring A is substituted with $R^dNHC(=O)$— or (C1-C6 alkyl)C(=O)NH—; and $R^d$ is C1-C6 alkyl, C1-C6 alkoxy, $Cyc^1$, $Cyc^1CH_2$—, phenyl or $hetAr^2$.

Compound 120 (wherein $R^x$ is as defined for Scheme 24) which may be prepared according to Scheme 24 may be subjected to Wittig olefination reaction (e.g., with ethyl 2-(triphenyl-λ5-phosphanylidene)acetate) to provide compound 130. Reduction of the olefin moiety in 130 provides compound 131, whereupon iodination (e.g., with N-iodo-succinimide) affords compound 132. Reduction of the ester moiety in 132 (e.g., with DIBAL-H) provides alcohol-containing compound 133. Protection of the alcohol in 133 with a reagent of formula $P^5$—X wherein $P^5$ is a suitable hydroxy protecting group (e.g., a silyl protecting group, e.g., tert-butyldimethyl silyl) and X is a leaving group (e.g., halogen) affords compound 134. Treatment of 134 with $P^6$—$NH_2$ wherein $P^6$ is an amino protecting group (e.g., benzyl, e.g., 2,4-dimethoxybenzyl, DMB) can provide compound 135. Subjecting 135 to appropriate palladium-catalyzed cross-coupling (e.g., Suzuki coupling) conditions with a boronic acid or boronic ester of formula 125 can provide compound 136. In compound 125, each R' is independently H or (1-6C)alkyl, or each R' together with the atoms to which they are connected form a 5-6 membered ring optionally substituted with 1-4 substituents selected from (C1-C3 alkyl); and R'' is C1-C6 alkyl. Removal of the hydroxy protecting group in 136 (e.g., with TBAF) can provide compound 137. Exposure of 137 to mesyl chloride allows methanesulfonylation of the primary alcohol group. Therefore, the NH group of ring A can displace this ensuing mesylate intramolecularly upon treatment with a base (e.g., cesium carbonate) to provide compound 138. Hydrolysis of the ester group in 138 affords 139, whereupon coupling with $R^dNH_2$ under standard amide coupling conditions followed by removal of the amino protecting group provides compound 140 which is a compound of Formula I-L, wherein $R^x$ is C1-C6 alkyl, fluoroC1-C6 alkyl, $Cyc^2$, or $Cyc^3$; ring A is substituted with $R^dNHC(=O)$, and $R^d$ is C1-C6 alkyl, C1-C6 alkoxy, $Cyc^1$, $Cyc^1CH_2$—, phenyl or $hetAr^2$. Alternatively, compound 140 can be obtained from compound 139 by sequential removal of the amino protecting group and coupling with $R^dNH_2$ under standard amide coupling conditions.

Further, compound 139 may be treated with diphenylphosphoryl azide (DPPA) and trimethylamine in a Curtius-type rearrangement. Treatment of the intermediate (not shown) to (C1-C6 alkylCO)$_2$O followed by removal of the amino protecting group can provide compound 141 which is a compound of Formula I-L, wherein $R^x$ is C1-C6 alkyl, fluoroC1-C6 alkyl, $Cyc^2$, or $Cyc^3$; and ring A is substituted with (C1-C6 alkyl)C(=O)NH—.

The term "amino protecting group" as used herein refers to a derivative of the groups commonly employed to block or protect an amino group while reactions are carried out on other functional groups on the compound. Examples of suitable protecting groups for use in any of the processes described herein include carbamates, amides, alkyl and aryl groups, benzyl groups and substituted benzyl groups, imines, as well as many N-heteroatom derivatives which can be removed to regenerate the desired amine group. Non-limiting examples of amino protecting groups are 2,4-dimethoxybenzyl (DMB), acetyl, trifluoroacetyl, t-butyloxycarbonyl ("Boc"), benzyloxycarbonyl ("CBz") [2-(trimethylsilyl)ethoxy]methyl (SEM), dimethylformamide dimethyl acetal, and 9-fluorenylmethyleneoxycarbonyl ("Fmoc"). Further examples of these groups, and other protecting groups, are found in T. W. Greene, et al. Greene's Protective Groups in Organic Synthesis. New York: Wiley Interscience, 2006.

Nitrogen atoms in compounds described in any of the above methods may be protected with one or more of any convenient nitrogen protecting group, for example, as described in Greene & Wuts, eds., "Protecting Groups in Organic Synthesis", $2^{nd}$ ed. New York; John Wiley & Sons, Inc., 1991. A nitrogen protecting group can be any "amino protecting group" as described above. Examples of nitrogen protecting groups include acyl and alkoxycarbonyl groups, such as t-butoxycarbonyl (BOC), phenoxycarbonyl, and [2-(trimethylsilyl)ethoxy]methyl (SEM).

Hydroxy groups may be protected with any convenient hydroxy protecting group, for example, as described in T. W. Greene, et al., Greene's Protective Groups in Organic Synthesis. New York: Wiley Interscience, 2006. Examples include benzyl, trityl, silyl ethers (e.g., tert-butyldimethylsilyl), and the like.

Accordingly, further provided herein is a process for preparing a compound of Formula I or a pharmaceutically acceptable salt thereof as defined herein which comprises:

(a) for a compound of Formula I, wherein W is $CR^3R^4$; X is $CR^7R^8$; Y is C(=O); Z is N; ------- is a single bond; $R^7$ and $R^8$ are hydrogen; $R^x$ is C1-C6 alkyl, fluoroC1-C6 alkyl, $Cyc^2$, or $Cyc^3$; and Ring A is a monocyclic heteroaryl ring or bicyclic heteroaryl ring as defined for Formula I, subjecting a compound of the following formula:

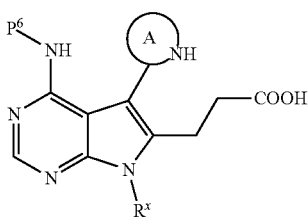

wherein R$^x$ is C1-C6 alkyl, fluoroC1-C6 alkyl, Cyc$^2$, or Cyc$^3$, Ring A is a monocyclic heteroaryl ring or bicyclic heteroaryl ring as defined for Ring A in Formula I, and P$^6$ is an amino protecting group, to an intramolecular cyclization; and removing the amino protecting group P$^6$ on the resulting intermediate;

(b) for a compound of Formula I, wherein W is CR$^3$R$^4$; X is CR$^7$R$^8$; Y is C(=O); Z is N; ------- is a single bond; R$^7$ and R$^8$ are hydrogen; R$^x$ is C1-C6 alkyl, fluoroC1-C6 alkyl, Cyc$^2$, or Cyc$^3$; ring A is a monocyclic heteroaryl ring or bicyclic heteroaryl ring as defined for Formula I, wherein ring A is substituted with NHR$^d$C(=O)—, and R$^d$ is C1-C6 alkyl, C1-C6 alkoxy, Cyc$^1$, Cyc$^1$CH$_2$—, phenyl or hetAr$^2$, coupling a compound of the following formula:

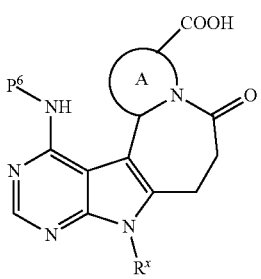

wherein R$^x$ is C1-C6 alkyl, fluoroC1-C6 alkyl, Cyc$^2$, or Cyc$^3$, ring A is a monocyclic heteroaryl ring or bicyclic heteroaryl ring as defined for Formula I, and P$^6$ is an amino protecting group, with a compound of formula R$^d$NH$_2$ wherein R$^d$ is C1-C6 alkyl, C1-C6 alkoxy, Cyc$^1$, Cyc$^1$CH$_2$—, phenyl or hetAr$^2$;

and removing the amino protecting group P$^6$;

(c) for a compound of formula I, wherein W is CR$^3$R$^4$; X is NR$^9$; Y is C(=O); Z is N, and ------- is a single bond; R$^9$ is hydrogen; R$^x$ is C1-C6 alkyl, fluoroC1-C6 alkyl, Cyc$^2$, or Cyc$^3$; and Ring A is a monocyclic heteroaryl ring or a bicyclic heteroaryl ring as defined for Formula I, reacting a compound of the following formula:

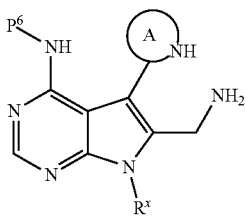

wherein R$^x$ is C1-C6 alkyl, fluoroC1-C6 alkyl, Cyc$^2$, or Cyc$^3$; Ring A is a monocyclic heteroaryl ring or a bicyclic heteroaryl ring as defined for Formula I; and P$^6$ is an amino protecting group, with Boc$_2$O; and removing the amino protecting group P$^6$;

(d) for a compound of Formula I, wherein W is CR$^3$R$^4$; X is NR$^9$; Y is C(=O); Z is N; ------- is a single bond; R$^9$ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, hetCyc$^1$, (hetCyc$^1$)C1-C6 alkyl-, (Ar$^1$)C1-C6 alkyl-, or (hetAr$^1$)C1-C6 alkyl-; R$^x$ is C1-C6 alkyl, fluoroC1-C6 alkyl, Cyc$^2$, or Cyc$^3$; and Ring A is

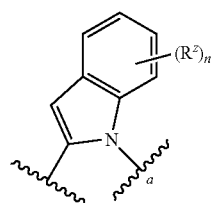

wherein the bond labeled "a" indicates the point of attachment to Y, n is 0, 1, 2, 3 or 4, and each R$^z$ is independently selected from R$^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH— wherein R$^d$ is C1-C6 alkyl, C1-C6 alkoxy, Cyc$^1$, Cyc$^1$CH$_2$—, phenyl or hetAr$^2$, reacting a compound of the following formula:

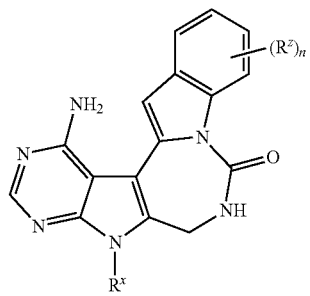

wherein R$^x$ is C1-C6 alkyl, fluoroC1-C6 alkyl, Cyc$^2$, or Cyc$^3$; n is 0, 1, 2, 3 or 4, and each R$^z$ is independently selected from R$^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH— wherein R$^d$ is C1-C6 alkyl, C1-C6 alkoxy, Cyc$^1$, Cyc$^1$CH$_2$—, phenyl or hetAr$^2$, with a compound of formula R$^9$—X, wherein X is a leaving group; and R$^9$ is C1-C6 alkyl, hydroxyC1-C6 alkyl- wherein the hydroxy group is protected with a hydroxy protecting group, (C1-C6 alkoxy)C1-C6 alkyl, C3-C6 cycloalkyl, (C3-C6 cycloalkyl)C1-C6 alkyl-, hetCyc$^1$, (hetCyc$^1$)C1-C6 alkyl-, (Ar$^1$)C1-C6 alkyl-, or (hetAr$^1$)C1-C6 alkyl-; and removing the hydroxy protecting group if present;

(e) for a compound of Formula I, wherein W is CR$^3$R$^4$, X is NR$^9$; Y is C(=O); Z is N; ------- is a single bond); R$^9$ is hydrogen; R$^x$ is C1-C6 alkyl, fluoroC1-C6 alkyl, Cyc$^2$, or Cyc$^3$; and Ring A is

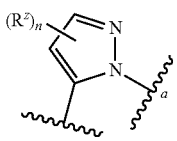

wherein the bond labeled "a" indicates the point of attachment to Y, each $R^z$ is independently selected from C1-C6 alkyl and C3-C6 cycloalkyl, n is 0, 1 or 2, and Ring A is further optionally substituted with one occurrence of halo, reacting a compound of the following formula

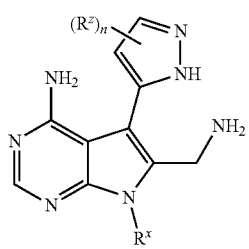

wherein $R^x$ is C1-C6 alkyl, fluoroC1-C6 alkyl, $Cyc^2$, or $Cyc^3$, each $R^z$ is independently selected from halogen, C1-C6 alkyl and C3-C6 cycloalkyl, n is 0, 1 or 2, and the pyrazolyl ring is further optionally substituted with one occurrence of halo, with a reagent of formula $(p\text{-}NO_2C_6H_5O)_2CO$;

(f) for a compound of Formula I, wherein W is $CR^3R^4$; X is $NR^9$; Y is C(=O), Z is C; ------ is a single bond; $R^9$ is hydrogen; $R^x$ is C1-C6 alkyl, fluoroC1-C6 alkyl, $Cyc^2$, or $Cyc^3$; and Ring A is

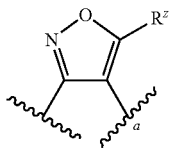

wherein the bond labeled "a" indicates the point of attachment to Y and $R^z$ is C1-C6 alkyl or C3-C6 cycloalkyl, reacting a compound of the following formula:

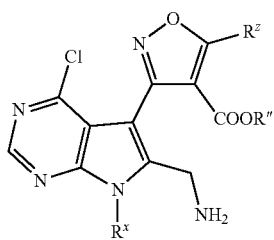

wherein $R^x$ is C1-C6 alkyl, fluoroC1-C6 alkyl, $Cyc^2$, or $Cyc^3$, and $R^z$ is C1-C6 alkyl or C3-C6 cycloalkyl with ammonium hydroxide;

(g) for a compound of Formula I, wherein W is $CR^3R^4$; X is $NR^9$; Y is C(=O), Z is C; ------ is a single bond; $R^9$ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, (hetCyc$^1$)C1-C6 alkyl-, (Ar$^1$) C1-C6 alkyl-, or (hetAr$^1$)C1-C6 alkyl-; $R^x$ is C1-C6 alkyl, fluoroC1-C6 alkyl, $Cyc^2$, or $Cyc^3$; and Ring A is

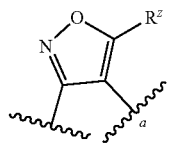

wherein the bond labeled "a" indicates the point of attachment to Y, and $R^z$ is C1-C6 alkyl or C3-C6 cycloalkyl, reacting a compound of the following formula:

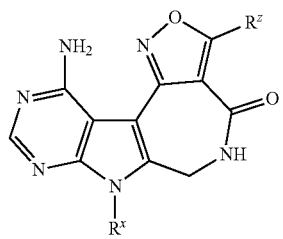

wherein $R^x$ is C1-C6 alkyl, fluoroC1-C6 alkyl, $Cyc^2$, or $Cyc^3$, and $R^z$ is C1-C6 alkyl or C3-C6 cycloalkyl, with a compound of formula $R^9$—X wherein $R^9$ is C1-C6 alkyl, hydroxyC1-C6 alkyl- the hydroxy group is protected with a suitable hydroxy protecting group, (C1-C6 alkoxy)C1-C6 alkyl, C3-C6 cycloalkyl, (C3-C6 cycloalkyl)C1-C6 alkyl-, (hetCyc$^1$)C1-C6 alkyl-, (Ar$^1$)C1-C6 alkyl-, or (hetAr$^1$)C1-C6 alkyl-; and removing the hydroxy protecting group if present;

(h) for a compound of Formula I, wherein W is $CR^3R^4$, X is $NR^9$; Y is C(=O); Z is C; and ------ is a single bond; $R^9$ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, (hetCyc$^1$)C1-C6 alkyl-, (Ar$^1$) C1-C6 alkyl-, or (hetAr$^1$)C1-C6 alkyl-; $R^x$ is as defined for Formula I; and Ring A is

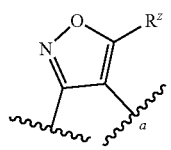

wherein the bond labeled "a" indicates the point of attachment to Y and $R^z$ is C1-C6 alkyl or C3-C6 cycloalkyl, removing the amino protecting group $P^2$ on a compound of the following formula:

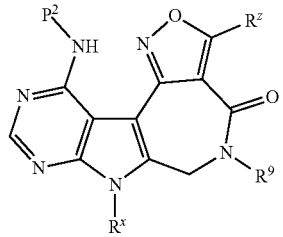

wherein $R^x$ is as defined for Formula I, $R^z$ is C1-C6 alkyl or C3-C6 cycloalkyl, $R^9$ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, (hetCyc¹)C1-C6 alkyl-, (Ar¹)C1-C6 alkyl-, or (hetAr¹)C1-C6 alkyl-, and P² is an amino protecting group;

(i) for a compound of Formula I, wherein W is CR³R⁴; X is NR⁹; Y is C(=O); Z is C; ------ is a single bond; Ring A is a 6-membered aryl ring optionally substituted with one or more substituents independently selected from halogen, C3-C6 cycloalkyl, C1-C6 alkoxy, R^cNHC(=O)—, R^cC(=O)NH—, or R^cNHC(=O)NH— wherein R^c is C3-C6 cycloalkyl or (C3-C6 cycloalkyl)CH₂—; R⁹ is hydrogen; and R^x is C1-C6 alkyl, fluoroC1-C6 alkyl, Cyc², or Cyc³, subjecting a compound of the following formula:

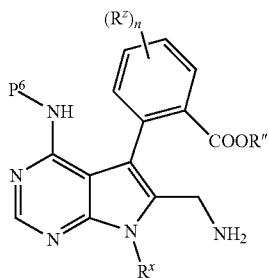

wherein R^x is C1-C6 alkyl, fluoroC1-C6 alkyl, Cyc², or Cyc³, n is 0, 1, 2, 3, or 4, each R^z is independently halogen, C3-C6 cycloalkyl, C1-C6 alkoxy, R^cNHC(=O)—, R^cC(=O)NH—, or R^cNHC(=O)NH— wherein R^c is C3-C6 cycloalkyl or (C3-C6 cycloalkyl)CH₂—, and P⁶ is an amino protecting group, to an intramolecular cyclization; and removing the amino protecting group P⁶;

(j) for a compound of Formula I, wherein W is CR³R⁴; X is NR⁹; Y is C(=O); Z is C; ------ is a single bond; Ring A is a 6-membered aryl ring optionally substituted with one or more substituents independently selected from halogen, C3-C6 cycloalkyl, C1-C6 alkoxy, R^cNHC(=O)—, R^cC(=O)NH—, or R^cNHC(=O)NH— wherein R^c is C3-C6 cycloalkyl or (C3-C6 cycloalkyl)CH₂—; R⁹ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, (hetCyc¹)C1-C6 alkyl-, (Ar¹)C1-C6 alkyl-, or (hetAr¹)C1-C6 alkyl-; and R^x is C1-C6 alkyl, fluoroC1-C6 alkyl, Cyc², or Cyc³, reacting a compound of the following formula:

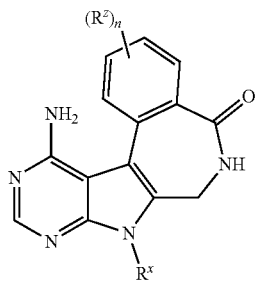

wherein R^x is C1-C6 alkyl, fluoroC1-C6 alkyl, Cyc², or Cyc³, n is 0, 1, 2, 3, or 4, and each R^z is independently selected from halogen, C3-C6 cycloalkyl, C1-C6 alkoxy, R^cNHC(=O)—, R^cC(=O)NH—, or R^cNHC(=O)NH— wherein R^c is C3-C6 cycloalkyl or (C3-C6 cycloalkyl)CH₂—, with a compound of formula R⁹—X, wherein R⁹ is C1-C6 alkyl, hydroxyC1-C6 alkyl- wherein the hydroxy group is protected with a suitable hydroxy protecting group, (C1-C6 alkoxy)C1-C6 alkyl, C3-C6 cycloalkyl, (C3-C6 cycloalkyl)C1-C6 alkyl-, (hetCyc¹)C1-C6 alkyl-, (Ar¹)C1-C6 alkyl-, or (hetAr¹)C1-C6 alkyl-, and X is a leaving group; and removing the hydroxy protecting group if present;

(k) for a compound of Formula I wherein W is CR³R⁴; X is NR⁹; Y is C(=O); Z is C; ------ is a single bond; R⁹ is hydrogen; R^x is hydrogen, C1-C6 alkyl, fluoroC1-C6 alkyl, Cyc², or Cyc³; and Ring A is

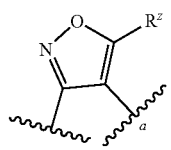

wherein the bond labeled "a" indicates the point of attachment to Y; and R^z is C1-C6 alkyl or C3-C6 cycloalkyl, reacting a compound of the following formula:

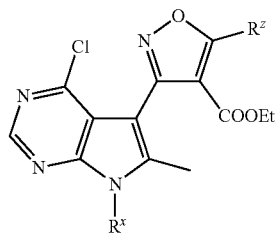

wherein R^x is C1-C6 alkyl, fluoroC1-C6 alkyl, Cyc², or Cyc³, and R^z is C1-C6 alkyl or C3-C6 cycloalkyl, with N-bromosuccinimide and AIBN; and reacting the resulting intermediate with ammonium hydroxide; or reacting a compound of the following formula:

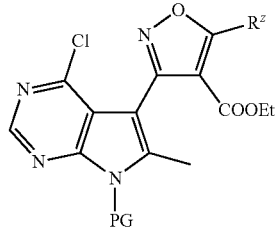

wherein PG is an amino protecting group, and R^z is C1-C6 alkyl or C3-C6 cycloalkyl, with N-bromosuccinimide and AIBN; reacting the resulting intermediate with ammonium hydroxide; and removing the amino protecting group PG on the resulting intermediate;

(l) for a compound of Formula I wherein W is CR³R⁴; X is NR⁹; Y is C(=O); Z is C; ------ is a single bond; R⁹ is C1-C6 alkyl, hydroxyC1-C6 alkyl-, (C1-C6 alkyl) SO₂—, (C1-C6 alkoxy)C1-C6 alkyl, C3-C6 cycloalkyl, (C3-C6 cycloalkyl)C1-C6 alkyl-, hetCyc¹, (hetCyc¹) C1-C6 alkyl-, Ar¹, (Ar¹)C1-C6 alkyl-, hetAr¹, (hetAr¹) C1-C6 alkyl-, (C1-C6 alkyl)C(=O)—, (fluoroC1-C6 alkyl)C(=O)—, H₂NC(=O)—, Ar¹CH₂C(=O)— or (C3-C6 cycloalkyl)C(=O)—; R^x is C1-C6 alkyl, fluoroC1-C6 alkyl, Cyc², or Cyc³; and Ring A is

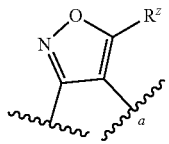

wherein the bond labeled "a" indicates the point of attachment to Y and R^z is C1-C6 alkyl or C3-C6 cycloalkyl, reacting a compound of the following formula:

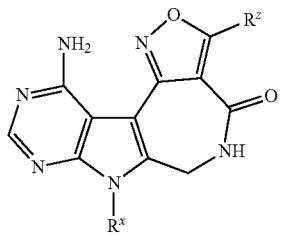

wherein R^x is C1-C6 alkyl, fluoroC1-C6 alkyl, Cyc², or Cyc³; and R^z is C1-C6 alkyl or C3-C6 cycloalkyl, with a compound of formula R⁹—X wherein R⁹ is C1-C6 alkyl, hydroxyC1-C6 alkyl- wherein the hydroxy group is protected with a suitable hydroxy protecting group, (C1-C6 alkyl)SO₂—, (C1-C6 alkoxy)C1-C6 alkyl, C3-C6 cycloalkyl, (C3-C6 cycloalkyl)C1-C6 alkyl-, hetCyc¹, (hetCyc¹)C1-C6 alkyl-, Ar¹, (Ar¹)C1-C6 alkyl-, hetAr¹, (hetAr¹)C1-C6 alkyl-, (C1-C6 alkyl)C(=O)—, (fluoroC1-C6 alkyl)C(=O)—, H₂NC(=O)—, Ar¹CH₂C(=O)— or (C3-C6 cycloalkyl)C(=O)—, and X is a leaving group; and removing the hydroxy protecting group if present;

(m) for a compound of Formula I wherein W is CR³R⁴; X is NR⁹; Y is C(=O); Z is C; and ------- is a single bond); R⁹ is hydrogen; R^x is C1-C6 alkyl, fluoroC1-C6 alkyl, Cyc², or Cyc³; and Ring A is as defined for Formula I, subjecting a compound of the following formula:

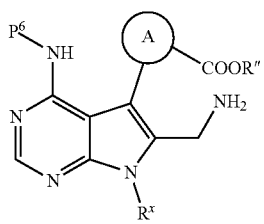

wherein R^x is C1-C6 alkyl, fluoroC1-C6 alkyl, Cyc², or Cyc³, P⁶ is an amino protecting group, and R" is C1-C6 alkyl, to an intramolecular cyclization; and removing the amino protecting group P⁶;

(n) for a compound of Formula I wherein W is CR³R⁴; X is O; Y is C(=O); Z is C; and ------- is a single bond; R^x is C1-C6 alkyl, fluoroC1-C6 alkyl, Cyc², or Cyc³, and Ring A is

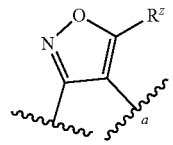

wherein the bond labeled "a" indicates the point of attachment to Y and R^z is C1-C6 alkyl or C3-C6 cycloalkyl, removing the amino protecting group P² on a compound of the following formula:

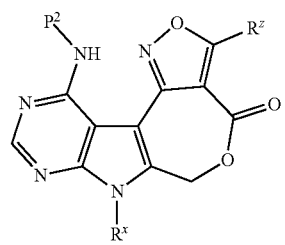

wherein R^x is C1-C6 alkyl, fluoroC1-C6 alkyl, Cyc², or Cyc³, R^z is C1-C6 alkyl or C3-C6 cycloalkyl, and P² is an amino protecting group;

(o) for a compound of Formula I wherein W is CR³R⁴; X is NR⁹; Y is SO₂; Z is C, and ------- is a single bond; R⁹ is hydrogen; R^x is C1-C6 alkyl, fluoroC1-C6 alkyl, Cyc², or Cyc³; and Ring A is

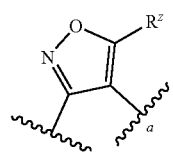

wherein the bond labeled "a" indicates the point of attachment to Y and R^z is C1-C6 alkyl or C3-C6 cycloalkyl, reacting a compound of the following formula

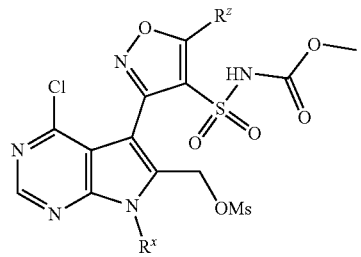

wherein R^x is C1-C6 alkyl, fluoroC1-C6 alkyl, Cyc², or Cyc³, and R^z is C1-C6 alkyl or C3-C6 cycloalkyl, with ammonium hydroxide;

(p) for a compound of Formula I wherein W is CR³R⁴; X is NR⁹; Y is SO₂; Z is C, and ------- is a single bond; R⁹ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, (hetCyc¹)C1-C6 alkyl-, (Ar¹)C1-C6 alkyl-, or (hetAr¹)C1-C6 alkyl-; R^x is C1-C6 alkyl, fluoroC1-C6 alkyl, Cyc², or Cyc³; and Ring A is

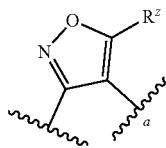

wherein the bond labeled "a" indicates the point of attachment to Y and $R^z$ is C1-C6 alkyl or C3-C6 cycloalkyl, reacting a compound of the following formula

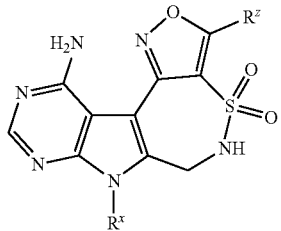

wherein $R^x$ is C1-C6 alkyl, fluoroC1-C6 alkyl, $Cyc^2$, or $Cyc^3$, and $R^z$ is C1-C6 alkyl or C3-C6 cycloalkyl, with a compound of formula $R^9$—X wherein $R^9$ is hydrogen, C1-C6 alkyl, hydroxyC1-C6 alkyl- wherein the hydroxy group is protected with a suitable hydroxy protecting group, (C1-C6 alkoxy)C1-C6 alkyl, C3-C6 cycloalkyl, (C3-C6 cycloalkyl)C1-C6 alkyl-, (hetCyc¹)C1-C6 alkyl-, (Ar¹)C1-C6 alkyl-, or (hetAr¹)C1-C6 alkyl-; and removing the hydroxy protecting group if present;

(q) for a compound of Formula I, wherein W is $CR^3R^4$; X is $CR^7R^8$; Y is $SO_2$; Z is C; and ------- is a single bond; $R^7$ and $R^8$ are hydrogen; $R^x$ is C1-C6 alkyl, fluoroC1-C6 alkyl, $Cyc^2$, or $Cyc^3$; and Ring A is

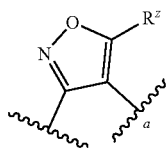

wherein the bond labeled "a" indicates the point of attachment to Y and $R^z$ is C1-C6 alkyl or C3-C6 cycloalkyl, reacting a compound of the following formula

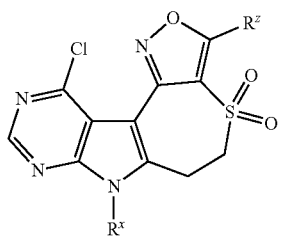

wherein $R^x$ is C1-C6 alkyl, fluoroC1-C6 alkyl, $Cyc^2$, or $Cyc^3$, and $R^z$ is C1-C6 alkyl or C3-C6 cycloalkyl with ammonium hydroxide;

(r) for a compound of Formula I wherein W is $CR^3R^4$; X is $CR^7R^8$; Y is C(=O); Z is C; ------- is a single bond; $R^7$ and $R^8$ are hydrogen; $R^x$ is C1-C6 alkyl, fluoroC1-C6 alkyl, $Cyc^2$, or $Cyc^3$; and Ring A is

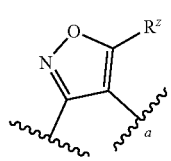

wherein the bond labeled "a" indicates the point of attachment to Y and $R^z$ is C1-C6 alkyl or C3-C6 cycloalkyl, reacting a compound of the following formula:

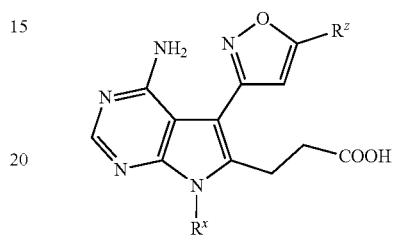

wherein $R^x$ is C1-C6 alkyl, fluoroC1-C6 alkyl, $Cyc^2$, or $Cyc^3$, and $R^z$ is C1-C6 alkyl or C3-C6 cycloalkyl, with polyphosphoric acid;

(s) for a compound of Formula I wherein W is $CR^3R^4$; X is $CR^7R^8$; Y is C(=O); Z is C; ------- is a single bond; $R^7$ and $R^8$ are hydrogen; $R^x$ is hydrogen, C1-C6 alkyl, fluoroC1-C6 alkyl, $Cyc^2$, $Cyc^3$, $hetCyc^3$, $Ar^3$ or $hetAr^3$; and Ring A is

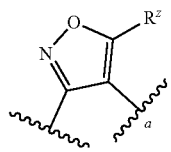

wherein the bond labeled "a" indicates the point of attachment to Y, and $R^z$ is C1-C6 alkyl or C3-C6 cycloalkyl, reacting a compound of the following formula:

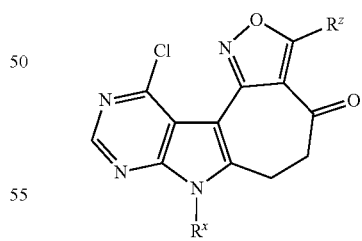

wherein $R^x$ is hydrogen, C1-C6 alkyl, fluoroC1-C6 alkyl, $Cyc^2$, $Cyc^3$, $hetCyc^3$, $Ar^3$ or $hetAr^3$, and $R^z$ is C1-C6 alkyl or C3-C6 cycloalkyl, with ammonium hydroxide;

(t) for a compound of Formula I wherein W is $CR^3R^4$; X is $CR^7R^8$; Y is C(=O); Z is C; ------- is a single bond; $R^7$ and $R^8$ are hydrogen; $R^x$ is C1-C6 alkyl, fluoroC1-C6 alkyl, $Cyc^2$, $Cyc^3$, $hetCyc^3$, $Ar^3$ or $hetAr^3$; and Ring A is

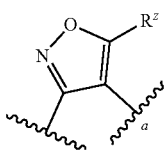

wherein the bond labeled "a" indicates the point of attachment to Y, and $R^z$ is C1-C6 alkyl or C3-C6 cycloalkyl, removing the amino protecting group $P^6$ on a compound of the following formula:

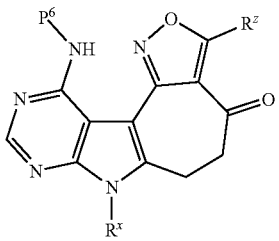

wherein $R^x$ is C1-C6 alkyl, fluoroC1-C6 alkyl, $Cyc^2$, $Cyc^3$, $hetCyc^3$, $Ar^3$ or $hetAr^3$, $R^z$ is C1-C6 alkyl or C3-C6 cycloalkyl, and $P^6$ is an amino protecting group;

(u) for a compound of Formula I wherein W is $CR^3R^4$; X is $CR^7R^8$; Y is C(=O); Z is C; ------- is a single bond; $R^7$ and $R^8$ are hydrogen; $R^x$ is C1-C6 alkyl, fluoroC1-C6 alkyl, $Cyc^2$, $Cyc^3$, $hetCyc^3$, $Ar^3$ or $hetAr^3$; and Ring A is

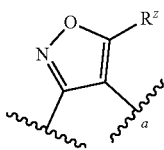

wherein the bond labeled "a" indicates the point of attachment to Y, and $R^z$ is C1-C6 alkyl or C3-C6 cycloalkyl, reacting a compound of the following formula:

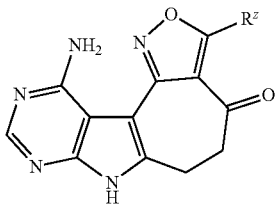

wherein $R^z$ is C1-C6 alkyl or C3-C6 cycloalkyl, with a compound of formula $R^x$—X wherein $R^x$ is C1-C6 alkyl, fluoroC1-C6 alkyl, $Cyc^2$, $Cyc^3$, $hetCyc^3$, $Ar^3$ or $hetAr^3$, a compound of formula $R^x$—OH wherein $R^x$ is C1-C6 alkyl, fluoroC1-C6 alkyl, $Cyc^2$, $Cyc^3$, or $hetCyc^3$, or a compound of formula $R^xB(OR')_2$ wherein $R^x$ is C1-C6 alkyl, fluoroC1-C6 alkyl, $Cyc^2$, $Cyc^3$, $hetCyc^3$, $Ar^3$ or $hetAr^3$, and each $R^1$ is independently H or (1-6C)alkyl, or each $R^1$ together with the atoms to which they are connected form a 5-6 membered ring optionally substituted with 1-4 substituents selected from (C1-C3 alkyl);

(v) for a compound of formula I, wherein W is $CR^3R^4$; X is $CR^7R^8$; Y is $CR^{10}R^{11}$; Z is C; ------- is a single bond; $R^7$ and $R^8$ are hydrogen; $R^x$ is as defined for Formula I, $R^{10}$ and $R^{11}$ are as defined for Formula I, and Ring A is

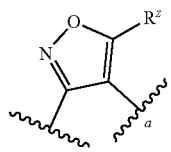

wherein the bond labeled "a" indicates the point of attachment to Y and $R^z$ is C1-C6 alkyl or C3-C6 cycloalkyl, functionalizing a compound of the following formula:

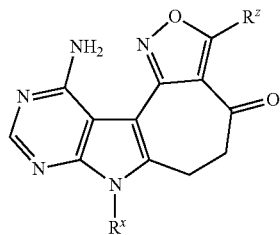

wherein $R^x$ is as defined for Formula I, and $R^z$ is C1-C6 alkyl or C3-C6 cycloalkyl; and
optionally subjecting the resulting product to chiral separation;

(w) for a compound of Formula I, wherein W is $CR^3R^4$; X is $CR^7R^8$; Y is $CR^{10}R^{11}$; Z is C; ------- is a single bond; $R^7$ and $R^8$ are hydrogen; $R^x$ is as defined for Formula I, $R^{10}$ is hydroxyl, $R^{11}$ is hydrogen, and Ring A is

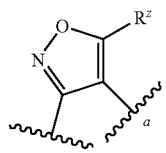

wherein the bond labeled "a" indicates the point of attachment to Y and $R^z$ is C1-C6 alkyl or C3-C6 cycloalkyl, reacting a compound of the following formula:

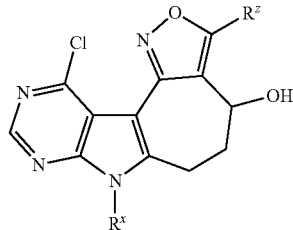

wherein $R^x$ is as defined for Formula I, and $R^z$ is C1-C6 alkyl or C3-C6 cycloalkyl, with ammonium hydroxide; and
optionally subjecting the resulting product to chiral separation;

(x) for a compound of Formula I, wherein W is CR³R⁴; X is CR⁷R⁸; Y is CR¹⁰R¹¹; Z is C; ------- is a single bond; R⁷ and R⁸ are hydrogen; R$^x$ is C1-C6 alkyl, fluoroC1-C6 alkyl, Cyc², Cyc³, hetCyc³, Ar³ or hetAr³, R¹⁰ is hydroxyl, and R¹¹ is hydrogen, and Ring A is

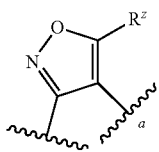

wherein the bond labeled "a" indicates the point of attachment to Y and R$^z$ is C1-C6 alkyl or C3-C6 cycloalkyl, subjecting a compound of the following formula:

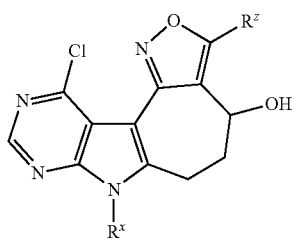

wherein R$^x$ is as defined for Formula I, and R$^z$ is C1-C6 alkyl or C3-C6 cycloalkyl, to chiral separation; and
    reacting the resulting intermediate with ammonium hydroxide;
(y) for a compound of Formula I, wherein W is CR³R⁴; X is NR⁹; Y is CR¹⁰R¹¹; Z is C; ------- is a single bond; R¹⁰ and R¹¹ are hydrogen; R$^x$ is C1-C6 alkyl, fluoroC1-C6 alkyl, Cyc², or Cyc³; R⁹ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, hetCyc¹, (hetCyc¹)C1-C6 alkyl-, Ar¹, (Ar¹)C1-C6 alkyl-, hetAr¹ or (hetAr¹)C1-C6 alkyl-, and Ring A is

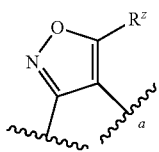

wherein the bond labeled "a" indicates the point of attachment to Y and R$^z$ is C1-C6 alkyl or C3-C6 cycloalkyl, reacting a compound of the following formula:

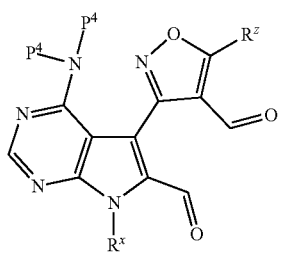

wherein R$^x$ is C1-C6 alkyl, fluoroC1-C6 alkyl, Cyc², or Cyc³, R$^z$ is C1-C6 alkyl or C3-C6 cycloalkyl, and each P⁴ is independently an amino protecting group, with a compound of formula R⁹NH₂, wherein R⁹ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, hetCyc¹, (hetCyc¹)C1-C6 alkyl-, Ar¹, (Ar¹)C1-C6 alkyl-, hetAr¹ or (hetAr¹)C1-C6 alkyl-, in the presence of a reducing agent; and
    removing the amino protecting groups P⁴ on the resulting intermediate;
(z) for a compound of Formula I, wherein W is CR³R⁴; X is NR⁹; Y is CR¹⁰R¹¹; Z is C; ------- is a single bond; R¹⁰ and R¹¹ are hydrogen; R$^x$ is C1-C6 alkyl, fluoroC1-C6 alkyl, Cyc², or Cyc³; R⁹ is (C1-C6 alkyl)SO₂ or R⁹'C(=O) wherein R⁹' is C1-C6 alkyl or fluoroC1-C6 alkyl, and Ring A is

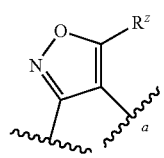

wherein the bond labeled "a" indicates the point of attachment to Y and R$^z$ is C1-C6 alkyl or C3-C6 cycloalkyl, reacting a compound of the following formula:

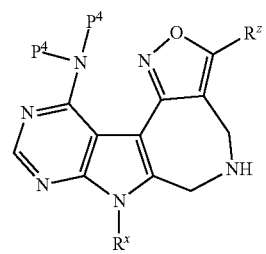

wherein R$^x$ is C1-C6 alkyl, fluoroC1-C6 alkyl, Cyc², or Cyc³, R$^z$ is C1-C6 alkyl or C3-C6 cycloalkyl, and each P⁴ is independently an amino protecting group, with a compound of formula (C1-C6 alkyl)SO₂Cl or R⁹'C(=O)Cl wherein R⁹' is C1-C6 alkyl or fluoroC1-C6 alky; and
    removing the amino protecting groups P⁴ on the resulting intermediate;
(aa) for a compound of Formula I, wherein W is CR³R⁴; X is O; Y is CR¹⁰R¹¹; Z is C; ------- is a single bond; R¹⁰ and R¹¹ are hydrogen; R$^x$ is C1-C6 alkyl, fluoroC1-C6 alkyl, Cyc², or Cyc³; and Ring A is

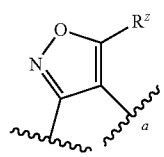

wherein the bond labeled "a" indicates the point of attachment to Y and R$^z$ is C1-C6 alkyl or C3-C6 cycloalkyl, reacting a compound of the following formula:

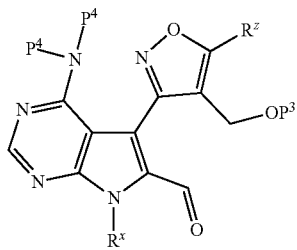

wherein $R^x$ is C1-C6 alkyl, fluoroC1-C6 alkyl, $Cyc^2$, or $Cyc^3$, $R^z$ is C1-C6 alkyl or C3-C6 cycloalkyl, each $P^4$ is independently an amino protecting group, and $P^3$ is a hydroxy protecting group, with $CF_3SO_3TMS$ and $Et_3SiH$;

(bb) for a compound of Formula I, wherein W is $CR^3R^4$; X is $CR^5$; Y is $CR^6$; Z is C; ------ is a double bond; $R^5$ and $R^6$ are hydrogen; $R^x$ is C1-C6 alkyl, fluoroC1-C6 alkyl, $Cyc^2$, or $Cyc^3$; and Ring A is

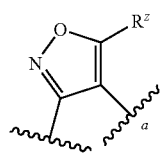

wherein the bond labeled "a" indicates the point of attachment to Y and $R^z$ is C1-C6 alkyl or C3-C6 cycloalkyl, reacting a compound of the following formula:

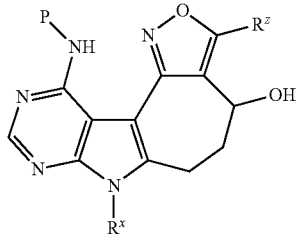

wherein $R^x$ is C1-C6 alkyl, fluoroC1-C6 alkyl, $Cyc^2$, or $Cyc^3$, $R^z$ is C1-C6 alkyl or C3-C6 cycloalkyl, and P is an amino protecting group, with iodomethane in the presence of a base; and removing the amino protecting group P on the resulting intermediate;

(cc) for a compound of Formula I, wherein W is $CR^3R^4$; X is $CR^7R^8$; Y is $CR^{10}R^{11}$; Z is N; ------ is a single bond; $R^7$ and $R^8$ are hydrogen; $R^{10}$ and $R^{11}$ are hydrogen; $R^x$ is C1-C6 alkyl, fluoroC1-C6 alkyl, $Cyc^2$, or $Cyc^3$; ring A is a monocyclic heteroaryl ring or bicyclic heteroaryl ring as defined for Formula I, wherein ring A is substituted with $NHR^dC(=O)$—, and $R^d$ is C1-C6 alkyl, C1-C6 alkoxy, $Cyc^1$, $Cyc^1CH_2$—, phenyl or $hetAr^2$, removing the amino protecting group $P^6$ on a compound of the following formula:

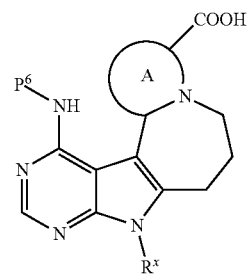

wherein $R^x$ is C1-C6 alkyl, fluoroC1-C6 alkyl, $Cyc^2$, or $Cyc^3$, ring A is a monocyclic heteroaryl ring or bicyclic heteroaryl ring as defined for Formula I, and $P^6$ is an amino protecting group;

and coupling the resulting intermediate with a compound of formula $R^dNH_2$ wherein $R^d$ is C1-C6 alkyl, C1-C6 alkoxy, $Cyc^1$, $Cyc^1CH_2$—, phenyl or $hetAr^2$;

(dd) for a compound of Formula I, wherein W is $CR^3R^4$; X is $CR^7R^8$; Y is $CR^{10}R^{11}$; Z is N; ------ is a single bond; $R^7$ and $R^8$ are hydrogen; $R^{10}$ and $R^{11}$ are hydrogen; $R^x$ is C1-C6 alkyl, fluoroC1-C6 alkyl, $Cyc^2$, or $Cyc^3$; ring A is a monocyclic heteroaryl ring or bicyclic heteroaryl ring as defined for Formula I, wherein ring A is substituted with $NHR^dC(=O)$—, and $R^d$ is C1-C6 alkyl, C1-C6 alkoxy, $Cyc^1$, $Cyc^1CH_2$—, phenyl or $hetAr^2$, coupling a compound of the following formula:

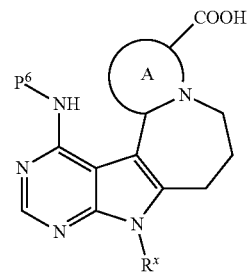

wherein $R^x$ is C1-C6 alkyl, fluoroC1-C6 alkyl, $Cyc^2$, or $Cyc^3$, A is a monocyclic heteroaryl ring or bicyclic heteroaryl ring as defined for Formula I, and $P^6$ is an amino protecting group, with a compound of formula $R^dNH_2$ wherein $R^d$ is C1-C6 alkyl, C1-C6 alkoxy, $Cyc^1$, $Cyc^1CH_2$—, phenyl or $hetAr^2$;

and removing the amino protecting group $P^6$; or (ee) for a compound of Formula I, wherein W is $CR^3R^4$; X is $CR^7R^8$; Y is $CR^{10}R^{11}$; Z is N; ------ is a single bond; $R^7$ and $R^8$ are hydrogen; $R^{10}$ and $R^{11}$ are hydrogen; $R^x$ is C1-C6 alkyl, fluoroC1-C6 alkyl, $Cyc^2$, or $Cyc^3$; ring A is a monocyclic heteroaryl ring or bicyclic heteroaryl ring as defined for Formula I, wherein ring A is substituted with (C1-C6 alkyl)C(=O)NH—, reacting a compound of the following formula:

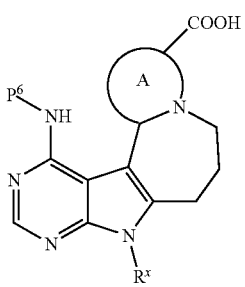

wherein $R^x$ is C1-C6 alkyl, fluoroC1-C6 alkyl, $Cyc^2$, or $Cyc^3$, ring A is a monocyclic heteroaryl ring or bicyclic heteroaryl ring as defined for Formula I, and $P^6$ is an amino protecting group, with diphenylphosphoryl azide (DPPA);

reacting the resulting intermediate with a compound of formula (C1-C6 alkylCO)$_2$O; and removing the amino protecting group $P^6$ on the resulting intermediate, optionally removing any remaining protecting groups, and optionally forming a pharmaceutically acceptable salt thereof.

The ability of test compounds to act as RET inhibitors may be demonstrated by the assay described in Examples A, B, C, and D. IC$_{50}$ values are shown in Table 5.

In some embodiments, the compounds provided herein exhibit potent and selective RET inhibition. For example, the compounds provided herein exhibit nanomolar potency against wild type RET and a RET kinase encoded by a RET gene including an activating mutation or a RET kinase inhibitor resistance mutation, including, for example, the KIF5B-RET fusion, G810R and G810S ATP cleft front mutations, M918T activating mutation, and V804M, V804L, and V804E gatekeeper mutations, with minimal activity against related kinases.

In some embodiments, the compounds provided herein exhibit nanomolar potency against an altered RET fusion protein encoded by a RET gene encoding the RET fusion protein (e.g. any of the RET fusion proteins described herein including, without limitation, CCDC6-RET or KIF5B-RET) which RET gene includes a RET kinase inhibitor resistance mutation (e.g., any of the RET mutations described herein including, without limitation, V804M, V804L, or V804E) such that the altered RET protein is a RET fusion protein that exhibits RET kinase resistance due to the presence of a RET kinase inhibitor resistance amino acid substitution or deletion. Non-limiting examples include CCDC6-RET-V804M and KIF5B-RET-V804M. In some embodiments, the compounds provided herein exhibit nanomolar potency against an altered RET protein encoded by a RET gene that that includes a RET mutation (e.g. any of the RET mutations described herein including, without limitation, C634W or M918T) and that includes a RET kinase inhibitor resistance mutation (e.g., any of the RET kinase inhibitor resistance mutations described herein including, without limitation, V804M, V804L, or V804E) such that the altered RET protein includes a RET substitution caused by the RET mutation (e.g., a RET primary mutation) and the altered RET protein exhibits RET kinase resistance due to the presence of a RET kinase inhibitor resistance amino acid substitution or deletion.

In some embodiments, the compounds of Formula I (e.g., any one of Formulas I-A to I-L), or a pharmaceutically acceptable salt thereof, selectively target a RET kinase. For example, a compound of Formula I (e.g., any one of Formulas I-A to I-L), or a pharmaceutically acceptable salt or solvate thereof, can selectively target a RET kinase over another kinase or non-kinase target.

In some embodiments, a compound of Formula I (e.g., any one of Formulas I-A to I-L), or a pharmaceutically acceptable salt or solvate thereof, exhibits at least a 30-fold selectivity for a RET kinase over another kinase. For example, a compound of Formula I (e.g., any one of Formulas I-A to I-L), or a pharmaceutically acceptable salt or solvate thereof, exhibits at least a 40-fold selectivity; at least a 50-fold selectivity; at least a 60-fold selectivity; at least a 70-fold selectivity; at least a 80-fold selectivity; at least a 90-fold selectivity; at least 100-fold selectivity; at least 200-fold selectivity; at least 300-fold selectivity; at least 400-fold selectivity; at least 500-fold selectivity; at least 600-fold selectivity; at least 700-fold selectivity; at least 800-fold selectivity; at least 900-fold selectivity; or at least 1000-fold selectivity for a RET kinase over another kinase. In some embodiments, selectivity for a RET kinase over another kinase is measured in a cellular assay (e.g., a cellular assay as provided herein).

In some embodiments, the compounds provided herein can exhibit selectivity for a RET kinase over a KDR kinase (e.g., VEGFR2). In some embodiments, the selectivity for a RET kinase over a KDR kinase is observed without loss of potency for a RET kinase encoded by a RET gene including an activating mutation or a RET kinase inhibitor resistance mutation (e.g., a gatekeeper mutant). In some embodiments, the selectivity over a KDR kinase is at least 10-fold (e.g., at least a 40-fold selectivity; at least a 50-fold selectivity; at least a 60-fold selectivity; at least a 70-fold selectivity; at least a 80-fold selectivity; at least a 90-fold selectivity; at least 100-fold selectivity; at least 150-fold selectivity; at least 200-fold selectivity; at least 250-fold selectivity; at least 300-fold selectivity; at least 350-fold selectivity; or at least 400-fold selectivity) as compared to the inhibition of KIF5B-RET (e.g., the compounds are more potent against KIF5B-RET than KDR). In some embodiments, the selectivity for a RET kinase over a KDR kinase is about 30-fold. In some embodiments, the selectivity for a RET kinase over a KDR kinase is at least 100-fold. In some embodiments, the selectivity for a RET kinase over a KDR kinase is at least 150-fold. In some embodiments, the selectivity for a RET kinase over a KDR kinase is at least 400-fold. Without being bound by any theory, potent KDR kinase inhibition is believed to be a common feature among multikinase inhibitors (MKIs) that target RET and may be the source of the dose-limiting toxicities observed with such compounds.

In some embodiments, inhibition of V804M is similar to that observed for wild-type RET. For example, inhibition of V804M is within about 2-fold (e.g., about 5-fold, about 7-fold, about 10-fold) of inhibition of wild-type RET (e.g., the compounds were similarly potent against wild-type RET and V804M). In some embodiments, selectivity for a wild-type or V804M RET kinase over another kinase is measured in an enzyme assay (e.g., an enzyme assay as provided herein). In some embodiments, the compounds provided herein exhibit selective cytotoxicity to RET-mutant cells.

In some embodiments, inhibition of G810S and/or G810R is similar to that observed for wild-type RET. For example, inhibition of G810S and/or G810R is within about 2-fold (e.g., about 5-fold, about 7-fold, about 10-fold) of inhibition of wild-type RET (e.g., the compounds were similarly potent against wild-type RET and G810S and/or G810R). In some embodiments, selectivity for a wildtype or G810S and/or G810R RET kinase over another kinase is measured in an enzyme assay (e.g., an enzyme assay as provided herein). In some embodiments, the compounds provided herein exhibit selective cytotoxicity to RET-mutant cells.

In some embodiments, the compounds provided herein exhibit brain and/or central nervous system (CNS) penetrance. Such compounds are capable of crossing the blood brain barrier and inhibiting a RET kinase in the brain and/or other CNS structures. In some embodiments, the compounds provided herein are capable of crossing the blood brain barrier in a therapeutically effective amount. For example, treatment of a patient with cancer (e.g., a RET-associated cancer such as a RET-associated brain or CNS cancer) can include administration (e.g., oral administration) of the compound to the patient. In some such embodiments, the compounds provided herein are useful for treating a primary brain tumor or metastatic brain tumor. For example, a RET-associated primary brain tumor or metastatic brain tumor.

In some embodiments, the compounds of Formula I (e.g., any one of Formulas I-A to I-L), or a pharmaceutically acceptable salt or solvate thereof, exhibit one or more of high GI absorption, low clearance, and low potential for drug-drug interactions.

Compounds of Formula I (e.g., any one of Formulas I-A to I-L), or a pharmaceutically acceptable salt or solvate thereof are useful for treating diseases and disorders which can be treated with a RET kinase inhibitor, such as RET-associated diseases and disorders, e.g., proliferative disorders such as cancers, including hematological cancers and solid tumors (e.g., advanced solid tumors and/or RET-fusion positive solid tumors), and gastrointestinal disorders such as IBS.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

As used herein, the terms "subject," "individual," or "patient," are used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer with a dysregulation of a RET gene, a RET protein, or expression or activity, or level of any of the same (a RET-associated cancer) (e.g., as determined using a regulatory agency-approved, e.g., FDA-approved, assay or kit). In some embodiments, the subject has a tumor that is positive for a dysregulation of a RET gene, a RET protein, or expression or activity, or level of any of the same (e.g., as determined using a regulatory agency-approved assay or kit). The subject can be a subject with a tumor(s) that is positive for a dysregulation of a RET gene, a RET protein, or expression or activity, or level of any of the same (e.g., identified as positive using a regulatory agency-approved, e.g., FDA-approved, assay or kit). The subject can be a subject whose tumors have a dysregulation of a RET gene, a RET protein, or expression or activity, or a level of the same (e.g., where the tumor is identified as such using a regulatory agency-approved, e.g., FDA-approved, kit or assay). In some embodiments, the subject is suspected of having a RET-associated cancer. In some embodiments, the subject has a clinical record indicating that the subject has a tumor that has a dysregulation of a RET gene, a RET protein, or expression or activity, or level of any of the same (and optionally the clinical record indicates that the subject should be treated with any of the compositions provided herein). In some embodiments, the patient is a pediatric patient.

The term "pediatric patient" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

In certain embodiments, compounds of Formula I (e.g., any one of Formulas I-A to I-L), or a pharmaceutically acceptable salt or solvate thereof are useful for preventing diseases and disorders as defined herein (for example, autoimmune diseases, inflammatory diseases, and cancer). The term "preventing" as used herein means the prevention of the onset, recurrence or spread, in whole or in part, of the disease or condition as described herein, or a symptom thereof.

The term "RET-associated disease or disorder" as used herein refers to diseases or disorders associated with or having a dysregulation of a RET gene, a RET kinase (also called herein RET kinase protein), or the expression or activity or level of any (e.g., one or more) of the same (e.g., any of the types of dysregulation of a RET gene, a RET kinase, a RET kinase domain, or the expression or activity or level of any of the same described herein). Non-limiting examples of a RET-associated disease or disorder include, for example, cancer and gastrointestinal disorders such as irritable bowel syndrome (IBS).

The term "RET-associated cancer" as used herein refers to cancers associated with or having a dysregulation of a RET gene, a RET kinase (also called herein RET kinase protein), or expression or activity, or level of any of the same. Non-limiting examples of a RET-associated cancer are described herein.

The phrase "dysregulation of a RET gene, a RET kinase, or the expression or activity or level of any of the same" refers to a genetic mutation (e.g., a chromosomal translocation that results in the expression of a fusion protein including a RET kinase domain and a fusion partner, a mutation in a RET gene that results in the expression of a RET protein that includes a deletion of at least one amino acid as compared to a wildtype RET protein, a mutation in a RET gene that results in the expression of a RET protein with one or more point mutations as compared to a wildtype RET protein, a mutation in a RET gene that results in the expression of a RET protein with at least one inserted amino acid as compared to a wildtype RET protein, a gene duplication that results in an increased level of RET protein in a cell, or a mutation in a regulatory sequence (e.g., a promoter and/or enhancer) that results in an increased level of RET protein in a cell), an alternative spliced version of a RET mRNA that results in a RET protein having a deletion of at least one amino acid in the RET protein as compared to the wild-type RET protein), or increased expression (e.g., increased levels) of a wildtype RET kinase in a mammalian cell due to aberrant cell signaling and/or dysregulated autocrine/paracrine signaling (e.g., as compared to a control non-cancerous cell). As another example, a dysregulation of a RET gene, a RET protein, or expression or activity, or level of any of the same, can be a mutation in a RET gene that encodes a RET protein that is constitutively active or has increased activity as compared to a protein encoded by a RET gene that does not include the mutation. For example, a dysregulation of a RET gene, a RET protein, or expression or activity, or level of any of the same, can be the result of a gene or chromosome translocation which results in the expression of a fusion protein that contains a first portion of RET that includes a functional kinase domain, and a second portion of a partner protein (i.e., that is not RET). In some examples, dysregulation of a RET gene, a RET protein, or expression or activity or level of any of the same can be a result of a gene translocation of one RET gene with another non-RET gene. Non-limiting examples of fusion proteins are described in Table 1. Non-limiting examples of RET kinase protein point mutations/insertions/deletions are described in Tables 2 and 2a. Additional examples of RET kinase protein mutations (e.g., point mutations) are RET inhibitor resistance mutations. Non-limiting examples of RET inhibitor resistance mutations are described in Tables 3 and 4.

In some embodiments, dysregulation of a RET gene, a RET kinase, or the expression or activity or level of any of the same can be caused by an activating mutation in a RET gene (see, e.g., chromosome translocations that result in the expression of any of the fusion proteins listed in Table 1). In some embodiments, dysregulation of a RET gene, a RET kinase, or the expression or activity or level of any of the same can be caused by a genetic mutation that results in the expression of a RET kinase that has increased resistance to inhibition by a RET kinase inhibitor and/or a multi-kinase inhibitor (MKI), e.g., as compared to a wildtype RET kinase (see, e.g., the amino acid substitutions in Tables 3 and 4). In some embodiments, dysregulation of a RET gene, a RET kinase, or the expression or activity or level of any of the same can be caused by a mutation in a nucleic acid encoding an altered RET protein (e.g., a RET fusion protein or a RET protein having a mutation (e.g., a primary mutation)) that results in the expression of an altered RET protein that has increased resistance to inhibition by a RET kinase inhibitor and/or a multi-kinase inhibitor (MKI), e.g., as compared to a wildtype RET kinase (see, e.g., the amino acid substitutions in Tables 3 and 4). The exemplary RET kinase point mutations, insertions, and deletions shown in Tables 2 and 2a can be caused by an activating mutation and/or can result in the expression of a RET kinase that has increased resistance to inhibition by a RET kinase inhibitor and/or a multi-kinase inhibitor (MKI).

The term "activating mutation" describes a mutation in a RET kinase gene that results in the expression of a RET kinase that has an increased kinase activity, e.g., as compared to a wildtype RET kinase, e.g., when assayed under identical conditions. For example, an activating mutation can result in the expression of a fusion protein that includes a RET kinase domain and a fusion partner. In another example, an activating mutation can be a mutation in a RET kinase gene that results in the expression of a RET kinase that has one or more (e.g., two, three, four, five, six, seven, eight, nine, or ten) amino acid substitutions (e.g., any combination of any of the amino acid substitutions described herein) that has increased kinase activity, e.g., as compared to a wildtype RET kinase, e.g., when assayed under identical conditions. In another example, an activating mutation can be a mutation in a RET kinase gene that results in the expression of a RET kinase that has one or more (e.g., two, three, four, five, six, seven, eight, nine, or ten) amino acids deleted, e.g., as compared to a wildtype RET kinase, e.g., when assayed under identical conditions. In another example, an activating mutation can be a mutation in a RET kinase gene that results in the expression of a RET kinase that has at least one (e.g., at least 2, at least 3, at least 4, at least 5, at least 6, at least 7, at least 8, at least 9, at least 10, at least 12, at least 14, at least 16, at least 18, or at least 20) amino acid inserted as compared to a wildtype RET kinase, e.g., the exemplary wildtype RET kinase described herein, e.g., when assayed under identical conditions. Additional examples of activating mutations are known in the art.

The term "wildtype" or "wild-type" describes a nucleic acid (e.g., a RET gene or a RET mRNA) or protein (e.g., a RET protein) that is found in a subject that does not have a RET-associated disease, e.g., a RET-associated cancer (and optionally also does not have an increased risk of developing a RET-associated disease and/or is not suspected of having a RET-associated disease), or is found in a cell or tissue from a subject that does not have a RET-associated disease, e.g., a RET-associated cancer (and optionally also does not have an increased risk of developing a RET-associated disease and/or is not suspected of having a RET-associated disease).

The term "regulatory agency" refers to a country's agency for the approval of the medical use of pharmaceutical agents with the country. For example, a non-limiting example of a regulatory agency is the U.S. Food and Drug Administration (FDA).

Provided herein is a method of treating cancer (e.g., a RET-associated cancer) in a patient in need of such treatment, the method comprising administering to the patient a therapeutically effective amount of a compound of Formula I (e.g., any one of Formulas I-A to I-L), or a pharmaceutically acceptable salt or solvate thereof or a pharmaceutical composition thereof. For example, provided herein are methods for treating a RET-associated cancer in a patient in need of such treatment, the method comprising a) detecting a dysregulation of a RET gene, a RET kinase, or the expression or activity or level of any of the same in a sample from the patient; and b) administering a therapeutically effective amount of a compound of Formula I (e.g., any one of Formulas I-A to I-L), or a pharmaceutically acceptable salt or solvate thereof. In some embodiments, the dysregulation of a RET gene, a RET kinase, or the expression or activity or level of any of the same includes one or more fusion proteins. Non-limiting examples of RET gene fusion proteins are described in Table 1. In some embodiments, the fusion protein is KIF5B-RET. In some embodiments, the dysregulation of a RET gene, a RET kinase, or the expression or activity or level of any of the same includes one or more RET kinase protein point mutations/insertions. Non-limiting examples of RET kinase protein point mutations/insertions/deletions are described in Tables 2 and 2a. In some embodiments, the RET kinase protein point mutations/insertions/deletions are selected from the group consisting of M918T, M918V, C634W, V804L, V804M, G810S, and G810R. In some embodiments, the RET kinase protein point mutations/insertions/deletions occur in a RET fusion protein (e.g., any of the RET gene fusion proteins described in Table 1). In some embodiments, a compound of Formula I is selected from: i) Examples 1-20, ii) Examples 21-40, iii) Examples 41-60, iv) Examples 61-80, v) Examples 81-100, vi) Examples 101-120, vii) Examples 121-140, or viii) Examples 141-151.

In some embodiments of any of the methods or uses described herein, the cancer (e.g., RET-associated cancer) is a hematological cancer. In some embodiments of any of the methods or uses described herein, the cancer (e.g., RET-associated cancer) is a solid tumor (e.g., an advanced solid tumor and/or a RET-fusion positive solid tumor). In some embodiments of any of the methods or uses described herein, the cancer (e.g., RET-associated cancer) is a lung cancer (e.g., small cell lung carcinoma or non-small cell lung carcinoma), thyroid cancer (e.g., papillary thyroid cancer, medullary thyroid cancer (e.g., sporadic medullary thyroid cancer or hereditary medullary thyroid cancer), differentiated thyroid cancer, recurrent thyroid cancer, or refractory differentiated thyroid cancer), thyroid ademona, endocrine gland neoplasms, lung adenocarinoma, bronchioles lung cell carcinoma, multiple endocrine neoplasia type 2A or 2B (MEN2A or MEN2B, respectively), pheochromocytoma, parathyroid hyperplasia, breast cancer, mammary cancer, mammary carcinoma, mammary neoplasm, colorectal cancer (e.g., metastatic colorectal cancer), papillary renal cell carcinoma, ganglioneuromatosis of the gastroenteric mucosa, inflammatory myofibroblastic tumor, or cervical cancer. In some embodiments of any of the methods or uses described herein, the cancer (e.g., RET-associated cancer) is selected from the group of: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, neoplasms by site, neoplasms, colon cancer, colorectal cancer, craniopharyngioma, cutaneous T-cell lymphoma, cutaneous angiosarcoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, thoracic neoplasms, head and neck neoplasms, CNS tumor, primary CNS tumor, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, neoplasms by site, neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, lung neoplasm, pulmonary cancer, pulmonary neoplasms, respiratory tract neoplasms, bronchogenic carcinoma, bronchial neoplasms, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy-associated breast cancer, primary central nervous system lymphoma, primary peritoneal cancer, prostate cancer, rectal cancer, colon cancer, colonic neoplasms, renal cell cancer, retinoblastoma, rhabdomyosarcoma, salivary gland cancer, sarcoma, Sezary syndrome, skin cancer, Spitz tumors, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, and Wilms' tumor.

In some embodiments, a hematological cancer (e.g., hematological cancers that are RET-associated cancers) is selected from the group consisting of leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF). In one embodiment, the hematological cancer (e.g., the hematological cancer that is a RET-associated cancer) is AML or CMML.

In some embodiments, the cancer (e.g., the RET-associated cancer) is a solid tumor. Examples of solid tumors (e.g., solid tumors that are RET-associated cancers) include, for example, thyroid cancer (e.g., papillary thyroid carcinoma, medullary thyroid carcinoma), lung cancer (e.g., lung adenocarcinoma, small-cell lung carcinoma), pancreatic cancer, pancreatic ductal carcinoma, breast cancer, colon cancer, colorectal cancer, prostate cancer, renal cell carcinoma, head and neck tumors, neuroblastoma, and melanoma. See, for example, Nature Reviews Cancer, 2014, 14, 173-186.

In some embodiments, the cancer is selected from the group consisting of lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

In some embodiments, the patient is a human.

Compounds of Formula I (e.g., any one of Formulas I-A to I-L), or a pharmaceutically acceptable salt or solvate thereof are also useful for treating a RET-associated cancer.

Accordingly, also provided herein is a method for treating a patient diagnosed with or identified as having a RET-associated cancer, e.g., any of the exemplary RET-associated cancers disclosed herein, comprising administering to the patient a therapeutically effective amount of a compound of Formula I (e.g., any one of Formulas I-A to I-L), or a pharmaceutically acceptable salt or solvate thereof, or a pharmaceutical composition thereof as defined herein.

Dysregulation of a RET kinase, a RET gene, or the expression or activity or level of any (e.g., one or more) of the same can contribute to tumorigenesis. For example, a dysregulation of a RET kinase, a RET gene, or expression or activity or level of any of the same can be a translocation, overexpression, activation, amplification, or mutation of a RET kinase, a RET gene, or a RET kinase domain. Translocation can include a gene translocation resulting in the expression of a fusion protein that includes a RET kinase domain and a fusion partner. For example, a fusion protein can have increased kinase activity as compared to a wildtype RET protein. In some embodiments, a mutation in a RET gene can involve mutations in the RET ligand-binding site, extracellular domains, kinase domain, and in regions involved in protein:protein interactions and downstream signaling. In some embodiments, a mutation (e.g., an activating mutation) in a RET gene can result in the expression of a RET kinase having one or more (e.g., two, three, four, five, six, seven, eight, nine, or ten) amino acid substitutions (e.g., one or more amino acid substitutions in the kinase domain (e.g., amino acid positions 723 to 1012 in a wildtype RET protein), a gatekeeper amino acid (e.g., amino acid position 804 in a wildtype RET protein), the P-loop (e.g., amino acid positions 730-737 in a wildtype RET protein), the DFG motif (e.g., amino acid positions 892-894 in a wildtype RET protein), ATP cleft solvent front amino acids (e.g., amino acid positions 758, 811, and 892 in a wildtype RET protein), the activation loop (e.g., amino acid positions 891-916 in a wildtype RET protein), the C-helix and loop preceeding the C-helix (e.g., amino acid positions 768-788 in a wildtype RET protein), and/or the ATP binding site (e.g., amino acid positions 730-733, 738, 756, 758, 804, 805, 807, 811, 881, and 892 in a wildtype RET protein). In some embodiments, a mutation can be a gene amplification of a RET gene. In some embodiments, a mutation (e.g., an activating mutation) in a RET gene can result in the expression of a RET kinase or RET receptor that lacks at least one amino acid (e.g., at least 2, at least 3, at least 4, at least 5, at least 6, at least 7, at least 8, at least 9, at least 10, at least 12, at least 14, at least 16, at least 18, at least 20, at least 25, at least 30, at least 35, at least 40, at least 45, or at least 50 amino acids) as compared to a wildtype RET protein. In some embodiments, dysregulation of a RET kinase can be increased expression (e.g., increased levels) of a wildtype RET kinase in a mammalian cell due to aberrant cell signaling and/or dysregulated autocrine/paracrine signaling (e.g., as compared to a control non-cancerous cell). In some embodiments, a mutation (e.g., an activating mutation) in a RET gene can result in the expression of a RET kinase or RET receptor that has at least one amino acid (e.g., at least 2, at least 3, at least 4, at least 5, at least 6, at least 7, at least 8, at least 9, at least 10, at least 12, at least 14, at least 16, at least 18, at least 20, at least 25, at least 30, at least 35, at least 40, at least 45, or at least 50 amino acids) inserted as compared to a wildtype RET protein. In some embodiments, dysregulation of a RET kinase can be increased expression (e.g., increased levels) of a wildtype RET kinase in a mammalian cell (e.g., as compared to a control non-cancerous cell), e.g., due to aberrant cell signaling and/or dysregulated autocrine/paracrine signaling. Other dysregulations can include RET mRNA splice variants. In some embodiments, the wildtype RET protein is the exemplary wildtype RET protein described herein.

In some embodiments, the dysregulation of a RET gene, a RET kinase, or expression or activity or level of any of the same, includes overexpression of wild-type RET kinase (e.g., leading to autocrine activation). In some embodiments, the dysregulation of a RET gene, a RET kinase protein, or expression or activity or level of any of the same, includes overexpression, activation, amplification, or mutation in a chromosomal segment comprising the RET gene or a portion thereof, including, for example, the kinase domain portion, or a portion capable of exhibiting kinase activity.

In some embodiments, the dysregulation of a RET gene, a RET kinase protein, or expression or activity or level of any of the same, includes one or more chromosome translocations or inversions resulting in a RET gene fusion. In some embodiments, the dysregulation of a RET gene, a RET kinase protein, or expression or activity or level of any of the same, is a result of genetic translocations in which the expressed protein is a fusion protein containing residues from a non-RET partner protein, and includes a minimum of a functional RET kinase domain.

Non-limiting examples of RET fusion proteins are shown in Table 1.

TABLE 1

Exemplary RET Fusion Partners and Cancers

| Fusion Partner | Non-limiting Exemplary RET-Associated Cancer(s) |
|---|---|
| BCR | Chronic Myelomonocytic Leukemia (CMML) |
| CLIP1 | Adenocarcinoma |
| KIF5B | NSCLC, Ovarian Cancer, Spitzoid Neoplasms; Lung Adenocarcinoma[3, 4, 14, 28]; Adenosquamous Carcinomas[15] |
| CCDC6 (also called PTC1, D10S170, or H4) | NSCLC, Colon Cancer, Papillary Thyroid Cancer; Adenocarcinomas; Lung Adenocarcinoma; Metastatic Colorectal Cancer[5]; Adenosquamous Carcinomas[15], Breast Cancer[30] |
| PTC1ex9 (a novel CCDC6 rearrangement) | Metastatic papillary thyroid cancer[2] |
| NCOA4 (also called PTC3, ELE1, and RFG) | Papillary Thyroid Cancer[21], NSCLC, Colon Cancer, Salivary Gland Cancer, Metastatic Colorectal Cancer[5]; Lung Adenocarcinoma[15]; Adenosquamous Carcinomas[15] Diffuse Sclerosing Variant of Papillary Thyroid Cancer[16], Breast Cancer[30], Acinic Cell Carcinoma[32], Mammary Analog Secretory Carcinoma[33] |
| TRIM33 (also called PTC7, RFG7, and TIF1G) | NSCLC, Papillary Thyroid Cancer, Lung Adenocarcinoma[46], Various[22] |
| ERC1 (also called ELKS and RAB61P2) | Papillary Thyroid Cancer, Breast Cancer |
| FGFR1OP | CMML, Primary Myelofibrosis with secondary Acute Myeloid Leukemia |
| MBD1(also known as PCM1) | Papillary Thyroid Cancer |

TABLE 1-continued

Exemplary RET Fusion Partners and Cancers

| Fusion Partner | Non-limiting Exemplary RET-Associated Cancer(s) |
|---|---|
| PRKAR1A (also called PTC2) | Papillary Thyroid Cancer |
| TRIM24 (also called PTC6) | Papillary Thyroid Cancer |
| KTN1 (also called PTC8) | Papillary Thyroid Cancer |
| GOLGA5 (also called PTC5) | Papillary Thyroid Cancer, Spitzoid Neoplasms |
| HOOK3 | Papillary Thyroid Cancer |
| KIAA1468 (also called PTC9 and RFG9) | Papillary Thyroid Cancer, Lung Adenocarcinomas[8, 12] |
| TRIM27 (also called RFP) | Papillary Thyroid Cancer |
| AKAP13 | Papillary Thyroid Cancer |
| FKBP15 | Papillary Thyroid Cancer, Acute Myeloid Leukemia[46] |
| SPECC1L | Papillary Thyroid Cancer; Thyroid Gland Carcinoma |
| TBL1XR1 | Papillary Thyroid Cancer; Thyroid Gland Carcinoma |
| CEP55 | Diffuse Gastric Cancer[7] |
| CUX1 | Lung Adenocarcinoma |
| ACBD5 | Papillary Thyroid Carcinoma |
| MYH13 | Medullary Thyroid Carcinoma[1] |
| Uncharacterized | Inflammatory Myofibroblastic Tumor[6] |
| PIBF1 | Bronchiolus Lung Cell Carcinoma[9] |
| KIAA1217 (also called SKT) | Papillary Thyroid Cancer[10, 13] Lung Adenocarcinoma[14] NSCLC[14] |
| MPRIP | NSCLC[11] |
| HRH4-RET | Thyroid Cancer and/or Paillary Thyroid Carcinoma[17] |
| Ria-RET | Thyroid Cancer and/or Papillary Thyroid Carcinoma[17] |
| RFG8 | Papillary Thyroid Carcinoma[18] |
| FOXP4 | Lung Adenocarcinoma[19] |
| MYH10 | Infantile Myofibromatosis[20] |
| HTIF1 | Various[22] |
| H4L | Various[22] |
| PTC4 (a novel NCO4/ELE1 rearrangement) | Papillary Thyroid Cancer[23] |
| FRMD4A | NSCLC[24] |
| SQSTM 1 | Papillary Thyroid Carcinoma[25] |
| AFAP1L2 | Papillary Thyroid Carcinoma[25] |
| AFAP1 | NSCLC[31] |
| PPFIBP2 | Papillary Thyroid Carcinoma[25] |
| EML4 | NSCLC |
| PARD3 | NSCLC[27] |
| RASGEF1A | Breast Cancer[30] |
| TEL | In vitro[34] |
| RUFY1 | Colorectal Cancer[35] |
| OLFM4 | Small-Bowel Cancer[36] |
| UEVLD | Papillary Thyroid Carcinoma[29] |
| DLG5 | Non-Anaplastic Thyroid (NAT) Cancer[37] |
| RRBP1 | Colon Cancer[38] |
| ANK3 | Papillary Thyroid Carcinoma[39] |
| PICALM | NSCLC[40] |
| MYO5C | NSCLC[41] |
| EPHA5 | NSCLC[40] |
| RUFY2 | Lung Cancer[42] |
| KIF13A | Lung Adenocarcinoma[43], NSCLC[45] |
| TNIP1 | Colorectal Cancer[44] |
| SNRNP70 | Colorectal Cancer[44] |
| MRLN | Thyroid Carcinoma[46] |
| LMNA | Spitzoid Melanoma[47] |
| RUFY3 | Papillary Thyroid Carcinoma |
| TFG | |
| MYO5A | Pigmented spindle cell nevus (PSCN) of Reed[48] |
| ADD3 | Lung adenocarcinoma[49] |
| JMJD1C | NSCLC[50] |
| RBPMS | |
| DOCK1 | |
| TAF3 | |

[1]Grubbs et al., J. Clin. Endocrinol. Metab. 100:788-793, 2015.
[2]Halkova et al., Human Pathology 46:1962-1969, 2015.
[3]U.S. Pat. No. 9,297,011
[4]U.S. Pat. No. 9,216,172
[5]Le Rolle et al., Oncotarget. 6(30):28929-37, 2015.
[6]Antonescu et al., Am J Surg Pathol. 39(7):957-67, 2015.
[7]U.S. Patent Application Publication No. 2015/0177246.
[8]U.S. Patent Application Publication No. 2015/0057335.
[9]Japanese Patent Application Publication No. 2015/109806A.
[10]Chinese Patent Application Publication No. 105255927A.
[11]Fang, et al. Journal of Thoracic Oncology 11.2 (2016): S21-S22.
[12]European Patent Application Publication No. EP3037547A1.
[13]Lee et al., Oncotarget. DOI: 10.18632/oncotarget.9137, e-published ahead of printing, 2016.
[14]Saito et al., Cancer Science 107:713-720, 2016.
[15]Pirker et al., Transl. Lung Cancer Res. 4(6):797-800, 2015.
[16]Joung et al., Histopathology 69(1):45-53, 2016.
[17]PCT Patent Application Publication No. WO 2016/141169.
[18]Klugbauer et al., Cancer Res., 60(24):7028-32, 2000.
[19]Bastian et al., Journal of Molecular Diagnostics, 18(6):1027, Abstract Number: S120, 2016 Annual Meeting of the Association for Molecular Pathology, Charlotte, NC, 2016.
[20]Rosenzweig et al., Pediatr Blood Cancer, doi:10.1002/pbc.26377, 2016.
[21]Su et al., PLoS One, 11(111): e0165596, 2016.
[22]U.S. Pat. No. 9,487,491.
[23]Fugazzola et al., Oncogene, 13(5):1093-7, 1996.
[24]Velcheti et al., J Thorac Oncol., 12(2):e15-e16. doi: 10.1016/j.jtho.2016.11.274, 2017.
[25]Kato et al, Clin Cancer Res. 2017 Apr. 15;23(8):1988-1997. doi: 10.1158/1078-0432.CCR-16-1679. Epub 2016 Sep. 28.
[26]Drilon, Alexander, et al. "A phase 1/1b study of RXDX-105, an oral RET and BRAF inhibitor, in patients with advanced solid tumors." Aug. 8 (2016): 7.
[27]Sabari et al., Oncoscience, Advance Publications, www.impactjournals.com/oncoscience/files/papers/1/345/345.pdf, 2017.
[28]U.S. Patent Application Publication No. 2017/0014413.
[29]Lu et al., Oncotarget, 8(28):45784-45792, doi: 10.18632/oncotarget.17412, 2017.
[30]Hirshfield et al., Cancer Research, (February 2017) Vol. 77, No. 4, Supp. 1. Abstract Number: P3-07-02. Meeting Info: 39th Annual CTRC-AACR San Antonio Breast Cancer Symposium. San Antonio, TX, United States. 06 Dec. 2016-10 Dec. 2016.
[31]Morgensztern et al., Journal of Thoracic Oncology, (January 2017) Vol. 12, No. 1, Supp. 1, pp. S717-S718, Abstract Number: P1.07-035, Meeting Info: 17th World Conference of the International Association for the Study of Lung Cancer, IASLC 2016. Vienna, Austria. 04 Dec. 2016.
[32]Dogan et al., Laboratory Investigation, (February 2017) Vol. 97, Supp. 1, pp. 323A. Abstract Number: 1298, Meeting Info: 106th Annual Meeting of the United States and Canadian Academy of Pathology, USCAP 2017. San Antonio, TX, United States.
[33]Dogan et al., MODERN PATHOLOGY, Vol. 30, Supp. [2], pp. 323A-323A. MA 1298, 2017.
[34]PCT Patent Application Publication No. WO 2017/146116.
[35]PCT Patent Application Publication No. WO 2017/122815.
[36]Reeser et al., J. Mol. Diagn., 19(5):682-696, doi: 10.1016/j.jmoldx.2017.05.006, 2017.
[37]Ibrahimpasic et al., Clin. Cancer Res., doi: 10.1158/1078-0432.CCR-17-1183, 2017.
[38]Kloosterman et al., Cancer Res., 77(14):3814-3822. doi: 10.1158/0008-5472.CAN-16-3563, 2017.
[39]Chai et al., Oncology Reports, 35(2): 962-970. doi: 10.3892/or.2015.4466, 2015.
[40]Gautschi et al. Journal of Clinical Oncology, 35(13) 1403-1410. doi: 10.1200/JCO.2016.70.9352, 2017.
[41]Lee et al. Annals of Oncology, 28(2), 292-297. doi: 10.1093/annonc/mdw559, 2016.
[42]Zheng et al. Nature Medicine, 20(12), 1479-1484. doi: 10.1038/nm.3729, 2014.
[43]Zhang et al. Lung Cancer, 118, 27-29. doi: 10.1016/j.lungcan.2017.08.019, 2018.
[44]Morano et al. Molecular Cancer Therapeutics, (January 2018) Vol. 17, No. 1, Supp. Supplement 1. Abstract Number: B049. Meeting Info: AACR-NCI-EORTC International Conference: Molecular Targets and Cancer Therapeutics 2017.
[45]Wang et al. Journal of Thoracic Oncology, (November 2017) Vol. 12, No. 11, Supp. Supplement 2, pp. S2105. Abstract Number: P2.02-018. Meeting Info: 18th World Conference on Lung Cancer of the International Association for the Study of Lung Cancer, IASLC 2017. Yokohama, Japan. 15 Oct. 2017-18 Oct. 2017.
[46]Gao et al. Cell Reports, 23(1), 227-238. doi: 10.1016/j.celrep.2018.03.050, 2018.
[47] U.S. Patent Application Publication No. 2016/0010068.
[48]VandenBoom, et al. Am. J. Surg. Pathol. 42(8): 1042-1051, 2018. doi: 10.1097/PAS.0000000000001074
[49]Cao, et al. Onco. Targets. Ther. 2018(11):2637-2646, 2018. doi: 10.2147/OTT.S155995
[50]Luo, et al. Int. J. Cancer, 2018. epub ahead of print. doi: 10.1002/ijc.31542

In some embodiments, the dysregulation of a RET gene, a RET kinase, or expression or activity or level of any of the same, includes one or more deletions (e.g., deletion of an amino acid at position 4), insertions, or point mutation(s) in a RET kinase. In some embodiments, the dysregulation of a RET gene, a RET kinase, or expression or activity or level of any of the same, includes a deletion of one or more residues from the RET kinase, resulting in constitutive activity of the RET kinase domain.

In some embodiments, the dysregulation of a RET gene, a RET kinase, or expression or activity or level of any of the same, includes at least one point mutation in a RET gene that results in the production of a RET kinase that has one or more amino acid substitutions, insertions, or deletions as compared to the wild-type RET kinase (see, for example, the point mutations listed in Table 2).

TABLE 2

| RET Kinase Protein Amino Acid Substitutions/Insertions/Deletions[A] |
| --- |
| Amino acid position 2 |
| Amino acid position 3 |
| Amino acid position 4 |
| Amino acid position 5 |
| Amino acid position 6 |
| Amino acid position 7 |
| Amino acid position 8 |
| Amino acid position 11 |
| Amino acid position 12 |
| Amino acid position 13 |
| Amino acid position 20 |
| Amino acid position 32 (e.g., S32L) |
| Amino acid position 34 (e.g., D34S) |
| Amino acid position 40 (e.g., L40P) |
| Amino acid position 45 (e.g., A45A)[39] |
| Amino acid position 56 (e.g., L56M)[30] |
| Amino acid position 64 (e.g., P64L) |
| Amino acid position 67 (e.g., R67H) |
| Amino acid position 77 (e.g., R77C)[65] |
| Amino acid position 114 (e.g., R114H) |
| Amino acid position 136 (e.g., glutamic acid to stop codon) |
| Amino acid position 145 (e.g., V145G) |
| Amino acid position 177 (e.g., R177L)[67] |
| Amino acid position 180 (e.g., arginine to stop codon) |
| Amino acid position 200 |
| Amino acid position 270 (e.g., P270L)[65] |
| Amino acid position 278 (e.g., T278N)[57] |
| Amino acid position 292 (e.g., V292M) |
| Amino acid position 294 |
| Amino acid position 321 (e.g., G321R) |
| Amino acid position 330 (e.g., R330Q) |
| Amino acid position 338 (e.g., T338I) |
| Amino acid position 360 (e.g., R360W) |
| Amino acid position 373 (e.g., alanine to frameshift) |
| Δ Amino acid positions 378-385 with insertion of one amino acid (e.g., D378-G385 > E) |
| Amino acid position 393 (e.g., F393L) |
| Amino acid position 423 (e.g., G423R)[27] |
| Amino acid position 428 (e.g., E428K)[57] |
| Amino acid position 432 (e.g., A432A[39]) |
| Amino acid position 446 (e.g., G446R)[28] |
| Δ Amino acid positions 505-506 (6-Base Pair In-Frame Germline Deletion in Exon 7)[3] |
| Amino acid position 510 (e.g., A510V) |
| Amino acid position 511 (e.g., E511K) |
| Amino acid position 513 (e.g., G513D)[7*] |
| Amino acid position 515 (e.g., C515S, C515W[4]) |
| Amino acid position 525 (e.g., R525W)[7*] |
| Amino acid position 531 (e.g., C531R, or 9 base pair duplication[2]) |
| Amino acid position 532 (e.g., duplication)[2] |
| Amino acid position 533 (e.g., G533C, G533S) |
| Amino acid position 534 (e.g., L534L)[6] |
| Amino acid position 550 (e.g., G550E) |
| Amino acid position 591 (e.g., V591I) |
| Amino acid position 593 (e.g., G593E) |
| Amino acid position 595 (e.g., E595D and E595A)[18] |
| Amino acid position 600 (e.g., R600Q) |
| Amino acid position 602 (e.g., I602V)[6] |
| Amino acid position 603 (e.g., K603Q, K603E[2]) |
| Amino acid position 606 (e.g., Y606C) |
| Amino acid position 609 (e.g., C609Y, C609S, C609G, C609R, C609F, C609W, C609C[32]) |
| Amino acid position 611 (e.g., C611R, C611S, C611G, C611Y, C611F, C611W) |
| Amino acid position 616 (e.g., E616Q)[23] |
| Δ Amino acid position 616[64] |
| Amino acid position 618 (e.g., C618S, C618Y, C618R, C618G, C618F, C618W, stop[56]) |
| Amino acid position 619 (e.g., F619F) |
| Amino acid position 620 (e.g., C620S, C620W, C620R, C620G, C620L, C620Y, C620F, C620A[47]) |
| Amino acid position 622 (e.g., P622L)[68] |
| Amino acid position 623 (e.g., E623K) |
| Amino acid position 624 (e.g., D624N) |
| Amino acid position 630 (e.g., C630A, C630R, C630S, C630Y, C630F, C630W) |
| Δ Amino acid position 630[56] |

TABLE 2-continued

RET Kinase Protein Amino Acid Substitutions/Insertions/Deletions[4]

Amino acid position 631 (e.g., D631N, D631Y, D631A, D631G, D631V, D631E, )
Δ Amino acid position 631[69]
Amino acid positions 631-633 > V (i.e., residues 631-633 are replaced with a single valine residue)
Amino acid positions 631-633 > A (i.e., residues 631-633 are replaced with a single alanine residue)
Amino acid positions 631-633 > E (i.e., residues 631-633 are replaced with a single glutamic acid residue)
Δ Amino acid positions 631-633 (e.g., D631-L633)
Δ Amino acid positions 631-634 (e.g., D631-C634)
Amino acid position 632 (e.g., E632K, E632G[5,11], E632V[62], 632 to frameshift[47])
Δ Amino acid positions 632-633 (e.g., E632-L633 in either the somatic cells, or a 6-Base Pair In-Frame Germline Deletion in Exon 11[9])
Amino acid positions 632-639>HR (i.e., residues 632-639 are replaced with two residues, histidine and arginine)
Amino acid position 633 (e.g., L633R[62], 9 base pair duplication[2])
Amino acid position 634 (e.g., C634W, C634Y, C634S, C634R, C634F, C634G, C634L, C634A, or C634T, a 9 base pair deletion[62], a 9 base pair duplication[56], or a 12 base pair duplication[2]) (e.g., causing MTC)
Δ Amino acid position 634[56]
Amino acid position 632/633/634 (E632V/L633R/634 9 base pair deletion)[62]
Amino acid position 635 (e.g., R635G or an insertion ELCR[2])
Amino acid position 636 (e.g., T636P[2], T636M[4])
Amino acid position 638 (e.g., isoleucine to frameshift[47])
Amino acid position 640 (e.g., A640G)
Amino acid position 634/640 (e.g., C634R/A640G)[56]
Amino acid position 641 (e.g., A641S, A641T[8])
Amino acid position 634/641 (e.g., C634S/A641S)[56]
Amino acid position 639/641 (e.g., A639G/A641R)[56]
Amino acid position 644 (e.g., T644M)[59]
Amino acid position 648 (e.g., V648I)
Amino acid position 649 (e.g., S649L)[28]
Amino acid position 661 (e.g., H661H)[6]
Amino acid position 664 (e.g., A664D)
Amino acid position 665 (e.g., H665Q)
Amino acid position 666 (e.g., K666E, K666M, K666N, K666R)
Amino acid position 675 (T675T, silent nucleotide change)[18]
Amino acid position 679 (e.g., P679P)[6]
Amino acid position 680 (e.g., A680T, alanine to frameshift)[6]
Amino acid position 686 (e.g., S686N)
Amino acid position 689 (e.g., S689T)[18]
Amino acid position 691 (e.g., G691S)
Amino acid position 694 (e.g., R694Q)
Amino acid position 700 (e.g., M700L)
Amino acid position 706 (e.g., V706M, V706A)
Amino acid position 713 splice variant (e.g., E713K (e.g., a splice variant))[6]
Amino acid position 714 (e.g., D714Y)[57]
Amino acid position 727 (e.g., G727E)[6]
Amino acid position 732 (e.g., E732K)[20]
Amino acid position 734 (e.g., E734K)[48]
Amino acid position 736 (e.g., G736R)[6]
Amino acid position 738 (e.g., V738V)[6]
Amino acid position 742 (e.g., T742M)[51]
Amino acid position 748 (e.g., G748C)
Amino acid position 749 (e.g., R749T)[36]
Amino acid position 750 (e.g., A750P, A750G)[6]
Amino acid position 752 (e.g., Y752Y)[6]
Amino acid position 751 (e.g., G751G)[6]
Amino acid position 762 (e.g., E762Q)[36]
Amino acid position 765 (e.g., S765P, S765F)
Amino acid position 766 (e.g., P766S, P766M)[6]
Amino acid position 768 (e.g., E768Q, E768D, E768N)[46]
Amino acid position 769 (e.g., L769L)[6]
Amino acid position 770 (e.g., R770Q)
Amino acid position 771 (e.g., D771N)
Amino acid position 777 (e.g., N777S)
Amino acid position 778 (e.g., V778I)
Amino acid position 781 (e.g., Q781R)
Amino acid position 788 (e.g., I788I)[32]
Amino acid position 790 (e.g., L790F)
Amino acid position 768/790 (e.g., E768D/L790T)[40]
Amino acid position 791 (e.g., Y791F, Y791N)[24]
Amino acid position 634/791 (e.g., C634Y/Y791F)[55]
Amino acid position 790/791 (e.g., L790F/Y791F)[55]
Amino acid position 802
Amino acid position 804 (e.g., V804L[15, 16], V804M[15, 16], V804E[12]) (e.g., causing MTC)
Amino acid position 778/804[50] (e.g., V778I/V804M)[54]
Amino acid position 781/804 (e.g., Q781R/V804M)[41]

TABLE 2-continued

RET Kinase Protein Amino Acid Substitutions/Insertions/Deletions[a]

Amino acid position 805 (e.g., E805K)
Amino acid position 804/805 (e.g., V804M/E805K)[17]
Amino acid position 806 (e.g., Y806F, Y806S[12], Y806G, Y806C[2, 12, 14], Y806E[14], Y806H[12], Y806N[12], Y806Y[32])
Amino acid position 804/806 (e.g., V804M/Y806C)[38]
Amino acid position 810 (e.g., G810R[12], G810S[12], G810A[13], G810C, G810V, and G810D)
Amino acid position 818 (e.g., E818K)
Amino acid position 819 (e.g., S819I)
Amino acid position 820 (e.g., R820L)[57]
Amino acid position 823 (e.g., G823E)
Amino acid position 826 (e.g., Y826M, Y826S)[10]
Amino acid position 828 (e.g., G828R)[57]
Amino acid position 833 (e.g., R833C)
Amino acid position 836 (e.g., S836S)[19]
Amino acid position 841 (e.g., P841L, P841P)
Amino acid position 843 (e.g., E843D)
Amino acid position 844 (e.g., R844W, R844Q, R844L)
Amino acid position 845 (e.g., A845A)[63]
Amino acid position 848 (e.g., M848T)
Amino acid position 852 (e.g., I852M)
Amino acid position 853 (e.g., S853T)[57]
Amino acid position 865 (e.g., L865V)[12]
Amino acid position 866 (e.g., A866W)[33]
Amino acid position 867 (e.g., E867K)[37]
Amino acid position 870 (e.g., L870F)[12]
Amino acid position 873 (e.g., R873W, R873Q[42])
Amino acid position 876 (e.g., A876V)
Amino acid position 881 (e.g., L881V)
Amino acid position 882
Amino acid position 883 (e.g., A883F, A883S, A883T, A883Y[53], A883V)
Amino acid position 884 (e.g., E884K, E884V[35])
Amino acid position 886 (e.g., R886W)
Amino acid position 891 (e.g., S891A, S891S[32], S891L[35])
Amino acid position 893 (e.g., F893L)[42]
Amino acid position 894 (e.g., G894S)[43]
Amino acid position 897 (e.g., R897Q, R897P)
Amino acid position 898 (e.g., D898V, D898Y[66])
Δ Amino acid position 898
Δ Amino acid positions 898-902[58]
Δ Amino acid positions 899-902[47]
Δ Amino acid positions 898-901[47]
Δ Amino acid positions 632-633/Δ Amino acid positions 898-901[47]
Amino acid position 900 (e.g., Y900F)[22]
Amino acid position 901 (e.g., E901K)
Amino acid position 904 (e.g., S904F, S904S, S904C[2], S904T[57])
Amino acid position 691/904 (e.g., G691S/S904S)[49]
Amino acid position 804/904 (e.g., V804M/S904C)[38]
Amino acid position 905 (e.g., Y905F)[22]
Amino acid position 907 (e.g., K907E, K907M)
Amino acid position 908 (e.g., R908K)
Amino acid position 911 (e.g., G911D, G911G (e.g., a splice variant)[6])
Amino acid position 912 (e.g., R912P, R912Q)
Amino acid position 918 (e.g., M918T[2], M918V, M918L[6]) (e.g., causing MTC)
Amino acid position 591/918 (e.g., V591I/M918T)[61]
Amino acid position 620/918 (e.g., C620F/M918T)[47]
Amino acid position 891/918 (e.g., S891A/M918T)[47]
Δ Amino acid position 898-901/M918T[47]
Amino acid position 919 (e.g., A919V, A919P[52])
Amino acid position 768/919[54]
Amino acid position 921 (e.g., E921K, E921D)
Amino acid position 911/918/921 (e.g., G911E/M918T/E921K)[61]
Amino acid position 922 (e.g., S922P, S922Y)
Amino acid position 924 (e.g., F924S)[6]
Amino acid position 930 (e.g., T930M)
Amino acid position 961 (e.g., F961L)
Amino acid position 972 (e.g., R972G)
Amino acid position 973 (e.g., P973T)[57]
Amino acid position 977 (e.g., S977R)[37]
Amino acid position 981 (e.g., Y981F)[22]
Amino acid position 982 (e.g., R982C)[70]
Amino acid position 634/691/982 (e.g., C634R/G691S/R982C)[45]
Amino acid position 1009 (e.g., M1009V)
Amino acid position 1015 (e.g., Y1015F)[22]
Amino acid position 1017 (e.g., D1017N)
Amino acid position 1041 (e.g., V1041G)
Amino acid position 1047 (e.g., P1047S)[65]
Amino acid position 1051 (e.g., A1051T)[57]
Δ Amino acid position 1059[57]

TABLE 2-continued

RET Kinase Protein Amino Acid Substitutions/Insertions/Deletions[A]

Amino acid position 1064 (e.g., M1064T)
Amino acid position 1096 (e.g., Y1096F)[21]
Amino acid position 1105 (e.g., A1105V)[57]
Amino acid position 1109 (e.g., M1109T)[34]
RET+3[1]
(In-Frame Deletion in Exons 6 and 11)[25]
(3bp In-Frame Deletion in Exon 15)[26]
Nucleotide position 2136 + 2 (e.g., 2136 + 2T > G)[29]
(del632-636 ins6)[31]
Amino acid positions 791 and 852 (e.g., Y791F + I852M)[31]
Amino acid positions 634 and 852 (e.g., C634R + I852M)[31]
c.1893_1895del[44]

[A]The RET kinase mutations shown may be activating mutations and/or confer increased resistance of the RET kinase to a RET kinase inhibitor and/or a multi-kinase inhibitor (MKI), e.g., as compared to a wildtype RET kinase.
[1]U.S. Patent Application Publication No. 2014/0272951.
[2]Krampitz et al., Cancer 120:1920-1931, 2014.
[3]Latteyer, et al., J. Clin. Endocrinol. Metab. 101(3): 1016-22, 2016.
[4]Silva, et al. Endocrine 49.2: 366-372, 2015.
[5]Scollo, et al., Endocr. J. 63(1): 87-91, 2016.
[6]Jovanovic, et al., Prilozi 36(1): 93-107, 2015.
[7]Qi, et al., Oncotarget. 6(32): 33993-4003, 2015. *R525W and G513D appear to act in combination with S891A to enchance oncogenic activity.
[8]Kim, et al. ACTA ENDOCRINOLOGICA-BUCHAREST 11.2, 189-194, 2015.
[9]Cecchirini, et al. Oncogene, 14, 2609-2612, 1997.
[10]Karrasch, et al. Eur. Thyroid J., 5(1): 73-7, 2016.
[11]Scollo et al., Endocr. J. 63: 87-91, 2016.
[12]PCT Patent Application Publication No. WO 2016/127074.
[13]Huang et al., Mol. Cancer Ther., Aug. 5, 2016 pii: molcanther.0258.2016. [Epub ahead of print].
[14]Carlomagno, et al., Endocr. Rel. Cancer 16(1): 233-41, 2009.
[15]Yoon et al., J. Med. Chem. 59(1): 358-73, 2016.
[16]U.S. Patent No. 8,629,135.
[17]Cranston, et al., Cancer Res. 66(20): 10179-87, 2006.
[18]Kheiroddin et al., Clin. Lab. 62(5): 871-6, 2016.
[19]Ceolin et al., PLoS One. 11(2): e0147840, doi: 10.1371/journal.pone.0147840, 2016.
[20]Mamedova et al., Summer Undergraduate Research Programs (SURP) Student Abstracts, University of Oklahoma Health Sciences Center, 2016.
[21]Liu et al., J. Biol. Chem., 271(10): 5309-12, 1995.
[22]Kato et al., Cancer Res., 62: 2414-22, 2002.
[23]Grey et al., Endocrine Pathology, doi: 10.1007/s12022-016-9451-6, 2016.
[24]De Almeida et al., Endocrine Reviews, 2016, Vol. 37, No. 2, Supp. Supplement 1. Abstract Number: SUN-068; 98th Annual Meeting and Expo of the Endocrine Society, ENDO 2016. Boston, MA, US. Apr. 1, 2016-Apr. 4, 2016.
[25]Vanden et al., Annals of Oncology, 2016, Vol. 27, Supp. Supplement 6. Abstract Number: 427PD; 41st European Society for Medical Oncology Congress, ESMP 2016. Copenhagen, Denmark. Oct. 7, 2016-Oct. 11, 2016.
[26]Romei et al., European Thyroid Journal (August 2016) Vol. 5, Supp. Supplement 1, pp. 75; 39th Annual Meeting of the European Thyroid Association, ETA 2016. Copenhagen, Denmark. Sep. 3, 2016-Sep. 6, 2016.
[27]Lee et al., Oncotarget, 8(4): 6579-6588, doi: 10.18632/oncotarget. 14172, 2017.
[28]Zhang et al., Laboratory Investigation, (February 2017) Vol. 97, Supp. 1, pp. 209A. Abstract Number: 840, Meeting Info: 106th Annual Meeting of the United States and Canadian Academy of Pathology, USCAP 2017. San Antonio, TX, United States.
[29]Borecka et al., European Journal of Cancer, (July 2016) Vol. 61, No. 1, pp. S26, Abstract Number: 162, Meeting Info: 24th Biennial Congress of the European Association for Cancer Research, EACR 2016. Manchester, United Kingdom.
[30]Corsello et al., Endocrine Reviews, (JUNE 2014) Vol. 35, No. 3, Suppl. S, pp. SUN-0322, Meeting Info.: 96th Annual Meeting and Expo of the Endocrine-Society, Chicago, IL, USA, Jun. 21-24, 2014.
[31]Gazizova et al., Endocrine Reviews, (JUNE 2014) Vol. 35, No. 3, Suppl. S, pp. SAT-0304, Meeting Info.: 96th Annual Meeting and Expo of the Endocrine-Society, Chicago, IL, USA, Jun. 21-24, 2014.
[32]Sromek et al., Endocr Pathol., doi: 10.1007/s12022-017-9487-2, 2017.
[33]U.S. Patent Application Publication No. 2017/0267661.
[34]Davila et. al., Rare Tumors, 2017; 9(2): 6834. doi: 10.4081/rt.2017.6834.
[35]U.S. Patent Application Publication No. 2018/0009818.
[36]PCT Patent Application Publication No. WO 2017/197051
[37]European Patent Application Publication No. 3271848
[38]Roskoski and Sadeghi-Nejad, Pharmacol. Res., 128, 1-17. doi: 10.1016/j.phrs.2017.12.021, 2018.
[39]Kaczmarek-Ryś, et al. Endocrine-related cancer 25(4): 421-436. doi: 10.1530/ERC-17-0452, 2018.
[40]Raue, et al. J. Clin Endocrinol Metab, 103(1): 235-243. doi: 10.1210/jc.2017-01884, 2018.
[41]Nakao, et al. Head and Neck, 35: E363-E368. doi: 10.1002/hed.23241, 2013.
[42]Attié, et al. Human Molecular Genetics 4(8): 1381-1386. doi: 10.1093/hmg/4.8.1381, 1995.
[43]Fitze, et al. Lancet, 393(9313): 1200-1205. doi: 10.1016/S0140-6736(02)08218-1, 2002.
[44]Weng, et al. Zhonghua Nei Ke Za Zhi, 57(2):134-137. doi: 10.3760/cma.j.issn.0578-1426.2018.02.010, 2018.
[45]Chen, et al. Medical Journal of Chinese People's Liberation Army 38.4 (2013): 308-312.
[46]Gudernova, et al. eLife, 6:e21536. doi: 10.7554/eLife.21536, 2017.
[47]Romei, et al. Oncotarget, 9(11): 9875-9884. doi: 10.18632/oncotarget.23986, 2018.
[48]Plaza-Menacho. Endocr Relat Cancer, 25(2): T79-T90. doi: 10.1530/ERC-17-0354, 2017.
[49]Guerin, et al. Endocr Relat Cancer, 25(2): T15-T28. doi: 10.1530/ERC-17-0266, 2017.
[50]Roy et al. Oncologist, 18(10): 1093-1100. doi: 10.1634/theoncologist.2013-0053, 2013
[51]U.S. Patent Application Publication No. 2017/0349953
[52]Santoro, et al. Endocrinology, 145(12), 5448-5451, 2004. doi: 10.1210/en.2004-0922
[53]U.S. Patent No. 9,006,256
[54]Yeganeh, et al. Asian Pac J Cancer Prev, 16(6), 2107-17. doi: 10.7314/APJCP.2015.16.6.2107
[55]Mulligan, L. M, Nature Reviews Cancer, 14(3), 173, 2014. doi: 10.1038/nrc3680
[56]Arighi, et al, Cytokine & Growth Factor Reviews, 16(4-5), 441-467, 2005. doi: 10.1016/j.cytogfr.2005.05.010
[57]Dabir, et al, Journal of Thoracic Oncology, 9(9), 1316-1323, 2014. doi: 10.1097/JTO.0000000000000234

TABLE 2-continued

RET Kinase Protein Amino Acid Substitutions/Insertions/Deletions[4]

[58]Uchino, et al, Cancer Science, 90(11), 1231-1237, 1999. doi: 10.1111/j.1349-7006.1999.tb00701.x
[59]Krampitz. Cancer, 120(13), 1920-1931, 2014: 10.1002/cncr.28661
[60]Jhiang et al, Thyroid 6(2), 1996. doi: 10.1089/thy.1996.6.115
[61]Dvořáková, et al, Thyroid, 16(3), 311-316, 2006. doi: 10.1089/thy.2006.16.311
[62]Severskaya et al, Genomics Transcriptomics Proteomics, 40(3) 425-435.
[63]Elisei, et al, Journal of Genetic Syndromes & Gene Therapy, 5(1), 1, 2014. doi: 10.4172/2157-7412.1000214
[64]Ahmed et al, The Journal of Molecular Diagnostics, 7(2), 283-288, 2005. doi: 10.1016/51525-1578(10)60556-9
[65]Oliveira, et al. J. Exp. Clin. Cancer Res. 37(84), 2018. doi: 10.1186/s13046-018-0746-y
[66]Yi, et al. Case Rep. Endocrinol. 2018:8657314, 2018. doi: 10.1155/2018/8657914
[67]Huang, et al. Cell. 173(2): 355-370, 2018. doi: 10.1016/j.cell.2018.03.039
[68]Bosic, et al. Pathology. 50(3):327-332, 2018. doi: 10.1016/j.pathol.2017.10.011
[69]Yao, et al. Zhonghua Yi Xue Za Zhi. 87(28): 1962-1965, 2007. PMID: 17923033
[70]Quintela-Fandino, et al. Mol. Oncol. 8(8): 1719-1728, 2014. doi: 10.1016nmolonc.2014.07.005

In some embodiments, the dysregulation of a RET gene, a RET kinase, or expression or activity or level of any of the same, includes at least one point mutation in a RET gene that results in the production of a RET kinase that has one or more amino acid substitutions, insertions, or deletions as compared to the wild-type RET kinase (see, for example, the point mutations listed in Table 2a).

TABLE 2a

RET Kinase Protein Amino Acid Substitutions/Insertions/Deletions[4]

Amino acid position 20
Amino acid position 32 (e.g., S32L)
Amino acid position 34 (e.g., D34S)
Amino acid position 40 (e.g., L40P)
Amino acid position 64 (e.g., P64L)
Amino acid position 67 (e.g., R67H)
Amino acid position 114 (e.g., R114H)
Amino acid position 145 (e.g., V145G)
Amino acid position 200
Amino acid position 292 (e.g., V292M)
Amino acid position 294
Amino acid position 321 (e.g., G321S)
Amino acid position 330 (e.g., R330Q)
Amino acid position 338 (e.g., T338I)
Amino acid position 360 (e.g., R360W)
Amino acid position 393 (e.g., F393L)
Amino acid position 432
Δ Amino acid residues 505-506 (6-Base Pair In-Frame Germline Deletion in Exon 7)
Amino acid position 510 (e.g., A510V)
Amino acid position 511 (e.g., E511K)
Amino acid position 513 (e.g., G513D)
Amino acid position 515 (e.g., C515S, C515W[4])
Amino acid position 525 (e.g., R525W)
Amino acid position 531 (e.g., C531R, or 9 base pair duplication)
Amino acid position 532 (e.g., duplication)
Amino acid position 533 (e.g., G533C, G533S)
Amino acid position 550 (e.g., G550E)
Amino acid position 591 (e.g., V591I)
Amino acid position 593 (e.g., G593E)
Amino acid position 595 (e.g., E595D and E595A)
Amino acid position 600 (e.g., R600Q)
Amino acid position 602 (e.g., I602V)
Amino acid position 603 (e.g., K603Q, K603E)
Amino acid position 606 (e.g., Y606C)
Amino acid position 609 (e.g., C609Y, C609S, C609G, C609R, C609F, C609W)
Amino acid position 611 (e.g., C611R, C611S, C611G, C611Y, C611F, C611W)
Amino acid position 616 (e.g., E616Q)
Amino acid position 618 (e.g., C618S, C618Y, C618R, C618G, C618F, C618W)
Amino acid position 620 (e.g., C620S, C620W, C620R, C620G, C620L, C620Y, C620F)
Amino acid position 623 (e.g., E623K)
Amino acid position 624 (e.g., D624N)
Amino acid position 630 (e.g., C630A, C630R, C630S, C630Y, C630F, C630W)
Amino acid position 631 (e.g., D631N, D631Y, D631A, D631G, D631V, D631E, )
Amino acid position 632 (e.g., E632K, E632G)
Δ Amino acid residues 632-633 (6-Base Pair In-Frame Germline Deletion in Exon 11)
Amino acid position 633 (e.g., 9 base pair duplication)
Amino acid position 634 (e.g., C634W, C634Y, C634S, C634R, C634F, C634G, C634L, C634A, or C634T, or an insertion ELCR, or a 12 base pair duplication)
(e.g., causing MTC)

TABLE 2a-continued

RET Kinase Protein Amino Acid Substitutions/Insertions/Deletions[A]

Amino acid position 635 (e.g., R635G)
Amino acid position 636 (e.g., T636P, T636M)
Amino acid position 640 (e.g., A640G)
Amino acid position 641 (e.g., A641S, A641T)
Amino acid position 648 (e.g., V648I)
Amino acid position 649 (e.g., S649L)
Amino acid position 664 (e.g., A664D)
Amino acid position 665 (e.g., H665Q)
Amino acid position 666 (e.g., K666E, K666M, K666N, K666R)
Amino acid position 686 (e.g., S686N)
Amino acid position 689 (e.g., S689T)
Amino acid position 691 (e.g., G691S)
Amino acid position 694 (e.g., R694Q)
Amino acid position 700 (e.g., M700L)
Amino acid position 706 (e.g., V706M, V706A)
Amino acid position 713 splice variant (e.g., E713K)
Amino acid position 732 (e.g., E732K)
Amino acid position 736 (e.g., G736R)
Amino acid position 748 (e.g., G748C)
Amino acid position 750 (e.g., A750P)
Amino acid position 765 (e.g., S765P)
Amino acid position 766 (e.g., P766S, P766M)
Amino acid position 768 (e.g., E768Q, E768D)
Amino acid position 769 (e.g., L769L)
Amino acid position 770 (e.g., R770Q)
Amino acid position 771 (e.g., D771N)
Amino acid position 777 (e.g., N777S)
Amino acid position 778 (e.g., V778I)
Amino acid position 781 (e.g., Q781R)
Amino acid position 790 (e.g., L790F)
Amino acid position 791 (e.g., Y791F, Y791N)
Amino acid position 802
Amino acid position 804 (e.g., V804L, V804M, V804E) (e.g., causing MTC)
Amino acid position 805 (e.g., E805K)
Amino acid position 804/805 (e.g., V804M/E805K)
Amino acid position 806 (e.g., Y806F, Y806S, Y806G, Y806C, Y806E, Y806H, Y806N)

Amino acid position 810 (e.g., G810R, G810S, G810A, G810C, G810V, and G810D)
Amino acid position 818 (e.g., E818K)
Amino acid position 819 (e.g., S819I)
Amino acid position 823 (e.g., G823E)
Amino acid position 826 (e.g., Y826M, Y826S)
Amino acid position 833 (e.g., R833C)
Amino acid position 836 (e.g., S836S)
Amino acid position 841 (e.g., P841L, P841P)
Amino acid position 843 (e.g., E843D)
Amino acid position 844 (e.g., R844W, R844Q, R844L)
Amino acid position 848 (e.g., M848T)
Amino acid position 852 (e.g., I852M)
Amino acid position 865 (e.g., L865V)
Amino acid position 870 (e.g., L870F)
Amino acid position 873 (e.g., R873W)
Amino acid position 876 (e.g., A876V)
Amino acid position 881 (e.g., L881V)
Amino acid position 882
Amino acid position 883 (e.g., A883F, A883S, A883T)
Amino acid position 884 (e.g., E884K)
Amino acid position 886 (e.g., R886W)
Amino acid position 891 (e.g., S891A)
Amino acid position 897 (e.g., R897Q)
Amino acid position 898 (e.g., D898V)
Amino acid position 900 (e.g., Y900F)
Amino acid position 901 (e.g., E901K)
Amino acid position 904 (e.g., S904F, S904S, S904C)
Amino acid position 907 (e.g., K907E, K907M)
Amino acid position 908 (e.g., R908K)
Amino acid position 911 (e.g., G911D)
Amino acid position 912 (e.g., R912P, R912Q)
Amino acid position 918 (e.g., M918T, M918V, M918L) (e.g., causing MTC)
Amino acid position 919 (e.g., A919V)
Amino acid position 921 (e.g., E921K)
Amino acid position 922 (e.g., S922P, S922Y)
Amino acid position 930 (e.g., T930M)
Amino acid position 961 (e.g., F961L)
Amino acid position 972 (e.g., R972G)
Amino acid position 982 (e.g., R982C)
Amino acid position 1009 (e.g., M1009V)
Amino acid position 1015 (e.g., Y1015F)

TABLE 2a-continued

RET Kinase Protein Amino Acid Substitutions/Insertions/Deletions[A]

Amino acid position 1017 (e.g., D1017N)
Amino acid position 1041 (e.g., V1041G)
Amino acid position 1064 (e.g., M1064T)
Amino acid position 1096 (e.g., Y1096F)
RET+3
(In-Frame Deletion in Exons 6 and 11)
(3bp In-Frame Deletion in Exon 15)

[A]The RET kinase mutations shown above may be activating mutations and/or may confer increased resistance of the RET kinase to a RET inhibitor and/or a multi-kinase inhibitor (MKI), e.g., as compared to a wildtype RET kinase.

In some embodiments, the dysregulation of a RET gene, a RET kinase, or expression or activity or level of any of the same, includes a splice variation in a RET mRNA which results in an expressed protein that is an alternatively spliced variant of RET having at least one residue deleted (as compared to the wild-type RET kinase) resulting in a constitutive activity of a RET kinase domain.

A "RET kinase inhibitor" as defined herein includes any compound exhibiting RET inhibition activity. In some embodiments, a RET kinase inhibitor is selective for a RET kinase. Exemplary RET kinase inhibitors can exhibit inhibition activity ($IC_{50}$) against a RET kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a RET kinase inhibitor can exhibit inhibition activity ($IC_{50}$) against a RET kinase of less than about 25 nM, less than about 10 nM, less than about 5 nM, or less than about 1 nM as measured in an assay as provided herein.

As used herein, a "first RET kinase inhibitor" or "first RET inhibitor" is a RET kinase inhibitor as defined herein, but which does not include a compound of Formula I (e.g., any one of Formulas I-A to I-L), or a pharmaceutically acceptable salt or solvate thereof as defined herein. As used herein, a "second RET kinase inhibitor" or a "second RET inhibitor" is a RET kinase inhibitor as defined herein, but which does not include a compound of Formula I (e.g., any one of Formulas I-A to I-L), or a pharmaceutically acceptable salt or solvate thereof as defined herein. When both a first and a second RET inhibitor are present in a method provided herein, the first and second RET kinase inhibitor are different.

In some embodiments, the dysregulation of a RET gene, a RET kinase, or expression or activity or level of any of the same, includes at least one point mutation in a RET gene that results in the production of a RET kinase that has one or more amino acid substitutions or insertions or deletions in a RET gene that results in the production of a RET kinase that has one or more amino acids inserted or removed, as compared to the wild-type RET kinase. In some cases, the resulting RET kinase is more resistant to inhibition of its phosphotransferase activity by one or more first RET kinase inhibitor(s), as compared to a wildtype RET kinase or a RET kinase not including the same mutation. Such mutations, optionally, do not decrease the sensitivity of the cancer cell or tumor having the RET kinase to treatment with a compound of Formula I (e.g., any one of Formulas I-A to I-L), or a pharmaceutically acceptable salt or solvate thereof (e.g., as compared to a cancer cell or a tumor that does not include the particular RET inhibitor resistance mutation). In such embodiments, a RET inhibitor resistance mutation can result in a RET kinase that has one or more of an increased $V_{max}$, a decreased $K_m$ for ATP, and an increased $K_D$ for a first RET kinase inhibitor, when in the presence of a first RET kinase inhibitor, as compared to a wildtype RET kinase or a RET kinase not having the same mutation in the presence of the same first RET kinase inhibitor.

In other embodiments, the dysregulation of a RET gene, a RET kinase, or expression or activity or level of any of the same, includes at least one point mutation in a RET gene that results in the production of a RET kinase that has one or more amino acid substitutions as compared to the wild-type RET kinase, and which has increased resistance to a compound of Formula I (e.g., any one of Formulas I-A to I-L), or a pharmaceutically acceptable salt or solvate thereof, as compared to a wildtype RET kinase or a RET kinase not including the same mutation. In such embodiments, a RET inhibitor resistance mutation can result in a RET kinase that has one or more of an increased $V_{max}$, a decreased $K_m$, and a decreased $K_D$ in the presence of a compound of Formula I (e.g., any one of Formulas I-A to I-L), or a pharmaceutically acceptable salt or solvate thereof, as compared to a wildtype RET kinase or a RET kinase not having the same mutation in the presence of the same compound of Formula I (e.g., any one of Formulas I-A to I-L), or a pharmaceutically acceptable salt or solvate thereof.

Examples of RET inhibitor resistance mutations can, e.g., include point mutations, insertions, or deletions in and near the ATP binding site in the tertiary structure of RET kinase (e.g., amino acid positions 730-733, 738, 756, 758, 804, 805, 807, 810, 811, 881, and 892 of a wildtype RET kinase, e.g., the exemplary wildtype RET kinase described herein), including but not limited to a gatekeeper residue (e.g., amino acid position 804 in a wildtype RET kinase), P-loop residues (e.g., amino acid positions 730-737 in a wildtype RET kinase), residues in or near the DFG motif (e.g., amino acid positions 888-898 in a wildtype RET kinase), and ATP cleft solvent front amino acid residues (e.g., amino acid positions 758, 811, and 892 of a wildtype RET kinase). Additional examples of these types of mutations include changes in residues that may affect enzyme activity and/or drug binding including but are not limited to residues in the activation loop (e.g., amino acid positions 891-916 of a wildtype RET kinase), residues near or interacting with the activation loop, residues contributing to active or inactive enzyme conformations, changes including mutations, deletions, and insertions in the loop proceeding the C-helix and in the C-helix (e.g., amino acid positions 768-788 in a wildtype RET protein). In some embodiments, the wildtype RET protein is the exemplary wildtype RET kinase described herein. Specific residues or residue regions that may be changed (and are RET inhibitor resistance mutations) include but are not limited to those listed in Table 3, with numbering based on the human wildtype RET protein sequence (e.g., SEQ ID NO: 1). As can be appreciated by those skilled in the art, an amino acid position in a reference protein sequence that corresponds to a specific amino acid position in SEQ ID NO: 1 can be determined by aligning the reference protein sequence with SEQ ID NO: 1 (e.g., using a software program, such as ClustalW2). Additional examples of RET inhibitor resistance mutation positions are shown in Table 4. Changes to these residues may include single or multiple amino acid changes, insertions within or flanking the sequences, and deletions within or flanking the sequences. See also J. Kooistra, G. K. Kanev, O. P. J. Van Linden, R. Leurs, I. J. P. De Esch, and C. De Graaf, "KLIFS: A structural kinase-ligand interaction database," *Nucleic Acids Res.*, vol. 44, no. D1, pp. D365-D371, 2016, which is incorporated by reference in its entirety herein.

Exemplary Sequence of Mature Human RET Protein (SEQ. ID NO: 1)

```
MAKATSGAAG LRLLLLLLLP LLGKVALGLY FSRDAYWEKL YVDQAAGTPL LYVHALRDAP EEVPSFRLGQ
HLYGTYRTRL HENNWICIQE DTGLLYLNRS LDHSSWEKLS VRNRGFPLLT VYLKVFLSPT SLREGECQWP
GCARVYFSFF NTSFPACSSL KPRELCFPET RPSFRIRENR PPGTFHQFRL LPVQFLCPNI SVAYRLLEGE
GLPFRCAPDS LEVSTRWALD REQREKYELV AVCTVHAGAR EEVVMVPFPV TVYDEDDSAP TFPAGVDTAS
AVVEFKRKED TVVATLRVFD ADVVPASGEL VRRYTSTLLP GDTWAQQTFR VEHWPNETSV QANGSFVRAT
VHDYRLVLNR NLSISENRTM QLAVLVNDSD FQGPGAGVLL LHFNVSVLPV SLHLPSTYSL SVSRRARRFA
QIGKVCVENC QAFSGINVQY KLHSSGANCS TLGVVTSAED TSGILFVNDT KALRRPKCAE LHYMVVATDQ
QTSRQAQAQL LVTVEGSYVA EEAGCPLSCA VSKRRLECEE CGGLGSPTGR CEWRQGDGKG ITRNFSTCSP
STKTCPDGHC DVVETQDINI CPQDCLRGSI VGGHEPGEPR GIKAGYGTCN CFPEEEKCFC EPEDIQDPLC
DELCRTVIAA AVLFSFIVSV LLSAFCIHCY HKFAHKPPIS SAEMTFRRPA QAFPVSYSSS GARRPSLDSM
ENQVSVDAFK ILEDPKWEFP RKNLVLGKTL GEGEFGKVVK ATAFHLKGRA GYTTVAVKML KENASPSELR
DLLSEFNVLK QVNHPHVIKL YGACSQDGPL LLIVEYAKYG SLRGFLRESR KVGPGYLGSG GSRNSSSLDH
PDERALTMGD LISFAWQISQ GMQYLAEMKL VHRDLAARNI LVAEGRKMKI SDFGLSRDVY EEDSYVKRSQ
GRIPVKWMAI ESLFDHIYTT QSDVWSFGVL LWEIVTLGGN PYPGIPPERL FNLLKTGHRM ERPDNCSEEM
YRLMLQCWKQ EPDKRPVFAD ISKDLEKMMV KRRDYLDLAA STPSDSLIYD DGLSEEETPL VDCNNAPLPR
ALPSTWIENK LYGMSDPNWP GESPVPLTRA DGTNTGFPRY PNDSVYANWM LSPSAAKLMD TFDS
```

In some embodiments, a RET inhibitor resistance mutation can include a dysregulation of a MET gene, a MET kinase, or the expression or activity or level of any of the same.

The phrase "dysregulation of a MET gene, a MET kinase, or the expression or activity or level of any of the same" refers to a genetic mutation (e.g., a MET gene translocation that results in the expression of a fusion protein, a deletion in a MET gene that results in the expression of a RET protein that includes a deletion of at least one amino acid as compared to the wild-type RET protein, or a mutation in a MET gene that results in the expression of a RET protein with one or more point mutations, or an alternative spliced version of a MET mRNA that results in a MET protein that results in the deletion of at least one amino acid in the MET protein as compared to the wild-type MET protein), or a MET gene amplification that results in overexpression of a MET protein or an autocrine activity resulting from the overexpression of a MET gene a cell, that results in a pathogenic increase in the activity of a kinase domain of a MET protein (e.g., a constitutively active kinase domain of a MET protein) in a cell. As another example, a dysregulation of a MET gene, a MET protein, or expression or activity, or level of any of the same, can be a mutation in a MET gene that encodes a MET protein that is constitutively active or has increased activity as compared to a protein encoded by a MET gene that does not include the mutation. For example, a dysregulation of a MET gene, a MET protein, or expression or activity, or level of any of the same, can be the result of a gene or chromosome translocation which results in the expression of a fusion protein that contains a first portion of MET that includes a functional kinase domain, and a second portion of a partner protein (i.e., that is not MET). In some examples, dysregulation of a MET gene, a MET protein, or expression or activity, can be a result of a gene translocation of one MET gene with another non-MET gene.

The term "wildtype MET" or "wild-type MET" describes a nucleic acid (e.g., a MET gene or a MET mRNA) or protein (e.g., a MET protein) that is found in a subject that does not have a MET-associated cancer (and optionally also does not have an increased risk of developing a MET-associated cancer and/or is not suspected of having a MET-associated cancer), or is found in a cell or tissue from a subject that does not have a MET-associated cancer (and optionally also does not have an increased risk of developing a MET-associated cancer and/or is not suspected of having a MET-associated cancer). The term "MET-associated cancer" as used herein refers to cancers associated with or having a dysregulation of a MET gene, a MET kinase, or expression or activity, or level of any of the same.

In some embodiments, compounds of Formula I (e.g., any one of Formulas I-A to I-L), or a pharmaceutically acceptable salt or solvate thereof are useful in treating patients that develop cancers with RET inhibitor resistance mutations (e.g., that result in an increased resistance to a first RET inhibitor, e.g., a substitution at amino acid position 804, e.g., V804M, V804L, or V804E, a substitution at amino acid position 810, e.g., G810S, G810R, G810C, G810A, G810V, and G810D, and/or one or more RET inhibitor resistance mutations listed in Tables 3 and 4) by either dosing in combination or as a subsequent or additional (e.g., follow-up) therapy to existing drug treatments (e.g., other RET kinase inhibitors; e.g., first and/or second RET kinase inhibitors). Exemplary first and second RET kinase inhibitors are described herein. In some embodiments, a first or second RET kinase inhibitor can be selected from the group consisting of cabozantinib, vandetanib, alectinib, apatinib, sitravatinib, sorafenib, lenvatinib, ponatinib, dovitinib, sunitinib, foretinib, BLU667, and BLU6864.

In some embodiments, compounds of Formula I (e.g., any one of Formulas I-A to I-L), or a pharmaceutically acceptable salt or solvate thereof are useful for treating a cancer that has been identified as having one or more RET inhibitor resistance mutations (that result in an increased resistance to a first or second RET inhibitor, e.g., a substitution at amino acid position 804, e.g., V804M, V804L, or V804E, or e.g., a substitution at amino acid position 810, e.g., G810S, G810R, G810C, G810A, G810V, and G810D). In some embodiments, the one or more RET inhibitor resistance mutations occur in a nucleic acid sequence encoding a RET fusion protein (e.g. any of the RET gene fusion proteins described in Table 1) resulting in a RET fusion protein that exhibits RET kinase inhibitor resistance. In some embodiments, the one or more RET inhibitor resistance mutations occurs in a nucleic acid sequence encoding a mutant RET protein (e.g. a mutant RET protein having any of the mutations described in Table 2) resulting in a mutant RET protein that exhibits RET kinase resistance. Non-limiting examples of RET inhibitor resistance mutations are listed in Tables 3 and 4.

TABLE 3

RET Inhibitor Resistance Mutations

Exemplary RET Resistance Mutations

Amino acid position 634 (e.g., C634W)[10]
Amino acid position 732 (e.g., E732K)[7]
Amino acid position 788 (e.g., I788N)[8]
Amino acid position 790 (e.g., L790F)[9]
Amino acid position 804 (e.g., V804M[1, 2], V804L[1, 2], V804E[6])
Amino acid position 778/804[13]
Amino acid position 804/805 (e.g., V804M/E805K)[3]
Amino acid position 806 (e.g., Y806C[4, 6], Y806E[4], Y806S[6], Y806H[6], Y806N[6])
Amino acid position 804/806 (e.g., V804M/Y806C)[11]
Amino acid position 810 (e.g., G810A[5], G810R[6], G810S[6], G810C, G810V, and G810D)
Amino acid position 865 (e.g., L865V[6])
Amino acid position 870 (e.g., L870F[6])
Amino acid position 891 (e.g., S891A)[10]
Amino acid position 904 (e.g., S904F)[12]
Amino acid position 804/904 (e.g., V804M/S904C)[11]
Amino acid position 918 (e.g., M918T)[10]

[1]Yoon et al., J. Med. Chem. 59(1): 358-73, 2016.
[2]U.S. Patent No. 8,629,135.
[3]Cranston, et al., Cancer Res. 66(20): 10179-87, 2006.
[4]Carlomagno, et al., Endocr. Rel. Cancer 16(1): 233-41, 2009.
[5]Huang et al., Mol. Cancer Ther., Aug. 5, 2016 . pii: molcanther.0258.2016. [Epub ahead of print].
[6]PCT Patent Application Publication No. WO 2016/127074.
[7]Mamedova et al., Summer Undergraduate Research Programs (SURP) Student Abstracts, University of Oklahoma Health Sciences Center, 2016.
[8]Plenker et al., Sci. Transl. Med., 9(394), doi: 10.1126/scitranslmed.aah6144, 2017.
[9]Kraft et al, Cancer Research, 2017, Vol. 77, No. 13, Supp. Supplement 1. Abstract Number: 4882; American Association for Cancer Research Annual Meeting 2017. Washington, DC, United States. Apr. 1, 2017-Apr. 5, 2017.
[10]U.S. Patent Application Publication No. 2018/0022732.
[11]Roskoski and Sadeghi-Nejad, Pharmacol. Res., 128, 1-17. doi: 10.1016/j.phrs.2017.12.021, 2018.
[12]Nakaoku, et al. Nat Commun, 9(1), 625. doi: 10.1038/s41467-018-02994-7, 2018.
[13]Roy et al. Oncologist, 18(10): 1093-1100. doi: 10.1634/theoncologist. 2013-0053, 2013.

TABLE 4

Additional Exemplary Amino Acid Positions of RET Inhibitor Resistance Mutations

| RET Amino Acid and Position | Exemplary Mutation | Mechanistic Resistance Rationale |
|---|---|---|
| L730 | P | Steric hindrance and/or active conformational effect |
| G731 | V | Steric hindrance and/or active conformational effect |
| E732 | K | Steric hindrance and/or active conformational effect |
| G733 | V | Steric hindrance and/or active conformational effect |
| E734 | K | Steric hindrance and/or active conformational effect |
| L760 | M | Active conformational effect |
| K761 | E | Active conformational effect |
| E762 | K | Active conformational effect |
| N763 | D | Active conformational effect |
| A764 | V | Active conformational effect |
| S765 | N | Active conformational effect |
| P766 | A | Active conformational effect |
| S767 | C | Active conformational effect |
| E768 | K | Active conformational effect |
| L779 | M | Steric hindrance and/or active conformational effect |
| I788 | M | Steric hindrance and/or active conformational effect |
| M868 | R | Steric hindrance and/or active conformational effect |
| K869 | E | Steric hindrance and/or active conformational effect |
| L870 | Q | Steric hindrance and/or active conformational effect |
| V871 | M | Steric hindrance and/or active conformational effect |
| H872 | R | Steric hindrance and/or active conformational effect |
| R873 | P | Steric hindrance and/or active conformational effect |
| D874 | Y | Steric hindrance and/or active conformational effect |
| L881 | R | Steric hindrance and/or active conformational effect |
| L895 | M | Active conformational effect |
| S896 | N | Active conformational effect |
| R897 | C | Active conformational effect |
| D898 | Y | Active conformational effect |
| V899 | G | Active conformational effect |
| Y900 | D | Active conformational effect |
| E901 | K | Active conformational effect |
| E902 | K | Active conformational effect |
| D903 | Y | Active conformational effect |
| S904 | C | Active conformational effect |
| Y905 | D | Active conformational effect |
| V906 | M | Active conformational effect |
| K907 | E | Active conformational effect |
| R908 | P | Active conformational effect |
| S909 | C | Active conformational effect |
| Q910 | R | Active conformational effect |
| G911 | C | Active conformational effect |
| R912 | P | Active conformational effect |

The oncogenic role of RET was first described in papillary thyroid carcinoma (PTC) (Grieco et al., *Cell*, 1990, 60, 557-63), which arises from follicular thyroid cells and is the most common thyroid malignancy. Approximately 20-30% of PTC harbor somatic chromosomal rearrangements (translocations or inversions) linking the promoter and the 5' portions of constitutively expressed, unrelated genes to the RET tyrosine kinase domain (Greco et al., *Q. J. Nucl. Med. Mol. Imaging*, 2009, 53, 440-54), therefore driving its ectopic expression in thyroid cells. Fusion proteins generated by such rearrangements are termed "RET/PTC" proteins. For example, RET/PTC 1 is a fusion between CCDD6 and RET that is commonly found in papillary thyroid carcinomas. Similarly, both RET/PTC3 and RET/PTC4 are fusions of ELE1 and RET that are commonly found in papillary thyroid carcinomas, although the fusion events resulting RET/PTC3 and RET/PTC4 lead to different proteins with different molecular weights (see e.g., Fugazzola et al., *Oncogene*, 13(5):1093-7, 1996). Some RET fusions associated with PTC are not referred to as "RET/PTC", but instead are referred to as the fusion protein inself. For example, fusion between RET and both ELKS and PCM1 are found in PTCs, but the fusion proteins are referred to as ELKS-RET and PCM1-RET (see e.g., Romei and Elisei, *Front. Endocrinol. (Lausanne)*, 3:54, doi: 10.3389/fendo.2012.00054, 2012).

The role of RET-PTC rearrangements in the pathogenesis of PTC has been confirmed in transgenic mice (Santoro et al., *Oncogene*, 1996, 12, 1821-6). To date, a variety of fusion partners have been identified, from PTC and other cancer types, all providing a protein/protein interaction domain that induces ligand-independent RET dimerization and constitutive kinase activity (see, e.g., Table 1). Recently, a 10.6 Mb pericentric inversion in chromosome 10, where RET gene maps, has been identified in about 2% of lung adenocarcinoma patients, generating different variants of the chimeric gene KIF5B-RET (Ju et al., *Genome Res.*, 2012, 22, 436-45; Kohno et al., 2012, *Nature Med.*, 18, 375-7; Takeuchi et al., *Nature Med.*, 2012, 18, 378-81; Lipson et al., 2012, *Nature Med.*, 18, 382-4). The fusion transcripts are highly expressed and all the resulting chimeric proteins contain the N-terminal portion of the coiled-coil region of KIF5B, which mediates homodimerization, and the entire RET kinase domain. None of RET positive patients harbor other known oncogenic alterations (such as EGFR or K-Ras mutation, ALK translocation), supporting the possibility that KIF5B-RET fusion could be a driver mutation of lung adenocarcinoma. The oncogenic potential of KIF5B-RET has been confirmed by transfecting the fusion gene into cultured cell lines: similarly to what has been observed with RET-PTC fusion proteins, KIF5B-RET is constitutively phosphorylated and induces NIH-3T3 transformation and IL-3 independent growth of BA-F3 cells. However, other RET fusion proteins have been identified in lung adenocarcinoma patients, such as the CCDC6-RET fusion protein, which has been found to play a key role in the proliferation of the human lung adenocarcinoma cell line LC-2/ad (*Journal of Thoracic Oncology*, 2012, 7(12):1872-1876). RET inhibitors have been shown to be useful in treating lung cancers involving RET rearrangements (Drilon, A. E. et al. *J Clin Oncol* 33, 2015 (suppl; abstr 8007)). RET fusion proteins have also been identified in patients having colorectal cancer (Song Eun-Kee, et al. *International Journal of Cancer*, 2015, 136: 1967-1975).

Besides rearrangements of the RET sequence, gain of function point mutations of RET proto-oncogene are also driving oncogenic events, as shown in medullary thyroid carcinoma (MTC), which arises from parafollicular calcitonin-producing cells (de Groot, et al., *Endocrine Rev.*, 2006, 27, 535-60; Wells and Santoro, *Clin. Cancer Res.*, 2009, 15, 7119-7122). Around 25% of MTC are associated with multiple endocrine neoplasia type 2 (MEN2), a group of inherited cancer syndromes affecting neuroendocrine organs caused by germline activating point mutations of RET. In MEN2 subtypes (MEN2A, MEN2B and Familial MTC/FMTC) RET gene mutations have a strong phenotype-genotype correlation defining different MTC aggressiveness and clinical manifestations of the disease. In MEN2A syndrome mutations involve one of the six cysteine residues (mainly C634) located in the cysteine-rich extracellular region, leading to ligand-independent homodimerization and constitutive RET activation. Patients develop MTC at a young age (onset at 5-25 years) and may also develop pheochromocytoma (50%) and hyperparathyroidism. MEN2B is mainly caused by M918T mutation, which is located in the kinase domain. This mutation constitutively activates RET in its monomeric state and alters substrate recognition by the kinase. MEN2B syndrome is characterized by an early onset (<1 year) and very aggressive form of MTC, pheochromocytoma (50% of patients) and ganglioneuromas. In FMTC the only disease manifestation is MTC, usually occurring at an adult age. Many different mutations have been detected, spanning the entire RET gene. The remaining 75% of MTC cases are sporadic and about 50% of them harbor RET somatic mutations: the most frequent mutation is M918T that, as in MEN2B, is associated with the most aggressive phenotype. Somatic point mutations of RET have also been described in other tumors such as colorectal cancer (Wood et al., *Science*, 2007, 318, 1108-13) and small cell lung carcinoma (*Jpn. J. Cancer Res.*, 1995, 86, 1127-30). In some embodiments, the MTC is RET-fusion positive MTC.

RET signaling components have been found to be expressed in primary breast tumors and to functionally interact with estrogen receptor-α pathway in breast tumor cell lines (Boulay et al., *Cancer Res.* 2008, 68, 3743-51; Plaza-Menacho et al., *Oncogene*, 2010, 29, 4648-57), while RET expression and activation by GDNF family ligands could play an important role in perineural invasion by different types of cancer cells (Ito et al., *Surgery*, 2005, 138, 788-94; Gil et al., J. Natl. Cancer Inst., 2010, 102, 107-18; Iwahashi et al., Cancer, 2002, 94, 167-74).

RET is also expressed in 30-70% of invasive breast cancers, with expression being relatively more frequent in estrogen receptor-positive tumors (Plaza-Menacho, I., et al., *Oncogene*, 2010, 29, 4648-4657; Esseghir, S., et al., *Cancer Res.*, 2007, 67, 11732-11741; Morandi, A., et al., *Cancer Res.*, 2013, 73, 3783-3795; Gattelli, A., *EMBO Mol. Med.*, 2013, 5, 1335-1350).

The identification of RET rearrangements has been reported in a subset of (patient-derived xenograft) PDX established from colorectal cancer. Although the frequency of such events in colorectal cancer patients remains to be defined, these data suggest a role of RET as a target in this indication (Gozgit et al., AACR Annual Meeting 2014). Studies have shown that the RET promoter is frequently methylated in colorectal cancers, and heterozygous missense mutations, which are predicted to reduce RET expression, are identified in 5-10% of cases, which suggests that RET might have some features of a tumor suppressor in sporadic colon cancers (Luo, Y., et al., *Oncogene*, 2013, 32, 2037-2047; Sjoblom, T., et al., *Science*, 2006, 268-274; Cancer Genome Atlas Network, *Nature*, 2012, 487, 330-337).

An increasing number of tumor types are now being shown to express substantial levels of wild-type RET kinase that could have implications for tumor progression and spread. RET is expressed in 50-65% of pancreatic ductal carcinomas, and expression is more frequent in metastatic and higher grade tumors (Ito, Y, et al., *Surgery*, 2005, 138, 788-794; Zeng, Q., et al., *J. Int. Med. Res.* 2008, 36, 656-664).

In neoplasms of hematopoietic lineages, RET is expressed in acute myeloid leukemia (AML) with monocytic differentiation, as well as in CMML (Gattei, V. et al., *Blood*, 1997, 89, 2925-2937; Gattei, V., et al., *Ann. Hematol*, 1998, 77, 207-210; Camos, M., *Cancer Res.* 2006, 66, 6947-6954). Recent studies have identified rare chromosomal rearrangements that involve RET in patients with chronic myelomonocytic leukemia (CMML). CMML is frequently associated with rearrangements of several tyrosine kinases, which result in the expression of chimeric cytosolic oncoproteins that lead to activation of RAS pathways (Kohlmann, A., et al., *J. Clin. Oncol.* 2010, 28, 2858-2865). In the case of RET, gene fusions that link RET with BCR (BCR-RET) or with fibroblast growth factor receptor 1 oncogene partner (FGFR1OP-RET) were transforming in early hematopoietic progenitor cells and could shift maturation of these cells towards monocytic paths, probably through the initiation of RET-mediated RAS signaling (Ballerini, P., et al., *Leukemia*, 2012, 26, 2384-2389).

RET expression has also been shown to occur in several other tumor types, including prostate cancer, small-cell lung carcinoma, melanoma, renal cell carcinoma, and head and neck tumors (Narita, N., et al., *Oncogene*, 2009, 28, 3058-3068; Mulligan, L. M., et al., *Genes Chromosomes Cancer*, 1998, 21, 326-332; Flavin, R., et al., *Urol. Oncol.*, 2012, 30, 900-905; Dawson, D. M., *J Natl Cancer Inst*, 1998, 90, 519-523).

In neuroblastoma, RET expression and activation by GFLs has roles in tumor cell differentiation, potentially collaborating with other neurotrophic factor receptors to down regulate N-Myc, the expression of which is a marker of poor prognosis (Hofstra, R. M., W., et al., *Hum. Genet.* 1996, 97, 362-364; Petersen, S. and Bogenmann, E., *Oncogene*, 2004, 23, 213-225; Brodeur, G. M., *Nature Ref. Cancer*, 2003, 3, 203-216).

Multitargeted inhibitors which cross react with RET are known (Borrello, M. G., et al., *Expert Opin. Ther. Targets*, 2013, 17(4), 403-419; International Patent Application Nos. WO 2014/141187, WO 2014/184069, and WO 2015/079251). Such multitargeted inhibitors (or multikinase inhibitors or MKIs) can also be associated with development of RET inhibitor resistance mutations. See, for example, Q.

Huang et al., "Preclinical Modeling of KIF5B-RET Fusion Lung Adenocarcinoma," *Mol. Cancer Ther.*, no. 18, pp. 2521-2529, 2016; Yasuyuki Kaneta et al., Abstract B173: Preclinical characterization and antitumor efficacy of DS-5010, a highly potent and selective RET inhibitor, *Mol Cancer Ther* Jan. 1, 2018 (17) (1 Supplement) B173; DOI:10.1158/1535-7163.TARG-17-B173, both of which are incorporated by reference in their entirety herein.

Accordingly, provided herein are methods for treating a patient diagnosed with (or identified as having) a cancer that include administering to the patient a therapeutically effective amount of a compound of Formula I (e.g., any one of Formulas I-A to I-L), or a pharmaceutically acceptable salt or solvate thereof. Also provided herein are methods for treating a patient identified or diagnosed as having a RET-associated cancer that include administering to the patient a therapeutically effective amount of a compound of Formula I (e.g., any one of Formulas I-A to I-L), or a pharmaceutically acceptable salt or solvate thereof or a pharmaceutical composition thereof. In some embodiments, the patient that has been identified or diagnosed as having a RET-associated cancer through the use of a regulatory agency-approved, e.g., FDA-approved test or assay for identifying dysregulation of a RET gene, a RET kinase, or expression or activity or level of any of the same, in a patient or a biopsy sample from the patient or by performing any of the non-limiting examples of assays described herein. In some embodiments, the test or assay is provided as a kit. In some embodiments, the cancer is a RET-associated cancer. For example, the RET-associated cancer can be a cancer that includes one or more RET inhibitor resistance mutations.

Also provided are methods for treating cancer in a patient in need thereof, the method comprising: (a) detecting a RET-associated cancer in the patient; and (b) administering to the patient a therapeutically effective amount of a compound of Formula I (e.g., any one of Formulas I-A to I-L), or a pharmaceutically acceptable salt or solvate thereof or a pharmaceutical composition thereof. Some embodiments of these methods further include administering to the subject another anticancer agent (e.g., a second RET inhibitor, a second compound of Formula I (e.g., any one of Formulas I-A to I-L), or a pharmaceutically acceptable salt or solvate thereof, or an immunotherapy). In some embodiments, the subject was previously treated with a first RET inhibitor or previously treated with another anticancer treatment, e.g., at least partial resection of the tumor or radiation therapy. In some embodiments, the patient is determined to have a RET-associated cancer through the use of a regulatory agency-approved, e.g., FDA-approved test or assay for identifying dysregulation of a RET gene, a RET kinase, or expression or activity or level of any of the same, in a patient or a biopsy sample from the patient or by performing any of the non-limiting examples of assays described herein. In some embodiments, the test or assay is provided as a kit. In some embodiments, the cancer is a RET-associated cancer. For example, the RET-associated cancer can be a cancer that includes one or more RET inhibitor resistance mutations.

Also provided are methods of treating a patient that include performing an assay on a sample obtained from the patient to determine whether the patient has a dysregulation of a RET gene, a RET kinase, or expression or activity or level of any of the same, and administering (e.g., specifically or selectively administering) a therapeutically effective amount of a compound of Formula I (e.g., any one of Formulas I-A to I-L), or a pharmaceutically acceptable salt or solvate thereof or a pharmaceutical composition thereof to the patient determined to have a dysregulation of a RET gene, a RET kinase, or expression or activity or level of any of the same. Some embodiments of these methods further include administering to the subject another anticancer agent (e.g., a second RET inhibitor, a second compound of Formula I (e.g., any one of Formulas I-A to I-L), or a pharmaceutically acceptable salt or solvate thereof, or immunotherapy). In some embodiments of these methods, the subject was previously treated with a first RET inhibitor or previously treated with another anticancer treatment, e.g., at least partial resection of a tumor or radiation therapy. In some embodiments, the patient is a patient suspected of having a RET-associated cancer, a patient presenting with one or more symptoms of a RET-associated cancer, or a patient having an elevated risk of developing a RET-associated cancer. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art. In some embodiments, the dysregulation of a RET gene, a RET kinase, or expression or activity or level of any of the same includes one or more RET inhibitor resistance mutations.

Also provided is a compound of Formula I (e.g., any one of Formulas I-A to I-L), or a pharmaceutically acceptable salt or solvate thereof or a pharmaceutical composition thereof for use in treating a RET-associated cancer in a patient identified or diagnosed as having a RET-associated cancer through a step of performing an assay (e.g., an in vitro assay) on a sample obtained from the patient to determine whether the patient has a dysregulation of a RET gene, a RET kinase, or expression or activity or level of any of the same, where the presence of a dysregulation of a RET gene, a RET kinase, or expression or activity or level of any of the same, identifies that the patient has a RET-associated cancer. Also provided is the use of a compound of Formula I (e.g., any one of Formulas I-A to I-L), or a pharmaceutically acceptable salt or solvate thereof for the manufacture of a medicament for treating a RET-associated cancer in a patient identified or diagnosed as having a RET-associated cancer through a step of performing an assay on a sample obtained from the patient to determine whether the patient has a dysregulation of a RET gene, a RET kinase, or expression or activity or level of any of the same where the presence of dysregulation of a RET gene, a RET kinase, or expression or activity or level of any of the same, identifies that the patient has a RET-associated cancer. Some embodiments of any of the methods or uses described herein further include recording in the patient's clinical record (e.g., a computer readable medium) that the patient is determined to have a dysregulation of a RET gene, a RET kinase, or expression or activity or level of any of the same, through the performance of the assay, should be administered a compound of Formula I (e.g., any one of Formulas I-A to I-L), or a pharmaceutically acceptable salt or solvate thereof or a pharmaceutical composition thereof. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. In some embodiments, the dysregulation of a RET gene, a RET kinase, or expression or activity or level of any of the same includes one or more RET inhibitor resistance mutations.

Also provided is a compound of Formula I (e.g., any one of Formulas I-A to I-L), or a pharmaceutically acceptable salt or solvate thereof, for use in the treatment of a cancer in a patient in need thereof or a patient identified or diagnosed as having a RET-associated cancer. Also provided is the use of a compound of Formula I (e.g., any one of Formulas I-A to I-L), or a pharmaceutically acceptable salt or solvate thereof for the manufacture of a medicament for treating a cancer in a patient identified or diagnosed as having a RET-associated cancer. In some embodiments, the cancer is a RET-associated cancer, for example, a RET-associated cancer having one or more RET inhibitor resistance mutations. In some embodiments, a patient is identified or diagnosed as having a RET-associated cancer through the use of a regulatory agency-approved, e.g., FDA-approved, kit for identifying dysregulation of a RET gene, a RET kinase, or expression or activity or level of any of the same, in a patient or a biopsy sample from the sample. As provided herein, a RET-associated cancer includes those described herein and known in the art.

In some embodiments of any of the methods or uses described herein, the patient has been identified or diagnosed as having a cancer with a dysregulation of a RET gene, a RET kinase, or expression or activity or level of any of the same. In some embodiments of any of the methods or uses described herein, the patient has a tumor that is positive for a dysregulation of a RET gene, a RET kinase, or expression or activity or level of any of the same. In some embodiments of any of the methods or uses described herein, the patient can be a patient with a tumor(s) that is positive for a dysregulation of a RET gene, a RET kinase, or expression or activity or level of any of the same. In some embodiments of any of the methods or uses described herein, the patient can be a patient whose tumors have a dysregulation of a RET gene, a RET kinase, or expression or activity or level of any of the same. In some embodiments of any of the methods or uses described herein, the patient is suspected of having a RET-associated cancer (e.g., a cancer having one or more RET inhibitor resistance mutations). In some embodiments, provided herein are methods for treating a RET-associated cancer in a patient in need of such treatment, the method comprising a) detecting a dysregulation of a RET gene, a RET kinase, or the expression or activity or level of any of the same in a sample from the patient; and b) administering a therapeutically effective amount of a compound of Formula I (e.g., any one of Formulas I-A to I-L), or a pharmaceutically acceptable salt or solvate thereof. In some embodiments, the dysregulation of a RET gene, a RET kinase, or the expression or activity or level of any of the same includes one or more fusion proteins. Non-limiting examples of RET gene fusion proteins are described in Table 1. In some embodiments, the fusion protein is KIF5B-RET. In some embodiments, the dysregulation of a RET gene, a RET kinase, or the expression or activity or level of any of the same includes one or more RET kinase protein point mutations/insertions/deletions. Non-limiting examples of RET kinase protein point mutations/insertions/deletions are described in Tables 2 and 2a. In some embodiments, the RET kinase protein point mutations/insertions/deletions are selected from the group consisting of M918T, M918V, C634W, V804L, V804M, G810S, and G810R. In some embodiments, the dysregulation of a RET gene, a RET kinase, or the expression or activity or level of any of the same includes one or more RET inhibitor resistance mutations. Non-limiting examples of RET inhibitor resistance mutations are described in Tables 3 and 4. In some embodiments, the RET inhibitor resistance mutation is V804M. In some embodiments, the RET inhibitor resistance mutation is G810S. In some embodiments, the RET inhibitor resistance mutation is G810R. In some embodiments, the cancer with a dysregulation of a RET gene, a RET kinase, or expression or activity or level of any of the same is determined using a regulatory agency-approved, e.g., FDA-approved, assay or kit. In some embodiments, the tumor that is positive for a dysregulation of a RET gene, a RET kinase, or expression or activity or level of any of the same is a tumor positive for one or more RET inhibitor resistance mutations. In some embodiments, the tumor with a dysregulation of a RET gene, a RET kinase, or expression or activity or level of any of the same is determined using a regulatory agency-approved, e.g., FDA-approved, assay or kit.

In some embodiments of any of the methods or uses described herein, the patient has a clinical record indicating that the patient has a tumor that has a dysregulation of a RET gene, a RET kinase, or expression or activity or level of any of the same (e.g., a tumor having one or more RET inhibitor resistance mutations). In some embodiments, the clinical record indicates that the patient should be treated with one or more of the compounds of Formula I (e.g., any one of Formulas I-A to I-L), or a pharmaceutically acceptable salt or solvate thereof or compositions provided herein. In some embodiments, the cancer with a dysregulation of a RET gene, a RET kinase, or expression or activity or level of any of the same is a cancer having one or more RET inhibitor resistance mutations. In some embodiments, the cancer with a dysregulation of a RET gene, a RET kinase, or expression or activity or level of any of the same is determined using a regulatory agency-approved, e.g., FDA-approved, assay or kit. In some embodiments, the tumor that is positive for a dysregulation of a RET gene, a RET kinase, or expression or activity or level of any of the same is a tumor positive for one or more RET inhibitor resistance mutations. In some embodiments, the tumor with a dysregulation of a RET gene, a RET kinase, or expression or activity or level of any of the same is determined using a regulatory agency-approved, e.g., FDA-approved, assay or kit.

Also provided are methods of treating a patient that include administering a therapeutically effective amount of a compound of Formula I (e.g., any one of Formulas I-A to I-L), or a pharmaceutically acceptable salt or solvate thereof to a patient having a clinical record that indicates that the patient has a dysregulation of a RET gene, a RET kinase, or expression or activity or level of any of the same. Also provided is the use of a compound of Formula I (e.g., any one of Formulas I-A to I-L), or a pharmaceutically acceptable salt or solvate thereof for the manufacture of a medicament for treating a RET-associated cancer in a patient having a clinical record that indicates that the patient has a dysregulation of a RET gene, a RET kinase, or expression or activity or level of any of the same. Some embodiments of these methods and uses can further include: a step of performing an assay (e.g., an in vitro assay) on a sample obtained from the patient to determine whether the patient has a dysregulation of a RET gene, a RET kinase, or expression or activity or level of any of the same, and recording the information in a patient's clinical file (e.g., a computer readable medium) that the patient has been identified to have a dysregulation of a RET gene, a RET kinase, or expression or activity or level of any of the same. In some embodiments, the assay is an in vitro assay. For example, an assay that utilizes next generation sequencing, immunohistochemistry, or break apart FISH analysis. In some embodiments, the assay is a regulatory agency-approved, e.g., FDA-approved, kit. In some embodiments, the assay is a liquid biopsy. In some embodiments, the dysregulation of a RET gene, RET kinase, or expression or activity or level of any of the same includes one or more RET inhibitor resistance mutations.

Also provided herein is a method of treating a subject. In some embodiments, the method includes performing an assay on a sample obtained from the subject to determine whether the subject has a dysregulation of a RET gene, a RET protein, or expression or level of any of the same. In some such embodiments, the method also includes administering to a subject determined to have a dysregulation of a RET gene, a RET protein, or expression or activity, or level of any of the same a therapeutically effective amount of a compound of Formula I (e.g., any one of Formulas I-A to I-L), or a pharmaceutically acceptable salt or solvate thereof. In some embodiments, the method includes determining that a subject has a dysregulation of a RET gene, a RET protein, or expression or level of any of the same via an assay performed on a sample obtained from the subject. In such embodiments, the method also includes administering to a subject a therapeutically effective amount of a compound of Formula I (e.g., any one of Formulas I-A to I-L), or a pharmaceutically acceptable salt or solvate thereof. In some embodiments, the dysregulation in a RET gene, a RET kinase protein, or expression or activity of the same is a gene or chromosome translocation that results in the expression of a RET fusion protein (e.g., any of the RET fusion proteins described herein). In some embodiments, the RET fusion can be selected from a KIF5B-RET fusion and a CCDC6-RET fusion. In some embodiments, the dysregulation in a RET gene, a RET kinase protein, or expression or activity or level of any of the same is one or more point mutation in the RET gene (e.g., any of the one or more of the RET point mutations described herein). The one or more point mutations in a RET gene can result, e.g., in the translation of a RET protein having one or more of the following amino acid substitutions: M918T, M918V, C634W, V804L, V804M, G810S, and G810R. In some embodiments, the dysregulation in a RET gene, a RET kinase protein, or expression or activity or level of any of the same is one or more RET inhibitor resistance mutations (e.g., any combination of the one or more RET inhibitor resistance mutations described herein). Some embodiments of these methods further include administering to the subject another anticancer agent (e.g., a second RET inhibitor a second compound of Formula I (e.g., any one of Formulas I-A to I-L), or a pharmaceutically acceptable salt or solvate thereof, or immunotherapy).

In some embodiments, the compounds provided herein exhibit brain and/or central nervous system (CNS) penetrance. Such compounds are capable of crossing the blood brain barrier and inhibiting a RET kinase in the brain and/or other CNS structures. In some embodiments, the compounds provided herein are capable of crossing the blood brain barrier in a therapeutically effective amount. For example, treatment of a patient with cancer (e.g., a RET-associated cancer such as a RET-associated brain or CNS cancer) can include administration (e.g., oral administration) of the compound to the patient. In some such embodiments, the compounds provided herein are useful for treating a primary brain tumor or metastatic brain tumor. For example, the compounds can be used in the treatment of one or more of gliomas such as glioblastoma (also known as glioblastoma multiforme), astrocytomas, oligodendrogliomas, ependymomas, and mixed gliomas, meningiomas, medulloblastomas, gangliogliomas, schwannomas (neurilemmomas), and craniopharyngiomas (see, for example, the tumors listed in Louis, D. N. et al. *Acta Neuropathol* 131(6), 803-820 (June 2016)). In some embodiments, the brain tumor is a primary brain tumor. In some embodiments, the patient has previously been treated with another anticancer agent, e.g., another RET inhibitor (e.g., a compound that is not a compound of General Formula I) or a multi-kinase inhibitor. In some embodiments, the brain tumor is a metastatic brain tumor. In some embodiments, the patient has previously been treated with another anticancer agent, e.g., another RET inhibitor (e.g., a compound that is not a compound of General Formula I) or a multi-kinase inhibitor.

Also provided are methods (e.g., in vitro methods) of selecting a treatment for a patient identified or diagnosed as having a RET-associated cancer. Some embodiments can further include administering the selected treatment to the patient identified or diagnosed as having a RET-associated cancer. For example, the selected treatment can include administration of a therapeutically effective amount of a compound of Formula I (e.g., any one of Formulas I-A to I-L), or a pharmaceutically acceptable salt or solvate thereof. Some embodiments can further include a step of performing an assay on a sample obtained from the patient to determine whether the patient has a dysregulation of a RET gene, a RET kinase, or expression or activity or level of any of the same, and identifying and diagnosing a patient determined to have a dysregulation of a RET gene, a RET kinase, or expression or activity or level of any of the same, as having a RET-associated cancer. In some embodiments, the cancer is a RET-associated cancer having one or more RET inhibitor resistance mutations. In some embodiments, the patient has been identified or diagnosed as having a RET-associated cancer through the use of a regulatory agency-approved, e.g., FDA-approved, kit for identifying dysregulation of a RET gene, a RET kinase, or expression or activity or level of any of the same, in a patient or a biopsy sample from the patient. In some embodiments, the RET-associated cancers is a cancer described herein or known in the art. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy.

Also provided herein are methods of selecting a treatment for a patient, wherein the methods include a step of performing an assay on a sample obtained from the patient to determine whether the patient has a dysregulation of a RET gene, a RET kinase, or expression or activity or level of any of the same (e.g., one or more RET inhibitor resistance mutations), and identifying or diagnosing a patient determined to have a dysregulation of a RET gene, a RET kinase, or expression or activity or level of any of the same, as having a RET-associated cancer. Some embodiments further include administering the selected treatment to the patient identified or diagnosed as having a RET-associated cancer. For example, the selected treatment can include administration of a therapeutically effective amount of a compound of Formula I (e.g., any one of Formulas I-A to I-L), or a pharmaceutically acceptable salt or solvate thereof to the patient identified or diagnosed as having a RET-associated cancer. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy.

Also provided are methods of selecting a patient for treatment, wherein the methods include selecting, identifying, or diagnosing a patient having a RET-associated cancer, and selecting the patient for treatment including administration of a therapeutically-effective amount of a compound of Formula I (e.g., any one of Formulas I-A to I-L), or a pharmaceutically acceptable salt or solvate thereof. In some embodiments, identifying or diagnosing a patient as having a RET-associated cancer can include a step of performing an assay on a sample obtained from the patient to determine whether the patient has a dysregulation of a RET gene, a RET kinase, or expression or activity or level of any of the same, and identifying or diagnosing a patient determined to have a dysregulation of a RET gene, a RET kinase, or expression or activity or level of any of the same, as having a RET-associated cancer. In some embodiments, the method of selecting a patient for treatment can be used as a part of a clinical study that includes administration of various treatments of a RET-associated cancer. In some embodiments, a RET-associated cancer is a cancer having one or more RET inhibitor resistance mutations. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy. In some embodiments, the dysregulation of the RET gene, the RET kinase, or expression or activity or level of any of the same includes one or more RET inhibitor resistance mutations.

In some embodiments of any of the methods or uses described herein, an assay used to determine whether the patient has a dysregulation of a RET gene, or a RET kinase, or expression or activity or level of any of the same, using a sample from a patient can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a RET gene, a RET kinase, or expression or activity or levels of any of the same (see, e.g., the references cited herein). In some embodiments, the dysregulation of the RET gene, the RET kinase, or expression or activity or level of any of the same includes one or more RET inhibitor resistance mutations. In some embodiments, the sample is a biological sample or a biopsy sample (e.g., a paraffin-embedded biopsy sample) from the patient. In some embodiments, the patient is a patient suspected of having a RET-associated cancer, a patient having one or more symptoms of a RET-associated cancer, and/or a patient that has an increased risk of developing a RET-associated cancer).

In some embodiments, dysregulation of a RET gene, a RET kinase, or the expression or activity or level of any of the same can be identified using a liquid biopsy (variously referred to as a fluid biopsy or fluid phase biopsy). See, e.g., Karachialiou et al., "Real-time liquid biopsies become a reality in cancer treatment", *Ann. Transl. Med.*, 3(3):36, 2016. Liquid biopsy methods can be used to detect total tumor burden and/or the dysregulation of a RET gene, a RET kinase, or the expression or activity or level of any of the same. Liquid biopsies can be performed on biological samples obtained relatively easily from a subject (e.g., via a simple blood draw) and are generally less invasive than traditional methods used to detect tumor burden and/or dysregulation of a RET gene, a RET kinase, or the expression or activity or level of any of the same. In some embodiments, liquid biopsies can be used to detect the presence of dysregulation of a RET gene, a RET kinase, or the expression or activity or level of any of the same at an earlier stage than traditional methods. In some embodiments, the biological sample to be used in a liquid biopsy can include, blood, plasma, urine, cerebrospinal fluid, saliva, sputum, broncho-alveolar lavage, bile, lymphatic fluid, cyst fluid, stool, ascites, and combinations thereof. In some embodiments, a liquid biopsy can be used to detect circulating tumor cells (CTCs). In some embodiments, a liquid biopsy can be used to detect cell-free DNA. In some embodiments, cell-free DNA detected using a liquid biopsy is circulating tumor DNA (ctDNA) that is derived from tumor cells. Analysis of ctDNA (e.g., using sensitive detection techniques such as, without limitation, next-generation sequencing (NGS), traditional PCR, digital PCR, or microarray analysis) can be used to identify dysregulation of a RET gene, a RET kinase, or the expression or activity or level of any of the same.

In some embodiments, ctDNA derived from a single gene can be detected using a liquid biopsy. In some embodiments, ctDNA derived from a plurality of genes (e.g., 2, 3, 4, 5, 6, 7, 8, 9, 10, 15, 20, 25, 30, 35, 40, 45, 50, 55, 60, 65, 70, 75, 80, 85, 90, 95, 100 or more, or any number of genes in between these numbers) can be detected using a liquid biopsy. In some embodiments, ctDNA derived from a plurality of genes can be detected using any of a variety of commercially-available testing panels (e.g., commercially-available testing panels designed to detect dysregulation of a RET gene, a RET kinase, or the expression or activity or level of any of the same). Liquid biopsies can be used to detect dysregulation of a RET gene, a RET kinase, or the expression or activity or level of any of the same including, without limitation, point mutations or single nucleotide variants (SNVs), copy number variants (CNVs), genetic fusions (e.g., translocations or rearrangements), insertions, deletions, or any combination thereof. In some embodiments, a liquid biopsy can be used to detect a germline mutation. In some embodiments, a liquid biopsy can be used to detect a somatic mutation. In some embodiments, a liquid biopsy can be used to detect a primary genetic mutation (e.g., a primary mutation or a primary fusion that is associated with initial development of a disease, e.g., cancer). In some embodiments, a liquid biopsy can be used to detect a genetic mutation that develops after development of the primary genetic mutation (e.g., a resistance mutation that arises in response to a treatment administered to a subject). In some embodiments, a dysregulation of a RET gene, a RET kinase, or the expression or activity or level of any of the same identified using a liquid biopsy is also present in a cancer cell that is present in the subject (e.g., in a tumor). In some embodiments, any of the types of dysregulation of a RET gene, a RET kinase, or the expression or activity or level of any of the same described herein can be detected using a liquid biopsy. In some embodiments, a genetic mutation identified via a liquid biopsy can be used to identify the subject as a candidate for a particular treatment. For example, detection of dysregulation of a RET gene, a RET kinase, or the expression or activity or level of any of the same in the subject can indicate that the subject will be responsive to a treatment that includes administration of a compound of Formula I (e.g., any one of Formulas I-A to I-L), or a pharmaceutically acceptable salt or solvate thereof.

Liquid biopsies can be performed at multiple times during a course of diagnosis, a course of monitoring, and/or a course of treatment to determine one or more clinically relevant parameters including, without limitation, progression of the disease, efficacy of a treatment, or development of resistance mutations after administering a treatment to the subject. For example, a first liquid biopsy can be performed at a first time point and a second liquid biopsy can be performed at a second time point during a course of diagnosis, a course of monitoring, and/or a course of treatment. In some embodiments, the first time point can be a time point prior to diagnosing a subject with a disease (e.g., when the subject is healthy), and the second time point can be a time point after subject has developed the disease (e.g., the second time point can be used to diagnose the subject with the disease). In some embodiments, the first time point can be a time point prior to diagnosing a subject with a disease (e.g., when the subject is healthy), after which the subject is monitored, and the second time point can be a time point after monitoring the subject. In some embodiments, the first time point can be a time point after diagnosing a subject with a disease, after which a treatment is administered to the subject, and the second time point can be a time point after the treatment is administered; in such cases, the second time point can be used to assess the efficacy of the treatment (e.g., if the genetic mutation(s) detected at the first time point are reduced in abundance or are undetectable) or to determine the presence of a resistance mutation that has arisen as a result of the treatment. In some embodiments, a treatment to be administered to a subject can include a compound of Formula I (e.g., any one of Formulas I-A to I-L), or a pharmaceutically acceptable salt or solvate thereof.

In some embodiments, the efficacy of a compound of Formula I (e.g., any one of Formulas I-A to I-L), or a pharmaceutically acceptable salt or solvate thereof, can be determined by assessing the allele frequency of a dysregulation of a RET gene in cfDNA obtained from a patient at different time points, e.g., cfDNA obtained from the patient at a first time point and cfDNA obtained from the patient at a second time point, where at least one dose of a compound of Formula I (e.g., any one of Formulas I-A to I-L) is administered to the patient between the first and second time points. Some embodiments of these methods can further include administering to the patient the at least one dose of the compound of Formula I, or a pharmaceutically acceptable salt or solvate thereof, between the first and second time points. For example, a reduction (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction) in the allele frequency (AF) of the dysregulation of a RET gene in the cfDNA obtained from the patient at the second time point as compared to the allele frequency (AF) of the dysregulation of a RET gene in the cfDNA obtained from the patient at the first time point indicates that the compound of Formula I, or a pharmaceutically acceptable salt or solvate thereof, was effective in the subject. In some embodiments, the AF is reduced such that the level is below the detection limit of the instrument. Alternatively, an increase in the allele frequency (AF) of the dysregulation of a RET gene in the cfDNA obtained from the patient at the second time point as compared to the allele frequency (AF) of the dysregulation of a RET gene in the cfDNA obtained from the patient at the first time point indicates that the compound of Formula I, or a pharmaceutically acceptable salt or solvate thereof, was not effective in the subject (e.g., the subject has developed a resistance mutation to the compound of Formula I, or a pharmaceutically acceptable salt or solvate thereof). Some embodiments of these methods can further include, administering additional doses of a compound of Formula I (e.g., any one of Formulas I-A to I-L), or a pharmaceutically acceptable salt or solvate thereof, to a patient in which a compound of Formula I (e.g., any one of Formulas I-A to I-L), or a pharmaceutically acceptable salt or solvate thereof, was determined to be effective. Some embodiments of these methods can further include, administering a different treatment (e.g., a treatment that does not include the administration of Formula I (e.g., any one of Formulas I-A to I-L), or a pharmaceutically acceptable salt or solvate thereof, as a monotherapy) to a patient in which a compound of Formula I (e.g., any one of Formulas I-A to I-L), or a pharmaceutically acceptable salt or solvate thereof, was determined not to be effective.

In some examples of these methods, the time difference between the first and second time points can be about 1 day to about 1 year, about 1 day to about 11 months, about 1 day to about 10 months, about 1 day to about 9 months, about 1 day to about 8 months, about 1 day to about 7 months, about 1 day to about 6 months, about 1 day to about 5 months, about 1 day to about 4 months, about 1 day to about 3 months, about 1 day to about 10 weeks, about 1 day to about 2 months, about 1 day to about 6 weeks, about 1 day to about 1 month, about 1 day to about 25 days, about 1 day to about 20 days, about 1 day to about 15 days, about 1 day to about 10 days, about 1 day to about 5 days, about 2 days to about 1 year, about 5 days to about 1 year, about 10 days to about 1 year, about 15 days to about 1 year, about 20 days to about 1 year, about 25 days to about 1 year, about 1 month to about 1 year, about 6 weeks to about 1 year, about 2 months to about 1 year, about 3 months to about 1 year, about 4 months to about 1 year, about 5 months to about 1 year, about 6 months to about 1 year, about 7 months to about 1 year, about 8 months to about 1 year, about 9 months to about 1 year, about 10 months to about 1 year, about 11 months to about 1 year, about 1 day to about 7 days, about 1 day to about 14 days, about 5 days to about 10 days, about 5 day to about 20 days, about 10 days to about 20 days, about 15 days to about 1 month, about 15 days to about 2 months, about 1 week to about 1 month, about 2 weeks to about 1 month, about 1 month to about 3 months, about 3 months to about 6 months, about 4 months to about 6 months, about 5 months to about 8 months, or about 7 months to about 9 months. In some embodiments of these methods, the patient can be previously identified as having a cancer having a dysregulated RET gene (e.g., any of the examples of a dysregulated RET gene described herein). In some embodiments of these methods, a patient can have been previously diagnosed as having any of the types of cancer described herein. In some embodiments of these methods, the patient can have one or more metastases (e.g., one or more brain metastases).

In some of the above embodiments, the cfDNA comprises ctDNA such as RET-associated ctDNA. For example, the cfDNA is ctDNA such as RET-associated ctDNA. In some embodiments, at least some portion of cfDNA is determined to be RET-associated ctDNA, for example, a sequenced and/or quantified amount of the total cfDNA is determined to have a RET fusion and/or a RET resistance mutation.

In the field of medical oncology it is normal practice to use a combination of different forms of treatment to treat each patient with cancer. In medical oncology the other component(s) of such conjoint treatment or therapy in addition to compositions provided herein may be, for example, surgery, radiotherapy, and chemotherapeutic agents, such as other kinase inhibitors, signal transduction inhibitors and/or monoclonal antibodies. For example, a surgery may be open surgery or minimally invasive surgery. Compounds of Formula I (e.g., any one of Formulas I-A to I-L), or a pharmaceutically acceptable salt or solvate thereof therefore may also be useful as adjuvants to cancer treatment, that is, they can be used in combination with one or more additional therapies or therapeutic agents, for example, a chemotherapeutic agent that works by the same or by a different mechanism of action. In some embodiments, a compound of Formula I (e.g., any one of Formulas I-A to I-L), or a pharmaceutically acceptable salt or solvate thereof, can be used prior to administration of an additional therapeutic agent or additional therapy. For example, a patient in need thereof can be administered one or more doses of a compound of Formula I (e.g., any one of Formulas I-A to I-L), or a pharmaceutically acceptable salt or solvate thereof for a period of time and then under go at least partial resection of the tumor. In some embodiments, the treatment with one or more doses of a compound of Formula I (e.g., any one of Formulas I-A to I-L), or a pharmaceutically acceptable salt or solvate thereof reduces the size of the tumor (e.g., the tumor burden) prior to the at least partial resection of the tumor. In some embodiments, a patient in need thereof can be administered one or more doses of a compound of Formula I (e.g., any one of Formulas I-A to I-L), or a pharmaceutically acceptable salt or solvate thereof for a period of time and under one or more rounds of radiation therapy. In some embodiments, the treatment with one or more doses of a compound of Formula I (e.g., any one of Formulas I-A to I-L), or a pharmaceutically acceptable salt or solvate thereof reduces the size of the tumor (e.g., the tumor burden) prior to the one or more rounds of radiation therapy.

In some embodiments, a patient has a cancer (e.g., a locally advanced or metastatic tumor) that is refractory or intolerant to standard therapy (e.g., administration of a chemotherapeutic agent, such as a first RET inhibitor or a multikinase inhibitor, immunotherapy, or radiation (e.g., radioactive iodine)). In some embodiments, a patient has a cancer (e.g., a locally advanced or metastatic tumor) that is refractory or intolerant to prior therapy (e.g., administration of a chemotherapeutic agent, such as a first RET inhibitor or a multikinase inhibitor, immunotherapy, or radiation (e.g., radioactive iodine)). In some embodiments, a patient has a cancer (e.g., a locally advanced or metastatic tumor) that has no standard therapy. In some embodiments, a patient is RET-kinase inhibitor naïve. For example, the patient is naïve to treatment with a selective RET-kinase inhibitor. In some embodiments, a patient is not RET-kinase inhibitor naïve.

In some embodiments, a patient has undergone prior therapy. In some embodiments, a patient having NSCLC (e.g, a RET-fusion positive NSCLS) has received treatment with a platinum-based chemotherapy, PD-1/PDL1 immunotherapy, or both prior to treatment with a compound of Formula I (e.g., any one of Formulas I-A to I-L), or a pharmaceutically acceptable salt or solvate thereof. In some embodiments, a patient having a thyroid cancer (e.g., a RET-fusion positive thyroid cancer) has received treatment with one or more of sorafenib, lenvatinib, and radioactive iodine prior to treatment with a compound of Formula I (e.g., any one of Formulas I-A to I-L), or a pharmaceutically acceptable salt or solvate thereof. In some embodiments, a patient having a colorectal cancer (e.g., a RET-fusion positive colorectal cancer) has received treatment with a fluoropyrimidine-based chemotherapy, with or without anti-VEGF-directed therapy or anti-EGFR-directed therapy, prior to treatment with a compound of Formula I (e.g., any one of Formulas I-A to I-L), or a pharmaceutically acceptable salt or solvate thereof. In some embodiments, a patient having a pancreatic cancer (e.g., a RET-fusion positive pancreatic cancer) has received treatment with one or more of a fluoropyrimidine-based chemotherapy, a gemcitabine-based chemotherapy, and a S-1 chemotherapy prior to treatment with a compound of Formula I (e.g., any one of Formulas I-A to I-L), or a pharmaceutically acceptable salt or solvate thereof. In some embodiments, a patient having a breast cancer (e.g., a RET-fusion positive breast cancer) has received treatment with one or more of anthracycline, taxane, HER2-directed therapy, and hormonal therapy prior to treatment with a compound of Formula I (e.g., any one of Formulas I-A to I-L), or a pharmaceutically acceptable salt or solvate thereof. In some embodiments, a patient having a MTC (e.g., a RET-fusion positive MTC cancer) has received treatment with one or more of caboxantinib and vandetanib prior to treatment with a compound of Formula I (e.g., any one of Formulas I-A to I-L), or a pharmaceutically acceptable salt or solvate thereof.

In some embodiments of any the methods described herein, the compound of Formula I, or a pharmaceutically acceptable salt or solvate thereof is administered in combination with a therapeutically effective amount of at least one additional therapeutic agent selected from one or more additional therapies or therapeutic (e.g., chemotherapeutic) agents.

Non-limiting examples of additional therapeutic agents include: other RET-targeted therapeutic agents (i.e. a first or second RET kinase inhibitor), other kinase inhibitors (e.g., receptor tyrosine kinase-targeted therapeutic agents (e.g., Trk inhibitors or EGFR inhibitors)), signal transduction pathway inhibitors, checkpoint inhibitors, modulators of the apoptosis pathway (e.g. obataclax); cytotoxic chemotherapeutics, angiogenesis-targeted therapies, immune-targeted agents, including immunotherapy, and radiotherapy.

In some embodiments, the other RET-targeted therapeutic is a multikinase inhibitor exhibiting RET inhibition activity. In some embodiments, the other RET-targeted therapeutic inhibitor is selective for a RET kinase. Exemplary RET kinase inhibitors can exhibit inhibition activity ($IC_{50}$) against a RET kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a RET kinase inhibitors can exhibit inhibition activity ($IC_{50}$) against a RET kinase of less than about 25 nM, less than about 10 nM, less than about 5 nM, or less than about 1 nM as measured in an assay as provided herein.

Non-limiting examples of RET-targeted therapeutic agents (e.g., a first RET inhibitor or a second RET inhibitor) include alectinib (9-Ethyl-6,6-dimethyl-8-[4-(morpholin-4-yl)piperidin-1-yl]-11-oxo-6,11-dihydro-5H-benzo[b]carbazole-3-carbonitrile); amuvatinib (MP470, HPK56) (N-(1,3-benzodioxol-5-ylmethyl)-4-([1]benzofuro[3,2-d]pyrimidin-4-yl)piperazine-1-carbothioamide); apatinib (YN968D1) (N-[4-(1-cyanocyclopentyl) phenyl-2-(4-picolyl)amino-3-Nicotinamide methanesulphonate); cabozantinib (Cometriq XL-184) (N-(4-((6,7-Dimethoxyquinolin-4-yl)oxy)phenyl)-N'-(4-fluorophenyl)cyclopropane-1,1-dicarboxamide); dovitinib (TKI258; GFKI-258; CHIR-258) ((3Z)-4-amino-5-fluoro-3-[5-(4-methylpiperazin-1-yl)-1,3-dihydrobenzimidazol-2-ylidene]quinolin-2-one); famitinib (5-[2-(diethylamino)ethyl]-2-[(Z)-(5-fluoro-2-oxo-1H-indol-3-ylidene)methyl]-3-methyl-6,7-dihydro-1H-pyrrolo[3,2-c]pyridin-4-one); fedratinib (SAR302503, TG101348) (N-(2-Methyl-2-propanyl)-3-{[5-methyl-2-({4-[2-(1-pyrrolidinyl)ethoxy]phenyl}amino)-4-pyrimidinyl]amino}benzenesulfonamide); foretinib (XL880, EXEL-2880, GSK1363089, GSK089) (N1'-[3-fluoro-4-[[6-methoxy-7-(3-morpholinopropoxy)-4-quinolyl]oxy]phenyl]-N1-(4-fluorophenyl)cyclopropane-1,1-dicarboxamide); fostamantinib (R788) (2H-Pyrido[3,2-b]-1,4-oxazin-3(4H)-one, 6-[[5-fluoro-2-[(3,4,5-trimethoxyphenyl)amino]-4-pyrimidinyl]amino]-2,2-dimethyl-4-[(phosphonooxy)methyl]-, sodium salt (1:2)); ilorasertib (ABT-348) (1-(4-(4-amino-7-(1-(2-hydroxyethyl)-1H-pyrazol-4-yl)thieno[3,2-c]pyridin-3-yl)phenyl)-3-(3-fluorophenyl)urea); lenvatinib (E7080, Lenvima) (4-[3-chloro-4-(cyclopropylaminocarbonyl)aminophenoxy]-7-methoxy-6-quinolinecarboxamide); motesanib (AMG 706) (N-(3,3-Dimethyl-2,3-dihydro-1H-indol-6-yl)-2-[(pyridin-4-ylmethyl)amino]pyridine-3-carboxamide); nintedanib (3-Z-[1-(4-(N-((4-methyl-piperazin-1-yl)-methylcarbonyl)-N-methyl-amino)-anilino)-1-phenyl-methylene]-6-methyoxycarbonyl-2-indolinone); ponatinib (AP24534) (3-(2-Imidazo[1,2-b]pyridazin-3-ylethynyl)-4-methyl-N-[4-[(4-methylpiperazin-1-yl)methyl]-3-(trifluoromethyl) phenyl]benzamide); PP242 (a TORKinib) (2-[4-Amino-1-(1-methylethyl)-1H-pyrazolo[3,4-d]pyrimidin-3-yl]-1H-indol-5-ol); quizartinib (1-(5-(tert-Butyl)isoxazol-3-yl)-3-(4-(7-(2-morpholinoethoxy)benzo[d]imidazo[2,1-b]thiazol-2-yl)phenyl)urea); regorfenib (BAY 73-4506, stivarga) (4-[4-({[4-Chloro-3-(trifluoromethyl)phenyl]carbamoyl}amino)-3-fluorophenoxy]-N-methylpyridine-2-carboxamide hydrate); RXDX-105 (CEP-32496, agerafenib) (1-(3-((6,7-dimethoxyquinazolin-4-yl)oxy)phenyl)-3-(5-(1,1,1-trifluoro-2-methylpropan-2-yl)isoxazol-3-yl)urea); semaxanib (SU5416) ((3Z)-3-[(3,5-dimethyl-1H-pyrrol-2-yl)methylidene]-1,3-dihydro-2H-indol-2-one); sitravatinib (MGCD516, MG516) (N-(3-Fluoro-4-{[2-(5-{[(2-methoxyethyl)amino]methyl}-2-pyridinyl)thieno[3,2-b]pyridin-7-yl]oxy}phenyl)-N?-(4-fluorophenyl)-1,1-cyclopropanedicarboxamide); sorafenib (BAY 43-9006) (4-[4-[[[[4-chloro-3-(trifluoromethyl)phenyl]amino]carbonyl] amino]phenoxy]-N-methyl-2-pyridinecarboxamide); vandetanib (N-(4-bromo-2-fluorophenyl)-6-methoxy-7-[(1-methylpiperidin-4-yl)methoxy]quinazolin-4-amine); vatalanib (PTK787, PTK/ZK, ZK222584) (N-(4-chlorophenyl)-4-(pyridin-4-ylmethyl)phthalazin-1-amine); AD-57 (N-[4-[4-amino-1-(1-methylethyl)-1H-pyrazolo[3,4-d]pyrimidin-3-yl]phenyl]-N'-[3-(trifluoromethyl)phenyl]-urea); AD-80 (1-[4-(4-amino-1-propan-2-ylpyrazolo[3,4-d]pyrimidin-3-yl)phenyl]-3-[2-fluoro-5-(trifluoromethyl)phenyl]urea); AD-81 (1-(4-(4-amino-1-isopropyl-1H-pyrazolo[3,4-d]pyrimidin-3-yl)phenyl)-3-(4-chloro-3-(trifluoromethyl)phenyl)urea); ALW-II-41-27 (N-(5-((4-((4-ethylpiperazin-1-yl)methyl)-3-(trifluoromethyl)phenyl)carbamoyl)-2-methylphenyl)-5-(thiophen-2-yl)nicotinamide); BPR1K871 (1-(3-chlorophenyl)-3-(5-(2-((7-(3-dimethylamino)propoxy)quinazolin-4-yl)amino)ethyl)thiazol-2-yl)urea); CLM3 (1-phenethyl-N-(1-phenylethyl)-1H-pyrazolo[3,4-d]pyrimidin-4-amine); EBI-907 (N-(2-chloro-3-(1-cyclopropyl-8-methoxy-3H-pyrazolo[3,4-c]isoquinolin-7-yl)-4-fluorophenyl)-3-fluoropropane-1-sulfonamide); NVP-AST-487 (N-[4-[(4-ethyl-1-piperazinyl)methyl]-3-(trifluoromethyl)phenyl]-N'-[4-[[6-(methylamino)-4-pyrimidinyl]oxy]phenyl]-urea); NVP-BBT594 (BBT594) (5-((6-acetamidopyrimidin-4-yl)oxy)-N-(4-((4-methylpiperazin-1-yl)methyl)-3-(trifluoromethyl)phenyl)indoline-1-carboxamide); PD173955 (6-(2,6-dichlorophenyl)-8-methyl-2-(3-methylsulfanylanilino)pyrido[2,3-d]pyrimidin-7-one); PP2 (4-amino-5-(4-chlorophenyl)-7-(dimethylethyl)pyrazolo[3,4-d]pyrimidine); PZ-1 (N-(5-(tert-butyl)isoxazol-3-yl)-2-(4-(5-(1-methyl-1H-pyrazol-4-yl)-1Hbenzo[d]imidazol-1-yl) phenyl)acetamide); RPI-1 (1,3-dihydro-5,6-dimethoxy-3-[(4-hydroxyphenyl)methylene]-H-indol-2-one; (3E)-3-[(4-hydroxyphenyl)methylidene]-5,6-dimethoxy-1H-indol-2-one); SGI-7079 (3-[2-[[3-fluoro-4-(4-methyl-1-piperazinyl) phenyl]amino]-5-methyl-7H-pyrrolo[2,3-d]pyrimidin-4-yl]-benzeneacetonitrile); SPP86 (1-Isopropyl-3-(phenylethynyl)-1H-pyrazolo[3,4-d]pyrimidin-4-amine); SU4984 (4-[4-[(E)-(2-oxo-1H-indol-3-ylidene)methyl]phenyl]piperazine-1-carbaldehyde); sunitinb (SU11248) (N-(2-Diethylaminoethyl)-5-[(Z)-(5-fluoro-2-oxo-1H-indol-3-ylidene)methyl]-2,4-dimethyl-1H-pyrrole-3-carboxamide); TG101209 (N-tert-butyl-3-(5-methyl-2-(4-(4-methylpiperazin-1-yl)phenylamino)pyrimidin-4-ylamino)benzenesulfonamide); Withaferin A ((4β,5β,6β,22R)-4,27-Dihydroxy-5,6:22,26-diepoxyergosta-2,24-diene-1,26-dione); XL-999 ((Z)-5-((1-ethylpiperidin-4-yl)amino)-3-((3-fluorophenyl)(5-methyl-1H-imidazol-2-yl)methylene)indolin-2-one); BPR1J373 (a 5-phenylthiazol-2-ylamine-pyriminide derivative); CG-806 (CG'806); DCC-2157; GTX-186; HG-6-63-01 ((E)-3-(2-(4-chloro-1H-pyrrolo[2,3-b]pyridin-5-yl)vinyl)-N-(4-((4-ethylpiperazin-1-yl)methyl)-3-(trifluoromethyl)phenyl)-4-methylbenzamide); SW-01 (Cyclobenzaprine hydrochloride); XMD15-44 (N-(4-((4-ethylpiperazin-1-yl)methyl)-3-(trifluoromethyl)phenyl)-4-methyl-3-(pyridin-3-ylethynyl)benzamide (generated from structure)); Y078-DM1 (an antibody drug conjugate composed of a RET antibody (Y078) linked to a derivative of the cytotoxic agent maytansine); Y078-DM4 (an antibody drug conjugate composed of a RET antibody (Y078) linked to a derivative of the cytotoxic agent maytansine); ITRI-305 (D0N5 TB, DIB003599); BLU-667 (((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl) amino)pyrimidin-2-yl)cyclohexane-1-carboxamide); BLU6864; DS-5010; GSK3179106; GSK3352589; and NMS-E668.

Further examples of RET-targeted therapeutics (e.g., a first RET kinase inhibitor or a second RET kinase inhibitor) include 5-amino-3-(5-cyclopropylisoxazol-3-yl)-1-isopropyl-1H-pyrazole-4-carboxamide; 3-(5-cyclopropylisoxazol-3-yl)-1-isopropyl-1H-pyrazolo[3,4-d]pyrimidin-4-amine; 3-((6,7-Dimethoxyquinazolin-4-yl)amino)-4-fluoro-2-methylphenol; N-(5-(tert-butyl)isoxazol-3-yl)-2-(4-(imidazo[1,2-a]pyridin-6-yl)phenyl)acetamide; N-(5-(tert-butyl)isoxazol-3-yl)-2-(3-(imidazo[1,2-b]pyridazin-6-yloxy)phenyl)acetamide; N-(2-fluoro-5-trifluoromethylphenyl)-N'-{4'-[(2"-benzamido)pyridin-4"-ylamino]phenyl}urea; 2-amino-6-{[2-(4-chlorophenyl)-2-oxoethyl]sulfanyl}-4-(3-thienyl)pyridine-3,5-dicarbonitrile; and 3-arylureidobenzylidene-indolin-2-ones.

Additional examples of other RET kinase inhibitors include those described in U.S. Pat. Nos. 9,150,517 and 9,149,464, and International Publication No. WO 2014075035, all of which are hereby incorporated by reference. For example, in some embodiments the other RET inhibitor is a compound of formula I:

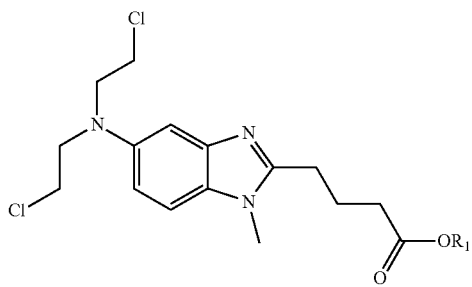

wherein $R_1$ is $C_6$-$C_{24}$alkyl or polyethylene glycol; or a pharmaceutically acceptable salt form thereof. In some embodiments, the other RET inhibitor is 4-{5-[bis-(chloroethyl)-amino]-1-methyl-1H-benzimidazol-2-yl}butyric acid dodecyl ester.

Additional examples of other RET kinase inhibitors include those described in International Publication No. WO 2016127074, which is hereby incorporated by reference. For example, in some embodiments the other RET inhibitor is a compound of Formula (I) or a pharmaceutically acceptable salt thereof, wherein:

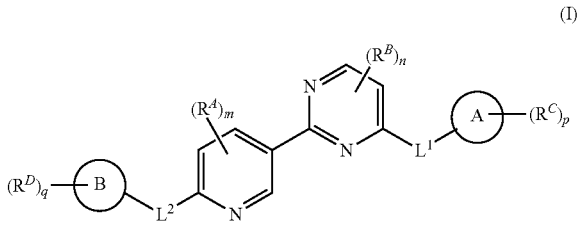

wherein Rings A and B are each independently selected from aryl, heteroaryl, cycloalkyl and heterocyclyl;

each $L^1$ and $L^2$ is independently selected from a bond, —(C1-C6 alkylene)-, —(C2-C6alkenylene)-, —(C2-C6 alkynylene)-, —(C1-C6 haloalkylene)-, —(C1-C6 heteroalkylene)-, —C(O)—, —O—, —S—, —S(O), —S(O)$_2$—, —N($R^1$)—, —O—(C1-C6 alkylene)-, —(C1-C6 alkylene)-O—, —N($R^1$)—C(O)—, —C(O)N($R^1$)—, —(C1-C6 alkylene)-N($R^1$)—, —N($R^1$)—(C1-C6 alkylene)-, —N($R^1$)—C(O)—(C1-C6 alkylene)-, —(C1-C6 alkylene)-N($R^1$)—C(O)—, —C(O)—N($R^1$)—(C1-C6 alkylene)-, —(C1-C6 alkylene)-C(O)—N($R^1$)—, —N($R^1$)—S(O)$_2$—, —S(O)$_2$—N($R^1$)—, —N($R^1$)—S(O)$_2$—(C1-C6 alkylene)-, and —S(O)$_2$—N($R^1$)—(C1-C6 alkylene)-; wherein each alkylene, alkenylene, alkynylene, haloalkylene, and heteroalkylene is independently substituted with 0-5 occurrences of $R^1$;

each $R^A$ and $R^B$ is independently selected from C1-C6 alkyl, C1-C6 alkoxy, halo, C1-C6 haloalkyl, C1-C6 hydroxyalkyl, C1-C6 heteroalkyl, and —N($R^1$)($R^1$); wherein each alkyl, alkoxy, haloalkyl, hydroxyalkyl, and hydroxyalkyl is independently substituted with 0-5 occurrences of Ra;

each $R^C$ and $R^D$ is independently selected from C1-C6 alkyl, C2-C6 alkenyl, C2-C6 alkynyl, C1-C6 alkoxy, halo, C1-C6 heteroalkyl, C1-C6 haloalkyl, C1-C6 haloalkoxy, C1-C6 hydroxyalkyl, cycloalkyl, aryl, heteroaryl, aryloxy, aralkyl, heterocyclyl, heterocyclylalkyl, nitro, cyano, —C(O)$R^1$, —OC(O)$R^1$, —C(O)O$R^1$, —(C1-C6 alkylene)-C(O)$R^1$, —S$R^1$, —S(O)$_2R^1$, —S(O)$_2$—N($R^1$)($R^1$), —(C1-C6 alkylene)-S(O)$_2R^1$, —(C1-C6 alkylene)-S(O)$_2$—N($R^1$)($R^1$), —N($R^1$)($R^1$)—C(O)—N($R^1$)($R^1$)—N($R^1$)—C(O)$R^1$, —N($R^1$)—C(O)O$R^1$, —(C1-C6 alkylene)-N($R^1$)—C(O)$R^1$, —N($R^1$)S(O)$_2R^1$, and —P(O)($R^1$)($R^1$); wherein each of alkyl, alkenyl, alkynyl, alkoxy, heteroalkyl, haloalkyl, haloalkoxy, hydroxyalkyl, cycloalkyl, aryl, heteroaryl, aryloxy, aralkyl, heterocyclyl, and heterocyclylalkyl is independently substituted with 0-5 occurrences of $R^a$; or 2 $R^C$ or 2 $R^D$ together with the carbon atom(s) to which they are attached form a cycloalkyl or heterocyclyl ring independently substituted with 0-5 occurrences of $R^a$;

each $R^1$ is independently selected from hydrogen, hydroxyl, halo, thiol, C1-C6 alkyl, C1-C6 thioalkyl, C1-C6 alkoxy, C1-C6 haloalkyl, C1-C6 hydroxyalkyl, C1-C6 heteroalkyl, cycloalkyl, cycloalkylalkyl, heteroarylalkyl, heterocyclyl, and heterocyclylalkyl, wherein each of alkyl, thioalkyl, alkoxy, haloalkyl, hydroxyalkyl, heteroalkyl, cycloalkyl, cycloalkylalkyl, heteroarylalkyl, heterocyclyl, and heterocyclylalkyl is independently substituted with 0-5 occurrences of $R^b$, or 2 $R^1$ together with the atom(s) to which they are attached form a cycloalkyl or heterocyclyl ring independently substituted with 0-5 occurrences of $R^b$;

each $R^a$ and $R^b$ is independently C1-C6 alkyl, halo, hydroxyl, C1-C6 haloalkyl, C1-C6 heteroalkyl, C1-C6 hydroxyalkyl, C1-C6 alkoxy, cycloalkyl, heterocyclyl, or cyano, wherein each of alkyl, haloalkyl, heteroalkyl, hydroxyalkyl, alkoxy, cycloalkyl and heterocyclyl is independently substituted with 0-5 occurrences of R';

each R' is C1-C6 alkyl, C1-C6 heteroalkyl, halo, hydroxyl, C1-C6 haloalkyl, C1-C6 hydroxyalkyl, cycloalkyl or cyano; or 2 R', together with the atom(s) to which they are attached form a cycloalkyl or heterocyclyl ring;

m is 0, 1, 2, or 3;

n is 0, 1, or 2; and p and q are each independently 0, 1, 2, 3, or 4. For example, a RET inhibitor can be selected from the group consisting of:

157
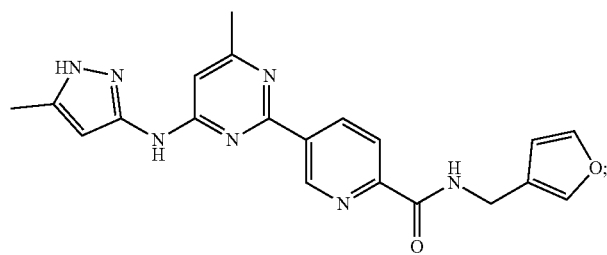
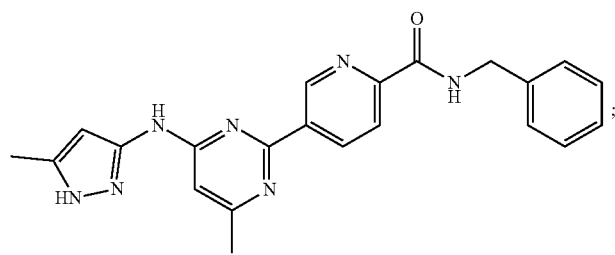
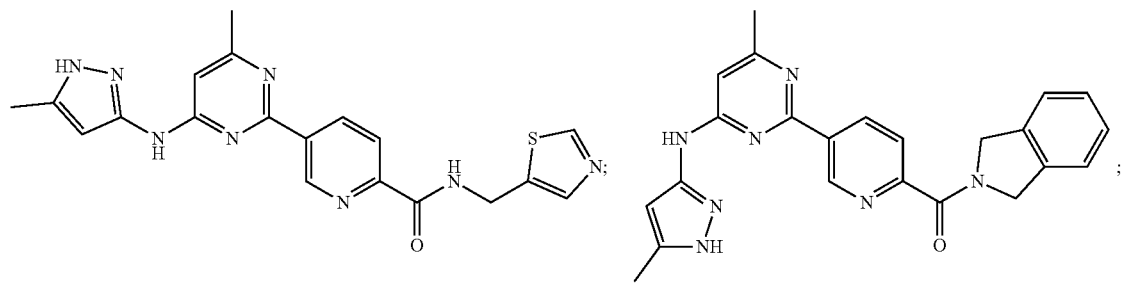
158
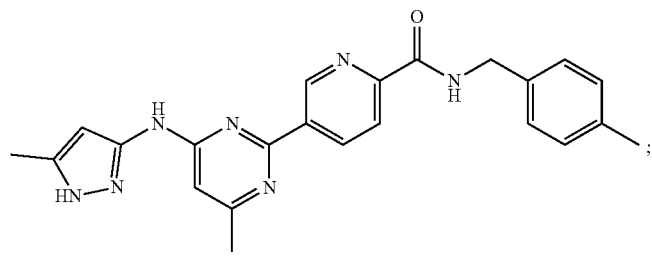
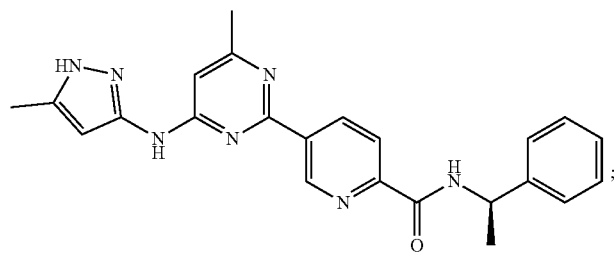
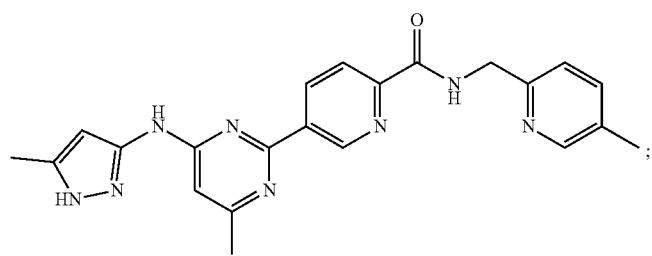

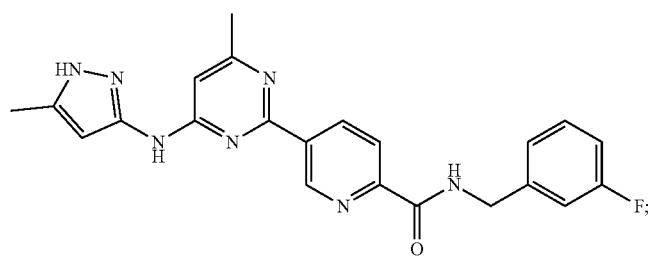
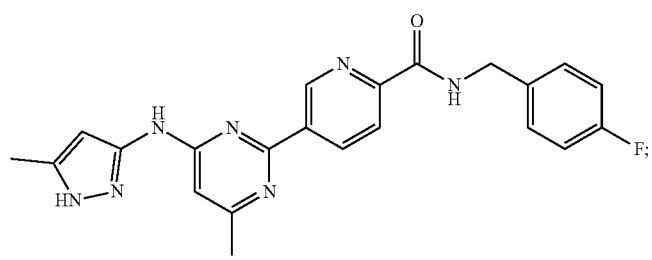
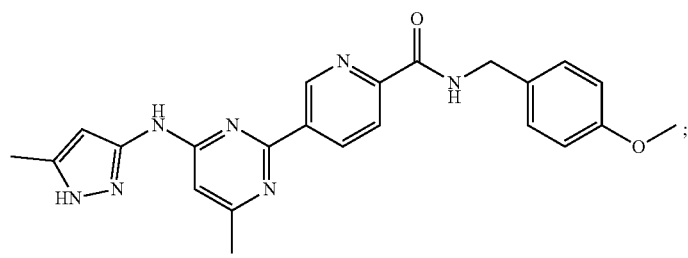
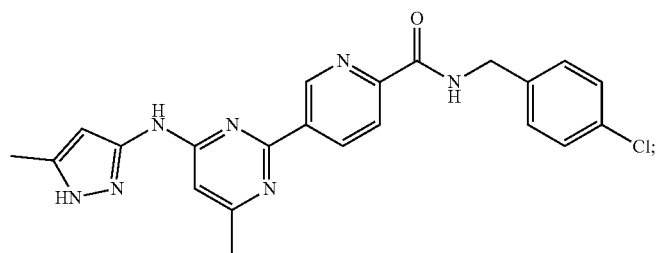
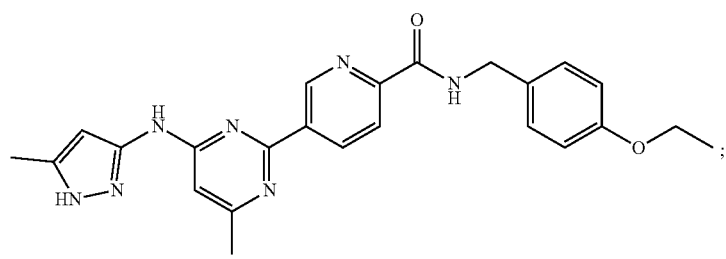
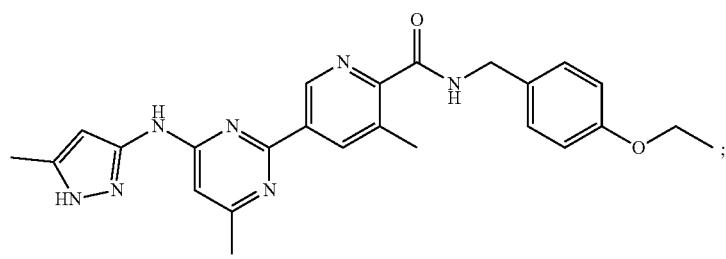

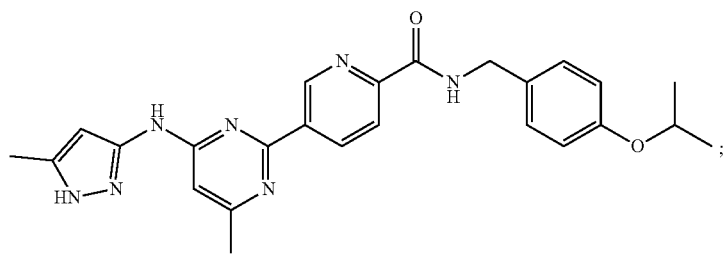
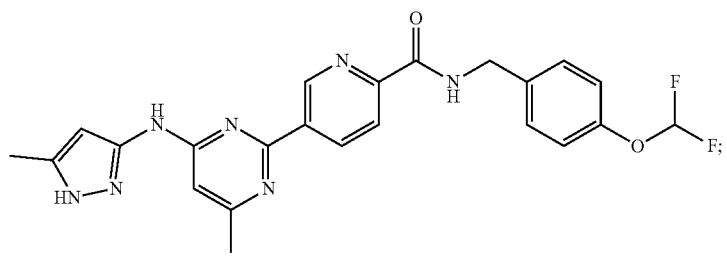
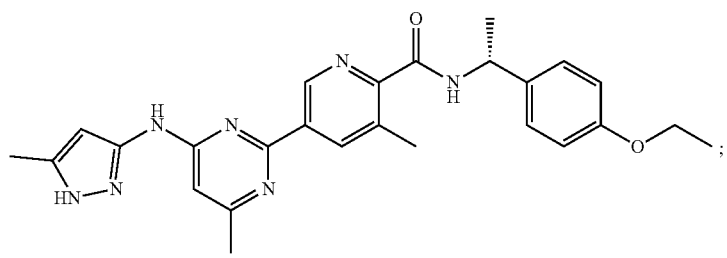
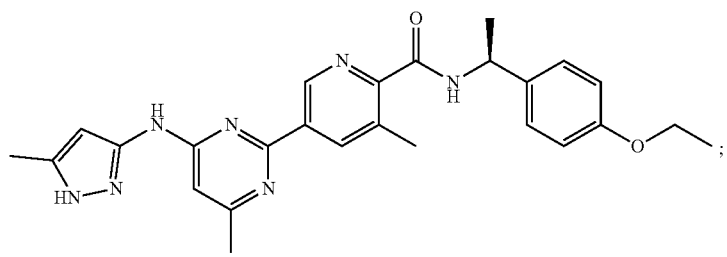
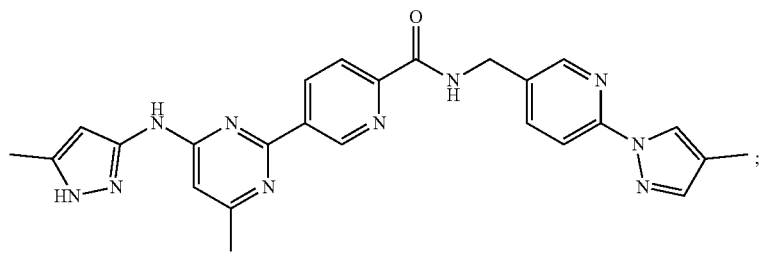
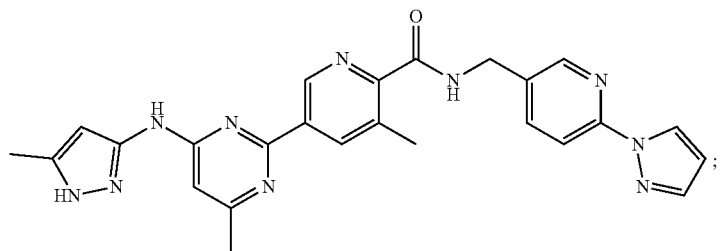

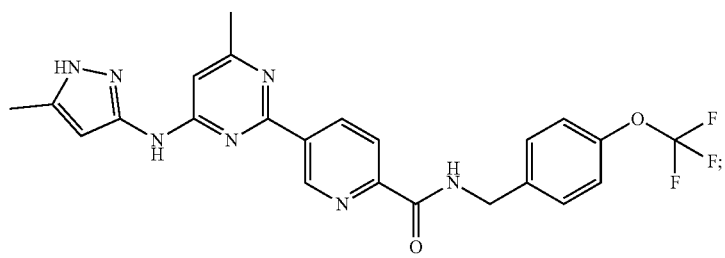
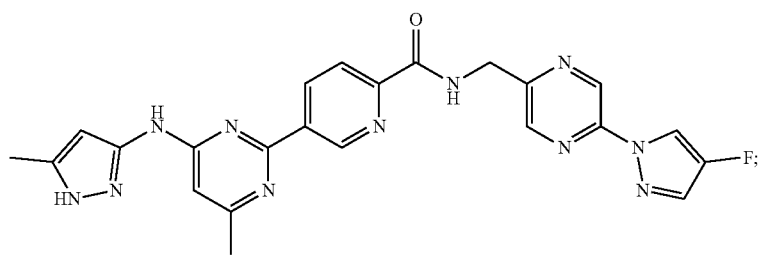
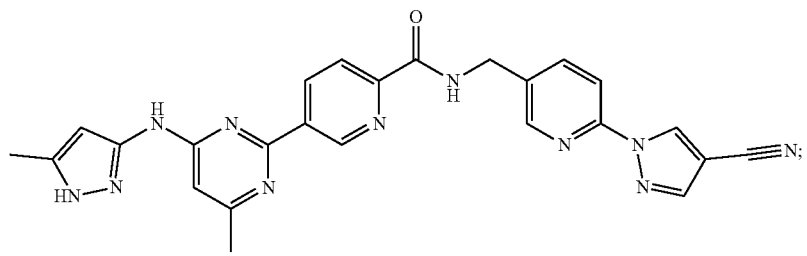
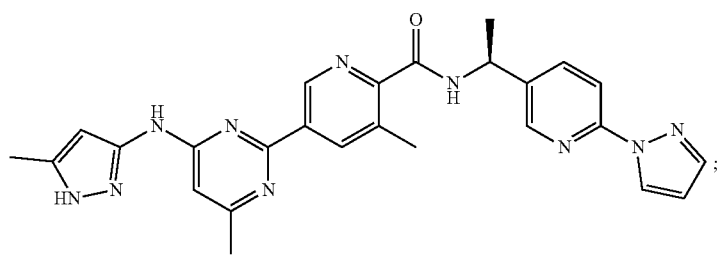
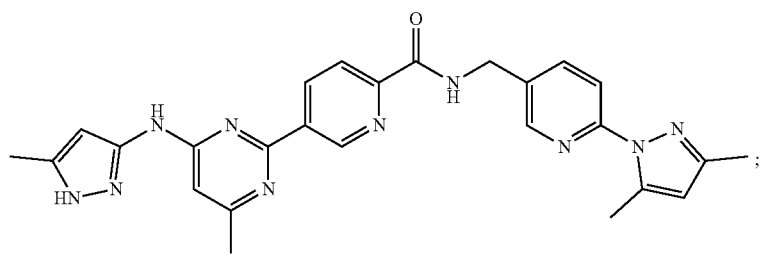
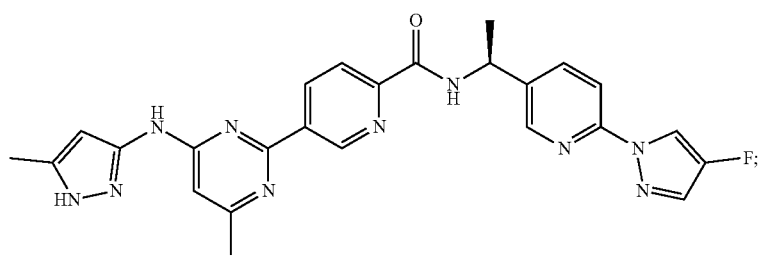

-continued
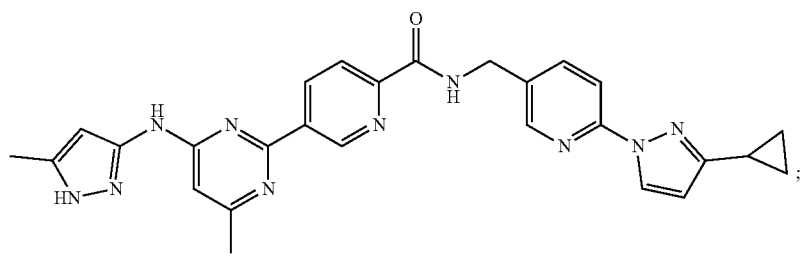
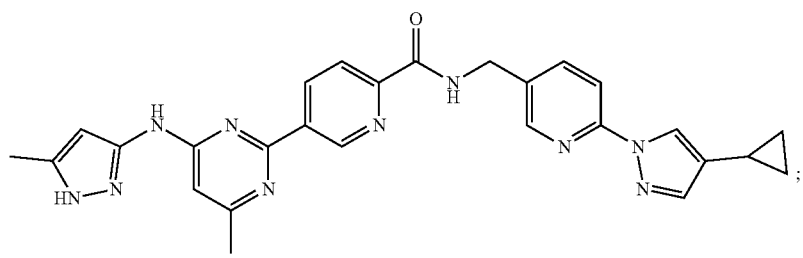
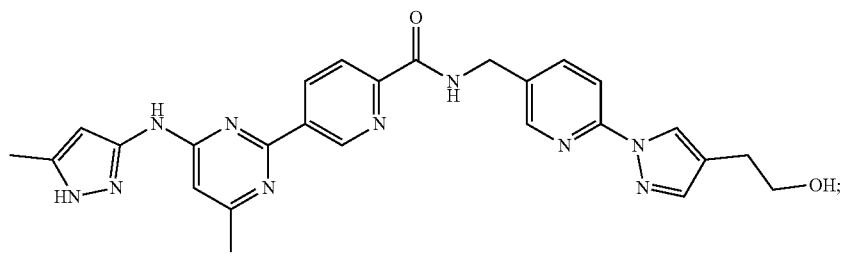
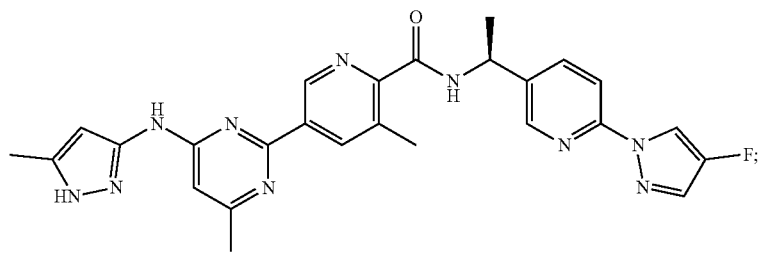
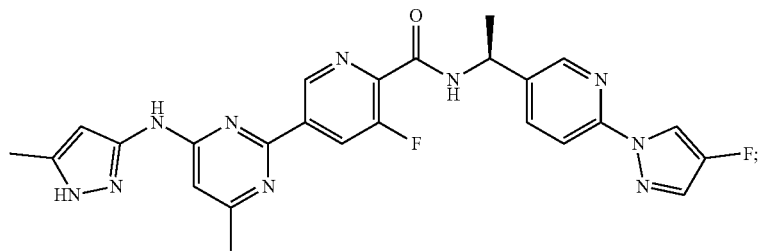
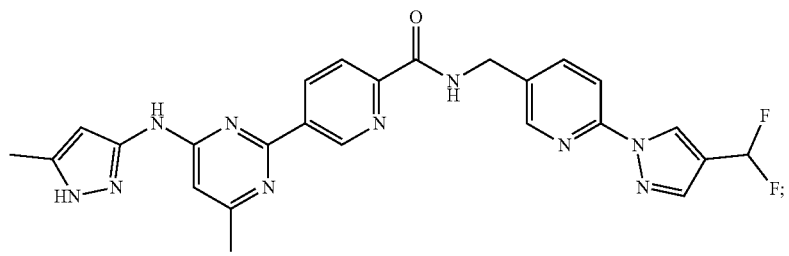

-continued

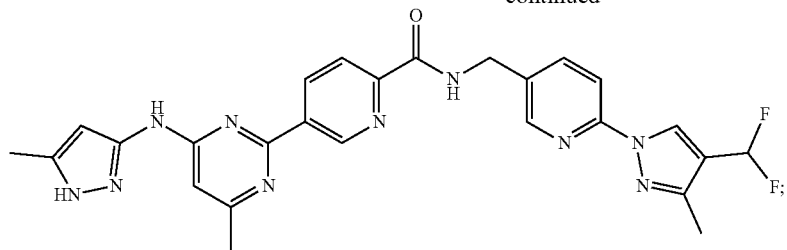

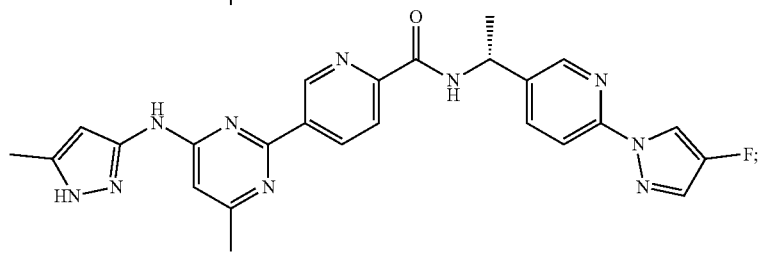

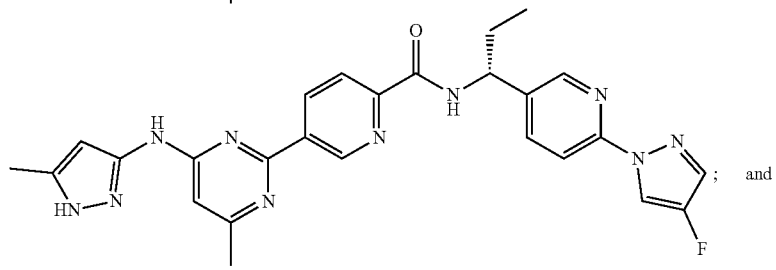

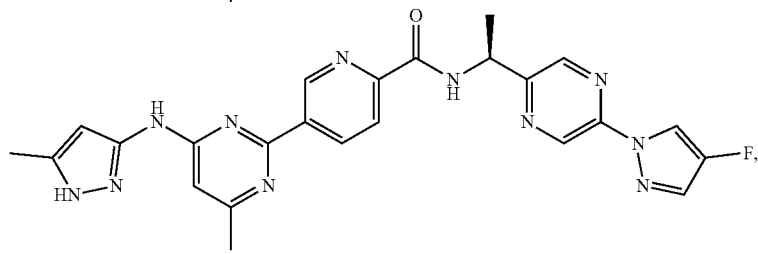

or a pharmaceutically acceptable salt thereof.

Additional examples of other RET kinase inhibitors include those described in International Publication No. WO 2016075224, which is hereby incorporated by reference. For example, in some embodiments, the other RET inhibitor is a compound of Formula (II) or a pharmaceutically acceptable salt thereof, wherein:

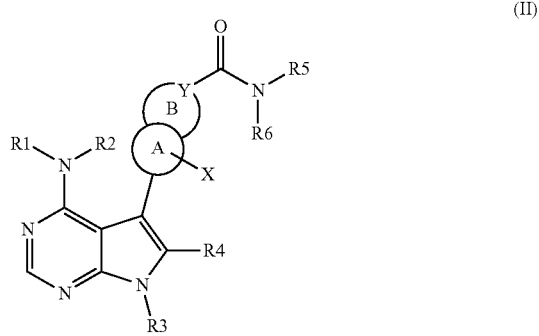

R1 and R2 are independently hydrogen or an optionally substituted group selected from straight or branched ($C_1$-$C_6$) alkyl, ($C_3$-$C_6$) cycloalkyl and COR', wherein R' is an optionally substituted group selected from straight or branched ($C_1$-$C_6$) alkyl and (C3-C6) cycloalkyl;

R3 is hydrogen or an optionally substituted group selected from straight or branched ($C_1$-$C_6$) alkyl, ($C_2$-$C_6$) alkenyl, (C2-C6) alkynyl, ($C_3$-$C_6$) cycloalkyl, aryl, heteroaryl and a 3- to 7-membered heterocyclyl ring;

R4 is hydrogen or an optionally substituted group selected from straight or branched ($C_1$-$C_6$) alkyl, ($C_2$-$C_6$) alkenyl, aryl, heteroaryl or heterocyclyl;

A is a 5- or 6-membered heteroaryl ring or a phenyl ring;

B is a 5- or 6-membered ring selected from heteroaryl, ($C_5$-$C_6$) cycloalkyl and heterocyclyl ring or a phenyl ring; wherein ring A and ring B are fused together to form a bicyclic system comprising a 6-membered aromatic or 5- to 6-membered heteroaromatic ring fused with a 6-membered aromatic or 5- to 6-membered heteroaromatic, ($C_5$-$C_6$) cycloalkyl or heterocyclyl ring;

Y is carbon or nitrogen;

X is hydrogen, halogen, hydroxyl, cyano or an optionally substituted group selected from straight or branched ($C_1$-$C_6$) alkyl and ($C_1$-$C_6$) alkoxyl; and R5 and R6 are independently hydrogen or an optionally substituted group selected from straight or branched (C$_1$-C$_6$) alkyl, (C$_3$-C$_6$) cycloalkyl, heterocyclyl, aryl and heteroaryl.

Additional examples of other RET kinase inhibitors include those described in International Publication No. WO 2015079251, which is hereby incorporated by reference. For example, in some embodiments, the other RET inhibitor is a compound of Formula (III) or a pharmaceutically acceptable salt or solvate thereof, wherein:

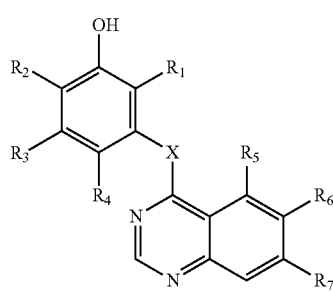

(III)

X is NH, NR$_x$, I or S, wherein R$_x$ is (1-3C)alkyl;

R$_1$ is selected from halo (e.g., fluoro, chloro, or bromo), trifluoromethyl, (1-4C)alkyl (e.g., methyl), (1-4C)alkoxy or (3-6C)cycloalkyl, wherein an alkyl, alkoxy or cycloalkyl group is optionally substituted with one or more fluoro;

R$_2$ is selected from hydrogen, halo (e.g., fluoro, chloro or bromo), hydroxyl, cyano, trifluoromethyl, trifluoromethoxy, (1-6C)alkyl (e.g., methyl), (3-8C)cycloalkyl, or (1-4C)alkoxy (e.g., OMe), wherein an alkyl, cycloalkyl or alkoxy group is optionally substituted with one or more fluoro;

R$_3$ is selected from hydrogen, halo (e.g. fluoro, chloro or bromo), hydroxyl, cyano, trifluoromethyl, trifluoromethoxy, (1-6C)alkyl (e.g., methyl), (3-8C)cycloalkyl, or (1-4C)alkoxy (e.g., OMe), wherein an alkyl, cycloalkyl or alkoxy group is optionally substituted with one or more fluoro;

R$_4$ is selected from hydrogen, halo (e.g., fluoro, chloro or bromo), hydroxyl, cyano, trifluoromethyl, trifluoromethoxy, (1-6C)alkyl (e.g., methyl), (3-8C)cycloalkyl, or (1-4C)alkoxy (e.g., OMe), wherein an alkyl, cycloalkyl or alkoxy group is optionally substituted with one or more fluoro;

R$_5$ is selected from hydrogen or a group defined by the formula:

—O-L$_5$-X$_5$-Q$_5$;

wherein

L$_5$ is absent or a linear or branched (1-4C)alkylene;

X$_5$ is absent or —C(O)O—, —O—, —C(O)—, —OC(O)—, —CH(QR$_{5L}$)—, —N(R$^J$)—, —N(R$_{5L}$)—C(O)—, —N(R$_{5L}$)—C(O)O—, —C(O)—N(R$_{5L}$)—, —S—, —SO—, —SO$_2$—, —S(O)$_2$N(R$_{5L}$)—, or —N(R$_{5L}$)SO$_2$— wherein R$_{5L}$ is selected from hydrogen or methyl; and Q$_5$ is (1-6C)alkyl, (2-6C)alkenyl, (2-6C)alkynyl, (3-8C)cycloalkyl, (3-8C)cycloalkyl-(1-4C)alkyl, aryl, aryl-(1-4C)alkyl, heteroaryl, heteroaryl-(1-4C)alkyl, heterocyclyl or heterocyclyl-(1-4C)alkyl;

R$_6$ is selected from hydrogen, or a group defined by the formula:

—O-L$_6$-X$_6$-Q$_6$ wherein

L$_6$ is absent or a linear or branched (1-4C)alkylene;

X$_6$ is absent or selected from —O—, —C(O)—, —C(O)O—, —OC(O)—, —CH(OR$_{6L}$)—, —N(R$_{6L}$), —N(R$_{6L}$)—C(O)—, —N(R$_{6L}$)—C(O)O—, —C(O)—N(R$_{6L}$)—, —S—, —SO—, —SO$_2$—, —S(O)$_2$N(R$_{6L}$)—, or —N(R$_{6L}$)SO$_2$— wherein R$_{6L}$ is selected from hydrogen or (1-3C)alkyl;

Q$_6$ is hydrogen, (1-8C)alkyl, (2-8C)alkenyl, (2-8C)alkynyl, (3-8C)cycloalkyl, (3-8C)cycloalkyl-(1-6C)alkyl, aryl, aryl-(1-6C)alkyl, heteroaryl, heteroaryl-(1-6C)alkyl, heterocyclyl, heterocyclyl-(1-6C)alkyl, or Q$_6$ and R$_{L6}$ are linked such that, together with the nitrogen atom to which they are attached, they form a heterocyclic ring;

wherein R$_6$ is optionally substituted (e.g. substituted on L$_6$ and/or Q$_6$) with one or more (1-6C)alkyl, (1-6C)alkanoyl, OR$_{6X}$, SR$_{6X}$, S(O)R$_{6X}$, S(O)$_2$R$_{6X}$, C(O)OR$_{6X}$ or C(O)NR$_{6X}$R'$_{6X}$, wherein Rex and R'$_{6X}$ are independently hydrogen, (1-8C)alkyl, or R$_{6X}$ and R'$_{6X}$ are linked such that, together with the nitrogen atom to which they are attached, they form a heterocyclic ring; and R$_7$ is selected from hydrogen, (1-6C)alkoxy, or a group defined by the formula:

—O-L$_7$-X$_7$-Q$_7$- wherein

L$_7$ is absent or a linear or branched (1-4C)alkylene;

X$_7$ is absent or selected from —O—, —C(O)—, —C(O)O—, —OC(O)—, —CH(OR$_{6L}$)—, —N(R$_{7L}$)—, —N(R$_{7L}$)—C(O)—, —N(R$_{7L}$)—C(O)O—, —C(O)—N(R$_{7L}$)—, —S—, —SO—, —SO$_2$—, —S(O)$_2$N(R$_{7L}$)—, or —N(R$_{7L}$)SO$_2$— wherein R$_{7L}$ is selected from hydrogen or (1-3C)alkyl;

Q$_7$ is hydrogen, (1-8C)alkyl, (2-8C)alkenyl, (2-8C)alkynyl, (3-8C)cycloalkyl, (3-8C)cycloalkyl-(1-6C)alkyl, aryl, aryl-(1-6C)alkyl, heteroaryl, heteroaryl-(1-6C)alkyl, heterocyclyl, heterocyclyl-(1-6C)alkyl, or Q$_7$ and R$_{7L}$ are linked such that, together with the nitrogen atom to which they are attached, they form a heterocyclic ring;

wherein R$_7$ is optionally substituted (e.g., substituted on L$_7$ and/or Q$_7$) with one or more halo, hydroxyl, nitro, cyano, (1-8C)alkyl, (1-8C)alkanoyl, OR$_{7X}$, SR$_{7X}$, S(O)R$_{7X}$, S(O)$_2$R$_{7X}$, C(O)OR$_{7X}$ or C(O)NR$_{7X}$R'$_{7X}$, wherein R$_{7X}$ and R'$_{7X}$ are independently hydrogen, (1-8C)alkyl, or R$_{7X}$ and R'$_{7X}$ are linked such that, together with the nitrogen atom to which they are attached, they form a heterocyclic ring; or R$_7$ is optionally substituted with one or more groups selected from oxo, (1-4C)haloalkyl, (1-4C)hydroxyalkyl, C(O)R$_{7y}$ or NR$_{7y}$R'$_{7y}$, wherein R$_{7y}$ and R'$_{7y}$ are independently hydrogen or (1-8C)alkyl.

Additional examples of other RET kinase inhibitors include those described in International Publication No. WO2017178845, which is hereby incorporated by reference. For example, in some embodiments, the other RET inhibitor is a compound of Formula (IV) or a pharmaceutically acceptable salt thereof, wherein:

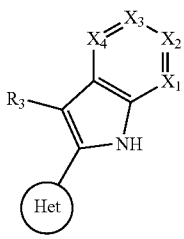

HET is selected from one of the following:

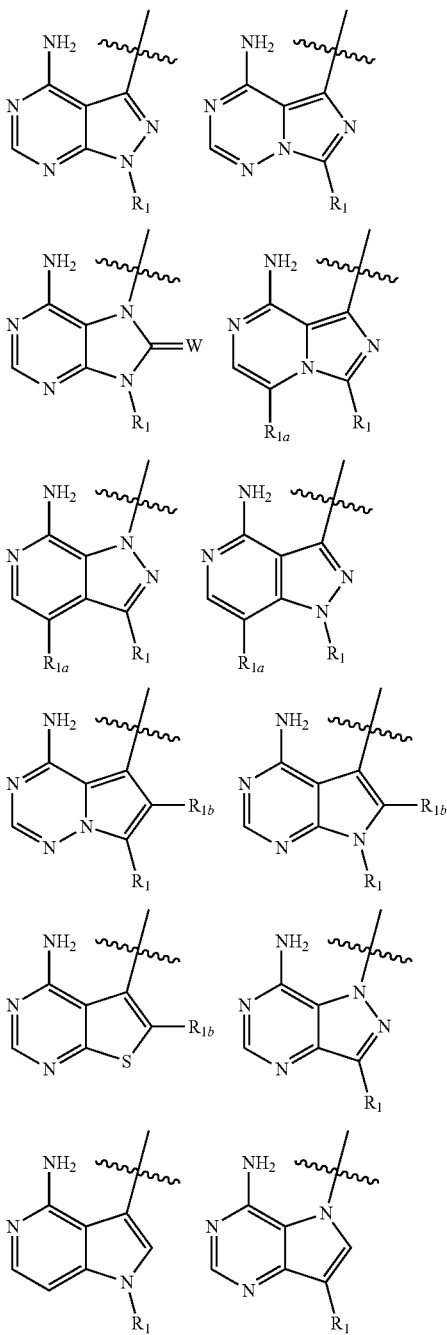

(IV)

denotes the point of attachment;

$R_1$ is selected from hydrogen, (1-4C)haloalkyl, (1-4C)haloalkoxy or a group of the formula:

-L-Y-Q wherein:
L is absent or (1-5C)alkylene optionally substituted by one or more substituents selected from (1-2C)alkyl or oxo;

Y is absent or O, S, SO, SO$_2$, N(R$_a$), C(O), C(O)O, OC(O), C(O)N(R$_a$), N(R$_a$)C(O), N(R$_a$)C(O)N(R$_b$), N(R$_a$)C(O)O, OC(O)N(R$_a$), S(O)$_2$N(R$_a$), or N(R$_a$)SO$_2$, wherein R$_a$ and R$_b$ are each independently selected from hydrogen or (1-4C)alkyl; and Q is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Q is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, NR$_c$R$_d$, OR$_c$, C(O)R$_c$, C(O)OR$_c$, OC(O)R$_c$, C(O)N(R$_d$)R$_c$, N(R$_d$)C(O)R$_c$, S(O)$_p$R$_c$ (where p is 0, 1 or 2), SO$_2$N(R$_d$)R$_c$, N(R$_d$)SO$_2$R$_c$, Si(R$_e$)(R$_d$)R$_c$ or (CH$_2$)$_q$NR$_c$R$_d$ (where q is 1, 2 or 3); wherein R$_c$, R$_d$ and R$_e$ are each independently selected from hydrogen, (1-6C)alkyl or (3-6C)cycloalkyl; or R$_c$ and R$_d$ are linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxy; or Q is optionally substituted by a group of the formula:

-L$_1$-L$_{Q1}$-W$_1$ wherein:
L$_1$ is absent or (1-3C)alkylene optionally substituted by one or more substituents selected from (1-2C)alkyl or oxo;

L$_{Q1}$ is absent or selected from O, S, SO, SO$_2$, N(R$_f$), C(O), C(O)O, OC(O), C(O)N(R$_f$), N(R$_f$)C(O), N(R$_f$)C(O)N(R$_g$), N(R$_f$)C(O)O, OC(O)N(R$_f$), S(O)$_2$N(R$_f$), or N(R$_f$)SO$_2$, wherein R$_f$ and R$_g$ are each independently selected from hydrogen or (1-2C)alkyl; and W$_1$ is hydrogen, (1-6C)alkyl, aryl, aryl(1-2C)alkyl, (3-8C)cycloalkyl, (3-8C)cycloalkenyl, heteroaryl or heterocyclyl; wherein W$_1$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl, mercapto, ureido, aryl, heteroaryl, heterocycyl, (3-6C)cycloalkyl, NR$_h$R$_i$, OR$_h$, C(O)R$_h$, C(O)OR$_h$, OC(O)R$_h$, C(O)N(R$_i$)R$_h$, N(R$_i$)C(O)R$_h$, S(O)$_r$R$_h$ (where r is 0, 1 or 2), SO$_2$N(R$_i$)R$_h$, N(R$_i$)SO$_2$R$_h$ or (CH$_2$)$_s$NR$_i$R$_h$ (where s is 1, 2 or 3);

wherein $R_h$ and $R_i$ are each independently selected from hydrogen, (1-4C)alkyl or (3-6C)cycloalkyl;

$R_{1a}$ and $R_{1b}$ are each selected from H, (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl or mercapto;

W is selected from O, S or $NR_{W1}$, wherein $R_{W1}$ is selected from H or (1-2C)alkyl;

$X_1$, $X_2$, $X_3$ and $X_4$ are independently selected from CH, $CR_2$ or N;

$R_2$ is selected from hydrogen, halo, (1-4C)alkyl, (1-4C)alkoxy, (1-4C)haloalkyl, (1-4C)haloalkoxy, amino, cyano, nitro, aryl, heteroaryl, heterocyclyl, cycloalkyl, (2-4C)alkynyl, $NR_jR_k$, $OR_j$, $C(O)R_j$, $C(O)OR_j$, $OC(O)R_j$, $C(O)N(R_k)R_j$, $N(R_k)C(O)R_j$, $N(R_k)C(O)N(R_j)$, $S(O)_{r1}R_k$ (where n is 0, 1 or 2), $SO_2N(R_j)R_k$, $N(R_j)SO_2R_k$ or $(CH_2)_vNR_jR_k$ (where v is 1, 2 or 3); wherein $R_j$ and $R_k$ are each independently selected from hydrogen or (1-4C)alkyl; and wherein said (1-4C)alkyl, aryl, heteroaryl, heterocycyl or cycloalkyl is optionally substituted by one or more substituents selected from halo, (1-4C)alkyl, (1-4C)alkoxy, (1-4C)haloalkyl, (1-4C)haloalkoxy, amino, cyano, nitro, phenyl, (2-4C)alkynyl, $NR_{j1}R_{k1}$, $OR_{j1}$, $C(O)R_{j1}$, $C(O)OR_{j1}$, $OC(O)R_{j1}$, $C(O)N(R_{k1})R_{j1}$, $N(R_{k1})C(O)R_{j1}$, $S(O)_{r2}R_h$ (where $r_2$ is 0, 1 or 2), $SO_2N(R_{j1})R_{k1}$, $N(R_{j1})SO_2R_{k1}$ or $(CH_2)_{v1}NR_{j1}R_{k1}$ (where $v_1$ is 1, 2 or 3); and wherein $R_{j1}$ and $R_{k1}$ are each independently selected from hydrogen or (1-4C)alkyl; and $R_3$ is selected from halo, (1-4C)alkyl, (1-4C)alkoxy, (1-4C)haloalkyl, (1-4C)haloalkoxy, amino, cyano, nitro, (2-4C)alkynyl, $NR_lR_m$, $OR_l$, $C(O)R_l$, $C(O)OR_l$, $OC(O)R_l$, $C(O)N(R_m)R_l$, $N(R_m)C(O)R_l$, or $(CH_2)_yNR_lR_m$ (where y is 1, 2 or 3); wherein said (1-4C)alkyl is optionally substituted by one or more substituents selected from amino, hydroxy, (1-2C)alkoxy or halo; and wherein $R_l$ and $R_m$ are each independently selected from hydrogen or (1-4C)alkyl.

Additional examples of other RET kinase inhibitors include those described in International Publication No. WO2017178844, which is hereby incorporated by reference. For example, in some embodiments, the other RET inhibitor is a compound of Formula (V) or a pharmaceutically acceptable salt thereof, wherein:

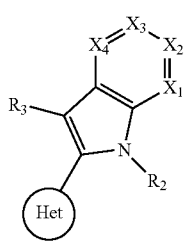

(V)

HET is selected from one of the following:

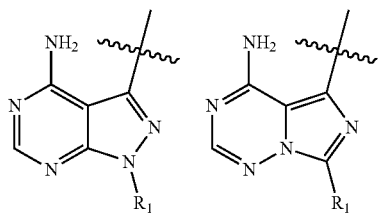

-continued

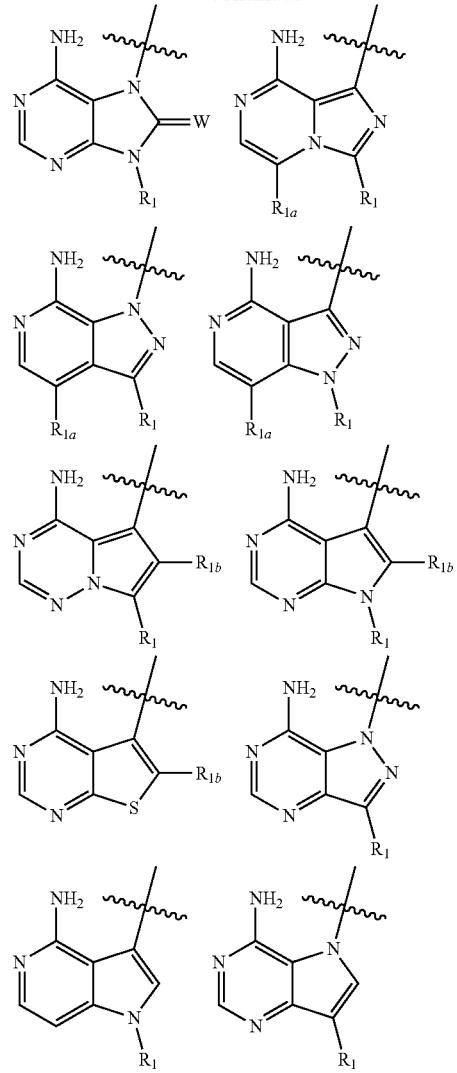

wherein

denotes the point of attachment;

$R_1$ is selected from hydrogen, (1-4C)haloalkyl, (1-4C)haloalkoxy or a group of the formula:

-L-Y-Q wherein:
L is absent or (1-5C)alkylene optionally substituted by one or more substituents selected from (1-2C)alkyl or oxo;

Y is absent or O, S, SO, $SO_2$, $N(R_a)$, C(O), C(O)O, OC(O), $C(O)N(R_a)$, $N(R_a)C(O)$, $N(R_a)C(O)N(R_b)$, $N(R_a)C(O)O$, $OC(O)N(R_a)$, $S(O)_2N(R_a)$, or $N(R_a)SO_2$, wherein $R_a$ and $R_b$ are each independently selected from hydrogen or (1-4C)alkyl; and Q is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Q is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, $NR_cR_d$, $OR_c$, $C(O)R_c$, $C(O)OR_c$, $OC(O)R_c$, $C(O)N(R_d)R_c$, $N(R_d)C(O)R_c$, $S(O)_yR_c$ (where y is 0, 1 or 2), $SO_2N(R_d)R_c$, $N(R_d)SO_2R_c$, $Si(R_d)(R_c)R_e$ or $(CH_2)_zNR_cR_d$ (where z is 1, 2 or 3); wherein $R_c$, $R_d$ and $R_e$ are each independently selected from hydrogen, (1-6C)alkyl or (3-6C)cycloalkyl; or $R_c$ and $R_d$ can be linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxyl; or Q is optionally substituted by a group of the formula:

-L₁-L_{Q1}-Z₁ wherein:
$L_1$ is absent or (1-3C)alkylene optionally substituted by one or more substituents selected from (1-2C)alkyl or oxo;

$L_{Q1}$ is absent or selected from O, S, SO, $SO_2$, $N(R_f)$, C(O), C(O)O, OC(O), $C(O)N(R_f)$, $N(R_f)C(O)$, $N(R_g)C(O)N(R_f)$, $N(R_f)C(O)O$, $OC(O)N(R_f)$, $S(O)_2N(R_f)$, or $N(R_f)SO_2$, wherein $R_f$ and $R_g$ are each independently selected from hydrogen or (1-2C)alkyl; and $Z_1$ is hydrogen, (1-6C)alkyl, aryl, aryl(1-2C)alkyl, (3-8C)cycloalkyl, (3-8C)cycloalkenyl, heteroaryl or heterocyclyl; wherein $Z_1$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl, mercapto, ureido, aryl, heteroaryl, heterocycyl, (3-6C)cycloalkyl, $NR_hR_i$, $OR_h$, $C(O)R_h$, $C(O)OR_h$, $OC(O)R_h$, $C(O)N(R_i)R_h$, $N(R_i)C(O)R_h$, $S(O)_{ya}R_h$ (where $y^a$ is 0, 1 or 2), $SO_2N(R_i)R_h$, $N(R_i)SO_2R_h$ or $(CH_2)_{za}NR_iR_h$ (where $z^a$ is 1, 2 or 3); wherein $R_h$ and $R_i$ are each independently selected from hydrogen, (1-4C)alkyl or (3-6C)cycloalkyl;

$R_{1a}$ and $R_{1b}$ are each selected from hydrogen, (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl or mercapto;

W is selected from O, S or $NR_j$, wherein $R_j$ is selected from H or (1-2C)alkyl;

$X_1$ and $X_2$ are each independently selected from N or $CR_k$; wherein
$R_k$ is selected from hydrogen, halo, (1-4C)alkyl, (1-4C)alkoxy, amino, (1-4C)alkylamino, (1-4C)dialkylamino, cyano, (2C)alkynyl, $C(O)R_{k1}$, $C(O)OR_{k1}$, $OC(O)R_{k1}$, $C(O)N(R_{k2})R_{k1}$, $N(R_{k2})C(O)R_{k1}$, $S(O)_{yb}R_{k1}$ (where $y^b$ is 0, 1 or 2), $SO_2N(R_{k2})R_{k1}$, $N(R_{k2})SO_2R_{k1}$ or $(CH_2)_{zb}NR_{k1}R_{k2}$ (where $z^b$ is 1, 2 or 3); wherein said (1-4C)alkyl is optionally substituted by one or more substituents selected from amino, hydroxy, (1-2C)alkoxy or halo; and $R_{k1}$ and $R_{k2}$ are each independently selected from hydrogen or (1-4C)alkyl;

$X_3$ is selected from N or $CR_m$;

wherein
$R_m$ is selected from hydrogen, halo, (1-4C)alkyl, (1-4C)alkoxy, amino, (1-4C)alkylamino, (1-4C)dialkylamino, cyano, (2C)alkynyl, $C(O)R_{m1}$, $C(O)OR_{m1}$, $OC(O)R_{m1}$, $C(O)N(R_{m2})R_{m1}$, $N(R_{m2})C(O)R_{m1}$, $S(O)_{yc}R_{m1}$ (where $y^c$ is 0, 1 or 2), $SO_2N(R_{m2})R_{m1}$, $N(R_{m2})SO_2R_{m1}$ or $(CH_2)_{zc}NR_{m1}R_{m2}$ (where zc is 1, 2 or 3); wherein said (1-4C)alkyl is optionally substituted by one or more substituents selected from amino, hydroxy, (1-2C)alkoxy or halo; and $R_{m1}$ and $R_{m2}$ are each independently selected from hydrogen or (1-4C)alkyl;

$R_o$ is selected from halo, (1-4C)alkyl, (1-4C)alkoxy, amino, (1-4C)alkylamino, (1-4C)dialkylamino, cyano, (2C)alkynyl, $C(O)R_{o1}$, $C(O)OR_{o1}$, $OC(O)R_{o1}$, $C(O)N(R_{o2})R_{o1}$, $N(R_{o2})C(O)R_{o1}$, $S(O)_{yd}R_{o1}$ (where $y^d$ is 0, 1 or 2), $SO_2N(R_{o2})R_{o1}$, $N(R_{o2})SO_2R_{o1}$ or $(CH_2)_{zd}NR_{o1}R_{o2}$ (where $z^d$ is 1, 2 or 3); wherein said (1-4C)alkyl is optionally substituted by one or more substituents selected from amino, hydroxy, (1-2C)alkoxy or halo; and $R_{o1}$ and $R_{o2}$ are each independently selected from hydrogen or (1-4C)alkyl;

$R_2$ is selected from hydrogen, (1-4C)alkyl or a group of the formula:

-L₂-Y₂-Q₂ wherein:
$L_2$ is absent or (1-3C)alkylene optionally substituted by one or more substituents selected from (1-2C)alkyl or oxo;

$Y_2$ is absent or C(O), C(O)O, $C(O)N(R_p)$, wherein $R_p$ is selected from hydrogen or (1-4C)alkyl; and $Q_2$ is hydrogen, (1-6C)alkyl, aryl, (3-8C)cycloalkyl, (3-8C)cycloalkenyl, heteroaryl or heterocyclyl; wherein $Q_2$ is optionally further substituted by one or more substituent groups independently selected from (1-4C)alkyl, halo, (1-4C)haloalkyl, (1-4C)haloalkoxy, amino, cyano, hydroxy, carboxy, carbamoyl, sulphamoyl, $NR_qR_r$, $OR_q$, wherein $R_q$ and $R_r$ are each independently selected from hydrogen, (1-4C)alkyl or (3-6C)cycloalkyl;

$R^3$ is selected from a group of the formula:

—Y₃-Q₃ wherein:
$Y_3$ is C(O), $C(O)N(R_y)$, $C(O)N(R_y)O$, $N(R_y)(O)C$, C(O)O, OC(O), $N(R_y)C(O)N(R_{y1})$, $SO_2N(R_y)$, $N(R_y)SO_2$, oxazolyl, triazolyl, oxadiazolyl, thiazolyl, imidazolyl, thiadiazolyl, pyridinyl, pyrazolyl, pyrrolyl or tetrazolyl, wherein $R_y$ and $R_{y1}$ are independently selected from hydrogen or (1-2C)alkyl; and $Q_3$ is hydrogen, (1-6C)alkyl, aryl, aryl(1-2C)alkyl, (3-8C)cycloalkyl, (3-8C)cycloalkenyl, heteroaryl or heterocyclyl; wherein $Q_3$ is optionally further substituted by one or more substituent groups independently selected from (1-4C)alkyl, halo, (1-4C)haloalkyl, (1-4C)haloalkoxy, amino, cyano, hydroxy, carboxy, carbamoyl, sulphamoyl, $NR_zR_{aa}$, $OR_z$, wherein $R_z$ and $R_{aa}$ are each independently selected from hydrogen, (1-4C)alkyl or (3-6C)cycloalkyl; or $Q_3$ is optionally substituted by a group of the formula:

-L₄-L_{Q4}-Z₄ wherein:
L₄ is absent or (1-3C)alkylene optionally substituted by one or more substituents selected from (1-2C)alkyl or oxo;
$L_{Q4}$ is absent or selected from or O, S, SO, SO₂, N(R$_a$b), C(O), C(O)O, OC(O), C(O)N(R$_{ab}$), N(R$_{ab}$)C(O), N(R$_{ac}$)C(O)N(R$_{ab}$), N(R$_{ab}$)C(O)O, OC(O)N(R$_{ab}$), S(O)₂N(R$_{ab}$), or N(R$_{ab}$)SO₂, wherein R$_a$b and R$_{ac}$ are each independently selected from hydrogen or (1-2C)alkyl; and
Z₄ is hydrogen, (1-6C)alkyl, aryl, aryl(1-2C)alkyl, (3-8C)cycloalkyl, (3-8C)cycloalkenyl, heteroaryl or heterocyclyl; wherein Z₄ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl, mercapto, ureido, aryl, heteroaryl, heterocycyl, (3-6C)cycloalkyl, NR$_{ad}$R$_{ae}$, OR$_{ad}$, C(O)R$_{ad}$, C(O)OR$_{ad}$, OC(O)R$_{ad}$, C(O)N(R$_{ae}$)R$_{ad}$, N(R$_{ae}$)C(O)R$_{ad}$, S(O)$_{y^e}$R$_{ad}$ (where $y^e$ is 0, 1 or 2), SO₂N(R$_{ae}$)R$_{ad}$, N(R$_{ae}$)SO₂R$_{ad}$ or (CH₂)$_{z^e}$-NR$_{ad}$R$_{ae}$ (where $z^e$ is 1, 2 or 3); wherein R$_{ad}$ and R$_{ae}$ are each independently selected from hydrogen, (1-4C)alkyl or (3-6C)cycloalkyl; or
Q₃ and R$_y$ are linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxyl;
with the proviso that only one or two of X₁, X₂ or X₃ can be N.

Additional examples of other RET kinase inhibitors include those described in International Publication No. WO 2017145050, which is hereby incorporated by reference. For example, in some embodiments, the other RET has the Formula (VI) or is a pharmaceutically acceptable salt thereof.

(VI)

Additional examples of other RET kinase inhibitors include those described in International Publication No. WO 2016038552 is hereby incorporated by reference. For example, in some embodiments, the other RET has the Formula (VII), or the Formula (VIII), or is a pharmaceutically acceptable salt thereof.

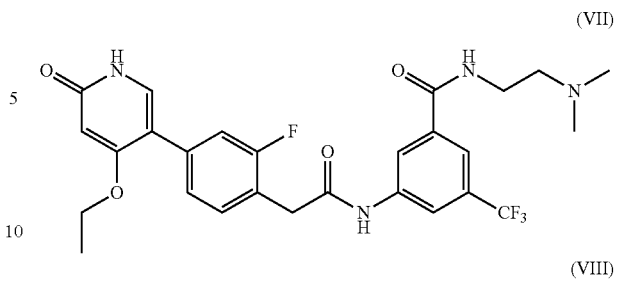

(VII)

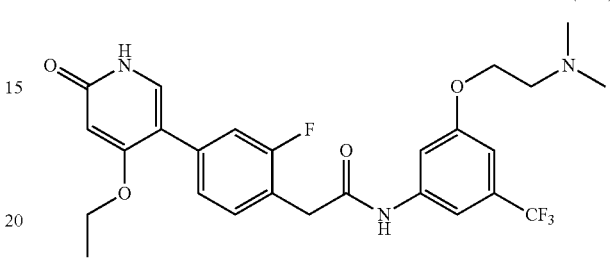

(VIII)

Yet other therapeutic agents include RET inhibitors such as those described, for example, in U.S. Pat. Nos. 9,738,660; 9,801,880; 9,682,083; 9,789,100; 9,550,772; 9,493,455; 9,758,508; 9,604,980; 9,321,772; 9,522,910; 9,669,028; 9,186,318; 8,933,230; 9,505,784; 8,754,209; 8,895,744; 8,629,135; 8,815,906; 8,354,526; 8,741,849; 8,461,161; 8,524,709; 8,129,374; 8,686,005; 9,006,256; 8,399,442; 7,795,273; 7,863,288; 7,465,726; 8,552,002; 8,067,434; 8,198,298; 8,106,069; 6,861,509; 8,299,057; 9,150,517; 9,149,464; 8,299,057; and 7,863,288; U.S. Publication Nos. 2018/0009818; 2018/0009817; 2017/0283404; 2017/0267661; 2017/0298074; 2017/0114032; 2016/0009709; 2015/0272958; 2015/0238477; 2015/0099721; 2014/0371219; 2014/0137274; 2013/0079343; 2012/0283261; 2012/0225057; 2012/0065233; 2013/0053370; 2012/0302567; 2011/0189167; 2016/0046636; 2013/0012703; 2011/0281841; 2011/0269739; 2012/0271048; 2012/0277424; 2011/0053934; 2011/0046370; 2010/0280012; 2012/0070410; 2010/0081675; 2010/0075916; 2011/0212053; 2009/0227556; 2009/0209496; 2009/0099167; 2010/0209488; 2009/0012045; 2013/0303518; 2008/0234267; 2008/0199426; 2010/0069395; 2009/0312321; 2010/0173954; 2011/0195072; 2010/0004239; 2007/0149523; 2017/0281632; 2017/0226100; 2017/0121312; 2017/0096425; 2017/0044106; 2015/0065468; 2009/0069360; 2008/0275054; 2007/0117800; 2008/0234284; 2008/0234276; 2009/0048249; 2010/0048540; 2008/0319005; 2009/0215761; 2008/0287427; 2006/0183900; 2005/0222171; 2005/0209195; 2008/0262021; 2008/0312192; 2009/0143399; 2009/0130229; 2007/0265274; 2004/0185547; and 2016/0176865; and International Publication Nos. WO 2017/079140; WO 2017/145050; WO 2017/097697; WO 2017/049462; WO 2017/043550; WO 2017/027883; WO 2017/013160; WO 2017/009644; WO 2016/168992; WO 2016/137060; WO 2016/127074; WO 2016/075224; WO 2016/038552; WO 2015/079251; WO 2014/086284; WO 2013/042137; WO 2013/036232; WO 2013/016720; WO 2012/053606; WO 2012/047017; WO 2007/109045; WO 2009/042646; WO 2009/023978; WO 2009/017838; WO 2017/178845; WO 2017/178844; WO 2017/146116; WO 2017/026718; WO 2016/096709; WO 2007/057397; WO 2007/057399; WO 2007/054357; WO 2006/130613; WO 2006/089298; WO 2005/070431; WO 2003/020698; WO 2001/062273; WO 2001/016169; WO 1997/044356; WO 2007/087245; WO 2005/044835; WO 2014/075035; and WO 2016/038519; and *J. Med. Chem.* 2012, 55 (10), 4872-4876, all of which are hereby incorporated by reference in their entireties.

In some embodiments, a RET inhibitor (e.g., a first RET inhibitor or a second RET inhibitor) is a compound of the Formula II:

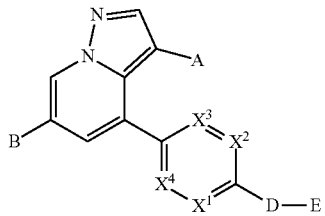

or a pharmaceutically acceptable salt or solvate thereof, wherein:

$X^1$ is CH, CCH$_3$, CF, CCl or N;
$X^2$ is CH, CF or N;
$X^3$ is CH, CF or N;
$X^4$ is CH, CF or N;
wherein zero, one or two of $X^1$, $X^2$, $X^3$ and $X^4$ is N;
A is H, Cl, CN, Br, CH$_3$, CH$_2$CH$_3$ or cyclopropyl;
B is hetAr$^1$;
hetAr$^1$ is a 5-membered heteroaryl ring having 1-3 ring heteroatoms independently selected from N, S and O, wherein said heteroaryl ring is optionally substituted with one or more substituents independently selected from the group consisting of halogen, C1-C6 alkyl, hydroxyC1-C6 alkyl, fluoroC1-C6 alkyl, difluoroC1-C6 alkyl, trifluoroC1-C6 alkyl, cyanoC1-C6 alkyl, (C1-C6 alkoxy)C1-C6 alkyl, (C1-C4 alkoxy)CH$_2$C(=O)—, (C1-C4 alkoxy)C(=O)C1-C3 alkyl, C3-C6 cycloalkyl, (R$^a$R$^b$N)C1-C6 alkyl, (R$^a$R$^b$N)C(=O)C1-C6 alkyl, (C1-C6 alkylSO$_2$)C1-C6 alkyl, hetCyc$^3$, and 4-methoxybenzyl;
R$^a$ and R$^b$ are independently H or C1-C6 alkyl;
hetCyc$^a$ is a 4-6 membered heterocyclic ring having a ring heteroatom selected from N and O, wherein said heterocyclic ring is optionally substituted with halogen, C1-C6 alkyl, fluoroC1-C6 alkyl, difluoroC1-C6 alkyl, trifluoroC1-C6 alkyl, (C1-C6 alkoxy)C1-C6 alkyl, di(C1-C3 alkyl)NCH$_2$C(=O), (C1-C6 alkoxy)C(=O) or (C1-C6 alkoxy)CH$_2$C(=O);
D is hetCyc$^1$, hetCyc$^2$, hetCyc$^3$ or hetCyc$^9$;
hetCyc$^1$ is a 4-6 membered heterocyclic ring having 1-2 ring atoms selected from N and O, wherein said heterocyclic ring is optionally substituted with one or more substituents independently selected from the group consisting of C1-C3 alkyl, fluoroC1-C3 alkyl, difluoroC1-C3 alkyl, trifluoroC1-C3 alkyl and OH, or said heterocyclic ring is substituted with a C3-C6 cycloalkylidene ring, or said heterocyclic ring is substituted with an oxo group;
hetCyc$^2$ is a 7-8 membered bridged heterocyclic ring having 1-3 ring heteroatoms independently selected from N and O, wherein said heterocyclic ring is optionally substituted with C1-C3 alkyl;
hetCyc$^3$ is a 7-11 membered heterospirocyclic ring having 1-2 ring heteroatoms independently selected from N and O, wherein said ring is optionally substituted with C1-C3 alkyl;
hetCyc$^9$ is a fused 9-10 membered heterocyclic ring having 1-3 ring nitrogen atoms and optionally substituted with oxo;

E is
(a) hydrogen,
(b) OH,
(c) R$^a$R$^b$N—, wherein R$^a$ is H or C1-C6 alkyl and R$^b$ is H, C1-C6 alkyl or phenyl;
(d) C1-C6 alkyl optionally substituted with one to three fluoros,
(e) hydroxyC1-C6 alkyl- optionally substituted with one to three fluoros,
(f) C1-C6 alkoxy optionally substituted with one to three fluoros,
(g) hydroxy(C1-C6 alkoxy) optionally substituted with one to three fluoros,
(h) (C1-C6 alkoxy)hydroxy C1-C6 alkyl- optionally substituted with one to three fluoros,
(i) (C1-C6 alkyl)C(=O)— optionally substituted with one to three fluoros,
(j) (hydroxy C1-C6 alkyl)C(=O)— optionally substituted with one to three fluoros,
(k) (C1-C6 alkoxy)C(=O)—,
(l) (C1-C6 alkoxy)(C1-C6 alkyl)C(=O)—,
(m) HC(=O)—,
(n) Cyc$^1$,
(o) Cyc$^1$C(=O)—,
(p) Cyc$^1$(C1-C6 alkyl)C(=O)— wherein said alkyl portion is optionally substituted with one or more groups independently selected from the group consisting of OH, fluoro, C1-C3 alkoxy and R$^c$R$^d$N—, where R$^c$ and R$^d$ are independently H or C1-C6 alkyl,
(q) hetCyc$^4$,
(r) hetCyc$^4$C(=O)—,
(s) hetCyc$^4$(C1-C3 alkyl)C(=O)—,
(t) (hetCyc$^4$)C(=O)C1-C2 alkyl-,
(u) hetCyc$^4$C(=O)NH—,
(v) Ar$^2$,
(w) Ar$^2$C(=O)—,
(x) Ar$^2$C1-C6 alkyl-,
(y) (Ar$^2$)hydroxy C2-C6 alkyl-,
(z) Ar$^2$(C1-C3 alkyl)C(=O)— wherein said alkyl portion is optionally substituted with one or two groups independently selected from the group consisting of OH, C1-C6 alkyl (optionally substituted with 1-3 fluoros), hydroxyC1-C6 alkyl, C1-C6 alkoxy and R$^e$R$^f$N—, where R$^e$ and R$^f$ are independently H or C1-C6 alkyl, or R$^e$ and R$^f$ together with the nitrogen to which they are attached form a 5-6 membered azacyclic ring optionally having an additional ring heteroatom selected from N and O,
(aa) hetAr$^2$C(=O)—,
(bb) (hetAr$^2$)hydroxyC2-C6 alkyl-,
(cc) hetAr$^2$(C1-C3 alkyl)C(=O)—, wherein said alkyl portion is optionally substituted with one or two groups independently selected from the group consisting of OH, C1-C6 alkyl, hydroxyC1-C6 alkyl, C1-C6 alkoxy and R$^e$R$^f$N—, wherein R$^e$ and R$^f$ are independently H or C1-C6 alkyl or R$^e$ and R$^f$ together with the nitrogen to which they are attached form a 5-6 membered azacyclic ring optionally having an additional ring heteroatom selected from N and O,
(dd) R$^1$R$^2$NC(=O)—,
(ee) R$^1$R$^2$N(C1-C3 alkyl)C(=O)—, wherein said alkyl portion is optionally substituted with phenyl,
(ff) R$^1$R$^2$NC(=O)C1-C2 alkyl-,
(gg) R$^1$R$^2$NC(=O)NH—,
(hh) CH$_3$SO$_2$(C1-C6 alkyl)C(=O)—, (ii) (C1-C6 alkyl)SO₂—,
(jj) (C3-C6 cycloalkyl)CH₂SO₂—,
(kk) hetCyc⁵-SO₂—,
(ll) R⁴R⁵NSO₂—,
(mm) R⁶C(=O)NH—,
(nn) hetCyc⁶,
(oo) hetAr²C1-C6 alkyl-,
(pp) (hetCyc⁴)C1-C6 alkyl-,
(qq) (C1-C6 alkoxy)C1-C6 alkyl- optionally substituted with 1-3 fluoros,
(rr) (C3-C6 cycloalkoxy)C1-C6 alkyl-,
(ss) (C3-C6 cycloalkyl)C1-C6 alkyl-, wherein said cycloalkyl is optionally substituted with 1-2 fluoros,
(tt) (RᵍRʰN)C1-C6 alkyl-, wherein Rᵍ and Rʰ are independently H or C1-C6 alkyl,
(uu) Ar²—O—,
(vv) (C1-C6 alkylSO₂)C1-C6 alkyl-,
(ww) (C1-C6 alkoxy)C(=O)NHC1-C6 alkyl-,
(xx) (C3-C6 cycloalkoxy)C(=O)—,
(yy) (C3-C6 cycloalkyl)SO₂—, wherein said cycloalkyl is optionally substituted with C1-C6 alkyl,
(zz) Ar⁴CH₂OC(=O)—,
(aaa) (N—(C1-C3 alkyl)pyridinonyl)C1-C3 alkyl-, and
(bbb) (Ar⁴SO₂)C1-C6 alkyl-;

Cyc¹ is a C3-C6 cycloalkyl, wherein (a) said cycloalkyl is optionally substituted with one or more substituents independently selected from the group consisting of OH, halogen, C1-C6 alkoxy, CN, hydroxyC1-C6 alkyl, (C1-C6 alkoxy)C1-C6 alkyl, and C1-C6 alkyl optionally substituted with 1-3 fluoros, or (b) said cycloalkyl is substituted with phenyl, wherein said phenyl is optionally substituted with one or more substituents independently selected from the group consisting of halogen, C1-C3 alkyl, C1-C3 alkoxy and CF, or (c) said cycloalkyl is substituted with a 5-6 membered heteroaryl ring having 1-3 ring heteroatoms independently selected from N and O, wherein said heteroaryl ring is optionally substituted with one or more substituents independently selected from the group consisting of halogen, C1-C3 alkyl, C1-C3 alkoxy and CF₃;

Ar² is phenyl optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, CN, a 5-6 membered heterocyclic ring having 1-2 ring heteroatoms independently selected from N and O, and RⁱRʲN— wherein Rⁱ and Rʲ are independently H or C1-C6 alkyl;

hetAr² is a 5-6 membered heteroaryl ring having 1-3 ring heteroatoms independently selected from N, O and S and optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, hydroxyC1-C6 alkyl, (C3-C6)cycloalkyl, (C1-C6 alkoxy)C1-C6 alkyl, CN, OH, and R'R"N—, wherein R' and R" are independently H or C1-C3 alkyl;

hetCyc⁴ is (a) a 4-6 membered heterocyclic ring having 1-2 ring heteroatoms independently selected from N, O and S wherein said S is optionally oxidized to SO₂, (b) a 7-8 membered bridged heterocyclic ring having 1-2 ring heteroatoms independently selected from N and O, (c) a 6-12 membered fused bicyclic heterocyclic ring having 1-2 ring heteroatoms independently selected from N and O and optionally independently substituted with 1-2 C1-C6 alkyl substituents, or (d) a 7-10 membered spirocyclic heterocyclic ring having 1-2 ring heteroatoms independently selected from N and O, wherein each of said heterocyclic rings is optionally substituted with one or more substituents independently selected from the group consisting of halogen, OH, CN, C1-C6 alkyl (optionally substituted with 1-3 fluoros), C1-C6 alkoxy, (C1-C6 alkoxy)C1-C6 alkyl, (C3-C6)cycloalkyl, (C1-C6 alkyl)C(=O)—, a 5-6 membered heterocyclic ring having 1-2 ring heteroatoms independently selected from N and O, and phenyl wherein said phenyl is optionally substituted with one or more substituents selected from halogen, C1-C6 alkyl and C1-C6 alkoxy;

hetCyc⁵ is a 5-6 membered heterocyclic ring having a ring heteroatom selected from O and N;

hetCyc⁶ is a 5 membered heterocyclic ring having one or two ring heteroatoms independently selected from N and O, wherein said ring is substituted with oxo and wherein said ring is further optionally substituted with one or more substituents independently selected from the group consisting of OH and C1-C6 alkyl;

R¹ is H, C1-C6 alkyl or (C1-C6 alkoxy)C1-C6 alkyl;

R² is H, C1-C6 alkyl (optionally substituted with 1-3 fluoros), (C1-C6 alkoxy)C1-C6 alkyl (optionally substituted with 1-3 fluoros), Cyc³, hydroxyC1-C6 alkyl (optionally substituted with 1-3 fluoros), C1-C6 alkoxy (optionally substituted with 1-3 fluoros), (C1-C6 alkoxy)C(=O), hetCyc⁷, Ar³, Ar³C1-C3 alkyl-, hydroxyC1-C6 alkoxy or (3-6C cycloalkyl)CH₂O—;

Cyc³ is a 3-6 membered carbocyclic ring optionally substituted with 1-2 groups independently selected from the group consisting of C1-C6 alkoxy, OH and halogen;

hetCyc⁷ is a 5-6 membered heterocyclic ring having a ring heteroatom selected from O and N wherein said ring is optionally substituted with C1-C6 alkyl;

Ar³ is phenyl optionally substituted with one or more substituents independently selected from halogen, C1-C3 alkyl, C1-C3 alkoxy, fluoroC1-C3 alkyl, difluoroC1-C3 alkyl and trifluoroC1-C3 alkyl;

R⁴ and R⁵ are independently H or C1-C6 alkyl;

R⁶ is C1-C6 alkyl, hydroxyC1-C6 alkyl, C1-C6 alkoxy, (C1-C6 alkoxy)C1-C6 alkyl, phenyl or hetCyc⁸;

hetCyc⁸ is a 5-6 membered heterocyclic ring having a ring heteroatom selected from O and N, wherein said heterocyclic ring is optionally substituted with C1-C6 alkyl; and Ar⁴ is phenyl optionally substituted with one or more halogens.

In some embodiments, a RET inhibitor (e.g., a first RET inhibitor or a second RET inhibitor) is a compound of the Formula III:

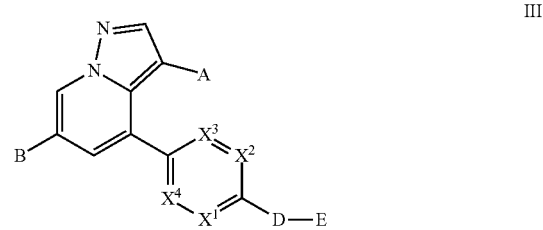

or a pharmaceutically acceptable salt or solvate thereof, wherein:

X¹ is CH or N;
X² is CH or N;
X³ is CH or N;
X⁴ is CH or N;
wherein one or two of X¹, X², X³ and X⁴ is N;
A is CN;
B is hetAr¹;
hetAr¹ is a 5-membered heteroaryl ring having 1-3 ring nitrogen atoms, wherein said heteroaryl ring is optionally substituted with one or more substituents independently selected from the group consisting of halogen, C1-C6 alkyl, hydroxyC1-C6 alkyl, fluoroC1-C6 alkyl, difluoroC1-C6 alkyl, trifluoroC1-C6 alkyl, cyanoC1-C6 alkyl, (C1-C6 alkoxy)C1-C6 alkyl, (C1-C4 alkoxy)CH₂C(=O)—, (C1-C4 alkoxy)C(=O)C1-C3 alkyl, C3-C6 cycloalkyl, (RᵃRᵇN)C1-C6 alkyl, (RᵃRᵇN)C(=O)C1-C6 alkyl, (C1-C6 alkylSO₂)C1-C6 alkyl, and 4-methoxybenzyl;
Rᵃ and Rᵇ are independently H or C1-C6 alkyl;
D is hetCyc¹;
hetCyc¹ is a 4-6 membered heterocyclic ring having 1-2 ring nitrogen atoms, wherein said heterocyclic ring is optionally substituted with one or more substituents independently selected from the group consisting of C1-C3 alkyl, fluoroC1-C3 alkyl, difluoroC1-C3 alkyl, trifluoroC1-C3 alkyl and OH, or said heterocyclic ring is substituted with a C3-C6 cycloalkylidene ring, or said heterocyclic ring is substituted with an oxo group;
E is
  (w) Ar²C(=O)—,
  (x) Ar²C1-C6 alkyl-,
  (z) Ar²(C1-C3 alkyl)C(=O)— wherein said alkyl portion is optionally substituted with one or two groups independently selected from the group consisting of OH, C1-C6 alkyl (optionally substituted with 1-3 fluoros), hydroxyC1-C6 alkyl, C1-C6 alkoxy and RᵉRᶠN—, where Rᵉ and Rᶠ are independently H or C1-C6 alkyl, or Rᵉ and Rᶠ together with the nitrogen to which they are attached form a 5-6 membered azacyclic ring optionally having an additional ring heteroatom selected from N and O,
  (cc) hetAr²(C1-C3 alkyl)C(=O)—, wherein said alkyl portion is optionally substituted with one or two groups independently selected from the group consisting of OH, C1-C6 alkyl, hydroxyC1-C6 alkyl, C1-C6 alkoxy and RᵉRᶠN—, wherein Rᵉ and Rᶠ are independently H or C1-C6 alkyl or Rᵉ and Rᶠ together with the nitrogen to which they are attached form a 5-6 membered azacyclic ring optionally having an additional ring heteroatom selected from N and O,
  (dd) R¹R²NC(=O)—,
  (oo) hetAr²C1-C6 alkyl-,
Ar² is phenyl optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, CN, a 5-6 membered heterocyclic ring having 1-2 ring heteroatoms independently selected from N and O, and RⁱRʲN— wherein Rⁱ and Rʲ are independently H or C1-C6 alkyl;
hetAr² is a 5-6 membered heteroaryl ring having 1-3 ring heteroatoms independently selected from N, O and S and optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, hydroxyC1-C6 alkyl, (C3-C6)cycloalkyl, (C1-C6 alkoxy)C1-C6 alkyl, CN, OH, and R'R"N—, wherein R' and R" are independently H or C1-C3 alkyl;
R¹ is H, C1-C6 alkyl or (C1-C6 alkoxy)C1-C6 alkyl; and
R² is H, C1-C6 alkyl (optionally substituted with 1-3 fluoros), (C1-C6 alkoxy)C1-C6 alkyl (optionally substituted with 1-3 fluoros), hydroxyC1-C6 alkyl (optionally substituted with 1-3 fluoros), C1-C6 alkoxy (optionally substituted with 1-3 fluoros), (C1-C6 alkoxy)C(=O), hydroxyC1-C6 alkoxy or (3-6C cycloalkyl)CH₂O.

In some embodiments, a RET inhibitor (e.g., a first RET inhibitor or a second RET inhibitor) is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridin-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof.

In some embodiments, a RET inhibitor (e.g., a first RET inhibitor or a second RET inhibitor) is a compound of the Formula IV:

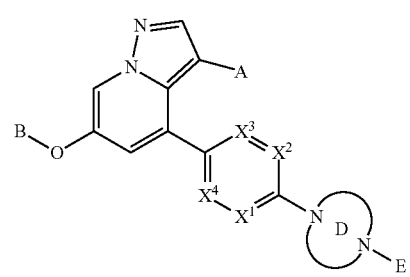

IV or a pharmaceutically acceptable salt or solvate thereof, wherein:
X¹, X², X³ and X⁴ are independently CH, CF, CCH₃ or N, wherein zero, one or two of X¹, X², X³ and X⁴ is N;
A is H, CN, Cl, CH₃—, CH₃CH₂—, cyclopropyl, —CH₂CN or —CH(CN)CH₃;
B is
  (a) hydrogen,
  (b) C1-C6 alkyl optionally substituted with 1-3 fluoros, (c) hydroxyC2-C6 alkyl-, wherein the alkyl portion is optionally substituted with 1-3 fluoros or a C3-C6 cycloalkylidene ring, (d) dihydroxyC3-C6 alkyl-, wherein the alkyl portion is optionally substituted with a C3-C6 cycloalkylidene ring, (e) (C1-C6 alkoxy)C1-C6 alkyl- optionally substituted with 1-3 fluoros, (f) $(R^1R^2N)$C1-C6 alkyl- wherein said alkyl portion is optionally substituted with OH and wherein $R^1$ and $R^2$ are independently H or C1-C6 alkyl (optionally substituted with 1-3 fluoros);

(g) hetAr$^1$C1-C3alkyl-, wherein hetAr$^1$ is a 5-6 membered heteroaryl ring having 1-3 ring heteroatoms independently selected from N, O and S and is optionally substituted with one or more independently selected C1-C6 alkyl substituents;

(h) (C3-C6 cycloalkyl)C1-C3 alkyl-, wherein said cycloalkyl is optionally substituted with OH, (i) (hetCyc$^a$)C1-C3 alkyl-, (j) hetCyc$^a$-, (k) C3-C6 cycloalkyl-, wherein said cycloalkyl is optionally substituted with OH, (l) (C1-C4 alkyl)C(=O)O—C1-C6 alkyl-, wherein each of the C1-C4 alkyl and C1-C6 alkyl portions is optionally and independently substituted with 1-3 fluoros, or (m) $(R^1R^2N)$C(=O)C1-C6 alkyl-, wherein $R^1$ and $R^2$ are independently H or C1-C6 alkyl (optionally substituted with 1-3 fluoros);

hetCyc$^a$- is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl-, C1-C6 alkoxy, (C1-C6 alkyl)C(=O)—, (C1-C6 alkoxy)C1-C6 alkyl-, and fluoro, or wherein hetCyc$^a$ is substituted with oxo;

Ring D is (i) a saturated 4-7 membered heterocyclic ring having two ring nitrogen atoms, (ii) a saturated 7-8 membered bridged heterocyclic ring having two ring nitrogen atoms and optionally having a third ring heteroatom which is oxygen, (iii) a saturated 7-11 membered heterospirocyclic ring having two ring nitrogen atoms, or (iv) a saturated 9-10 membered bicyclic fused heterocyclic ring having two ring nitrogen atoms, wherein each of said rings is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group;

E is (a) hydrogen, (b) C1-C6 alkyl optionally substituted with 1-3 fluoros, (c) (C1-C6 alkoxy)C1-C6 alkyl- optionally substituted with 1-3 fluoros, (d) (C1-C6 alkyl)C(=O)—, wherein said alkyl portion is optionally substituted with 1-3 fluoros or with a $R^gR^hN$— substituent wherein $R^g$ and $R^h$ are independently H or C1-C6 alkyl, (e) (hydroxyC2-C6 alkyl)C(=O)— optionally substituted with 1-3 fluoros, (f) (C1-C6 alkoxy)C(=O)—, (g) (C3-C6 cycloalkyl)C(=O)—, wherein said cycloalkyl is optionally substituted with one or more substituents independently selected from C1-C6 alkyl, C1-C6 alkoxy, OH, and (C1-C6 alkoxy)C1-C6 alkyl-, or said cycloalkyl is substituted with a 5-6 membered heteroaryl ring having 1-3 ring heteroatoms independently selected from N and O, (h) Ar$^1$C1-C6 alkyl-, (i) Ar$^1$(C1-C6 alkyl)C(=O)—, wherein said alkyl portion is optionally substituted with OH, hydroxyC1-C6 alkyl-, C1-C6 alkoxy, $R'''R''N$— or $R'''R''N$—CH$_2$—, wherein each $R'''$ and $R''$ is independently H or C1-C6 alkyl, (j) hetAr$^2$C1-C6 alkyl-, wherein said alkyl portion is optionally substituted with 1-3 fluoros, (k) hetAr$^2$(C1-C6 alkyl)C(=O)— wherein said alkyl portion is optionally substituted with OH, hydroxyC1-C6 alkyl- or C1-C6 alkoxy, (l) hetAr$^2$C(=O)—, (m) hetCyc$^1$C(=O)—, (n) hetCyc$^1$C1-C6 alkyl-, (o) $R^3R^4$NC(=O)—, (p) Ar$^1$N(R$^3$)C(=O)—, (q) hetAr$^2$N(R$^3$)C(=O)—, (r) (C1-C6 alkyl)SO$_2$—, wherein the alkyl portion is optionally substituted with 1-3 fluoros, (s) Ar$^1$SO$_2$—, (t) hetAr$^2$SO$_2$—, (u) N—(C1-C6 alkyl)pyridinonyl, (v) Ar$^1$C(=O)—;

(w) Ar$^1$O—C(=O)—, (x) (C3-C6 cycloalkyl)(C1-C6 alkyl)C(=O)—, (y) (C3-C6 cycloalkyl)(C1-C6 alkyl)SO$_2$—, wherein the alkyl portion is optionally substituted with 1-3 fluoros, (z) Ar$^1$(C1-C6 alkyl)SO$_2$—, (aa) hetCyc$^1$-O—C(=O)—, (bb) hetCyc$^1$CH$_2$C(=O)—, (cc) hetAr$^2$, or (dd) C3-C6 cycloalkyl;

Ar$^1$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), $R^eR^fN$— wherein $R^e$ and $R^f$ are independently H, C1-C6 alkyl, $(R^pR^qN)$C1-C6 alkoxy- wherein $R^p$ and $R^q$ are independently H or C1-C6 alkyl, and (hetAr$^a$)C1-C6 alkyl- wherein hetAr$^a$ is a 5-6 membered heteroaryl ring having 1-2 ring nitrogen atoms, or Ar$^1$ is a phenyl ring fused to a 5-6 membered heterocyclic ring having 1-2 ring heteroatoms independently selected from N and O;

hetAr$^2$ is a 5-6 membered heteroaryl ring having 1-3 ring heteroatoms independently selected from N, O and S or a 9-10 membered bicyclic heteroaryl ring having 1-3 ring nitrogen atoms, wherein hetAr$^2$ is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), $R^eR^fN$— wherein $R^e$ and $R^f$ are independently H or C1-C6 alkyl, OH, (C1-C6 alkoxy)C1-C6 alkoxy- and C3-C6 cycloalkyl;

hetCyc$^1$ is a 4-6 membered saturated heterocyclic ring having 1-2 ring heteroatoms independently selected from N, O and S wherein said heterocyclic ring is optionally substituted with one or more substituents independently selected from C1-C6 alkoxy and halogen;

$R^3$ is H or C1-C6 alkyl; and $R^4$ is C1-C6 alkyl.

In some embodiments, a RET inhibitor (e.g., a first RET inhibitor or a second RET inhibitor) is a compound of the Formula V:

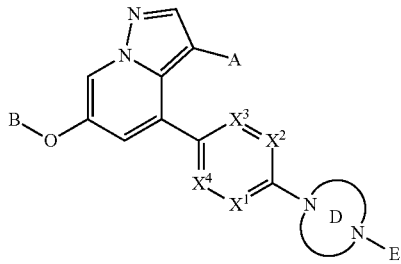

V or a pharmaceutically acceptable salt and solvate thereof, wherein:
$X^1$, $X^2$, $X^3$ and $X^4$ are independently CH or N, wherein zero, one or two of $X^1$, $X^2$, $X^3$ and $X^4$ is N;
A is CN;
B is
  (b) C1-C6 alkyl optionally substituted with 1-3 fluoros,
  (c) hydroxyC2-C6 alkyl-, wherein the alkyl portion is optionally substituted with 1-3 fluoros or a C3-C6 cycloalkylidene ring,
  (e) (C1-C6 alkoxy)C1-C6 alkyl- optionally substituted with 1-3 fluoros,
  (f) ($R^1R^2N$)C1-C6 alkyl-, wherein said alkyl portion is optionally substituted with OH and wherein $R^1$ and $R^2$ are independently H or C1-C6 alkyl (optionally substituted with 1-3 fluoros);
  (g) hetAr$^1$C1-C3 alkyl-, wherein hetAr$^1$ is a 5-6 membered heteroaryl ring having 1-3 ring heteroatoms independently selected from N, O and S and is optionally substituted with one or more independently selected C1-C6 alkyl substituents; or
  (i) (hetCyc$^a$)C1-C3 alkyl-,
hetCyc$^a$- is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl-, C1-C6 alkoxy, (C1-C6 alkyl)C(=O)—, (C1-C6 alkoxy)C1-C6 alkyl- and fluoro, or wherein hetCyc$^a$ is substituted with oxo;
Ring D is (i) a saturated 4-7 membered heterocyclic ring having two ring nitrogen atoms, or (ii) a saturated 7-9 membered bridged heterocyclic ring having two ring nitrogen atoms and optionally having a third ring heteroatom which is oxygen, wherein each of said rings is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group;
E is
  (h) Ar$^1$C1-C6 alkyl-,
  (j) hetAr$^2$C1-C6 alkyl-, wherein the alkyl portion is optionally substituted with 1-3 fluoros, or
  (l) hetAr$^2$C(=O)—,
Ar$^1$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), $R^eR^fN$— wherein $R^e$ and $R^f$ are independently H or C1-C6 alkyl, ($R^pR^qN$)C1-C6 alkoxy- wherein $R^p$ and $R^q$ are independently H or C1-C6 alkyl, and (hetAr$^a$)C1-C6 alkyl- wherein hetAr$^a$ is a 5-6 membered heteroaryl ring having 1-2 ring nitrogen atoms, or Ar$^1$ is a phenyl ring fused to a 5-6 membered heterocyclic ring having 1-2 ring heteroatoms independently selected from N and O; and
hetAr$^2$ is a 5-6 membered heteroaryl ring having 1-3 ring heteroatoms independently selected from N, O and S or a 9-10 membered bicyclic heteroaryl ring having 1-3 ring nitrogen atoms, wherein hetAr$^2$ is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), $R^eR^fN$— wherein $R^e$ and $R^f$ are independently H or C1-C6 alkyl, OH, (C1-C6 alkoxy)C1-C6 alkoxy- and C3-C6 cycloalkyl.

In some embodiments, a RET inhibitor (e.g., a first RET inhibitor or a second RET inhibitor) is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof.

In some embodiments, a RET inhibitor (e.g., a first RET inhibitor or a second RET inhibitor) is a compound of Formula VI:

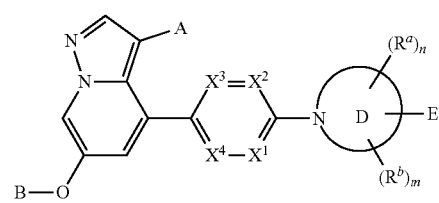

VI or a pharmaceutically acceptable salt or solvate thereof, wherein:

189

X$^1$, X$^2$, X$^3$ and X$^4$ are independently CH, CCH$_3$, CF or N, wherein zero, one or two of X$^1$, X$^2$, X$^3$ and X$^4$ is N;

A is H, CN, Cl, methyl, ethyl or cyclopropyl;

B is:
 (a) hydrogen,
 (b) C1-C6 alkyl optionally substituted with 1-3 fluoros,
 (c) hydroxyC2-C6 alkyl- wherein the alkyl portion is optionally substituted with a C3-C6 cycloalkylidene ring,
 (d) dihydroxyC3-C6 alkyl- wherein the alkyl portion is optionally substituted with a C3-C6 cycloalkylidene ring,
 (e) (C1-C6 alkoxy)C1-C6 alkyl- optionally substituted with 1-3 fluoros,
 (f) (R$^1$R$^2$N)C1-C6 alkyl- where R$^1$ and R$^2$ are independently selected from H, C1-C6 alkyl (optionally substituted with 1-3 fluoros), (C1-C6 alkoxy)C1-C6 alkyl-, (C1-C6 alkyl)C(=O)— and (C1-C6 alkoxy)C(=O)—;
 (g) hetAr$^1$C1-C6 alkyl-, where hetAr$^1$ is a 5-6 membered heteroaryl ring having 1-3 ring heteroatoms independently selected from N, O and S and is optionally substituted with one or more independently selected C1-C6 alkyl substituents;
 (h) (C3-C6 cycloalkyl)C1-C3 alkyl-, wherein said cycloalkyl is optionally substituted with OH,
 (i) (hetCyc$^a$)C1-C3 alkyl-,
 (j) hetCyc$^a$,
 (k) (R$^1$R$^2$N)C(=O)C1-C6 alkyl-, where R$^1$ and R$^2$ are independently selected from H and C1-C6 alkyl;
 (l) (R$^1$R$^2$N)C(=O)—, where R$^1$ and R$^2$ are independently selected from H and C1-C6 alkyl, or
 (m) hetCyc$^a$C(=O)C1-C6 alkyl-;

hetCyc$^a$ is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl, halogen, (C1-C6 alkyl)C(=O)—, C1-C6 alkoxy, oxo and (C1-C6 alkoxy)C(=O)—;

Ring D is (i) a saturated monocyclic 4-7 membered heterocyclic ring having one ring heteroatom which is nitrogen, (ii) a saturated 7-8 membered bridged heterocyclic ring having one ring heteroatom which is nitrogen, or (iii) a saturated 7-11 membered heterospirocyclic ring system having one ring heteroatom which is nitrogen;

each R$^a$ is independently C1-C6 alkyl (optionally substituted with 1-3 fluoros), hydroxyC1-C6 alkyl or (C1-C6 alkoxy)C1-C6 alkyl-;

R$^b$ is (a) hydroxy, (b) cyclopropyl, (c) hetCyc$^b$CH$_2$—, (d) R$^i$R$^j$NC(=O)CH$_2$OCH$_2$— where R$^i$ and R$^j$ are independently H or C1-C6 alkyl, (e) R$^c$R$^d$N—, (f) R$^c$R$^d$NCH$_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy(CH$_2$)$_n$— where n is 0 or 1 and R' and R" are independently hydrogen or C1-C6 alkyl, (j) hetCyc$^b$(C1-C3 alkyl)OCH$_2$—, (k) hetCyc$^b$C(=O)NH— or (l) hetAr$^a$C(=O)NH—;

hetCyc$^b$ is a 4-6 membered heterocyclic ring, a 7-8 membered bridged heterocyclic ring, or a 7-10 membered heterospirocyclic ring, each ring having 1-2 ring heteroatoms independently selected from N and O, wherein hetCyc$^b$ is optionally substituted with one or more substituents independently selected from OH, fluoro, C1-C6 alkyl (optionally substituted with 1-3 fluoros), hydroxyC1-C6 alkyl- (optionally substituted with 1-3 fluoros), (C1-C6 alkoxy)C1-C6 alkyl-, (C1-C6 alkoxy)C(=O)—, C1-C6 alkoxy, and R'R"N— where R' and R" are independently hydrogen or C1-C6 alkyl;

hetAr$^a$ is a 5-6 membered heteroaryl ring having 1-3 ring heteroatoms independently selected from N, O and S wherein hetAr$^a$ is optionally substituted with one or more substituents independently selected from the group consisting of halogen, CN, C1-C6 alkyl (optionally substituted with 1-3 fluoros), and C1-C6 alkoxy (optionally substituted with 1-3 fluoros), R$^c$ is hydrogen or C1-C6 alkyl;

R$^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, (R$^k$R$^l$N)C1-C6 alkyl- where R$^k$ and R$^l$ are independently H or C1-C6 alkyl, R$^m$R$^n$NC(=O)C1-C6 alkyl- where R$^m$ and R$^n$ are independently H or C1-C6 alkyl, PhCH$_2$— wherein the phenyl is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, hydroxyC1-C6 alkyl, (C1-C6 alkyl)SO$_2$—, R$^e$R$^f$N— and (R$^e$R$^f$N)C1-C6 alkyl- where each R$^e$ and R$^f$ is independently H or C1-C6 alkyl, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl;

n is 0, 1, 2, 3, 4, 5 or 6;

m is 0 or 1;

E is:
 (a) hydrogen,
 (b) hydroxy,
 (c) C1-C6 alkyl optionally substituted with 1-3 fluoros,
 (d) Ar$^1$C1-C6 alkyl- wherein said alkyl portion is optionally substituted with 1-3 fluoros,
 (e) hetAr$^2$C1-C6 alkyl-,
 (f) (C1-C6 alkoxy)C1-C6 alkoxy-,
 (g) Ar$^1$O—,
 (h) hetAr$^2$—O—,
 (i) Ar$^1$NR$^g$— where R$^g$ is H or C1-C6 alkyl,
 (j) hetAr$^2$NR$^g$— where R$^g$ is H or C1-C6 alkyl,
 (k) R$^3$C(=O)NR$^g$— where R$^g$ is H or C1-C6 alkyl;
 (l) Ar$^1$C(=O)NR$^g$— where R$^g$ is H or C1-C6 alkyl,
 (m) hetAr$^2$C(=O)NR$^g$(CH$_2$)$_p$— where p is 0 or 1 and R$^g$ is H or C1-C6 alkyl,
 (n) R$^4$R$^5$NC(=O)—,
 (o) Ar$^1$NR$^g$C(=O)—, where R$^g$ is H or C1-C6 alkyl,
 (p) hetAr$^2$NR$^g$C(=O)—, where R$^g$ is H or C1-C6 alkyl,
 (q) Ar$^1$)C1-C6 alkyl)C(=O)— wherein said alkyl portion is optionally substituted with OH, hydroxy(C1-C6 alkyl), C1-C6 alkoxy or NH$_2$,
 (r) hetCyc$^5$C(=O)—,
 (s) R$^4$R$^5$NC(=O)NR$^g$— where R$^g$ is H or C1-C6 alkyl, or
 (t) (C1-C6 alkyl)SO$_2$—;
 (u) Ar$^1$(C1-C6 alkyl)C(=O)NR$^g$— where R$^g$ is H or C1-C6 alkyl, (v) hetAr⁴C(=O)NR^g— where R^g is H or C1-C6 alkyl,
(w) hetAr²—S(=O)—,
(x) (C3-C6 cycloalkyl)CH₂SO₂—,
(y) Ar¹(C1-C6 alkyl)SO₂—,
(z) hetAr²SO₂—,
(aa) Ar¹,
(bb) hetAr²,
(cc) hetCyc⁵,
(dd) C1-C6 alkoxy,
(ee) Ar¹(C1-C6 alkyl)-O—,
(ff) hetAr²(C1-C6 alkyl)-O—,
(gg) hetAr²—O—C1-C6 alkyl-,
(hh) Ar¹)C1-C6 alkyl)NR^g— where R^g is H or C1-C6 alkyl,
(ii) hetAr²—S—,
(jj) Ar²SO₂NR^g(CH₂)_p— where p is 0 or 1 and R^g is H or C1-C6 alkyl,
(kk) (C1-C6 alkoxy)C(=O)—,
(ll) (C1-C6 alkyl)NR^gC(=O)O— where R^g is H or C1-C6 alkyl,
(mm) (C1-C6 alkyl)NR^gSO₂— where R^g is H or C1-C6 alkyl,
(nn) hetCyc⁵C(=O)NR^g— where R^g is H or C1-C6 alkyl,
(oo) Q-NR^h(C1-C3 alkyl)C(=O)NR^g— where R^g and R^h are independently H or C1-C6 alkyl and Q is H, C1-C6 alkyl or (C1-C6 alkyl)OC(=O)—,
(pp)

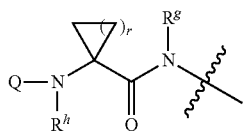

where R^g and R^h are independently H or C1-C6 alkyl, Q is H, C1-C6 alkyl or (C1-C6 alkyl)OC(=O)— and r is 1, 2, 3 or 4,
(qq)

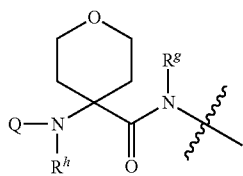

where R^g and R^h are independently H or C1-C6 alkyl and Q is H, C1-C6 alkyl or (C1-C6 alkyl)OC(=O)—,
(rr)

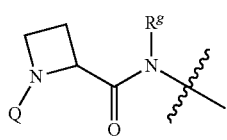

where R^g is H or C1-C6 alkyl and Q is H, C1-C6 alkyl or (C1-C6 alkyl)OC(=O)—, or
(ss) R^gR^hN— where R^g and R^h are independently H or C1-C6 alkyl,
(tt) (C3-C6 cycloalkyl)C(=O)NR^g— where the cycloalkyl is optionally and independently substituted with one or more halogens,
(uu) (C1-C6 alkyl)C(=O)NR^gCH₂— where R^g is H or C1-C6 alkyl, or
(vv) C1-C6 alkyl)SO₂NR^g— where R^g is H or C1-C6 alkyl;

Ar¹ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, hydroxyC1-C6 alkyl, (C1-C6 alkyl)SO₂—, R^eR^fN— and (R^eR^fN)C1-C6 alkyl- where each R^e and R^f is independently H or C1-C6 alkyl;

hetAr² is a 5-6 membered heteroaryl ring having 1-3 ring heteroatoms independently selected from N, O and S, or a 9-10 membered bicyclic heteroaryl having 1-2 ring nitrogen atoms, wherein hetAr² is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros) and hydroxyC1-C6 alkoxy-;

hetCyc⁵ is a 4-6 membered saturated heterocyclic ring having 1-2 ring heteroatoms independently selected from N, O and S wherein said heterocyclic ring is optionally substituted with one or more substituents independently selected from C1-C6 alkoxy and oxo;

R³ is C1-C6 alkyl (optionally substituted with 1-3 fluoros), hydroxyC1-C6 alkyl-, C1-C6 alkoxy, C3-C6 cycloalkyl, (C3-C6 cycloalkyl)CH₂—, (C3-C6 cycloalkyl)O—, (C3-C6 cycloalkyl)CH₂O—, hetCyc⁷O—, Ph-O—, or (C1-C6 alkoxy)C1-C6 alkyl-; wherein each of said C3-C6 cycloalkyl moieties is optionally substituted with C1-C6 alkyl (optionally substituted with 1-3 fluoros), C1-C6 alkoxy, OH or R'R"N— where R' and R" are independently hydrogen or C1-C6 alkyl;

R⁴ is H or C1-C6 alkyl;
R⁵ is Ar², hetAr³, Ar²CH₂—, hetCyc⁶-CH₂—, hydroxyC1-C6 alkyl-, (C3-C6 cycloalkyl)CH₂—, or C1-C6 alkyl optionally substituted with 1-3 fluoros;

Ar² is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, and R^gR^hN— where R^g and R^h are independently H or C1-C6 alkyl, or Ar² is phenyl fused to a 6 membered heterocyclic ring having a ring nitrogen atom and optionally substituted with C1-C6 alkyl;

hetAr³ is a 5-6 membered heteroaryl ring having 1-3 ring heteroatoms independently selected from N, O and S and optionally substituted with one or more substituents independently selected from the group consisting of halogen, CN, C1-C6 alkyl (optionally substituted with 1-3 fluoros), C1-C6 alkoxy (optionally substituted with 1-3 fluoros), and (C1-C6 alkoxy)C1-C6 alkyl- (optionally substituted with 1-3 fluoros);

hetAr⁴ is pyridin-4(1H)-onyl or pyridin-2(1H)-onyl optionally substituted with one or more substituents independently selected from C1-C6 alkyl and halogen;

hetCyc⁶ is a 5-7 membered heterocyclic ring having 1-3 ring heteroatoms independently selected from N, O and S; and hetCyc⁷ is a 5-7 membered heterocyclic ring having 1-3 ring heteroatoms independently selected from N, O and S.

In some embodiments, a RET inhibitor (e.g., a first RET inhibitor or a second RET inhibitor) is a compound of the Formula VII:

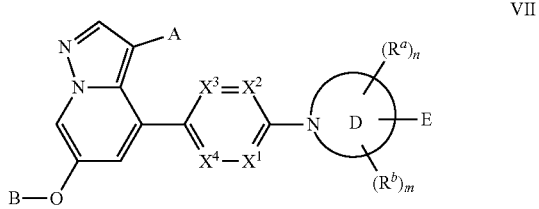

VII or a pharmaceutically acceptable salt or solvate thereof, wherein:

$X^1$, $X^2$, $X^3$ and $X^4$ are independently CH or N, wherein zero, one or two of $X^1$, $X^2$, $X^3$ and $X^4$ is N;

A is CN;

B is:
  (b) C1-C6 alkyl optionally substituted with 1-3 fluoros,
  (c) hydroxyC2-C6 alkyl- wherein the alkyl portion is optionally substituted with a C3-C6 cycloalkylidene ring, or
  (i) (hetCyc$^a$)C1-C3 alkyl-;

hetCyc$^a$ is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl, halogen, (C1-C6 alkyl)C(=O)—, C1-C6 alkoxy, oxo, and (C1-C6 alkoxy)C(=O)—;

Ring D is a saturated monocyclic 4-7 membered heterocyclic ring having one ring heteroatom which is nitrogen;

each $R^a$ is independently C1-C6 alkyl (optionally substituted with 1-3 fluoros);

$R^b$ is (a) hydroxy;

n is 0 or 1;

m is 0 or 1;

E is:
  (e) hetAr²C1-C6 alkyl-,
  (h) hetAr²—O—,
  (k) R³C(=O)NR$^g$— where $R^g$ is H or C1-C6 alkyl,
  (l) Ar¹C(=O)NR$^g$— where $R^g$ is H or C1-C6 alkyl, or
  (m) hetAr²C(=O)NR$^g$(CH₂)$_p$— where p is 0 or 1 and $R^g$ is H or C1-C6 alkyl;

Ar¹ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, hydroxyC1-C6 alkyl, (C1-C6 alkyl)SO₂—, R$^e$R$^f$N— and (R$^e$R$^f$N)C1-C6 alkyl- where each $R^e$ and $R^f$ is independently H or C1-C6 alkyl;

hetAr² is a 5-6 membered heteroaryl ring having 1-3 ring heteroatoms independently selected from N, O and S, or a 9-10 membered bicyclic heteroaryl having 1-2 ring nitrogen atoms, wherein hetAr² is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros) and hydroxyC1-C6 alkoxy-; and $R^3$ is C1-C6 alkyl (optionally substituted with 1-3 fluoros), hydroxyC1-C6 alkyl-, C1-C6 alkoxy, C3-C6 cycloalkyl, (C3-C6 cycloalkyl)CH₂—, (C3-C6 cycloalkyl)O—, (C3-C6 cycloalkyl)CH₂O—, hetCyc⁷O—, Ph-O—, or (C1-C6 alkoxy)C1-C6 alkyl-; wherein each of said C3-C6 cycloalkyl moieties is optionally substituted with C1-C6 alkyl (optionally substituted with 1-3 fluoros), C1-C6 alkoxy, OH, or R'R"N— where R' and R" are independently hydrogen or C1-C6 alkyl.

In some embodiments, a RET inhibitor (e.g., a first RET inhibitor or a second RET inhibitor) is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl) piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof.

Non-limiting examples of receptor tyrosine kinase (e.g., Trk) targeted therapeutic agents, include afatinib, cabozantinib, cetuximab, crizotinib, dabrafenib, entrectinib, erlotinib, gefitinib, imatinib, lapatinib, lestaurtinib, nilotinib, pazopanib, panitumumab, pertuzumab, sunitinib, trastuzumab, 1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea, AG 879, AR-772, AR-786, AR-256, AR-618, AZ-23, AZ623, DS-6051, Gö 6976, GNF-5837, GTx-186, GW 441756, LOXO-101, MGCD516, PLX7486, RXDX101, VM-902A, TPX-0005, and TSR-011. Additional Trk targeted therapeutic agents include those described in U.S. Pat. Nos. 8,450,322; 8,513,263; 8,933,084; 8,791,123; 8,946,226; 8,450,322; 8,299,057; and 8,912,194; U.S. Publication No. 2016/0137654; 2015/0166564; 2015/0051222; 2015/0283132; and 2015/0306086; International Publication No. WO 2010/033941; WO 2010/048314; WO 2016/077841; WO 2011/146336; WO 2011/006074; WO 2010/033941; WO 2012/158413; WO 2014078454; WO 2014078417; WO 2014078408; WO 2014078378; WO 2014078372; WO 2014078331; WO 2014078328; WO 2014078325; WO 2014078323; WO 2014078322; WO 2015175788; WO 2009/013126; WO 2013/174876; WO 2015/124697; WO 2010/058006; WO 2015/017533; WO 2015/112806; WO 2013/183578; and WO 2013/074518, all of which are hereby incorporated by reference in their entireties.

Further examples of Trk inhibitors can be found in U.S. Pat. No. 8,637,516, International Publication No. WO 2012/034091, U.S. Pat. No. 9,102,671, International Publication No. WO 2012/116217, U.S. Publication No. 2010/0297115, International Publication No. WO 2009/053442, U.S. Pat. No. 8,642,035, International Publication No. WO 2009092049, U.S. Pat. No. 8,691,221, International Publication No. WO2006131952, all of which are incorporated by reference in their entireties herein. Exemplary Trk inhibitors include GNF-4256, described in *Cancer Chemother. Pharmacol.* 75(1):131-141, 2015; and GNF-5837 (N-[3-[[2,3-dihydro-2-oxo-3-(1H-pyrrol-2-ylmethylene)-1H-indol-6-yl]amino]-4-methylphenyl]-N'-[2-fluoro-5-(trifluoromethyl)phenyl]-urea), described in *ACS Med. Chem. Lett.* 3(2):140-145, 2012, each of which is incorporated by reference in its entirety herein.

Additional examples of Trk inhibitors include those disclosed in U.S. Publication No. 2010/0152219, U.S. Pat. No. 8,114,989, and International Publication No. WO 2006/123113, all of which are incorporated by reference in their entireties herein. Exemplary Trk inhibitors include AZ623, described in *Cancer* 117(6):1321-1391, 2011; AZD6918, described in *Cancer Biol. Ther.* 16(3):477-483, 2015; AZ64, described in *Cancer Chemother. Pharmacol.* 70:477-486, 2012; AZ-23 ((S)-5-Chloro-N2-(1-(5-fluoropyridin-2-yl)ethyl)-N4-(5-isopropoxy-1H-pyrazol-3-yl)pyrimidine-2,4-diamine), described in *Mol. Cancer Ther.* 8:1818-1827, 2009; and AZD7451; each of which is incorporated by reference in its entirety.

A Trk inhibitor can include those described in U.S. Pat. Nos. 7,615,383; 7,384,632; 6,153,189; 6,027,927; 6,025,166; 5,910,574; 5,877,016; and 5,844,092, each of which is incorporated by reference in its entirety.

Further examples of Trk inhibitors include CEP-751, described in *Int. J. Cancer* 72:672-679, 1997; CT327, described in *Acta Derm. Venereol.* 95:542-548, 2015; compounds described in International Publication No. WO 2012/034095; compounds described in U.S. Pat. No. 8,673,347 and International Publication No. WO 2007/022999; compounds described in U.S. Pat. No. 8,338,417; compounds described in International Publication No. WO 2016/027754; compounds described in U.S. Pat. No. 9,242,977; compounds described in U.S. Publication No. 2016/0000783; sunitinib (N-(2-diethylaminoethyl)-5-[(Z)-(5-fluoro-2-oxo-1H-indol-3-ylidene)methyl]-2,4-dimethyl-1H-pyrrole-3-carboxamide), as described in *PLoS One* 9:e95628, 2014; compounds described in International Publication No. WO 2011/133637; compounds described in U.S. Pat. No. 8,637,256; compounds described in *Expert. Opin. Ther. Pat.* 24(7):731-744, 2014; compounds described in *Expert Opin. Ther. Pat.* 19(3):305-319, 2009; (R)-2-phenylpyrrolidine substituted imidazopyridazines, e.g., GNF-8625, (R)-1-(6-(6-(2-(3-fluorophenyl)pyrrolidin-1-yl)imidazo[1,2-b]pyridazin-3-yl)-[2,4'-bipyridin]-2'-yl)piperidin-4-ol as described in ACS Med. Chem. Lett. 6(5):562-567, 2015; GTx-186 and others, as described in *PLoS One* 8(12):e83380, 2013; K252a ((9S-(9α,10β,12α))-2,3,9,10,11,12-hexahydro-10-hydroxy-10-(methoxycarbonyl)-9-methyl-9,12-epoxy-1H-diindolo[1,2,3-fg:3',2',1'-kl]pyrrolo[3,4-i][1,6]benzodiazocin-1-one), as described in *Mol. Cell Biochem.* 339(1-2):201-213, 2010; 4-aminopyrazolylpyrimidines, e.g., AZ-23 (((S)-5-chloro-N2-(1-(5-fluoropyridin-2-yl)ethyl)-N4-(5-isopropoxy-1H-pyrazol-3-yl)pyrimidine-2,4-diamine)), as described in *J. Med. Chem.* 51(15): 4672-4684, 2008; PFIA-739358 (danusertib), as described in *Mol. Cancer Ther.* 6:3158, 2007; Gö 6976 (5,6,7,13-tetrahydro-13-methyl-5-oxo-12H-indolo[2,3-a]pyrrolo[3,4-c]carbazole-12-propanenitrile), as described in *J. Neurochem.* 72:919-924, 1999; GW441756 ((3Z)-3-[(1-methylindol-3-yl)methylidene]-1H-pyrrolo[3,2-b]pyridin-2-one), as described in *IJAE* 115:117, 2010; milciclib (PHA-848125AC), described in *J. Carcinog.* 12:22, 2013; AG-879 ((2E)-3-[3,5-Bis(1,1-dimethylethyl)-4-hydroxyphenyl]-2-cyano-2-propenethioamide); altiratinib (N-(4-((2-(cyclopropanecarboxamido)pyridin-4-yl)oxy)-2,5-difluorophenyl)-N-(4-fluorophenyl)cyclopropane-1,1-dicarboxamide); cabozantinib (N-(4-((6,7-Dimethoxyquinolin-4-yl)oxy)phenyl)-N'-(4-fluorophenyl)cyclopropane-1,1-dicarboxamide); lestaurtinib ((5S,6S,8R)-6-Hydroxy-6-(hydroxymethyl)-5-methyl-7,8,14,15-tetrahydro-5H-16-oxa-4b,8a,14-triaza-5,8-methanodibenzo[b,h]cycloocta[jkl]cyclopenta[e]-as-indacen-13(6H)-one); dovatinib (4-amino-5-fluoro-3-[6-(4-methylpiperazin-1-yl)-1H-benzimidazol-2-yl]quinolin-2(1H)-one mono 2-hydroxypropanoate hydrate); sitravatinib (N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide); ONO-5390556; regorafenib (4-[4-({[4-Chloro-3-(trifluoromethyl)phenyl]carbamoyl}amino)-3-fluorophenoxy]-N-methylpyridine-2-carboxamide hydrate); and VSR-902A; all of the references above are incorporated by reference in their entireties herein.

The ability of a Trk inhibitor to act as a TrkA, TrkB, and/or Trk C inhibitor may be tested using the assays described in Examples A and B in U.S. Pat. No. 8,513,263, which is incorporated herein by reference.

In some embodiments, the receptor tyrosine kinase inhibitor is an epidermal growth factor receptor typrosine kinase inhibitor (EGFR). For example, EGFR inhibitors can include osimertinib (merelectinib, Tagrisso), erlotinib (Tarceva), gefitinib (Iressa), cetuximab (Erbitux), necitumumab (Portrazza), neratinib (Nerlynx), lapatinib (Tykerb), panitumumab (Vectibix), and vandetanib (Caprelsa). In some embodiments, the EGFR inhibitor is osimertinib.

In some embodiments, signal transduction pathway inhibitors include Ras-Raf-MEK-ERK pathway inhibitors (e.g., binimetinib, selumetinib, encorafinib, sorafenib, trametinib, and vemurafenib), PI3K-Akt-mTOR-S6K pathway inhibitors (e.g. everolimus, rapamycin, perifosine, temsirolimus), and other kinase inhibitors, such as baricitinib, brigatinib, capmatinib, danusertib, ibrutinib, milciclib, quercetin, regorafenib, ruxolitinib, semaxanib, AP32788, BLU285, BLU554, INCB39110, INCB40093, INCB50465, INCB52793, INCB54828, MGCD265, NMS-088, NMS-1286937, PF 477736 ((R)-amino-N-[5,6-dihydro-2-(1-methyl-1H-pyrazol-4-yl)-6-oxo-1Hpyrrolo[4,3,2-ef][2,3]benzodiazepin-8-yl]-cyclohexaneacetamide), PLX3397, PLX7486, PLX8394, PLX9486, PRN1008, PRN1371, RXDX103, RXDX106, RXDX108, and TG101209 (N-tert-butyl-3-(5-methyl-2-(4-(4-methylpiperazin-1-yl)phenylamino)pyrimidin-4-ylamino)benzenesulfonamide).

Non-limiting examples of checkpoint inhibitors include ipilimumab, tremelimumab, nivolumab, pidilizumab, MPDL3208A, MEDI4736, MSB0010718C, BMS-936559, BMS-956559, BMS-935559 (MDX-1105), AMP-224, and pembrolizumab.

In some embodiments, cytotoxic chemotherapeutics are selected from arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

Non-limiting examples of angiogenesis-targeted therapies include aflibercept and bevacizumab.

The term "immunotherapy" refers to an agent that modulates the immune system. In some embodiments, an immunotherapy can increase the expression and/or activity of a regulator of the immune system. In some embodiments, an immunotherapy can decrease the expression and/or activity of a regulator of the immune system. In some embodiments, an immunotherapy can recruit and/or enhance the activity of an immune cell.

In some embodiments, the immunotherapy is a cellular immunotherapy (e.g., adoptive T-cell therapy, dendritic cell therapy, natural killer cell therapy). In some embodiments, the cellular immunotherapy is sipuleucel-T (APC8015; Provenge™; Plosker (2011) Drugs 71(1): 101-108). In some embodiments, the cellular immunotherapy includes cells that express a chimeric antigen receptor (CAR). In some embodiments, the cellular immunotherapy is a CAR-T cell therapy. In some embodiments, the CAR-T cell therapy is tisagenlecleucel (Kymriah™).

In some embodiments, the immunotherapy is an antibody therapy (e.g., a monoclonal antibody, a conjugated antibody). In some embodiments, the antibody therapy is bevacizumab (Mvasti™, Avastin®), trastuzumab (Herceptin®), avelumab (Bavencio®), rituximab (MabThera™, Rituxan®), edrecolomab (Panorex), daratumuab (Darzalex®), olaratumab (Lartruvo™), ofatumumab (Arzerra®), alemtuzumab (Campath®), cetuximab (Erbitux®), oregovomab, pembrolizumab (Keytruda®), dinutiximab (Unituxin®), obinutuzumab (Gazyva®), tremelimumab (CP-675,206), ramucirumab (Cyramza®), ublituximab (TG-1101), panitumumab (Vectibix®), elotuzumab (Empliciti™), avelumab (Bavencio®), necitumumab (Portrazza™), cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), ganitumab, urelumab, pidilizumab or amatuximab.

In some embodiments, the immunotherapy is an antibody-drug conjugate. In some embodiments, the antibody-drug conjugate is gemtuzumab ozogamicin (Mylotarg™), inotuzumab ozogamicin (Besponsa®), brentuximab vedotin (Adcetris®), ado-trastuzumab emtansine (TDM-1; Kadcyla®), mirvetuximab soravtansine (IMGN853) or anetumab ravtansine In some embodiments, the immunotherapy includes blinatumomab (AMG103; Blincyto®) or midostaurin (Rydapt).

In some embodiments, the immunotherapy includes a toxin. In some embodiments, the immunotherapy is denileukin diftitox (Ontak®).

In some embodiments, the immunotherapy is a cytokine therapy. In some embodiments, the cytokine therapy is an interleukin 2 (IL-2) therapy, an interferon alpha (IFNα) therapy, a granulocyte colony stimulating factor (G-CSF) therapy, an interleukin 12 (IL-12) therapy, an interleukin 15 (IL-15) therapy, an interleukin 7 (IL-7) therapy or an erythropoietin-alpha (EPO) therapy. In some embodiments, the IL-2 therapy is aldesleukin (Proleukin®). In some embodiments, the IFNα therapy is IntronA® (Roferon-A®). In some embodiments, the G-CSF therapy is filgrastim (Neupogen®).

In some embodiments, the immunotherapy is an immune checkpoint inhibitor. In some embodiments, the immunotherapy includes one or more immune checkpoint inhibitors. In some embodiments, the immune checkpoint inhibitor is a CTLA-4 inhibitor, a PD-1 inhibitor or a PD-L1 inhibitor. In some embodiments, the CTLA-4 inhibitor is ipilimumab (Yervoy®) or tremelimumab (CP-675,206). In some embodiments, the PD-1 inhibitor is pembrolizumab (Keytruda®) or nivolumab (Opdivo®). In some embodiments, the PD-L1 inhibitor is atezolizumab (Tecentriq®), avelumab (Bavencio®) or durvalumab (Imfinzi™).

In some embodiments, the immunotherapy is mRNA-based immunotherapy. In some embodiments, the mRNA-based immunotherapy is CV9104 (see, e.g., Rausch et al. (2014) Human Vaccin Immunother 10(11): 3146-52; and Kubler et al. (2015) J. Immunother Cancer 3:26).

In some embodiments, the immunotherapy is bacillus Calmette-Guerin (BCG) therapy.

In some embodiments, the immunotherapy is an oncolytic virus therapy. In some embodiments, the oncolytic virus therapy is talimogene alherparepvec (T-VEC; Imlygic®).

In some embodiments, the immunotherapy is a cancer vaccine. In some embodiments, the cancer vaccine is a human papillomavirus (HPV) vaccine. In some embodiments, the HPV vaccine is Gardasil®, Gardasil9® or Cervarix®. In some embodiments, the cancer vaccine is a hepatitis B virus (HBV) vaccine. In some embodiments, the HBV vaccine is Engerix-B®, Recombivax HB® or GI-13020 (Tarmogen®). In some embodiments, the cancer vaccine is Twinrix® or Pediarix®. In some embodiments, the cancer vaccine is BiovaxlD®, Oncophage®, GVAX, ADXS11-001, ALVAC-CEA, PROSTVAC®, Rindopepimut®, CimaVax-EGF, lapuleucel-T (APC8024; Neuvenge™), GRNVAC1, GRNVAC2, GRN-1201, hepcortespenlisimut-L (Hepko-V5), DCVAX®, SCIB1, BMT CTN 1401, PrCa VBIR, PANVAC, ProstAtak®, DPX-Survivac, or viagenpumatucel-L (HS-110).

In some embodiments, the immunotherapy is a peptide vaccine. In some embodiments, the peptide vaccine is nelipepimut-S (E75) (NeuVax™), IMA901, or SurVaxM (SVN53-67). In some embodiments, the cancer vaccine is an immunogenic personal neoantigen vaccine (see, e.g., Ott et al. (2017) Nature 547: 217-221; Sahin et al. (2017) Nature 547: 222-226). In some embodiments, the cancer vaccine is RGSH4K, or NEO-PV-01. In some embodiments, the cancer vaccine is a DNA-based vaccine. In some embodiments, the DNA-based vaccine is a mammaglobin-A DNA vaccine (see, e.g., Kim et al. (2016) OncoImmunology 5(2): e1069940).

In some embodiments, immune-targeted agents are selected from aldesleukin, interferon alfa-2b, ipilimumab, lambrolizumab, nivolumab, prednisone, and sipuleucel-T.

Non-limiting examples of radiotherapy include radioiodide therapy, external-beam radiation, and radium 223 therapy.

Additional kinase inhibitors include those described in, for example, U.S. Pat. Nos. 7,514,446; 7,863,289; 8,026, 247; 8,501,756; 8,552,002; 8,815,901; 8,912,204; 9,260, 437; 9,273,051; U.S. Publication No. US 2015/0018336; International Publication No. WO 2007/002325; WO 2007/ 002433; WO 2008/080001; WO 2008/079906; WO 2008/ 079903; WO 2008/079909; WO 2008/080015; WO 2009/ 007748; WO 2009/012283; WO 2009/143018; WO 2009/ 143024; WO 2009/014637; 2009/152083; WO 2010/ 111527; WO 2012/109075; WO 2014/194127; WO 2015/ 112806; WO 2007/110344; WO 2009/071480; WO 2009/ 118411; WO 2010/031816; WO 2010/145998; WO 2011/ 092120; WO 2012/101032; WO 2012/139930; WO 2012/ 143248; WO 2012/152763; WO 2013/014039; WO 2013/

102059; WO 2013/050448; WO 2013/050446; WO 2014/019908; WO 2014/072220; WO 2014/184069; and WO 2016/075224 all of which are hereby incorporated by reference in their entireties.

Further examples of kinase inhibitors include those described in, for example, WO 2016/081450; WO 2016/022569; WO 2016/011141; WO 2016/011144; WO 2016/011147; WO 2015/191667; WO 2012/101029; WO 2012/113774; WO 2015/191666; WO 2015/161277; WO 2015/161274; WO 2015/108992; WO 2015/061572; WO 2015/058129; WO 2015/057873; WO 2015/017528; WO/2015/017533; WO 2014/160521; and WO 2014/011900, each of which is hereby incorporated by reference in its entirety.

Further examples of kinase inhibitors include luminespib (AUY-922, NVP-AUY922) (5-(2,4-dihydroxy-5-isopropylphenyl)-N-ethyl-4-(4-(morpholinomethyl)phenyl)isoxazole-3-carboxamide) and doramapimod (BIRB-796) (1-[5-tert-butyl-2-(4-methylphenyl)pyrazol-3-yl]-3-[4-(2-morpholin-4-ylethoxy)naphthalen-1-yl]urea).

Accordingly, also provided herein is a method of treating cancer, comprising administering to a patient in need thereof a pharmaceutical combination for treating cancer which comprises (a) a compound of Formula I (e.g., any one of Formulas I-A to I-L), or a pharmaceutically acceptable salt or solvate thereof, (b) an additional therapeutic agent, and (c) optionally at least one pharmaceutically acceptable carrier for simultaneous, separate or sequential use for the treatment of cancer, wherein the amounts of the compound of Formula I, or a pharmaceutically acceptable salt or solvate thereof and the additional therapeutic agent are together effective in treating the cancer.

In some embodiments, the additional therapeutic agent(s) includes any one of the above listed therapies or therapeutic agents which are standards of care in cancers wherein the cancer has a dysregulation of a RET gene, a RET protein, or expression or activity, or level of any of the same.

These additional therapeutic agents may be administered with one or more doses of the compound of Formula I, or a pharmaceutically acceptable salt or solvate thereof, or pharmaceutical composition thereof, as part of the same or separate dosage forms, via the same or different routes of administration, and/or on the same or different administration schedules according to standard pharmaceutical practice known to one skilled in the art.

Also provided herein is (i) a pharmaceutical combination for treating a cancer in a patient in need thereof, which comprises (a) a compound of Formula I (e.g., any one of Formulas I-A to I-L), or a pharmaceutically acceptable salt or solvate thereof, (b) at least one additional therapeutic agent (e.g., any of the exemplary additional therapeutic agents described herein or known in the art), and (c) optionally at least one pharmaceutically acceptable carrier for simultaneous, separate or sequential use for the treatment of cancer, wherein the amounts of the compound of Formula I, or a pharmaceutically acceptable salt or solvate thereof and of the additional therapeutic agent are together effective in treating the cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer in a patient in need thereof. In one embodiment the patient is a human. In some embodiments, the cancer is a RET-associated cancer. For example, a RET-associated cancer having one or more RET inhibitor resistance mutations.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of Formula I (e.g., any one of Formulas I-A to I-L), or a pharmaceutically acceptable salt or solvate thereof and at least one additional therapeutic agent (e.g., a chemotherapeutic agent), are both administered to a patient simultaneously in the form of a single composition or dosage. The term "non-fixed combination" means that a compound of Formula I (e.g., any one of Formulas I-A to I-L), or a pharmaceutically acceptable salt or solvate thereof and at least one additional therapeutic agent (e.g., chemotherapeutic agent) are formulated as separate compositions or dosages such that they may be administered to a patient in need thereof simultaneously, concurrently or sequentially with variable intervening time limits, wherein such administration provides effective levels of the two or more compounds in the body of the patient. These also apply to cocktail therapies, e.g. the administration of three or more active ingredients Accordingly, also provided herein is a method of treating a cancer, comprising administering to a patient in need thereof a pharmaceutical combination for treating cancer which comprises (a) a compound of Formula I (e.g., any one of Formulas I-A to I-L), or a pharmaceutically acceptable salt or solvate thereof, (b) an additional therapeutic agent, and (c) optionally at least one pharmaceutically acceptable carrier for simultaneous, separate or sequential use for the treatment of cancer, wherein the amounts of the compound of Formula I, or a pharmaceutically acceptable salt or solvate thereof and the additional therapeutic agent are together effective in treating the cancer. In one embodiment, the compound of Formula I, or a pharmaceutically acceptable salt or solvate thereof, and the additional therapeutic agent are administered simultaneously as separate dosages. In one embodiment, the compound of Formula I, or a pharmaceutically acceptable salt or solvate thereof, and the additional therapeutic agent are administered as separate dosages sequentially in any order, in jointly therapeutically effective amounts, e.g. in daily or intermittently dosages. In one embodiment, the compound of Formula I, or a pharmaceutically acceptable salt or solvate thereof, and the additional therapeutic agent are administered simultaneously as a combined dosage. In some embodiments, the cancer is a RET-associated cancer. For example, a RET-associated cancer having one or more RET inhibitor resistance mutations. In some embodiments, the additional therapeutic agent is crizotinib. In some embodiments, the additional therapeutic agent is osimertinib. In some embodiments, the patient has been administered one or more doses of a compound of Formula I (e.g., any one of Formulas I-A to I-L), or a pharmaceutically acceptable salt or solvate thereof, prior to administration of the pharmaceutical composition. In some embodiments, the cancer is a lung cancer (e.g., a RET-associated lung cancer).

Also provided herein is a method of treating a disease or disorder mediated by RET in a patient in need of such treatment, the method comprising administering to the patient a therapeutically effective amount of a compound of Formula I (e.g., any one of Formulas I-A to I-L), or a pharmaceutically acceptable salt or solvate thereof or a pharmaceutical composition thereof. In some embodiments, the disease or disorder mediated by RET is a dysregulation of RET gene, a RET kinase, or expression or activity or level of any of the same. For example the dysregulation of a RET gene, a RET kinase, or expression or activity or level of any of the same includes one or more RET inhibitor resistance mutations. A disease or disorder mediated by RET can include any disease, disorder or condition that is directly or indirectly linked to expression or activity of RET, including overexpression and/or abnormal activity levels. In one embodiment, the disease is cancer (e.g., a RET-associated cancer). In one embodiment, the cancer is any of the cancers or RET-associated cancers described herein. In some embodiments, the additional therapeutic agent is crizotinib. In some embodiments, the additional therapeutic agent is osimertinib. In some embodiments, the patient has been administered one or more doses of a compound of Formula I (e.g., any one of Formulas I-A to I-L), or a pharmaceutically acceptable salt or solvate thereof, prior to administration of the pharmaceutical composition. In some embodiments, the cancer is a lung cancer (e.g., a RET-associated lung cancer).

Although the genetic basis of tumorigenesis may vary between different cancer types, the cellular and molecular mechanisms required for metastasis appear to be similar for all solid tumor types. During a metastatic cascade, the cancer cells lose growth inhibitory responses, undergo alterations in adhesiveness and produce enzymes that can degrade extracellular matrix components. This leads to detachment of tumor cells from the original tumor, infiltration into the circulation through newly formed vasculature, migration and extravasation of the tumor cells at favorable distant sites where they may form colonies. A number of genes have been identified as being promoters or suppressors of metastasis. For example, overexpression of glial cell-derived neurotrophic factor (GDNF) and its RET receptor tyrosine kinase have been correlated with cancer proliferation and metastasis. See, e.g., Zeng, Q. et al. *J. Int. Med. Res.* (2008) 36(4): 656-64.

Accordingly, also provided herein are methods for inhibiting, preventing, aiding in the prevention, or decreasing the symptoms of metastasis of a cancer in a patient in need thereof, the method comprising administering to the patient a therapeutically effective amount of a compound of Formula I (e.g., any one of Formulas I-A to I-L), or a pharmaceutically acceptable salt or solvate thereof or a pharmaceutical composition thereof. Such methods can be used in the treatment of one or more of the cancers described herein. See, e.g., US Publication No. 2013/0029925; International Publication No. WO 2014/083567; and U.S. Pat. No. 8,568, 998. See also, e.g., Hezam K et al., *Rev Neurosci* 2018 Jan. 26; 29:93-98; Gao L, et al., *Pancreas* 2015 January; 44:134-143; Ding K et al., *J Biol Chem* 2014 Jun. 6; 289:16057-71; and Amit M et al., *Oncogene* 2017 Jun. 8; 36:3232-3239. In some embodiments, the cancer is a RET-associated cancer. In some embodiments, the compound of Formula I, or a pharmaceutically acceptable salt or solvate thereof is used in combination with an additional therapy or another therapeutic agent, including a chemotherapeutic agent, such as a kinase inhibitor. For example, a first or second RET kinase inhibitor. In some embodiments, the additional therapeutic agent is crizotinib. In some embodiments, the additional therapeutic agent is osimertinib. In some embodiments, the patient has been administered one or more doses of a compound of Formula I (e.g., any one of Formulas I-A to I-L), or a pharmaceutically acceptable salt or solvate thereof, prior to administration of the pharmaceutical composition. In some embodiments, the cancer is a lung cancer (e.g., a RET-associated lung cancer).

The term "metastasis" is an art known term and means the formation of an additional tumor (e.g., a solid tumor) at a site distant from a primary tumor in a subject or patient, where the additional tumor includes the same or similar cancer cells as the primary tumor.

Also provided are methods of decreasing the risk of developing a metastasis or an additional metastasis in a patient having a RET-associated cancer that include: selecting, identifying, or diagnosing a patient as having a RET-associated cancer, and administering a therapeutically effective amount of a compound of Formula I (e.g., any one of Formulas I-A to I-L), or a pharmaceutically acceptable salt or solvate thereof to the patient selected, identified, or diagnosed as having a RET-associated cancer. Also provided are methods of decreasing the risk of developing a metastasis or an additional metastasis in a patient having a RET-associated cancer that includes administering a therapeutically effective amount of a Formula I (e.g., any one of Formulas I-A to I-L), or a pharmaceutically acceptable salt or solvate thereof to a patient having a RET-associated cancer. The decrease in the risk of developing a metastasis or an additional metastasis in a patient having a RET-associated cancer can be compared to the risk of developing a metastasis or an additional metastasis in the patient prior to treatment, or as compared to a patient or a population of patients having a similar or the same RET-associated cancer that has received no treatment or a different treatment. In some embodiments, the RET-associated cancer is a RET-associated cancer having one or more RET inhibitor resistance mutations. In some embodiments, the additional therapeutic agent is crizotinib. In some embodiments, the additional therapeutic agent is osimertinib. In some embodiments, the patient has been administered one or more doses of a compound of Formula I (e.g., any one of Formulas I-A to I-L), or a pharmaceutically acceptable salt or solvate thereof, prior to administration of the pharmaceutical composition. In some embodiments, the cancer is a lung cancer (e.g., a RET-associated lung cancer).

The phrase "risk of developing a metastasis" means the risk that a subject or patient having a primary tumor will develop an additional tumor (e.g., a solid tumor) at a site distant from a primary tumor in a subject or patient over a set period of time, where the additional tumor includes the same or similar cancer cells as the primary tumor. Methods for reducing the risk of developing a metastasis in a subject or patient having a cancer are described herein.

The phrase "risk of developing additional metastases" means the risk that a subject or patient having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

In some embodiments, the presence of one or more RET inhibitor resistance mutations in a tumor causes the tumor to be more resistant to treatment with a first RET inhibitor. Methods useful when a RET inhibitor resistance mutation causes the tumor to be more resistant to treatment with a first RET inhibitor are described below. For example, provided herein are methods of treating a subject having a cancer that include: identifying a subject having a cancer cell that has one or more RET inhibitor resistance mutations; and administering to the identified subject a compound of Formula I (e.g., any one of Formulas I-A to I-L), or a pharmaceutically acceptable salt or solvate thereof. In some embodiments, the compound of Formula I, or a pharmaceutically acceptable salt or solvate thereof is administered in combination with the first RET inhibitor. Also provided are methods of treating a subject identified as having a cancer cell that has one or more RET inhibitor resistance mutations that include administering to the subject a compound of Formula I (e.g., any one of Formulas I-A to I-L), or a pharmaceutically acceptable salt or solvate thereof. In some embodiments, the compound of Formula I, or a pharmaceutically acceptable salt or solvate thereof is administered in combination with the first RET inhibitor. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D.

For example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668. In some embodiments, the methods further comprise (after (b)) (c) determining whether a cancer cell in a sample obtained from the subject has at least one RET inhibitor resistance mutation; and (d) administering a compound selected from Examples 1-151, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668. In some embodiments, the methods further comprise (after (b)) (c) determining whether a cancer cell in a sample obtained from the subject has at least one RET inhibitor resistance mutation; and (d) administering a compound selected from Examples 1-151, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a first RET inhibitor, wherein the first RET inhibitor is selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668. In some embodiments, the methods further comprise (after (b)) (c) determining whether a cancer cell in a sample obtained from the subject has at least one RET inhibitor resistance mutation of Tables 3 or 4; and (d) administering a compound selected from Examples 1-151, or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a first RET inhibitor, wherein the first RET inhibitor is selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668. In some embodiments, the methods further comprise (after (b)) (c) determining whether a cancer cell in a sample obtained from the subject has the RET inhibitor resistance mutation V804M, G810S, or G810R; and (d) administering a compound of Formula I selected from Examples 1-151, or a pharmaceutically acceptable salt of solvate thereof, as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I (e.g., any one of Formulas I-A to I-L), or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668, as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from Examples 1-151, or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668, as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a compound of Formula I selected from Examples 1-151, or a pharmaceutically acceptable salt of solvate thereof. In some embodiments, the methods further comprise (after (b)) (c) determining whether a cancer cell in a sample obtained from the subject has at least one RET inhibitor resistance mutation of Tables 3 or 4; and (d) administering a second RET inhibitor, wherein the second RET inhibitor is selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668, as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I (e.g., any one of Formulas I-A to I-L) selected from Examples 1-151, or a pharmaceutically acceptable salt or solvate thereof. In some embodiments, the methods further comprise (after (b)) (c) determining whether a cancer cell in a sample obtained from the subject has the RET inhibitor resistance mutation V804M, G810S, or G810R; and (d) administering a second RET inhibitor, wherein the second RET inhibitor is selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668, as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I (e.g., any one of Formulas I-A to I-L), or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a second therapeutic agent, wherein the second therapeutic agent is selected from the group consisting of crizotinib and osimertinib, as a monotherapy or in conjunction with a compound of Formula I (e.g., any one of Formulas I-A to I-L), or a pharmaceutically acceptable salt or solvate thereof to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions of Table 2 in a sample from the subject; and (b) administering to the subject a therapeutically effective amount of a compound of Formula I (e.g., any one of Formulas I-A to I-L), or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a second therapeutic agent, wherein the second therapeutic agent is selected from the group consisting of crizotinib and osimertinib, as a monotherapy or in conjunction with a compound of Formula I (e.g., any one of Formulas I-A to I-L), or a pharmaceutically acceptable salt or solvate thereof to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some embodiments of the above, the RET-associated cancer is a lung cancer.

In some embodiments, the presence of one or more RET inhibitor resistance mutations in a tumor causes the tumor to be more resistant to treatment with a first RET inhibitor. Methods useful when a RET inhibitor resistance mutation causes the tumor to be more resistant to treatment with a first RET inhibitor are described below. For example, provided herein are methods of treating a subject having a cancer that include: identifying a subject having a cancer cell that has one or more RET inhibitor resistance mutations; and administering to the identified subject a compound of Formula I (e.g., any one of Formulas I-A to I-L), or a pharmaceutically acceptable salt or solvate thereof. In some embodiments, the compound of Formula I, or a pharmaceutically acceptable salt or solvate thereof is administered in combination with the first RET inhibitor. Also provided are methods of treating a subject identified as having a cancer cell that has one or more RET inhibitor resistance mutations that include administering to the subject a compound of Formula I (e.g., any one of Formulas I-A to I-L), or a pharmaceutically acceptable salt or solvate thereof. In some embodiments, the compound of Formula I, or a pharmaceutically acceptable salt or solvate thereof is administered in combination with the first RET inhibitor. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D.

For example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a compound of Formula I (e.g., any one of Formulas I-A to I-L), or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a compound of Formula I (e.g., any one of Formulas I-A to I-L) selected from Examples 1-151, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a first RET inhibitor, wherein the first RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a compound of Formula I (e.g., any one of Formulas I-A to I-L) selected from Examples 1-151, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a first RET inhibitor, wherein the first RET inhibitor is selected from the group consisting of ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl) piperazin-1-yl)pyridin-3-yl)-6-(1-methyl-1H-pyrazol-4-yl) pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has the RET inhibitor resistance mutation V804M, G810S, or G810R; and (d) administering a compound of Formula I selected from Examples 1-151, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I (e.g., any one of Formulas I-A to I-L), or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H- pyrazol-4-yl)-4-(6-(4-(pyridine-2-ylmethyl)piperazin-1-yl) pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from Examples 1-151, or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a compound of Formula I selected from Examples 1-151, or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a second RET inhibitor, wherein the second RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile; bis(2,2,2-trifluoroacetate); 4-(6-(4-(2,6-difluorobenzyl)piperazin-1-yl)pyridin-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I selected from Examples 1-151, or a pharmaceutically acceptable salt or solvate thereof. In some embodiments, the methods further comprise (after (b)) (c) determining whether a cancer cell in a sample obtained from the subject has the RET inhibitor resistance mutation V804M, G810S, or G810R; and (d) administering a second RET inhibitor, wherein the second RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl- 1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a compound of Formula I (e.g., any one of Formulas I-A to I-L), or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-

(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-(((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-(((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a compound of Formula I selected from Examples 1-151, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a first RET inhibitor, wherein the first RET inhibitor is selected from the group consisting of 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-(((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-(((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has the RET inhibitor resistance mutation V804M, G810S, or G810R; and (d) administering a compound of Formula I selected from Examples 1-151 or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I (e.g., any one of Formulas I-A to I-L), or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-(((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-(((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from Examples 1-151 or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a compound of Formula I selected from Examples 1-151, or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a second RET inhibitor, wherein the second RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I selected from Examples 1-151, or a pharmaceutically acceptable salt or solvate thereof. In some embodiments, the methods further comprise (after (b)) (c) determining whether a cancer cell in a sample obtained from the subject has the RET inhibitor resistance mutation V804M, G810S, or G810R; and (d) administering a second RET inhibitor, wherein the second RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a compound of Formula I (e.g., any one of Formulas I-A to I-L), or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a compound of Formula I selected from Examples 1-151, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a first RET inhibitor, wherein the first RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a compound of Formula I selected from Examples 1-151, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting the fusion protein KIF5B-RET in a sample from the subject; and (b)

administering to the subject a therapeutically effective amount of a first RET inhibitor, wherein the first RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof. In some embodiments, the methods further comprise (after (b)) (c) determining whether a cancer cell in a sample obtained from the subject has the RET inhibitor resistance mutation V804M, G810S, or G810R; and (d) administering a compound of Formula I selected from Examples 1-151, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I (e.g., any one of Formulas I-A to I-L), or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from Examples 1-151, or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a compound of Formula I selected from Examples 1-151, or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a second RET inhibitor, wherein the second RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I selected from Examples 1-151, or a pharmaceutically acceptable salt or solvate thereof. In some embodiments, the methods further comprise (after (b)) (c) determining whether a cancer cell in a sample obtained from the subject has the RET inhibitor resistance mutation V804M, G810S, or G810R; and (d) administering a second RET inhibitor, wherein the second RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation.

In some embodiments provided herein, circulating tumor DNA can be used to monitor the responsiveness of a patient to a particular therapy (e.g., a first RET inhibitor, a second RET inhibitor, or a compound of Formula I (e.g., any one of Formulas I-A to I-L), or a pharmaceutically acceptable salt or solvate thereof). For example, prior to starting treatment with a therapy as described herein (e.g., a first RET inhibitor, a second RET inhibitor, or a compound of Formula I (e.g., any one of Formulas I-A to I-L), or a pharmaceutically acceptable salt or solvate thereof), a biological sample can be obtained from the subject and the level of circulating tumor DNA determined in the biological sample. This sample can be considered a base-line sample. The subject can then be administered one or more doses of a therapy as described herein (e.g., a first RET inhibitor, a second RET inhibitor, or a compound of Formula I (e.g., any one of Formulas I-A to I-L), or a pharmaceutically acceptable salt or solvate thereof) and the levels of circulating tumor DNA can be monitored (e.g., after the first dose, second dose, third dose, etc. or after one week, two weeks, three weeks, four weeks, etc.). If the level of circulating tumor DNA is lower than the baseline sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction etc.), this is indicative of responsiveness to the therapy. In some embodiments, the level of circulating tumor DNA is reduced such that it is below the detection limit of the instrument. In some embodiments, the level of circulating tumor DNA in a biological sample obtained from the patient (n) is compared to the sample taken just previous (n−1). If the level of circulating tumor DNA in the n sample is lower than the n−1 sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction, etc.), this is indicative of responsiveness to the therapy. In some embodiments, the level of circulating tumor DNA is reduced such that it is below the detection limit of the instrument. In the case of responsiveness to therapy, the subject can to be administered one or more doses of the therapy and the circulating tumor DNA can be continued to be monitored.

If the level of circulating tumor DNA in the sample is higher than the baseline (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase, etc.), this can be indicative of resistance to the therapy. If the level of circulating tumor DNA in the n sample is higher than the n−1 sample (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase etc.), this can be indicative of resistance to the therapy. When resistance to therapy is suspected, the subject can undergo one or more of imaging, biopsy, surgery, or other diagnostic tests. In some embodiments, when resistance to the therapy is suspected, the subject can be administered (either as a monotherapy or in combination with the previous therapy) a compound capable of treating a RET inhibitor resistance (e.g., a compound of Formula I (e.g., any one of Formulas I-A to I-L), or a pharmaceutically acceptable salt or solvate thereof, as provided herein). See, for example, Cancer Discov; 7(12); 1368-70 (2017); and Cancer Discov; 7(12); 1394-403 (2017).

In some embodiments provided herein, a protein biomarker can be used to monitor the responsiveness of a patient to a particular therapy (e.g., a first RET inhibitor, a second RET inhibitor, or a compound of Formula I (e.g., any one of Formulas I-A to I-L), or a pharmaceutically acceptable salt or solvate thereof). For example, prior to starting treatment with a therapy as described herein (e.g., a first RET inhibitor, a second RET inhibitor, or a compound of Formula I (e.g., any one of Formulas I-A to I-L), or a pharmaceutically acceptable salt or solvate thereof), a biological sample can be obtained from the subject and the level of a protein biomarker can be determined in the biological sample. This sample can be considered a base-line sample. The subject can then be administered one or more doses of a therapy as described herein (e.g., a first RET inhibitor, a second RET inhibitor, or a compound of Formula I (e.g., any one of Formulas I-A to I-L), or a pharmaceutically acceptable salt or solvate thereof) and the levels of the protein biomarker can be monitored (e.g., after the first dose, second dose, third dose, etc. or after one week, two weeks, three weeks, four weeks, etc.). If the level of the protein biomarker is lower than the baseline sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction etc.), this is indicative of responsiveness to the therapy. In some embodiments, the level of the protein biomarker is reduced such that it is below the detection limit of the instrument. In some embodiments, the level of the protein biomarker in a biological sample obtained from the patient (n) is compared to the sample taken just previous (n-1). If the level of the protein biomarker in the n sample is lower than the n-1 sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction, etc.), this is indicative of responsiveness to the therapy. In some embodiments, the level of the protein biomarker is reduced such that it is below the detection limit of the instrument. In the case of responsiveness to therapy, the subject can to be administered one or more doses of the therapy and the protein biomarker can be continued to be monitored.

If the level of the protein biomarker in the sample is higher than the baseline (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase, etc.), this can be indicative of resistance to the therapy. If the level of the protein biomarker in the n sample is higher than the n−1 sample (e.g., a 1% to about a 99% increase, a 1% to about a 95% increase, a 1% to about a 90% increase, a 1% to about a 85% increase, a 1% to about a 80% increase, a 1% to about a 75% increase, a 1% increase to about a 70% increase, a 1% increase to about a 65% increase, a 1% increase to about a 60% increase, a 1% increase to about a 55% increase, a 1% increase to about a 50% increase, a 1% increase to about a 45% increase, a 1% increase to about a 40% increase, a 1% increase to about a 35% increase, a 1% increase to about a 30% increase, a 1% increase to about a 25% increase, a 1% increase to about a 20% increase, a 1% increase to about a 15% increase, a 1% increase to about a 10% increase, a 1% to about a 5% increase, about a 5% to about a 99% increase, about a 10% to about a 99% increase, about a 15% to about a 99% increase, about a 20% to about a 99% increase, about a 25% to about a 99% increase, about a 30% to about a 99% increase, about a 35% to about a 99% increase, about a 40% to about a 99% increase, about a 45% to about a 99% increase, about a 50% to about a 99% increase, about a 55% to about a 99% increase, about a 60% to about a 99% increase, about a 65% to about a 99% increase, about a 70% to about a 99% increase, about a 75% to about a 95% increase, about a 80% to about a 99% increase, about a 90% increase to about a 99% increase, about a 95% to about a 99% increase, about a 5% to about a 10% increase, about a 5% to about a 25% increase, about a 10% to about a 30% increase, about a 20% to about a 40% increase, about a 25% to about a 50% increase, about a 35% to about a 55% increase, about a 40% to about a 60% increase, about a 50% increase to about a 75% increase, about a 60% increase to about 80% increase, or about a 65% to about a 85% increase etc.), this can be indicative of resistance to the therapy. When resistance to therapy is suspected, the subject can undergo one or more of imaging, biopsy, surgery, or other diagnostic tests. In some embodiments, when resistance to the therapy is suspected, the subject can be administered (either as a monotherapy or in combination with the previous therapy) a compound capable of treating a RET inhibitor resistance (e.g., a compound of Formula I (e.g., any one of Formulas I-A to I-L), or a pharmaceutically acceptable salt or solvate thereof, as provided herein).

In some embodiments, one or more protein biomarkers are monitored. The particular protein biomarkers to be monitored can depend on the type of cancer and can be readily identified by one having ordinary skill in the art. Non-limiting examples of protein biomarkers include: CA 125, carcinoembryonic antigen (CEA), calcitonin, thyroglobulin, adrenocorticotropic hormone (ACTH), cortisol, CA 19-9, prolactin, hepatocyte growth factor, osteopontin, myeloperoxidase, tissue inhibitor of metalloproteinases 1, angiopoietin-1 (Ang-1), cytokeratin 19 (CK-19), tissue inhibitor of metalloproteinase-1 (TIMP-1), chitinase 3 like-1 (YKL-40), galectin-3 (GAL-3), CYFRA 21-1 (cytokeratins), EPCAM (epithelial cell adhesion molecule), ProGRP (pro-gastrin-releasing peptide), and CEACAM (carcinoembryonic antigen). See, for example, Cohen J D, Li L, Wang Y, et al. Detection and localization of surgically resectable cancers with a multi-analyte blood test. *Science*; Published online 18 Jan. 2018. pii: eaar3247. DOI: 10.1126/science.aar3247; Fawaz M Makki et al. Serum biomarkers of papillary thyroid cancer. *J Otolaryngol Head Neck Surg.* 2013; 42(1): 16; and Tatiana N. Zamay et al. Current and Prospective Protein Biomarkers of Lung Cancer. *Cancers* (Basel). 2017 November; 9(11): 155. In some embodiments, the biomarkers include one or more of CEA, calcitonin, thyroglobulin, ACTH, and cortisol. In some embodiments, the cancer is medullary thyroid cancer and the protein biomarkers include CEA and calcitonin. In some embodiments, the cancer is non-medullary thyroid cancer and the protein biomarker include thyroglobulin. In some embodiments, the biomarkers are ACTH and cortisol (e.g., when a patient as Cushing's disease related to their cancer).

Also provided herein are methods of treating a RET-associated cancer in a subject that include (a) administering one or more (e.g., two or more, three or more, four or more, five or more, or ten or more) doses of a first RET kinase inhibitor to a subject identified or diagnosed as having a RET-associated cancer (e.g., any of the types of RET-associated cancers described herein)(e.g., identified or diagnosed as having a RET-associated cancer using any of the exemplary methods described herein or known in the art); (b) after step (a), determining a level of circulating tumor DNA in a biological sample (e.g., a biological sample comprising blood, serum, or plasma) obtained from the subject; (c) administering a therapeutically effective amount of a second RET inhibitor or a compound of Formula I (e.g., any one of Formulas I-A to I-L), or a pharmaceutically acceptable salt or solvate thereof as a monotherapy or in conjunction with another anticancer agent to a subject identified as having about the same or an elevated level of circulating tumor DNA as compared to a reference level of circulating tumor DNA (e.g., any of the reference levels of circulating tumor DNA described herein). In some examples of these methods, the reference level of circulating tumor DNA is a level of circulating tumor DNA in a biological sample obtained from the subject prior to step (a). Some embodiments of these methods further include determining the level of circulating tumor DNA in the biological sample obtained from the subject prior to step (a). In some examples of these methods, the reference level of circulating tumor DNA is a threshold level of circulating tumor DNA (e.g., an average level of circulating tumor DNA in a population of subjects having a similar RET-associated cancer and having a similar stage of the RET-associated cancer, but receiving a non-effective treatment or a placebo, or not yet receiving therapeutic treatment, or a level of circulating tumor DNA in a subject having a similar RET-associated cancer and having a similar stage of the RET-associated cancer, but receiving a non-effective treatment or a placebo, or not yet receiving therapeutic treatment). In some examples of these methods, the first RET inhibitor is selected from the group of: cabozantinib, vandetanib, alectinib, apatinib, sitravatinib, sorafenib, lenvatinib, ponatinib, dovitinib, sunitinib, foretinib, BLU667, and BLU6864.

Also provided herein are methods of treating a RET-associated cancer in a subject that include administering a therapeutically effective amount of a compound of Formula I (e.g., any one of Formulas I-A to I-L), or a pharmaceutically acceptable salt or solvate thereof, to a subject (i) identified or diagnosed as having a RET-associated cancer (e.g., any of the types of RET-associated cancers described herein) (e.g., identified or diagnosed as having a RET-associated cancer using any of the exemplary methods described herein or known in the art), (ii) previously administered one or more (e.g., two or more, three or more, four or more, five or more, or ten or more) doses of a second RET kinase inhibitor, and (ii) after the prior administration of the one or more doses of the second RET kinase inhibitor, identified as having about the same or an elevated level of circulating tumor DNA as compared to a reference level of circulating tumor DNA (e.g., any of the reference levels of circulating tumor DNA described herein or known in the art). In some embodiments of these methods, the reference level of circulating tumor DNA is a level of circulating tumor DNA in a biological sample (e.g., a biological sample comprising blood, plasma, or serum) obtained from the subject prior to the administration of the one or more doses of the second RET kinase inhibitor. Some embodiments of these methods further include determining the level of circulating tumor DNA in the biological sample obtained from the subject prior to administration of the one or more doses of the second RET kinase inhibitor. In some examples of these methods, the reference level of circulating tumor DNA is a threshold level of circulating tumor DNA (e.g., an average level of circulating tumor DNA in a population of subjects having a similar RET-associated cancer and having a similar stage of the RET-associated cancer, but receiving a non-effective treatment or a placebo, or not yet receiving therapeutic treatment, or a level of circulating tumor DNA in a subject having a similar RET-associated cancer and having a similar stage of the RET-associated cancer, but receiving a non-effective treatment or a placebo, or not yet receiving therapeutic treatment). In some embodiments of these methods, the second RET kinase inhibitor is selected from the group consisting of: cabozantinib, vandetanib, alectinib, apatinib, sitravatinib, sorafenib, lenvatinib, ponatinib, dovitinib, sunitinib, foretinib, BLU667, and BLU6864.

Also provided herein are methods of treating a RET-associated cancer in a subject that include: (a) administering one or more doses of a compound of Formula I (e.g., any one of Formulas I-A to I-L), or a pharmaceutically acceptable salt or solvate thereof, as a monotherapy to a subject identified or diagnosed as having a RET-associated cancer (e.g., any of the types of RET-associated cancer described herein) (e.g., a subject identified or diagnosed as having a RET-associated cancer using any of the methods described herein or known in the art); (b) after step (a), determining a level of circulating tumor DNA in a biological sample (e.g., a biological sample comprising blood, serum, or plasma) obtained from the subject; (c) administering a therapeutically effective amount of a compound of Formula I (e.g., any one of Formulas I-A to I-L), or a pharmaceutically acceptable salt or solvate thereof, and an additional therapeutic agent or treatment (e.g., any of the additional therapeutic agents or treatments of a RET-associated cancer described herein or known in the art) to a subject identified as having about the same or an elevated level of circulating tumor DNA as compared to a reference level of circulating tumor DNA (e.g., any of the exemplary reference levels of circulating tumor DNA described herein or known in the art). In some embodiments of these methods, the additional therapeutic agent is a second RET kinase inhibitor (e.g., a RET kinase inhibitor selected from the group of: cabozantinib, vandetanib, alectinib, apatinib, sitravatinib, sorafenib, lenvatinib, ponatinib, dovitinib, sunitinib, foretinib, BLU667, and BLU6864. In some examples of any of these methods, the additional therapeutic agent or treatment comprises one or more of: radiation therapy, a chemotherapeutic agent (e.g., any of the exemplary chemotherapeutic agents described herein or known in the art), a checkpoint inhibitor (e.g., any of the exemplary checkpoint inhibitors described herein or known in the art), surgery (e.g., at least partial resection of the tumor) and one or more other kinase inhibitors (e.g., any of the exemplary kinase inhibitors described herein or known in the art). In some examples of these methods, the reference level of circulating tumor DNA is a level of circulating tumor DNA in a biological sample (e.g., a biological sample comprising blood, serum, or plasma) obtained from the subject prior to step (a). In some examples of these methods, the reference level of circulating tumor DNA is a threshold level of circulating tumor DNA (e.g., an average level of circulating tumor DNA in a population of subjects having a similar RET-associated cancer and having a similar stage of the RET-associated cancer, but receiving a non-effective treatment or a placebo, or not yet receiving therapeutic treatment, or a level of circulating tumor DNA in a subject having a similar RET-associated cancer and having a similar stage of the RET-associated cancer, but receiving a non-effective treatment or a placebo, or not yet receiving therapeutic treatment).

Also provided herein are methods of treating a RET-associated cancer in a subject that include: administering a therapeutically effective amount of a compound of Formula I (e.g., any one of Formulas I-A to I-L), or a pharmaceutically acceptable salt or solvate thereof, and an additional therapeutic agent or treatment to a subject (i) identified or diagnosed as having a RET-associated cancer (e.g., any of the types of RET-associated cancer described herein) (e.g., a subject identified or diagnosed as having a RET-associated cancer using any of the methods described herein or known in the art), (ii) previously administered one or more doses of the compound of Formula I, or a pharmaceutically acceptable salt or solvate thereof, as a monotherapy, and (ii) after administration of the one or more (e.g., two or more, three or more, four or more, five or more, or ten or more) doses of the compound of Formula I, or a pharmaceutically acceptable salt or solvate thereof, as a monotherapy, identified as having about the same or an elevated level of circulating tumor DNA as compared to a reference level of circulating tumor DNA (e.g., any of the exemplary reference levels of circulating tumor DNA described herein). In some embodiments of these methods, the reference level of circulating tumor DNA is a level of circulating tumor DNA in a biological sample obtained from the subject prior to administration of the one or more (e.g., two or more, three or more, four or more, five or more, or ten or more) doses of the compound of Formula I, or a pharmaceutically acceptable salt or solvate thereof, as a monotherapy. Some embodiments of these methods further include determining the level of circulating tumor DNA in the biological sample obtained from the subject prior to administration of the one or more doses of the compound of Formula I, or a pharmaceutically acceptable salt or solvate thereof, as a monotherapy. In some examples of these methods, the reference level of circulating tumor DNA is a threshold level of circulating tumor DNA (e.g., an average level of circulating tumor DNA in a population of subjects having a similar RET-associated cancer and having a similar stage of the RET-associated cancer, but receiving a non-effective treatment or a placebo, or not yet receiving therapeutic treatment, or a level of circulating tumor DNA in a subject having a similar RET-associated cancer and having a similar stage of the RET-associated cancer, but receiving a non-effective treatment or a placebo, or not yet receiving therapeutic treatment). In some embodiments of this method, the additional therapeutic agent is a second RET kinase inhibitor (e.g., a second RET kinase inhibitor selected from the group of cabozantinib, vandetanib, alectinib, apatinib, sitravatinib, sorafenib, lenvatinib, ponatinib, dovitinib, sunitinib, foretinib, BLU667, and BLU6864. In some embodiments of these methods, the additional therapeutic agent or treatment includes one or more of radiation therapy, a chemotherapeutic agent (e.g., any of the exemplary chemotherapeutic agents described herein or known in the art), a checkpoint inhibitor (e.g., any of the exemplary checkpoint inhibitors described herein or known in the art), surgery (e.g., at least partial resection of the tumor), and one or more other kinase inhibitors (e.g., any of the kinase inhibitors described herein or known in the art).

Also provided herein are methods of selecting a treatment for a subject that include: selecting a therapeutically effective amount of a compound of Formula I (e.g., any one of Formulas I-A to I-L), or a pharmaceutically acceptable salt or solvate thereof, for a subject (i) identified or diagnosed as having a RET-associated cancer (e.g., any of the RET-associated cancers described herein) (e.g., a subject identified or diagnosed as having a RET-associated cancer using any of the methods described herein or known in the art), (ii) previously administered one or more (e.g., two or more, three or more, four or more, five or more, or ten or more) doses of a second RET kinase inhibitor (e.g., any of the RET kinase inhibitors described herein or known in the art), and (ii) after administration of the one or more doses of the second RET kinase inhibitor, identified as having about the same or an elevated level of circulating tumor DNA as compared to a reference level of circulating tumor DNA. In some embodiments of any of these methods, the reference level of circulating tumor DNA is a level of circulating tumor DNA in a biological sample (e.g., a biological sample comprising blood, serum, or plasma) obtained from the subject prior to administration of the one or more doses of the second RET kinase inhibitor. Some embodiments of these methods further include determining the level of circulating tumor DNA in the biological sample obtained from the subject prior to administration of the one or more doses of the second RET kinase inhibitor. In some examples of these methods, the reference level of circulating tumor DNA is a threshold level of circulating tumor DNA (e.g., an average level of circulating tumor DNA in a population of subjects having a similar RET-associated cancer and having a similar stage of the RET-associated cancer, but receiving a non-effective treatment or a placebo, or not yet receiving therapeutic treatment, or a level of circulating tumor DNA in a subject having a similar RET-associated cancer and having a similar stage of the RET-associated cancer, but receiving a non-effective treatment or a placebo, or not yet receiving therapeutic treatment). In some embodiments of any these methods, the second RET kinase inhibitor is selected from the group of cabozantinib, vandetanib, alectinib, apatinib, sitravatinib, sorafenib, lenvatinib, ponatinib, dovitinib, sunitinib, foretinib, BLU667, and BLU6864.

Also provided herein are methods of selecting a treatment for a subject that include selecting a therapeutically effective amount of a compound of Formula I (e.g., any one of Formulas I-A to I-L), or a pharmaceutically acceptable salt or solvate thereof, and an additional therapeutic agent or treatment for a subject (i) identified or diagnosed as having a RET-associated cancer (e.g., any of the RET-associated cancers described herein or known in the art) (e.g., a subject diagnosed or identified as having a RET-associated cancer using any of the methods described herein or known in the art), (ii) previously administered one or more doses (e.g., two or more, three or more, four or more, five or more, or ten or more) of the compound of Formula I, or a pharmaceutically acceptable salt or solvate thereof, as a monotherapy, and (ii) after administration of the one or more doses of the compound of Formula I, or a pharmaceutically acceptable salt or solvate thereof, identified as having about the same or an elevated level of circulating tumor DNA as compared to a reference level of circulating tumor DNA. In some embodiments of these methods, the reference level of circulating tumor DNA is a level of circulating tumor DNA in a biological sample (e.g., a biological sample comprising blood, serum, or plasma) obtained from the subject prior to administration of the one or more doses of the compound of Formula I, or a pharmaceutically acceptable salt or solvate thereof, as a monotherapy. Some embodiments further include determining the level of circulating tumor DNA in the biological sample obtained from the subject prior to administration of the one or more doses of the compound of Formula I, or a pharmaceutically acceptable salt or solvate thereof, as a monotherapy. In some examples of these methods, the reference level of circulating tumor DNA is a threshold level of circulating tumor DNA (e.g., an average level of circulating tumor DNA in a population of subjects having a similar RET-associated cancer and having a similar stage of the RET-associated cancer, but receiving a non-effective treatment or a placebo, or not yet receiving therapeutic treatment, or a level of circulating tumor DNA in a subject having a similar RET-associated cancer and having a similar stage of the RET-associated cancer, but receiving a non-effective treatment or a placebo, or not yet receiving therapeutic treatment). In some embodiments of any of these methods, the additional therapeutic agent is a second RET kinase inhibitor (e.g., a second RET kinase inhibitor selected from the group of: cabozantinib, vandetanib, alectinib, apatinib, sitravatinib, sorafenib, lenvatinib, ponatinib, dovitinib, sunitinib, foretinib, BLU667, and BLU6864. In some embodiments of any of the methods described herein, the additional therapeutic agent or treatment includes one or more of radiation therapy, a chemotherapeutic agent (e.g., any of the examples of a chemotherapeutic agent described herein or known in the art), a checkpoint inhibitor (e.g., any of the checkpoint inhibitors described herein or known in the art), surgery (e.g., at least partial resection of the tumor), and one or more other kinase inhibitors (e.g., any of the other kinase inhibitors described herein or known in the art).

Also provided herein are methods of determining the efficacy of a treatment in a subject that include: (a) determining a first level of circulating tumor DNA in a biological sample (e.g., a biological sample including blood, serum, or plasma) obtained from a subject identified or diagnosed as having a RET-associated cancer at a first time point; (b) administering a treatment including one or more doses of a compound of Formula I (e.g., any one of Formulas I-A to I-L), or a pharmaceutically acceptable salt or solvate thereof to the subject, after the first time point and before a second time point; (c) determining a second level of circulating tumor DNA in a biological sample (e.g., a biological sample comprising blood, serum, or plasma) obtained from the subject at the second time point; and (d) identifying that the treatment is effective in a subject determined to have a decreased second level of circulating tumor DNA as compared to the first level of circulating tumor DNA; or identifying the treatment is not effective in a subject determined to have about the same or an elevated second level of circulating tumor DNA as compared to the first level of circulating tumor DNA. In some embodiments of these methods, the first time point and the second time point are about 1 week to about 1 year apart (e.g., about 1 week to about 10 months, about 1 week to about 8 months, about 1 week to about 6 months, about 1 week to about 4 months, about 1 week to about 3 months, about 1 week to about 2 months, about 1 week to about 1 month, or about 1 week to about 2 weeks).

Also provided herein are methods of determining whether a subject has developed resistance to a treatment that include: (a) determining a first level of circulating tumor DNA in a biological sample (e.g., a biological sample comprising blood, serum, or plasma) obtained from a subject identified or diagnosed as having a RET-associated cancer at a first time point; (b) administering a treatment including one or more (e.g., two or more, three or more, four or more, five or more, or ten or more) doses of a compound of Formula I (e.g., any one of Formulas I-A to I-L), or a pharmaceutically acceptable salt or solvate thereof to the subject, after the first time point and before a second time point; (c) determining a second level of circulating tumor DNA in a biological sample obtained from the subject at the second time point; and (d) determining that a subject having a decreased second level of circulating tumor DNA as compared to the first level of circulating tumor DNA has not developed resistance to the treatment; or determining that a subject having about the same or an elevated second level of circulating tumor DNA as compared to the first level of circulating tumor DNA has developed resistance to the treatment. In some embodiments of these methods, the first time point and the second time point are about 1 week to about 1 year apart (e.g., about 1 week to about 10 months, about 1 week to about 8 months, about 1 week to about 6 months, about 1 week to about 4 months, about 1 week to about 3 months, about 1 week to about 2 months, about 1 week to about 1 month, or about 1 week to about 2 weeks).

Exemplary methods for detecting circulating tumor DNA are described in Moati et al., *Clin. Res. Hepatol. Gastroenterol.* Apr. 4, 2018; Oussalah et al., *E Bio Medicine* Mar. 28, 2018; Moon et al., *Adv. Drug Deliv. Rev.* Apr. 4, 2018; Solassaol et al., *Clin. Chem. Lab. Med.* Apr. 7, 2018; Arriola et al., *Clin. Transl. Oncol.* Apr. 5, 2018; Song et al., *J. Circ. Biomark.* Mar. 25, 2018; Aslibekyan et al., *JAMA Cardiol.* Apr. 4, 2018; Isbell et al., *J. Thorac. Cardiovasc. Surg.* Mar. 13, 2018; Boeckx et al., *Clin. Colorectal Cancer* Feb. 22, 2018; Anunobi et al., *J. Surg. Res.* Mar. 28, 2018; Tan et al., *Medicine* 97(13):e0197, 2018; Reithdorf et al., *Transl. Androl. Urol.* 6(6):1090-1110, 2017; Volckmar et al., *Genes Chromosomes Cancer* 57(3): 123-139, 2018; and Lu et al., *Chronic Dis. Transl. Med.* 2(4):223-230, 2016. Additional methods for detecting circulating tumor DNA are known in the art.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a multikinase inhibitor, wherein the multikinase inhibitor is selected from vandetanib or cabozantinib; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a compound of Formula I (e.g., any one of Formulas I-A to I-L), or a pharmaceutically acceptable salt or solvate thereof as a monotherapy or in conjunction with another anticancer agent to the subject if the subject has a cancer cell that has at least one RET inhibitor resistance mutation; or (e) administering additional doses of the multikinase inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first multikinase inhibitor, wherein the multikinase inhibitor is selected from the group consisting of: vandetanib or cabozantinib; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a compound of Formula I selected from Examples 1-151, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the multikinase inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a multikinase inhibitor, wherein the multikinase inhibitor is selected from the group consisting of: vandetanib or cabozantinib; or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a compound of Formula I selected from Examples 1-151, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the multikinase inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a multikinase inhibitor, wherein the multikinase inhibitor is selected from the group consisting of vandetanib or cabozantinib; or a pharmaceutically acceptable salt or solvate thereof. In some embodiments, the methods further comprise (after (b)) (c) determining whether a cancer cell in a sample obtained from the subject has the RET inhibitor resistance mutation V804M, G810S, or G810R; and (d) administering a compound of Formula I selected from Examples 1-151, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the multikinase inhibitor of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I (e.g., any one of Formulas I-A to I-L), or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a multikinase inhibitor (e.g., vandetanib or cabozantinib, as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from Examples 1-151, or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a multikinase inhibitor (e.g., vandetanib or cabozantinib), as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a compound of Formula I (e.g., any one of Formulas I-A to I-L), or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a multikinase inhibitor (e.g., vandetanib or cabozantinib), as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I selected from Examples 1-151, or a pharmaceutically acceptable salt or solvate thereof. In some embodiments, the methods further comprise (after (b)) (c) determining whether a cancer cell in a sample obtained from the subject has the RET inhibitor resistance mutation V804M, G810S, or G810R; and (d) administering a multikinase inhibitor (e.g., vandetanib or cabozantinib) as a monotherapy or in conjunction with another anticancer agent to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation.

Also, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I (e.g., any one of Formulas I-A to I-L), or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering additional doses of the compound of Formula, or a pharmaceutically acceptable salt or solvate thereof of step (b) to the subject as a monotherapy or in conjunction with another anticancer agent (e.g., a second RET inhibitor, a second compound of Formula I (e.g., any one of Formulas I-A to I-L), or a pharmaceutically acceptable salt or solvate thereof, or immunotherapy) or anticancer therapy (e.g., surgery or radiation) if the subject has a cancer cell that has at least one RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from Examples 1-151, or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering additional doses of the compound of Formula I, or a pharmaceutically acceptable salt or solvate thereof of step (b) to the subject as a monotherapy or in conjunction with another anticancer agent (e.g., a second RET inhibitor, a second compound of Formula I (e.g., any one of Formulas I-A to I-L), or a pharmaceutically acceptable salt or solvate thereof, or immunotherapy) or anticancer therapy (e.g., surgery or radiation) if the subject has a cancer cell that has at least one RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a compound of Formula I selected from Examples 151 or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering additional doses of the compound of Formula I, or a pharmaceutically acceptable salt or solvate thereof of step (b) to the subject as a monotherapy or in conjunction with another anticancer agent (e.g., a second RET inhibitor, a second compound of Formula I (e.g., any one of Formulas I-A to I-L), or a pharmaceutically acceptable salt or solvate thereof, or immunotherapy) or anticancer therapy (e.g., surgery or radiation) if the subject has a cancer cell that has at least one RET inhibitor resistance mutation. In some embodiments, a second RET inhibitor selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668 is administered in step (d). In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I selected from Examples 1-151, or a pharmaceutically acceptable salt or solvate thereof. In some embodiments, the methods further comprise (after (b)) (c) determining whether a cancer cell in a sample obtained from the subject has the RET inhibitor resistance mutation V804M, G810S, or G810R; and (d) administering additional doses of the compound of Formula I, or a pharmaceutically acceptable salt or solvate thereof of step (b) to the subject as a monotherapy or in conjunction with another anticancer agent (e.g., a second RET inhibitor, a second compound of Formula I (e.g., any one of Formulas I-A to I-L), or a pharmaceutically acceptable salt or solvate thereof, or immunotherapy) or anticancer therapy (e.g., surgery or radiation) if the subject has a cancer cell that has at least one RET inhibitor resistance mutation. In some embodiments, a second RET inhibitor selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668 is administered in step (d).

Also, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I (e.g., any one of Formulas I-A to I-L), or a pharmaceutically acceptable salt or solvate thereof. In some embodiments, the methods further comprise (after (b)) (c) detecting at least one RET inhibitor resistance mutation in a cancer cell in a sample obtained from the subject; and (d) administering additional doses of the compound of Formula I, or a pharmaceutically acceptable salt or solvate thereof of step (b) to the subject as a monotherapy or in conjunction with another anticancer agent (e.g., a second RET inhibitor, a second compound of Formula I (e.g., any one of Formulas I-A to I-L), or a pharmaceutically acceptable salt or solvate thereof, or immunotherapy) or anticancer therapy (e.g., surgery or radiation). In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from Examples 1-151, or a pharmaceutically acceptable salt or solvate thereof. In some embodiments, the methods further comprise (after (b)) (c) detecting at least one RET inhibitor resistance mutation in a cancer cell in a sample obtained from the subject; and (d) administering additional doses of the compound of Formula I, or a pharmaceutically acceptable salt or solvate thereof of step (b) to the subject as a monotherapy or in conjunction with another anticancer agent (e.g., a second RET inhibitor, a second compound of Formula I (e.g., any one of Formulas I-A to I-L), or a pharmaceutically acceptable salt or solvate thereof, or immunotherapy) or anticancer therapy (e.g., surgery or radiation). In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a compound of Formula I selected from Examples 1-151 or a pharmaceutically acceptable salt or solvate thereof. In some embodiments, the methods further comprise (after (b)) (c) detecting at least one RET inhibitor resistance mutation of Tables 3 or 4 in a cancer cell in a sample obtained from the subject; and (d) administering additional doses of the compound of Formula I, or a pharmaceutically acceptable salt or solvate thereof of step (b) to the subject as a monotherapy or in conjunction with another anticancer agent (e.g., a second RET inhibitor, a second compound of Formula I (e.g., any one of Formulas I-A to I-L), or a pharmaceutically acceptable salt or solvate thereof, or immunotherapy) or anticancer therapy (e.g., surgery or radiation). In some embodiments, a second RET inhibitor selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668 is administered in step (d). In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I selected from Examples 1-151, or a pharmaceutically acceptable salt or solvate thereof. In some embodiments, the methods further comprise (after (b)) (c) detecting the RET inhibitor resistance mutation V804M, G810S, or G810R in a cancer cell in a sample obtained from the subject; and (d) administering additional doses of the compound of Formula I, or a pharmaceutically acceptable salt or solvate thereof of step (b) to the subject as a monotherapy or in conjunction with another anticancer agent (e.g., a second RET inhibitor, a second compound of Formula I (e.g., any one of Formulas I-A to I-L), or a pharmaceutically acceptable salt or solvate thereof, or immunotherapy) or anticancer therapy (e.g., surgery or radiation). In some embodiments, a second RET inhibitor selected from the group consisting of alectinib, cabozantinib, lenvatinib, nintedanib, ponatinib, regorfenib, sorafenib, sunitinib, vandetanib, RXDX-105 (agerafenib), BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide), BLU6864, DS-5010, GSK3179106, GSK3352589, and NMS-E668 is administered in step (d).

Further provided herein is a method for treating lung cancer in a patient in need thereof, the method comprising administering to the patient a therapeutically effective amount of a compound of Formula I (e.g., any one of Formulas I-A to I-L), or a pharmaceutically acceptable salt or solvate thereof, crizotinib, osimertinib, or any combination thereof.

In some embodiments, the lung cancer is a RET-associated cancer. For example, the method can include: (a) detecting a dysregulation of a RET gene, a RET kinase, or the expression or activity or level of any of the same in a sample from the subject; and (b) administering to the subject a therapeutically effective amount of a compound of Formula I (e.g., any one of Formulas I-A to I-L), or a pharmaceutically acceptable salt or solvate thereof. In some embodiments, the methods further comprises (after (b)) (c) determining whether a cancer cell in a sample obtained from the subject has at least one RET inhibitor resistance mutation (e.g., a MET dysregulation such as a MET gene amplification); and (d) administering a second therapeutic agent, wherein the second therapeutic agent is crizotinib, as a monotherapy or in conjunction with a compound of Formula I (e.g., any one of Formulas I-A to I-L), or a pharmaceutically acceptable salt or solvate thereof to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation. In some such embodiments, the method comprises (a) detecting one or more fusion proteins of Table 1 and/or one or more RET kinase protein point mutations/insertions of Table 2 in a sample from the subject; and (b) administering to the subject a therapeutically effective amount of a compound of Formula I (e.g., any one of Formulas I-A to I-L), or a pharmaceutically acceptable salt or solvate thereof. In further embodiments, the methods further comprise (after (b)) (c) determining whether a cancer cell in a sample obtained from the subject has at least one RET inhibitor resistance mutation (e.g., a MET dysregulation such as a MET gene amplification); and (d) administering a second therapeutic agent, wherein the second therapeutic agent is crizotinib, as a monotherapy or in conjunction with a compound of Formula I (e.g., any one of Formulas I-A to I-L), or a pharmaceutically acceptable salt or solvate thereof to the subject if the subject has a cancer cell that has at least one RET inhibitor resistance mutation; or (e) administering additional doses of the compound of Formula I, or a pharmaceutically acceptable salt or solvate thereof of step (b) to the subject if the subject has a cancer cell that does not have a RET inhibitor resistance mutation.

In some embodiments, the lung cancer is an EGFR-associated cancer. For example, the method can include: (a) detecting a dysregulation of an EGFR gene, an EGFR kinase, or the expression or activity or level of any of the same in a sample from the subject; and (b) administering to the subject a therapeutically effective amount of an EGFR inhibitor (e.g., osimertinib). In some embodiments, the methods further comprises (after (b)) (c) determining whether a cancer cell in a sample obtained from the subject has at least one dysregulation of a RET gene, a RET kinase, or the expression or activity or level of any of the same (e.g., a RET gene fusion); and (d) administering a compound of Formula I (e.g., any one of Formulas I-A to I-L), or a pharmaceutically acceptable salt or solvate thereof, as a monotherapy or in conjunction with the EGFR inhibitor (e.g., osimertinib) to the subject if the subject has a cancer cell that has at least one dysregulation of a RET gene, a RET kinase, or the expression or activity or level of any of the same (e.g., a RET gene fusion); or (e) administering additional doses of the EGFR inhibitor (e.g., osimertinib) of step (b) to the subject if the subject has a cancer cell that does not have a dysregulation of a RET gene, a RET kinase, or the expression or activity or level of any of the same (e.g., a RET gene fusion). In some such embodiments, the method comprises (a) detecting a dysregulation of an EGFR gene, an EGFR kinase, or the expression or activity or level of any of the same in a sample from the subject; and (b) administering to the subject a therapeutically effective amount of osimertinib. In further embodiments, the methods further comprise (after (b)) (c) determining whether a cancer cell in a sample obtained from the subject has one or more fusion proteins of Table 1 and/or one or more RET kinase protein point mutations/insertions of Table 2; and (d) administering a compound of Formula I (e.g., any one of Formulas I-A to I-L), or a pharmaceutically acceptable salt or solvate thereof, as a monotherapy or in conjunction with osimertinib to the subject if the subject has a cancer cell that has one or more fusion proteins of Table 1 and/or one or more RET kinase protein point mutations/insertions of Table 2; or (e) administering additional doses of the osimertinib of step (b) to the subject if the subject has a cancer cell that does not have one or more fusion proteins of Table 1 and/or one or more RET kinase protein point mutations/insertions of Table 2.

The term "EGFR-associated cancer" as used herein refers to cancers associated with or having a dysregulation of a EGFR gene, a EGFR kinase, or expression or activity, or level of any of the same.

The phrase "dysregulation of a EGFR gene, a EGFR kinase, or the expression or activity or level of any of the same" refers to a genetic mutation (e.g., a EGFR gene translocation that results in the expression of a fusion protein, a deletion in a EGFR gene that results in the expression of a EGFR protein that includes a deletion of at least one amino acid as compared to the wild-type EGFR protein, or a mutation in a EGFR gene that results in the expression of a EGFR protein with one or more point mutations, or an alternative spliced version of a EGFR mRNA that results in a EGFR protein that results in the deletion of at least one amino acid in the EGFR protein as compared to the wild-type EGFR protein), or a EGFR gene amplification that results in overexpression of a EGFR protein or an autocrine activity resulting from the overexpression of a EGFR gene a cell, that results in a pathogenic increase in the activity of a kinase domain of a EGFR protein (e.g., a constitutively active kinase domain of a EGFR protein) in a cell. As another example, a dysregulation of a EGFR gene, a EGFR protein, or expression or activity, or level of any of the same, can be a mutation in a EGFR gene that encodes a EGFR protein that is constitutively active or has increased activity as compared to a protein encoded by a EGFR gene that does not include the mutation. For example, a dysregulation of a EGFR gene, a EGFR protein, or expression or activity, or level of any of the same, can be the result of a gene or chromosome translocation which results in the expression of a fusion protein that contains a first portion of EGFR that includes a functional kinase domain, and a second portion of a partner protein (i.e., that is not EGFR). In some examples, dysregulation of a EGFR gene, a EGFR protein, or expression or activity, can be a result of a gene translocation of one EGFR gene with another non-EGFR gene.

The term "wildtype EGFR" or "wild-type EGFR" describes a nucleic acid (e.g., a EGFR gene or a EGFR mRNA) or protein (e.g., a EGFR protein) that is found in a subject that does not have a EGFR-associated cancer (and optionally also does not have an increased risk of developing a EGFR-associated cancer and/or is not suspected of having a EGFR-associated cancer), or is found in a cell or tissue from a subject that does not have a EGFR-associated cancer (and optionally also does not have an increased risk of developing a EGFR-associated cancer and/or is not suspected of having a EGFR-associated cancer).

Also provided are methods of selecting a treatment for a subject having a cancer that include: identifying a subject having a cancer cell that has one or more RET inhibitor resistance mutations; and selecting a treatment that includes administration of a compound of Formula I (e.g., any one of Formulas I-A to I-L), or a pharmaceutically acceptable salt or solvate thereof. In some embodiments, the one or more RET inhibitor resistance mutations confer increased resistance to a cancer cell or tumor to treatment with a first RET inhibitor. In some embodiments, the compound of Formula I, or a pharmaceutically acceptable salt or solvate thereof is administered in combination with the first RET inhibitor. Also provided are methods of selecting a treatment for a subject having a cancer that include: selecting a treatment that includes administration of a compound of Formula I (e.g., any one of Formulas I-A to I-L), or a pharmaceutically acceptable salt or solvate thereof for a subject identified as having a cancer cell that has one or more RET inhibitor resistance mutations. Also provided are methods of selecting a subject having a cancer for a treatment that does not include a first RET inhibitor as a monotherapy that include: identifying a subject having a cancer cell that has one or more RET inhibitor resistance mutations; and selecting the identified subject for a treatment that includes a compound of Formula I (e.g., any one of Formulas I-A to I-L), or a pharmaceutically acceptable salt or solvate thereof. Also provided are methods of selecting a subject having a cancer for a treatment that does not include a first RET inhibitor as a monotherapy that include: selecting a subject identified as having a cancer cell that has one or more RET inhibitor resistance mutations for a treatment that includes administration of a compound of Formula I (e.g., any one of Formulas I-A to I-L), or a pharmaceutically acceptable salt or solvate thereof. In some embodiments, the one or more RET inhibitor resistance mutations include one or more RET inhibitor resistance mutations listed in Tables 3 and 4. In some embodiments, the one or more RET inhibitor resistance mutations can include a substitution at amino acid position 804, e.g., V804M, V804L, or V804E, or a substitution amino acid position 810, e.g., G810S, G810R, G810C, G810A, G810V, and G810D.

Also provided are methods of determining the likelihood that a subject having a cancer (e.g., a RET-associated cancer) will have a positive response to treatment with a first RET inhibitor as a monotherapy that include: determining whether a cancer cell in a sample obtained from the subject has one or more RET inhibitor resistance mutations; and determining that a subject having a cancer cell that has one or more RET inhibitor resistance mutations has a decreased likelihood of having a positive response (i.e. an increased likelihood of having a negative response) to treatment with a first RET inhibitor as a monotherapy. Also provided are methods of determining the likelihood that a subject having a cancer (e.g., a RET-associated cancer) will have a positive response to treatment with a first RET inhibitor as a monotherapy that include: determining whether a cancer cell in a sample obtained from the subject has one or more RET inhibitor resistance mutations; and determining that a subject not having a cancer cell that has one or more RET inhibitor resistance mutations has an increased likelihood of having a positive response to treatment with a first RET inhibitor as a monotherapy as compared to a subject having a cancer cell that has one or more RET inhibitor resistance mutations. Also provided are methods of predicting the efficacy of treatment with a first RET inhibitor as a monotherapy in a subject having cancer that include: determining whether a cancer cell in a sample obtained from the subject has one or more RET inhibitor resistance mutations; and determining that treatment with a first RET inhibitor as a monotherapy is less likely to be effective in a subject having a cancer cell in a sample obtained from the subject that has one or more RET inhibitor resistance mutations. Also provided are methods of predicting the efficacy of treatment with a first RET inhibitor as a monotherapy in a subject having cancer that include: determining that treatment with a first RET inhibitor as a monotherapy is less likely to be effective in a subject having a cancer cell in a sample obtained from the subject that has one or more RET inhibitor resistance mutations. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D.

Also provided are methods of treating a subject having a cancer that include: (a) administering one or more doses of a first RET inhibitor to the subject for a period of time; (b) after (a), determining whether a cancer cell in a sample obtained from the subject has at least one RET inhibitor resistance mutation; and (c) administering a compound of Formula I (e.g., any one of Formulas I-A to I-L), or a pharmaceutically acceptable salt or solvate thereof as a monotherapy or in conjunction with another anticancer agent to the subject if the subject has a cancer cell that has at least one RET inhibitor resistance mutation; or (d) administering additional doses of the first RET inhibitor of step (a) to the subject if the subject has a cancer cell that does not have a RET inhibitor resistance mutation. In some embodiments, where the subject is administered additional doses of the first RET inhibitor of step (a), the subject can also be administered another anticancer agent (e.g., a second RET inhibitor or a compound of Formula I (e.g., any one of Formulas I-A to I-L), or a pharmaceutically acceptable salt or solvate thereof, or immunotherapy). In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (c), another RET inhibitor can be the first RET inhibitor administered in step (a). In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D.

Also provided are methods of treating a subject having a cancer that include: (a) administering one or more doses of a first RET inhibitor to the subject for a period of time; (b) after (a), determining whether a cancer cell in a sample obtained from the subject has at least one RET inhibitor resistance mutation; and (c) administering a second RET inhibitor as a monotherapy or in conjunction with another anticancer agent to the subject if the subject has a cancer cell that has at least one RET inhibitor resistance mutation; or (d) administering additional doses of the first RET inhibitor step (a) to the subject if the subject has a cancer cell that does not have a RET inhibitor resistance mutation. In some embodiments, where the subject is administered additional doses of the first RET inhibitor of step (a), the subject can also be administered another anticancer agent. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D. In some embodiments, the additional anticancer agent is any anticancer agent known in the art. For example, the additional anticancer agent is another RET inhibitor (e.g., a compound of Formula I (e.g., any one of Formulas I-A to I-L), or a pharmaceutically acceptable salt or solvate thereof). In some embodiments, the additional anticancer agent is an immunotherapy.

Also provided are methods of treating a subject having a cancer (e.g., a RET-associated cancer) that include: (a) determining whether a cancer cell in a sample obtained from a subject having a cancer and previously administered one or more doses of a first RET inhibitor, has one or more RET inhibitor resistance mutations; and (b) administering a compound of Formula I (e.g., any one of Formulas I-A to I-L), or a pharmaceutically acceptable salt or solvate thereof as a monotherapy or in conjunction with another anticancer agent to the subject if the subject has a cancer cell that has at least one RET inhibitor resistance mutation; or (c) administering additional doses of the first RET inhibitor previously administered to the subject if the subject has cancer cell that does not have a RET inhibitor resistance mutation. In some embodiments, where the subject is administered additional doses of the first RET inhibitor previously administered to the subject, the subject can also be administered another anticancer agent (e.g., a compound of Formula I (e.g., any one of Formulas I-A to I-L), or a pharmaceutically acceptable salt or solvate thereof, or immunotherapy). In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (b), another anticancer agent can be the first RET inhibitor administered in step (a).

Also provided are methods of treating a subject having a cancer that include: (a) determining whether a cancer cell in a sample obtained from a subject having a cancer and previously administered one or more doses of a first RET inhibitor has one or more RET inhibitor resistance mutations; and (b) administering a second RET inhibitor as a monotherapy or in conjunction with another anticancer agent to the subject if the subject has a cancer cell that has at least one RET inhibitor resistance mutation; or (c) administering additional doses of the first RET inhibitor previously administered to the subject if the subject has a cancer cell that does not have a RET inhibitor resistance mutation. In some embodiments, where the subject is administered additional doses of the first RET inhibitor previously administered to the subject, the subject can also be administered another anticancer agent. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D. In some embodiments, the additional anticancer agent is any anticancer agent known in the art. For example, the additional anticancer agent is another RET inhibitor (e.g., a compound of Formula I (e.g., any one of Formulas I-A to I-L), or a pharmaceutically acceptable salt or solvate thereof). In some embodiments, the additional anticancer agent is an immunotherapy. In some embodiments of (b), another anticancer agent can be the first RET inhibitor administered in step (a).

In some embodiments, a RET-associated cancer as described herein can occur in a subject along with a dysregulation of another gene, another protein, or the expression or activity or level of any of the same.

For example, a RET-associated cancer that exhibits a RET fusion can occur in a subject along with one or more of: a dysregulation of a MET gene, a MET protein, or the expression or activity or level of any of the same; a dysregulation of a PIK3CA gene, a PIK3CA protein, or the expression or activity or level of any of the same; a dysregulation of a KRAS gene, a KRAS protein, or the expression or activity or level of any of the same; a dysregulation of a EGFR gene, a EGFR protein, or the expression or activity or level of any of the same (e.g., an amplification of a EGFR gene); a dysregulation of a FGFR2 gene, a FGFR2 protein, or the expression or activity or level of any of the same (eg., a fusion of an FGFR2 gene or an FGFR2 protein); a dysregulation of a CDK4 gene, a CDK4 protein, or the expression or activity or level of any of the same (e.g., an amplification of a CDK4 gene); a dysregulation of a mTOR gene, a mTOR protein, or the expression or activity or level of any of the same; a dysregulation of a CDKN2A gene, a CDKN2A protein, or the expression or activity or level of any of the same (e.g., a deletion in a CDKN2A gene or a CDKN2A protein); a dysregulation of a CDKN2B gene, a CDKN2B protein, or the expression or activity or level of any of the same (e.g., a deletion in a CDKN2B gene or a CDKN2B protein); a dysregulation of a NF1 gene, a NF1 protein, or the expression or activity or level of any of the same; a dysregulation of a MYC gene, a MYC protein, or the expression or activity or level of any of the same (e.g., an amplification in a MYC gene); a dysregulation of a MDM2 gene, a MDM2 protein, or the expression or activity or level of any of the same (e.g., an amplification in a MDM2 gene); a dysregulation of a GNAS gene, a GNAS protein, or the expression or activity or level of any of the same; a dysregulation of a BRCA2 gene, a BRCA2 protein, or the expression or activity or level of any of the same.

In some embodiments, a RET-associated cancer that exhibits a mutation of a RET gene and/or a RET protein can occur in a subject along with one or more of: a dysregulation of a PIK3CA gene, a PIK3CA protein, or the expression or activity or level of any of the same; a dysregulation of a KRAS gene, a KRAS protein, or the expression or activity or level of any of the same; a dysregulation of a EGFR gene, a EGFR protein, or the expression or activity or level of any of the same; a dysregulation of a FGFR1 gene, a FGFR1 protein, or the expression or activity or level of any of the same (e.g, an amplification of a FGFR1 gene); a dysregulation of a FGFR2 gene, a FGFR2 protein, or the expression or activity or level of any of the same (e.g., an amplification of a FGFR2 gene); a dysregulation of a FGFR3 gene, a FGFR3 protein, or the expression or activity or level of any of the same (e.g., a fusion of a FGFR3 gene or a FGFR3 protein); a dysregulation of a ERBB2 gene, a ERBB2 protein, or the expression or activity or level of any of the same (e.g., an amplification of ERBB2 gene); and a dysregulation of a KIT gene, a KIT protein, or the expression or activity or level of any of the same.

In some embodiments, a RET-associated cancer that exhibits an amplification of a RET gene can occur in a patient along with one or more additional kinase amplifications. For example, am amplification in a FGFR1 gene; an amplification in a FGFR2 gene; an amplification in a FGFR3 gene; an amplification of a FGFR4 gene; an amplification of a CDK4 gene; and an amplification in a CDK6 gene.

In some embodiments, wherein a RET-associated cancer as described herein can occur in a subject along with a dysregulation in another kinase, the methods described herein can further comprise administration of an additional therapeutic agent that targets and/or treats the dysregulation in the other kinase. For example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I (e.g., any one of Formulas I-A to I-L), or a pharmaceutically acceptable salt or solvate thereof. In some embodiments, the method further comprises (c) detecting a dysregulation in another kinase in a sample from the subject; and (d) administering to the subject a therapeutic agent that targets and/or treats the dysregulation in the other kinase. In some embodiments, the administration of a compound of Formula I (e.g., any one of Formulas I-A to I-L), or a pharmaceutically acceptable salt or solvate thereof is done concurrently, sequentially, or serially. In some embodiments, the detecting steps (a) and (c) can be done simultaneously or sequentially in any order.

Additional therapeutic agents that target and/or treat the dysregulation of the other kinase can include any known inhibitor of the other kinase. Examples of such agents are as follows:

Exemplary PARP inhibitors include: 3-aminobenzamide (INO-1001), 5-aminoisoquinoline, ABT472, ABT767, AG140361, AG14032, ANG2864, ANG3186, AZD2281, AZD2461, BGP-15, BSI101, BSI401, CEP6800, CEP8983, CK102, CEP9722 (prodrug of CEP8983), CPH101 with CPH102, DR2313, E7016 (GPI-21016), E7449, GP16150, IMP4297, IMP04149, INO1002, INO1003, JPI283, JPI289, KU0687, KU58948, niraparib (MK-4827), NT125, olaparib (AZD2281), ONO-1924H, ONO2231, pamiparib (BGB-290), PJ-34, rucaparib (AG014699), SC10914, SOMCL9112, talazoparib (BMN-673), and veliparib (ABT-888).

Exemplary CDK 4/6 inhibitors include: palbociclib (PD0332991), abemaciclib (LY2835219), ribociclib (LEE011), trilaciclib (G1T28), voruciclib, and G1T38.

Exemplary ERBB2 (HER2/neu) inhibitors include: afatinib, afatinib, dacomitinib (PF-00299804), DS8201-a, erlontinib, gefitinib, KU004, lapatinib, laptinib ditosylate, MM-111, mubritinib (TAK-165), neratinib, pyrotinib (HTI-1001), tucatinib (ONT-380, ARRY-380), 7C3, cetuximab, HER2-BsAb, hersintuzumab, margetuximab, MI130004, NeuVax, paitumumab, pertuzumab, SYD985, trastuzumab, and trastuzumab emtansine.

Exemplary inhibitors of amplified ERBB2 (HER2/neu) include dacomitinib (PF-00299804), lapatinib, neratinib, pertuzumab, trastuzumab, and trastuzumab emtansine.

Exemplary EGFR inhibitors include: AC0010, afatinib, AP26113, ASP8273, avatinib, avitinib, AZD3759, BMS-690514, brigatinib, canertinib, Cap-701, CHMFL-EGFR-202, CUDC-101, dacomitinib, EAI045, EGF816, erlontinib, erlotinib, gefitinib, GNS-1481, GNS-1486, Gö6976, HS-10296, icotinib, KU004, lapatinib, nazartinib, neratinib, olmutinib (HM61713, BI 1482694), osimertinib, osimertinib (AZD9291), pelitinib, PF-06747775, PKC412, pyrotinib (HTI-1001), rocilentinib, vandetanib, varlitinib, XL647, 7C3, cetuximab, depatuxizumab mafodotin (ABT-414), matuzumab, nimotuzumab, panitumumab, and zalutumumab.

Exemplary wild-type EGFR inhibitors include: afatinib, BMS-690514, canertinib, CUDC-101, dacomitinib, erlotinib, gefitinib, lapatinib, neratinib, pelitinib, vandetanib, varlitinib, XL647, cetuximab, matuzumab, nimotuzumab, panitumumab, and zalutumumab.

Exemplary inhibitors of mutated EGFR include: AC0010, afatinib, AP26113, ASP8273, avatinib, avitinib, AZD3759, BMS-690514, brigatinib, canertinib, Cap-701, CHMFL-EGFR-202, CUDC-101, dacomitinib, EAI045, EGF816, GNS-1481, GNS-1486, Gö6976, HS-10296, icotinib, nazartinib, neratinib, olmutinib (HM61713, BI 1482694), osimertinib (AZD9291), PF-06747775, PKC412, rocilentinib, vandetanib, varlitinib, and cetuximab.

An exemplary inhibitor of amplified EGFR is depatuxizumab mafodotin (ABT-414).

Exemplary inhibitors of FGFR include: ASP5878, AZD4547, BGJ398, BLU9931, brivatinib, cediranib, DEBIO 1347, derazantinib (ARQ-087), dovitinib (CHIR258), E7090, ENMD-2076, erdafitinib (JNJ-42756293), FGF401, FIIN-1, FRIN-1, INCB054828, L16H50, lenvatinib, lucitanib, LY2874455, nintedanib, NP603, orantinib (SU6668), pazopanib, PBI05204, PD173074, ponatinib, PRN1371, regorafenib, rogaratinib (BAY-1163877), S49076, SOMCL-085, SU5402, sunitinib, TAS-120, FP-1039, GAL-F2, GAL-FR21, GAL-FR22, GAL-FR23, GP369, hLD1.vb, LD1, MFGR1877S, MM-161, PRO-001, and R3Mab.

Exemplary inhibitors of FGFR fusions include: BGJ398, DEBIO 1347, derazantinib (ARQ-087), E7090, erdafitinib (JNJ-42756293), lucitanib, and TAS-120.

Exemplary inhibitors of FGFR1, FGFR2, and FGFR3 include: AZD4547, BGJ398, DEBIO 1347, E7090, INCB054828, S49076, SOMCL-085, and TAS-120.

Exemplary inhibitors of FGF4 include: BLU-554, BLU9931, NVP-FGF401, and hLD1.vb.

Exemplary inhibitors of amplified FGFR1 include: AZD4547, BGJ398, DEBIO 1347, derazantinib (ARQ-087), erdafitinib (JNJ-42756293), INCB054828, and lucitanib.

Exemplary inhibitors of amplified FGFR2 include: AZD4547, DEBIO 1347, derazantinib (ARQ-087), lucitanib, regorafenib, and TAS-120.

An exemplary inhibitor of amplified FGFR3 is AZD4547.

Exemplary MEK inhibitors include: AZD8330 (ARRY-424704), AZD6244 (ARRY-142866), BI-847325, binimetinib, BIX02188, BIX02189, CH4987655, CH5126766, CI-1040, cobemetinib (GDC-0973), EBI-1051, G-573, G8935, GDC-0623, Myricetin, nobiletin, PD0325901, PD184161, PD318088, PD98059, PD334581, pimasertib (AS-703026), refametinib (RDEA119, BAY 869766), selumentinib (AZD6244), SL-327, TAK-733, trametinib, and U0126.

Exemplary KRAS inhibitors include: 0375-0604, a covalent quinazoline-based switch II pocket (SIIP) compound, ARS-1620, AZD4785, and LP1.

Exemplary PI3K inhibitors include: 3-methyladenine, A66, alpelisib (BYL719), AMG319, apitolisib (GDC-0980, RG7422), AS-252424, AS-604850, AS-605240, AZD6842, AZD8186, AZD8835, BGT226 (NVP-BGT226), buparlisib (BKM120), CAY10505, CH5132799, copanlisib (BAY 80-6946), CUDC-907, CZC24832, dactolisib (BEZ235, NVP-BEZ235), DS7423, duvelisib (IPI-145, INK1197), GDC-0032, GDC-0084, GDC-0326, gedatolisib (PF-05212384, PKI-5587), GNE-317, GS-9820, GSK1059615, GSK2292767, GSK2636771, HS-173, IC-87114, Idelalisib (CAL-101, GS-1101), IPI-145, IPI-3063, IPI-549, LY294002, LY3023414, nemiralisib (GSK2269557), omipalisib (GSK2126458, GSK458), PF-04691502, PF-4989216, PI-103, PI-3065, pictilisib (GDC-0941), PIK-293, PIK-294, PIK-75, PIK-90, PIK-93, PIK-III, pilaralisib (XL147), PKI-587, PP-110, PQR309, PQR309, PW-12, PX-866, quercetin, S14161, SAR245409 (XL765), SAR260301, SAR405, serabelisib (INK-1117, MLN-1117, TAK-1117), SF-1126, SF-2523, SN32976, taselisib (GDC-0032), TB101110, TG100-115, TG100-713, TGR-1202, TGX-221, umbralisib (TGR-1202), voxtalisib (XL765, SAR245409), VPS34-IN1, VS-5584 (SB2343), WJD008, wortmannin, and ZSTK474.

Exemplary KIT inhibitors include: AMG 706, amuvatinib (MP-470), APcK110, axitinib (AG-013736), AZD2932, dasatinib (BMS-354825), dovitinib (TKI-258, CHIR-258), EXEL-0862, imatinib, KI-328, masitinib (AB1010), midostaurin, MLN518, motesanib, N3-(6-aminopyridin-3-yl)-N1-(2-cyclopentylethyl)-4-methylisophthalamide, nilotinib, OSI-930, pazopanib (GW786034), pexidartinib (PLX3397), PKC412, PLX647, PP1, quizartinib (AC220), regorafenib (BAY 73-4506), semaxinib (SU 5416), sitravatinib (MGCD516), sorafenib, STI571, SU11248, SU9529, sunitinib, telatinib, tivozanib (AV-951), tyrphostin AG 1296, VX-322, and WBZ_4.

Exemplary MDM2 inhibitors include: (−)-parthenolide, ALRN6924, AM-8553, AMG232, CGM-097, DS-3032b, GEM240, HDM201, HLI98, idasanutlin (RG-7338), JapA, MI-219, MI-219, MI-319, MI-77301 (SAR405838), MK4828, MK-8242, MX69, NSC 207895 (XI-006), Nutlin-3, Nutlin-3a, Nutlin-3b, NVP-CFC218, NVP-CGM097, PXn727/822, RG7112, RO2468, RO5353, RO5503781, serdemetan (JNJ-26854165), SP-141, and YH239-EE.

Exemplary inhibitors of amplified MDM2 include: AM-8553, AMG232, DS-3032b, MI-77301 (SAR405838), NSC 207895 (XI-006), Nutlin-3a, NVP-CFC218, NVP-CGM097, and RG7112.

Exemplary inhibitors of MET include: (−)-Oleocanthal, ABBV-399, AMG-208, AMG-337, AMG-458, BAY-853474, BMS-754807, BMS-777607, BMS-794833, cabozantinib (XL184, BMS-907351), capmatinib (INCB28060), crizotinib (PF-02341066), DE605, foretinib (GSK1363089, XL880), glesatinib (MGCD265), golvatinib (E7050), INCB028060, JNJ-38877605, KRC-408, merestinib (LY2801653), MK-2461, MK8033, NPS-1034, NVP-BVU972, PF-04217903, PHA-665752, S49076, savolitinib (AZD6094, HMPL-504), SGX-523, SU11274, TAS-115, tepotinib (EMD 1214063, MSC2156119J), volitinib, CE-355621, and Onartuzumab.

Exemplary inhibitors of mTOR include: anthracimycin, apitolisib (GDC-0980, RG7422), AZD-8055, BGT226 (NVP-BGT226), CC-223, CZ415, dactolisib (BEZ235, NVP-BEZ235), DS7423, everolimus (RAD001), GDC-0084, GDC-0349, gedatolisib (PF-05212384, PKI-5587), GSK1059615, INK128, KU-0063794, LY3023414, MLN0128, omipalisib (GSK2126458, GSK458), OSI-027, OSU-53, Palomid 529 (P529), PF-04691502, PI-103, PKI-587, PP242, PQR309, ridafarolimus (AP-23573), sapanisertib (INK 128, MLN0128), SAR245409 (XL765), SF-1126, SF2523, sirolimus (rapamycin), SN32976, TAK228, temsirolimus (CCI-779, NSC 683864), Torin 1, Torin 2, torkinib (PP242), umirolimus, vistusertib (AZD2014), voxtalisib (XL765, SAR245409), VS-5584, VS-5584 (SB2343), WAY-600, WYE-125132 (WYE-132), WYE-354, WYE-687, XL388, and zotarolimus (ABT-578).

Exemplary inhibitors of MYC include: 10058-F4, 10074-G5, and KSI-3716.

The phrase "dysregulation of a gene, a protein, or the expression or activity or level of any of the same" refers to a genetic mutation (e.g., a chromosomal translocation that results in the expression of a fusion protein including a kinase domain and a fusion partner, a mutation in a gene that results in the expression of a protein that includes a deletion of at least one amino acid as compared to a wildtype protein, a mutation in a gene that results in the expression of a protein with one or more point mutations as compared to a wildtype protein, a mutation in a gene that results in the expression of a protein with at least one inserted amino acid as compared to a wildtype protein, a gene duplication that results in an increased level of protein in a cell, or a mutation in a regulatory sequence (e.g., a promoter and/or enhancer) that results in an increased level of protein in a cell), an alternative spliced version of a mRNA that results in a protein having a deletion of at least one amino acid in the protein as compared to the wild-type protein), or increased expression (e.g., increased levels) of a wildtype protein in a mammalian cell due to aberrant cell signaling and/or dysregulated autocrine/paracrine signaling (e.g., as compared to a control non-cancerous cell). As another example, a dysregulation of a gene, a protein, or expression or activity, or level of any of the same, can be a mutation in a gene that encodes a protein that is constitutively active or has increased activity as compared to a protein encoded by a gene that does not include the mutation. For example, a dysregulation of a gene, a protein, or expression or activity, or level of any of the same, can be the result of a gene or chromosome translocation which results in the expression of a fusion protein that contains a first portion of a protein that includes a functional kinase domain, and a second portion of a partner protein (i.e., that is not the primary protein). In some examples, dysregulation of a gene, a protein, or expression or activity or level of any of the same can be a result of a gene translocation of one gene with a different gene.

Treatment of a patient having a cancer with a multi-kinase inhibitor (MKI) or target-specific kinase inhibitor (e.g., a BRAF inhibitor, a EGFR inhibitor, a MEK inhibitor, an ALK inhibitor, a ROS1 inhibitor, a MET inhibitor, an aromatase inhibitor, a RAF inhibitor, or a RAS inhibitor) can result in dysregulation of a RET gene, a RET kinase, or the expression or activity or level of the same in the cancer, and/or resistance to a RET inhibitor. See, e.g., Bhinge et al., *Oncotarget* 8:27155-27165, 2017; Chang et al., *Yonsei Med. J.* 58:9-18, 2017; and Lopez-Delisle et al., doi: 10.1038/s41388-017-0039-5, *Oncogene* 2018.

Treatment of a patient having a cancer with a RET inhibitor in combination with a multi-kinase inhibitor or a target-specific kinase inhibitor (e.g., a BRAF inhibitor, a EGFR inhibitor, a MEK inhibitor, an ALK inhibitor, a ROS1 inhibitor, a MET inhibitor, an aromatase inhibitor, a RAF inhibitor, or a RAS inhibitor) can have increased therapeutic efficacy as compared to treatment of the same patient or a similar patient with the RET inhibitor as a monotherapy, or the multi-kinase inhibitor or the target-specific kinase inhibitor as a monotherapy. See, e.g., Tang et al., doi: 10.1038/modpathol.2017.109, *Mod. Pathol.* 2017; Andreucci et al., *Oncotarget* 7:80543-80553, 2017; Nelson-Taylor et al., *Mol. Cancer Ther.* 16:1623-1633, 2017; and Kato et al., *Clin. Cancer Res.* 23:1988-1997, 2017.

Provided herein are methods of treating a patient having a cancer (e.g., any of the cancers described herein) and previously administered a multi-kinase inhibitor (MKI) or a target-specific kinase inhibitor (e.g., a BRAF inhibitor, a EGFR inhibitor, a MEK inhibitor, an ALK inhibitor, a ROS1 inhibitor, a MET inhibitor, an aromatase inhibitor, a RAF inhibitor, or a RAS inhibitor) (e.g., as a monotherapy) that include: administering to the patient (i) a therapeutically effective dose of a compound of Formula I (e.g., any one of Formulas I-A to I-L), or a pharmaceutically acceptable salt or solvate thereof as a monotherapy, or (ii) a therapeutically effective dose of a compound of Formula I (e.g., any one of Formulas I-A to I-L), or a pharmaceutically acceptable salt or solvate thereof, and a therapeutically effective dose of the previously administered MKI or the previously administered target-specific kinase inhibitor.

Provided herein are methods of treating a patient having a cancer (e.g., any of the cancers described herein) previously administered a MKI or a target specific kinase inhibitor (e.g., a BRAF inhibitor, a EGFR inhibitor, a MEK inhibitor, an ALK inhibitor, a ROS1 inhibitor, a MET inhibitor, an aromatase inhibitor, a RAF inhibitor, or a RAS inhibitor) (e.g., as a monotherapy) that include: identifying a patient having a cancer cell that has a dysregulation of a RET gene, a RET kinase, or the expression or activity or level of the same; and administering to the identified patient (i) a therapeutically effective dose of a compound of Formula I (e.g., any one of Formulas I-A to I-L), or a pharmaceutically acceptable salt or solvate thereof as a monotherapy, or (ii) a therapeutically effective dose of a compound of Formula I (e.g., any one of Formulas I-A to I-L), or a pharmaceutically acceptable salt or solvate thereof, and a therapeutically effective dose of the previously administered MKI or the previously administered target-specific kinase inhibitor.

Provided herein are methods of treating a patient having a cancer (e.g., any of the cancers described herein) that include: administering to a patient a therapeutically effective amount of a MKI or a target-specific kinase inhibitor (e.g., a BRAF inhibitor, a EGFR inhibitor, a MEK inhibitor, an ALK inhibitor, a ROS1 inhibitor, a MET inhibitor, an aromatase inhibitor, a RAF inhibitor, or a RAS inhibitor) (e.g., as a monotherapy) for a first period of time; after the period of time, identifying a patient having a cancer cell that has a dysregulation of a RET gene, a RET kinase, or the expression or activity or level of the same; and administering to the identified patient (i) a therapeutically effective dose of a compound of Formula I (e.g., any one of Formulas I-A to I-L), or a pharmaceutically acceptable salt or solvate thereof as a monotherapy, or (ii) a therapeutically effective dose of a compound of Formula I (e.g., any one of Formulas I-A to I-L), or a pharmaceutically acceptable salt or solvate thereof, and a therapeutically effective dose of the previously administered MKI or the previously administered target-specific kinase inhibitor.

Provided herein are methods of treating a patient having a cancer (e.g., any of the cancers described herein) that has dysregulation of a BRAF gene, a BRAF kinase, or the expression or activity or level of the same that include administering to the patient (i) a therapeutically effective amount of a compound of Formula I (e.g., any one of Formulas I-A to I-L), or a pharmaceutically acceptable salt or solvate thereof and (ii) a therapeutically effective amount of a BRAF inhibitor (e.g., any of the BRAF inhibitors described herein or known in the art).

Provided herein are methods of treating a patient having a cancer (e.g., any of the cancers described herein) that include: identifying a patient having a cancer cell that has dysregulation of a BRAF gene, a BRAF kinase, or the expression or activity or level of the same; and administering to the identified patient (i) a therapeutically effective amount of a compound of Formula I (e.g., any one of Formulas I-A to I-L), or a pharmaceutically acceptable salt or solvate thereof and (ii) a therapeutically effective amount of a BRAF inhibitor (e.g., any of the BRAF inhibitors described herein or known in the art).

Provided herein are methods of treating a patient having a cancer (e.g., any of the cancers described herein) that has dysregulation of an EGFR gene, an EGFR protein, or the expression or activity or level of the same that include administering to the patient (i) a therapeutically effective amount of a compound of Formula I (e.g., any one of Formulas I-A to I-L), or a pharmaceutically acceptable salt or solvate thereof and (ii) a therapeutically effective amount of an EGFR inhibitor (e.g., any of the EGFR inhibitors described herein or known in the art).

Provided herein are methods of treating a patient having a cancer (e.g., any of the cancers described herein) that include: identifying a patient having a cancer cell that has dysregulation of an EGFR gene, an EGFR protein, or the expression or activity or level of the same; and administering to the identified patient (i) a therapeutically effective amount of a compound of Formula I (e.g., any one of Formulas I-A to I-L), or a pharmaceutically acceptable salt or solvate thereof and (ii) a therapeutically effective amount of an EGFR inhibitor (e.g., any of the EGFR inhibitors described herein or known in the art).

Provided herein are methods of treating a patient having a cancer (e.g., any of the cancers described herein) that has dysregulation of a MEK gene, a MEK protein, or the expression or activity or level of the same that include administering to the patient (i) a therapeutically effective amount of a compound of Formula I (e.g., any one of Formulas I-A to I-L), or a pharmaceutically acceptable salt or solvate thereof and (ii) a therapeutically effective amount of a MEK inhibitor (e.g., any of the MEK inhibitors described herein or known in the art).

Provided herein are methods of treating a patient having a cancer (e.g., any of the cancers described herein) that include: identifying a patient having a cancer cell that has dysregulation of a MEK gene, a MEK protein, or the expression or activity or level of the same; and administering to the identified patient (i) a therapeutically effective amount of a compound of Formula I (e.g., any one of Formulas I-A to I-L), or a pharmaceutically acceptable salt or solvate thereof and (ii) a therapeutically effective amount of a MEK inhibitor (e.g., any of the MEK inhibitors described herein or known in the art).

Provided herein are methods of treating a patient having a cancer (e.g., any of the cancers described herein) that has dysregulation of an ALK gene, an ALK protein, or the expression or activity or level of the same that include administering to the patient (i) a therapeutically effective amount of a compound of Formula I (e.g., any one of Formulas I-A to I-L), or a pharmaceutically acceptable salt or solvate thereof and (ii) a therapeutically effective amount of an ALK inhibitor (e.g., any of the ALK inhibitors described herein or known in the art).

Provided herein are methods of treating a patient having a cancer (e.g., any of the cancers described herein) that include: identifying a patient having a cancer cell that has dysregulation of an ALK gene, an ALK protein, or the expression or activity or level of the same; and administering to the identified patient (i) a therapeutically effective amount of a compound of Formula I (e.g., any one of Formulas I-A to I-L), or a pharmaceutically acceptable salt or solvate thereof and (ii) a therapeutically effective amount an ALK inhibitor (e.g., any of the ALK inhibitors described herein or known in the art).

Provided herein are methods of treating a patient having a cancer (e.g., any of the cancers described herein) that has dysregulation of a ROS gene, a ROS protein, or the expression or activity or level of the same that include administering to the patient (i) a therapeutically effective amount of a compound of Formula I (e.g., any one of Formulas I-A to I-L), or a pharmaceutically acceptable salt or solvate thereof and (ii) a therapeutically effective amount of a ROS inhibitor (e.g., any of the ROS inhibitors described herein or known in the art).

Provided herein are methods of treating a patient having a cancer (e.g., any of the cancers described herein) that include: identifying a patient having a cancer cell that has dysregulation of a ROS gene, a ROS protein, or the expression or activity or level of the same; and administering to the identified patient (i) a therapeutically effective amount of a compound of Formula I (e.g., any one of Formulas I-A to I-L), or a pharmaceutically acceptable salt or solvate thereof and (ii) a therapeutically effective amount a ROS inhibitor (e.g., any of the ROS inhibitors described herein or known in the art).

Provided herein are methods of treating a patient having a cancer (e.g., any of the cancers described herein) that has dysregulation of a MET gene, a MET protein, or the expression or activity or level of the same that include administering to the patient (i) a therapeutically effective amount of a compound of Formula I (e.g., any one of Formulas I-A to I-L), or a pharmaceutically acceptable salt or solvate thereof and (ii) a therapeutically effective amount of a MET inhibitor (e.g., any of the MET inhibitors described herein or known in the art).

Provided herein are methods of treating a patient having a cancer (e.g., any of the cancers described herein) that include: identifying a patient having a cancer cell that has dysregulation of a MET gene, a MET protein, or the expression or activity or level of the same; and administering to the identified patient (i) a therapeutically effective amount of a compound of Formula I (e.g., any one of Formulas I-A to I-L), or a pharmaceutically acceptable salt or solvate thereof and (ii) a therapeutically effective amount a MET inhibitor (e.g., any of the MET inhibitors described herein or known in the art).

Provided herein are methods of treating a patient having a cancer (e.g., any of the cancers described herein) that has dysregulation of an aromatase gene, an aromatase protein, or the expression or activity or level of the same that include administering to the patient (i) a therapeutically effective amount of a compound of Formula I (e.g., any one of Formulas I-A to I-L), or a pharmaceutically acceptable salt or solvate thereof and (ii) a therapeutically effective amount of an aromatase inhibitor (e.g., any of the aromatase inhibitors described herein or known in the art).

Provided herein are methods of treating a patient having a cancer (e.g., any of the cancers described herein) that include: identifying a patient having a cancer cell that has dysregulation of an aromatase gene, an aromatase protein, or the expression or activity or level of the same; and administering to the identified patient (i) a therapeutically effective amount of a compound of Formula I (e.g., any one of Formulas I-A to I-L), or a pharmaceutically acceptable salt or solvate thereof and (ii) a therapeutically effective amount an aromatase inhibitor (e.g., any of the aromatase inhibitors described herein or known in the art).

Provided herein are methods of treating a patient having a cancer (e.g., any of the cancers described herein) that has dysregulation of a RAF gene, a RAF protein, or the expression or activity or level of the same that include administering to the patient (i) a therapeutically effective amount of a compound of Formula I (e.g., any one of Formulas I-A to I-L), or a pharmaceutically acceptable salt or solvate thereof and (ii) a therapeutically effective amount of a RAF inhibitor (e.g., any of the RAF inhibitors described herein or known in the art).

Provided herein are methods of treating a patient having a cancer (e.g., any of the cancers described herein) that include: identifying a patient having a cancer cell that has dysregulation of a RAF gene, a RAF protein, or the expression or activity or level of the same; and administering to the identified patient (i) a therapeutically effective amount of a compound of Formula I (e.g., any one of Formulas I-A to I-L), or a pharmaceutically acceptable salt or solvate thereof and (ii) a therapeutically effective amount a RAF inhibitor (e.g., any of the RAF inhibitors described herein or known in the art).

Provided herein are methods of treating a patient having a cancer (e.g., any of the cancers described herein) that has dysregulation of a RAS gene, a RAS protein, or the expression or activity or level of the same that include administering to the patient (i) a therapeutically effective amount of a compound of Formula I (e.g., any one of Formulas I-A to I-L), or a pharmaceutically acceptable salt or solvate thereof and (ii) a therapeutically effective amount of a RAS inhibitor (e.g., any of the RAS inhibitors described herein or known in the art).

Provided herein are methods of treating a patient having a cancer (e.g., any of the cancers described herein) that include: identifying a patient having a cancer cell that has dysregulation of a RAS gene, a RAS protein, or the expression or activity or level of the same; and administering to the identified patient (i) a therapeutically effective amount of a compound of Formula I (e.g., any one of Formulas I-A to I-L), or a pharmaceutically acceptable salt or solvate thereof and (ii) a therapeutically effective amount a RAS inhibitor (e.g., any of the RAS inhibitors described herein or known in the art).

The phrase "dysregulation of a BRAF gene, a BRAF protein, or the expression or activity or level of any of the same" refers to a genetic mutation (e.g., a chromosomal translocation that results in the expression of a fusion protein including a BRAF kinase domain and a fusion partner, a mutation in a BRAF gene that results in the expression of a BRAF protein that includes a deletion of at least one amino acid as compared to a wildtype BRAF protein, a mutation in a BRAF gene that results in the expression of a BRAF protein with one or more point mutations as compared to a wildtype BRAF protein, a mutation in a BRAF gene that results in the expression of a BRAF protein with at least one inserted amino acid as compared to a wildtype BRAF protein, a gene duplication that results in an increased level of BRAF protein in a cell, or a mutation in a regulatory sequence (e.g., a promoter and/or enhancer) that results in an increased level of BRAF protein in a cell), an alternative spliced version of a BRAF mRNA that results in a BRAF protein having a deletion of at least one amino acid in the BRAF protein as compared to the wild-type BRAF protein), or increased expression (e.g., increased levels) of a wildtype BRAF protein in a mammalian cell due to aberrant cell signaling and/or dysregulated autocrine/paracrine signaling (e.g., as compared to a control non-cancerous cell). As another example, a dysregulation of a BRAF gene, a BRAF protein, or expression or activity, or level of any of the same, can be a mutation in a BRAF gene that encodes a BRAF protein that is constitutively active or has increased activity as compared to a protein encoded by a BRAF gene that does not include the mutation. For example, a dysregulation of a BRAF gene, a BRAF protein, or expression or activity, or level of any of the same, can be the result of a gene or chromosome translocation which results in the expression of a fusion protein that contains a first portion of a BRAF protein that includes a functional kinase domain, and a second portion of a partner protein (i.e., that is not BRAF). In some examples, dysregulation of a BRAF gene, a BRAF protein, or expression or activity or level of any of the same can be a result of a gene translocation of one BRAF gene with another non-BRAF gene.

Non-limiting examples of a BRAF inhibitor include dabrafenib, vemurafenib (also called RG7204 or PLX4032), sorafenib tosylate, PLX-4720, GDC-0879, BMS-908662 (Bristol-Meyers Squibb), LGX818 (Novartis), PLX3603 (Hofmann-LaRoche), RAF265 (Novartis), RO5185426 (Hofmann-LaRoche), and GSK2118436 (GlaxoSmithKline). Additional examples of a BRAF inhibitor are known in the art.

The phrase "dysregulation of an EGFR gene, an EGFR protein, or the expression or activity or level of any of the same" refers to a genetic mutation (e.g., a chromosomal translocation that results in the expression of a fusion protein including an EGFR kinase domain and a fusion partner, a mutation in an EGFR gene that results in the expression of an EGFR protein that includes a deletion of at least one amino acid as compared to a wildtype EGFR protein, a mutation in an EGFR gene that results in the expression of an EGFR protein with one or more point mutations as compared to a wildtype EGFR protein, a mutation in an EGFR gene that results in the expression of an EGFR protein with at least one inserted amino acid as compared to a wildtype EGFR protein, a gene duplication that results in an increased level of EGFR protein in a cell, or a mutation in a regulatory sequence (e.g., a promoter and/or enhancer) that results in an increased level of EGFR protein in a cell), an alternative spliced version of a EGFR mRNA that results in an EGFR protein having a deletion of at least one amino acid in the EGFR protein as compared to the wild-type EGFR protein), or increased expression (e.g., increased levels) of a wildtype EGFR protein in a mammalian cell due to aberrant cell signaling and/or dysregulated autocrine/paracrine signaling (e.g., as compared to a control non-cancerous cell). As another example, a dysregulation of an EGFR gene, an EGFR protein, or expression or activity, or level of any of the same, can be a mutation in an EGFR gene that encodes an EGFR protein that is constitutively active or has increased activity as compared to a protein encoded by an EGFR gene that does not include the mutation. For example, a dysregulation of an EGFR gene, an EGFR protein, or expression or activity, or level of any of the same, can be the result of a gene or chromosome translocation which results in the expression of a fusion protein that contains a first portion of a EGFR protein that includes a functional kinase domain, and a second portion of a partner protein (i.e., that is not EGFR). In some examples, dysregulation of an EGFR gene, an EGFR protein, or expression or activity or level of any of the same can be a result of a gene translocation of one EGFR gene with another non-EGFR gene.

Non-limiting examples of an EGFR inhibitor include gefitinib, erlotinib, brigatinib, lapatinib, neratinib, icotinib, afatinib, dacomitinib, poziotinib, vandetanib, afatinib, AZD9291, CO-1686, HM61713, AP26113, CI-1033, PKI-166, GW-2016, EKB-569, PDI-168393, AG-1478, CGP-59326A. Additional examples of an EGFR inhibitor are known in the art.

The phrase "dysregulation of a MEK gene, a MEK protein, or the expression or activity or level of any of the same" refers to a genetic mutation (e.g., a chromosomal translocation that results in the expression of a fusion protein including a MEK kinase domain and a fusion partner, a mutation in a MEK gene that results in the expression of a MEK protein that includes a deletion of at least one amino acid as compared to a wildtype MEK protein, a mutation in a MEK gene that results in the expression of a MEK protein with one or more point mutations as compared to a wildtype MEK protein, a mutation in a MEK gene that results in the expression of a MEK protein with at least one inserted amino acid as compared to a wildtype MEK protein, a gene duplication that results in an increased level of MEK protein in a cell, or a mutation in a regulatory sequence (e.g., a promoter and/or enhancer) that results in an increased level of MEK protein in a cell), an alternative spliced version of a MEK mRNA that results in a MEK protein having a deletion of at least one amino acid in the MEK protein as compared to the wild-type MEK protein), or increased expression (e.g., increased levels) of a wildtype MEK protein in a mammalian cell due to aberrant cell signaling and/or dysregulated autocrine/paracrine signaling (e.g., as compared to a control non-cancerous cell). As another example, a dysregulation of a MEK gene, a MEK protein, or expression or activity, or level of any of the same, can be a mutation in a MEK gene that encodes a MEK protein that is constitutively active or has increased activity as compared to a protein encoded by a MEK gene that does not include the mutation. For example, a dysregulation of a MEK gene, a MEK protein, or expression or activity, or level of any of the same, can be the result of a gene or chromosome translocation which results in the expression of a fusion protein that contains a first portion of a MEK protein that includes a functional kinase domain, and a second portion of a partner protein (i.e., that is not MEK). In some examples, dysregulation of a MEK gene, a MEK protein, or expression or activity or level of any of the same can be a result of a gene translocation of one MEK gene with another non-MEK gene.

Non-limiting examples of a MEK inhibitor include mekinist, trametinib (GSK1120212), cobimetinib (XL518), binimetinib (MEK162), selumetinib, PD-325901, CI-1040, PD035901, TAK-733, PD098059, U0126, AS703026/MSC1935369, XL-518/GDC-0973, BAY869766/RDEA119, and GSK1120212. Additional examples of a MEK inhibitor are known in the art.

The phrase "dysregulation of an ALK gene, an ALK protein, or the expression or activity or level of any of the same" refers to a genetic mutation (e.g., a chromosomal translocation that results in the expression of a fusion protein including an ALK kinase domain and a fusion partner, a mutation in an ALK gene that results in the expression an ALK protein that includes a deletion of at least one amino acid as compared to a wildtype ALK protein, a mutation in an ALK gene that results in the expression of an ALK protein with one or more point mutations as compared to a wildtype ALK protein, a mutation in an ALK gene that results in the expression of an ALK protein with at least one inserted amino acid as compared to a wildtype ALK protein, a gene duplication that results in an increased level of ALK protein in a cell, or a mutation in a regulatory sequence (e.g., a promoter and/or enhancer) that results in an increased level of ALK protein in a cell), an alternative spliced version of an ALK mRNA that results in an ALK protein having a deletion of at least one amino acid in the ALK protein as compared to the wild-type ALK protein), or increased expression (e.g., increased levels) of a wildtype ALK protein in a mammalian cell due to aberrant cell signaling and/or dysregulated autocrine/paracrine signaling (e.g., as compared to a control non-cancerous cell). As another example, a dysregulation of an ALK gene, an ALK protein, or expression or activity, or level of any of the same, can be a mutation in an ALK gene that encodes an ALK protein that is constitutively active or has increased activity as compared to a protein encoded by an ALK gene that does not include the mutation. For example, a dysregulation of an ALK gene, an ALK protein, or expression or activity, or level of any of the same, can be the result of a gene or chromosome translocation which results in the expression of a fusion protein that contains a first portion of an ALK protein that includes a functional kinase domain, and a second portion of a partner protein (i.e., that is not ALK). In some examples, dysregulation of an ALK gene, an ALK protein, or expression or activity or level of any of the same can be a result of a gene translocation of one ALK gene with another non-ALK gene.

Non-limiting examples of an ALK inhibitor include crizotinib (Xalkori), ceritinib (Zykadia), alectinib (Alecensa), dalantercept, ACE-041 (Brigatinib) (AP26113), entrectinib (NMS-E628), PF-06463922 (Pfizer), TSR-011 (Tesaro), CEP-37440 (Teva), CEP-37440 (Teva), X-396 (Xcovery), and ASP-3026 (Astellas). Additional examples of an ALK inhibitor are known in the art.

The phrase "dysregulation of a ROS1 gene, a ROS1 protein, or the expression or activity or level of any of the same" refers to a genetic mutation (e.g., a chromosomal translocation that results in the expression of a fusion protein including a ROS1 kinase domain and a fusion partner, a mutation in a ROS1 gene that results in the expression a ROS1 protein that includes a deletion of at least one amino acid as compared to a wildtype ROS1 protein, a mutation in a ROS1 gene that results in the expression of a ROS1 protein with one or more point mutations as compared to a wildtype ROS1 protein, a mutation in a ROS1 gene that results in the expression of a ROS1 protein with at least one inserted amino acid as compared to a wildtype ROS1 protein, a gene duplication that results in an increased level of ROS1 protein in a cell, or a mutation in a regulatory sequence (e.g., a promoter and/or enhancer) that results in an increased level of ROS1 protein in a cell), an alternative spliced version of a ROS1 mRNA that results in a ROS1 protein having a deletion of at least one amino acid in the ROS1 protein as compared to the wild-type ROS1 protein), or increased expression (e.g., increased levels) of a wildtype ROS1 protein in a mammalian cell due to aberrant cell signaling and/or dysregulated autocrine/paracrine signaling (e.g., as compared to a control non-cancerous cell). As another example, a dysregulation of a ROS1 gene, a ROS1 protein, or expression or activity, or level of any of the same, can be a mutation in a ROS1 gene that encodes a ROS1 protein that is constitutively active or has increased activity as compared to a protein encoded by a ROS1 gene that does not include the mutation. For example, a dysregulation of a ROS1 gene, a ROS1 protein, or expression or activity, or level of any of the same, can be the result of a gene or chromosome translocation which results in the expression of a fusion protein that contains a first portion of a ROS1 protein that includes a functional kinase domain, and a second portion of a partner protein (i.e., that is not ROS1). In some examples, dysregulation of a ROS1 gene, a ROS1 protein, or expression or activity or level of any of the same can be a result of a gene translocation of one ROS1 gene with another non-ROS1 gene.

Non-limiting examples of a ROS1 inhibitor include crizotinib, entrectinib (RXDX-101), lorlatinib (PF-06463922), certinib, TPX-0005, DS-605, and cabozantinib. Additional examples of a ROS1 inhibitor are known in the art.

The phrase "dysregulation of a MET gene, a MET protein, or the expression or activity or level of any of the same" refers to a genetic mutation (e.g., a chromosomal translocation that results in the expression of a fusion protein including a MET kinase domain and a fusion partner, a mutation in a MET gene that results in the expression a MET protein that includes a deletion of at least one amino acid as compared to a wildtype MET protein, a mutation in a MET gene that results in the expression of a MET protein with one or more point mutations as compared to a wildtype MET protein, a mutation in a MET gene that results in the expression of a MET protein with at least one inserted amino acid as compared to a wildtype MET protein, a gene duplication that results in an increased level of MET protein in a cell, or a mutation in a regulatory sequence (e.g., a promoter and/or enhancer) that results in an increased level of MET protein in a cell), an alternative spliced version of a MET mRNA that results in a MET protein having a deletion of at least one amino acid in the MET protein as compared to the wild-type MET protein), or increased expression (e.g., increased levels) of a wildtype MET protein in a mammalian cell due to aberrant cell signaling and/or dysregulated autocrine/paracrine signaling (e.g., as compared to a control non-cancerous cell). As another example, a dysregulation of a MET gene, a MET protein, or expression or activity, or level of any of the same, can be a mutation in a MET gene that encodes a MET protein that is constitutively active or has increased activity as compared to a protein encoded by a MET gene that does not include the mutation. For example, a dysregulation of a MET gene, a MET protein, or expression or activity, or level of any of the same, can be the result of a gene or chromosome translocation which results in the expression of a fusion protein that contains a first portion of a MET protein that includes a functional kinase domain, and a second portion of a partner protein (i.e., that is not MET). In some examples, dysregulation of a MET gene, a MET protein, or expression or activity or level of any of the same can be a result of a gene translocation of one MET gene with another non-MET gene.

Non-limiting examples of a MET inhibitor include crizotinib, cabozantinib, JNJ-38877605, PF-04217903 (Pfizer), MK-2461, GSK 1363089, AMG 458 (Amgen), tivantinib, INCB28060 (Incyte), PF-02341066 (Pfizer), E7050 (Eisai), BMS-777607 (Bristol-Meyers Squibb), JNJ-38877605 (Johnson & Johnson), ARQ197 (ArQule), GSK/1363089/XL880 (GSK/Exeilixis), and XL174 (BMS/Exelixis). Additional examples of a MET inhibitor are known in the art.

The phrase "dysregulation of a aromatase gene, an aromatase protein, or the expression or activity or level of any of the same" refers to a genetic mutation (e.g., a mutation in an aromatase gene that results in the expression an aromatase protein that includes a deletion of at least one amino acid as compared to a wildtype aromatase protein, a mutation in an aromatase gene that results in the expression of an aromatase protein with one or more point mutations as compared to a wildtype aromatase protein, a mutation in an aromatase gene that results in the expression of an aromatase protein with at least one inserted amino acid as compared to a wildtype aromatase protein, a gene duplication that results in an increased level of aromatase protein in a cell, or a mutation in a regulatory sequence (e.g., a promoter and/or enhancer) that results in an increased level of aromatase protein in a cell), an alternative spliced version of an aromatase mRNA that results in an aromatase protein having a deletion of at least one amino acid in the aromatase protein as compared to the wild-type aromatase protein), or increased expression (e.g., increased levels) of a wildtype aromatase in a mammalian cell due to aberrant cell signaling and/or dysregulated autocrine/paracrine signaling (e.g., as compared to a control non-cancerous cell). As another example, a dysregulation of an aromatase gene, an aromatase protein, or expression or activity, or level of any of the same, can be a mutation in an aromatase gene that encodes an aromatase protein that is constitutively active or has increased activity as compared to a protein encoded by an aromatase gene that does not include the mutation.

Non-limiting examples of an aromatase inhibitor include Arimidex (anastrozole), Aromasin (exemestane), Femara (letrozole), Teslac (testolactone), and formestane. Additional examples of an aromatase inhibitor are known in the art.

The phrase "dysregulation of a RAF gene, a RAF protein, or the expression or activity or level of any of the same" refers to a genetic mutation (e.g., a chromosomal translocation that results in the expression of a fusion protein including a RAF kinase domain and a fusion partner, a mutation in a RAF gene that results in the expression a RAF protein that includes a deletion of at least one amino acid as compared to a wildtype RAF protein, a mutation in a RAF gene that results in the expression of a RAF protein with one or more point mutations as compared to a wildtype RAF protein, a mutation in a RAF gene that results in the expression of a RAF protein with at least one inserted amino acid as compared to a wildtype RAF protein, a gene duplication that results in an increased level of RAF protein in a cell, or a mutation in a regulatory sequence (e.g., a promoter and/or enhancer) that results in an increased level of RAF protein in a cell), an alternative spliced version of a RAF mRNA that results in a RAF protein having a deletion of at least one amino acid in the RAF protein as compared to the wild-type RAF protein), or increased expression (e.g., increased levels) of a wildtype RAF protein in a mammalian cell due to aberrant cell signaling and/or dysregulated autocrine/paracrine signaling (e.g., as compared to a control non-cancerous cell). As another example, a dysregulation of a RAF gene, a RAF protein, or expression or activity, or level of any of the same, can be a mutation in a RAF gene that encodes a RAF protein that is constitutively active or has increased activity as compared to a protein encoded by a RAF gene that does not include the mutation. For example, a dysregulation of a RAF gene, a RAF protein, or expression or activity, or level of any of the same, can be the result of a gene or chromosome translocation which results in the expression of a fusion protein that contains a first portion of a RAF protein that includes a functional kinase domain, and a second portion of a partner protein (i.e., that is not RAF). In some examples, dysregulation of a RAF gene, a RAF protein, or expression or activity or level of any of the same can be a result of a gene translocation of one RAF gene with another non-RAF gene.

Non-limiting examples of a RAF inhibitor include sorafenib, vemurafenib, dabrafenib, BMS-908662/XL281, GSK2118436, RAF265, RO5126766, and RO4987655. Additional examples of a RAF inhibitor are known in the art.

The phrase "dysregulation of a RAS gene, a RAS protein, or the expression or activity or level of any of the same" refers to a genetic mutation (e.g., a chromosomal translocation that results in the expression of a fusion protein including a RAS kinase domain and a fusion partner, a mutation in a RAS gene that results in the expression a RAS protein that includes a deletion of at least one amino acid as compared to a wildtype RAS protein, a mutation in a RAS gene that results in the expression of a RAS protein with one or more point mutations as compared to a wildtype RAS protein, a mutation in a RAS gene that results in the expression of a RAS protein with at least one inserted amino acid as compared to a wildtype RAS protein, a gene duplication that results in an increased level of RAS protein in a cell, or a mutation in a regulatory sequence (e.g., a promoter and/or enhancer) that results in an increased level of RAS protein in a cell), an alternative spliced version of a RAS mRNA that results in a RAS protein having a deletion of at least one amino acid in the RAS protein as compared to the wild-type RAS protein), or increased expression (e.g., increased levels) of a wildtype RAS protein in a mammalian cell due to aberrant cell signaling and/or dysregulated autocrine/paracrine signaling (e.g., as compared to a control non-cancerous cell). As another example, a dysregulation of a RAS gene, a RAS protein, or expression or activity, or level of any of the same, can be a mutation in a RAS gene that encodes a RAS protein that is constitutively active or has increased activity as compared to a protein encoded by a RAS gene that does not include the mutation. For example, a dysregulation of a RAS gene, a RAS protein, or expression or activity, or level of any of the same, can be the result of a gene or chromosome translocation which results in the expression of a fusion protein that contains a first portion of a RAS protein that includes a functional kinase domain, and a second portion of a partner protein (i.e., that is not RAS). In some examples, dysregulation of a RAS gene, a RAS protein, or expression or activity or level of any of the same can be a result of a gene translocation of one RAS gene with another non-RAS gene.

Non-limiting examples of a RAS inhibitor include Kobe0065 and Kobe2602. Additional examples of a RAS inhibitor are known in the art.

Non-limiting examples of multi-kinase inhibitors (MKIs) include dasatinib and sunitinib.

In some embodiments, provided herein are methods of treating a subject having a cancer that include: (a) administering one or more doses of a first RET inhibitor or a compound of Formula I (e.g., any one of Formulas I-A to I-L), or a pharmaceutically acceptable salt or solvate thereof to the subject for a period of time; (b) after (a), determining whether a cancer cell in a sample obtained from the subject has at least one dysregulation of a gene, a protein, or the expression or activity or level of any of the same, wherein the gene or protein is selected from the group consisting of EGFR, MET, ALK, ROS1, KRAS, BRAF, RAS, PIK3CA, and HER2; and (c) 1) administering a second RET inhibitor as a monotherapy or in conjunction with another anticancer agent, 2) administering additional doses of the first RET inhibitor or a compound of Formula I (e.g., any one of Formulas I-A to I-L), or a pharmaceutically acceptable salt or solvate thereof in combination with an inhibitor targeting the gene or protein (e.g., an inhibitor of EGFR, MET, ALK, ROS1, KRAS, BRAF, RAS, PIK3CA, and HER2), or 3) stopping administration of the RET inhibitor of step a) and administering an inhibitor targeting the gene or protein (e.g., an inhibitor of EGFR, MET, ALK, ROS1, KRAS, BRAF, RAS, PIK3CA, and HER2) to the subject if the subject has a cancer cell that has at least one dysregulation of a gene, a protein, or the expression or activity or level of the same, wherein the gene or protein is selected from the group consisting of EGFR, MET, ALK, ROS1, KRAS, BRAF, RAS, PIK3CA, and HER2; or (d) administering additional doses of the first RET inhibitor step (a) to the subject if the subject has a cancer cell that does not have a RET inhibitor resistance mutation. In some embodiments, the one or more dysregulations of a gene, a protein, or the expression or activity or level of any of the same, wherein the gene or protein is selected from the group consisting of EGFR, MET, ALK, ROS1, KRAS, BRAF, RAS, PIK3CA, and HER2 confer increased resistance to a cancer cell or tumor to treatment with the first RET inhibitor or the compound of Formula I, or a pharmaceutically acceptable salt or solvate thereof. In some embodiments, the tumor is a NSCLC tumor and the one or more dysregulations of a gene, a protein, or the expression or activity or level of any of the same are selected from targetable mutations in EGFR or MET, targetable rearrangements involving ALK or ROS1, or activating mutations in KRAS. In some embodiments, the tumor is a thyroid (non-MTC) tumor and the one or more dysregulations of a gene, a protein, or the expression or activity or level of any of the same are selected from targetable mutations in BRAF or activating mutations in RAS. In some embodiments, the tumor is a MTC tumor and the one or more dysregulations of a gene, a protein, or the expression or activity or level of any of the same are selected from targetable mutations in ALK or activating mutations in RAS. In some embodiments, the tumor is a pancreatic tumor and the one or more dysregulations of a gene, a protein, or the expression or activity or level of any of the same is an activating mutations in KRAS. In some embodiments, the tumor is a colorectal tumor and the one or more dysregulations of a gene, a protein, or the expression or activity or level of any of the same are selected from targetable mutations in BRAF or PIK3CA or an activating mutation in RAS. In some embodiments, the tumor is a breast tumor and the one or more dysregulations of a gene, a protein, or the expression or activity or level of any of the same are selected from targetable mutations in PIK3CA or alteration in HER2.

Also provided are methods of selecting a treatment for a subject having a cancer that include (a) administering one or more doses of a first RET inhibitor to the subject for a period of time; (b) after (a), determining whether a cancer cell in a sample obtained from the subject has at least one RET inhibitor resistance mutation; and (c) selecting a compound of Formula I (e.g., any one of Formulas I-A to I-L), or a pharmaceutically acceptable salt or solvate thereof as a monotherapy or in conjunction with another anticancer agent for the subject if the subject has a cancer cell that has one or more RET inhibitor resistance mutations; or (d) selecting additional doses of the first RET inhibitor of step (a) for the subject if the subject has a cancer cell that does not have a RET inhibitor resistance mutation. In some embodiments, when additional doses of the first RET inhibitor of step (a) are selected for the subject, the method can further include selecting doses of another anticancer agent for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (c), another RET inhibitor can be the first RET inhibitor administered in step (a).

Also provided are methods of selecting a treatment for a subject having a cancer that include (a) administering one or more doses of a first RET inhibitor to the subject for a period of time; (b) after (a), determining whether a cancer cell in a sample obtained from the subject has at least one RET inhibitor resistance mutation; and (c) selecting a second RET inhibitor as a monotherapy or in conjunction with another anticancer agent if the subject has a cancer cell that has one or more RET inhibitor resistance mutations; or (d) selecting additional doses of the first RET inhibitor of step (a) for the subject if the subject has a cancer cell that does not have a RET inhibitor resistance mutation. In some embodiments, when additional doses of the first RET inhibitor of step (a) are selected for the subject, the method can further include selecting doses of another anticancer agent for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D. In some embodiments, the additional anticancer agent is any anticancer agent known in the art. For example, the additional anticancer agent is another RET inhibitor (e.g., a compound of Formula I (e.g., any one of Formulas I-A to I-L), or a pharmaceutically acceptable salt or solvate thereof). In some embodiments, the additional anticancer agent is an immunotherapy. In some embodiments, another RET can be the first RET inhibitor administered in step (a).

Also provided are methods of selecting a treatment for a subject having a cancer that include (a) determining whether a cancer cell in a sample obtained from a subject having a cancer and previously administered one or more doses of a first RET inhibitor has one or more RET inhibitor resistance mutations; (b) selecting a compound of Formula I (e.g., any one of Formulas I-A to I-L), or a pharmaceutically acceptable salt or solvate thereof as a monotherapy or in conjunction with another anticancer agent for the subject if the subject has a cancer cell that has at least one RET inhibitor resistance mutation; or (c) selecting additional doses of the first RET inhibitor previously administered to the subject if the subject has a cancer cell that does not have a RET inhibitor resistance mutation. In some embodiments, when additional doses of the first RET inhibitor previously administered to the subject are selected for the subject, the method can further include selecting doses of another anticancer agent (e.g., a compound of Formula I (e.g., any one of Formulas I-A to I-L), or a pharmaceutically acceptable salt or solvate thereof or immunotherapy) for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (c), another RET inhibitor can be the first RET inhibitor administered in step (a).

Also provided are methods of selecting a treatment for a subject having a cancer that include (a) determining whether a cancer cell in a sample obtained from a subject having a cancer and previously administered one or more doses of a first RET inhibitor has one or more RET inhibitor resistance mutations; (b) selecting a second RET inhibitor as a monotherapy or in conjunction with another anticancer agent for the subject if the subject has a cancer cell that has at least one RET inhibitor resistance mutation; or (c) selecting additional doses of the first RET inhibitor previously administered to the subject if the subject has a cancer cell that does not have a RET inhibitor resistance mutation. In some embodiments, when additional doses of the first RET inhibitor previously administered to the subject are selected for the subject, the method can further include selecting doses of another anticancer agent (e.g., a compound of Formula I (e.g., any one of Formulas I-A to I-L), or a pharmaceutically acceptable salt or solvate thereof, or an immunotherapy) for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D. In some embodiments, the additional anticancer agent is any anticancer agent known in the art. For example, the additional anticancer agent is another RET inhibitor (e.g., a compound of Formula I (e.g., any one of Formulas I-A to I-L), or a pharmaceutically acceptable salt or solvate thereof). In some embodiments, the additional anticancer agent is an immunotherapy. In some embodiments, another RET can be the first RET inhibitor administered in step (a).

Also provided are methods of determining a subject's risk for developing a cancer that has some resistance to a first RET inhibitor that include: determining whether a cell in a sample obtained from the subject has one or more RET inhibitor resistance mutations; and identifying a subject having a cell that has one or more RET inhibitor resistance mutations, as having an increased likelihood of developing a cancer that has some resistance to the first RET inhibitor. Also provided are methods of determining a subject's risk for developing a cancer that has some resistance to a first RET inhibitor that include: identifying a subject having a cell that has one or more RET inhibitor resistance mutations, as having an increased likelihood of developing a cancer that has some resistance to the first RET inhibitor. Also provided are methods of determining the presence of a cancer that has some resistance to a first RET inhibitor that include: determining whether a cancer cell in a sample obtained from the subject has one or more RET inhibitor resistance mutations; and determining that the subject having a cancer cell that has one or more RET inhibitor resistance mutations has a cancer that has some resistance to the first RET inhibitor. Also provided are methods of determining the presence of a cancer that has some resistance to a first RET inhibitor in a subject that include: determining that a subject having a cancer cell that has one or more RET inhibitor resistance mutations, has a cancer that has some resistance to the first RET inhibitor. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E, or a substitution at amino acid position 810, e.g., G810S, G810R, G810C, G810A, G810V, and G810D.

In some embodiments of any of the methods described herein, a RET inhibitor resistance mutation that confers increased resistance to a cancer cell or tumor to treatment with a first RET inhibitor can be any of the RET inhibitor resistance mutations listed in Table 3 or 4 (e.g., a substitution at amino acid position 804, e.g., V804M, V804L, or V804E, or a substitution at amino acid position 810, e.g., G810S, G810R, G810C, G810A, G810V, and G810D).

In some embodiments, the presence of one or more RET inhibitor resistance mutations in a tumor causes the tumor to be more resistant to treatment with a compound of Formula I (e.g., any one of Formulas I-A to I-L), or a pharmaceutically acceptable salt or solvate thereof. Methods useful when a RET inhibitor resistance mutation causes the tumor to be more resistant to treatment with a compound of Formula I (e.g., any one of Formulas I-A to I-L), or a pharmaceutically acceptable salt or solvate thereof are described below. For example, provided herein are methods of treating a subject having a cancer that include: identifying a subject having a cancer cell that has one or more RET inhibitor resistance mutations; and administering to the identified subject a treatment that does not include a compound of Formula I (e.g., any one of Formulas I-A to I-L), or a pharmaceutically acceptable salt or solvate thereof as a monotherapy (e.g., a second RET kinase inhibitor). Also provided are methods of treating a subject identified as having a cancer cell that has one or more RET inhibitor resistance mutations that include administering to the subject a treatment that does not include a compound of Formula I (e.g., any one of Formulas I-A to I-L), or a pharmaceutically acceptable salt or solvate thereof as a monotherapy (e.g., a second RET kinase inhibitor). In some embodiments, the one or more RET inhibitor resistance mutations confer increased resistance to a cancer cell or tumor to treatment with a compound of Formula I (e.g., any one of Formulas I-A to I-L), or a pharmaceutically acceptable salt or solvate thereof.

Also provided are methods of selecting a treatment for a subject having a cancer that include: identifying a subject having a cancer cell that has one or more RET inhibitor resistance mutations; and selecting a treatment that does not include a compound of Formula I (e.g., any one of Formulas I-A to I-L), or a pharmaceutically acceptable salt or solvate thereof as a monotherapy for the identified subject (e.g., a second RET kinase inhibitor). Also provided are methods of selecting a treatment for a subject having a cancer that include: selecting a treatment that does not include a compound of Formula I (e.g., any one of Formulas I-A to I-L), or a pharmaceutically acceptable salt or solvate thereof as a monotherapy (e.g., a second RET kinase inhibitor) for a subject identified as having a cancer cell that has one or more RET inhibitor resistance mutations. Also provided are methods of selecting a subject having a cancer for a treatment that does not include a compound of Formula I (e.g., any one of Formulas I-A to I-L), or a pharmaceutically acceptable salt or solvate thereof as a monotherapy (e.g., a second RET kinase inhibitor) that include: identifying a subject having a cancer cell that has one or more RET inhibitor resistance mutations; and selecting the identified subject for a treatment that does not include a compound of Formula I (e.g., any one of Formulas I-A to I-L), or a pharmaceutically acceptable salt or solvate thereof as a monotherapy (e.g., a second RET kinase inhibitor). Also provided are methods of selecting a subject having a cancer for a treatment that does not include a compound of Formula I (e.g., any one of Formulas I-A to I-L), or a pharmaceutically acceptable salt or solvate thereof as a monotherapy (e.g., a second RET kinase inhibitor) that include: selecting a subject identified as having a cancer cell that has one or more RET inhibitor resistance mutations for a treatment that does not include a compound of Formula I (e.g., any one of Formulas I-A to I-L), or a pharmaceutically acceptable salt or solvate thereof as a monotherapy. In some embodiments, the one or more RET inhibitor resistance mutations confer increased resistance to a cancer cell or tumor to treatment with a compound of Formula I (e.g., any one of Formulas I-A to I-L), or a pharmaceutically acceptable salt or solvate thereof.

Also provided are methods of determining the likelihood that a subject having a cancer will have a positive response to treatment with a compound of Formula I (e.g., any one of Formulas I-A to I-L), or a pharmaceutically acceptable salt or solvate thereof as a monotherapy that include: determining whether a cancer cell in a sample obtained from the subject has one or more RET inhibitor resistance mutations; and determining that the subject having the cancer cell that has one or more RET inhibitor resistance mutations has a decreased likelihood of having a positive response to treatment with a compound of Formula I (e.g., any one of Formulas I-A to I-L), or a pharmaceutically acceptable salt or solvate thereof as a monotherapy. Also provided are methods of determining the likelihood that a subject having cancer will have a positive response to treatment with a compound of Formula I (e.g., any one of Formulas I-A to I-L), or a pharmaceutically acceptable salt or solvate thereof as a monotherapy that include: determining that a subject having a cancer cell that has one or more RET inhibitor resistance mutations has a decreased likelihood of having a positive response to treatment with a compound of Formula I (e.g., any one of Formulas I-A to I-L), or a pharmaceutically acceptable salt or solvate thereof as a monotherapy. Also provided are methods of predicting the efficacy of treatment with a compound of Formula I (e.g., any one of Formulas I-A to I-L), or a pharmaceutically acceptable salt or solvate thereof as a monotherapy in a subject having cancer that include: determining whether a cancer cell in a sample obtained from the subject has one or more RET inhibitor resistance mutations; and determining that treatment with a compound of Formula I (e.g., any one of Formulas I-A to I-L), or a pharmaceutically acceptable salt or solvate thereof as a monotherapy is less likely to be effective in a subject having a cancer cell in a sample obtained from the subject that has one or more RET inhibitor resistance mutations. Also provided are methods of predicting the efficacy of treatment with a compound of Formula I (e.g., any one of Formulas I-A to I-L), or a pharmaceutically acceptable salt or solvate thereof as a monotherapy in a subject having cancer that include: determining that treatment with a compound of Formula I (e.g., any one of Formulas I-A to I-L), or a pharmaceutically acceptable salt or solvate thereof as a monotherapy is less likely to be effective in a subject having a cancer cell in a sample obtained from the subject that has one or more RET inhibitor resistance mutations. In some embodiments, the one or more RET inhibitor resistance mutations confer increased resistance to a cancer cell or tumor to treatment with a compound of Formula I (e.g., any one of Formulas I-A to I-L), or a pharmaceutically acceptable salt or solvate thereof.

Also provided are methods of treating a subject having a cancer that include: (a) administering one or more doses of a compound of Formula I (e.g., any one of Formulas I-A to I-L), or a pharmaceutically acceptable salt or solvate thereof for a period of time; (b) after (a), determining whether a cancer cell in a sample obtained from the subject has one or more RET inhibitor resistance mutations; and (c) administering a second RET inhibitor or a second compound of Formula I (e.g., any one of Formulas I-A to I-L), or a pharmaceutically acceptable salt or solvate thereof as a monotherapy or in conjunction with another anticancer agent to a subject having a cancer cell that has one or more RET inhibitor resistance mutations; or (d) administering additional doses of the compound of Formula I, or a pharmaceutically acceptable salt or solvate thereof of step (a) to a subject having a cancer cell that does not have a RET inhibitor resistance mutation. In some embodiments, where the subject is administered additional doses of the compound of Formula I, or a pharmaceutically acceptable salt or solvate thereof of step (a), the subject can also be administered another anticancer agent or a second compound of Formula I (e.g., any one of Formulas I-A to I-L), or a pharmaceutically acceptable salt or solvate thereof. In some embodiments, the one or more RET inhibitor resistance mutations confer increased resistance to a cancer cell or tumor to treatment with a compound of Formula I (e.g., any one of Formulas I-A to I-L), or a pharmaceutically acceptable salt or solvate thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula I, or a pharmaceutically acceptable salt or solvate thereof administered in step (a).

Also provided are methods of treating a subject having a cancer that include: (a) determining whether a cancer cell in a sample obtained from a subject having a cancer and previously administered one or more doses of a compound of Formula I (e.g., any one of Formulas I-A to I-L), or a pharmaceutically acceptable salt or solvate thereof, has one or more RET inhibitor resistance mutations; (b) administering a second RET inhibitor or a second compound of Formula I (e.g., any one of Formulas I-A to I-L), or a pharmaceutically acceptable salt or solvate thereof as a monotherapy or in conjunction with another anticancer agent to a subject having a cancer cell that has one or more RET inhibitor resistance mutations; or (c) administering additional doses of the compound of Formula I, or a pharmaceutically acceptable salt or solvate thereof previously administered to a subject having a cancer cell that does not have a RET inhibitor resistance mutation. In some embodiments, where the subject is administered additional doses of the compound of Formula I, or a pharmaceutically acceptable salt or solvate thereof of step (a), the subject can also be administered another anticancer agent. In some embodiments, the one or more RET inhibitor resistance mutations confer increased resistance to a cancer cell or tumor to treatment with a compound of Formula I (e.g., any one of Formulas I-A to I-L), or a pharmaceutically acceptable salt or solvate thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula I, or a pharmaceutically acceptable salt or solvate thereof administered in step (a).

Also provided are methods of selecting a treatment for a subject having a cancer that include: (a) administering one or more doses of a compound of Formula I (e.g., any one of Formulas I-A to I-L), or a pharmaceutically acceptable salt or solvate thereof to the subject for a period of time; (b) after (a), determining whether a cancer cell in a sample obtained from the subject has one or more RET inhibitor resistance mutations; and (c) selecting a second RET inhibitor or a second compound of Formula I (e.g., any one of Formulas I-A to I-L), or a pharmaceutically acceptable salt or solvate thereof as a monotherapy or in conjunction with another anticancer agent for the subject if the subject has a cancer cell that has a RET inhibitor resistance mutation; or (d) selecting additional doses of the compound of Formula I, or a pharmaceutically acceptable salt or solvate thereof of step (a) for the subject if the subject has a cancer cell that does not have a RET inhibitor resistance mutation. In some embodiments, where additional doses of a compound of Formula I (e.g., any one of Formulas I-A to I-L), or a pharmaceutically acceptable salt or solvate thereof of step (a) are selected for the subject, the method can also include further selecting another anticancer agent. In some embodiments, the one or more RET inhibitor resistance mutations confer increased resistance to a cancer cell or tumor to treatment with a compound of Formula I (e.g., any one of Formulas I-A to I-L), or a pharmaceutically acceptable salt or solvate thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula I, or a pharmaceutically acceptable salt or solvate thereof administered in step (a).

Also provided are methods of selecting a treatment for a subject having a cancer that include: (a) determining whether a cancer cell in a sample obtained from a subject having a cancer and previously administered one or more doses of a compound of Formula I (e.g., any one of Formulas I-A to I-L), or a pharmaceutically acceptable salt or solvate thereof, has one or more RET inhibitor resistance mutations; (b) selecting a second RET inhibitor or a second compound of Formula I (e.g., any one of Formulas I-A to I-L), or a pharmaceutically acceptable salt or solvate thereof as a monotherapy or in conjunction with another anticancer agent for the subject if the subject has a cancer cell that has a RET inhibitor resistance mutation; or (c) selecting additional doses of the compound of Formula I, or a pharmaceutically acceptable salt or solvate thereof previously administered to the subject if the subject has a cancer cell that does not have a RET inhibitor resistance mutation. In some embodiments, where additional doses of the compound of Formula I, or a pharmaceutically acceptable salt or solvate thereof of step (a) are selected for the subject, the method can also include further selecting another anticancer agent. In some embodiments, the one or more RET inhibitor resistance mutations confer increased resistance to a cancer cell or tumor to treatment with a compound of Formula I (e.g., any one of Formulas I-A to I-L), or a pharmaceutically acceptable salt or solvate thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula I, or a pharmaceutically acceptable salt or solvate thereof administered in step (a).

Also provided are methods of determining a subject's risk for developing a cancer that has some resistance to a compound of Formula I (e.g., any one of Formulas I-A to I-L), or a pharmaceutically acceptable salt or solvate thereof that include: determining whether a cell in a sample obtained from the subject has one or more RET inhibitor resistance mutations; and identifying the subject if the subject has a cell that has one or more RET inhibitor resistance mutations as having an increased likelihood of developing a cancer that has some resistance to a compound of Formula I (e.g., any one of Formulas I-A to I-L), or a pharmaceutically acceptable salt or solvate thereof. Also provided are methods of determining a subject's risk for developing a cancer that has some resistance to a compound of Formula I (e.g., any one of Formulas I-A to I-L), or a pharmaceutically acceptable salt or solvate thereof that include: identifying a subject having a cell that has one or more RET inhibitor resistance mutations as having an increased likelihood of developing a cancer that has some resistance to a compound of Formula I (e.g., any one of Formulas I-A to I-L), or a pharmaceutically acceptable salt or solvate thereof. Also provided are methods of determining the presence of a cancer that has some resistance to a compound of Formula I (e.g., any one of Formulas I-A to I-L), or a pharmaceutically acceptable salt or solvate thereof that includes: determining whether a cancer cell in a sample obtained from the subject has one or more RET inhibitor resistance mutations; and determining that the subject having the cancer cell that has one or more RET inhibitor resistance mutations has a cancer that has some resistance to a compound of Formula I (e.g., any one of Formulas I-A to I-L), or a pharmaceutically acceptable salt or solvate thereof. Also provided are methods of determining the presence of a cancer that has some resistance to a compound of Formula I (e.g., any one of Formulas I-A to I-L), or a pharmaceutically acceptable salt or solvate thereof in a subject that include: determining that a subject having a cancer cell that has one or more RET inhibitor resistance mutations has a cancer that has some resistance to a compound of Formula I (e.g., any one of Formulas I-A to I-L), or a pharmaceutically acceptable salt or solvate thereof. In some embodiments, the one or more RET inhibitor resistance mutations confer increased resistance to a cancer cell or tumor to treatment with a compound of Formula I (e.g., any one of Formulas I-A to I-L), or a pharmaceutically acceptable salt or solvate thereof.

In some embodiments of any of the methods described herein, a RET inhibitor resistance mutation that confers increased resistance to a cancer cell or tumor to treatment with a compound of Formula I (e.g., any one of Formulas I-A to I-L), or a pharmaceutically acceptable salt or solvate thereof, can be any of the RET inhibitor resistance mutations listed in Table 3 or 4.

Methods of determining the level of resistance of a cancer cell or a tumor to a RET inhibitor (e.g., any of the RET inhibitors described herein or known in the art) can be determined using methods known in the art. For example, the level of resistance of a cancer cell to a RET inhibitor can be assessed by determining the $IC_{50}$ of a RET inhibitor (e.g., any of the RET inhibitors described herein or known in the art) on the viability of a cancer cell. In other examples, the level of resistance of a cancer cell to a RET inhibitor can be assessed by determining the growth rate of the cancer cell in the presence of a RET inhibitor (e.g., any of the RET inhibitors described herein). In other examples, the level of resistance of a tumor to a RET inhibitor can be assessed by determining the mass or size of one or more tumors in a subject over time during treatment with a RET inhibitor (e.g., any of the RET inhibitors described herein). In other examples, the level of resistance of a cancer cell or a tumor to a RET inhibitor can be indirectly assessed by determining the activity of a RET kinase including one or more of the RET inhibitor resistance mutations (i.e., the same RET kinase expressed in a cancer cell or a tumor in a subject). The level of resistance of a cancer cell or tumor having one or more RET inhibitor resistance mutations to a RET inhibitor is relative to the level of resistance in a cancer cell or tumor that does not have a RET inhibitor resistance mutation (e.g., a cancer cell or tumor that does not have the same RET inhibitor resistance mutations, a cancer cell or a tumor that does not have any RET inhibitor resistance mutations, or a cancer cell or a tumor that expresses a wildtype RET protein). For example, the determined level of resistance of a cancer cell or a tumor having one or more RET inhibitor resistance mutations can be greater than about 1%, greater than about 2%, greater than about 3%, greater than about 4%, greater than about 5%, greater than about 6%, greater than about 7%, greater than about 8%, greater than about 9%, greater than about 10%, greater than about 11%, greater than about 12%, greater than about 13%, greater than about 14%, greater than about 15%, greater than about 20%, greater than about 25%, greater than about 30%, greater than about 35%, greater than about 40%, greater than about 45%, greater than about 50%, greater than about 60%, greater than about 70%, greater than about 80%, greater than about 90%, greater than about 100%, greater than about 110%, greater than about 120%, greater than about 130%, greater than about 140%, greater than about 150%, greater than about 160%, greater than about 170%, greater than about 180%, greater than about 190%, greater than about 200%, greater than about 210%, greater than about 220%, greater than about 230%, greater than about 240%, greater than about 250%, greater than about 260%, greater than about 270%, greater than about 280%, greater than about 290%, or greater than about 300% of the level of resistance in a cancer cell or tumor that does not have a RET inhibitor resistance mutation (e.g., a cancer cell or tumor that does not have the same RET inhibitor resistance mutations, a cancer cell or a tumor that does not have any RET inhibitor resistance mutations, or a cancer cell or a tumor that expresses a wildtype RET protein).

RET is thought to play an important role in the development and survival of afferent nociceptors in the skin and gut. RET kinase knock-out mice lack enteric neurons and have other nervous system anomalies suggesting that a functional RET kinase protein product is necessary during development (Taraviras, S. et al., *Development*, 1999, 126:2785-2797). Moreover population studies of patients with Hirschsprung's disease characterized by colonic obstruction due to lack of normal colonic enervation have a higher proportion of both familial and sporadic loss of function RET mutations (Butler Tjaden N., et al., *Transl. Res.*, 2013, 162:1-15). Irritable bowel syndrome (IBS) is a common illness affecting 10-20% of individuals in developed countries and is characterized by abnormal bowel habits, bloating and visceral hypersensitivity (Camilleri, M., *N. Engl. J. Med.*, 2012, 367: 1626-1635). While the etiology of IBS is unknown it is thought to result from either a disorder between the brain and gastrointestinal tract, a disturbance in the gut microbiome or increased inflammation. The resulting gastrointestinal changes affect normal bowel transit resulting in either diarrhea or constipation. Furthermore in many IBS patients the sensitization of the peripheral nervous system results in visceral hypersensitivity or allodynia (Keszthelyi, D., *Eur. J. Pain*, 2012, 16: 1444-1454). See, e.g., U.S. Publication No. 2015/0099762.

Accordingly, provided herein are methods for treating a patient diagnosed with (or identified as having) an irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, and inflammatory bowel disease that include administering to the patient a therapeutically effective amount of a compound of Formula I (e.g., any one of Formulas I-A to I-L), or a pharmaceutically acceptable salt or solvate thereof.

Also provided herein are methods for treating a patient identified or diagnosed as having a RET-associated irritable bowel syndrome (IBS) (e.g., a patient that has been identified or diagnosed as having a RET-associated irritable bowel syndrome (IBS) through the use of a regulatory agency-approved, e.g., FDA-approved, kit for identifying dysregulation of a RET gene, a RET kinase, or expression or activity or level of any of the same, in a patient or a biopsy sample from the patient) that include administering to the patient a therapeutically effective amount of a compound of Formula I (e.g., any one of Formulas I-A to I-L), or a pharmaceutically acceptable salt or solvate thereof.

Also provided herein are methods for treating pain associated with IBS that include administering to the patient a therapeutically effective amount of a compound of Formula I (e.g., any one of Formulas I-A to I-L), or a pharmaceutically acceptable salt or solvate thereof. In some embodiments, a compound of Formula I (e.g., any one of Formulas I-A to I-L), or a pharmaceutically acceptable salt or solvate thereof is administered in combination with another therapeutic agent useful for treating one or more symptoms of IBS.

Also provided are methods for treating an irritable bowel syndrome (IBS) in a patient in need thereof, the method comprising: (a) determining if the irritable bowel syndrome (IBS) in the patient is a RET-associated IBS (e.g., using a regulatory-agency approved, e.g., FDA-approved, kit for identifying dysregulation of a RET gene, a RET kinase, or expression or activity or level of any of the same, in a patient or a biopsy sample from the patient, or by performing any of the non-limiting examples of assays described herein); and (b) if the IBS is determined to be a RET-associated IBS, administering to the patient a therapeutically effective amount of a compound of Formula I (e.g., any one of Formulas I-A to I-L), or a pharmaceutically acceptable salt or solvate thereof.

In some embodiments, the compounds of the present invention are useful for treating irritable bowel syndrome (IBS) in combination with one or more additional therapeutic agents or therapies effective in treating the irritable bowel syndrome that work by the same or a different mechanism of action. The at least one additional therapeutic agent may be administered with a compound of Formula I (e.g., any one of Formulas I-A to I-L), or a pharmaceutically acceptable salt or solvate thereof as part of the same or separate dosage forms, via the same or different routes of administration, and on the same or different administration schedules according to standard pharmaceutical practice known to one skilled in the art.

Non-limiting examples of additional therapeutics for the treatment of irritable bowel syndrome (IBS) include probiotics, fiber supplements (e.g., psyllium, methylcellulose), anti-diarrheal medications (e.g., loperamide), bile acid binders (e.g., cholestyramine, colestipol, colesevelam), anticholinergic and antispasmodic medications (e.g., hyoscyamine, dicyclomine), antidepressant medications (e.g., tricyclic antidepressant such as imipramine or nortriptyline or a selective serotonin reuptake inhibitor (SSRI) such as fluoxetine or paroxetine), antibiotics (e.g., rifaximin), alosetron, and lubiprostone.

Accordingly, also provided herein are methods of treating irritable bowel syndrome (IBS), comprising administering to a patient in need thereof a pharmaceutical combination for treating IBS which comprises (a) a compound of Formula I (e.g., any one of Formulas I-A to I-L), or a pharmaceutically acceptable salt or solvate thereof, (b) an additional therapeutic agent, and (c) optionally at least one pharmaceutically acceptable carrier for simultaneous, separate or sequential use for the treatment of IBS, wherein the amounts of the compound of Formula I, or a pharmaceutically acceptable salt or solvate thereof and the additional therapeutic agent are together effective in treating the IBS. In one embodiment, the compound of Formula I, or a pharmaceutically acceptable salt or solvate thereof, and the additional therapeutic agent are administered simultaneously as separate dosages. In one embodiment, the compound of Formula I, or a pharmaceutically acceptable salt or solvate thereof, and the additional therapeutic agent are administered as separate dosages sequentially in any order, in jointly therapeutically effective amounts, e.g. in daily or intermittently dosages. In one embodiment, compound of Formula I (e.g., any one of Formulas I-A to I-L), or a pharmaceutically acceptable salt or solvate thereof, and the additional therapeutic agent are administered simultaneously as a combined dosage.

Also provided herein is (i) a pharmaceutical combination for treating irritable bowel syndrome in a patient in need thereof, which comprises (a) a compound of Formula I (e.g., any one of Formulas I-A to I-L), or a pharmaceutically acceptable salt or solvate thereof, (b) at least one additional therapeutic agent (e.g., any of the exemplary additional therapeutic agents described herein for treating irritable bowel syndrome or known in the art), and (c) optionally at least one pharmaceutically acceptable carrier for simultaneous, separate or sequential use for the treatment of irritable bowel syndrome, wherein the amounts of the compound of Formula I, or a pharmaceutically acceptable salt or solvate thereof and of the additional therapeutic agent are together effective in treating the irritable bowel syndrome; (ii) a pharmaceutical composition comprising such a combination; (iii) the use of such a combination for the preparation of a medicament for the treatment of irritable bowel syndrome; and (iv) a commercial package or product comprising such a combination as a combined preparation for simultaneous, separate or sequential use; and to a method of treatment of irritable bowel syndrome in a patient in need thereof. In one embodiment the patient is a human.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of Formula I (e.g., any one of Formulas I-A to I-L), or a pharmaceutically acceptable salt or solvate thereof and at least one additional therapeutic agent (e.g., an agent effective in treating irritable bowel syndrome), are both administered to a patient simultaneously in the form of a single composition or dosage. The term "non-fixed combination" means that a compound of Formula I (e.g., any one of Formulas I-A to I-L), or a pharmaceutically acceptable salt or solvate thereof and at least one additional therapeutic agent (e.g., an agent effective in treating irritable bowel syndrome) are formulated as separate compositions or dosages, such that they may be administered to a patient in need thereof simultaneously, concurrently or sequentially with variable intervening time limits, wherein such administration provides effective levels of the two or more compounds in the body of the patient. In one embodiment, the compound of Formula I, or a pharmaceutically acceptable salt or solvate thereof and the additional therapeutic agent are formulated as separate unit dosage forms, wherein the separate dosages forms are suitable for either sequential or simultaneous administration. These also apply to cocktail therapies, e.g. the administration of three or more active ingredients.

In some embodiments, a compound provided herein can be used as an agent for supportive care for a patient undergoing cancer treatment. For example, a compound of Formula I (e.g., any one of Formulas I-A to I-L), or a pharmaceutically acceptable salt or solvate thereof, can be useful to reduce one or more symptoms associated with treatment with one or more cancer therapies such as diarrheal or constipations complications and/or abdominal pain. See, for example, U.S. Publication No. 2015/0099762 and Hoffman, J. M. et al. *Gastroenterology* (2012) 142:844-854. Accordingly, a compound, or a pharmaceutically acceptable salt thereof, or composition provided herein can be administered to a patient to address one or more complications associated with cancer treatment (e.g., gastrointestinal complications such as diarrhea, constipation, or abdominal pain).

In some embodiments, a therapeutically effective amount of a compound of Formula I (e.g., any one of Formulas I-A to I-L), or a pharmaceutically acceptable salt or solvate thereof, can be administered to a patient undergoing cancer treatment (e.g., a patient experiencing an adverse event associated with cancer treatment such as an immune-related adverse event or a gastrointestinal complication including diarrhea, constipation, and abdominal pain). For example, a compound provided herein, or a pharmaceutically acceptable salt thereof, can be used in the treatment of colitis or IBS associated with administration of a checkpoint inhibitor; see, e.g., Postow, M. A. et al. *Journal of Clinical Oncology* (2015) 33:1974-1982. In some such embodiments, a compound provided herein, or a pharmaceutically acceptable salt thereof, can be formulated to exhibit low bioavailability and/or be targeted for delivery in the gastrointestinal tract. See, for example, U.S. Pat. No. 6,531,152.

Also provided is a method for inhibiting RET kinase activity in a cell, comprising contacting the cell with a compound of Formula I. In one embodiment, the contacting is in vitro. In one embodiment, the contacting is in vivo. In one embodiment, the contacting is in vivo, wherein the method comprises administering an effective amount of a compound of Formula I (e.g., any one of Formulas I-A to I-L), or a pharmaceutically acceptable salt or solvate thereof to a subject having a cell having RET kinase activity. In some embodiments, the cell is a cancer cell. In one embodiment, the cancer cell is any cancer as described herein. In some embodiments, the cancer cell is a RET-associated cancer cell. In some embodiments, the cell is a gastrointestinal cell.

Also provided is a method for inhibiting RET kinase activity in a mammalian cell, comprising contacting the cell with a compound of Formula I. In one embodiment, the contacting is in vitro. In one embodiment, the contacting is in vivo. In one embodiment, the contacting is in vivo, wherein the method comprises administering an effective amount of a compound of Formula I (e.g., any one of Formulas I-A to I-L), or a pharmaceutically acceptable salt or solvate thereof to a mammal having a cell having RET kinase activity. In some embodiments, the mammalian cell is a mammalian cancer cell. In one embodiment, the mammalian cancer cell is any cancer as described herein. In some embodiments, the mammalian cancer cell is a RET-associated cancer cell. In some embodiments, the mammalian cell is a gastrointestinal cell.

As used herein, the term "contacting" refers to the bringing together of indicated moieties in an in vitro system or an in vivo system. For example, "contacting" a RET kinase with a compound provided herein includes the administration of a compound provided herein to an individual or patient, such as a human, having a RET kinase, as well as, for example, introducing a compound provided herein into a sample containing a cellular or purified preparation containing the RET kinase.

Also provided herein is a method of inhibiting cell proliferation, in vitro or in vivo, the method comprising contacting a cell with an effective amount of a compound of Formula I (e.g., any one of Formulas I-A to I-L), or a pharmaceutically acceptable salt or solvate thereof, or a pharmaceutical composition thereof as defined herein.

The phrase "effective amount" means an amount of compound that, when administered to a patient in need of such treatment, is sufficient to (i) treat a RET kinase-associated disease or disorder, (ii) attenuate, ameliorate, or eliminate one or more symptoms of the particular disease, condition, or disorder, or (iii) delay the onset of one or more symptoms of the particular disease, condition, or disorder described herein. The amount of a compound of Formula I (e.g., any one of Formulas I-A to I-L), or a pharmaceutically acceptable salt or solvate thereof that will correspond to such an amount will vary depending upon factors such as the particular compound, disease condition and its severity, the identity (e.g., weight) of the patient in need of treatment, but can nevertheless be routinely determined by one skilled in the art.

When employed as pharmaceuticals, the compound of Formula I (e.g., any one of Formulas I-A to I-L), including pharmaceutically acceptable salts or solvates thereof, can be administered in the form of pharmaceutical compositions. These compositions can be prepared in a manner well known in the pharmaceutical art, and can be administered by a variety of routes, depending upon whether local or systemic treatment is desired and upon the area to be treated. Administration can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided herein are pharmaceutical compositions which contain, as the active ingredient, a compound of Formula I (e.g., any one of Formulas I-A to I-L) or pharmaceutically acceptable salt or solvate thereof, in combination with one or more pharmaceutically acceptable carriers (excipients). For example, a pharmaceutical composition prepared using a compound of Formula I (e.g., any one of Formulas I-A to I-L) or a pharmaceutically acceptable salt or solvate thereof. In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is a solid oral formulation. In some embodiments, the composition is formulated as a tablet or capsule.

Further provided herein are pharmaceutical compositions containing a compound of Formula I (e.g., any one of Formulas I-A to I-L) or a pharmaceutically acceptable salt or solvate thereof with a pharmaceutically acceptable carrier. Pharmaceutical compositions containing a compound of Formula I (e.g., any one of Formulas I-A to I-L) or a pharmaceutically acceptable salt or solvate thereof as the active ingredient can be prepared by intimately mixing the compound of Formula I or a pharmaceutically acceptable salt or solvate thereof with a pharmaceutical carrier according to conventional pharmaceutical compounding techniques. The carrier can take a wide variety of forms depending upon the desired route of administration (e.g., oral, parenteral). In some embodiments, the composition is a solid oral composition.

Suitable pharmaceutically acceptable carriers are well known in the art. Descriptions of some of these pharmaceutically acceptable carriers can be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded,* Volumes 1-3, edited by Lieberman et al; *Pharmaceutical Dosage Forms: Parenteral Medications,* Volumes 1-2, edited by Avis et al; and *Pharmaceutical Dosage Forms: Disperse Systems,* Volumes 1-2, edited by Lieberman et al; published by Marcel Dekker, Inc.

In preparing the compositions in oral dosage form, any of the usual pharmaceutical media can be employed. Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Solid oral preparations can also be coated with substances such as sugars or be enteric-coated so as to modulate major site of absorption. For parenteral administration, the carrier will usually consist of sterile water and other ingredients can be added to increase solubility or preservation. Injectable suspensions or solutions can also be prepared utilizing aqueous carriers along with appropriate additives. The pharmaceutical compositions herein will contain, per dosage unit, e.g., tablet, capsule, powder, injection, teaspoonful and the like, an amount of the active ingredient necessary to deliver an effective dose as described herein.

The compositions comprising a compound of Formula I (e.g., any one of Formulas I-A to I-L) or a pharmaceutically acceptable salt or solvate thereof can be formulated in a unit dosage form, each dosage containing from about 5 to about 1,000 mg (1 g), more usually about 100 mg to about 500 mg, of the active ingredient. The term "unit dosage form" refers to physically discrete units suitable as unitary dosages for human subjects and other patients, each unit containing a predetermined quantity of active material (i.e., a compound of Formula I (e.g., any one of Formulas I-A to I-L) or a pharmaceutically acceptable salt or solvate thereof) calculated to produce the desired therapeutic effect, in association with a suitable pharmaceutical excipient.

In some embodiments, the compositions provided herein contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient. In some embodiments, the compositions provided herein contain about 10 mg, about 20 mg, about 80 mg, or about 160 mg of the active ingredient.

In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The daily dosage of the compound of Formula I (e.g., any one of Formulas I-A to I-L) or a pharmaceutically acceptable salt or solvate thereof can be varied over a wide range from 1.0 to 10,000 mg per adult human per day, or higher, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 160, 200, 250 and 500 milligrams of the active ingredient for the symptomatic adjustment of the dosage to the patient to be treated. An effective amount of the drug is ordinarily-supplied at a dosage level of from about 0.1 mg/kg to about 1000 mg/kg of body weight per day, or any range therein. Preferably, the range is from about 0.5 to about 500 mg/kg of body weight per day, or any range therein. More preferably, from about 1.0 to about 250 mg/kg of body weight per day, or any range therein. More preferably, from about 0.1 to about 100 mg/kg of body weight per day, or any range therein. In an example, the range can be from about 0.1 to about 50.0 mg/kg of body weight per day, or any amount or range therein. In another example, the range can be from about 0.1 to about 15.0 mg/kg of body weight per day, or any range therein. In yet another example, the range can be from about 0.5 to about 7.5 mg/kg of body weight per day, or any amount to range therein. Pharmaceutical compositions containing a compound of Formula I (e.g., any one of Formulas I-A to I-L) or a pharmaceutically acceptable salt or solvate thereof can be administered on a regimen of 1 to 4 times per day or in a single daily dose.

The active compound may be effective over a wide dosage range and is generally administered in a pharmaceutically effective amount. Optimal dosages to be administered can be readily determined by those skilled in the art. It will be understood, therefore, that the amount of the compound actually administered will usually be determined by a physician, and will vary according to the relevant circumstances, including the mode of administration, the actual compound administered, the strength of the preparation, the condition to be treated, and the advancement of the disease condition. In addition, factors associated with the particular patient being treated, including patient response, age, weight, diet, time of administration and severity of the patient's symptoms, will result in the need to adjust dosages.

In some embodiments, the compounds provided herein can be administered in an amount ranging from about 1 mg/kg to about 100 mg/kg. In some embodiments, the compound provided herein can be administered in an amount of about 1 mg/kg to about 20 mg/kg, about 5 mg/kg to about 50 mg/kg, about 10 mg/kg to about 40 mg/kg, about 15 mg/kg to about 45 mg/kg, about 20 mg/kg to about 60 mg/kg, or about 40 mg/kg to about 70 mg/kg. For example, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg. In some embodiments, such administration can be once-daily or twice-daily (BID) administration.

In some embodiments, the compounds provided herein can be administered in an amount of about 10 mg twice a day (BID), 20 mg BID, about 40 mg BID, about 60 mg BID, about 80 mg BID, about 120 mg BID, about 160 mg BID, and about 240 mg BID. In some embodiments, each dose is administered at least six hours after the previous dose. In some embodiments, each dose is administered at least twelve hours after the previous dose.

In some embodiments, a compound of Formula I (e.g., any one of Formulas I-A to I-L), or a pharmaceutically acceptable salt or solvate thereof exhibits pH dependent solubility at lower pH values. Accordingly, patients also receiving proton pump inhibitors (PPIs) and/or antacids may need to adjust the dosage of the compound of Formula I, or a pharmaceutically acceptable salt or solvate thereof (e.g., increase the dose of the compound of Formula I, or a pharmaceutically acceptable salt or solvate thereof). In some embodiments, the isoform of cytochrome P450 (CUP) that metabolizes a compound of Formula I (e.g., any one of Formulas I-A to I-L), or a pharmaceutically acceptable salt or solvate thereof, is CYP3A4. Accordingly, patients also receiving agents that inhibit or induce CYP3A4 may need to adjust the dosage of the compound of Formula I, or a pharmaceutically acceptable salt or solvate thereof (e.g., increase the dose of the compound of Formula I, or a pharmaceutically acceptable salt or solvate thereof, in the case of a CYP3A4 inducer or decrease the dose of the compound of Formula I, or a pharmaceutically acceptable salt or solvate thereof, in the case of a CYP3A4 inhibitor).

One skilled in the art will recognize that both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, can be completed according to methods well known in the clinical and medical arts.

Provided herein are pharmaceutical kits useful, for example, in the treatment of RET-associated diseases or disorders, such as cancer or irritable bowel syndrome (IBS), which include one or more containers containing a pharmaceutical composition comprising a therapeutically effective amount of a compound provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The following examples illustrate the invention.

Biological Examples

Example A

RET Enzyme Assay

The potency of compounds inhibiting several different RET kinase forms (Wild Type, V804M, G810R, & G810S) were determined using CisBio's HTRF® KinEASE™-TK assay technology. The kinases were incubated with 250 nM TK-substrate biotin (CisBio, part of cat #62TK0PEC) at 1 mM ATP along with test compounds in a buffer consisting of 25 mM HEPES, pH 7.4, 10 mM $MgCl_2$, 0.01% Triton X-100, and 2% DMSO in a volume of 8 μL. Compounds were typically prepared as a three-fold serial dilution in DMSO and added to the assay to give the appropriate final concentration. After a 30-min incubation at 22° C., the reaction was quenched by adding 8 μL of quench solution containing 31.25 nM Sa-XL665 and 1×TK-Ab-Cryptate in HTRF detection buffer (all from CisBio, part of cat #62TK0PEC). After a 1 hour incubation at 22° C., the extent of reaction was determined using a PerkinElmer EnVision multimode plate reader via HTRF dual wavelength detection, and the percent of control (POC) was calculated using a ratiometric emission factor. One hundred POC was determined using DMSO only samples (no compound present), and 0 POC was determined using pre-quenched control reactions. A 4-parameter logistic curve was fit to the POC values as a function of the concentration of compound, and the $IC_{50}$ value was the point where the best-fit curve crossed 50 POC. Enzyme lots and concentrations used as shown in the Table below, and the averaged $IC_{50}$ values for the compounds tested in these assay are provided in Table 5.

| Enzyme form | Vendor | Lot Number | Enzyme Concentration (nM) |
|---|---|---|---|
| Wild Type | Eurofins | 3654890-B | 0.25 |
| V804M | Millipore | D8KN029U-C | 0.2 |
| G810R | Array BioPharma Inc. | 160713 | 2.5 |
| G810S | Array BioPharma Inc. | 170322A | 0.25 |

Example B

RET Cell Assay

The cellular potency of compounds inhibiting RET kinase were determined in HEK-293 cells expressing a Kif5b-RET fusion protein. Briefly, HEK-293 cells expressing a Kif5b-RET fusion protein were plated at 50K cells/well in 96 well poly-D-Lysine coated plates the day prior to the assay. The cells were incubated for 1 hour with test compound in DMEM (Dulbecco's Modified Eagle Medium) at a final DMSO concentration of 0.5%. Compounds were typically prepared in a three-fold serial dilution in DMSO and added to the assay to give the appropriate final concentration. After 1 hour the media was removed, the cells were fixed with 3.8% formaldehyde for 20 min, washed with PBS, and permeabilized for 10 min with 100% methanol. The plates were then washed with PBS-0.05% Tween20, and blocked with LI-COR Blocking solution (LI-COR Catalog No. 927-40000) for 1 hour. Plates were washed with PBS-0.05% Tween20, then incubated with anti-phospho-RET (Tyr1062) (Santa Cruz Catalog No. sc-20252-R) antibody and anti-GAPDH (Millipore Catalog No. MAB374) antibody for 2 hours. The plates were washed with PBS-0.05% Tween20, and incubated with anti-rabbit 680 (Molecular Probes Catalog No. A21109) and anti-mouse 800 (LI-COR Catalog No. 926-32210) secondary antibodies for 1 hour. All antibodies were diluted in LI-COR Block containing 0.05% Tween. The plates were washed with PBS-0.05% Tween20,100 µL PBS is added to each well, and the plates were read on a LI-COR Aerius fluorescent plate reader. The phospho-RET signal was normalized to the GAPDH signal. 100 POC (percent of control) was determined using no test compounds and 0 POC was determined using 1 µM of a control inhibitor. The POC values were fit to a 4 parameter logistic curve. The $IC_{50}$ value is the point where the curve crosses 50 POC. $IC_{50}$ values for the compounds tested in these assay are provided in Table 5.

Example C

RET G810R and G810S Mutant Assay

The potency of a compound inhibiting G810R or G810S mutant RET kinase was determined using CisBio's HTRF® KinEASE™-TK assay technology. The assays contained G810R or G810S mutant RET produced at Array Biopharma, Inc. (1 nM enzyme). The kinase was incubated with 250 nM TK-substrate biotin (CisBio, part of Catalog No. 62TK0PEC) and 1 mM ATP along with test compound in a buffer consisting of 25 mM HEPES, pH 7.4, 10 mM $MgCl_2$, 0.01% Triton X-100, and 2% DMSO in a volume of 8 µL. Compounds were typically prepared as a three-fold serial dilution in DMSO and added to the assay to give the appropriate final concentration. After a 60-min incubation at 22° C., the reaction was quenched by adding 8 µL of quench solution containing 31.25 nM Sa-XL665 and 1×TK-Ab-Cryptate in HTRF detection buffer (all from CisBio, part of Catalog No. 62TK0PEC). After a 1-h incubation at 22° C., the extent of reaction was determined using a PerkinElmer EnVision multimode plate reader via HTRF dual wavelength detection, and the percent of control (POC) was calculated using a ratiometric emission factor. One hundred POC was determined using no test compounds, and 0 POC was determined using pre-quenched control reactions. A 4-parameter logistic curve was fit to the POC values as a function of the concentration of compound, and the $IC_{50}$ value is the point where the best-fit curve crossed 50 POC. $IC_{50}$ values for the compounds tested in these assay are provided in Table 5.

Example D

RET G810R and G810S Mutant Cell Assay

The cellular potency of compounds inhibiting RET kinase were determined in HEK-293 cells expressing a G810R or G810S mutant RET Kif5b-RET fusion protein. Briefly, HEK-293 cells expressing a G810R or G810S mutant RET Kif5b-RET fusion protein were plated at 50K cells/well in 96 well poly-D-Lysine coated plates the day prior to the assay. The cells were incubated for 1 hour with test compound in DMEM (Dulbecco's Modified Eagle Medium) at a final DMSO concentration of 0.5%. Compounds were typically prepared in a three-fold serial dilution in DMSO and added to the assay to give the appropriate final concentration. After 1 hour the media was removed, the cells were fixed with 3.8% formaldehyde for 20 min, washed with PBS, and permeabilized for 10 min with 100% methanol. The plates were then washed with PBS-0.05% Tween20, and blocked with LI-COR Blocking solution (LI-COR Catalog No. 927-40000) for 1 hour. Plates were washed with PBS-0.05% Tween20, then incubated with anti-phospho-RET (Tyr1062) (Santa Cruz Catalog No. sc-20252-R) antibody and anti-GAPDH (Millipore Catalog No. MAB374) antibody for 2 hours. The plates were washed with PBS-0.05% Tween20, and incubated with anti-rabbit 680 (Molecular Probes Catalog No. A21109) and anti-mouse 800 (LI-COR Catalog No. 926-32210) secondary antibodies for 1 hour. All antibodies were diluted in LI-COR Block containing 0.05% Tween. The plates were washed with PBS-0.05% Tween20, 100 µL PBS was added to each well, and the plates were read on a LI-COR Aerius fluorescent plate reader. The phospho-RET signal was normalized to the GAPDH signal. 100 POC (percent of control) was determined using no test compounds and 0 POC was determined using 1 µM of a control inhibitor. The POC values are fit to a 4 parameter logistic curve. The $IC_{50}$ value is the point where the curve crosses 50 POC. $IC_{50}$ values for the compounds tested in these assay are provided in Table 5.

TABLE 5

| | $IC_{50}$'s of compounds tested in the assay of Example A. | | | | | | |
|---|---|---|---|---|---|---|---|
| Ex# | RET Enz FRET_WT $IC_{50}$ (nM) | RET V804M Enz FRET $IC_{50}$ (nM) | RET G810R Enz FRET $IC_{50}$ (nM) | RET G810S Enz FRET $IC_{50}$ (nM) | KIF5B-RET pTYR1062 Cell $IC_{50}$ (nM) | KIF5B-RET G810R Cell $IC_{50}$ (nM) | KIF5B-RET G810S Cell $IC_{50}$ (nM) |
| 1 | 52 | 202 | 145 | 117 | 17 | 179 | N/A |
| 2 | 114 | 324 | 243 | 248 | 99 | 406 | N/A |
| 3 | 16 | 105 | 151 | 84 | 40 | 195 | 81 |
| 4 | 16 | 106 | 157 | 135 | 60 | 290 | N/A |
| 5 | 17 | 99 | 157 | 138 | 75 | 459 | N/A |
| 6 | 58 | 297 | 143 | 178 | 64 | 287 | N/A |
| 7 | 91 | 340 | 171 | 356 | 135 | 660 | N/A |
| 8 | 41 | 227 | 95 | 123 | 91 | 302 | N/A |
| 9 | 103 | 533 | 224 | 298 | N/A | N/A | N/A |
| 10 | 20 | 106 | 114 | 46 | 28 | 254 | N/A |
| 11 | 136 | 516 | 345 | 507 | N/A | N/A | N/A |
| 12 | 47 | 399 | 176 | 112 | 143 | 705 | N/A |
| 13 | 36 | 275 | 137 | 72 | 119 | 596 | N/A |

TABLE 5-continued

IC$_{50}$'s of compounds tested in the assay of Example A.

| Ex# | RET Enz FRET_WT IC$_{50}$ (nM) | RET V804M Enz FRET IC$_{50}$ (nM) | RET G810R Enz FRET IC$_{50}$ (nM) | RET G810S Enz FRET IC$_{50}$ (nM) | KIF5B-RET pTYR1062 Cell IC$_{50}$ (nM) | KIF5B-RET G810R Cell IC$_{50}$ (nM) | KIF5B-RET G810S Cell IC$_{50}$ (nM) |
|---|---|---|---|---|---|---|---|
| 14 | 112 | 865 | 252 | 293 | N/A | N/A | N/A |
| 15 | 58 | 607 | 361 | 307 | N/A | N/A | N/A |
| 16 | 205 | 1794 | 354 | 648 | N/A | N/A | N/A |
| 17 | 49 | 241 | 533 | 433 | N/A | N/A | N/A |
| 18 | 153 | 692 | 253 | 397 | N/A | N/A | N/A |
| 19 | 45 | 202 | 103 | 215 | 53 | 262 | 184 |
| 20 | 53 | 254 | 135 | 123 | 28 | 160 | 111 |
| 21 | 9 | 44 | 31 | N/A | 28 | 87 | 83 |
| 22 | 31 | 323 | 102 | 75 | 65 | 496 | N/A |
| 23 | 18 | 189 | 63 | 54 | 20 | 133 | 107 |
| 24 | 25 | 92 | 70 | 87 | 40 | 181 | N/A |
| 25 | 14 | 123 | 37 | N/A | 7 | 142 | N/A |
| 26 | 20 | 145 | 62 | 45 | 22 | 196 | N/A |
| 27 | 142 | 595 | 308 | 581 | N/A | N/A | N/A |
| 28 | 307 | 2833 | 641 | 1025 | N/A | N/A | N/A |
| 29 | 8 | 26 | 27 | 25 | 12 | 71 | 37 |
| 30 | 93 | 259 | 180 | 300 | 155 | 2161 | N/A |
| 31 | 571 | 2207 | 1315 | 1322 | N/A | N/A | N/A |
| 32 | 188 | 10000 | 1232 | 10000 | N/A | N/A | N/A |
| 33 | 1185 | 10000 | 10000 | 10000 | N/A | N/A | N/A |
| 34 | 227 | 805 | 288 | 397 | N/A | N/A | N/A |
| 35 | 47 | 114 | 124 | 110 | 35 | 831 | N/A |
| 36 | 58 | 235 | 130 | 217 | 53 | 144 | 255 |
| 37 | 318 | 10000 | 1284 | 1222 | N/A | N/A | N/A |
| 38 | 342 | 3122 | 649 | 921 | N/A | N/A | N/A |
| 39 | 893 | 10000 | 3066 | 4137 | N/A | N/A | N/A |
| 40 | 621 | 2205 | 724 | 973 | N/A | N/A | N/A |
| 41 | 198 | 659 | 415 | 564 | N/A | N/A | N/A |
| 42 | 72 | 594 | 166 | 176 | 45 | 385 | N/A |
| 43 | 104 | 187 | 90 | 223 | 105 | 298 | 213 |
| 44 | 104 | 248 | 196 | 245 | 142 | 1888 | N/A |
| 45 | 194 | 10000 | 275 | 557 | 344 | 814 | N/A |
| 46 | 330 | 10000 | 400 | 973 | N/A | N/A | N/A |
| 47 | 112 | 9371 | 269 | 303 | 134 | 1949 | N/A |
| 48 | 2443 | 10000 | 7876 | 10000 | N/A | N/A | N/A |
| 49 | 8422 | 10000 | 10000 | 10000 | N/A | N/A | N/A |
| 50 | 2183 | 10000 | 2570 | 5082 | N/A | N/A | N/A |
| 51 | 7364 | 10000 | 10000 | 10000 | N/A | N/A | N/A |
| 52 | 1055 | 10000 | 877 | 3199 | N/A | N/A | N/A |
| 53 | 16 | 34 | 102 | 94 | 64 | 485 | N/A |
| 54 | 13 | 41 | 70 | 54 | 22 | 103 | 92 |
| 55 | 8 | 21 | 31 | 29 | 10 | 46 | 40 |
| 56 | 9 | 51 | 79 | 42 | 7 | 50 | 37 |
| 57 | 29 | 178 | 123 | 176 | 38 | 131 | 121 |
| 58 | 23 | 66 | 64 | 159 | 49 | 186 | 181 |
| 59 | 275 | 749 | 308 | 859 | N/A | N/A | N/A |
| 60 | 21 | 98 | 45 | 40 | 29 | 157 | 101 |
| 61 | 31 | 136 | 89 | 58 | 33 | 281 | 101 |
| 62 | 34 | 138 | 96 | 74 | 52 | 349 | 192 |
| 63 | 61 | 211 | 118 | 108 | 72 | 439 | 352 |
| 64 | 39 | 182 | 169 | 76 | 47 | 119 | 90 |
| 65 | 43 | 163 | 64 | 133 | 45 | 621 | 290 |
| 66 | 1792 | 6834 | 2185 | 2302 | N/A | N/A | N/A |
| 67 | 23 | 92 | 53 | 69 | 60 | 467 | N/A |
| 68 | 386 | 10000 | 485 | 1165 | 1775 | 4747 | N/A |
| 69 | 34 | 10000 | 47 | 65 | 103 | 394 | N/A |
| 70 | 92 | 10000 | 183 | 312 | 166 | 607 | 388 |
| 71 | 1161 | 10000 | 3735 | 4753 | 2529 | 6525 | 3623 |
| 72 | 512 | 10000 | 3091 | 2629 | 3957 | 16180 | 6351 |
| 73 | 531 | 10000 | 2738 | 2478 | 13910 | 16667 | 16667 |
| 74 | 353 | 6004 | 2083 | 289 | N/A | 2944 | 918 |
| 75 | 82 | 2031 | 421 | 51 | N/A | 170 | 191 |
| 76 | 117 | 10000 | 118 | 292 | 143 | 845 | 570 |
| 77 | 27 | 10000 | 135 | 73 | 13 | 89 | 32 |
| 78 | 638 | 10000 | 507 | 720 | N/A | N/A | N/A |
| 79 | 356 | 10000 | 270 | 591 | N/A | N/A | N/A |
| 80 | 195 | 10000 | 320 | 404 | N/A | N/A | N/A |
| 81 | 19 | 5488 | 94 | 52 | 11 | 76 | 39 |
| 82 | 358 | 10000 | 420 | 821 | N/A | N/A | N/A |
| 83 | 63 | 10000 | 58 | 97 | 293 | 1062 | 812 |
| 84 | 182 | 10000 | 244 | 634 | N/A | N/A | N/A |

TABLE 5-continued

IC$_{50}$'s of compounds tested in the assay of Example A.

| Ex# | RET Enz FRET_WT IC$_{50}$ (nM) | RET V804M Enz FRET IC$_{50}$ (nM) | RET G810R Enz FRET IC$_{50}$ (nM) | RET G810S Enz FRET IC$_{50}$ (nM) | KIF5B-RET pTYR1062 Cell IC$_{50}$ (nM) | KIF5B-RET G810R Cell IC$_{50}$ (nM) | KIF5B-RET G810S Cell IC$_{50}$ (nM) |
|---|---|---|---|---|---|---|---|
| 85 | 389 | 10000 | 501 | 960 | N/A | N/A | N/A |
| 86 | 37 | 8320 | 150 | 98 | 73 | N/A | 169 |
| 87 | 47 | 5783 | 202 | 204 | 32 | 89 | 71 |
| 88 | 62 | 6257 | 288 | 297 | 50 | 53 | 44 |
| 89 | 311 | 10000 | 544 | 1583 | 233 | N/A | 269 |
| 90 | 353 | 10000 | 1059 | 1597 | 222 | N/A | 408 |
| 91 | 166 | 10000 | 624 | 596 | 66 | N/A | 98 |
| 92 | 114 | 10000 | 285 | 168 | 56 | N/A | 301 |
| 93 | 1263 | 10000 | 1914 | 5573 | 1000 | N/A | 1000 |
| 94 | 568 | 10000 | 840 | 2001 | 388 | N/A | 297 |
| 95 | 546 | 10000 | 816 | 2080 | 318 | N/A | 376 |
| 96 | 27 | 10000 | 187 | 393 | 85 | 142 | 116 |
| 97 | 73 | 4457 | 478 | 457 | 26 | 47 | 47 |
| 98 | 2212 | 10000 | 4069 | 7952 | N/A | N/A | N/A |
| 99 | 881 | 10000 | 2210 | 3251 | N/A | N/A | N/A |
| 100 | 233 | 2856 | 1605 | 914 | 10 | N/A | 15 |
| 101 | 135 | 10000 | 1416 | 805 | 43 | 75 | 62 |
| 102 | 128 | 483 | 760 | 183 | 35 | N/A | 86 |
| 103 | 43 | 6096 | 190 | 196 | 41 | N/A | 141 |
| 104 | 54 | 8234 | 186 | 259 | 36 | N/A | 92 |
| 105 | 639 | 10000 | 742 | 2584 | 1355 | 15535 | N/A |
| 106 | 404 | 10000 | 2425 | 3266 | N/A | N/A | N/A |
| 107 | 10000 | 10000 | 10000 | 10000 | N/A | N/A | N/A |
| 108 | 10000 | 10000 | 8385 | 10000 | 12859 | 16667 | N/A |
| 109 | 1776 | 10000 | 1810 | 2268 | N/A | N/A | N/A |
| 110 | 411 | 1742 | 214 | 284 | N/A | 537 | 201 |
| 111 | 3443 | 6237 | 3296 | 2708 | N/A | N/A | N/A |
| 112 | 1776 | 3735 | 2017 | 958 | N/A | N/A | N/A |
| 113 | 102 | 169 | 106 | 63 | 513 | N/A | 274 |
| 114 | 357 | 1051 | 435 | 282 | N/A | N/A | N/A |
| 115 | 346 | 1090 | 179 | 153 | N/A | N/A | N/A |
| 116 | 1296 | 1059 | 238 | 491 | N/A | N/A | N/A |
| 117 | 373 | 863 | 300 | 304 | N/A | N/A | N/A |
| 118 | 131 | 99 | 80 | 75 | 125 | 206 | 108 |
| 119 | 24 | 79 | 45 | 67 | 66 | 593 | 131 |
| 120 | 10 | 20 | 74 | 24 | 15 | 35 | 33 |
| 121 | 41 | 120 | 87 | 84 | 74 | N/A | 118 |
| 122 | 14 | 38 | 28 | 26 | 31 | N/A | 77 |
| 123 | 39 | 87 | 103 | 86 | 21 | N/A | 42 |
| 124 | 24 | 80 | 89 | 49 | 19 | 44 | 33 |
| 125 | 11 | 19 | 41 | 19 | 7 | 16 | 16 |
| 126 | 6 | 30 | 15 | 9 | 5 | 29 | 26 |
| 127 | 6 | 21 | 28 | 23 | 9 | 57 | 52 |
| 128 | 88 | 349 | 98 | 160 | 157 | N/A | 435 |
| 129 | 8 | 21 | 23 | 19 | 18 | 46 | 65 |
| 130 | 12 | 64 | 40 | 32 | 34 | N/A | 131 |
| 131 | 14 | 41 | 97 | 18 | 14 | 30 | 60 |
| 132 | 1709 | 1936 | 4462 | 2318 | N/A | N/A | N/A |
| 133 | 2642 | 6204 | 6142 | 3402 | N/A | N/A | N/A |
| 134 | 112 | 355 | 560 | 488 | N/A | N/A | N/A |
| 135 | 45 | 152 | 150 | 229 | 54 | N/A | 103 |
| 136 | 201 | 551 | 274 | 817 | N/A | N/A | N/A |
| 137 | 38 | 60 | 52 | 155 | 67 | N/A | 280 |
| 138 | 143 | 376 | 272 | 646 | N/A | N/A | N/A |
| 139 | 75 | 10000 | 1032 | 474 | 16 | 49 | 36 |
| 140 | 554 | 8965 | 876 | 3072 | 884 | N/A | 1000 |
| 141 | 139 | 415 | 211 | 405 | N/A | N/A | N/A |
| 142 | 124 | 505 | 157 | 425 | N/A | N/A | N/A |
| 143 | 53 | 438 | 109 | 261 | 151 | N/A | 447 |
| 144 | 24 | 57 | 61 | 101 | 40 | N/A | 177 |
| 145 | 20 | 31 | 85 | 101 | 73 | 120 | 93 |
| 146 | 26 | 87 | 43 | 116 | 63 | 98 | 68 |
| 147 | 14 | 32 | 74 | 94 | 21 | 56 | 90 |
| 148 | 183 | 216 | 154 | 758 | N/A | N/A | N/A |
| 149 | 7 | 22 | 70 | 41 | 2 | N/A | 20 |
| 150 | 12 | 15 | 84 | 46 | 4 | 40 | 18 |
| 151 | 9 | 27 | 86 | 55 | 14 | 113 | 57 |

Synthetic Examples

Preparation of Synthetic Intermediates

Intermediate P1

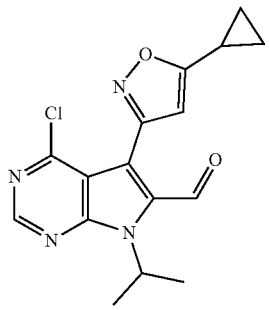 [SMILES: CC(C)n1c(C=O)c(-c2cc(C3CC3)on2)c2c(Cl)ncnc21]

4-chloro-5-(5-cyclopropylisoxazol-3-yl)-7-isopropyl-7H-pyrrolo[2,3-d]pyrimidine-6-carbaldehyde Step 1: Preparation of 4-chloro-7-isopropyl-7H-pyrrolo[2,3-d]pyrimidine-5-carbaldehyde To a mixture of 4-chloro-7H-pyrrolo[2,3-d]pyrimidine-5-carboxaldehyde (25.0 g, 138 mmol) and $Cs_2CO_3$ (53.8 g, 165 mmol) in DMF (275 mL) was added 2-bromopropane (15.5 mL, 165 mmol). The reaction was stirred overnight at 60° C. It was diluted with EtOAc (100 mL), washed with water (2×100 mL) and brine (1×), then dried ($Na_2SO_4$), filtered and concentrated in vacuo. The crude residue was purified by silica chromatography (0-40% acetone in DCM) to afford the title compound as a pale yellowish solid (21.7 g, 70% yield). MS (apci) m/z=224.1 (M+H).

Step 2: Preparation of 4-chloro-7-isopropyl-7H-pyrrolo[2,3-d]pyrimidine-5-carbaldehyde Oxime A solution of 4-chloro-7-isopropyl-7H-pyrrolo[2,3-d]pyrimidine-5-carbaldehyde (4.75 g, 21.2 mmol) in EtOH (21 mL) was treated with hydroxylamine hydrochloride (3.69 g, 53.1 mmol) and NaOAc (4.36 g, 53.1 mmol), then stirred for 1 h at RT. The mixture was then diluted with DCM, and the solids were filtered off. The filtrate was concentrated in vacuo, and the residue was purified by silica chromatography (0-20% MeOH in DCM) to afford the title compound (4.98 g, 98% yield). LCMS m/z=239.1 (M+H).

Step 3: Preparation of 3-(4-chloro-7-isopropyl-7H-pyrrolo[2,3-d]pyrimidin-5-yl)-5-Cyclopropyl-isoxazole A mixture of 4-chloro-7-isopropyl-7H-pyrrolo[2,3-d]pyrimidine-5-carbaldehyde oxime (12.4 g, 52.0 mmol), 1-chloropyrrolidine-2,5-dione (7.63 g, 57.1 mmol), $KHCO_3$ (6.76 g, 67.5 mmol) and ethynylcyclopropane (13.2 mL, 156 mmol) in DMF (260 mL) was stirred for 2 d at RT. The mixture was poured into water (800 mL) and filtered. The solids collected were rinsed with hexanes (200 mL), and dried in vacuo to afford the title compound (15.7 g, quantitative yield). MS (apci) m/z=303.1 (M+H).

Step 4: Preparation of 4-chloro-5-(5-cyclopropylisoxazol-3-yl)-7-isopropyl-7H-pyrrolo[2,3-d]-pyrimidine-6-carbaldehyde To a solution of 3-(4-chloro-7-isopropyl-7H-pyrrolo[2,3-d]pyrimidin-5-yl)-5-cyclopropylisoxazole (5.27 g, 17.4 mmol) and diisopropylamine (0.98 mL, 6.96 mmol) in THF (58 mL) was slowly added n-BuLi (2.5 M in THF; 9.75 mL, 24.37 mmol) at −78° C. After stirring 30 min, the mixture was cannulated into a solution of ethyl formate (4.2 mL, 52.23 mmol) in THF (5 mL) at −78° C. The reaction was stirred for 1 h, after which it was quenched with saturated $NH_4Cl_{(aq)}$. The mixture was partitioned between EtOAc and water. After phase separation, the aqueous phase was extracted with EtOAc (2×). The combined organic extracts were washed with brine, then dried over anhydrous $Na_2SO_{4(s)}$, filtered, and concentrated in vacuo. The crude residue was purified by silica chromatography (10-50% EtOAc in hexanes) to give the title compound (3.7 g, 64% yield). MS (apci) m/z=331.1 (M+H).

Intermediate P2

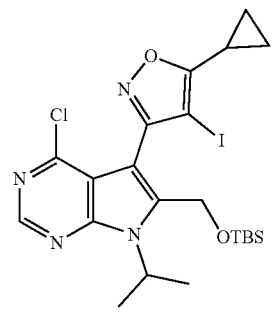 [SMILES: CC(C)n1c(CO[Si](C)(C)C(C)(C)C)c(-c2noc(C3CC3)c2I)c2c(Cl)ncnc21]

3-(6-(((tert-butyldimethylsilyl)oxy)methyl)-4-chloro-7-isopropyl-7H-pyrrolo[2,3-d]pyrimidin-5-yl)-5-cyclopropyl-4-iodoisoxazole Step 1: Preparation of (4-chloro-5-(5-cyclopropylisoxazol-3-yl)-7-isopropyl-7H-pyrrolo[2,3-d]pyrimidin-6-yl)methanol A solution of 4-chloro-5-(5-cyclopropylisoxazol-3-yl)-7-isopropyl-7H-pyrrolo[2,3-d]pyrimidine-6-carbaldehyde (Intermediate P1) (3.54 g, 10.7 mmol) in methanol (36 mL) was cooled to 0° C., and treated with $NaBH_4$ (0.40 g, 10.7 mmol). After 1 h stirring, the reaction was diluted with EtOAc, and washed with water (2×) and brine (2×). The organic extracts were dried over anhydrous $Na_2SO_{4(s)}$, filtered, and concentrated in vacuo to afford the title compound as white solid (3.6 g, quantitative yield). MS (apci) m/z=333.1 (M+H).

Step 2: Preparation of (4-chloro-5-(5-cyclopropyl-4-iodoisoxazol-3-yl)-7-isopropyl-7H-pyrrolo[2,3-d]pyrimidin-6-yl)methanol A suspension of (4-chloro-5-(5-cyclopropylisoxazol-3-yl)-7-isopropyl-7H-pyrrolo[2,3-d]pyrimidin-6-yl)methanol (3.56 g, 10.7 mmol) in ACN (70 mL) was treated sequentially with NIS (3.61 g, 16.0 mmol) and TFA (7.13 mL, 10.7 mmol). After 90 min stirring at RT, the reaction was diluted with EtOAc, washed successively with water (1×), saturated NaHCO$_{3(aq)}$ (1×), 10% Na$_2$S$_2$O$_3$, and brine. The organic extracts then were dried over anhydrous Na$_2$SO$_{4(s)}$, filtered, and concentrated in vacuo to afford the title compound as white solid (4.9 g, quantitative yield). MS (apci) m/z=459.0 (M+H).

Step 3: Preparation of 3-(6-(((tert-butyldimethylsilyl)oxy)methyl)-4-chloro-7-isopropyl-7H-pyrrolo[2,3-d]pyrimidin-5-yl)-5-cyclopropyl-4-iodoisoxazole A solution of (4-chloro-5-(5-cyclopropyl-4-iodoisoxazol-3-yl)-7-isopropyl-7H-pyrrolo[2,3-d]pyrimidin-6-yl)methanol (5.53 g, 12.1 mmol) in DMF (80 mL) was treated with TBDMSCl (2.73 g, 18.1 mmol) and 1H-imidazole (1.64 g, 24.1 mmol). After stirring overnight, the reaction was diluted with EtOAc, washed with water and brine, then dried over anhydrous Na$_2$SO$_{4(s)}$, filtered and concentrated in vacuo. The crude was purified by silica chromatography (0-25% EtOAc in hexanes) to give the title compound as a clear yellowish oil (6.2 g, 90% yield). MS (apci) m/z=573.1 (M+H).

Intermediate P3

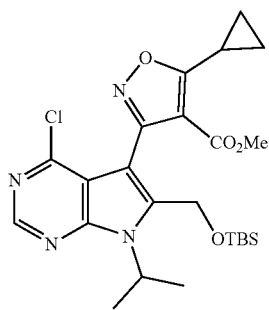 [SMILES: COC(=O)c1c(-c2c(CO[Si](C)(C)C(C)(C)C)n(C(C)C)c3ncnc(Cl)c23)noc1C1CC1]

methyl 3-(6-(((tert-butyldimethylsilyl)oxy)methyl)-4-chloro-7-isopropyl-7H-pyrrolo[2,3-d]pyrimidin-5-yl)-5-cyclopropylisoxazole-4-carboxylate A cold (−78° C.) solution of 3-(6-(((tert-butyldimethylsilyl)oxy)methyl)-4-chloro-7-isopropyl-7H-pyrrolo[2,3-d]pyrimidin-5-yl)-5-cyclopropyl-4-iodoisoxazole (Intermediate P2; 594 mg, 1.04 mmol) in THF (6.912 mL) was treated dropwise with n-BuLi (2.5 M in THF; 580.6 μL, 1.451 mmol). The resulting mixture was stirred for 30 min at −78° C. Subsequently, the mixture was treated slowly with dimethyl carbonate (349.4 μL, 4.147 mmol), and then stirred for 1 h at −10° C. The reaction mixture was quenched with saturated NH$_4$Cl$_{(aq)}$, and allowed to warm to RT. The quenched mixture was partitioned between EtOAc and water. After phase-separation, the organic extracts were washed with brine, then dried over anhydrous Na$_2$SO$_{4(s)}$, filtered, and concentrated in vacuo. The residue was purified by silica chromatography (10-50% hexanes: EtOAc) to afford the title compound (279 mg, 53% yield). MS (apci) m/z=505.2 (M+H).

Intermediate P4

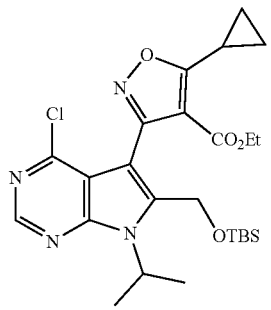 [SMILES: CCOC(=O)c1c(-c2c(CO[Si](C)(C)C(C)(C)C)n(C(C)C)c3ncnc(Cl)c23)noc1C1CC1]

Ethyl 3-(6-(((tert-butyldimethylsilyl)oxy)methyl)-4-chloro-7-isopropyl-7H-pyrrolo[2,3-d]pyrimidin-5-yl)-5-cyclopropylisoxazole-4-carboxylate The title compound (1.1 g, 51% yield) was prepared, worked up and purified using a similar procedure to that described for methyl 3-(6-(((tert-butyldimethylsilyl)oxy)methyl)-4-chloro-7-isopropyl-7H-pyrrolo[2,3-d]pyrimidin-5-yl)-5-cyclopropylisoxazole-4-carboxylate (Intermediate P3), replacing dimethyl carbonate with diethyl carbonate. MS (apci) m/z=519.2 (M+H).

Intermediate P5

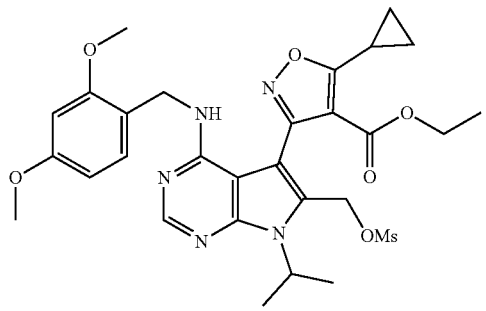 [SMILES: CCOC(=O)c1c(-c2c(COS(C)(=O)=O)n(C(C)C)c3ncnc(NCc4ccc(OC)cc4OC)c23)noc1C1CC1]

Ethyl 5-cyclopropyl-3-(4-((2,4-dimethoxybenzyl)amino)-7-isopropyl-6-(((methylsulfonyl)oxy)methyl)-7H-pyrrolo[2,3-d]pyrimidin-5-yl)isoxazole-4-carboxylate Step 1: Preparation of ethyl 3-(6-(((tert-butyldimethylsilyl)oxy)methyl)-4-((2,4-dimethoxybenzyl)amino)-7-isopropyl-7H-pyrrolo[2,3-d]pyrimidin-5-yl)-5-cyclopropylisoxazole-4-carboxylate A solution of ethyl 3-(6-(((tert-butyldimethylsilyl)oxy)methyl)-4-chloro-7-isopropyl-7H-pyrrolo[2,3-d]pyrimidin-5-yl)-5-cyclopropylisoxazole-4-carboxylate (Intermediate P4; 700 mg, 1.35 mmol) and (2,4-dimethoxyphenyl)methylamine (607.7 μL, 4.045 mmol) in DMSO (8.99 mL) was stirred overnight at 60° C. After cooling to RT, the reaction mixture was partitioned between EtOAc and water. Following phase separation, the organic extracts were washed sequentially with additional water (3×) and brine. The combined organic extracts were dried over anhydrous Na$_2$SO$_{4(s)}$, filtered, and concentrated in vacuo. The crude residue was purified by silica chromatography (10-90% hexanes: EtOAc as the gradient eluent) to afford the title compound (826 mg, 94% yield). MS (apci) m/z=650.3 (M+H).

Step 2: Preparation of ethyl 5-cyclopropyl-3-(4-((2, 4-dimethoxybenzyl)amino)-6-(hydroxymethyl)-7-isopropyl-7H-pyrrolo[2,3-d]pyrimidin-5-yl)isoxazole-4-carboxylate TBAF (1.0 M THF) (1.65 mL, 1.65 mmol) was added to a cold (0° C.) solution of ethyl 3-(6-(((tert-butyldimethylsilyl)oxy)methyl)-4-((2,4-dimethoxybenzyl)amino)-7-isopropyl-7H-pyrrolo[2,3-d]pyrimidin-5-yl)-5-cyclopropylisoxazole-4-carboxylate (826 mg, 1.27 mmol) and acetic acid (17.4 M; 219 µL, 3.81 mmol) in THF (8.47 mL). After being allowed to slowly warm to RT, the reaction mixture was stirred overnight at RT. The mixture was then partitioned between DCM and water. Following phase separation, the organic extracts were washed with brine, then dried over anhydrous Na$_2$SO$_{4(s)}$, filtered, and concentrated in vacuo to afford the title compound (446 mg, 66% yield). MS (apci) m/z=536.2 (M+H).

Step 3: Preparation of ethyl 5-cyclopropyl-3-(4-((2, 4-dimethoxybenzyl)amino)-7-isopropyl-6-(((methylsulfonyl)oxy)methyl)-7H-pyrrolo[2,3-d]pyrimidin-5-yl)isoxazole-4-carboxylate A cold (0° C.) solution of ethyl 5-cyclopropyl-3-(4-((2, 4-dimethoxybenzyl)amino)-6-(hydroxymethyl)-7-isopropyl-7H-pyrrolo[2,3-d]pyrimidin-5-yl)isoxazole-4-carboxylate (446 mg, 0.833 mmol) and methanesulfonyl chloride (67.7 µL, 0.874 mmol) in DCM (8.33 mL) was treated with DIEA (580 µL, 3.33 mmol), and stirred overnight at RT. The reaction mixture was then partitioned between DCM and water. Following phase separation, the organic extracts were washed with brine, then dried over anhydrous Na$_2$SO$_{4(s)}$, filtered, and concentrated in vacuo to afford the title compound, which was used directly in the next step without further purifications, assuming quantitative yield.

Intermediate P6

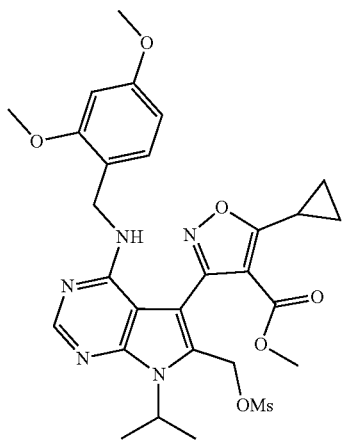 [SMILES: COC(=O)c1c(-c2c(COS(C)(=O)=O)n(C(C)C)c3ncnc(NCc4ccc(OC)cc4OC)c23)noc1C1CC1]

methyl 5-cyclopropyl-3-(4-((2,4-dimethoxybenzyl) amino)-7-isopropyl-6-(((methylsulfonyl)oxy) methyl)-7H-pyrrolo[2,3-d]pyrimidin-5-yl)isoxazole-4-carboxylate The title compound was prepared in a similar fashion as described for Intermediate P5, replacing ethyl 3-(6-(((tert-butyldimethylsilyl)oxy)methyl)-4-chloro-7-isopropyl-7H-pyrrolo[2,3-d]pyrimidin-5-yl)-5-cyclopropylisoxazole-4-carboxylate (Intermediate P4) in step 1 with methyl 3-(6-(((tert-butyldimethylsilyl)oxy)methyl)-4-chloro-7-isopropyl-7H-pyrrolo[2,3-d]pyrimidin-5-yl)-5-cyclopropylisoxazole-4-carboxylate (Intermediate P3) instead.

Intermediate P7

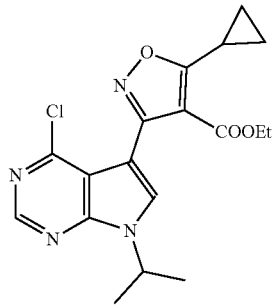 [SMILES: CCOC(=O)c1c(-c2cn(C(C)C)c3ncnc(Cl)c23)noc1C1CC1]

Ethyl 3-(4-chloro-7-isopropyl-7H-pyrrolo[2,3-d] pyrimidin-5-yl)-5-cyclopropylisoxazole-4-carboxylate Step 1: Preparation of 4-chloro-7-isopropyl-7H-pyrrolo[2,3-d]pyrimidine-5-carbaldehyde A solution of 4-chloro-7H-pyrrolo[2,3-d]pyrimidine-5-carbaldehyde (3.6 g, 19.8 mmol) in DMF (40 mL) was treated with Cs$_2$CO$_{3(s)}$ (7.1 g, 21.8 mmol) and 2-bromopropane (2.2 mL, 23.8 mmol). The reaction mixture was then stirred overnight at 50° C. After cooling to RT, the reaction was diluted with water (100 mL) and filtered. The filter cake was rinsed with water (30 mL) and then air-dried to afford the title compound as off-white solid (3.1 g, 70% yield). MS (apci) m/z=224.1 (M+H).

Step 2: Preparation of 4-chloro-7-isopropyl-7H-pyrrolo[2,3-d]pyrimidine-5-carbaldehyde Oxime A mixture of 4-chloro-7-isopropyl-7H-pyrrolo[2,3-d]pyrimidine-5-carbaldehyde (1.15 g, 5.14 mmol), NH$_2$OH—HCl (0.39 g, 5.66 mmol) and NaOAc (0.46 g, 5.66 mmol) in EtOH (26 mL) was stirred for 30 min at 50° C. After cooling to RT, the reaction was diluted with DCM (50 mL), and filtered through a celite pad. The filtrate was concentrated in vacuo to afford the title compound as yellowish solid (1.25 g, quantitative yield). MS (apci) m/z=239.1 (M+H).

Step 3: Preparation of ethyl 3-(4-chloro-7-isopropyl-7H-pyrrolo[2,3-d]pyrimidin-5-yl)-5-cyclopropylisoxazole-4-carboxylate In a pressure vessel, a solution of 4-chloro-7-isopropyl-7H-pyrrolo[2,3-d]pyrimidine-5-carbaldehyde oxime (96.6 mg, 0.40 mmol) in 1,2-dimethoxyethane (8.1 mL) was treated with NCS (59.4 mg, 0.44 mmol). The vessel was then sealed, and the reaction was stirred overnight at RT. Ethyl 3-cyclopropylpropiolate (Intermediate R1) (559 µL, 4.05 mmol) and KHCO$_3$ (122 mg, 1.21 mmol) were then introduced, and the reaction was again sealed and heated at 65° C. for 2 h. The reaction mixture then was filtered. The filtrate was concentrated and purified by silica chromatography (0-70% EtOAc in hexanes as the gradient eluent) to afford the title compound (82.4 mg, 54% yield). MS (apci) m/z=375.1 (M+H).

Intermediate P8

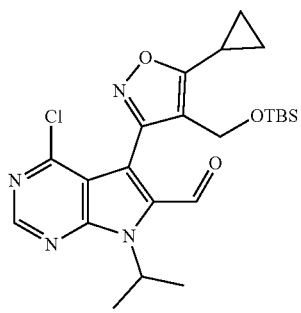 [SMILES: CC(C)n1c(C=O)c(-c2noc(C3CC3)c2CO[Si](C)(C)C(C)(C)C)c2c(Cl)ncnc21]

5-(4-(((tert-butyldimethylsilyl)oxy)methyl)-5-cyclopropylisoxazol-3-yl)-4-chloro-7-isopropyl-7H-pyrrolo[2,3-d]pyrimidine-6-carbaldehyde Step 1: Preparation of (3-(4-chloro-7-isopropyl-7H-pyrrolo[2,3-d]pyrimidin-5-yl)-5-cyclopropylisoxazol-4-yl)methanol A cold (−78° C.) solution of ethyl 3-(4-chloro-7-isopropyl-7H-pyrrolo[2,3-d]pyrimidin-5-yl)-5-cyclopropylisoxazole-4-carboxylate (Intermediate P7; 128 mg, 0.342 mmol) in DCM (1.366 µL) was treated dropwise with DIBAL-H (25 wt. % in toluene; 459 µL, 0.68 mmol). After stirring the resulting mixture for 30 min at −78° C., additional DIBAL-H (230 µL, 0.34 mmol) was introduced. The mixture was stirred for an additional 30 min at −78° C. before quenching with water. The aqueous phase of the quench solidified at −78° C., and the organic phase was separated by decanting. The organic extracts were washed successively with water and brine, then passed through a phase separator column and concentrated in vacuo to afford the title compound (100.6 mg, 89% yield). MS (apci) m/z=333.1 (M+H).

Step 2: Preparation of 4-(((tert-butyldimethylsilyl)oxy)methyl)-3-(4-chloro-7-isopropyl-7H-pyrrolo[2,3-d]pyrimidin-5-yl)-5-cyclopropylisoxazole A solution of (3-(4-chloro-7-isopropyl-7H-pyrrolo[2,3-d]pyrimidin-5-yl)-5-cyclopropylisoxazol-4-yl)methanol (501.4 mg, 1.51 mmol) in DMF (6.027 mL) was treated with tert-butylchlorodimethylsilane (454.2 mg, 3.013 mmol) and 1H-imidazole (307.7 mg, 4.520 mmol) then stirred for 45 min at RT. The resulting mixture was quenched with water and extracted with EtOAc. The combined organic extracts were washed successively with water and brine then dried over anhydrous Na$_2$SO$_{4(s)}$, filtered, and concentrated in vacuo. The crude residue was purified by silica chromatography (0-50% EtOAc in Hexanes as the gradient eluent) to afford the title compound (597.3 mg, 89% yield). MS (apci) m/z=447.2 (M+H).

Step 3: Preparation of 5-(4-(((tert-butyldimethylsilyl)oxy)methyl)-5-cyclopropylisoxazol-3-yl)-4-chloro-7-isopropyl-7H-pyrrolo[2,3-d]pyrimidine-6-carbaldehyde A cold (−78° C.) solution of 4-(((tert-butyldimethylsilyl)oxy)methyl)-3-(4-chloro-7-isopropyl-7H-pyrrolo[2,3-d]pyrimidin-5-yl)-5-cyclopropylisoxazole (338 mg, 0.756 mmol) in THF (7.561 mL) was treated with LDA (2 M THF) (1.13 mL, 2.27 mmol). After stirring the mixture for 30 min at −78° C., ethyl formate (123.1 µL, 1.512 mmol) was added. The resulting mixture was stirred overnight at −20° C. After being allowed to warm to RT, the reaction mixture was quenched with saturated NH$_4$Cl$_{(aq)}$. The quenched mixture was diluted with water and extracted with EtOAc. The organic extracts were washed with brine, dried over anhydrous Na$_2$SO$_{4(s)}$, filtered, and concentrated in vacuo. The crude residue was purified by silica chromatography (0-50% EtOAc in hexanes as the gradient eluent) to afford the title compound (179.3 mg, 50% yield). MS (apci) m/z=475.2 (M+H).

Intermediate P9

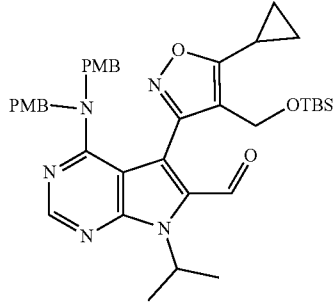

4-(bis(4-methoxybenzyl)amino)-5-(4-(((tert-butyldimethylsilyl)oxy)methyl)-5-cyclopropylisoxazol-3-yl)-7-isopropyl-7H-pyrrolo[2,3-d]pyrimidine-6-carbaldehyde A solution of 5-(4-(((tert-butyldimethylsilyl)oxy)methyl)-5-cyclopropylisoxazol-3-yl)-4-chloro-7-isopropyl-7H-pyrrolo[2,3-d]pyrimidine-6-carbaldehyde (Intermediate P8; 106 mg, 0.22 mmol) in DMSO (444 µL) was treated with bis(4-methoxybenzyl)amine (336.2 mg, 1.110 mmol) and DIEA (387.9 µL, 2.221 mmol). The resulting mixture was stirred for 1 h at 95° C. After subsequently cooling to RT, the reaction was quenched with water and extracted with EtOAc (×3). The combined organic extracts were washed with brine, dried over anhydrous Na$_2$SO$_{4(s)}$, filtered, and concentrated in vacuo. The crude residue was purified by silica chromatography (0-50% EtOAc in hexanes as the gradient eluent) to afford the title compound (140 mg, 91% yield). MS (apci) m/z=696.3 (M+H).

Intermediate P10

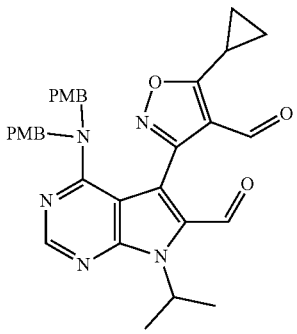

3-(4-(bis(4-methoxybenzyl)amino)-6-formyl-7-isopropyl-7H-pyrrolo[2,3-d]pyrimidin-5-yl)-5-cyclopropylisoxazole-4-carbaldehyde

Step 1: Preparation of (4-(bis(4-methoxybenzyl)amino)-5-(5-cyclopropyl-4-(hydroxymethyl)isoxazol-3-yl)-7-isopropyl-7H-pyrrolo[2,3-d]pyrimidine-6-carbaldehyde A solution of 4-(bis(4-methoxybenzyl)amino)-5-(4-(((tert-butyldimethylsilyl)oxy)methyl)-5-cyclopropylisoxazol-3-yl)-7-isopropyl-7H-pyrrolo[2,3-d]pyrimidine-6-carbaldehyde (Intermediate P9; 170.2 mg, 0.2446 mmol) in THF (2.446 mL) was treated with TBAF (1.0 M in THF) (269 µL, 0.27 mmol). After stirring for 20 min at RT, the reaction mixture was quenched with saturated $NH_4Cl_{(aq)}$ and extracted with EtOAc. The combined organic extracts were dried over anhydrous $Na_2SO_{4(s)}$, filtered, and concentrated in vacuo to afford the title compound (141.4 mg, 99% yield). MS (apci) m/z=582.3 (M+H).

Step 2: Preparation of 3-(4-(bis(4-methoxybenzyl)amino)-6-formyl-7-isopropyl-7H-pyrrolo[2,3-d]pyrimidin-5-yl)-5-cyclopropylisoxazole-4-carbaldehyde A solution of 4-(bis(4-methoxybenzyl)amino)-5-(5-cyclopropyl-4-(hydroxymethyl)isoxazol-3-yl)-7-isopropyl-7H-pyrrolo[2,3-d]pyrimidine-6-carbaldehyde (141.4 mg, 0.2431 mmol) in DCM (2.431 mL) was treated with DMP (154.7 mg, 0.3646 mmol) and stirred for 30 min at RT. The reaction mixture then was washed with saturated $NaHCO_{3(aq)}$. The organic extracts were passed through a phase separator column, and concentrated in vacuo. The crude residue was purified by silica chromatography (0-70% EtOAc in hexanes as the gradient eluent) to afford the title compound (106.5 mg, 76% yield). MS (apci) m/z=580.2 (M+H).

Intermediate P11

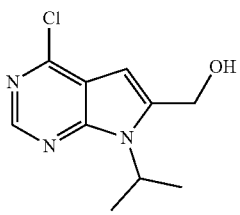

(4-chloro-7-isopropyl-7H-pyrrolo[2,3-d]pyrimidin-6-yl)methanol

Step 1: Preparation of ethyl 4-chloro-7-isopropyl-7H-pyrrolo[2,3-d]pyrimidine-6-carboxylate A solution of ethyl 4-chloro-7H-pyrrolo[2,3-d]pyrimidine-6-carboxylate (1.56 g, 6.91 mmol) in THF (70 mL) was treated with iPrOH (794 µL, 10.4 mmol) and $PPh_3$ (2.72 g, 10.4 mmol), and the resulting mixture was then cooled to 0° C. The cold (0° C.) mixture was treated dropwise with DIAD (2.04 mL, 10.4 mmol), after which it was stirred for 16 h at RT. The resulting mixture was concentrated in vacuo. The crude residue was purified by silica chromatography (5-60% hexanes-EtOAc as the gradient eluent) to afford the title compound (1.76 g, 95% yield). MS (apci) m/z=268.1 (M+H).

Step 2: Preparation of (4-chloro-7-isopropyl-7H-pyrrolo[2,3-d]pyrimidin-6-yl)methanol A cold (−78° C.) solution of ethyl 4-chloro-7-isopropyl-7H-pyrrolo[2,3-d]pyrimidine-6-carboxylate (1.76 g, 6.57 mmol) in DCM (66 mL) was treated with DIBAL-H (25 wt. % in toluene; 13.3 mL, 19.7 mmol), and stirred for 30 min at −78° C. The cold (−78° C.) reaction mixture was quenched with the addition of an aqueous solution of sodium potassium tartrate (1.0 M, ~50 mL). The quenched mixture then was stirred for 60 h at RT, before diluting with additional water. The biphasic mixture was extracted with DCM (2×). The organic extracts were combined, dried over anhydrous $Na_2SO_{4(s)}$, filtered, and concentrated in vacuo. The crude residue was purified by silica chromatography (5-60% hexanes-Acetone as the gradient eluent) to afford the title product (1.43 g, 96% yield). MS (apci) m/z=226.1 (M+H).

Intermediate P12

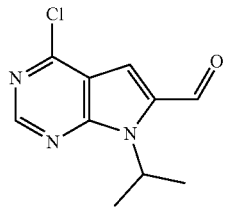

4-chloro-7-isopropyl-7H-pyrrolo[2,3-d]pyrimidine-6-carbaldehyde

A solution of (4-chloro-7-isopropyl-7H-pyrrolo[2,3-d]pyrimidin-6-yl)methanol (Intermediate P11) (3.0 g, 13 mmol) in DCM (66 mL) was treated with 1,1,1-tris(acetyloxy)-1,1-dihydro-1,2-benziodoxol-3-(1H)-one (Dess-Martin periodinane) (8.5 g, 20 mmol) at RT, and the resulting mixture was stirred for 1 h. The reaction was then washed with sat. $NaHCO_3$ (3×) and water (1×), dried ($Na_2SO_4$), filtered and concentrated to afford the title compound as white solid, which was directly used in the next step without further purifications, assuming quantitative yield. MS (apci) m/z=224.1 (M+H).

Intermediate P13

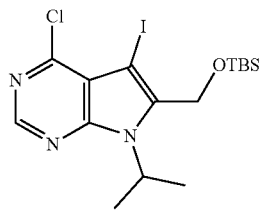 [SMILES: CC(C)n1c(CO[Si](C)(C)C(C)(C)C)c(I)c2c(Cl)ncnc21]

6-(((tert-butyldimethylsilyl)oxy)methyl)-4-chloro-5-iodo-7-isopropyl-7H-pyrrolo[2,3-d]pyrimidine

Step 1: Preparation of (4-chloro-5-iodo-7-isopropyl-7H-pyrrolo[2,3-d]pyrimidin-6-yl)methanol A solution of (4-chloro-7-isopropyl-7H-pyrrolo[2,3-d]pyrimidin-6-yl)methanol (Intermediate P11) (1.43 g, 6.34 mmol) in DMF (25 mL) was treated with NIS (1.57 g, 6.97 mmol), and the mixture was then stirred for 16 h at RT. The resulting mixture was diluted with water and extracted with EtOAc (2×). The combined organic extracts were washed with water (3×) and brine (1×), and then dried over anhydrous Na$_2$SO$_{4(s)}$, filtered, and concentrated in vacuo to afford the title compound (2.12 g, 95% yield). MS (apci) m/z=352.0 (M+H).

Step 2: Preparation of 6-(((tert-butyldimethylsilyl)oxy)methyl)-4-chloro-5-iodo-7-isopropyl-7H-pyrrolo[2,3-d]pyrimidine A solution of (4-chloro-5-iodo-7-isopropyl-7H-pyrrolo[2,3-d]pyrimidin-6-yl)methanol (2.12 g, 6.03 mmol) in DMF (30 mL) was treated with TBDMSCl (1.36 g, 9.05 mmol) and imidazole (821 mg, 12.1 mmol), and then stirred for 1 h at RT. The resulting mixture was quenched with water, and extracted with EtOAc (2×). The combined organic extracts were washed with water (3×) and brine (1×), then dried over anhydrous Na$_2$SO$_{4(s)}$, filtered, and concentrated in vacuo. The crude residue was purified by silica chromatography (5-50% hexanes-EtOAc as the gradient eluent) to afford the title compound (2.58 g, 92% yield). MS (apci) m/z=466 (M+H).

Intermediate P14

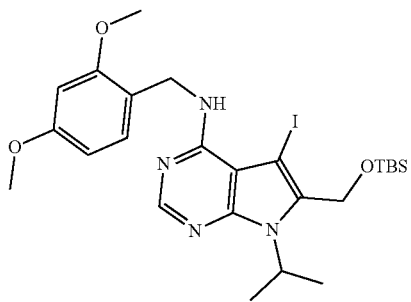 [SMILES: COc1ccc(CNc2ncnc3c2c(I)c(CO[Si](C)(C)C(C)(C)C)n3C(C)C)c(OC)c1]

6-(((tert-butyldimethylsilyl)oxy)methyl)-N-(2,4-dimethoxybenzyl)-5-iodo-7-isopropyl-7H-pyrrolo[2,3-d]pyrimidin-4-amine A solution of 6-(((tert-butyldimethylsilyl)oxy)methyl)-4-chloro-5-iodo-7-isopropyl-7H-pyrrolo[2,3-d]pyrimidine (Intermediate P13; 1.49 g, 3.20 mmol) in DMSO (13 mL) was treated with 2,4-dimethoxybenzylamine (1.201 mL, 7.996 mmol), and the resulting mixture was then stirred for 16 h at 60° C. After cooling to RT, the reaction mixture was diluted with water, and extracted with EtOAc (2×). The combined organic extracts were washed with water (3×) and brine (1×), then dried over anhydrous Na$_2$SO$_{4(s)}$, filtered, and concentrated in vacuo. The crude residue was purified by silica chromatography (5-75% MTBE in hexanes) to afford the title compound (1.88 g, 99% yield). MS (apci) m/z=597.1 (M+H).

Intermediate P15

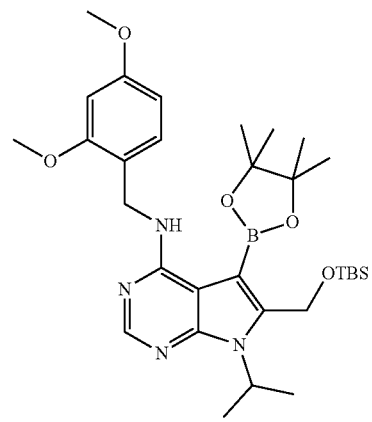

6-(((tert-butyldimethylsilyl)oxy)methyl)-N-(2,4-dimethoxybenzyl)-7-isopropyl-5-(4,4,5,5-tetramethyl-1,3,2-dioxaborolan-2-yl)-7H-pyrrolo[2,3-d]pyrimidin-4-amine To a mixture of 6-(((tert-butyldimethylsilyl)oxy)methyl)-N-(2,4-dimethoxybenzyl)-5-iodo-7-isopropyl-7H-pyrrolo[2,3-d]pyrimidin-4-amine (0.30 g, 0.50 mmol) (Intermediate P14) and Pd(PPh$_3$)$_4$ (58 mg, 0.05 mmol) in 1,4-dioxane (2.5 mL) was added Et$_3$N (0.1 mL, 0.75 mmol) under nitrogen. The mixture was degassed and purged with N$_2$ before 4,4,5,5-tetramethyl-1,3,2-dioxaborolane (95 μL, 0.65 mmol) was introduced. The resulting mixture was heated at 90° C. for 3 h then cooled to rt, after which it was concentrated, and the resulting residue was purified by silica chromatography (0-50% EtOAc in hexanes) to afford the title product as light yellowish solid (0.24 g, 80%). MS (apci) m/z=597.4 (M+H).

Intermediate P16

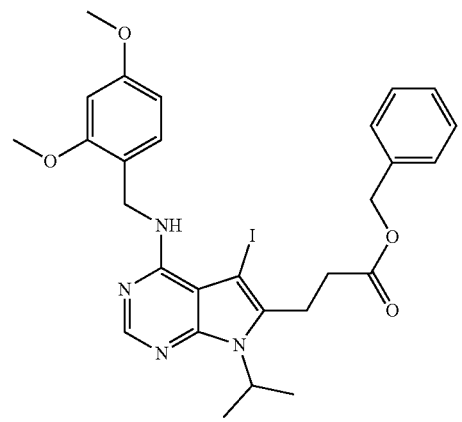 [SMILES: COc1ccc(CNc2ncnc3c2c(I)c(CCC(=O)OCc2ccccc2)n3C(C)C)c(OC)c1]

Benzyl 3-(4-((2,4-dimethoxybenzyl)amino)-5-iodo-7-isopropyl-7H-pyrrolo[2,3-d]pyrimidin-6-yl)propanoate Step 1: Preparation of benzyl (E)-3-(4-chloro-7-isopropyl-7H-pyrrolo[2,3-d]pyrimidin-6-yl)acrylate To a solution of 4-chloro-7-isopropyl-7H-pyrrolo[2,3-d]pyrimidine-6-carbaldehyde (Intermediate P12) (2.1 g, 9.34 mmol) in DCM (47 mL) was added benzyl 2-(triphenyl-λ5-phosphanylidene)acetate (4.22 g, 10.3 mmol) at RT and stirred for 30 min. The reaction was partitioned between DCM and water. After phase-separation, the organic layer was washed with brine then dried (Na₂SO₄), filtered, concentrated and purified by silica chromatography (10-90% EtOAc in hexanes) to afford the title compound (1.6 g, 47%). MS (apci) m/z=356.1 (M+H).

Step 2: Preparation of benzyl 3-(4-chloro-7-isopropyl-7H-pyrrolo[2,3-d]pyrimidin-6-yl)propanoate To a solution of Cu(OAC)₂ (0.080 g, 0.44 mmol) and Xantphos (0.51 g, 0.88 mmol) in THF (20 mL) was added phenylsilane (5.4 mL, 43.9 mmol) at RT. The resulting mixture was stirred for 5 min. Then a solution of benzyl (E)-3-(4-chloro-7-isopropyl-7H-pyrrolo[2,3-d]pyrimidin-6-yl)acrylate (1.56 g, 4.39 mmol) in THF (10 mL) was introduced, and stirring was continued for another 1 h. The reaction was partitioned between EtOAc and water. After phase-separation, the organic layer was washed with brine then dried (Na₂SO₄), filtered, concentrated and purified by silica chromatography (10-90% EtOAc in hexanes) to afford the title compound (1.24 g, 79%). MS (apci) m/z=358.1 (M+H).

Step 3: Preparation of benzyl 3-(4-((2,4-dimethoxybenzyl)amino)-7-isopropyl-7H-pyrrolo[2,3-d]pyrimidin-6-yl)propanoate A mixture of benzyl 3-(4-chloro-7-isopropyl-7H-pyrrolo[2,3-d]pyrimidin-6-yl)propanoate (1.24 g, 3.47 mmol) and (2,4-dimethoxyphenyl)methanamine (1.6 mL, 10.4 mmol) in DMSO (23 mL) was heated at 90° C. overnight. After cooled to RT, the reaction was partitioned between EtOAc and water. After phase-separation, the organic layer was washed with brine then dried (Na₂SO₄), filtered, concentrated and purified by silica chromatography (10-90% EtOAc in hexanes) to afford the title compound (0.50 g, 30%). MS (apci) m/z=489.2 (M+H).

Step 4: Preparation of benzyl 3-(4-((2,4-dimethoxybenzyl)amino)-5-iodo-7-isopropyl-7H-pyrrolo[2,3-d]pyrimidin-6-yl)propanoate To a solution of benzyl 3-(4-((2,4-dimethoxybenzyl)amino)-7-isopropyl-7H-pyrrolo[2,3-d]pyrimidin-6-yl)propanoate (148 mg, 0.30 mmol) in DMF (3 mL) was added NIS (72 mg, 0.32 mmol) at RT and stirred for 2 h. The reaction was partitioned between EtOAc and water. After phase-separation, the organic layer was washed with brine then dried (Na₂SO₄), filtered, concentrated and purified by silica chromatography (10-90% EtOAc in hexanes) to afford the title product (108 mg, 58%). MS (apci) m/z=615.2 (M+H).

Intermediate P17

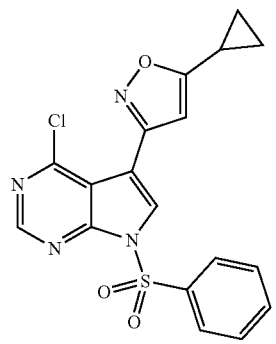 [SMILES: O=S(=O)(c1ccccc1)n1cc(-c2cc(C3CC3)on2)c2c(Cl)ncnc21]

3-(4-chloro-7-(phenylsulfonyl)-7H-pyrrolo[2,3-d]pyrimidin-5-yl)-5-cyclopropylisoxazole Step 1: Preparation of 4-chloro-7H-pyrrolo[2,3-d]pyrimidine-5-carbaldehyde Under an atmosphere of N₂(g), n-BuLi (2.5 M, hexanes) (9.2 mL, 23.0 mmol) was dropwise added to a suspension of 5-bromo-4-chloro-7H-pyrrolo[2,3-d]pyrimidine (2.32 g, 9.98 mmol) in THF (50 mL) cooled to −78° C. The reaction was stirred for 1 h before DMF (1.00 mL, 13.0 mmol) was introduced dropwise. After stirring at −78° C. for another 30 min, the reaction was slowly warmed to RT, then quenched with saturated NH₄Cl(aq) and water. The biphasic mixture was concentrated in vacuo to remove the organic solvents, and the resulting suspension was filtered. The solids collected were rinsed with water and hexanes, and then dried in vacuo to afford the title compound (1.52 g, 84% yield).

Step 2: Preparation of 4-chloro-7-(phenylsulfonyl)-7H-pyrrolo[2,3-d]pyrimidine-5-carbaldehyde A solution of 4-chloro-7H-pyrrolo[2,3-d]pyrimidine-5-carbaldehyde (400 mg, 2.2 mmol) in DMF (11 mL) was treated with 60 wt. % NaH (110 mg, 2.75 mmol) and stirred for 15 min at RT. The resulting yellow solution was treated dropwise with benzenesulfonyl chloride (340 μL, 2.6 mmol). After stirring for 20 min at RT, the reaction mixture was quenched with ice (2 g) and water (20 mL). The quenched mixture was stirred at RT for 3 min, and then the resulting suspension was filtered. The solids collected were rinsed with water (10 mL) and hexanes (10 mL), and then air dried to afford the title compound (650 mg, 92% yield).

Step 3: Preparation of 4-chloro-7-(phenylsulfonyl)-7H-pyrrolo[2,3-d]pyrimidine-5-carbaldehyde Oxime A mixture of 4-chloro-7-(phenylsulfonyl)-7H-pyrrolo[2,3-d]pyrimidine-5-carbaldehyde (650 mg, 2.0 mmol), NH₂OH—HCl (170 mg, 2.4 mmol) and NaOAc (200 mg, 2.4 mmol) in EtOH (20 mL) was stirred for 20 h at RT. The resulting mixture was diluted with DCM (20 mL), and the resulting suspension was filtered through a pad of Celite®. The filtrate was concentrated in vacuo to afford the title compound (680 mg, quantitative yield).

Step 4: Preparation of 3-(4-chloro-7-(phenylsulfonyl)-7H-pyrrolo[2,3-d]pyrimidin-5-yl)-5-cyclopropylisoxazole A solution of 4-chloro-7-(phenylsulfonyl)-7H-pyrrolo[2,3-d]pyrimidine-5-carbaldehyde oxime (170 mg, 0.505 mmol), NCS (80.9 mg, 0.606 mmol), KHCO$_{3(s)}$ (92 mg, 1.52 mmol) and cyclopropylacetylene (128 µL, 1.51 mmol) in DMF (5.048 mL) was stirred for 45 min at 50° C. After cooling to RT, the reaction mixture was diluted with EtOAc and then quenched with water. The resulting suspension was filtered, and the solids were rinsed with EtOAc and water. The biphasic filtrate was separated, and the organic extracts were concentrated in vacuo. The crude residue was purified by silica chromatography (0-30% EtOAc in hexanes) to afford the title compound (101 mg, 50% yield). MS (apci) m/z=401.0 (M+H).

Intermediate P18

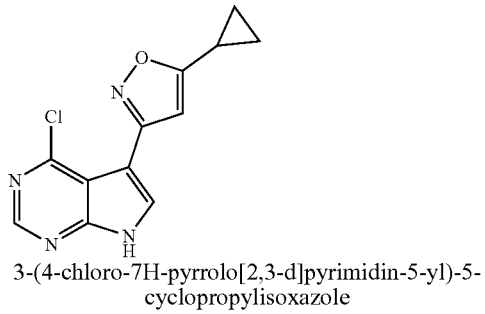

3-(4-chloro-7H-pyrrolo[2,3-d]pyrimidin-5-yl)-5-cyclopropylisoxazole

To a solution of tetrabutylammonium fluoride (TBAF) in THF (1 M) (14.6 mL, 14.6 mmol) was added 3-(4-chloro-7-(phenylsulfonyl)-7H-pyrrolo[2,3-d]pyrimidin-5-yl)-5-cyclopropylisoxazole (Intermediate P17) (2.93 g, 7.31 mmol). The mixture was heated at 60° C. for 1 h, then cooled to RT, diluted with EtOAc (50 mL) and washed with water (2×30 mL). After phase-separation, the organic layer was dried (Na$_2$SO$_4$), filtered and concentrated to give the title product as beige solid, assuming quantitative yield. MS (apci neg) m/z=259.1 (M–H).

Intermediate P19

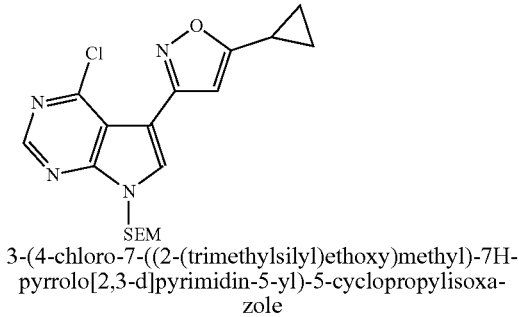

3-(4-chloro-7-((2-(trimethylsilyl)ethoxy)methyl)-7H-pyrrolo[2,3-d]pyrimidin-5-yl)-5-cyclopropylisoxazole

Method A

Step 1: Preparation of 4-chloro-7-((2-(trimethylsilyl)ethoxy)methyl)-7H-pyrrolo[2,3-d]pyrimidine-5-carbaldehyde To a suspension of 4-chloro-7H-pyrrolo[2,3-d]pyrimidine-5-carbaldehyde (1.82 g, 10.0 mmol) in DMF (33 mL) was added NaH (60 wt %) (0.44 g, 11.0 mmol) at 0° C. After 20 min stirring 2-(trimethylsilyl)ethoxymethyl chloride (SEM-Cl) (2.13 mL, 12.0 mmol) was introduced. The reaction was allowed to warm to RT and stirred for 3 h. This was followed by the addition of more NaH (0.24 g, 6 mmol) and SEM-Cl (0.84 g, 5 mmol). After another 30 min of stirring, the reaction mixture was quenched with ice and NH$_4$Cl (sat.), and then extracted with EtOAc. The combined organic extracts were washed with water, dried (Na$_2$SO$_4$), filtered, concentrated and purified by silica chromatography (0-25% EtOAc in hexanes) to give the title product as yellowish solid (1.33 g, 43%). MS (apci) m/z=312.1 (M+H).

Step 2: Preparation of 4-chloro-7-((2-(trimethylsilyl)ethoxy)methyl)-7H-pyrrolo[2,3-d]pyrimidine-5-carbaldehyde Oxime A mixture of 4-chloro-7-((2-(trimethylsilyl)ethoxy)methyl)-7H-pyrrolo[2,3-d]pyrimidine-5-carbaldehyde (1.33 g, 4.26 mmol), hydroxylamine hydrochloride (0.33 g, 4.7 mmol) and NaOAc (0.38 g, 4.7 mmol) in EtOH (21 mL) was stirred at 40° C. for 1 h, after which it was concentrated. The residue thus obtained was taken up in DCM and filtered through a short pad of celite. The filtrate was concentrated to afford the title product as white solid, assuming quantitative yield. LCMS m/z=327.1 (M+H).

Step 3: Preparation of 3-(4-chloro-7-((2-(trimethylsilyl)ethoxy)methyl)-7H-pyrrolo[2,3-d]pyrimidin-5-yl)-5-cyclopropylisoxazole A mixture of 4-chloro-7-((2-(trimethylsilyl)ethoxy)methyl)-7H-pyrrolo[2,3-d]pyrimidine-5-carbaldehyde oxime (1.37 g, 4.2 mmol), NCS (0.617 g, 4.62 mmol), KHCO$_3$ (0.631 g, 6.30 mmol) and cyclopropylacetylene (1.07 mL, 12.6 mmol) in DMF (21 mL) was stirred at RT for 5 d. The reaction was diluted with water and extracted with EtOAc (3×). The combined organic extracts were washed with brine, dried (Na$_2$SO$_4$), filtered, concentrated and purified by silica chromatography (0-30% EtOAc in hexanes) to afford the title product (0.83 g, 50%). MS (apci) m/z=391.2 (M+H).

Method B

To a solution of 3-(4-chloro-7H-pyrrolo[2,3-d]pyrimidin-5-yl)-5-cyclopropylisoxazole (Intermediate P18) (5.87 g, 22.52 mmol) in DMF (113 mL) was added NaH (60 wt %) (1.08 g, 27.0 mmol) followed by (2-(chloromethoxy)ethyl)trimethylsilane (SEM-Cl) (4.4 mL, 24.8 mmol) at RT. After 30 min stirring, the reaction was diluted with water and extracted with EtOAc (2×). The combined organic extracts were washed with brine, dried (Na$_2$SO$_4$), filtered, concentrated and purified by silica chromatography (0-50% EtOAc in hexanes) to afford the title product as clear brownish oil (2.7 g, 31%). MS (apci) m/z=391.1 (M+H).

Intermediate P20

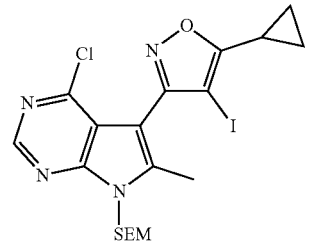 [SMILES: Cc1c(-c2noc(C3CC3)c2I)c2c(Cl)ncnc2n1COCC[Si](C)(C)C]

3-(4-chloro-6-methyl-7-((2-(trimethylsilyl)ethoxy)methyl)-7H-pyrrolo[2,3-d]pyrimidin-5-yl)-5-cyclopropyl-4-iodoisoxazole Step 1: Preparation of 3-(4-chloro-6-methyl-7-((2-(trimethylsilyl)ethoxy)methyl)-7H-pyrrolo[2,3-d]pyrimidin-5-yl)-5-cyclopropylisoxazole To a solution of 3-(4-chloro-7-((2-(trimethylsilyl)ethoxy)methyl)-7H-pyrrolo[2,3-d]pyrimidin-5-yl)-5-cyclopropylisoxazole (Intermediate P19) (1.96 g, 5.01 mmol) in THF (25 mL) was added n-BuLi (2.5 M THF) (3.0 mL, 7.5 mmol) at −78° C. After 10 min stirring, iodomethane (0.63 mL, 10.0 mmol) was introduced, and the resulting solution was stirred at −78° C. for 30 min before warming up to −20° C. The reaction was quenched with NH₄Cl (sat.) and extracted with EtOAc. The combined organic extracts were dried (Na₂SO₄), filtered and concentrated to give the title product as brownish oil, assuming quantitative yield. MS (apci) m/z=405.1 (M+H).

Step 2: Preparation of 3-(4-chloro-6-methyl-7-((2-(trimethylsilyl)ethoxy)methyl)-7H-pyrrolo[2,3-d]pyrimidin-5-yl)-5-cyclopropyl-4-iodoisoxazole A solution of 3-(4-chloro-6-methyl-7-((2-(trimethylsilyl)ethoxy)methyl)-7H-pyrrolo[2,3-d]pyrimidin-5-yl)-5-cyclopropylisoxazole (2.0 g, 5.0 mmol) in MeCN (25 mL) and treated with NIS (1.69 g, 7.52 mmol) and TFA (1.16 mL, 15.0 mmol). The resulting mixture was stirred at RT for 3 h, after which it was quenched with 10% Na₂S₂O₃ (aq) (5 mL) and sat. NaHCO₃ (20 mL). This was followed by extraction with EtOAc (3×). The combined organic extracts were dried (Na₂SO₄), filtered, concentrated and purified by silica chromatography (0-30% EtOAc in hexanes) to afford the title product as yellowish oil (1.5 g, 56%). LCMS m/z=531.0 (M+H).

Intermediate P21

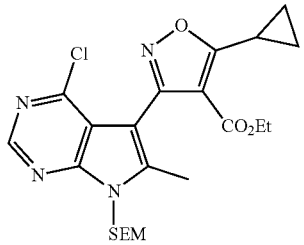 [SMILES: CCOC(=O)c1c(-c2c(C)n(COCC[Si](C)(C)C)c3ncnc(Cl)c23)noc1C1CC1]

Ethyl 3-(4-chloro-6-methyl-7-((2-(trimethylsilyl)ethoxy)methyl)-7H-pyrrolo[2,3-d]pyrimidin-5-yl)-5-cyclopropylisoxazole-4-carboxylate To a solution of 3-(4-chloro-6-methyl-7-((2-(trimethylsilyl)ethoxy)methyl)-7H-pyrrolo[2,3-d]pyrimidin-5-yl)-5-cyclopropyl-4-iodoisoxazole (Intermediate P20) (1.50 g, 2.83 mmol) in THF (14 mL) was dropwise added isopropylmagnesium(II) lithium chloride (1.3 M) (2.8 mL, 3.67 mmol) at 0° C. After 10 min stirring ethyl chloroformate (0.54 mL, 5.65 mmol) was introduced, and the resulting mixture was warmed to RT and stirred for 1 h. The reaction was quenched with NH₄Cl (sat.) and extracted with EtOAc. The combined organic extracts were dried (Na₂SO₄), filtered, concentrated and purified by silica chromatography (0-30% EtOAc in hexanes) to afford the title product along with a side product 3-(4-chloro-6-methyl-7-((2-(trimethylsilyl)ethoxy)methyl)-7H-pyrrolo[2,3-d]pyrimidin-5-yl)-5-cyclopropylisoxazole (ca. 25%) as yellowish oil. The title product was used directly in the next step without further purifications (1.2 g, 90%). MS (apci) m/z=477.2 (M+H).

Intermediate P22

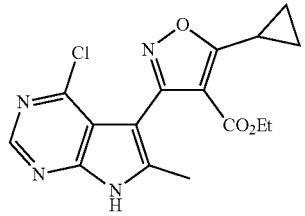 [SMILES: CCOC(=O)c1c(-c2c(C)[nH]c3ncnc(Cl)c23)noc1C1CC1]

Ethyl 3-(4-chloro-6-methyl-7H-pyrrolo[2,3-d]pyrimidin-5-yl)-5-cyclopropylisoxazole-4-carboxylate A solution of ethyl 3-(4-chloro-6-methyl-7-((2-(trimethylsilyl)ethoxy)methyl)-7H-pyrrolo[2,3-d]pyrimidin-5-yl)-5-cyclopropylisoxazole-4-carboxylate (Intermediate P21) (150 mg, 0.31 mmol) in TFA (0.5 mL) was stirred at RT for 16 h. The mixture was then concentrated and the resulting residue purified by reverse phase chromatography (0-95% MeCN in water with 0.1% TFA). The combined product fractions were partitioned between sat. NaHCO₃ and DCM. After phase-separation the organic layer was concentrated to afford the title product as off-white solid (82 mg, 75%). MS (apci) m/z=347.0 (M+H).

Intermediate P23

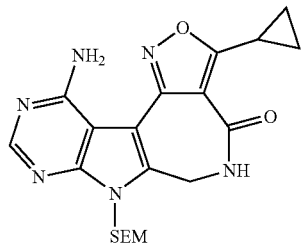 [SMILES: C[Si](C)(C)CCOCn1c2c(c3c(N)ncnc31)-c1noc(C3CC3)c1C(=O)NC2]

11-amino-3-cyclopropyl-7-((2-(trimethylsilyl)ethoxy)methyl)-6,7-dihydroisoxazolo[4,3-c]pyrimido[5′,4′:4,5]pyrrolo[3,2-e]azepin-4(5H)-one A mixture of ethyl 3-(4-chloro-6-methyl-7-((2-(trimethylsilyl)ethoxy)methyl)-7H-pyrrolo[2,3-d]pyrimidin-5-yl)-5-cyclopropylisoxazole-4-carboxylate (Intermediate P21) (189 mg, 0.40 mmol), NBS (84.6 mg, 0.48 mmol) and AIBN (9.8 mg, 0.059 mmol) in 1,2-DCE (4 mL) was flushed with nitrogen, sealed in a pressure vessel and stirred at 80° C. for 2 h. Upon cooling to RT, the reaction was concentrated. The residue thus obtained was then taken up in 1,4-dioxane (4 mL) and NH₄OH (28-30%) (2 mL). The mixture was re-sealed in the vessel and stirred at 90° C. for 16 h, then cooled to RT and concentrated. The crude residue was subjected to reverse phase chromatography (0-95% MeCN in water with 0.1% TFA). The combined product fractions were neutralized with 10% Na₂CO₃ (aq) and extracted with DCM. The organic extracts were dried (Na₂SO₄), filtered and concentrated to afford the title product as off-white solid (15 mg, 8.8%). MS (apci) m/z=427.1 (M+H).

303
Intermediate P24

304
Intermediate P25

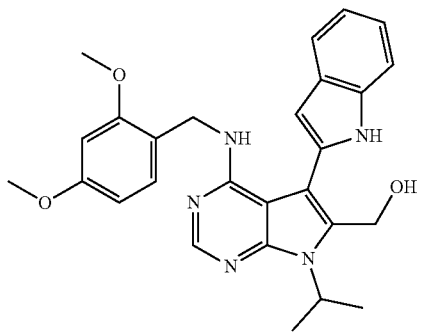 [SMILES: COc1ccc(CNc2ncnc3c2c(-c2cc4ccccc4[nH]2)c(CO)n3C(C)C)c(OC)c1]

(4-((2,4-dimethoxybenzyl)amino)-5-(1H-indol-2-yl)-7-isopropyl-7H-pyrrolo[2,3-d]pyrimidin-6-yl)methanol

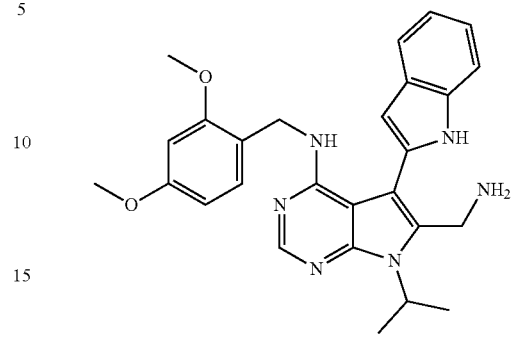

6-(aminomethyl)-N-(2,4-dimethoxybenzyl)-5-(1H-indol-2-yl)-7-isopropyl-7H-pyrrolo[2,3-d]pyrimidin-4-amine

Step 1: Preparation of 6-((((tert-butyldimethylsilyl)oxy)methyl)-N-(2,4-dimethoxybenzyl)-5-(1H-indol-2-yl)-7-isopropyl-7H-pyrrolo[2,3-d]pyrimidin-4-amine A mixture of 6-((((tert-butyldimethylsilyl)oxy)methyl)-N-(2,4-dimethoxybenzyl)-5-iodo-7-isopropyl-7H-pyrrolo[2,3-d]pyrimidin-4-amine (Intermediate P14) (218 mg, 0.36 mmol), $(PPh_3)_2Pd(II)Cl_2$ (51.3 mg, 0.073 mmol), 2-(4,4,5,5-tetramethyl-1,3,2-dioxaborolan-2-yl)-1H-indole (178 mg, 0.73 mmol) and $Na_2CO_3$ (2 N aq) (365 µL, 0.73 mmol) in dioxane (5.2 mL) was sparged with Ar and stirred at 80° C. overnight. After cooled to RT, the reaction was partitioned between DCM and water. The aqueous was phase extracted with 4:1 DCM:IPA (3×). The combined organic extracts were concentrated and purified using silica chromatography (0-100% EtOAc in hexanes) to give the title compound (164 mg, 76% yield). MS (apci) m/z=586.3 (M+H).

Step 2: Preparation of (4-((2,4-dimethoxybenzyl)amino)-5-(1H-indol-2-yl)-7-isopropyl-7H-pyrrolo[2,3-d]pyrimidin-6-yl)methanol To a solution of 6-((((tert-butyldimethylsilyl)oxy)methyl)-N-(2,4-dimethoxybenzyl)-5-(1H-indol-2-yl)-7-isopropyl-7H-pyrrolo[2,3-d]pyrimidin-4-amine (164 mg, 0.28 mmol) in THF (2.8 mL) was added acetic acid (32 µL, 0.56 mmol) at 0° C., followed by tetrabutylammonium fluoride (TBAF) (1 M, THF; 308 µL, 0.31 mmol). The reaction was allowed to warm to RT and stirred for 3 h before it was concentrated and purified using silica chromatography (0-100% EtOAc in hexanes) to give the title compound (109 mg, 82% yield). MS (apci) m/z=472.2 (M+H).

Step 1: Preparation of 6-(azidomethyl)-N-(2,4-dimethoxybenzyl)-5-(1H-indol-2-yl)-7-isopropyl-7H-pyrrolo[2,3-d]pyrimidin-4-amine To a solution of (4-((2,4-dimethoxybenzyl)amino)-5-(1H-indol-2-yl)-7-isopropyl-7H-pyrrolo[2,3-d]pyrimidin-6-yl)methanol (Intermediate P24) (99 mg, 0.21 mmol) in toluene (2.1 mL) was added 1,8-diazabicyclo[5.4.0]undec-7-ene (DBU) (38 µL, 0.25 mmol) at 0° C., followed by diphenylphosphoryl azide (DPPA) (54 µL, 0.25 mmol). The reaction was allowed to warm to rt. After stirring overnight, the reaction mixture was diluted with EtOAc and washed with water and brine, then dried ($Na_2SO_4$), filtered and concentrated. The residue was purified using silica chromatography (0-100% EtOAc in hexanes) to afford the title compound (71 mg, 68% yield). MS (apci) m/z=497.2 (M+H).

Step 2: Preparation of 6-(aminomethyl)-N-(2,4-dimethoxybenzyl)-5-(1H-indol-2-yl)-7-isopropyl-7H-pyrrolo[2,3-d]pyrimidin-4-amine To a solution of 6-(azidomethyl)-N-(2,4-dimethoxybenzyl)-5-(1H-indol-2-yl)-7-isopropyl-7H-pyrrolo[2,3-d]pyrimidin-4-amine (70 mg, 0.14 mmol) in 1:1 THF:water (1.4 mL) was added $PPh_3$ (74 mg, 0.28 mmol) at RT and stirred for 16 h. The reaction was diluted with 4:1 DCM:IPA and washed with sat. $NaHCO_3$. The combined organic phase was then dried ($Na_2SO_4$), filtered, concentrated and purified by silica chromatography (0-100% EtOAc in hexanes) to afford the title product (51 mg, 77%). MS (apci) m/z=471.2 (M+H).

Intermediate P26

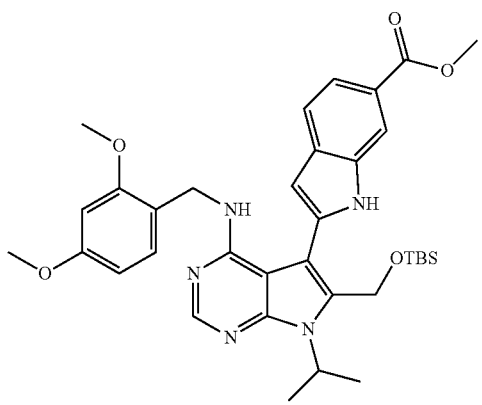

Methyl 2-(6-(((tert-butyldimethylsilyl)oxy)methyl)-4-((2,4-dimethoxybenzyl)amino)-7-isopropyl-7H-pyrrolo[2,3-d]pyrimidin-5-yl)-1H-indole-6-carboxylate A mixture of 6-methoxycarbonyl-1H-indole-2-boronic acid pinacol ester (852 mg, 2.83 mmol), (PPh$_3$)$_2$Pd(II)Cl$_2$ (99.3 mg, 0.141 mmol), 6-(((tert-butyldimethylsilyl)oxy)methyl)-N-(2,4-dimethoxybenzyl)-5-iodo-7-isopropyl-7H-pyrrolo[2,3-d]pyrimidin-4-amine (Intermediate P14) (422 mg, 0.707 mmol) and Na$_2$CO$_3$ (2 N aq) (707 µL, 1.41 mmol) in dioxane (10 mL) was sparged with Ar and heated at 80° C. for 2 h. The reaction was partitioned between DCM and water then extracted with 4:1 DCM:IPA (3×). The combined organic extracts were concentrated and purified using silica chromatography (0-40% EtOAc in hexanes) to yield the title product (415 mg, 91%). MS (apci) m/z=644.3 (M+H).

Intermediate P27

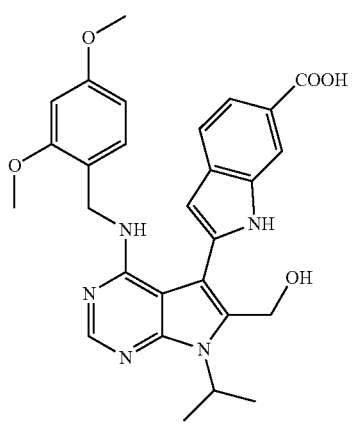 [SMILES: COc1ccc(CNc2ncnc3c2c(-c2cc4ccc(C(=O)O)cc4[nH]2)c(CO)n3C(C)C)c(OC)c1]

2-(4-((2,4-Dimethoxybenzyl)amino)-6-(hydroxymethyl)-7-isopropyl-7H-pyrrolo[2,3-d]pyrimidin-5-yl)-1H-indole-6-carboxylic Acid To a solution of methyl 2-(6-(((tert-butyldimethylsilyl)oxy)methyl)-4-((2,4-dimethoxybenzyl)amino)-7-isopropyl-7H-pyrrolo[2,3-d]pyrimidin-5-yl)-1H-indole-6-carboxylate (Intermediate P26) (339 mg, 0.53 mmol) in THF (10 mL) and MeOH (1 mL) was added LiOH (2 M aq) (1.3 mL, 2.6 mmol) at RT. The reaction mixture was stirred overnight. Additional LiOH (2 M aq) (1.3 mL, 2.6 mmol) was then introduced and the reaction was stirred for another 48 h before it was acidified with HCl (1 M aq) to pH ~5. It was then diluted with water (3 mL) and extracted with DCM (3×5 mL). The combined organic extracts were concentrated and purified with silica chromatography (0-10% MeOH in DCM) to yield the title product (140 mg, 50%). MS (apci) m/z=516.2 (M+H).

Intermediate P28

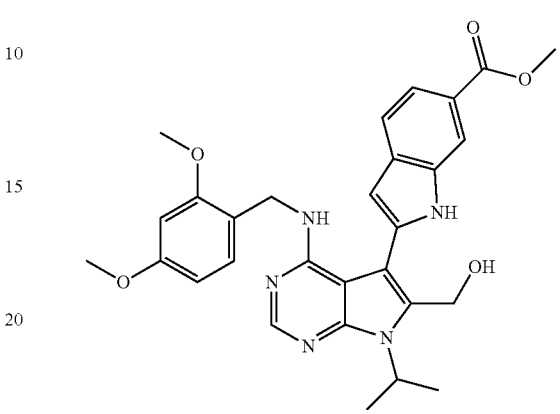

Methyl 2-(4-((2,4-dimethoxybenzyl)amino)-6-(hydroxymethyl)-7-isopropyl-7H-pyrrolo[2,3-d]pyrimidin-5-yl)-1H-indole-6-carboxylate The title product was prepared in a similar fashion as described for the synthesis of (4-((2,4-dimethoxybenzyl)amino)-5-(1H-indol-2-yl)-7-isopropyl-7H-pyrrolo[2,3-d]pyrimidin-6-yl)methanol (Intermediate P24), replacing 2-(4,4,5,5-tetramethyl-1,3,2-dioxaborolan-2-yl)-1H-indole with methyl 2-(4,4,5,5-tetramethyl-1,3,2-dioxaborolan-2-yl)-1H-indole-6-carboxylate during step 1 instead. MS (apci) m/z=530.2 (M+H).

Intermediate P29

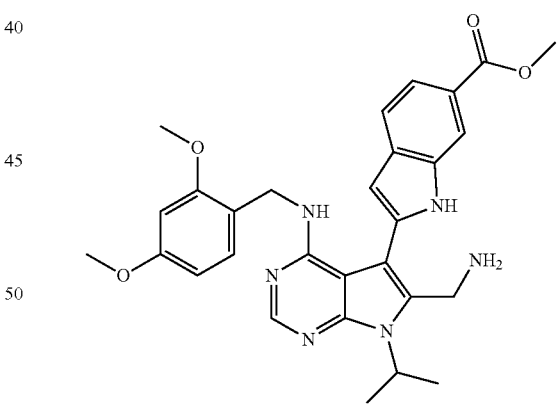

Methyl 2-(6-(aminomethyl)-4-((2,4-dimethoxybenzyl)amino)-7-isopropyl-7H-pyrrolo[2,3-d]pyrimidin-5-yl)-1H-indole-6-carboxylate The title product was prepared in a similar fashion as described for the synthesis of 6-(aminomethyl)-N-(2,4-dimethoxybenzyl)-5-(1H-indol-2-yl)-7-isopropyl-7H-pyrrolo[2,3-d]pyrimidin-4-amine (Intermediate P25), replacing (4-((2,4-dimethoxybenzyl)amino)-5-(1H-indol-2-yl)-7-isopropyl-7H-pyrrolo[2,3-d]pyrimidin-6-yl)methanol (Intermediate P24) with methyl 2-(4-((2,4-dimethoxybenzyl)amino)-6-(hydroxymethyl)-7-isopropyl-7H-pyrrolo[2, 3-d]pyrimidin-5-yl)-1H-indole-6-carboxylate (Intermediate P28) during step 1 instead. MS (apci) m/z=529.2 (M+H).

Intermediate P30

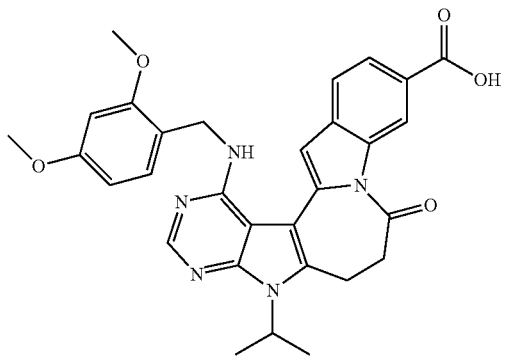 [SMILES: COc1ccc(CNc2ncnc3c2c2c(n3C(C)C)CCC(=O)n3c-2cc2ccc(C(=O)O)cc23)c(OC)c1]

1-((2,4-dimethoxybenzyl)amino)-5-isopropyl-8-oxo-5,6,7,8-tetrahydropyrimido[5'',4'':4',5']pyrrolo[3',2':3,4]azepino[1,2-a]indole-11-carboxylic Acid Step 1: Preparation of methyl 2-(6-(3-(benzyloxy)-3-oxopropyl)-4-((2,4-dimethoxybenzyl)amino)-7-isopropyl-7H-pyrrolo[2,3-d]pyrimidin-5-yl)-1H-indole-6-carboxylate A mixture of methyl 2-(4,4,5,5-tetramethyl-1,3,2-dioxaborolan-2-yl)-1H-indole-6-carboxylate (0.318 g, 1.05 mmol), benzyl 3-(4-((2,4-dimethoxybenzyl)amino)-5-iodo-7-isopropyl-7H-pyrrolo[2,3-d]pyrimidin-6-yl)propanoate (Intermediate P16) (0.108 g, 0.176 mmol), PdCl$_2$(PPh$_3$)$_2$ (0.0123 g, 0.0176 mmol) and Na$_2$CO$_3$ (2 N, aq) (0.27 ml, 0.54 mmol) in dioxane (0.88 mL) was heated to 90° C. overnight. The reaction mixture was then filtered, concentrated and purified by silica chromatography (1-15% MeOH in DCM) to give the title compound (0.116 g, 99%). MS (apci) m/z=662.3 (M+H).

Step 2: Preparation of 2-(6-(2-carboxyethyl)-4-((2,4-dimethoxybenzyl)amino)-7-isopropyl-7H-pyrrolo[2,3-d]pyrimidin-5-yl)-1H-indole-6-carboxylic Acid A mixture of methyl 2-(6-(3-(benzyloxy)-3-oxopropyl)-4-((2,4-dimethoxybenzyl)amino)-7-isopropyl-7H-pyrrolo[2,3-d]pyrimidin-5-yl)-1H-indole-6-carboxylate (0.10 g, 0.15 mmol) and LiOH (2 N, aq) (0.23 mL, 0.46 mmol) in MeOH (0.76 mL) was refluxed overnight. The mixture was concentrated and purified by silica chromatography (1-15% MeOH in DCM with 1% AcOH) to give the title compound (0.058 g, 69%). MS (apci) m/z=558.2 (M+H).

Step 3: Preparation of 1-((2,4-dimethoxybenzyl)amino)-5-isopropyl-8-oxo-5,6,7,8-tetrahydropyrimido[5'',4'':4',5']pyrrolo[3',2':3,4]azepino[1,2-a]indole-11-carboxylic Acid A mixture of 2-(6-(2-carboxyethyl)-4-((2,4-dimethoxybenzyl)amino)-7-isopropyl-7H-pyrrolo[2,3-d]pyrimidin-5-yl)-1H-indole-6-carboxylic acid (0.034 g, 0.061 mmol), BOC-anhydride (0.050 mL, 0.213 mmol), DMAP (0.022 g, 0.18 mmol) and 2,6-lutidine (0.021 mL, 0.183 mmol) in MeCN (0.61 mL) was stirred at RT for 2 h. The reaction was partitioned between DCM and water. After phase-separation, the organic layer was washed with brine then dried (Na$_2$SO$_4$), filtered and concentrated to afford the title compound, which was used directly in the next step without further purifications, assuming quantitative yield. MS (apci) m/z=540.2 (M+H).

Intermediate P31

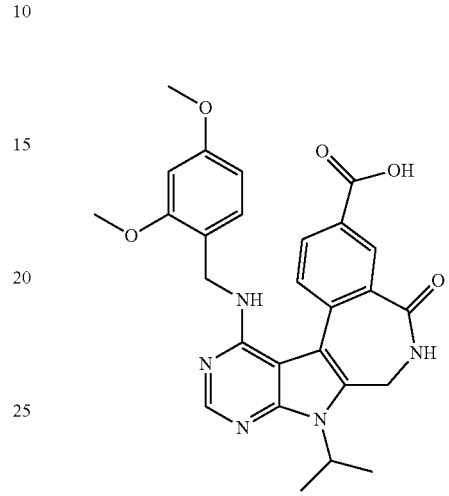

12-((2,4-Dimethoxybenzyl)amino)-8-isopropyl-5-oxo-5,6,7,8-tetrahydrobenzo[c]pyrimido[5',4':4,5]pyrrolo[3,2-e]azepine-3-carboxylic Acid Step 1: Preparation of dimethyl 4-(6-(((tert-butyldimethylsilyl)oxy)methyl)-4-((2,4-dimethoxybenzyl)amino)-7-isopropyl-7H-pyrrolo[2,3-d]pyrimidin-5-yl)isophthalate A mixture of 6-(((tert-butyldimethylsilyl)oxy)methyl)-N-(2,4-dimethoxybenzyl)-7-isopropyl-5-(4,4,5,5-tetramethyl-1,3,2-dioxaborolan-2-yl)-7H-pyrrolo[2,3-d]pyrimidin-4-amine (Intermediate P15) (159 mg, 0.27 mmol), dimethyl 4-bromoisophthalate (109 mg, 0.40 mmol), Pd(PPh$_3$)$_4$ (31 mg, 0.027 mmol), and K$_2$CO$_3$ (111 mg, 0.80 mmol) in 4:1 dioxane:water (2.7 mL) was sparged with argon, sealed in a pressure vessel and stirred at 80° C. for 16 h. After cooled to RT, the reaction was diluted with 4:1 DCM:IPA and washed with water. The organic layer was then dried (Na$_2$SO$_4$), filtered, concentrated, and purified by silica chromatography (5-95% acetone in hexanes) to afford the title compound (125 mg, 70%). MS (apci) m/z=663.3 (M+H).

Step 2: Preparation of dimethyl 4-(4-((2,4-dimethoxybenzyl)amino)-6-(hydroxymethyl)-7-isopropyl-7H-pyrrolo[2,3-d]pyrimidin-5-yl)isophthalate To a solution of dimethyl 4-(6-(((tert-butyldimethylsilyl)oxy)methyl)-4-((2,4-dimethoxybenzyl)amino)-7-isopropyl-7H-pyrrolo[2,3-d]pyrimidin-5-yl)isophthalate (125 mg, 0.18 mmol) in THF (1.9 mL) was added acetic acid (27 µL, 0.47 mmol) followed by TBAF (1 M THF) (470 µL, 0.47 mmol) at RT and stirred for 48 h. The reaction was concentrated and purified by silica chromatography (5-95% acetone in hexanes) to afford the title compound (92 mg, 89%). MS (apci) m/z=549.2 (M+H).

Step 3: Preparation of dimethyl 4-(6-(azidomethyl)-4-((2,4-dimethoxybenzyl)amino)-7-isopropyl-7H-pyrrolo[2,3-d]pyrimidin-5-yl)isophthalate To a solution of dimethyl 4-(4-((2,4-dimethoxybenzyl)amino)-6-(hydroxymethyl)-7-isopropyl-7H-pyrrolo[2,3-d]pyrimidin-5-yl)isophthalate (92 mg, 0.17 mmol) in toluene (1.7 mL) was added DBU (50 μL, 0.34 mmol) followed by DPPA (72 μL, 0.34 mmol) at 0° C. The reaction was warmed to RT and stirred for 2 h before it was diluted with EtOAc and washed with water and brine, then dried (Na$_2$SO$_4$), filtered, concentrated, and purified by silica chromatography (5-95% acetone in hexanes) to give the title compound (75 mg, 78%). MS (apci) m/z=574.2 (M+H).

Step 4: Preparation of dimethyl 4-(6-(aminomethyl)-4-((2,4-dimethoxybenzyl)amino)-7-isopropyl-7H-pyrrolo[2,3-d]pyrimidin-5-yl)isophthalate To a solution of dimethyl 4-(6-(azidomethyl)-4-((2,4-dimethoxybenzyl)amino)-7-isopropyl-7H-pyrrolo[2,3-d]pyrimidin-5-yl)isophthalate (75 mg, 0.13 mmol) in 1:1 THF:water (1.3 mL) was added PPh$_3$ (68 mg, 0.26 mmol) at RT and stirred for 16 h. The reaction was diluted with 4:1 DCM:IPA and washed with sat. NaHCO$_3$, then dried (Na$_2$SO$_4$), filtered, concentrated, and purified by reverse phase chromatography (5-95% MeCN in water with 0.1% TFA). The combined product fractions were partitioned between 4:1 DCM:IPA and sat. NaHCO$_3$, then dried over Na$_2$SO$_4$, filtered, and concentrated to give the title compound (52 mg, 73%). MS (apci) m/z=548.3 (M+H).

Step 5: Preparation of methyl 12-((2,4-dimethoxybenzyl)amino)-8-isopropyl-5-oxo-5,6,7,8-tetrahydrobenzo[c]pyrimido[5',4':4,5]pyrrolo[3,2-e]azepine-3-carboxylate A solution of dimethyl 4-(6-(aminomethyl)-4-((2,4-dimethoxybenzyl)amino)-7-isopropyl-7H-pyrrolo[2,3-d]pyrimidin-5-yl)isophthalate (52 mg, 0.095 mmol) in dioxane (1.9 mL) was stirred at 90° C. for 24 h. After cooled to RT, the reaction was concentrated and purified by silica chromatography (5-95% acetone in DCM) to afford the title compound, which was directly used in the next step assuming quantitative yield. MS (apci) m/z=516.2 (M+H).

Step 6: Preparation of 12-((2,4-dimethoxybenzyl)amino)-8-isopropyl-5-oxo-5,6,7,8-tetrahydrobenzo[c]pyrimido[5',4':4,5]pyrrolo[3,2-e]azepine-3-carboxylic Acid To a solution of methyl 12-((2,4-dimethoxybenzyl)amino)-8-isopropyl-5-oxo-5,6,7,8-tetrahydrobenzo[c]pyrimido[5',4':4,5]pyrrolo[3,2-e]azepine-3-carboxylate (49 mg, 0.095 mmol) in THF (1.9 mL) was added KOH (2 N aq) (475 μL, 0.95 mmol) at RT and stirred for 16 h. The reaction was then diluted with water and acidified to pH~5 using 1.0 M HCl, followed by extracting with 4:1 DCM:IPA (2×). The combined organics were dried over Na$_2$SO$_4$, filtered, and concentrated to afford the title product (33 mg, 70%). MS (apci) m/z=502.2 (M+H).

Intermediate P32

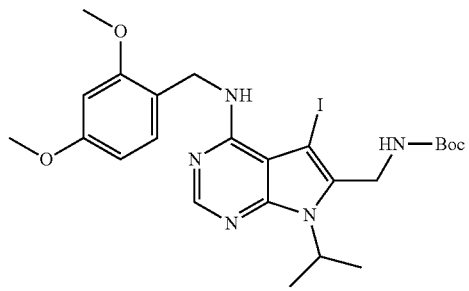 [SMILES: COc1ccc(CNc2ncnc3c2c(I)c(CNC(=O)OC(C)(C)C)n3C(C)C)c(OC)c1]

Tert-butyl ((4-((2,4-dimethoxybenzyl)amino)-5-iodo-7-isopropyl-7H-pyrrolo[2,3-d]pyrimidin-6-yl)methyl)carbamate

Step 1: Preparation of (4-((2,4-dimethoxybenzyl)amino)-5-iodo-7-isopropyl-7H-pyrrolo[2,3-d]pyrimidin-6-yl)methanol A mixture of 6-(((tert-butyldimethylsilyl)oxy)methyl)-N-(2,4-dimethoxybenzyl)-5-iodo-7-isopropyl-7H-pyrrolo[2,3-d]pyrimidin-4-amine (Intermediate P14) (1.30 g, 2.18 mmol), acetic acid (0.125 mL, 2.18 mmol) and TBAF (1 M THF) (2.40 mL, 2.40 mmol) in THF (14.5 mL) was stirred at rt for 2 h. The reaction was diluted with water and extracted with EtOAc. The combined organic extracts were washed with brine, then dried (Na$_2$SO$_4$), filtered, concentrated, and purified by silica chromatography (1-10% MeOH in DCM) to afford the title compound (1.05 g, 99%). MS (apci) m/z=483.1 (M+H).

Step 2: Preparation of 6-(azidomethyl)-N-(2,4-dimethoxybenzyl)-5-iodo-7-isopropyl-7H-pyrrolo[2,3-d]pyrimidin-4-amine To a solution of (4-((2,4-dimethoxybenzyl)amino)-5-iodo-7-isopropyl-7H-pyrrolo[2,3-d]pyrimidin-6-yl)methanol (1.05 g, 2.18 mmol) in toluene (14.5 mL) cooled to 0° C. was added diphenyl phosphorazidate (0.94 mL, 4.35 mmol), followed by 2,3,4,6,7,8,9,10-octahydropyrimido[1,2-a]azepine (0.65 mL, 4.35 mmol). The reaction was warmed up to rt and stirred overnight. It was then diluted with water and extracted with DCM. The combined organic extracts were washed with brine, then dried (Na$_2$SO$_4$), filtered, and purified by silica chromatography (1-10% MeOH in DCM) to afford the title compound (1.09 g, 99%). MS (apci) m/z=508.1 (M+H).

Step 3: Preparation of 6-(aminomethyl)-N-(2,4-dimethoxybenzyl)-5-iodo-7-isopropyl-7H-pyrrolo[2,3-d]pyrimidin-4-amine A mixture of 6-(azidomethyl)-N-(2,4-dimethoxybenzyl)-5-iodo-7-isopropyl-7H-pyrrolo[2,3-d]pyrimidin-4-amine (1.09 g, 2.160 mmol) and PPh₃ (1.13 g, 4.32 mmol) in THF (8.6 mL) and water (8.6 mL) was stirred at rt overnight. It was then diluted with water and extracted with DCM. The combined organic extracts were washed with brine, then dried (Na₂SO₄), filtered, concentrated, and purified by silica chromatography (1-10% MeOH in DCM) to afford the title compound (0.44 g, 42%). MS (apci) m/z=482.1 (M+H).

Step 4: Preparation of tert-butyl ((4-((2,4-dimethoxybenzyl)amino)-5-iodo-7-isopropyl-7H-pyrrolo[2,3-d]pyrimidin-6-yl)methyl)carbamate To a solution of 6-(aminomethyl)-N-(2,4-dimethoxybenzyl)-5-iodo-7-isopropyl-7H-pyrrolo[2,3-d]pyrimidin-4-amine (56 mg, 0.12 mmol) in THF (2.3 mL) was added di-tert-butyl dicarbonate (27 µL, 0.12 mmol) at rt and stirred for 2 h. The reaction was then diluted with water (20 mL) and extracted with DCM (3×20 mL). The combined organic extracts were washed with brine, then dried (Na₂SO₄), filtered, concentrated, and purified by silica chromatography (0-100% EtOAc in hexanes) to afford the title compound (59 mg, 88%). MS (apci) m/z=582.2 (M+H).

Intermediate P33

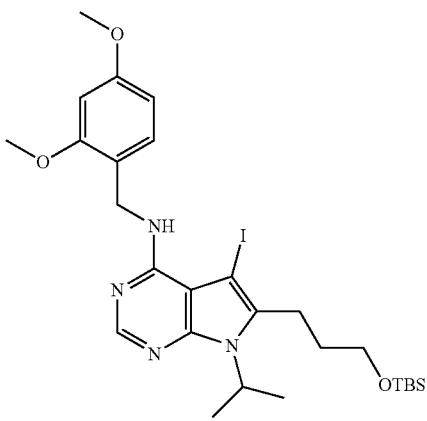 [SMILES: COc1ccc(CNc2ncnc3c2c(I)c(CCCO[Si](C)(C)C(C)(C)C)n3C(C)C)c(OC)c1]

6-(3-((tert-butyldimethylsilyl)oxy)propyl)-N-(2,4-dimethoxybenzyl)-5-iodo-7-isopropyl-7H-pyrrolo[2,3-d]pyrimidin-4-amine Step 1: Preparation of ethyl (E)-3-(4-chloro-7-isopropyl-7H-pyrrolo[2,3-d]pyrimidin-6-yl)acrylate To a solution of 4-chloro-7-isopropyl-7H-pyrrolo[2,3-d]pyrimidine-6-carbaldehyde (Intermediate P12) (14.9 g, 32.0 mmol) in DCM (300 mL) was added carbethoxymethylene triphenylphosphorane (13.4 g, 38.4 mmol) at rt and stirred for 16 h. The reaction was concentrated and purified by silica chromatography (5 to 75% acetone in hexanes) to afford the title compound (8 g, 85%). MS (apci) m/z=294.1 (M+H).

Step 2: Preparation of ethyl 3-(4-chloro-7-isopropyl-7H-pyrrolo[2,3-d]pyrimidin-6-yl)propanoate To a solution of Cu(OAC)₂ (0.17 g, 0.95 mmol) in THF (50 mL) was added (9,9-dimethyl-9H-xanthene-4,5-diyl)bis(diphenylphosphane) (1.10 g, 1.90 mmol) followed by phenylsilane (5.85 mL, 47.5 mmol). After 15 min stirring at rt, a solution of ethyl (E)-3-(4-chloro-7-isopropyl-7H-pyrrolo[2,3-d]pyrimidin-6-yl)acrylate (2.79 g, 9.50 mmol) in THF (50 mL) was introduced, and stirring continued at rt for 3 h. The reaction was cooled to 0° C. and treated slowly with sat. NaHCO₃. It was diluted with water and extracted with DCM (2×). The combined organic extracts was dried (Na₂SO₄), filtered, concentrated, and purified by silica chromatography (5 to 75% EtOAc in hexanes) to afford the title compound (2.7 g, 97%). MS (apci) m/z=296.1 (M+H).

Step 3: Preparation of ethyl 3-(4-chloro-5-iodo-7-isopropyl-7H-pyrrolo[2,3-d]pyrimidin-6-yl)propanoate To a solution of ethyl 3-(4-chloro-7-isopropyl-7H-pyrrolo[2,3-d]pyrimidin-6-yl)propanoate (2.46 g, 8.32 mmol) in DMF (55 mL) was added N-iodosuccinimide (1.96 g, 8.73 mmol) at rt and stirred for 60 h. The reaction was diluted with water and extracted with EtOAc (2×). The combined organic extracts were washed with water and brine, then dried (Na₂SO₄), filtered, concentrated, and purified by silica chromatography (5 to 75% EtOAc in hexanes) to afford the title compound (3.05 g, 87%). MS (apci) m/z=422.0 (M+H).

Step 4: Preparation of 3-(4-chloro-5-iodo-7-isopropyl-7H-pyrrolo[2,3-d]pyrimidin-6-yl)propan-1-ol To a solution of ethyl 3-(4-chloro-5-iodo-7-isopropyl-7H-pyrrolo[2,3-d]pyrimidin-6-yl)propanoate (5.06 g, 12.0 mmol) in THF (60 mL) cooled to −78° C. was added DIBAL-H (25 wt %) (24.2 mL, 36.0 mmol). After stirred at −78° C. for 30 min, the reaction was quenched with water and allowed to warm to rt and stirred overnight. After phase-separation, the aqueous phase was extracted with DCM (2×). The combined organic extracts was washed with water, then dried (Na₂SO₄), filtered and concentrated to afford the title compound as white solid (2.9 g, 64%). MS (apci) m/z=380.0 (M+H).

Step 5: Preparation of 6-(3-((tert-butyldimethylsilyl)oxy)propyl)-4-chloro-5-iodo-7-isopropyl-7H-pyrrolo[2,3-d]pyrimidine To a solution of 3-(4-chloro-5-iodo-7-isopropyl-7H-pyrrolo[2,3-d]pyrimidin-6-yl)propan-1-ol (2.9 g, 7.6 mmol) in DMF (38 mL) were added imidazole (1.0 g, 15 mmol) and tert-butyldimethylsilyl chloride (1.7 g, 11 mmol). After stirred at rt for 1 h, the reaction was diluted with EtOAc, washed with water and brine, then dried (Na₂SO₄), filtered, concentrated, and purified by silica chromatography (0 to 50% EtOAc in hexanes) to afford the title compound as clear oil (3.6 g, 95%). MS (apci) m/z=494.1 (M+H).

Step 6: Preparation of 6-(3-((tert-butyldimethylsilyl)oxy)propyl)-N-(2,4-dimethoxybenzyl)-5-iodo-7-isopropyl-7H-pyrrolo[2,3-d]pyrimidin-4-amine To a solution of 6-(3-((tert-butyldimethylsilyl)oxy)propyl)-4-chloro-5-iodo-7-isopropyl-7H-pyrrolo[2,3-d]pyrimidine (1.53 g, 3.1 mmol) in DMSO (15.5 mL) was added (2,4-dimethoxyphenyl)methanamine (1.16 mL, 7.74 mmol). The reaction was heated to 60° C. and stirred overnight. After cooled to rt, the reaction was diluted with EtOAc, washed with water and brine, then dried (Na₂SO₄), filtered, concentrated, and purified by silica chromatography (0-100% MTBE in hexanes) to afford the title product as clear oil (1.8 g, 92%). MS (apci) m/z=625.2 (M+H).

Intermediate P34

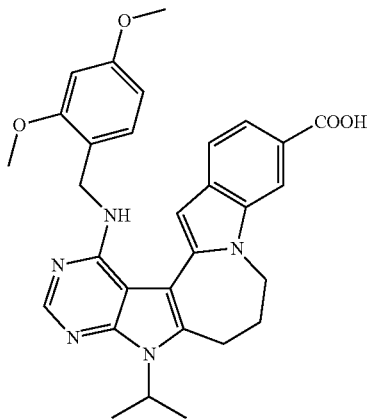 [SMILES: COc1ccc(CNc2ncnc3c2c2c(n3C(C)C)CCCn3c-2cc2ccc(C(=O)O)cc23)c(OC)c1]

1-((2,4-dimethoxybenzyl)amino)-5-isopropyl-5,6,7,8-tetrahydropyrimido[5",4":4',5']pyrrolo[3',2':3,4]azepino[1,2-a]indole-11-carboxylic Acid To a solution of methyl 1-((2,4-dimethoxybenzyl)amino)-5-isopropyl-5,6,7,8-tetrahydropyrimido[5",4":4',5']pyrrolo[3',2':3,4]azepino[1,2-a]indole-11-carboxylate (Example 86, Step 3) (458 mg, 0.85 mmol) in THF (17 mL) and MeOH (17 mL) was added LiOH (2 M aq) (4.2 mL, 8.4 mmol) at ambient temperature and stirred overnight. The reaction was neutralized with sat. NH$_4$Cl (aq) (20 mL) and extracted with DCM (3×50 mL) through a Phase Separator frit. The combined organic extracts were concentrated and purified using silica chromatography (0-100% EtOAc in hexanes followed by 0-10% MeOH in EtOAc) to yield the title product (319 mg, 72%). MS (apci) m/z=526.2 (M+H).

Intermediate P35

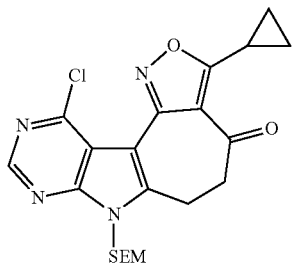 [SMILES: C[Si](C)(C)CCOCn1c2c(c3c(Cl)ncnc31)-c1noc(C3CC3)c1C(=O)CC2]

11-chloro-3-cyclopropyl-7-((2-(trimethylsilyl)ethoxy)methyl)-6,7-dihydroisoxazolo[4",3":6',7']cyclohepta[1',2':4,5]pyrrolo[2,3-d]pyrimidin-4(5H)-one Step 1: Preparation of 1-(3-(6-(bromomethyl)-4-chloro-7-((2-(trimethylsilyl)ethoxy)methyl)-7H-pyrrolo[2,3-d]pyrimidin-5-yl)-5-cyclopropylisoxazol-4-yl)ethan-1-one To a solution of 3-(4-chloro-6-methyl-7-((2-(trimethylsilyl)ethoxy)methyl)-7H-pyrrolo[2,3-d]pyrimidin-5-yl)-5-cyclopropyl-4-iodoisoxazole (Intermediate P20) (2.9 g, 5.46 mmol) in THF (27 mL) cooled to −78° C. was dropwise added isopropylmagnesium chloride lithium chloride complex (1.3 M THF) (5.46 mL, 7.10 mmol), maintaining an internal temperature below −60° C. After addition, stirring was continued for 20 min before acetic anhydride (0.77 mL, 8.2 mmol) was introduced at −70° C. The resulting mixture was warmed to rt and quenched with sat. NH$_4$Cl (50 mL) and water (50 mL), after which it was extracted with EtOAc (100 mL). The combined organic extracts was dried (Na$_2$SO$_4$), and then filtered through a short pad of celite, rinsing the pad with 50% EtOAc in hexanes (30 mL). The filtrate was concentrated, taken up in DCE (27 mL) and treated with AIBN (90 mg, 0.55 mmol) and NBS (1.2 g, 6.74 mmol). The resulting mixture was heated at 80° C. for 90 min. After cooled to rt, the reaction was washed with Na$_2$S$_2$O$_3$ (10% aq), water and brine, then dried (Na$_2$SO$_4$), filtered, concentrated and purified with silica chromatography (0-30% EtOAc in hexanes) to give the title compound as white solid (1.38 g, 48%). MS (apci) m/z=525.1 (M+H).

Step 2: Preparation of 11-chloro-3-cyclopropyl-7-((2-(trimethylsilyl)ethoxy)methyl)-6,7-dihydroisoxazolo[4",3":6',7']cyclohepta[1',2':4,5]pyrrolo[2,3-d]pyrimidin-4(5H)-one To a solution of LHMDS (1 M THF) (5.90 mL, 5.90 mmol) in THF (22 mL) cooled to −78° C. was dropwise added a solution of 1-(3-(6-(bromomethyl)-4-chloro-7-((2-(trimethylsilyl)ethoxy)methyl)-7H-pyrrolo[2,3-d]pyrimidin-5-yl)-5-cyclopropylisoxazol-4-yl)ethan-1-one (1.15 g, 2.19 mmol) in THF (8 mL). The resulting mixture was slowly warmed to −40° C. over 1 h, then to −20° C. over 30 min. It was quenched with NH$_4$Cl (sat.) and water, then extracted with EtOAc. The combined organic extracts was dried (Na$_2$SO$_4$), filtered, concentrated and purified with silica chromatography (0-40% EtOAc in hexanes) to give the title product as yellowish solid (0.53 g, 54%). MS (apci) m/z=445.2 (M+H).

Intermediate P36

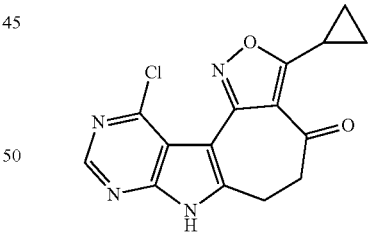

11-chloro-3-cyclopropyl-6,7-dihydroisoxazolo[4",3":6',7']cyclohepta[1',2':4,5]pyrrolo[2,3-d]pyrimidin-4(5H)-one A solution of 11-chloro-3-cyclopropyl-7-((2-(trimethylsilyl)ethoxy)methyl)-6,7-dihydroisoxazolo[4",3":6',7']cyclohepta[1',2':4,5]pyrrolo[2,3-d]pyrimidin-4(5H)-one (Intermediate P35) (0.52 g, 1.2 mmol) in DCM (2.9 mL) and TFA (5.8 mL) was stirred at rt for 2 h, then concentrated to near dryness. It was taken up in dioxane and re-concentrated. The residue was dissolved in 1,4-dioxane (5.8 mL), followed by addition of NH$_4$OH (28% aq) (2.9 mL). The mixture was concentrated to near dryness and treated with water (15 mL), then vacuum-filtered, rinsing the solid with water and hexanes, giving the title product as yellowish solid after air-drying (0.37 g, 101%). MS (apci) m/z=315.1 (M+H).

Intermediate P37

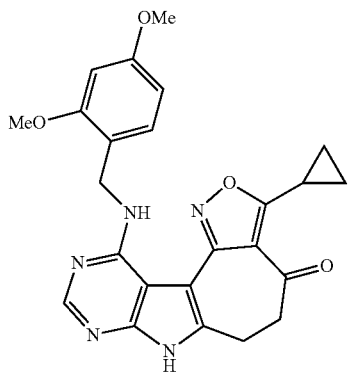 [SMILES: COc1ccc(CNc2ncnc3[nH]c4c(c23)-c2noc(C3CC3)c2C(=O)CC4)c(OC)c1]

3-cyclopropyl-11-((2,4-dimethoxybenzyl)amino)-6,7-dihydroisoxazolo[4'',3'':6',7']cyclohepta[1',2':4,5]pyrrolo[2,3-d]pyrimidin-4(5H)-one A mixture of 11-chloro-3-cyclopropyl-6,7-dihydroisoxazolo[4'',3'':6',7']cyclohepta[1',2':4,5]pyrrolo[2,3-d]pyrimidin-4(5H)-one (Intermediate P36) (158 mg, 0.50 mmol), 2,4-dimethoxybenzylamine (302 μL, 2.0 mmol) and DMA (2.5 mL) was stirred at 75° C. for 1 h. After cooled to rt, the reaction was quenched with water (10 mL) and citric acid (10% aq) (2 mL) then filtered, rinsing the collected solid with water (2 mL) and hexanes (2 mL). The solid was further triturated with aid of sonication in a mixture of water (10 mL) and citric acid (10% aq) (1 mL). The resulting suspension was filtered, rinsed with water and dried to afford the title product as yellowish solid (190 mg, 85%). MS (apci) m/z=446.2 (M+H).

Intermediate P38

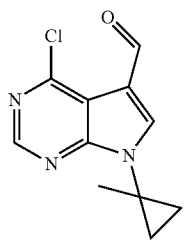 [SMILES: CC1(n2cc(C=O)c3c(Cl)ncnc32)CC1]

4-Chloro-7-(1-methylcyclopropyl)-7H-pyrrolo[2,3-d]pyrimidine-5-carbaldehyde

Step 1: Preparation of 4-chloro-7-(1-methylcyclopropyl)-7H-pyrrolo[2,3-d]pyrimidine To a solution of 2-(4,6-dichloropyrimidin-5-yl)acetaldehyde (5.0 g, 26.2 mmol) in 2-methoxyethan-1-ol (26 mL) in a pressure vessel was added DIEA (22.8 mL, 131 mmol) and 1-methylcyclopropan-1-amine hydrochloride (3.1 g, 28.8 mmol). The reaction was sealed and stirred at 70° C. overnight. After cooled to rt, the reaction was diluted with water and extracted with DCM. The combined organic extracts were concentrated and purified by silica chromatography (5-40% EtOAc in hexanes) to afford the title compound (4.6 g, 84%). MS (apci) m/z=208.1 (M+H).

Step 2: Preparation of 4-chloro-5-iodo-7-(1-methylcyclopropyl)-7H-pyrrolo[2,3-d]pyrimidine To a solution of 4-chloro-7-(1-methylcyclopropyl)-7H-pyrrolo[2,3-d]pyrimidine (4.6 g, 22.1 mmol) in DMF (55 mL) was added 1-iodopyrrolidine-2,5-dione (5.97 g, 26.5 mmol). The reaction was covered with aluminum foil and stirred at rt for 3 h. It was then diluted with sat. sodium thiosulfate (aq) and extracted with DCM. The combined organic extracts were concentrated and purified by silica chromatography (1-10% MeOH in DCM) to afford the title compound (5.79 g, 78.5%). MS (apci) m/z=334.0 (M+H).

Step 3: Preparation of 4-chloro-7-(1-methylcyclopropyl)-5-vinyl-7H-pyrrolo[2,3-d]pyrimidine A solution of 4-chloro-5-iodo-7-(1-methylcyclopropyl)-7H-pyrrolo[2,3-d]pyrimidine (5.76 g, 17.3 mmol), 4,4,5,5-tetramethyl-2-vinyl-1,3,2-dioxaborolane (3.08 mL, 18.1 mmol), Pd(PPh$_3$)$_4$ (1.20 g, 1.04 mmol), and potassium phosphate (2 N, aq) (34.5 mL, 69.1 mmol) in 1,4-dioxane (57.6 mL) was sparged with argon and heated under N$_2$ at 90° C. for 3 h. After cooled to rt, the reaction was diluted with sat NaHCO$_3$ (aq) and extracted with DCM. The combined organic extracts were concentrated and purified by silica chromatography (1-5% MeOH in DCM) to afford the title compound (4.0 g, 99%). MS (apci) m/z=234.1 (M+H).

Step 4: Preparation of 4-chloro-7-(1-methylcyclopropyl)-7H-pyrrolo[2,3-d]pyrimidine-5-carbaldehyde To a solution of 4-chloro-7-(1-methylcyclopropyl)-5-vinyl-7H-pyrrolo[2,3-d]pyrimidine (4.0 g, 17.1 mmol) in THF (86 mL) and water (34 mL) cooled to 0° C. was added 4-methylmorpholine N-oxide (2.0 g, 17.1 mmol) and OsO$_4$ (4%) (10.9 mL, 1.71 mmol). After 1 h stirring at 0° C., sodium periodate (7.322 g, 34.23 mmol) was introduced, and stirring continued for 2 h. The reaction was then diluted with sat. sodium thiosulfate (aq) and extracted with DCM. The combined organic extracts were concentrated and purified by silica chromatography (1-10% MeOH in DCM) to afford the title product (2.6 g, 65%). MS (apci) m/z=236.0 (M+H).

Intermediate P39

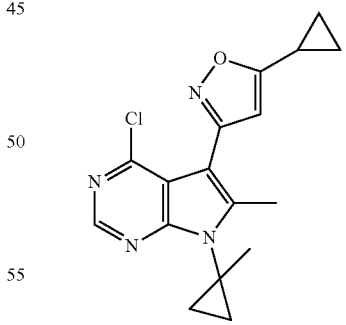

3-(4-Chloro-6-methyl-7-(1-methylcyclopropyl)-7H-pyrrolo[2,3-d]pyrimidin-5-yl)-5-cyclopropylisoxazole Step 1: Preparation of (E)-4-chloro-7-(1-methylcyclopropyl)-7H-pyrrolo[2,3-d]pyrimidine-5-carbaldehyde Oxime To a solution of 4-chloro-7-(1-methylcyclopropyl)-7H-pyrrolo[2,3-d]pyrimidine-5-carbaldehyde (Intermediate P38) (2.63 g, 11.16 mmol) in ethanol (37.2 mL) was added hydroxylamine (50%) (0.72 mL, 11.72 mmol) at 0° C. The reaction mixture was allowed to warm to rt and stirred for 90 min before it was diluted with water and extracted with DCM. The combined organic extracts were concentrated to afford the title compound, which was used directly in the next step assuming quantitative yield. MS (apci) m/z=251.1 (M+H).

Step 2: Preparation of 3-(4-chloro-7-(1-methylcyclopropyl)-7H-pyrrolo[2,3-d]pyrimidin-5-yl)-5-cyclopropylisoxazole To a solution of (E)-4-chloro-7-(1-methylcyclopropyl)-7H-pyrrolo[2,3-d]pyrimidine-5-carbaldehyde oxime (2.8 g, 11.2 mmol), potassium hydrogen carbonate (1.45 g, 14.5 mmol), and 1-chloropyrrolidine-2,5-dione (1.64 g, 12.3 mmol) in DMF (55.8 mL) was added ethynylcyclopropane (2.84 mL, 33.5 mmol) at rt. The reaction mixture was stirred overnight, after which it was diluted with sat. sodium thiosulfate (aq) and extracted with DCM. The combined organic extracts were concentrated and purified by silica chromatography (1-7% MeOH in DCM) to afford the title compound (3.14 g, 89%). MS (apci) m/z=315.1 (M+H).

Step 3: Preparation of 3-(4-chloro-6-methyl-7-(1-methylcyclopropyl)-7H-pyrrolo[2,3-d]pyrimidin-5-yl)-5-cyclopropylisoxazole To a solution of 3-(4-chloro-7-(1-methylcyclopropyl)-7H-pyrrolo[2,3-d]pyrimidin-5-yl)-5-cyclopropylisoxazole (3.14 g, 9.98 mmol) in THF (50 mL) cooled to −78° C. was added lithium diisopropylamide (1.96 M, THF) (8.1 mL, 16.0 mmol), followed by dropwise addition of iodomethane (2.48 ml, 39.9 mmol). The reaction was stirred at −78° C. for 20 min and then quenched with sat. NH$_4$Cl (aq). The reaction was diluted with sat NaHCO$_3$ (aq) and extracted with DCM. The combined organic extracts were concentrated and purified by silica chromatography (5-40% EtOAc in hexanes) to afford the title product (1.99 g, 61%). MS (apci) m/z=329.1 (M+H).

Intermediate P40

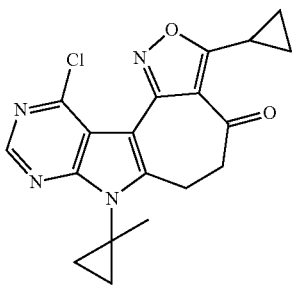 [SMILES: CC1(n2c3c(c4c(Cl)ncnc42)-c2noc(C4CC4)c2C(=O)CC3)CC1]

11-Chloro-3-cyclopropyl-7-(1-methylcyclopropyl)-6,7-dihydroisoxazolo[4",3":6',7']cyclohepta[1',2':4,5]pyrrolo[2,3-d]pyrimidin-4(5H)-one Step 1: Preparation of 3-(4-chloro-6-methyl-7-(1-methylcyclopropyl)-7H-pyrrolo[2,3-d]pyrimidin-5-yl)-5-cyclopropyl-4-iodoisoxazole A solution of 3-(4-chloro-6-methyl-7-(1-methylcyclopropyl)-7H-pyrrolo[2,3-d]pyrimidin-5-yl)-5-cyclopropylisoxazole (Intermediate P39) (1.99 g, 6.05 mmol), 1-iodopyrrolidine-2,5-dione (2.04 g, 9.08 mmol), and 2,2,2-trifluoroacetic acid (1.40 mL, 18.2 mmol) in acetonitrile (30 mL) was stirred for 90 min. The reaction was diluted with 1:1 sat. Na$_2$S$_2$O$_{3(aq)}$ and sat. NaHCO$_3$ $_{(aq)}$, after which it was extracted with DCM. The combined organic extracts were concentrated and purified by silica chromatography (1-5% MeOH in DCM) to afford the title compound (2.7 g, 98%). MS (apci) m/z=455.0 (M+H).

Step 2: Preparation of 1-(3-(4-chloro-6-methyl-7-(1-methylcyclopropyl)-7H-pyrrolo[2,3-d]pyrimidin-5-yl)-5-cyclopropylisoxazol-4-yl)ethan-1-one To a solution of 3-(4-chloro-6-methyl-7-(1-methylcyclopropyl)-7H-pyrrolo[2,3-d]pyrimidin-5-yl)-5-cyclopropyl-4-iodoisoxazole (2.3 g, 5.0 mmol) in THF (25 mL) cooled to 0° C. was added isopropylmagnesium(II) lithium chloride (1.2 M THF) (5.5 mL, 6.6 mmol) and acetic anhydride (0.72 mL, 7.6 mmol). The reaction was allowed to warm to rt and stirred for 15 min. It was then quenched with sat. NH$_4$Cl (aq), then diluted with sat. NaHCO$_3$ (aq) and extracted with DCM. The combined organic extracts were concentrated and purified by silica chromatography (5-100% EtOAc in hexanes) to afford the title compound (1.3 g, 70%). MS (apci) m/z=371.1 (M+H).

Step 3: Preparation of 1-(3-(6-(bromomethyl)-4-chloro-7-(1-methylcyclopropyl)-7H-pyrrolo[2,3-d]pyrimidin-5-yl)-5-cyclopropylisoxazol-4-yl)ethan-1-one A solution of 1-(3-(4-chloro-6-methyl-7-(1-methylcyclopropyl)-7H-pyrrolo[2,3-d]pyrimidin-5-yl)-5-cyclopropylisoxazol-4-yl)ethan-1-one (1.45 g, 3.91 mmol), 1-bromopyrrolidine-2,5-dione (0.84 g, 4.69 mmol), and (E)-2,2'-(diazene-1,2-diyl)-bis(2-methylpropanenitrile) (0.038 g, 0.24 mmol) in 1,2-dichloroethane (20 mLl) was heated to 75° C. for 90 min. The reaction was diluted with sat. Na$_2$S$_2$O$_{3(aq)}$ then extracted with DCM. The combined organic extracts were concentrated and purified by silica chromatography (5-70% EtOAc in hexanes) to afford the title compound (1.30 g, 2.89 mmol, 74% yield). MS (apci) m/z=451.0 (M+H).

Step 4: Preparation of 11-chloro-3-cyclopropyl-7-(1-methylcyclopropyl)-6,7-dihydroisoxazolo[4",3":6',7']cyclohepta[1',2':4,5]pyrrolo[2,3-d]pyrimidin-4(5H)-one To a solution of 1-(3-(6-(bromomethyl)-4-chloro-7-(1-methylcyclopropyl)-7H-pyrrolo[2,3-d]pyrimidin-5-yl)-5-cyclopropylisoxazol-4-yl)ethan-1-one (1.32 g, 2.94 mmol) in THF (294 mL) cooled to −78° C. was added LiHMDS (1 M THF) (5.88 mL, 5.88 mmol). The reaction was warmed to −40° C. and stirred for 1 h. The reaction was then quenched with sat. NH$_4$Cl, then diluted with sat. NaHCO$_3$ (aq) and extracted with DCM. The combined organic extracts were concentrated and purified first by silica chromatography (5-80% EtOAc in hexanes), followed by reverse-phase chromatography (5 to 95% MeCN in water with 0.1% TFA). The combined product fractions was diluted with sat. NaHCO$_3$ (aq) and extracted with DCM. The combined organic extracts was dried (Na$_2$SO$_4$), filtered, and concentrated to afford the title product (0.48 g, 45%). MS (apci) m/z=369.1 (M+H).

Intermediate R1

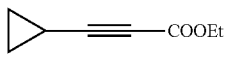

Ethyl 3-cyclopropylpropiolate

A solution of ethynylcyclopropane (0.78 g, 11.8 mmol) in THF (8 mL) was sparged with $Ar_{(g)}$ and cooled to −78° C., followed by dropwise addition of n-BuLi (2.5 M in THF; 5.2 mL, 13.0 mmol). The mixture was stirred for 30 min at −78° C. and for 45 min at −10° C. The reaction mixture then was re-cooled to −78° C. before ethyl carbonochloridate (1.24 mL, 13.0 mmol) was added dropwise. The resulting mixture was allowed to warm to RT, then was stirred overnight before partitioning between EtOAc and saturated $NH_4Cl_{(aq)}$. After phase-separation, the organic layer was washed with water, then dried over anhydrous $Na_2SO_{4(s)}$, filtered, and concentrated in vacuo to afford the title compound (1.6 g, 98% yield). MS (apci) m/z=139.1 (M+H).

Intermediate R2

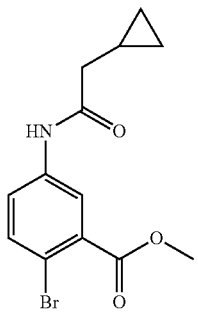 [SMILES: COC(=O)c1cc(NC(=O)CC2CC2)ccc1Br]

Methyl 2-bromo-5-(2-cyclopropylacetamido)benzoate

To a mixture of methyl 5-amino-2-bromobenzoate (1.0 g, 4.3 mmol), cyclopropylacetic acid (0.48 mL, 5.2 mmol) and HATU (4.9 g, 13.0 mmol) in DCM (22 mL) was added DIEA (3.8 mL, 21.7 mmol) at RT, and the reaction mixture was stirred overnight. The reaction was concentrated and purified by silica chromatography (0-100% acetone in DCM) to afford the title product (1.36 g, 100%). MS (apci) m/z=312.0 (M+H).

Intermediate R3

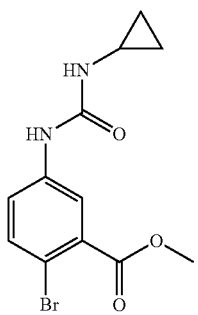 [SMILES: COC(=O)c1cc(NC(=O)NC2CC2)ccc1Br]

Methyl 2-bromo-5-(3-cyclopropylureido)benzoate

To a solution of triphosgene (297 mg, 1.0 mmol) in DCM (15 mL) was added a solution of methyl 5-amino-2-bromobenzoate (576 mg, 2.5 mmol) and DIEA (2.2 mL, 12.5 mmol) in DCM (10 mL) at 0° C. After 1 h stirring, cyclopropylamine (208 μL, 3.0 mmol) was introduced and the reaction was warmed to RT then stirred for 16 h. The reaction mixture was diluted with sat. $NaHCO_3$ and extracted with DCM (2×). The combined organics were dried ($Na_2SO_4$), filtered, concentrated and purified by silica chromatography (5 to 95% acetone in hexanes) to afford the title product (702 mg, 90%). $^1$H-NMR ($d^6$-DMSO) δ 8.65 (br s, 1H), 7.93 (m, 1H), 7.56 (d, 1H), 7.46 (m, 1H), 6.52 (br s, 1H), 3.84 (s, 3H), 2.53 (m, 1H), 0.63 (m, 2H), 0.41 (m, 2H).

Intermediate R4

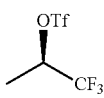

(R)-1,1,1-trifluoropropan-2-yl Trifluoromethanesulfonate

To a solution of (R)-1,1,1-trifluoropropan-2-ol (90 mg, 0.79 mmol) and pyridine (67 μL, 0.83 mmol) in DCM (1.6 mL) was slowly added triflic anhydride (133 μL, 0.79 mmol) at 0° C. The reaction was slowly warmed to rt and stirred for 15 min, after which it was filtered. The filter cake was rinsed with DCM to yield the title product as a 0.4 M solution, which was directly used in the next step assuming quantitative yield.

Intermediate R5

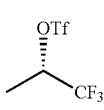

(S)-1,1,1-trifluoropropan-2-yl Trifluoromethanesulfonate

The title product was prepared in a similar fashion as described in Intermediate R4, replacing (R)-1,1,1-trifluoropropan-2-ol with (S)-1,1,1-trifluoropropan-2-ol instead.

Intermediate R6

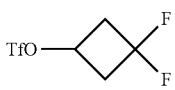

3,3-difluorocyclobutyl Trifluoromethanesulfonate

The title product was prepared in a similar fashion as described in Intermediate R4, replacing (R)-1,1,1-trifluoropropan-2-ol with 3,3-difluorocyclobutan-1-ol instead.

Preparation of Synthetic Examples

Example 1

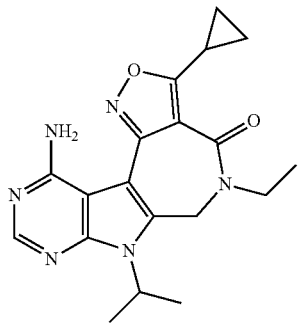 [SMILES: CCN1Cc2c(c3c(N)ncnc3n2C(C)C)-c2noc(C3CC3)c2C1=O]

11-amino-3-cyclopropyl-5-ethyl-7-isopropyl-6,7-dihydroisoxazolo[4,3-c]pyrimido[5',4':4,5]pyrrolo[3,2-e]azepin-4(5H)-one Step 1: Preparation of 3-cyclopropyl-11-((2,4-dimethoxybenzyl)amino)-5-ethyl-7-isopropyl-6,7-dihydroisoxazolo[4,3-c]pyrimido[5',4':4,5]pyrrolo[3,2-e]azepin-4(5H)-one A mixture of ethyl 5-cyclopropyl-3-(4-((2,4-dimethoxybenzyl)amino)-7-isopropyl-6-(((methylsulfonyl)oxy)methyl)-7H-pyrrolo[2,3-d]pyrimidin-5-yl)isoxazole-4-carboxylate (Intermediate P5; 27 mg, 0.044 mmol) and DIEA (15.3 µL, 0.0880 mmol) in DMF (440 µL) was treated with ethylamine (2 M in THF; 110 µL, 0.22 mmol). The resulting mixture was stirred for 2 h at RT and then overnight at 90° C. After cooling to RT, the reaction mixture was partitioned between DCM and water. The organic extracts were washed successively with water (2×) and brine, then dried over anhydrous $Na_2SO_{4(s)}$, filtered, and concentrated in vacuo to afford the title compound (22 mg, 97% yield). MS (apci) m/z=517.2 (M+H).

Step 2: Preparation of 11-amino-3-cyclopropyl-5-ethyl-7-isopropyl-6,7-dihydroisoxazolo[4,3-c]pyrimido[5',4':4,5]pyrrolo[3,2-e]azepin-4(5H)-one A solution of 3-cyclopropyl-11-((2,4-dimethoxybenzyl)amino)-5-ethyl-7-isopropyl-6,7-dihydroisoxazolo[4,3-c]pyrimido[5',4':4,5]pyrrolo[3,2-e]azepin-4(5H)-one (22 mg, 0.043 mmol) in TFA (1 mL, 12.9 mmol) and DCM (1 mL) was stirred for 1 h at RT. Subsequently, the mixture was concentrated in vacuo, then partitioned between DCM and saturated $NaHCO_{3(aq)}$. Following phase separation, the organic extracts were washed with brine, dried over anhydrous $Na_2SO_{4(s)}$, filtered, and concentrated in vacuo. The crude residue was purified by silica chromatography (1-10% DCM:MeOH as the gradient eluent) to afford the title compound (3.5 mg, 22% yield). MS (apci) m/z=367.2 (M+H).

The compounds in the following Table were prepared using a similar two-step procedure as described for the synthesis of 11-amino-3-cyclopropyl-5-ethyl-7-isopropyl-6,7-dihydroisoxazolo[4,3-c]pyrimido[5',4':4,5]pyrrolo[3,2-e]azepin-4(5H)-one (Example 1), replacing ethylamine with the appropriate amine in Step 1, followed by protection group(s) removal with the appropriate reagent(s). Reactions were monitored by LCMS, and the products purified by chromatography using appropriate eluents.

TABLE A

| Ex # | Structure | Chemical Name | MS apci (m/z) |
|---|---|---|---|
| 2 | 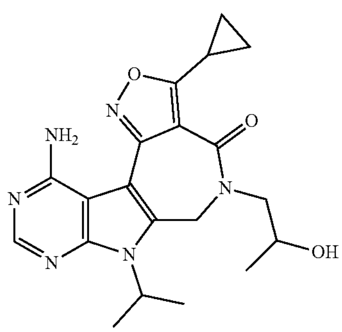 [SMILES: CC(O)CN1Cc2c(c3c(N)ncnc3n2C(C)C)-c2noc(C3CC3)c2C1=O] | 11-amino-3-cyclopropyl-5-(2-hydroxypropyl)-7-isopropyl-6,7-dihydroisoxazolo[4,3-c]pyrimido[5',4':4,5]pyrrolo[3,2-e]azepin-4(5H)-one | 397.2 (M + H) |
| 3 | 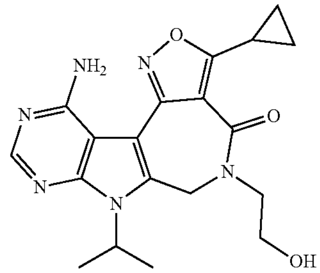 [SMILES: CC(C)n1c2c(c3c(N)ncnc31)-c1noc(C3CC3)c1C(=O)N(CCO)C2] | 11-amino-3-cyclopropyl-5-(2-hydroxyethyl)-7-isopropyl-6,7-dihydroisoxazolo[4,3-c]pyrimido[5',4':4,5]pyrrolo[3,2-e]azepin-4(5H)-one | 383.2 (M + H) |

TABLE A-continued

| Ex # | Structure | Chemical Name | MS apci (m/z) |
|---|---|---|---|
| 4 | 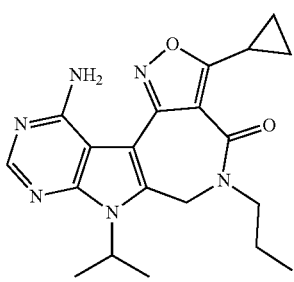 [SMILES: CCCN1Cc2c(c3c(N)ncnc3n2C(C)C)-c2noc(C3CC3)c2C1=O] | 11-amino-3-cyclopropyl-7-isopropyl-5-propyl-6,7-dihydroisoxazolo[4,3-c]pyrimido[5',4':4,5]pyrrolo[3,2-e]azepin-4(5H)-one | 381.2 (M + H) |
| 5 | 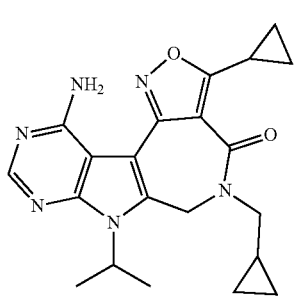 [SMILES: CC(C)n1c2c(c3c(N)ncnc31)-c1noc(C3CC3)c1C(=O)N(CC1CC1)C2] | 11-amino-3-cyclopropyl-5-(cyclopropylmethyl)-7-isopropyl-6,7-dihydroisoxazolo[4,3-c]pyrimido[5',4':4,5]pyrrolo[3,2-e]azepin-4(5H)-one | 393.2 (M + H) |
| 6 | 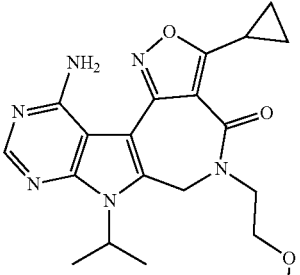 | 11-amino-3-cyclopropyl-7-isopropyl-5-(2-methoxyethyl)-6,7-dihydroisoxazolo[4,3-c]pyrimido[5',4':4,5]pyrrolo[3,2-e]azepin-4(5H)-one | 397.2 (M + H) |
| 7 | 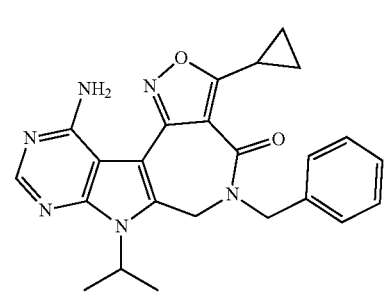 [SMILES: CC(C)n1c2c(c3c(N)ncnc31)-c1noc(C3CC3)c1C(=O)N(Cc1ccccc1)C2] | 11-amino-5-benzyl-3-cyclopropyl-7-isopropyl-6,7-dihydroisoxazolo[4,3-c]pyrimido[5',4':4,5]pyrrolo[3,2-e]azepin-4(5H)-one | 429.2 (M + H) |
| 8 | 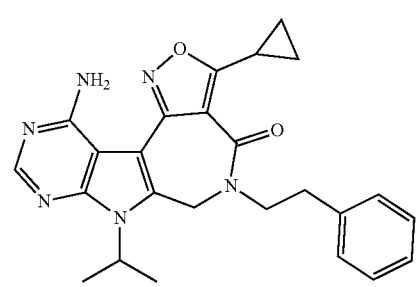 [SMILES: CC(C)n1c2c(c3c(N)ncnc31)-c1noc(C3CC3)c1C(=O)N(CCc1ccccc1)C2] | 11-amino-3-cyclopropyl-7-isopropyl-5-phenethyl-6,7-dihydroisoxazolo[4,3-c]pyrimido[5',4':4,5]pyrrolo[3,2-e]azepin-4(5H)-one | 443.2 (M + H) |

TABLE A-continued

| Ex # | Structure | Chemical Name | MS apci (m/z) |
|---|---|---|---|
| 9 | 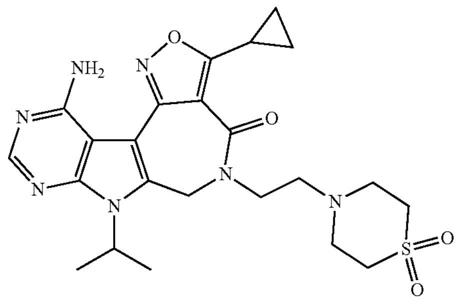 [SMILES: CC(C)n1c2c(c3c(N)ncnc31)-c1noc(C3CC3)c1C(=O)N(CCN1CCS(=O)(=O)CC1)C2] | 11-amino-3-cyclopropyl-5-(2-(1,1-dioxidothiomorpholino)ethyl)-7-isopropyl-6,7-dihydroisoxazolo[4,3-c]pyrimido[5',4':4,5]pyrrolo[3,2-e]azepin-4(5H)-one | 500.2 (M + H) |

Example 10

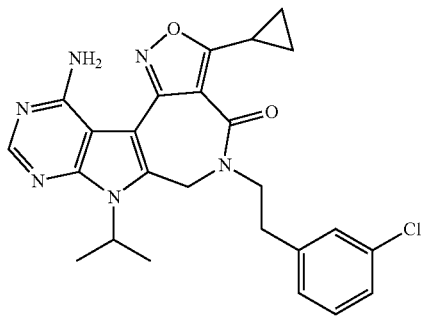 [SMILES: CC(C)n1c2c(c3c(N)ncnc31)-c1noc(C3CC3)c1C(=O)N(CCc1cccc(Cl)c1)C2]

11-amino-5-(3-chlorophenethyl)-3-cyclopropyl-7-isopropyl-6,7-dihydroisoxazolo[4,3-c]pyrimido[5',4':4,5]pyrrolo[3,2-e]azepin-4(5H)-one The title compound was prepared in a similar fashion as described in the synthesis of 11-amino-3-cyclopropyl-5-ethyl-7-isopropyl-6,7-dihydroisoxazolo[4,3-c]pyrimido[5',4':4,5]pyrrolo[3,2-e]azepin-4(5H)-one (Example 1), replacing ethyl 5-cyclopropyl-3-(4-((2,4-dimethoxybenzyl)amino)-7-isopropyl-6-(((methylsulfonyl)oxy)methyl)-7H-pyrrolo[2,3-d]pyrimidin-5-yl)isoxazole-4-carboxylate (Intermediate P5) with methyl 5-cyclopropyl-3-(4-((2,4-dimethoxybenzyl)amino)-7-isopropyl-6-(((methylsulfonyl)oxy)methyl)-7H-pyrrolo[2,3-d]pyrimidin-5-yl)isoxazole-4-carboxylate (Intermediate P6), and ethylamine with 2-(3-chlorophenyl)ethan-1-amine in step 1 instead. MS (apci) m/z=477.2 (M+H).

The compounds in the following Table were prepared in a similar fashion as described for the synthesis of 11-amino-5-(3-chlorophenethyl)-3-cyclopropyl-7-isopropyl-6,7-dihydroisoxazolo[4,3-c]pyrimido[5',4':4,5]pyrrolo[3,2-e]azepin-4(5H)-one (Example 10), replacing 2-(3-chlorophenyl)ethan-1-amine with the appropriate amine in Step 1.

TABLE B

| Ex # | Structure | Chemical Name | MS apci (m/z) |
|---|---|---|---|
| 11 | 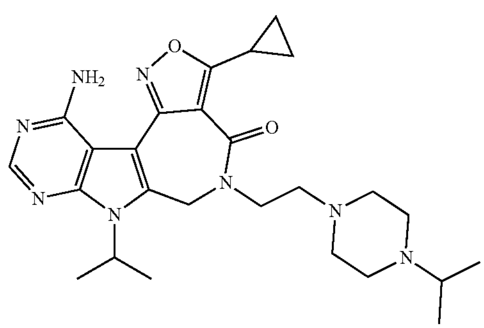 [SMILES: CC(C)N1CCN(CCN2Cc3c(c4c(N)ncnc4n3C(C)C)-c3noc(C4CC4)c3C2=O)CC1] | 11-amino-3-cyclopropyl-7-isopropyl-5-(2-(4-isopropylpiperazin-1-yl)ethyl)-6,7-dihydroisoxazolo[4,3-c]pyrimido[5',4':4,5]pyrrolo[3,2-e]azepin-4(5H)-one | 493.3 (M + H) |

TABLE B-continued

| Ex # | Structure | Chemical Name | MS apci (m/z) |
|---|---|---|---|
| 12 | 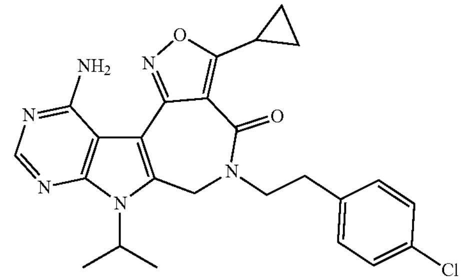 [SMILES: CC(C)n1c2c(c3c(N)ncnc31)-c1noc(C3CC3)c1C(=O)N(CCc1ccc(Cl)cc1)C2] | 11-amino-5-(4-chlorophenethyl)-3-cyclopropyl-7-isopropyl-6,7-dihydroisoxazolo[4,3-c]pyrimido[5',4':4,5]pyrrolo[3,2-e]azepin-4(5H)-one | 477.2 (M + H) |
| 13 | 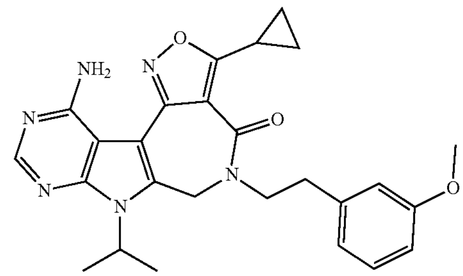 [SMILES: COc1cccc(CCN2Cc3c(c4c(N)ncnc4n3C(C)C)-c3noc(C4CC4)c3C2=O)c1] | 11-amino-3-cyclopropyl-7-isopropyl-5-(3-methoxyphenethyl)-6,7-dihydroisoxazolo[4,3-c]pyrimido[5',4':4,5]pyrrolo[3,2-e]azepin-4(5H)-one | 473.2 (M + H) |
| 14 | 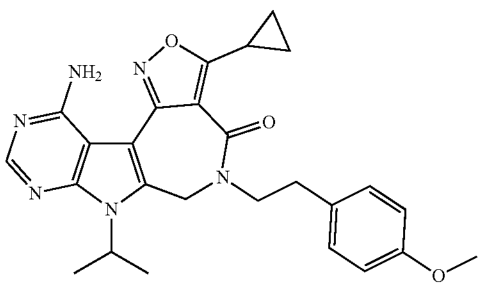 [SMILES: COc1ccc(CCN2Cc3c(c4c(N)ncnc4n3C(C)C)-c3noc(C4CC4)c3C2=O)cc1] | 11-amino-3-cyclopropyl-7-isopropyl-5-(4-methoxyphenethyl)-6,7-dihydroisoxazolo[4,3-c]pyrimido[5',4':4,5]pyrrolo[3,2-e]azepin-4(5H)-one | 473.2 (M + H) |
| 15 | 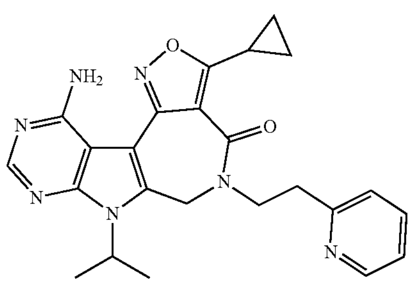 [SMILES: CC(C)n1c2c(c3c(N)ncnc31)-c1noc(C3CC3)c1C(=O)N(CCc1ccccn1)C2] | 11-amino-3-cyclopropyl-7-isopropyl-5-(2-(pyridin-2-yl)ethyl)-6,7-dihydroisoxazolo[4,3-c]pyrimido[5',4':4,5]pyrrolo[3,2-e]azepin-4(5H)-one | 444.2 (M + H) |
| 16 | 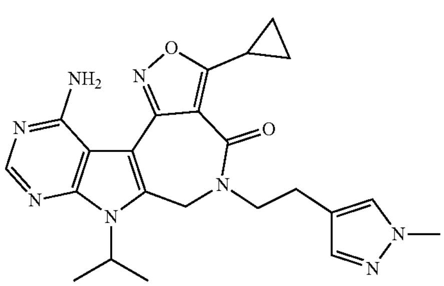 [SMILES: CC(C)n1c2c(c3c(N)ncnc31)-c1noc(C3CC3)c1C(=O)N(CCc1cnn(C)c1)C2] | 11-amino-3-cyclopropyl-7-isopropyl-5-(2-(1-methyl-1H-pyrazol-4-yl)ethyl)-6,7-dihydroisoxazolo[4,3-c]pyrimido[5',4':4,5]pyrrolo[3,2-e]azepin-4(5H)-one | 447.2 (M + H) |

TABLE B-continued

| Ex # | Structure | Chemical Name | MS apci (m/z) |
|---|---|---|---|
| 17 | 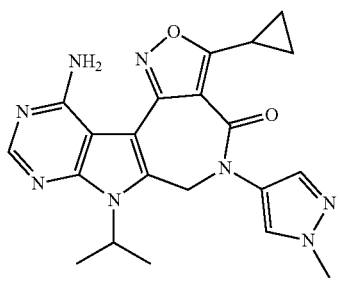 | 11-amino-5-(1-benzylpyrrolidin-3-yl)-3-cyclopropyl-7-isopropyl-6,7-dihydroisoxazolo[4,3-c]pyrimido[5',4':4,5]pyrrolo[3,2-e]azepin-4(5H)-one | 498.3 (M + H) |

Example 18

11-amino-3-cyclopropyl-7-isopropyl-5-(1-methyl-1H-pyrazol-4-yl)-6,7-dihydroisoxazolo[4,3-c]pyrimido[5',4':4,5]pyrrolo[3,2-e]azepin-4(5H)-one Step 1: Preparation of ethyl 5-cyclopropyl-3-(4-((2,4-dimethoxybenzyl)amino)-7-isopropyl-6-(((1-methyl-1H-pyrazol-4-yl)amino)methyl)-7H-pyrrolo[2,3-d]pyrimidin-5-yl)isoxazole-4-carboxylate A mixture of ethyl To a solution of ethyl 5-cyclopropyl-3-(4-((2,4-dimethoxybenzyl)amino)-7-isopropyl-6-(((methylsulfonyl)oxy)methyl)-7H-pyrrolo[2,3-d]pyrimidin-5-yl)isoxazole-4-carboxylate (Intermediate P5; 32 mg, 0.052 mmol) in DMF (0.6 mL) was added 1-methyl-1H-pyrazol-4-amine (25.3 mg, 0.26 mmol) followed by DIEA (19.1 µL, 0.110 mmol) and stirred overnight at RT, then at 90° C. for 18 h. After cooled to RT, the reaction was partioned between water and DCM. The combined organic extracts were concentrated and purified by silica chromatography (0-4% MeOH in DCM) to afford the title product (15 mg, 47% yield). MS (apci) m/z=615.3 (M+H).

Step 2: Preparation of 3-cyclopropyl-11-((2,4-dimethoxybenzyl)amino)-7-isopropyl-5-(1-methyl-1H-pyrazol-4-yl)-6,7-dihydroisoxazolo[4,3-c]pyrimido[5',4':4,5]pyrrolo[3,2-e]azepin-4(5H)-one To ethyl 5-cyclopropyl-3-(4-((2,4-dimethoxybenzyl)amino)-7-isopropyl-6-(((1-methyl-1H-pyrazol-4-yl)amino)methyl)-7H-pyrrolo[2,3-d]pyrimidin-5-yl)isoxazole-4-carboxylate (15 mg, 0.024 mmol) in MeOH (0.25 mL) was added LiOH (2 M, aq) (61 µL, 0.12 mmol) and stirred for 2 h. The reaction was partioned between water and DCM. After phase-separation and extracting the aqueous with DCM (2×), the combined organic extracts were concentrated to give the title product (12 mg, 86% yield). MS (apci) m/z=569.2 (M+H).

Step 3: Preparation of 11-amino-3-cyclopropyl-7-isopropyl-5-(1-methyl-1H-pyrazol-4-yl)-6,7-dihydroisoxazolo[4,3-c]pyrimido[5',4':4,5]pyrrolo[3,2-e]azepin-4(5H)-one To a solution of 3-cyclopropyl-11-((2,4-dimethoxybenzyl)amino)-7-isopropyl-5-(1-methyl-1H-pyrazol-4-yl)-6,7-dihydroisoxazolo[4,3-c]pyrimido[5',4':4,5]pyrrolo[3,2-e]azepin-4(5H)-one (12 mg, 0.021 mmol) in DCM (0.5 mL) was added triethylsilane (0.034 mL, 0.21 mmol) and 2,2,2-trifluoroacetic acid (0.5 mL, 0.021 mmol) and stirred overnight. The reaction mixture was then concentrated and partitioned between DCM and sat. NaHCO$_{3(aq)}$. After phase-separation and extracting the aqueous with DCM (2×), the combined organic extracts were concentrated and purified by silica chromatography (0-5% MeOH in DCM) to afford the title product (7 mg, 79% yield) MS (apci) m/z=419.2 (M+H).

Example 19

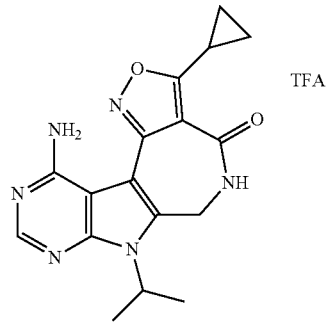 [SMILES: CC(C)n1c2c(c3c(N)ncnc31)-c1noc(C3CC3)c1C(=O)NC2]

11-amino-3-cyclopropyl-7-isopropyl-6,7-dihydroisoxazolo[4,3-c]pyrimido[5',4':4,5]pyrrolo[3,2-e]azepin-4(5H)-one 2,2,2-trifluoroacetate Step 1: Preparation of ethyl 3-(4-chloro-6-(hydroxymethyl)-7-isopropyl-7H-pyrrolo[2,3-d]pyrimidin-5-yl)-5-cyclopropylisoxazole-4-carboxylate A cold (0° C.) solution of ethyl 3-(6-(((tert-butyldimethylsilyl)oxy)methyl)-4-chloro-7-isopropyl-7H-pyrrolo[2,3- d]pyrimidin-5-yl)-5-cyclopropylisoxazole-4-carboxylate (Intermediate P4; 120 mg, 0.231 mmol) and acetic acid (14.7 M; 13.9 μL, 0.243 mmol) in THF (2.31 mL) was treated with TBAF (1.0 M in THF; 243 μL, 0.243 mmol). The resulting solution was stirred for 4 h at RT, after which the mixture was partitioned between DCM and saturated NaHCO$_{3(aq)}$. Following phase separation, the organic extracts were washed with brine, dried over anhydrous Na$_2$SO$_{4(s)}$, filtered, and concentrated in vacuo to afford the title compound (93 mg, 99% yield). MS (apci) m/z=405.1 (M+H).

Step 2: Preparation of ethyl 3-(6-(azidomethyl)-4-chloro-7-isopropyl-7H-pyrrolo[2,3-d]pyrimidin-5-yl)-5-cyclopropylisoxazole-4-carboxylate A solution of ethyl 3-(4-chloro-6-(hydroxymethyl)-7-isopropyl-7H-pyrrolo[2,3-d]pyrimidin-5-yl)-5-cyclopropylisoxazole-4-carboxylate (30 mg, 0.074 mmol) in toluene (741 μL) was treated sequentially with diphenylphosphoryl azide (32 μL, 0.15 mmol) and DBU (22 μL, 0.15 mmol), then stirred for 20 h at RT. Subsequently, the reaction mixture was diluted with EtOAc, and washed with water. The organic extracts then were dried over anhydrous Na$_2$SO$_{4(s)}$, filtered, and concentrated in vacuo. The crude residue was purified by silica chromatography (0-50% EtOAc in hexanes) to afford the title compound (20 mg, 63% yield). MS (apci) m/z=430.1 (M+H).

Step 3: Preparation of ethyl 3-(6-(aminomethyl)-4-chloro-7-isopropyl-7H-pyrrolo[2,3-d]pyrimidin-5-yl)-5-cyclopropylisoxazole-4-carboxylate A solution of ethyl 3-(6-(azidomethyl)-4-chloro-7-isopropyl-7H-pyrrolo[2,3-d]pyrimidin-5-yl)-5-cyclopropylisoxazole-4-carboxylate (20 mg, 0.047 mmol) in THF (931 μL) and water (93 μL) was treated with PPh$_3$ (24 mg, 0.093 mmol). The resulting solution was stirred for 1 h at RT before introducing additional THF (500 μL) and water (500 μL). After stirring for an additional 2 h at RT, the solution was concentrated in vacuo to afford the title compound (19 mg, quantitative yield). MS (apci) m/z=404.2 (M+H).

Step 4: Preparation of 11-amino-3-cyclopropyl-7-isopropyl-6,7-dihydroisoxazolo[4,3-c]pyrimido[5',4':4,5]pyrrolo[3,2-e]azepin-4(5H)-one 2,2,2-trifluoroacetate In a sealed tube, a mixture of ethyl 3-(6-(aminomethyl)-4-chloro-7-isopropyl-7H-pyrrolo[2,3-d]pyrimidin-5-yl)-5-cyclopropylisoxazole-4-carboxylate (19 mg, 0.047 mmol), NH$_4$OH (28-30%) (2 mL) and 1,4-dioxane (1 mL) was stirred for 2 h at 80° C. and then for 2 h at 100° C. After cooling to RT, the solution was concentrated in vacuo. The crude residue was purified by C18 reverse phase chromatography (0-95% ACN in water with 0.1% TFA) to afford the title compound as the TFA salt (10 mg, 47% yield). MS (apci) m/z=339.2 (M+H).

Example 20

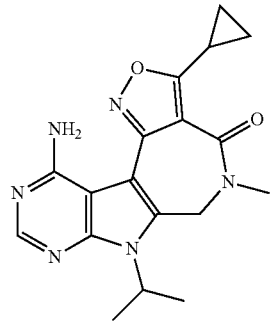 [SMILES: CC(C)n1c2c(c3c(N)ncnc31)-c1noc(C3CC3)c1C(=O)N(C)C2]

11-amino-3-cyclopropyl-7-isopropyl-5-methyl-6,7-dihydroisoxazolo[4,3-c]pyrimido[5',4':4,5]pyrrolo[3,2-e]azepin-4(5H)-one Method A:
The title product was prepared by as similar fashion as described for the synthesis of 11-amino-3-cyclopropyl-5-ethyl-7-isopropyl-6,7-dihydroisoxazolo[4,3-c]pyrimido[5',4':4,5]pyrrolo[3,2-e]azepin-4(5H)-one (Example 1), replacing ethylamine with methyl amine in Step 1 instead. MS (apci) m/z=353.1 (M+H).

Method B:
A suspension of 11-amino-3-cyclopropyl-7-isopropyl-6,7-dihydroisoxazolo[4,3-c]pyrimido[5',4':4,5]pyrrolo[3,2-e]azepin-4(5H)-one 2,2,2-trifluoroacetate (Example 19; 15 mg, 0.033 mmol) in DMF (554 μL) was treated with 60 wt. % NaH dispersion in mineral oil (2.1 mg, 0.053 mmol), and stirred for 10 min at RT. The resulting solution was cooled to 0° C. then treated with iodomethane (3.3 μL, 0.053 mmol), and stirred for 1 h at 0° C. After being allowed to warm to RT, the reaction mixture was directly purified by C18 reverse phase chromatography (0-95% ACN in water with 0.1% TFA) to afford the title compound as the TFA salt. The TFA salt then was dissolved in MeOH (500 μL), and treated with saturated NaHCO$_{3(aq)}$ (100 μL) and water (2 mL). The resulting mixture was concentrated in vacuo to about half of the original volume (1.5 mL). The resulting suspension was allowed to settle, and the supernatant was cannulated from the solid precipitate. The solids then were dried in vacuo to afford the title compound (4 mg, 34% yield). MS (apci) m/z=353.1 (M+H).

Example 21

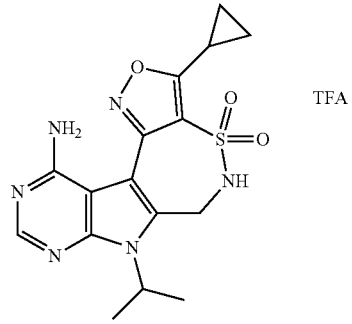

11-amino-3-cyclopropyl-7-isopropyl-6,7-dihydro-5H-isoxazolo[3,4-f]pyrimido[5',4':4,5]pyrrolo[2,3-d][1,2]thiazepine 4,4-dioxide 2,2,2-trifluoroacetate Step 1: Preparation of methyl ((3-(4-chloro-6-(hydroxymethyl)-7-isopropyl-7H-pyrrolo[2,3-d]pyrimidin-5-yl)-5-cyclopropylisoxazol-4-yl)sulfonyl)carbamate, Tetrabutylammonium Salt A cold (−78° C.) solution of 3-(6-(((tert-butyldimethylsilyl)oxy)methyl)-4-chloro-7-isopropyl-7H-pyrrolo[2,3-d]pyrimidin-5-yl)-5-cyclopropyl-4-iodoisoxazole (Intermediate P2; 387 mg, 0.675 mmol) in THF (3.38 mL) was treated with n-BuLi (2.5 M in THF; 324 μL, 0.811 mmol), and stirred for 10 min at −78° C. The resultant red-orange solution then was treated with Burgess reagent (145 mg, 0.608 mmol), and the solution was allowed to warm to −30° C. over a period of 1 h. Subsequently, the mixture was quenched with saturated NH$_4$Cl$_{(aq)}$ and water. After being allowed to warm to RT, the quenched mixture was extracted with EtOAc. The combined organic extracts were dried over anhydrous Na$_2$SO$_{4(s)}$, filtered, and concentrated in vacuo. The resulting foam residue was then dissolved in THF (6.5 mL), and treated with TBAF (1.0 M in THF; 878 μL, 0.878 mmol). After stirring for 15 min at RT, the reaction mixture was diluted with EtOAc, and washed with water. The organic extracts were dried over anhydrous Na$_2$SO$_{4(s)}$, filtered, and concentrated in vacuo. The crude residue was purified by silica chromatography (0-50% EtOAc in hexanes followed by 0-10% MeOH in DCM) to afford the title compound as the tetrabutylammonium salt (67 mg, 21% yield). MS (apci) m/z=470.1 (M+H).

Step 2: Preparation of 11-amino-3-cyclopropyl-7-isopropyl-6,7-dihydro-5H-isoxazolo[3,4-f]pyrimido[5',4':4,5]pyrrolo[2,3-d][1,2]thiazepine 4,4-dioxide 2,2,2-trifluoroacetate A solution of methyl ((3-(4-chloro-6-(hydroxymethyl)-7-isopropyl-7H-pyrrolo[2,3-d]pyrimidin-5-yl)-5-cyclopropylisoxazol-4-yl)sulfonyl)carbamate, tetrabutylammonium salt (48 mg, 0.067 mmol) in DCM (2.0 mL) was treated sequentially with MsCl (23.9 μL, 0.306 mmol) and DIPEA (89.2 μL, 0.511 mmol), then stirred for ~15 h at RT. The reaction mixture then was concentrated in vacuo. The resulting residue was dissolved in 1,4-dioxane (1.0 mL) and NH$_4$OH$_{(aq)}$ (28-30%) (511 μL). The resulting mixture was transferred to a sealed tube, and stirred for 30 min at 80° C. After cooling to RT, the resulting solution was concentrated in vacuo. The crude residue was purified by C18 reverse phase chromatography (0-95% ACN in water with 0.1% TFA). The desired fractions were combined and concentrated in vacuo to about 5 mL, as which point solid precipitated from the solution. The solids were collected by filtration and then dried in vacuo to afford the title compound as the TFA salt (23.5 mg, 71% yield). MS (apci) m/z=375.2 (M+H).

Example 22

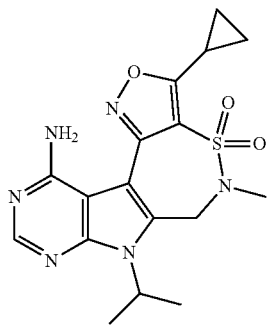 [SMILES: CC(C)n1c2c(c3c(N)ncnc31)-c1noc(C3CC3)c1S(=O)(=O)N(C)C2]

11-amino-3-cyclopropyl-7-isopropyl-5-methyl-6,7-dihydro-5H-isoxazolo[3,4-f]pyrimido[5',4':4,5]pyrrolo[2,3-d][1,2]thiazepine 4,4-dioxide A suspension of 11-amino-3-cyclopropyl-7-isopropyl-6,7-dihydro-5H-isoxazolo[3,4-f]pyrimido[5',4':4,5]pyrrolo[2,3-d][1,2]thiazepine 4,4-dioxide 2,2,2-trifluoroacetate (Example 21; 11 mg, 0.0225 mmol) in DMF (322 μL) was treated with 60 wt. % NaH dispersion in mineral oil (1.98 mg, 0.0496 mmol), and stirred for 10 min at RT. The resulting solution was cooled to 0° C., then treated with iodomethane (1.55 μL, 0.0248 mmol) and allowed to warm to RT. After stirring for 1 h at RT, the resulting mixture was directly purified by C18 reverse phase chromatography (0-95% ACN in water with 0.1% TFA) to afford the title compound as the TFA salt. The TFA salt then was dissolved in MeOH, and the solution was passed through a basic resin, PL-HCO$_3$ MP, filter plug. The filtrate was concentrated in vacuo to afford the title compound (1.5 mg, 17% yield). MS (apci) m/z=389.3 (M+H).

Example 23

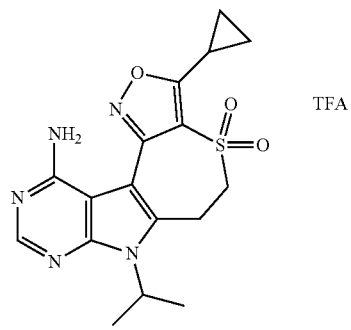 [SMILES: CC(C)n1c2c(c3c(N)ncnc31)-c1noc(C3CC3)c1S(=O)(=O)CC2]

11-amino-3-cyclopropyl-7-isopropyl-6,7-dihydro-5H-isoxazolo[4'',3'':2',3']thiepino[4',5':4,5]pyrrolo[2,3-d]pyrimidine 4,4-dioxide 2,2,2-trifluoroacetate Step 1: Preparation of 3-(6-(((tert-butyldimethylsilyl)oxy)methyl)-4-chloro-7-isopropyl-7H-pyrrolo[2,3-d]pyrimidin-5-yl)-5-cyclopropyl-4-(methylsulfonyl)isoxazole A cold (−78° C.) solution of 3-(6-(((tert-butyldimethylsilyl)oxy)methyl)-4-chloro-7-isopropyl-7H-pyrrolo[2,3-d]pyrimidin-5-yl)-5-cyclopropyl-4-iodoisoxazole (Intermediate P2; 130 mg, 0.227 mmol) in THF (1.51 mL) was treated with n-BuLi (2.5 M in THF; 127 μL, 0.318 mmol), and stirred for 15 min at −78° C. The resultant yellow-orange solution then was treated with DMDS (40.3 μL, 0.454 mmol), and the solution was allowed to warm to −30° C. over a period of 1 h. Subsequently, the mixture was quenched with saturated NH$_4$Cl$_{(aq)}$. After being allowed to warm to RT, the quenched mixture was extracted with EtOAc. The combined organic extracts were dried over anhydrous Na$_2$SO$_{4(s)}$, filtered, and concentrated in vacuo. The resulting residue then was dissolved in DCM (2.27 mL). The solution was cooled to 0° C. and treated with mCPBA (70 wt. %; 117 mg, 0.476 mmol). After overnight stirring at 0° C., additional mCPBA (70 wt.

%; 27.9 mg, 0.113 mmol) was introduced, and stirring was resumed for another 1.5 h at 0° C. The reaction was quenched with 10% Na$_2$S$_2$O$_{3(aq)}$ (2 mL) and saturated NaHCO$_{3(aq)}$ (5 mL) and extracted with DCM. The organic extracts were dried over anhydrous Na$_2$SO$_{4(s)}$, filtered, and concentrated in vacuo. The crude residue was purified by silica chromatography (0-50% EtOAc in hexanes) to afford the title compound (72 mg, 60% yield). MS (apci) m/z=525.2 (M+H).

Step 2: Preparation of 3-(6-(bromomethyl)-4-chloro-7-isopropyl-7H-pyrrolo[2,3-d]pyrimidin-5-yl)-5-cyclopropyl-4-(methylsulfonyl)isoxazole A solution of 3-(6-(((tert-butyldimethylsilyl)oxy)methyl)-4-chloro-7-isopropyl-7H-pyrrolo[2,3-d]pyrimidin-5-yl)-5-cyclopropyl-4-(methylsulfonyl)isoxazole (65 mg, 0.12 mmol) in THF (1.2 mL) was treated with TBAF (1.0 M THF) (186 µL, 0.19 mmol), and stirred for 15 min at RT. The reaction mixture then was diluted with EtOAc and washed with water. The organic extracts were dried over anhydrous Na$_2$SO$_{4(s)}$, filtered, and concentrated in vacuo. The residue was dissolved in DCM (1.2 mL) and treated with PBr$_3$ (97.4 mg, 0.36 mmol). The reaction mixture was stirred for 1 h at RT, before quenching with saturated NaHCO$_{3(aq)}$. The quenched mixture was extracted with DCM, and the organic extracts were dried over anhydrous Na$_2$SO$_{4(s)}$, filtered, and concentrated in vacuo. The crude residue was purified by silica chromatography (0-30% EtOAc in hexanes) to afford the title compound (50 mg, 85% yield). MS (apci) m/z=473.0 (M+H).

Step 3: Preparation of 11-chloro-3-cyclopropyl-7-isopropyl-6,7-dihydro-5H-isoxazolo[4'',3'':2',3']thiepino[4',5':4,5]pyrrolo[2,3-d]pyrimidine 4,4-dioxide A cold (-78° C.) solution of 3-(6-(bromomethyl)-4-chloro-7-isopropyl-7H-pyrrolo[2,3-d]pyrimidin-5-yl)-5-cyclopropyl-4-(methylsulfonyl)isoxazole (50 mg, 0.11 mmol) in THF (2.1 mL) was treated with LiHMDS (1 M in THF; 317 µL, 0.32 mmol). The resulting blue solution was stirred for 1 h at -78° C. before the mixture was quenched with saturated NH$_4$Cl$_{(aq)}$ and water. After being allowed to warm to RT, the quenched mixture was extracted with EtOAc. The organic extracts were dried over anhydrous Na$_2$SO$_{4(s)}$, filtered, and concentrated in vacuo to afford the title compound (43 mg, quantitative yield). MS (apci) m/z=393.0 (M+H).

Step 4: Preparation of 11-amino-3-cyclopropyl-7-isopropyl-6,7-dihydro-5H-isoxazolo[4'',3'':2',3']thiepino[4',5':4,5]pyrrolo[2,3-d]pyrimidine 4,4-dioxide 2,2,2-trifluoroacetate In a sealed tube, a solution of 11-chloro-3-cyclopropyl-7-isopropyl-6,7-dihydro-5H-isoxazolo[4'',3'':2',3']thiepino[4',5':4,5]pyrrolo[2,3-d]pyrimidine 4,4-dioxide (43 mg, 0.11 mmol) in 1,4-dioxane (1.1 mL) and NH$_4$OH$_{(aq)}$ (28-30%) (1.1 mL) was stirred for 45 min at 100° C. After cooling to RT, the resulting solution was concentrated in vacuo. The crude residue was purified by C18 reverse phase chromatography (0-95% ACN in water with 0.1% TFA) to afford the title compound as the TFA salt (8 mg, 15% yield). MS (apci) m/z=374.3 (M+H).

Example 24

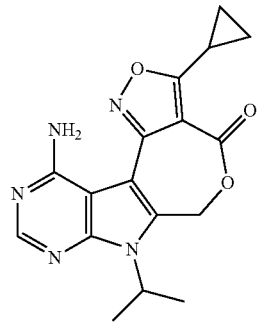 [SMILES: CC(C)n1c2c(c3c(N)ncnc31)-c1noc(C3CC3)c1C(=O)OC2]

11-amino-3-cyclopropyl-7-isopropyl-6,7-dihydro-4H-isoxazolo[3'',4'':5',6']oxepino[4',3':4,5]pyrrolo[2,3-d]pyrimidin-4-one Step 1: Preparation of methyl 3-(6-(((tert-butyldimethylsilyl)oxy)methyl)-4-((2,4-dimethoxybenzyl)amino)-7-isopropyl-7H-pyrrolo[2,3-d]pyrimidin-5-yl)-5-cyclopropylisoxazole-4-carboxylate A solution of methyl 3-(6-(((tert-butyldimethylsilyl)oxy)methyl)-4-chloro-7-isopropyl-7H-pyrrolo[2,3-d]pyrimidin-5-yl)-5-cyclopropylisoxazole-4-carboxylate (Intermediate P3; 279 mg, 0.552 mmol) and (2,4-dimethoxyphenyl)methanamine (207.5 µL, 1.381 mmol) in DMSO (3.683 mL) was stirred overnight at 60° C. After cooling to RT, the reaction mixture was diluted with EtOAc, then successively washed with water (4×) and brine. The organic extracts were dried over anhydrous Na$_2$SO$_{4(s)}$, filtered, and concentrated in vacuo to afford the title compound (351 mg, 100% yield). MS (apci) m/z=636.3 (M+H).

Step 2: Preparation of 3-cyclopropyl-11-((2,4-dimethoxybenzyl)amino)-7-isopropyl-6,7-dihydro-4H-isoxazolo[3'',4'':5',6']oxepino[4',3':4,5]pyrrolo[2,3-d]pyrimidin-4-one A solution methyl 3-(6-(((tert-butyldimethylsilyl)oxy)methyl)-4-((2,4-dimethoxybenzyl)amino)-7-isopropyl-7H-pyrrolo[2,3-d]pyrimidin-5-yl)-5-cyclopropylisoxazole-4-carboxylate (351 mg, 0.552 mmol) in THF (3.68 mL) was treated with TBAF (1 M in THF; 607 µL, 0.607 mmol), and stirred for 2 h at RT. The reaction mixture then was diluted with EtOAc and extracted successively with water and brine. The organic extracts were dried over anhydrous Na$_2$SO$_{4(s)}$, filtered, and concentrated in vacuo. The crude residue was purified by silica chromatography (10-90% EtOAc in hexanes) to afford the title compound (140 mg, 52% yield). MS (apci) m/z=490.2 (M+H).

Step 3: 11-amino-3-cyclopropyl-7-isopropyl-6,7-dihydro-4H-isoxazolo[3'',4'':5',6']oxepino[4',3':4,5]pyrrolo[2,3-d]pyrimidin-4-one A mixture of 3-cyclopropyl-11-((2,4-dimethoxybenzyl)amino)-7-isopropyl-6,7-dihydro-4H-isoxazolo[3'',4'':5',6']oxepino[4',3':4,5]pyrrolo[2,3-d]pyrimidin-4-one (54 mg, 0.11 mmol) and triethylsilane (17.6 µL, 0.110 mmol) in TFA (1 mL) and DCM (1 mL) was stirred for 1 h at RT. The resulting mixture was concentrated in vacuo, and the residue was partitioned between DCM and saturated NaHCO$_{3(aq)}$. The organics extracts then were washed with brine, dried over anhydrous Na$_2$SO$_{4(s)}$, filtered, and concentrated in vacuo. The crude residue was purified by silica chromatography (1-10% DCM:MeOH) to afford the title compound (19.5 mg, 52% yield). MS (apci) m/z=340.1 (M+H).

Example 25

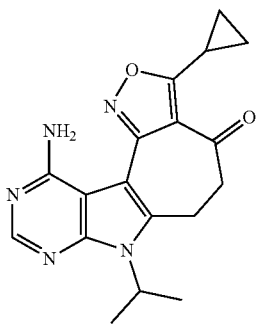 [SMILES: CC(C)n1c2c(c3c(N)ncnc31)-c1noc(C3CC3)c1C(=O)CC2]

11-amino-3-cyclopropyl-7-isopropyl-6,7-dihydroisoxazolo[4",3":6',7']cyclohepta[1',2':4,5]pyrrolo[2,3-d]pyrimidin-4(5H)-one Step 1: Preparation of benzyl (E)-3-(4-chloro-5-(5-cyclopropylisoxazol-3-yl)-7-isopropyl-7H-pyrrolo[2,3-d]pyrimidin-6-yl)acrylate A solution of 4-chloro-5-(5-cyclopropylisoxazol-3-yl)-7-isopropyl-7H-pyrrolo[2,3-d]pyrimidine-6-carbaldehyde (Intermediate P1; 100 mg, 0.302 mmol) in DCM (3.02 mL) was treated with benzyl (triphenylphosphoranylidene)acetate (149 mg, 0.363 mmol), and stirred for 1 h at RT. The resulting solution was concentrated in vacuo, and the residue was purified silica chromatography (0-25% EtOAc in hexanes) to afford the title compound (137 g, 98% yield). MS (apci) m/z=463.1 (M+H).

Step 2: Preparation of 3-(4-chloro-5-(5-cyclopropylisoxazol-3-yl)-7-isopropyl-7H-pyrrolo[2,3-d]pyrimidin-6-yl)propanoic Acid A solution of benzyl (E)-3-(4-chloro-5-(5-cyclopropylisoxazol-3-yl)-7-isopropyl-7H-pyrrolo[2,3-d]pyrimidin-6-yl)acrylate (137 mg, 0.296 mmol) in EtOAc (2.96 mL) was added 10% Pd/C (15.7 mg, 0.0148 mmol). The mixture was stirred under a balloon of H$_{2(g)}$ for 1 h at RT before introducing EtOH (3 mL) and additional 10% Pd/C (31.4 mg, 0.0296 mmol). The resulting mixture was placed back under a balloon of H$_{2(g)}$ and stirred for an additional 1.5 h at RT. The mixture was filtered through a short pad of celite, and the filtrate was concentrated in vacuo to afford title compound (100 mg), which was used directly in the next step without further purifications. MS (apci) m/z=375.1 (M+H).

Step 3: Preparation of 3-(4-amino-5-(5-cyclopropylisoxazol-3-yl)-7-isopropyl-7H-pyrrolo[2,3-d]pyrimidin-6-yl)propanoic Acid A solution of crude 3-(4-chloro-5-(5-cyclopropylisoxazol-3-yl)-7-isopropyl-7H-pyrrolo[2,3-d]pyrimidin-6-yl)propanoic acid (100 mg, 0.267 mmol) and NH$_4$OH$_{(aq)}$ (28-30%) (3 mL) in 1,4-dioxane (2 mL) was stirred for 16 h at 100° C. After cooling to RT, the solution was concentrated in vacuo to afford a product mixture containing the title compound, which was used directly in the next step without further purifications. MS (apci) m/z=356.2 (M+H).

Step 4: Preparation of 11-amino-3-cyclopropyl-7-isopropyl-6,7-dihydroisoxazolo[4",3":6',7']cyclohepta[1',2':4,5]pyrrolo[2,3-d]pyrimidin-4(5H)-one A solution of the crude mixture from the previous step containing 3-(4-amino-5-(5-cyclopropylisoxazol-3-yl)-7-isopropyl-7H-pyrrolo[2,3-d]pyrimidin-6-yl)propanoic acid (17 mg, 0.048 mmol) in polyphosphoric acid (PPA) (1 mL) was stirred for 1 h at 100° C. After cooling to RT, the mixture was neutralized with saturated NaHCO$_{3(aq)}$ and extracted with DCM (3×30 mL). The combined organic extracts were concentrated in vacuo, and the residue was purified by silica chromatography (0-10% MeOH/DCM) to afford the title compound (7.4 mg, 45% yield). MS (apci) m/z=338.1 (M+H).

Example 26

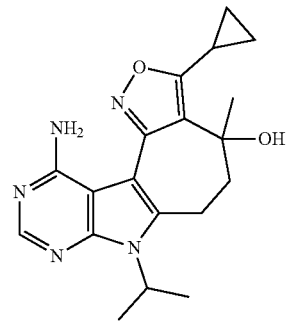 [SMILES: CC(C)n1c2c(c3c(N)ncnc31)-c1noc(C3CC3)c1C(C)(O)CC2]

11-amino-3-cyclopropyl-7-isopropyl-4-methyl-4,5,6,7-tetrahydroisoxazolo[4",3":6',7']cyclohepta[1',2':4,5]pyrrolo[2,3-d]pyrimidin-4-ol A solution of 11-amino-3-cyclopropyl-7-isopropyl-6,7-dihydroisoxazolo[4",3":6',7']cyclohepta[1',2':4,5]pyrrolo[2,3-d]pyrimidin-4(5H)-one (Example 25; 7 mg, 0.02 mmol) in THF (200 µL) was treated with anhydrous CeCl$_3$ (26 mg, 0.11 mmol) at 0° C., followed by MeMgBr (1.4M in toluene/THF 75:25) (300 µL, 0.4 mmol). After stirred for 1.5 h at 0° C., the reaction mixture was cooled to −78° C. before introducing MeLi (1.6 M Et$_2$O) (133 µL, 0.21 mmol). After stirred for 1 h at −78° C., the reaction mixture was quenched with MeOH, allowed to warm to RT and then partitioned between DCM and water (5 mL each). Following phase separation, the aqueous phase was back extracted with additional DCM (2×5 mL). The DCM extracts were combined and concentrated in vacuo. The crude residue was purified by silica chromatography (0-10% MeOH/DCM) to afford the title compound (4.5 mg, 60% yield). MS (apci) m/z=354.2 (M+H).

Example 27

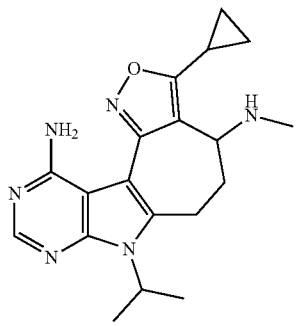 [SMILES: CNC1CCc2c(c3c(N)ncnc3n2C(C)C)-c2noc(C3CC3)c21]

3-cyclopropyl-7-isopropyl-N4-methyl-4,5,6,7-tetrahydroisoxazolo[4",3":6',7']cyclohepta[1',2':4,5]pyrrolo[2,3-d]pyrimidine-4,11-diamine A solution of 11-amino-3-cyclopropyl-7-isopropyl-6,7-dihydroisoxazolo[4",3":6',7']cyclohepta[1',2':4,5]pyrrolo[2,3-d]pyrimidin-4(5H)-one (Example 25; 10 mg, 0.03 mmol) in DCE (200 μL) was treated with methylamine (2 M THF) (74 μL, 0.15 mmol). The reaction mixture was stirred for 30 min at RT, and was then treated with NaBH(OAc)$_3$ (38 mg, 0.18 mmol). The resulting mixture was stirred for 45 min at RT, then overnight at 50° C. Subsequently, AcOH (10 drops) and additional methylamine (300 μL, 0.61 mmol) were introduced, and the reaction mixture was stirred for 30 min at 50° C. The resulting mixture was treated with additional NaBH(OAc)$_3$ (38 mg, 0.18 mmol). This mixture was stirred overnight at 50° C., then for 2 days at 65° C. and finally for 3 days at RT. The reaction then was concentrated in vacuo, and purified by silica chromatography (0-10% MeOH/DCM) to afford the title compound (2.8 mg, 27% yield). MS (apci) m/z=353.2 (M+H).

Example 28

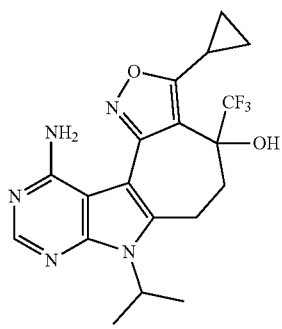 [SMILES: CC(C)n1c2c(c3c(N)ncnc31)-c1noc(C3CC3)c1C(O)(C(F)(F)F)CC2]

11-amino-3-cyclopropyl-7-isopropyl-4-(trifluoromethyl)-4,5,6,7-tetrahydroisoxazolo[4",3":6',7']cyclohepta[1',2':4,5]pyrrolo[2,3-d]pyrimidin-4-ol A solution of 11-amino-3-cyclopropyl-7-isopropyl-6,7-dihydroisoxazolo[4",3":6',7']cyclohepta[1',2':4,5]pyrrolo[2,3-d]pyrimidin-4(5H)-one (Example 25; 18 mg, 0.054 mmol) in THF (400 μL) was treated with TMSCF$_3$ (50 μL, 0.33 mmol) and CsF (4 mg, 0.027 mmol). The reaction mixture was stirred for 1.5 h at RT, and then HCl$_{(aq)}$ (5 M; 542 μL, 2.71 mmol) was added. The resulting mixture was stirred for 15 min at RT, then neutralized with saturated NaHCO$_{3(aq)}$ (5 mL). The neutralized mixture was extracted with DCM (3×5 mL). The organic extracts were concentrated in vacuo, and the residue was purified first by silica chromatography (0-10% MeOH/DCM), then by C18 reverse-phase chromatography (5-90% MeCN/water with 0.1% TFA) to afford the title compound as the TFA salt. The TFA salt was dissolved in DCM (5 mL) and extracted with saturated NaHCO$_{3(aq)}$ (5 mL). The aqueous phase then was back extracted with DCM (2×5 mL). The DCM extracts were combined, dried over anhydrous Na$_2$SO$_{4(s)}$, filtered, and concentrated in vacuo to afford the title compound (7 mg, 32% yield). MS (apci) m/z=408.1 (M+H).

Example 29

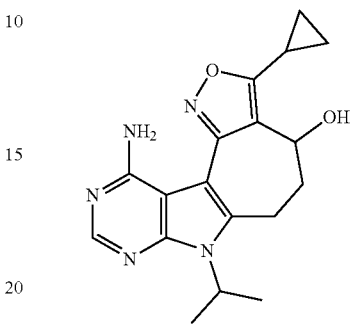

11-amino-3-cyclopropyl-7-isopropyl-4,5,6,7-tetrahydroisoxazolo[4",3":6',7']cyclohepta[1',2':4,5]pyrrolo[2,3-d]pyrimidin-4-ol A solution of 11-amino-3-cyclopropyl-7-isopropyl-6,7-dihydroisoxazolo[4",3":6',7']cyclohepta[1',2':4,5]pyrrolo[2,3-d]pyrimidin-4(5H)-one (Example 25; 18 mg, 0.055 mmol) in MeOH (600 μL) was treated with NaBH$_4$ (6.19 mg, 0.164 mmol), and the resulting mixture was stirred for 15 min at RT. The reaction mixture then was concentrated in vacuo, and the residue was purified by silica chromatography (0-10% MeOH/DCM) to afford the title compound (13.6 mg, 74% yield). MS (apci) m/z=340.2 (M+H).

Example 30

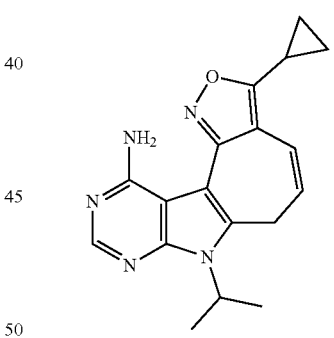

3-cyclopropyl-7-isopropyl-6,7-dihydroisoxazolo[4",3":6',7']cyclohepta[1',2':4,5]pyrrolo[2,3-d]pyrimidin-11-amine Step 1: Preparation of (E)-N'-(3-cyclopropyl-4-hydroxy-7-isopropyl-4,5,6,7-tetrahydroisoxazolo[4",3":6',7']cyclohepta[1',2':4,5]pyrrolo[2,3-d]pyrimidin-11-yl)-N,N-dimethylformimidamide A solution of 11-amino-3-cyclopropyl-7-isopropyl-4,5,6,7-tetrahydroisoxazolo[4",3":6',7']cyclohepta-[1',2':4,5]pyrrolo[2,3-d]pyrimidin-4-ol (Example 29; 22.2 mg, 0.0654 mmol) in EtOH (300 μL) was treated with 1,1-dimethoxy-N,N-dimethylmethylamine (87.2 μL, 0.654 mmol) and 2,2,2-trifluoroacetic acid (1.5 μL, 0.02 mmol) then stirred for 3 h at 65° C. After cooling to RT, the reaction mixture was concentrated in vacuo to afford the title compound, which was used directly in the next step without further purifications, assuming quantitative yield.

Step 2: Preparation of 3-cyclopropyl-7-isopropyl-6,7-dihydroisoxazolo[4",3":6',7']cyclohepta[1',2':4,5]pyrrolo[2,3-d]pyrimidin-11-amine A solution crude (E)-N'-(3-cyclopropyl-4-hydroxy-7-isopropyl-4,5,6,7-tetrahydroisoxazolo[4",3":6',7']cyclohepta[1',2':4,5]pyrrolo[2,3-d]pyrimidin-11-yl)-N,N-dimethylformimidamide (25 mg, 0.063 mmol) in DMF (300 µL) was treated with iodomethane (39.5 µL, 0.634 mmol) and DIEA (277 µL, 1.58 mmol), and stirred for 45 min at RT. The reaction mixture was partitioned between DCM (5 mL) and saturated NaHCO$_{3(aq)}$ (5 mL). Following phase separation, the aqueous extracts were back extracted with DCM (2×5 mL). The DCM extracts were combined and concentrated in vacuo. The crude residue was treated with 4 N HCl (1 mL), and stirred overnight at 65° C. After cooling to RT, the reaction mixture was partitioned between DCM (10 mL) and saturated NaHCO$_{3(aq)}$ (10 mL). Following phase separation, the aqueous extracts were back extracted with DCM (2×10 mL). The DCM extracts were combined and concentrated in vacuo. The residue was purified by silica chromatography (0-10% MeOH/DCM) to afford the title compound (2 mg, 10% yield). MS (apci) m/z=322.2 (M+H).

Example 31

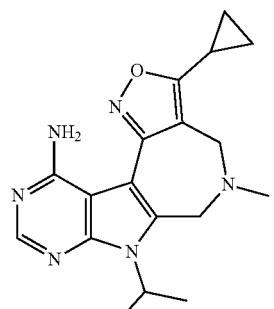

3-cyclopropyl-7-isopropyl-5-methyl-4,5,6,7-tetrahydroisoxazolo[4,3-c]pyrimido[5',4':4,5]pyrrolo[3,2-e]azepin-11-amine Step 1: Preparation of 3-cyclopropyl-7-isopropyl-N,N-bis(4-methoxybenzyl)-5-methyl-4,5,6,7-tetrahydroisoxazolo[4,3-c]pyrimido[5',4':4,5]pyrrolo[3,2-e]azepin-11-amine A solution of 3-(4-(bis(4-methoxybenzyl)amino)-6-formyl-7-isopropyl-7H-pyrrolo[2,3-d]pyrimidin-5-yl)-5-cyclopropylisoxazole-4-carbaldehyde (Intermediate P10; 25.7 mg, 0.0443 mmol) in DCE (887 µL) was treated with NaBH(OAc)$_3$ (37.6 mg, 0.177 mmol), stirred for 15 min at RT, and then treated dropwise with methylamine (2.0 M THF) (44.3 µL, 0.088 mmol). After stirring for 30 min at RT, the resulting mixture was diluted with DCM and washed with saturated NaHCO$_{3(aq)}$. Following phase separation, the aqueous extracts were back extracted with DCM. The DCM extracts were combined, then passed through a phase separator column and concentrated in vacuo. The crude residue was purified by silica chromatography (0-100% [15% MeOH+1.5% NH$_4$OH in DCM] in DCM) to afford the title compound (11.8 mg, 46% yield). MS (apci) m/z=579.4 (M+H).

Step 2: Preparation of 3-cyclopropyl-7-isopropyl-5-methyl-4,5,6,7-tetrahydroisoxazolo[4,3-c]pyrimido[5',4':4,5]pyrrolo[3,2-e]azepin-11-amine A solution of 3-cyclopropyl-7-isopropyl-N,N-bis(4-methoxybenzyl)-5-methyl-4,5,6,7-tetrahydroisoxazolo[4,3-c]pyrimido[5',4':4,5]pyrrolo[3,2-e]azepin-11-amine (11.8 mg, 0.0204 mmol) in DCM (408 µL) was treated with TFA (78.5 µL, 1.02 mmol), and stirred for 30 min at RT. The reaction mixture was then treated with triethylsilane (32.6 µL, 0.204 mmol), followed by stirring for an additional 30 min at RT before TfOH was introduced (1.81 µL, 0.0204 mmol). The resulting mixture was stirred for 10 min at RT, and then neutralized with saturated NaHCO$_{3(aq)}$. The neutralized mixture was extracted with DCM. The organic extracts were combined, passed through a phase separator column and concentrated in vacuo. After drying the residue under high-vacuum for 1 h, the title compound was cleanly isolated (4.1 mg, 59% yield). MS (apci) m/z=399.2 (M+H).

The compounds in the following Table were prepared in a similar fashion as described for the synthesis of 3-cyclopropyl-7-isopropyl-5-methyl-4,5,6,7-tetrahydroisoxazolo[4,3-c]pyrimido[5',4':4,5]pyrrolo[3,2-e]azepin-11-amine (Example 31), replacing methylamine with the appropriate amine in Step 1 instead.

TABLE C

| Ex # | Structure | Chemical Name | MS apci (m/z) |
|---|---|---|---|
| 32 | 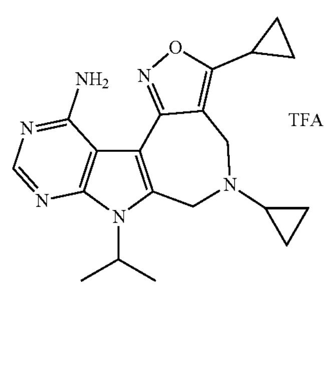 [SMILES: CC(C)n1c2c(c3c(N)ncnc31)-c1noc(C3CC3)c1CN(C1CC1)C2] | 3,5-dicyclopropyl-7-isopropyl-4,5,6,7-tetrahydroisoxazolo[4,3-c]pyrimido[5',4':4,5]pyrrolo[3,2-e]azepin-11-amine 2,2,2-trifluoroacetate | 365.2 (M + H) |

TABLE C-continued

| Ex # | Structure | Chemical Name | MS apci (m/z) |
|---|---|---|---|
| 33 | 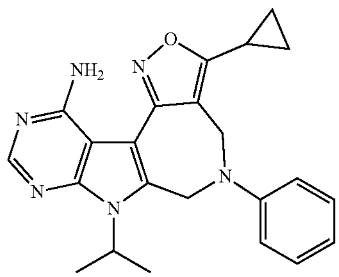 [SMILES: CC(C)n1c2c(c3c(N)ncnc31)-c1noc(C3CC3)c1CN(c1ccccc1)C2] | 3-cyclopropyl-7-isopropyl-5-phenyl-4,5,6,7-tetrahydroisoxazolo[4,3-c]pyrimido[5',4':4,5]pyrrolo[3,2-e]azepin-11-amine | 401.3 (M + H) |
| 34 | 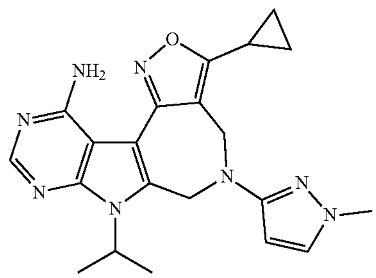 [SMILES: CC(C)n1c2c(c3c(N)ncnc31)-c1noc(C3CC3)c1CN(c1ccn(C)n1)C2] | 3-cyclopropyl-7-isopropyl-5-(1-methyl-1H-pyrazol-3-yl)-4,5,6,7-tetrahydroisoxazolo[4,3-c]pyrimido[5',4':4,5]pyrrolo[3,2-e]azepin-11-amine | 405.3 (M + H) |

Example 35

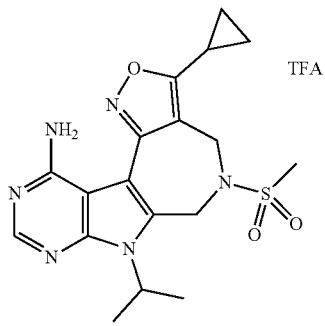 [SMILES: CC(C)n1c2c(c3c(N)ncnc31)-c1noc(C3CC3)c1CN(S(C)(=O)=O)C2]

3-cyclopropyl-7-isopropyl-5-(methylsulfonyl)-4,5,6,7-tetrahydroisoxazolo[4,3-c]pyrimido[5',4':4,5]pyrrolo[3,2-e]azepin-11-amine 2,2,2-trifluoroacetate Step 1: Preparation of 3-cyclopropyl-7-isopropyl-N,N-bis(4-methoxybenzyl)-4,5,6,7-tetrahydroisoxazolo[4,3-c]pyrimido[5',4':4,5]pyrrolo[3,2-e]azepin-11-amine A solution of 3-(4-(bis(4-methoxybenzyl)amino)-6-formyl-7-isopropyl-7H-pyrrolo[2,3-d]pyrimidin-5-yl)-5-cyclopropylisoxazole-4-carbaldehyde (Intermediate P10; 80.7 mg, 0.139 mmol) in DCE (2.78 mL) was treated with NaBH(OAc)₃ (148 mg, 0.696 mmol), stirred for 15 min at RT, and then treated dropwise with ammonium acetate (32.2 mg, 0.418 mmol). After stirring for 90 min at RT, the mixture was treated with AcOH (10 drops), and stirred for 1 h at 60° C. After cooling to RT, the reaction mixture was diluted with DCM and washed with saturated NaHCO₃(aq). Following phase separation, the aqueous extracts were back extracted with DCM. The DCM extracts were combined, then passed through a phase separator column and concentrated in vacuo. The crude residue was purified by silica chromatography (0-100% [15% MeOH+1.5% NH₄OH in DCM] in DCM) to afford the title compound (11.6 mg, 15% yield). MS (apci) m/z=565.3 (M+H).

Step 2: Preparation of 3-cyclopropyl-7-isopropyl-5-(methylsulfonyl)-4,5,6,7-tetrahydroisoxazolo[4,3-c]pyrimido[5',4':4,5]pyrrolo[3,2-e]azepin-11-amine 2,2,2-trifluoroacetate A solution of 3-cyclopropyl-7-isopropyl-N,N-bis(4-methoxybenzyl)-4,5,6,7-tetrahydroisoxazolo[4,3-c]pyrimido[5',4':4,5]pyrrolo[3,2-e]azepin-11-amine (11.6 mg, 0.0205 mmol) in DCM (205 µL, 0.0205 mmol) was treated with MsCl (3.53 mg, 0.0308 mmol) and DIEA (17.9 µL, 0.103 mmol), then stirred overnight at RT. The resulting mixture then was treated with TfOH (182.4 µL, 2.06 mmol) and TFA (a few drops). The resulting mixture was stirred for 120 min at RT, then extracted with DCM and saturated NaHCO₃(aq). The organic extracts were concentrated in vacuo and purified by C18 reverse phase chromatography (10-90% ACN in water with 0.1% TFA) to afford the title compound (1.6 mg, 15% yield). MS (apci) m/z=403.1 (M+H).

The compounds in the following Table were prepared by a similar fashion as described in the synthesis of 3-cyclopropyl-7-isopropyl-5-(methylsulfonyl)-4,5,6,7-tetrahydroisoxazolo[4,3-c]pyrimido[5',4':4,5]pyrrolo[3,2-e]azepin-11-amine 2,2,2-trifluoroacetate (Example 35), replacing MsCl with the appropriate electrophile reagent (e.g. an acyl chloride) in Step 2 instead.

TABLE D

| Ex # | Structure | Chemical Name | MS apci (m/z) |
|---|---|---|---|
| 36 | 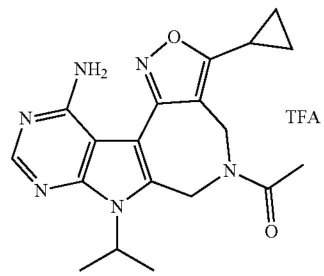 [SMILES: CC(=O)N1Cc2c(noc2C2CC2)-c2c(n(C(C)C)c3ncnc(N)c23)C1] | 1-(11-amino-3-cyclopropyl-7-isopropyl-6,7-dihydroisoxazolo[4,3-c]pyrimido[5',4':4,5]pyrrolo[3,2-e]azepin-5(4H)-yl)ethan-1-one 2,2,2-trifluoroacetate | 367.1 (M + H) |
| 37 | 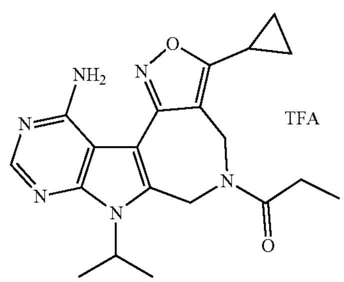 [SMILES: CCC(=O)N1Cc2c(noc2C2CC2)-c2c(n(C(C)C)c3ncnc(N)c23)C1] | 1-(11-amino-3-cyclopropyl-7-isopropyl-6,7-dihydroisoxazolo[4,3-c]pyrimido[5',4':4,5]pyrrolo[3,2-e]azepin-5(4H)-yl)propan-1-one 2,2,2-trifluoroacetate | 381.3 (M + H) |
| 38 | 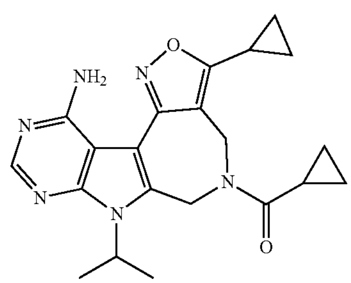 [SMILES: CC(C)n1c2c(c3c(N)ncnc31)-c1noc(C3CC3)c1CN(C(=O)C1CC1)C2] | (11-amino-3-cyclopropyl-7-isopropyl-6,7-dihydroisoxazolo[4,3-c]pyrimido[5',4':4,5]pyrrolo[3,2-e]azepin-5(4H)-yl)(cyclopropyl)methanone | 393.3 (M + H) |
| 39 | 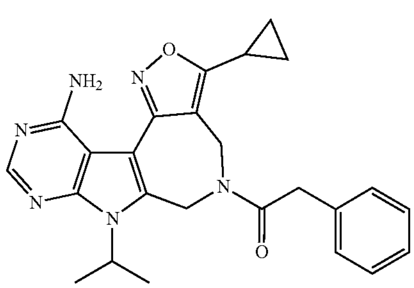 [SMILES: CC(C)n1c2c(c3c(N)ncnc31)-c1noc(C3CC3)c1CN(C(=O)Cc1ccccc1)C2] | 1-(11-amino-3-cyclopropyl-7-isopropyl-6,7-dihydroisoxazolo[4,3-c]pyrimido[5',4':4,5]pyrrolo[3,2-e]azepin-5(4H)-yl)-2-phenylethan-1-one | 443.3 (M + H) |

Example 40

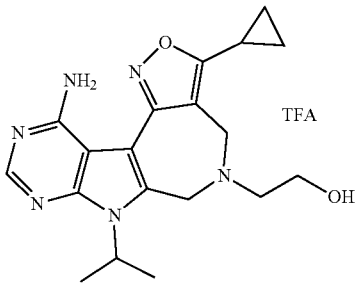 [SMILES: CC(C)n1c2c(c3c(N)ncnc31)-c1noc(C3CC3)c1CN(CCO)C2]

2-(11-amino-3-cyclopropyl-7-isopropyl-6,7-dihydroisoxazolo[4,3-c]pyrimido[5',4':4,5]pyrrolo[3,2-e]azepin-5(4H)-yl)ethan-1-ol 2,2,2-trifluoroacetate A solution of 3-cyclopropyl-7-isopropyl-N,N-bis(4-methoxybenzyl)-4,5,6,7-tetrahydroisoxazolo[4,3-c]pyrimido[5',4':4,5]pyrrolo[3,2-e]azepin-11-amine (Step 1, Example 35) (25 mg, 0.044 mmol) in DCM (443 μL) was treated with (2-bromoethoxy)(tert-butyl)dimethylsilane (16 mg, 0.066 mmol) and DIEA (39 μL, 0.22 mmol). The reaction mixture was then stirred at RT overnight, after which DMF (1 mL) was introduced, and the reaction vessel was sealed. The reaction was heated to 65° C. for 16 h to reach completion. After cooled to RT, the reaction mixture was treated with trifluoromethanesulfonic acid (197 μL, 2.2 mmol) then stirred for 20 min. It was partitioned between $Na_2CO_3$ (aq) and DCM. The combined organic extracts were concentrated and purified by prep HPLC (5-50% ACN in $H_2O$ with 0.1% TFA) to afford the title product (1.6 mg, 7.5% yield). MS (apci) m/z=369.2 (M+H).

Example 41

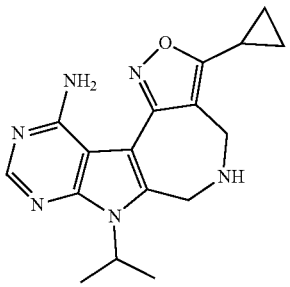 [SMILES: CC(C)n1c2c(c3c(N)ncnc31)-c1noc(C3CC3)c1CNC2]

3-cyclopropyl-7-isopropyl-4,5,6,7-tetrahydroisoxazolo[4,3-c]pyrimido[5',4':4,5]pyrrolo[3,2-e]azepin-11-amine Step 1: Preparation of 3-cyclopropyl-5-(2,4-dimethoxybenzyl)-7-isopropyl-N,N-bis(4-methoxybenzyl)-4,5,6,7-tetrahydroisoxazolo[4,3-c]pyrimido[5',4':4,5]pyrrolo[3,2-e]azepin-11-amine A solution of 3-(4-(bis(4-methoxybenzyl)amino)-6-formyl-7-isopropyl-7H-pyrrolo[2,3-d]pyrimidin-5-yl)-5-cyclopropylisoxazole-4-carbaldehyde (Intermediate P10) (169 mg, 0.29 mmol) in DCE (5.8 mL) was treated with NaBH(OAc)$_3$ (309.0 mg, 1.46 mmol) and stirred at rt for 5 min, followed by portion-wise addition of (2,4-dimethoxyphenyl)methanamine (0.22 mL, 1.45 mmol). After 5 h stirring at RT, the mixture was concentrated. The residue was taken up in DCM and washed with sat. NaHCO$_3$. The aqueous was extracted with DCM, and the combined organic extracts were concentrated and purified by silica chromatography (0-70% EtOAc in hexanes) to afford the title compound (130 mg, 62% yield). MS (apci) m/z=715.3 (M+H).

Step 2: Preparation of 3-cyclopropyl-7-isopropyl-4,5,6,7-tetrahydroisoxazolo[4,3-c]pyrimido[5',4':4,5]pyrrolo[3,2-e]azepin-11-amine A solution of 3-cyclopropyl-5-(2,4-dimethoxybenzyl)-7-isopropyl-N,N-bis(4-methoxybenzyl)-4,5,6,7-tetrahydroisoxazolo[4,3-c]pyrimido[5',4':4,5]pyrrolo[3,2-e]azepin-11-amine (109 mg, 0.15 mmol) in DCM (3 mL) was treated with TFA (234 μL, 3.0 mmol) and Et$_3$SiH (244 μL, 1.52 mmol). After 2 d stirring at RT, the reaction mixture was neutralized with sat. NaHCO$_3$ then extracted into DCM. The combined organic extracts were concentrated and purified by silica chromatography (0-100% [15% MeOH+1.5% NH$_4$OH in DCM] in DCM) to afford the title product (18.7 mg, 35% yield). MS (apci) m/z=325.2 (M+H).

Example 42

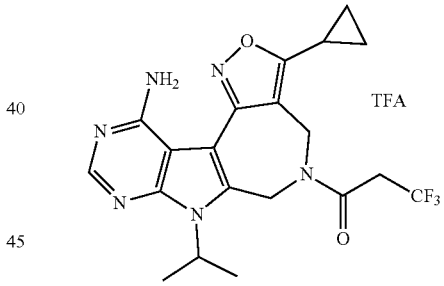

1-(11-amino-3-cyclopropyl-7-isopropyl-6,7-dihydroisoxazolo[4,3-c]pyrimido[5',4':4,5]pyrrolo[3,2-e]azepin-5(4H)-yl)-3,3,3-trifluoropropan-1-one 2,2,2-trifluoroacetate A solution of 3-cyclopropyl-7-isopropyl-4,5,6,7-tetrahydroisoxazolo[4,3-c]pyrimido[5',4':4,5]pyrrolo[3,2-e]azepin-11-amine (Example 41) (14 mg, 0.043 mmol) in DCM (0.86 mL) was treated with 3,3,3-trifluoropropanoyl chloride (6.7 μL, 0.065 mmol) and DIEA (38 μL, 0.22 mmol) then stirred at rt overnight. The reaction was diluted with water and extracted with DCM. The combined organic extracts were concentrated and purified by prep HPLC (10-90% ACN in H$_2$O with 0.1% TFA) to afford the title product (1.3 mg, 7% yield). MS (apci) m/z=435.2 (M+H).

Example 43

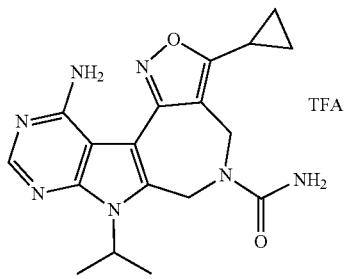 [SMILES: CC(C)n1c2c(c3c(N)ncnc31)-c1noc(C3CC3)c1CN(C(N)=O)C2]

11-amino-3-cyclopropyl-7-isopropyl-6,7-dihydroisoxazolo[4,3-c]pyrimido[5',4':4,5]pyrrolo[3,2-e]azepine-5(4H)-carboxamide 2,2,2-trifluoroacetate To a solution of 3-cyclopropyl-7-isopropyl-4,5,6,7-tetrahydroisoxazolo[4,3-c]pyrimido[5',4':4,5]pyrrolo[3,2-e]azepin-11-amine (Example 41) (1.2 mg, 0.0037 mmol) in THF (1 mL) was added trimethylsilyl isocyanate (0.015 mL, 0.11 mmol) at. The reaction mixture was stirred for 3 d, after which it was directly purified by reverse phase chromatography (0-95% MeCN in water with 0.1% TFA) to afford the title compound as white solid (1.3 mg, 73%). MS (apci) m/z=368.2 (M+H).

Example 44

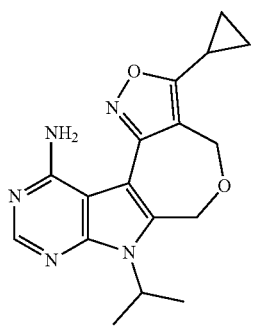 [SMILES: CC(C)n1c2c(c3c(N)ncnc31)-c1noc(C3CC3)c1COC2]

3-cyclopropyl-7-isopropyl-6,7-dihydro-4H-isoxazolo[3",4":5',6']oxepino[4',3':4,5]pyrrolo[2,3-d]pyrimidin-11-amine A cold (−78° C.) solution of 4-(bis(4-methoxybenzyl)amino)-5-(4-(((tert-butyldimethylsilyl)oxy)methyl)-5-cyclopropylisoxazol-3-yl)-7-isopropyl-7H-pyrrolo[2,3-d]pyrimidine-6-carbaldehyde (Intermediate P9; 8.00 mg, 0.0115 mmol) in DCM (1.15 mL) was treated with TMSOTf (1.11 µL, 0.00575 mmol). After stirring for 1.5 h at −78° C., the reaction mixture was treated with triethylsilane (2.02 µL, 0.0126 mmol). The resulting mixture was stirred for an additional 1.5 h at −78° C., and it was then allowed to warm to RT. The reaction mixture was then partitioned between water and DCM. Following phase separation, the aqueous extracts were back extracted with DCM (3×). The DCM extracts were combined, passed through a phase separator column, and then concentrated in vacuo. The crude residue was purified by silica chromatography (0-10% MeOH in DCM with 0.1% NH₄OH) to afford the title compound (2.34 mg, 63% yield). MS (apci) m/z=326.1 (M+H).

Example 45

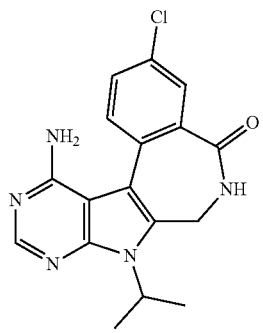 [SMILES: CC(C)n1c2c(c3c(N)ncnc31)-c1ccc(Cl)cc1C(=O)NC2]

12-amino-3-chloro-8-isopropyl-7,8-dihydrobenzo[c]pyrimido[5',4':4,5]pyrrolo[3,2-e]azepin-5(6H)-one Step 1: Preparation of methyl 2-(6-(((tert-butyldimethylsilyl)oxy)methyl)-4-((2,4-dimethoxybenzyl)amino)-7-isopropyl-7H-pyrrolo[2,3-d]pyrimidin-5-yl)-5-chlorobenzoate In a pressure vessel, solution of 6-(((tert-butyldimethylsilyl)oxy)methyl)-N-(2,4-dimethoxybenzyl)-5-iodo-7-isopropyl-7H-pyrrolo[2,3-d]pyrimidin-4-amine (Intermediate P14; 299 mg, 0.501 mmol) in 4:1 dioxane:water (4.2 mL) was treated with 4-chloro-2-(methoxycarbonyl)phenylboronic acid (322 mg, 1.50 mmol), PdCl₂(PPh₃)₂ (87.9 mg, 0.125 mmol), and K₂CO₃(s) (208 mg, 1.50 mmol). After sparging the mixture with Ar(g), the vessel was sealed. The resulting mixture was stirred for 16 h at 90° C. After cooling to RT, the mixture was treated with additional 4-chloro-2-(methoxycarbonyl)phenylboronic acid (107 mg, 0.499 mmol) and PdCl₂(PPh₃)₂ (35 mg, 0.0499 mmol), and sparged with Ar(g). The vessel was sealed, and the mixture was stirred for an additional 1 h at 90° C. After cooling to RT, the reaction mixture was diluted with 4:1 DCM:iPrOH, and washed with water (1×). The organic extracts were dried over anhydrous Na₂SO₄(s), filtered, and concentrated in vacuo. The crude residue was purified by silica chromatography (5-95% DCM-EtOAc) to afford the title compound (160.6 mg, 50% yield). MS (apci) m/z=639.3 (M+H).

Step 2: Preparation of methyl 5-chloro-2-(4-((2,4-dimethoxybenzyl)amino)-6-(hydroxymethyl)-7-isopropyl-7H-pyrrolo[2,3-d]pyrimidin-5-yl)benzoate A cold (0° C.) solution of methyl 2-(6-(((tert-butyldimethylsilyl)oxy)methyl)-4-((2,4-dimethoxybenzyl)amino)-7-isopropyl-7H-pyrrolo[2,3-d]pyrimidin-5-yl)-5-chlorobenzoate (160.6 mg, 0.2512 mmol) in THF (2.5 mL) was treated sequentially with AcOH (15.82 µL, 0.2763 mmol) and TBAF (1.0 M THF) (76.3 µL, 0.28 mmol). The resulting mixture was stirred for 16 h at RT, before introducing additional TBAF (276 µL, 0.28 mmol). The mixture was stirred for an additional 24 h at RT, and then was concentrated in vacuo. The crude residue was purified by silica chromatography (5-95% DCM-EtOAc) to afford the title compound (114.8 mg, 87% yield). MS (apci) m/z=525.2 (M+H).

Step 3: Preparation of methyl 2-(6-(azidomethyl)-4-((2,4-dimethoxybenzyl)amino)-7-isopropyl-7H-pyrrolo[2,3-d]pyrimidin-5-yl)-5-chlorobenzoate A cold (0° C.) solution of methyl 5-chloro-2-(4-((2,4-dimethoxybenzyl)amino)-6-(hydroxymethyl)-7-isopropyl-7H-pyrrolo[2,3-d]pyrimidin-5-yl)benzoate (114.8 mg, 0.2187 mmol) in toluene (2.2 mL) was treated sequentially with DBU (39.24 μL, 0.2624 mmol) and DPPA (56.55 μL, 0.2624 mmol), then warmed to RT, and stirred for 2 h. The resulting mixture was diluted with EtOAc, and washed successively with water (1×) and brine (1×). The combined organic extracts were dried over anhydrous Na$_2$SO$_{4(s)}$, filtered, and concentrated in vacuo. The crude residue was purified by silica chromatography (5-95% hexanes-Acetone) to afford the title compound (95.7 mg, 80% yield). MS (apci) m/z=550.2 (M+H).

Step 4: Preparation of methyl 2-(6-(aminomethyl)-4-((2,4-dimethoxybenzyl)amino)-7-isopropyl-7H-pyrrolo[2,3-d]pyrimidin-5-yl)-5-chlorobenzoate A solution of methyl 2-(6-(azidomethyl)-4-((2,4-dimethoxybenzyl)amino)-7-isopropyl-7H-pyrrolo[2,3-d]pyrimidin-5-yl)-5-chlorobenzoate (95.7 mg, 0.174 mmol) in 1:1 THF:water (1.7 mL) was treated with PPh$_3$ (91.3 mg, 0.348 mmol), then stirred for 16 h at RT. Subsequently, the reaction mixture was diluted with 4:1 DCM:iPrOH, and washed with saturated NaHCO$_{3(aq)}$ (1×). The organic extracts were dried over anhydrous Na$_2$SO$_{4(s)}$, filtered, and concentrated in vacuo. The crude residue was purified by C18 reverse-phase chromatography (5-95% ACN/water with 0.1% TFA) to afford the title compound as the TFA salt. The TFA salt was dissolved in 4:1 DCM:iPrOH and extracted with saturated NaHCO$_{3(aq)}$. The organic extracts were dried over anhydrous Na$_2$SO$_{4(s)}$, filtered, and concentrated in vacuo to afford the title compound (78.8 g, 86% yield). MS (apci) m/z=524.2 (M+H).

Step 5: 12-amino-3-chloro-8-isopropyl-7,8-dihydrobenzo[c]pyrimido[5',4':4,5]pyrrolo[3,2-e]azepin-5(6H)-one A solution of methyl 2-(6-(aminomethyl)-4-((2,4-dimethoxybenzyl)amino)-7-isopropyl-7H-pyrrolo[2,3-d]pyrimidin-5-yl)-5-chlorobenzoate (78.8 mg, 0.150 mmol) in dioxane (3.0 mL) was stirred for 24 h at 90° C. Subsequently, the mixture was cooled to RT, and concentrated in vacuo. The residue thus obtained was re-dissolved in TFA (1.5 mL), stirred for 1 h at RT, and concentrated in vacuo. The crude residue was purified by C18 reverse phase chromatography (5-95% water-ACN with 0.1% TFA) to afford the title compound as the TFA salt. The TFA salt was dissolved in 4:1 DCM:iPrOH, and extracted with saturated NaHCO$_{3(aq)}$. The organic extracts were dried over anhydrous Na$_2$SO$_{4(s)}$, filtered, and concentrated in vacuo to afford the title compound (35.9 mg, 70% yield). MS (apci) m/z=342.1 (M+H).

The compounds in the following Table were prepared in a similar fashion as described for the synthesis of 12-amino-3-chloro-8-isopropyl-7,8-dihydrobenzo[c]pyrimido[5',4':4,5]pyrrolo[3,2-e]azepin-5(6H)-one (Example 45), replacing 4-chloro-2-(methoxycarbonyl)phenylboronic acid with the appropriate boronic acid or boronate starting material in Step 1 instead.

TABLE E

| Ex # | Structure | Chemical Name | MS apci (m/z) |
|---|---|---|---|
| 46 | 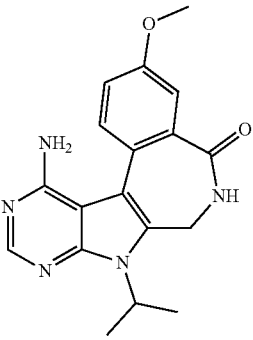 [SMILES: COc1ccc2c(c1)C(=O)NCc1c-2c2c(N)ncnc2n1C(C)C] | 12-amino-8-isopropyl-3-methoxy-7,8-dihydrobenzo[c]pyrimido[5',4':4,5]pyrrolo[3,2-e]azepin-5(6H)-one | 338.1 (M + H) |

TABLE E-continued

| Ex # | Structure | Chemical Name | MS apci (m/z) |
|---|---|---|---|
| 47 | 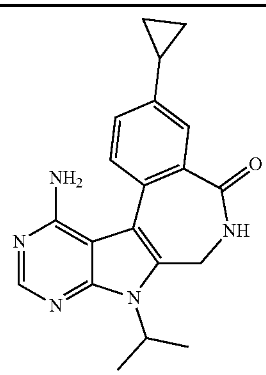 | 12-amino-3-cyclopropyl-8-isopropyl-7,8-dihydrobenzo[c]pyrimido[5',4':4,5]pyrrolo[3,2-e]azepin-5(6H)-one | 348.2 (M + H) |

The compounds in the following Table were prepared in a similar fashion as described for the synthesis of 12-amino-3-chloro-8-isopropyl-7,8-dihydrobenzo[c]pyrimido[5',4':4,5]pyrrolo[3,2-e]azepin-5(6H)-one (Example 45), replacing 6-(((tert-butyldimethylsilyl)oxy)methyl)-N-(2,4-dimethoxybenzyl)-5-iodo-7-isopropyl-7H-pyrrolo[2,3-d]pyrimidin-4-amine (Intermediate P14) with 6-(((tert-butyldimethylsilyl)oxy)methyl)-N-(2,4-dimethoxybenzyl)-7-isopropyl-5-(4,4,5,5-tetramethyl-1,3,2-dioxaborolan-2-yl)-7H-pyrrolo[2,3-d]pyrimidin-4-amine (Intermediate P15), and 4-chloro-2-(methoxycarbonyl)phenylboronic acid with the appropriate halide reagent (e.g. methyl 2-bromo-5-(2-cyclopropylacetamido)benzoate/Intermediate R2 for Example 48 and methyl 2-bromo-5-(3-cyclopropylureido)benzoate/Intermediate R3 for Example 49) in Step 1 instead.

TABLE F

| Ex # | Structure | Chemical Name | MS apci (m/z) |
|---|---|---|---|
| 48 | 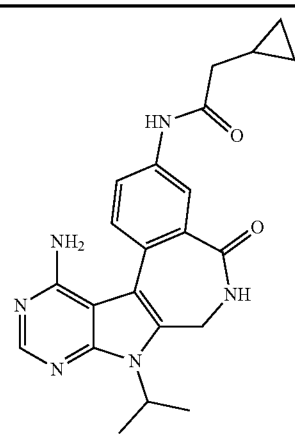 | N-(12-amino-8-isopropyl-5-oxo-5,6,7,8-tetrahydrobenzo[c]pyrimido[5',4':4,5]pyrrolo[3,2-e]azepin-3-yl)-2-cyclopropylacetamide | 405.2 (M + H) |
| 49 | 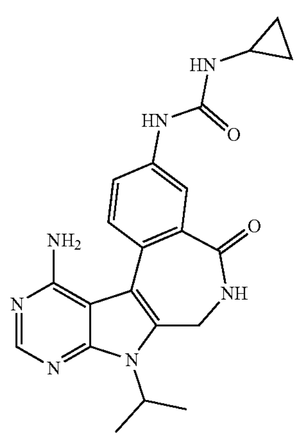 [SMILES: CC(C)n1c2c(c3c(N)ncnc31)-c1ccc(NC(=O)NC3CC3)cc1C(=O)NC2] | 1-(12-amino-8-isopropyl-5-oxo-5,6,7,8-tetrahydrobenzo[c]pyrimido[5',4':4,5]pyrrolo[3,2-e]azepin-3-yl)-3-cyclopropylurea | 406.2 (M + H) |

| Ex # | Structure | Chemical Name | MS apci (m/z) |
|---|---|---|---|
| 50 | 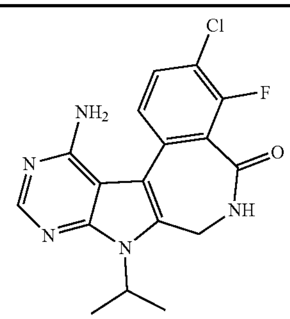 | 12-amino-3-chloro-4-fluoro-8-isopropyl-7,8-dihydrobenzo[c]pyrimido[5',4':4,5]pyrrolo[3,2-e]azepin-5(6H)-one | 360.1 (M + H) |

Example 51

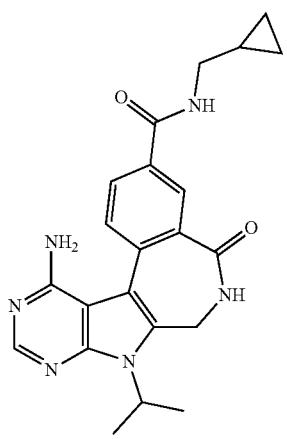 [SMILES: CC(C)n1c2c(c3c(N)ncnc31)-c1ccc(C(=O)NCC3CC3)cc1C(=O)NC2]

12-Amino-N-(cyclopropylmethyl)-8-isopropyl-5-oxo-5,6,7,8-tetrahydrobenzo[c]pyrimido[5',4':4,5]pyrrolo[3,2-e]azepine-3-carboxamide Step 1: Preparation of N-(cyclopropylmethyl)-12-((2,4-dimethoxybenzyl)amino)-8-isopropyl-5-oxo-5,6,7,8-tetrahydrobenzo[c]pyrimido[5',4':4,5]pyrrolo[3,2-e]azepine-3-carboxamide To a solution of 12-((2,4-dimethoxybenzyl)amino)-8-isopropyl-5-oxo-5,6,7,8-tetrahydrobenzo[c]pyrimido[5',4':4,5]pyrrolo[3,2-e]azepine-3-carboxylic acid (Intermediate P31) (33 mg, 0.066 mmol) in DCM (1.3 mL) was added cyclopropanemethylamine (9.5 mg, 0.13 mmol), HATU (51 mg, 0.13 mmol), and DIEA (23 µL, 0.13 mmol) at RT. The resulting mixture was stirred for 1 h, after which it was concentrated and purified by silica chromatography (5-95% acetone in DCM) to afford the title compound assuming quantitative yield. MS (apci) m/z=555.3 (M+H).

Step 2: Preparation of 12-amino-N-(cyclopropylmethyl)-8-isopropyl-5-oxo-5,6,7,8-tetrahydrobenzo[c]pyrimido[5',4':4,5]pyrrolo[3,2-e]azepine-3-carboxamide A solution of N-(cyclopropylmethyl)-12-((2,4-dimethoxybenzyl)amino)-8-isopropyl-5-oxo-5,6,7,8-tetrahydrobenzo[c]pyrimido[5',4':4,5]pyrrolo[3,2-e]azepine-3-carboxamide (36 mg, 0.066 mmol) in TFA (1.0 mL) was stirred at RT for 2 h, then concentrated and purified by reverse phase chromatography (5-95% MeCN in water with 0.1% TFA). The combined desired fractions were partitioned between 4:1 DCM:IPA and sat. NaHCO₃. After phase-separation, the organic layer was dried (Na₂SO₄), filtered, and concentrated to afford the title product (12 mg, 44%). MS (apci) m/z=405.2 (M+H).

Example 52

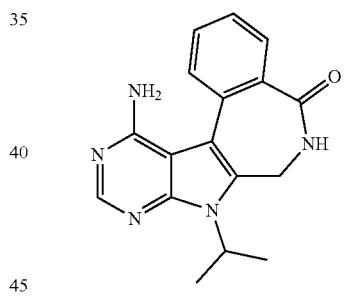

12-amino-8-isopropyl-7,8-dihydrobenzo[c]pyrimido[5',4':4,5]pyrrolo[3,2-e]azepin-5(6H)-one A mixture of 12-amino-3-chloro-8-isopropyl-7,8-dihydrobenzo[c]pyrimido[5',4':4,5]pyrrolo[3,2-e]azepin-5(6H)-one (Example 45) (9.5 mg, 0.028 mmol) and Pd/C (5 wt %) (5.9 mg, 0.0028 mmol) in MeOH (0.5 mL) was sparged and then stirred under an atmosphere of hydrogen-filled balloon at RT for 16 h. The reaction mixture was filtered, rinsed with MeOH, and concentrated. The crude was purified by reverse phase chromatography (5-95% ACN in water with 0.1% TFA). The combined product fractions were partitioned between 4:1 DCM:IPA and sat. NaHCO₃. After phase-separation, the aqueous was extracted with 4:1 DCM:IPA (1×). The combined organic extracts were dried (Na₂SO₄), filtered, and concentrated to afford the title product (6.3 mg, 74% yield). MS (apci) m/z=308.1 (M+H).

Example 53

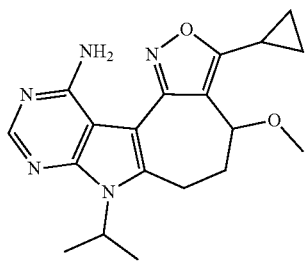 [SMILES: COC1CCc2c(c3c(N)ncnc3n2C(C)C)-c2noc(C3CC3)c21]

3-cyclopropyl-7-isopropyl-4-methoxy-4,5,6,7-tetra-hydroisoxazolo[4",3":6',7']cyclohepta[1',2':4,5]pyrrolo[2,3-d]pyrimidin-11-amine To a solution of 11-amino-3-cyclopropyl-7-isopropyl-4,5,6,7-tetrahydroisoxazolo[4",3":6',7']cyclohepta[1',2':4,5]pyrrolo[2,3-d]pyrimidin-4-ol (Example 29) (12.1 mg, 0.0357 mmol) in THF (0.35 mL) and DMF (5 drops) was added NaH (1.43 mg, 0.0357 mmol) at 0° C. After 15-min stirring, iodomethane (2.22 μL, 0.0357 mmol) was introduced and the reaction was stirred overnight. The reaction was then quenched with MeOH (0.2 mL), concentrated and purified by silica chromatography (0-4% MeOH in DCM) to afford the title product (2.5 mg, 20% yield). MS (apci) m/z=354.2 (M+H).

Example 54

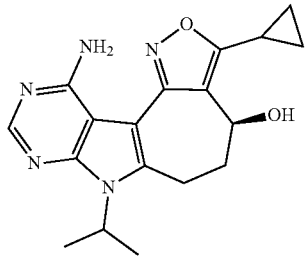 [SMILES: CC(C)n1c2c(c3c(N)ncnc31)-c1noc(C3CC3)c1[C@@H](O)CC2]

(S)-11-amino-3-cyclopropyl-7-isopropyl-4,5,6,7-tetrahydroisoxazolo[4",3":6',7']cyclohepta[1',2':4,5]pyrrolo[2,3-d]pyrimidin-4-ol The title product was prepared by chiral SFC separation of the racemic compound 11-amino-3-cyclopropyl-7-isopropyl-4,5,6,7-tetrahydroisoxazolo[4",3":6',7']cyclohepta[1',2':4,5]pyrrolo[2,3-d]pyrimidin-4-ol (Example 29) (Chiral Tech IA column; 4.6×250 mm, 5μ; 4 mL/min; eluent=A: CO₂ B: 5-70% (MeOH:IPA:DEA 80:20:0.1)). The combined product fractions from the first eluted peak ("peak 1") was first arbitrarily assigned as the S-enantiomer, which was later confirmed through X-ray structural determination. MS (apci) m/z=340.2 (M+H).

Example 55

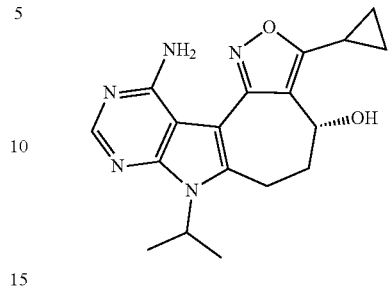

(R)-11-amino-3-cyclopropyl-7-isopropyl-4,5,6,7-tetrahydroisoxazolo[4",3":6',7']cyclohepta[1',2':4,5]pyrrolo[2,3-d]pyrimidin-4-ol The title product was prepared by chiral SFC separation of the racemic compound 11-amino-3-cyclopropyl-7-isopropyl-4,5,6,7-tetrahydroisoxazolo[4",3":6',7']cyclohepta[1',2':4,5]pyrrolo[2,3-d]pyrimidin-4-ol (Example 29) (Chiral Tech IA column; 4.6×250 mm, 5μ; 4 mL/min; eluent=A: CO₂ B: 5-70% (MeOH:IPA:DEA 80:20:0.1)). The combined product fractions from the second eluted peak ("peak 2") was first arbitrarily assigned as the R-enantiomer, which was later confirmed through X-ray structural determination. MS (apci) m/z=340.2 (M+H).

Example 56

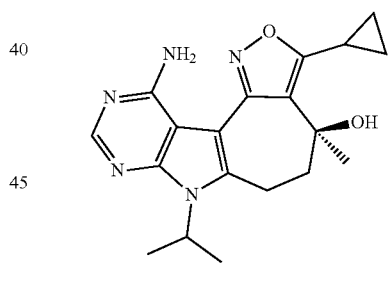

(S)-11-amino-3-cyclopropyl-7-isopropyl-4-methyl-4,5,6,7-tetrahydroisoxazolo[4",3":6',7']cyclohepta[1',2':4,5]pyrrolo[2,3-d]pyrimidin-4-ol The title product was prepared by chiral SFC separation of the racemic compound 11-amino-3-cyclopropyl-7-isopropyl-4-methyl-4,5,6,7-tetrahydroisoxazolo[4",3":6',7']cyclohepta[1',2':4,5]pyrrolo[2,3-d]pyrimidin-4-ol (Example 26) (Chiral Tech AS-H; eluent=A: CO₂ B: 5-50% (MeOH:IPA:tBuOH:DEA 80:10:10:0.1)). The combined product fractions from the first eluted peak ("peak 1") was arbitrarily assigned as the S-enantiomer, which was later confirmed through X-ray structural determination. MS (apci) m/z=354.2 (M+H).

Example 57

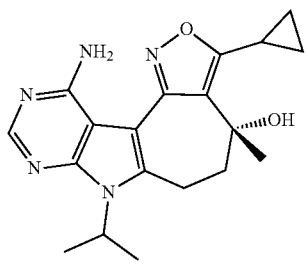 [SMILES: CC(C)n1c2c(c3c(N)ncnc31)-c1noc(C3CC3)c1[C@](C)(O)CC2]

(R)-11-amino-3-cyclopropyl-7-isopropyl-4-methyl-4,5,6,7-tetrahydroisoxazolo[4",3":6',7']cyclohepta[1',2':4,5]pyrrolo[2,3-d]pyrimidin-4-ol The title product was prepared by chiral SFC separation of the racemic compound 11-amino-3-cyclopropyl-7-isopropyl-4-methyl-4,5,6,7-tetrahydroisoxazolo[4",3":6',7']cyclohepta[1',2':4,5]pyrrolo[2,3-d]pyrimidin-4-ol (Example 26) (Chiral Tech AS-H; eluent=A: $CO_2$ B: 5-50% (MeOH:IPA:tBuOH:DEA 80:10:10:0.1)). The combined product fractions from the second eluted peak ("peak 2") was arbitrarily assigned as the R-enantiomer, which was later confirmed through X-ray structural determination. MS (apci) m/z=354.2 (M+H).

Example 58

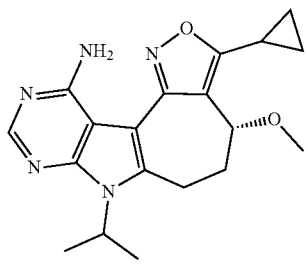 [SMILES: CO[C@@H]1CCc2c(c3c(N)ncnc3n2C(C)C)-c2noc(C3CC3)c21]

(R)-3-cyclopropyl-7-isopropyl-4-methoxy-4,5,6,7-tetrahydroisoxazolo[4",3":6',7']cyclohepta[1',2':4,5]pyrrolo[2,3-d]pyrimidin-11-amine The title product was prepared by chiral SFC separation of the racemic compound 3-cyclopropyl-7-isopropyl-4-methoxy-4,5,6,7-tetrahydroisoxazolo[4",3":6',7']cyclohepta[1',2':4,5]pyrrolo[2,3-d]pyrimidin-11-amine (Example 53) (Chiral Tech AS-H column; 4.6×250 mm; 4 mL/min; eluent=A: $CO_2$ B: 5-50% (MeOH:IPA:DEA 80:20:0.1)). The combined product fractions from the first eluted peak ("peak 1") was arbitrarily assigned as the (R)-enantiomer, which was later confirmed through X-ray structural determination. MS (apci) m/z=354.2 (M+H).

Example 59

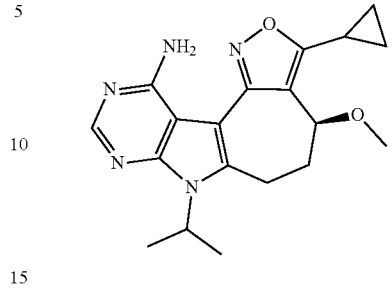

(S)-3-cyclopropyl-7-isopropyl-4-methoxy-4,5,6,7-tetrahydroisoxazolo[4",3":6',7']cyclohepta[1',2':4,5]pyrrolo[2,3-d]pyrimidin-11-amine The title product was prepared by chiral SFC separation of the racemic compound 3-cyclopropyl-7-isopropyl-4-methoxy-4,5,6,7-tetrahydroisoxazolo[4",3":6',7']cyclohepta[1',2':4,5]pyrrolo[2,3-d]pyrimidin-11-amine (Example 53) (Chiral Tech AS-H column; 4.6×250 mm; 4 mL/min; eluent=A: $CO_2$ B: 5-50% (MeOH:IPA:DEA 80:20:0.1)). The combined product fractions from the second eluted peak ("peak 2") was arbitrarily assigned as the (S)-enantiomer, which was later confirmed through X-ray structural determination. MS (apci) m/z=354.2 (M+H).

Example 60

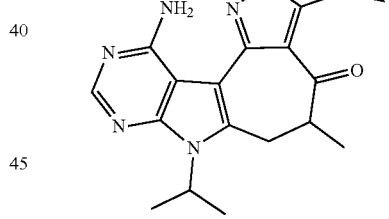

11-amino-3-cyclopropyl-7-isopropyl-5-methyl-6,7-dihydroisoxazolo[4",3":6',7']cyclohepta[1',2':4,5]pyrrolo[2,3-d]pyrimidin-4(5H)-one To a solution of 11-amino-3-cyclopropyl-7-isopropyl-6,7-dihydroisoxazolo[4",3":6',7']cyclohepta[1',2':4,5]pyrrolo[2,3-d]pyrimidin-4(5H)-one (Example 25) (19 mg, 0.056 mmol) in THF (375 µL) cooled to −78° C. was added LiHMDS (1 M, THF) (56 µL, 0.056 mmol) and iodomethane (3.5 µL, 0.056 mmol). The reaction was allowed to warm to rt and stirred overnight. It was then diluted with sat. $NaHCO_3$ (aq) and extracted with DCM. The combined organic extracts were dried ($Na_2SO_4$), filtered, concentrated, and purified by silica chromatography (5-50% acetone in DCM) followed by reverse-phase chromatography (5-95% MeCN in water) to afford the title product (5.4 mg, 27%). MS (apci) m/z=352.2 (M+H).

Example 61

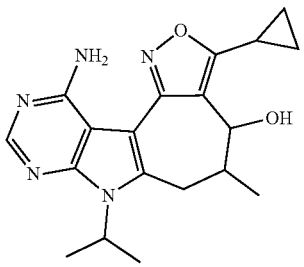 [SMILES: CC1Cc2c(c3c(N)ncnc3n2C(C)C)-c2noc(C3CC3)c2C1O]

11-amino-3-cyclopropyl-7-isopropyl-5-methyl-4,5,6,7-tetrahydroisoxazolo[4",3":6',7']cyclohepta[1',2':4,5]pyrrolo[2,3-d]pyrimidin-4-ol To a solution of 11-amino-3-cyclopropyl-7-isopropyl-5-methyl-6,7-dihydroisoxazolo[4",3":6',7']cyclohepta[1',2':4,5]pyrrolo[2,3-d]pyrimidin-4(5H)-one (Example 60) (3 mg, 0.0085 mmol) in MeOH (0.085 mL) was added NaBH$_4$ (0.00065 g, 0.017 mmol) at rt and stirred for 2 h. It was then diluted with water and extracted with DCM. The combined organic extracts was washed with brine, then dried (Na$_2$SO$_4$), filtered, concentrated, and purified by prep-TLC (10% MeOH in DCM) to afford the title product as a mixture of cis:trans isomers (~1:2 ratio) (2.9 mg, 96%). MS (apci) m/z=354.2 (M+H).

Example 62 Example 63

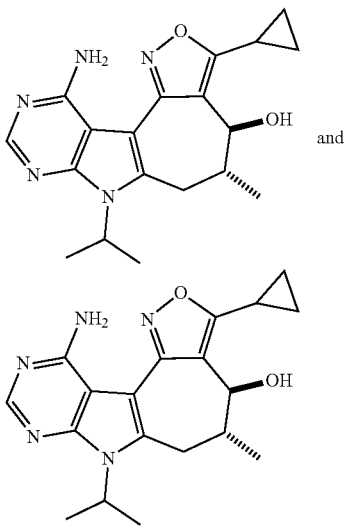

(Trans)-11-amino-3-cyclopropyl-7-isopropyl-5-methyl-4,5,6,7-tetrahydroisoxazolo[4",3":6',7']cyclohepta[1',2':4,5]pyrrolo[2,3-d]pyrimidin-4-ol (Example 62)

(Cis)-11-amino-3-cyclopropyl-7-isopropyl-5-methyl-4,5,6,7-tetrahydroisoxazolo[4",3":6',7']cyclohepta[1',2':4,5]pyrrolo[2,3-d]pyrimidin-4-ol (Example 63)

To a solution of 11-amino-3-cyclopropyl-7-isopropyl-5-methyl-6,7-dihydroisoxazolo[4",3":6',7']cyclohepta[1',2':4,5]pyrrolo[2,3-d]pyrimidin-4(5H)-one (Example 60) (11 mg, 0.031 mmol) in MeOH (0.31 mL) was added NaBH$_4$ (2.4 mg, 0.063 mmol) at rt and stirred for 2 h. It was then diluted with water and extracted with DCM. The combined organic extracts was washed with brine, then dried (Na$_2$SO$_4$), filtered, concentrated, and purified by prep HPLC (5-95% acetonitrile in water with 0.1% TFA) to afford the trans title product (3.5 mg, 32%) and the cis title product (1.3 mg, 12%). The stereochemistry for each product was first arbitrarily assigned and later confirmed through X-ray structural determination. MS (apci) m/z=354.2 (M+H).

Example 64 Example 65

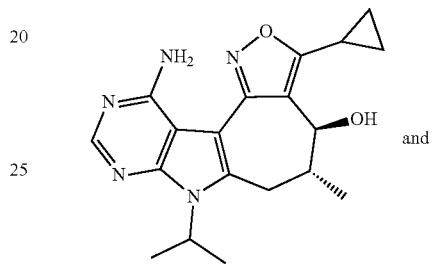

and

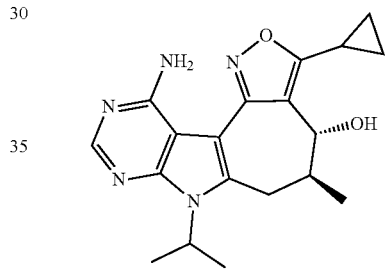

(4S,5R)-11-amino-3-cyclopropyl-7-isopropyl-5-methyl-4,5,6,7-tetrahydroisoxazolo[4",3":6',7']cyclohepta[1',2':4,5]pyrrolo[2,3-d]pyrimidin-4-ol (Example 64)

(4R,5S)-11-amino-3-cyclopropyl-7-isopropyl-5-methyl-4,5,6,7-tetrahydroisoxazolo[4",3":6',7']cyclohepta[1',2':4,5]pyrrolo[2,3-d]pyrimidin-4-ol (Example 65)

The title products were obtained by subjecting (trans)-11-amino-3-cyclopropyl-7-isopropyl-5-methyl-4,5,6,7-tetrahydroisoxazolo[4",3":6',7']cyclohepta[1',2':4,5]pyrrolo[2,3-d]pyrimidin-4-ol (Example 62) (4 mg, 0.011 mmol) to chiral SFC (ChiralTech IA column, 19 mL/min, 220 nM, 5µ, 10-35% MeOH:IPA:DEA 80:20:0.1), giving two enantiomerically pure isomer products (1.7 mg, 85%). The first eluent fractions (peak 1) were assigned as the (4S, 5R)- and the second eluent fractions (peak 2), (4R,5S)-enantiomer. The absolute stereochemistry was arbitrarily assigned. MS (apci) m/z=354.2 (M+H).

Example 66

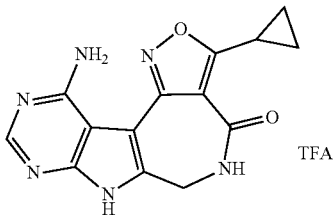 [SMILES: Nc1ncnc2[nH]c3c(c12)-c1noc(C2CC2)c1C(=O)NC3]

11-amino-3-cyclopropyl-6,7-dihydroisoxazolo[4,3-c]pyrimido[5',4':4,5]pyrrolo[3,2-e]azepin-4(5H)-one 2,2,2-trifluoroacetate To a suspension of 11-amino-3-cyclopropyl-7-((2-(trimethylsilyl)ethoxy)methyl)-6,7-dihydroisoxazolo[4,3-c]pyrimido[5',4':4,5]pyrrolo[3,2-e]azepin-4(5H)-one (Intermediate P23) (14 mg, 0.033 mmol) in DCM (0.5 mL) was added TFA (1 mL, 0.033 mmol) at RT. After stirred for 60 h the reaction was concentrated and directly purified by reverse phase chromatography (0-95% MeCN in water with 0.1% TFA) to give the title product as white solid (5 mg, 37%). MS (apci) m/z=297.0 (M+H).

Example 67

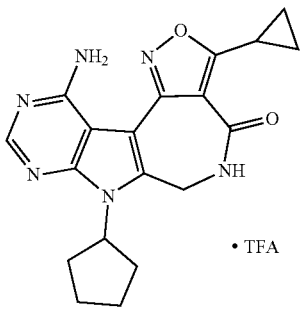 [SMILES: Nc1ncnc2c1c1c(n2C2CCCC2)CNC(=O)c2c-1noc2C1CC1]

11-amino-7-cyclopentyl-3-cyclopropyl-6,7-dihydroisoxazolo[4,3-c]pyrimido[5',4':4,5]pyrrolo[3,2-e]azepin-4(5H)-one 2,2,2-trifluoroacetate Step 1: Preparation of ethyl 3-(4-chloro-7-cyclopentyl-6-methyl-7H-pyrrolo[2,3-d]pyrimidin-5-yl)-5-cyclopropylisoxazole-4-carboxylate To a suspension of ethyl 3-(4-chloro-6-methyl-7H-pyrrolo[2,3-d]pyrimidin-5-yl)-5-cyclopropylisoxazole-4-carboxylate (Intermediate P22) (30 mg, 0.087 mmol) in THF (865 µL) was added cyclopentanol (16 µL, 0.17 mmol), PPh$_3$ (45 mg, 0.17 mmol) and DIAD (34 µL, 0.17 mmol) at RT. The mixture was stirred for 30 min then concentrated and purified with silica chromatography (0-50% EtOAc in hexanes) to afford the title compound (24 mg, 67%). MS (apci) m/z=415.2 (M+H).

Step 2: Preparation of 11-amino-7-cyclopentyl-3-cyclopropyl-6,7-dihydroisoxazolo[4,3-c]pyrimido[5',4':4,5]pyrrolo[3,2-e]azepin-4(5H)-one 2,2,2-trifluoroacetate A mixture of ethyl 3-(4-chloro-7-cyclopentyl-6-methyl-7H-pyrrolo[2,3-d]pyrimidin-5-yl)-5-cyclopropylisoxazole-4-carboxylate (24 mg, 0.058 mmol), NBS (15 mg, 0.087 mmol) and AIBN (1.4 mg, 0.0087 mmol) in DCE (578 µL) was sealed in a pressure vessel under N$_2$. The reaction was then heated at 80° C. for 2 h. After cooled to RT, the reaction mixture was concentrated, then taken up in dioxane (0.5 mL) and concentrated again to remove all DCE. The residue was taken up in a mixture of 1,4-dioxane (578 µL) and NH$_4$OH (aq) (289 µL). The reaction vessel was subsequently sealed and the mixture heated at 90-100° C. for 2 d. After cooled to RT, the reaction was concentrated and purified by reverse-phase chromatography (0-95% MeCN in water with 0.1% TFA) to afford the title product as off-white solid (5 mg, 19%). MS (apci) m/z=365.3 (M+H).

Example 68

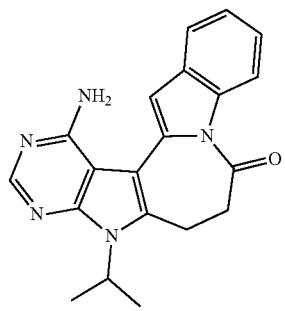 [SMILES: CC(C)n1c2c(c3c(N)ncnc31)-c1cc3ccccc3n1C(=O)CC2]

1-amino-5-isopropyl-6,7-dihydropyrimido[5'',4'':4',5']pyrrolo[3',2':3,4]azepino[1,2-a]indol-8(5H)-one Step 1: Preparation of 4-((2,4-dimethoxybenzyl)amino)-5-(1H-indol-2-yl)-7-isopropyl-7H-pyrrolo[2,3-d]pyrimidine-6-carbaldehyde To a solution of (4-((2,4-dimethoxybenzyl)amino)-5-(1H-indol-2-yl)-7-isopropyl-7H-pyrrolo[2,3-d]pyrimidin-6-yl)methanol (Intermediate P24) (109 mg, 0.23 mmol) in DCM (1.5 mL) was added 1,1,1-tris(acetyloxy)-1,1-dihydro-1,2-benziodoxol-3-(1H)-one (Dess-Martin periodinane) (98.0 mg, 0.23 mmol) at RT. The reaction mixture was then stirred for 30 min. Subsequently, the reaction was diluted with DCM (5 mL) and filtered (GF/F), washing with DCM (10 mL). The filtrate was diluted with sat. NaHCO$_3$ (20 mL) and extracted with DCM (3×20 mL). The combined organic extracts were concentrated and purified using silica chromatography (0-10% MeOH in DCM) to afford the title compound (14 mg, 13% yield). MS (apci) m/z=470.2 (M+H).

Step 2: Preparation of ethyl (E)-3-(4-((2,4-dimethoxybenzyl)amino)-5-(1H-indol-2-yl)-7-isopropyl-7H-pyrrolo[2,3-d]pyrimidin-6-yl)acrylate To a solution of 4-((2,4-dimethoxybenzyl)amino)-5-(1H-indol-2-yl)-7-isopropyl-7H-pyrrolo[2,3-d]pyrimidine-6-carbaldehyde (14 mg, 0.030 mmol) in DCM (149 μL) was added ethyl 2-(triphenyl-l5-phosphanylidene)acetate (11.9 mg, 0.034 mmol) at RT. After 30 min stirring, reaction was concentrated and purified using silica chromatography (0-100% EtOAc in hexanes) to yield the title compound (13 mg, 81% yield). MS (apci) m/z=540.3 (M+H).

Step 3: Preparation of ethyl 3-(4-((2,4-dimethoxybenzyl)amino)-5-(1H-indol-2-yl)-7-isopropyl-7H-pyrrolo[2,3-d]pyrimidin-6-yl)propanoate To a solution of Cu(OAc)₂ (0.44 mg, 0.0024 mmol) and Xantphos (2.8 mg, 0.0048 mmol) in THF (1.6 mL) was added phenylsilane (30 μL, 0.24 mmol). After 5 min stirring at RT, a solution of ethyl (E)-3-(4-((2,4-dimethoxybenzyl)amino)-5-(1H-indol-2-yl)-7-isopropyl-7H-pyrrolo[2,3-d]pyrimidin-6-yl)acrylate (13 mg, 0.024 mmol) in THF (0.5 mL) was introduced and stirred for another 1 h. The reaction was then partitioned between sat. NaHCO₃ and DCM (5 mL ea.). After phase separation, the aqueous was extracted with DCM (3×5 mL). The combined organic extracts were concentrated and purified using silica chromatography (0-100% EtOAc in hexanes) to yield the title compound (13 mg, quant.). MS (apci) m/z=542.3 (M+H).

Step 4: Preparation of 3-(4-((2,4-dimethoxybenzyl)amino)-5-(1H-indol-2-yl)-7-isopropyl-7H-pyrrolo[2,3-d]pyrimidin-6-yl)propanoic Acid To a solution of ethyl 3-(4-((2,4-dimethoxybenzyl)amino)-5-(1H-indol-2-yl)-7-isopropyl-7H-pyrrolo[2,3-d]pyrimidin-6-yl)propanoate (13 mg, 0.024 mmol) in THF (1 mL) and MeOH (0.1 mL) was added LiOH (2M aq) (36 μL, 0.072 mmol). After stirred at RT for 2 d, the reaction was acidified with 1 N HCl to pH ~5, then diluted with water (3 mL) and extracted with DCM (3×5 mL). The combined organic extracts were concentrated in vacuo to afford the title compound (11 mg, 83% yield). MS (apci) m/z=514.2 (M+H).

Step 5: Preparation of 1-((2,4-dimethoxybenzyl)amino)-5-isopropyl-6,7-dihydropyrimido[5",4":4',5']pyrrolo[3',2':3,4]azepino[1,2-a]indol-8(5H)-one To a solution of 3-(4-((2,4-dimethoxybenzyl)amino)-5-(1H-indol-2-yl)-7-isopropyl-7H-pyrrolo[2,3-d]pyrimidin-6-yl)propanoic acid (11 mg, 0.021 mmol), di-tert-butyl dicarbonate (12.4 μL, 0.0535 mmol) and DMAP (0.1 mg, 0.0011 mmol) in MeCN (2.1 mL) was added one drop of 2,6-lutidine. After 30 min stirring at RT, the reaction was partioned between DCM and water (5 ml each). After phase separation, the aqueous was extracted with DCM (3×5 mL). The combined organic extracts were concentrated and purified using silica chromatography (0-100% EtOAc in hexanes) to yield the title compound (5 mg, 47% yield). MS (apci) m/z=496.2 (M+H).

Step 6: Preparation of 1-amino-5-isopropyl-6,7-dihydropyrimido[5",4":4',5']pyrrolo[3',2':3,4]azepino[1,2-a]indol-8(5H)-one To a solution of 1-((2,4-dimethoxybenzyl)amino)-5-isopropyl-6,7-dihydropyrimido[5",4":4',5']pyrrolo[3',2':3,4]azepino[1,2-a]indol-8(5H)-one (5 mg, 0.010 mmol) in DCM (1.0 mL) was added Et₃SiH (0.2 mL) and TFA (0.5 mL). After overnight stirring at RT, the reaction was diluted with sat. NaHCO₃ (10 mL) and extracted with DCM (3×10 mL). The combined organic extracts were concentrated and purified using silica chromatography (0-100% DCM in hexanes followed by 0-10% MeOH in DCM with 0.1% NH₄OH) to yield the title product (1.8 mg, 49% yield). MS (apci) m/z=346.2 (M+H).

Example 69

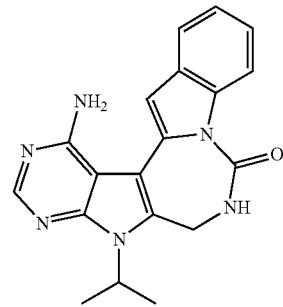 [SMILES: CC(C)n1c2c(c3c(N)ncnc31)-c1cc3ccccc3n1C(=O)NC2]

1-amino-5-isopropyl-6,7-dihydropyrimido[5",4":4',5']pyrrolo[2',3':5,6][1,3]diazepino[1,7-a]indol-8(5H)-one To a solution of 6-(aminomethyl)-N-(2,4-dimethoxybenzyl)-5-(1H-indol-2-yl)-7-isopropyl-7H-pyrrolo[2,3-d]pyrimidin-4-amine (Intermediate P25) (11.8 mg, 0.025 mmol), di-tert-butyl dicarbonate (6.6 μL, 0.028 mmol) and DMAP (1 mg, 0.008 mmol) in MeCN (2.5 mL) was added 2,6-lutidine (1 drop) at RT then stirred for overnight. TFA and Et₃SiH (0.2 mL each) were then added and stirred for 2 d at RT and 4 h at 50° C. The reaction was diluted with sat. NaHCO₃ (10 mL) and extracted with DCM (5×10 mL). The combined organic extracts were concentrated and purified by silica chromatography (0-10% MeOH in DCM with 0.1% NH₄OH) to afford the title product (1.8 mg, 20% yield). MS (apci) m/z=347.1 (M+H).

Example 70

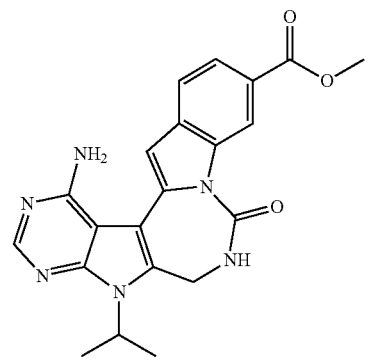 [SMILES: COC(=O)c1ccc2cc3n(c2c1)C(=O)NCc1c-3c2c(N)ncnc2n1C(C)C]

Methyl 1-amino-5-isopropyl-8-oxo-5,6,7,8-tetrahydropyrimido[5",4":4',5']pyrrolo[2',3':5,6][1,3]diazepino[1,7-a]indole-11-carboxylate Step 1: Preparation of methyl 1-((2,4-dimethoxybenzyl)amino)-5-isopropyl-8-oxo-5,6,7,8-tetrahydropyrimido[5",4":4',5']pyrrolo[2',3':5,6][1,3]diazepino[1,7-a]indole-11-carboxylate To a solution of methyl 2-(6-(aminomethyl)-4-((2,4-dimethoxybenzyl)amino)-7-isopropyl-7H-pyrrolo[2,3-d]pyrimidin-5-yl)-1H-indole-6-carboxylate (Intermediate P29) (11.7 mg, 0.022 mmol) in DMF (443 µL) was added bis(4-nitrophenyl) carbonate (6.7 mg, 0.022 mmol) at RT. The resulting mixture was stirred overnight. TEA (1 drop) was then introduced and the reaction was stirred for another 1 h before it was partitioned between DCM and water (5 mL each). The aqueous phase was extracted with DCM (3×10 mL). The combined organic extracts were concentrated and purified using silica chromatography (0-100% EtOAc in hexanes) to yield the title compound (8 mg, 42%). MS (apci) m/z=555.2 (M+H).

Step 2: Preparation of methyl 1-amino-5-isopropyl-8-oxo-5,6,7,8-tetrahydropyrimido[5",4":4',5']pyrrolo[2',3':5,6][1,3]diazepino[1,7-a]indole-11-carboxylate To a solution of methyl 1-((2,4-dimethoxybenzyl)amino)-5-isopropyl-8-oxo-5,6,7,8-tetrahydropyrimido[5",4":4',5']pyrrolo[2',3':5,6][1,3]diazepino[1,7-a]indole-11-carboxylate (8 mg, 0.0094 mmol) in DCE (1.8 mL) was added TFA (36 µL, 0.47 mmol) and triethylsilane (75 µL, 0.47 mmol) at RT. The reaction mixture was then stirred overnight. The reaction was diluted with sat. NaHCO₃ (aq) (30 mL) and extracted with 25% IPA in DCM (3×10 mL). The combined organic extracts were concentrated in vacuo and purified using silica chromatography (0-10% MeOH in DCM) to yield the title product (3 mg, 79%). MS (apci) m/z=405.1 (M+H).

Example 71

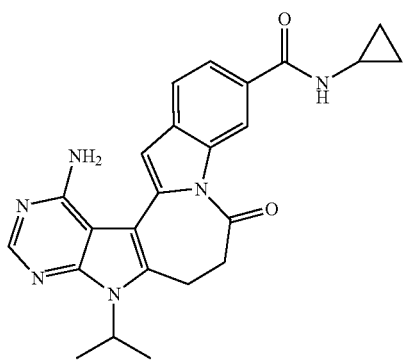 [SMILES: CC(C)n1c2c(c3c(N)ncnc31)-c1cc3ccc(C(=O)NC4CC4)cc3n1C(=O)CC2]

1-amino-N-cyclopropyl-5-isopropyl-8-oxo-5,6,7,8-tetrahydropyrimido[5",4":4',5']pyrrolo[3',2':3,4]azepino[1,2-a]indole-11-carboxamide Step 1: Preparation of N-cyclopropyl-1-((2,4-dimethoxybenzyl)amino)-5-isopropyl-8-oxo-5,6,7,8-tetrahydropyrimido[5",4":4',5']pyrrolo[3',2':3,4]azepino[1,2-a]indole-11-carboxamide A mixture of 1-((2,4-dimethoxybenzyl)amino)-5-isopropyl-8-oxo-5,6,7,8-tetrahydropyrimido[5",4":4',5']pyrrolo[3',2':3,4]azepino[1,2-a]indole-11-carboxylic acid (Intermediate P30) (35 mg, 0.065 mmol), cyclopropanamine (9 µL, 0.13 mmol), HATU (25 mg, 0.065 mmol) and DIEA (23 µL, 0.13 mmol) in DCM (0.65 mL) was stirred for 1 h at RT. The reaction was partitioned between DCM and water. After phase-separation, the organic layer was washed with brine then dried (Na₂SO₄), filtered and concentrated to afford the title compound, which was used directly in the next step without further purifications, assuming quantitative yield. MS (apci) m/z=579.2 (M+H).

Step 2: Preparation of 1-amino-N-cyclopropyl-5-isopropyl-8-oxo-5,6,7,8-tetrahydropyrimido[5",4":4',5']pyrrolo[3',2':3,4]azepino[1,2-a]indole-11-carboxamide A mixture of N-cyclopropyl-1-((2,4-dimethoxybenzyl)amino)-5-isopropyl-8-oxo-5,6,7,8-tetrahydropyrimido[5",4":4',5']pyrrolo[3',2':3,4]azepino[1,2-a]indole-11-carboxamide (0.035 g, 0.060 mmol) and triethylsilane (0.019 mL, 0.12 mmol) in TFA (1 mL) and DCM (1 mL) was stirred at RT for 1 h. It was then concentrated, partitioned between DCM and sat. NaHCO₃, followed by extracting the aqueous with DCM. The combined organic extracts were washed with brine, dried (Na₂SO₄), filtered, concentrated and purified by silica chromatography (1-10% MeOH in DCM) to give the title product (1.2 mg, 4%). MS (apci) m/z=429.2 (M+H).

Example 72

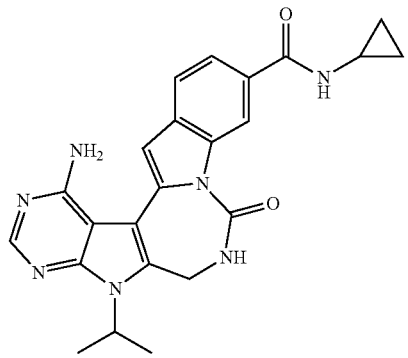 [SMILES: CC(C)n1c2c(c3c(N)ncnc31)-c1cc3ccc(C(=O)NC4CC4)cc3n1C(=O)NC2]

1-amino-N-cyclopropyl-5-isopropyl-8-oxo-5,6,7,8-tetrahydropyrimido[5",4":4',5']pyrrolo[2',3':5,6][1,3]diazepino[1,7-a]indole-11-carboxamide Step 1: Preparation of N-cyclopropyl-2-(4-((2,4-dimethoxybenzyl)amino)-6-(hydroxymethyl)-7-isopropyl-7H-pyrrolo[2,3-d]pyrimidin-5-yl)-1H-indole-6-carboxamide To a solution of 2-(4-((2,4-dimethoxybenzyl)amino)-6-(hydroxymethyl)-7-isopropyl-7H-pyrrolo[2,3-d]pyrimidin-5-yl)-1H-indole-6-carboxylic acid (Intermediate P27) (68 mg, 0.13 mmol) in DCM (2.6 mL) was added TEA (10 µL, 0.13 mmol) followed by cyclopropylamine (36.6 µL, 0.53 mmol) and HATU (55 mg, 0.14 mmol). After stirred at ambient temperature for 30 min, the reaction was concentrated and purified by silica chromatography (0-10% MeOH in DCM) to afford the title compound (58 mg, 79%). MS (apci) m/z=555.3 (M+H).

Step 2: Preparation of 2-(6-(azidomethyl)-4-((2,4-dimethoxybenzyl)amino)-7-isopropyl-7H-pyrrolo[2,3-d]pyrimidin-5-yl)-N-cyclopropyl-1H-indole-6-carboxamide To a solution of N-cyclopropyl-2-(4-((2,4-dimethoxybenzyl)amino)-6-(hydroxymethyl)-7-isopropyl-7H-pyrrolo[2, 3-d]pyrimidin-5-yl)-1H-indole-6-carboxamide (55 mg, 0.099 mmol) in toluene (1 mL) was added DBU (18 µL, 0.12 mmol) followed by DPPA (26 µL, 0.12 mmol) at 0° C. The reaction was allowed to warm to RT and stirred for 4.5 h before additional DBU (54 µL, 0.36 mmol) and DPPA (78 µL, 0.36 mmol) were added in three portions during the next 18 h until most starting material was consumed. The reaction was partitioned between DCM and water. The aqueous phase was then extracted with DCM (5×20 mL). The combined organic extracts were concentrated and purified using silica chromatography (0-10% MeOH in DCM) to afford the title compound (45 mg, 78%). MS (apci) m/z=580.3 (M+H).

Step 3: Preparation of 2-(6-(aminomethyl)-4-((2,4-dimethoxybenzyl)amino)-7-isopropyl-7H-pyrrolo[2,3-d]pyrimidin-5-yl)-N-cyclopropyl-1H-indole-6-carboxamide To a solution of 2-(6-(azidomethyl)-4-((2,4-dimethoxybenzyl)amino)-7-isopropyl-7H-pyrrolo[2,3-d]pyrimidin-5-yl)-N-cyclopropyl-1H-indole-6-carboxamide (45 mg, 0.078 mmol) in 1:1 THF:water was added PPh$_3$ (41 mg, 0.16 mmol) at RT and stirred for 2 h. The reaction was diluted with 4:1 DCM:IPA, washed with sat. NaHCO$_3$, then dried (Na$_2$SO$_4$), filtered, concentrated and purified by silica chromatography (0-20% MeOH in DCM) to afford the title compound (10 mg, 23%). MS (apci) m/z=554.3 (M+H).

Step 4: Preparation of N-cyclopropyl-1-((2,4-dimethoxybenzyl)amino)-5-isopropyl-8-oxo-5,6,7,8-tetrahydropyrimido[5'',4'':4',5']pyrrolo[2',3':5,6][1,3]diazepino[1,7-a]indole-11-carboxamide To a solution of 2-(6-(aminomethyl)-4-((2,4-dimethoxybenzyl)amino)-7-isopropyl-7H-pyrrolo[2,3-d]pyrimidin-5-yl)-N-cyclopropyl-1H-indole-6-carboxamide (10 mg, 0.018 mmol) in DMF (0.36 mL) was added bis(4-nitrophenyl) carbonate (5.5 mg, 0.018 mmol) at RT. The reaction was stirred for 1 h, followed by introduction of TEA (2.5 µL, 0.018 mmol). After 30 min stirring the reaction mixture was partitioned between EtOAc and water. The organic layer was washed with water and brine then dried (Na$_2$SO$_4$), filtered, concentrated and purified by silica chromatography (1-10% MeOH in DCM) to give the title compound (9 mg, 86% yield). MS (apci) m/z=580.3 (M+H).

Step 5: Preparation of 1-amino-N-cyclopropyl-5-isopropyl-8-oxo-5,6,7,8-tetrahydropyrimido[5'',4'':4',5']pyrrolo[2',3':5,6][1,3]diazepino[1,7-a]indole-11-carboxamide A mixture of N-cyclopropyl-1-((2,4-dimethoxybenzyl)amino)-5-isopropyl-8-oxo-5,6,7,8-tetrahydropyrimido[5'',4'':4',5']pyrrolo[2',3':5,6][1,3]diazepino[1,7-a]indole-11-carboxamide (9 mg, 0.016 mmol) and triethylsilane (7.4 µL, 0.046 mmol) in TFA (0.048 mL) and DCM (0.16 mL) was stirred overnight at RT. It was then concentrated and partitioned between DCM and sat. NaHCO$_3$. The organics were washed with brine then dried (Na$_2$SO$_4$), filtered, concentrated and purified by silica chromatography (1-10% MeOH in DCM) to afford the title product (2 mg, 30%). MS (apci) m/z=430.2 (M+H).

Example 73

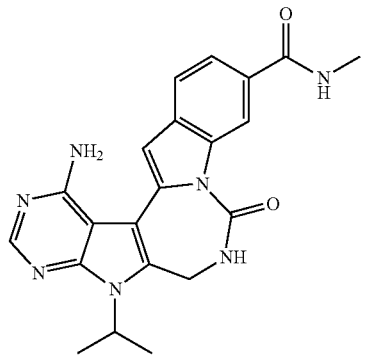 [SMILES: CNC(=O)c1ccc2cc3n(c2c1)C(=O)NCc1c-3c2c(N)ncnc2n1C(C)C]

1-Amino-5-isopropyl-N-methyl-8-oxo-5,6,7,8-tetrahydropyrimido[5'',4'':4',5']pyrrolo[2',3':5,6][1,3]diazepino[1,7-a]indole-11-carboxamide The title product was prepared in a similar fashion as described in the synthesis of 1-amino-N-cyclopropyl-5-isopropyl-8-oxo-5,6,7,8-tetrahydropyrimido[5'',4'':4',5']pyrrolo[2',3':5,6][1,3]diazepino[1,7-a]indole-11-carboxamide (Example 72), replacing cyclopropylamine in step 1 with methanamine instead (10 mg, 92%). MS (apci) m/z=404.2 (M+H).

Example 74

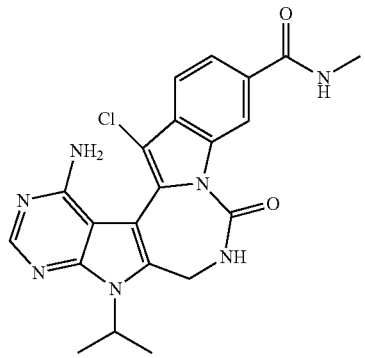 [SMILES: CNC(=O)c1ccc2c(Cl)c3n(c2c1)C(=O)NCc1c-3c2c(N)ncnc2n1C(C)C]

1-Amino-14-chloro-5-isopropyl-N-methyl-8-oxo-5,6,7,8-tetrahydropyrimido[5'',4'':4',5']pyrrolo[2',3':5,6][1,3]diazepino[1,7-a]indole-11-carboxamide To a solution of 1-amino-5-isopropyl-N-methyl-8-oxo-5,6,7,8-tetrahydropyrimido[5'',4'':4',5']pyrrolo[2',3':5,6][1,3]diazepino[1,7-a]indole-11-carboxamide (Example 73) (7 mg, 0.017 mmol) in DMF (174 µL) was added NCS (2.3 mg, 0.017 mmol) at RT and stirred overnight, followed by stirring at 50° C. for 2 d. The reaction was purified using silica chromatography (0-100% DCM in hexanes then 0-10% MeOH in DCM) to yield the title product (2.8 mg, 35%). MS (apci) m/z=438.1 (M+H).

Example 75

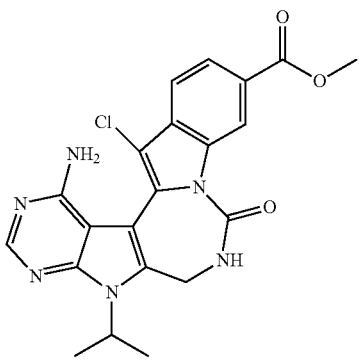 [SMILES: COC(=O)c1ccc2c(Cl)c3n(c2c1)C(=O)NCc1c-3c2c(N)ncnc2n1C(C)C]

Methyl 1-amino-14-chloro-5-isopropyl-8-oxo-5,6,7,8-tetrahydropyrimido[5",4":4',5']pyrrolo[2',3':5,6][1,3]diazepino[1,7-a]indole-11-carboxylate The title compound was prepared in a similar fashion as described in the synthesis of 1-amino-14-chloro-5-isopropyl-N-methyl-8-oxo-5,6,7,8-tetrahydropyrimido[5",4":4',5']pyrrolo[2',3':5,6][1,3]diazepino[1,7-a]indole-11-carboxamide (Example 74), replacing 1-amino-5-isopropyl-N-methyl-8-oxo-5,6,7,8-tetrahydropyrimido[5",4":4',5']pyrrolo[2',3':5,6][1,3]diazepino[1,7-a]indole-11-carboxamide (Example 73) with methyl 1-amino-5-isopropyl-8-oxo-5,6,7,8-tetrahydropyrimido[5",4":4',5']pyrrolo[2',3':5,6][1,3]diazepino[1,7-a]indole-11-carboxylate (Example 70) instead. MS (apci) m/z=439.2 (M+H).

Example 76

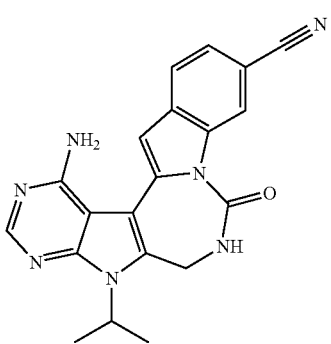 [SMILES: CC(C)n1c2c(c3c(N)ncnc31)-c1cc3ccc(C#N)cc3n1C(=O)NC2]

1-amino-5-isopropyl-8-oxo-5,6,7,8-tetrahydropyrimido[5",4":4',5']pyrrolo[2',3':5,6][1,3]diazepino[1,7-a]indole-11-carbonitrile Step 1: Preparation of 2-(6-(((tert-butyldimethylsilyl)oxy)methyl)-4-((2,4-dimethoxybenzyl)amino)-7-isopropyl-7H-pyrrolo[2,3-d]pyrimidin-5-yl)-1H-indole-6-carbonitrile A mixture of 6-((((tert-butyldimethylsilyl)oxy)methyl)-N-(2,4-dimethoxybenzyl)-5-iodo-7-isopropyl-7H-pyrrolo[2,3-d]pyrimidin-4-amine (Intermediate P14) (0.21 g, 0.35 mmol), (6-cyano-1H-indol-2-yl)boronic acid (0.20 g, 1.06 mmol), PdCl$_2$(PPh$_3$)$_2$ (0.037 g, 0.053 mmol) and Na$_2$CO$_3$ (2N, aq) (0.37 mL, 0.74 mmol) in dioxane (1.76 mL) was heated to 90° C. overnight. The reaction was then directly purified by silica chromatography (10-90% EtOAc in hexanes) to afford the title compound (0.21 g, 98%). MS (apci) m/z=611.3 (M+H).

Step 2: Preparation of 2-(4-((2,4-dimethoxybenzyl)amino)-6-(hydroxymethyl)-7-isopropyl-7H-pyrrolo[2,3-d]pyrimidin-5-yl)-1H-indole-6-carbonitrile A mixture of 2-(6-(((tert-butyldimethylsilyl)oxy)methyl)-4-((2,4-dimethoxybenzyl)amino)-7-isopropyl-7H-pyrrolo[2,3-d]pyrimidin-5-yl)-1H-indole-6-carbonitrile (0.21 g, 0.34 mmol) and TBAF (1 M, THF) (0.38 mL, 0.38 mmol) in THF (3.44 mL) was stirred at rt for 2 h. The reaction was diluted with water and extracted with EtOAc. The combined organic extracts were washed with brine, then dried (Na$_2$SO$_4$), filtered, concentrated, and purified by silica chromatography (1-10% MeOH in DCM) to afford the title compound (170 mg, 99%). MS (apci) m/z=497.2 (M+H).

Step 3: Preparation of 2-(6-(azidomethyl)-4-((2,4-dimethoxybenzyl)amino)-7-isopropyl-7H-pyrrolo[2,3-d]pyrimidin-5-yl)-1H-indole-6-carbonitrile To a solution of 2-(4-((2,4-dimethoxybenzyl)amino)-6-(hydroxymethyl)-7-isopropyl-7H-pyrrolo[2,3-d]pyrimidin-5-yl)-1H-indole-6-carbonitrile (0.17 g, 0.34 mmol) in toluene (3.4 mL) cooled to 0° C. was added diphenyl phosphorazidate (0.15 mL, 0.68 mmol), followed by 2,3,4,6,7,8,9,10-octahydropyrimido[1,2-a]azepine (0.10 mL, 0.68 mmol). The reaction was allowed to warm to rt and stirred overnight. It was diluted with water and extracted with DCM. The combined organic extracts were washed with brine, then dried (Na$_2$SO$_4$), filtered, concentrated, and purified by silica chromatography (1-10% MeOH in DCM) to afford the title compound (170 mg, 95%). MS (apci) m/z=522.3 (M+H).

Step 4: Preparation of 2-(6-(aminomethyl)-4-((2,4-dimethoxybenzyl)amino)-7-isopropyl-7H-pyrrolo[2,3-d]pyrimidin-5-yl)-1H-indole-6-carbonitrile A mixture of 2-(6-(azidomethyl)-4-((2,4-dimethoxybenzyl)amino)-7-isopropyl-7H-pyrrolo[2,3-d]pyrimidin-5-yl)-1H-indole-6-carbonitrile (0.17 g, 0.33 mmol) and PPh$_3$ (0.17 g, 0.65 mmol) in THF (1.6 mL) and water (1.6 mL) was stirred at rt overnight. It was then diluted with water and extracted with DCM. The combined organic extracts were washed with brine, then dried (Na$_2$SO$_4$), filtered, concentrated, and purified by silica chromatography (1-10% MeOH in DCM) to afford the title compound (67 mg, 41%). MS (apci) m/z=496.2 (M+H).

Step 5: Preparation of 1-((2,4-dimethoxybenzyl)amino)-5-isopropyl-8-oxo-5,6,7,8-tetrahydropyrimido[5",4":4',5']pyrrolo[2',3':5,6][1,3]diazepino[1,7-a]indole-11-carbonitrile To a solution of 2-(6-(aminomethyl)-4-((2,4-dimethoxybenzyl)amino)-7-isopropyl-7H-pyrrolo[2,3-d]pyrimidin-5-yl)-1H-indole-6-carbonitrile (0.067 g, 0.14 mmol) in DMF (1.4 mL) was added bis(4-nitrophenyl) carbonate (0.041 g, 0.14 mmol) at rt. After 1 h stirring, TEA (0.019 mL, 0.14 mmol) was introduced and stirring continued for 30 min.

The reaction was then diluted with water and extracted with EtOAc. The combined organic extracts were washed with water, brine, then dried (Na$_2$SO$_4$), filtered, concentrated, and purified by silica chromatography (1-10% MeOH in DCM) to afford the title compound (36 mg, 51%). MS (apci) m/z=522.2 (M+H).

Step 6: Preparation of 1-amino-5-isopropyl-8-oxo-5,6,7,8-tetrahydropyrimido[5'',4'':4',5']pyrrolo[2',3':5,6][1,3]diazepino[1,7-a]indole-11-carbonitrile A mixture of 1-((2,4-dimethoxybenzyl)amino)-5-isopropyl-8-oxo-5,6,7,8-tetrahydropyrimido[5'',4'':4',5']pyrrolo[2',3':5,6][1,3]diazepino[1,7-a]indole-11-carbonitrile (0.036 g, 0.069 mmol) and triethylsilane (0.022 mL, 0.138 mmol) in TFA (0.53 mL) and DCM (0.69 mL) was stirred overnight at rt. The reaction was diluted with sat. NaHCO$_3$ (aq) and extracted with DCM. The combined organic extracts were washed with brine, dried (Na$_2$SO$_4$), filtered, concentrated, and purified by silica chromatography (1-10% MeOH in DCM) to afford the title product (14.8 mg, 58%). MS (apci) m/z=372.2 (M+H).

The compounds in the following Table were prepared in a similar fashion as described in the synthesis of 1-amino-5-isopropyl-8-oxo-5,6,7,8-tetrahydropyrimido[5'',4'':4',5']pyrrolo[2',3':5,6][1,3]diazepino[1,7-a]indole-11-carbonitrile (Example 76), replacing (6-cyano-1H-indol-2-yl)boronic acid in step 1 with the appropriate boronate or boronic acid instead.

TABLE G

| Ex # | Structure | Chemical Name | MS apci (m/z) |
|---|---|---|---|
| 77 | 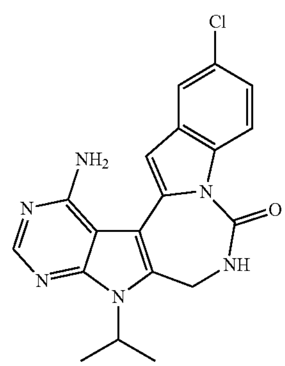 [SMILES: CC(C)n1c2c(c3c(N)ncnc31)-c1cc3cc(Cl)ccc3n1C(=O)NC2] | 1-amino-12-chloro-5-isopropyl-6,7-dihydropyrimido[5'',4'':4',5']pyrrolo[2',3':5,6][1,3]diazepino[1,7-a]indol-8(5H)-one | 381.1 (M + H) |
| 78 | 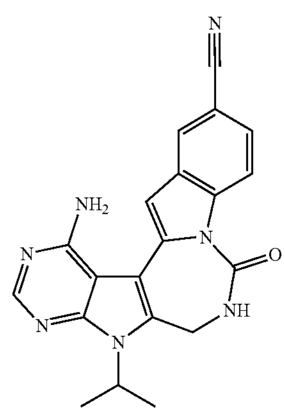 [SMILES: CC(C)n1c2c(c3c(N)ncnc31)-c1cc3cc(C#N)ccc3n1C(=O)NC2] | 1-amino-5-isopropyl-8-oxo-5,6,7,8-tetrahydropyrimido[5'',4'':4',5']pyrrolo[2',3':5,6][1,3]diazepino[1,7-a]indole-12-carbonitrile | 372.2 (M + H) |
| 79 | 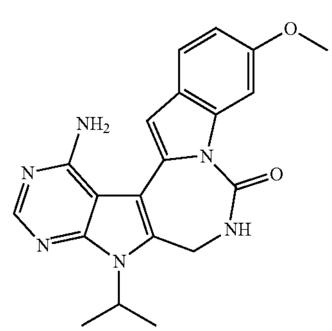 [SMILES: COc1ccc2cc3n(c2c1)C(=O)NCc1c-3c2c(N)ncnc2n1C(C)C] | 1-amino-5-isopropyl-11-methoxy-6,7-dihydropyrimido[5'',4'':4',5']pyrrolo[2',3':5,6][1,3]diazepino[1,7-a]indol-8(5H)-one | 377.2 (M + H) |

TABLE G-continued

| Ex # | Structure | Chemical Name | MS apci (m/z) |
|---|---|---|---|
| 80 | 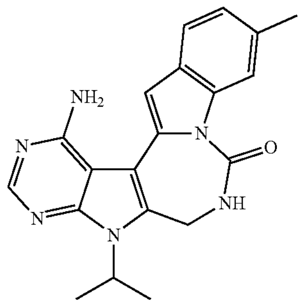 [SMILES: Cc1ccc2cc3n(c2c1)C(=O)NCc1c-3c2c(N)ncnc2n1C(C)C] | 1-amino-5-isopropyl-11-methyl-6,7-dihydropyrimido[5'',4'':4',5']pyrrolo[2',3':5,6][1,3]diazepino[1,7-a]indol-8(5H)-one | 361.2 (M + H) |
| 81 | 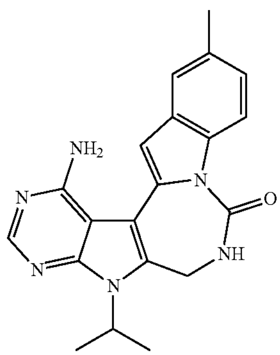 [SMILES: Cc1ccc2c(c1)cc1n2C(=O)NCc2c-1c1c(N)ncnc1n2C(C)C] | 1-amino-5-isopropyl-12-methyl-6,7-dihydropyrimido[5'',4'':4',5']pyrrolo[2',3':5,6][1,3]diazepino[1,7-a]indol-8(5H)-one | 361.2 (M + H) |
| 82 | 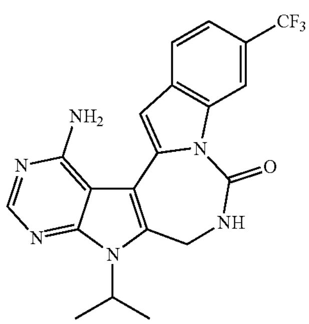 [SMILES: CC(C)n1c2c(c3c(N)ncnc31)-c1cc3ccc(C(F)(F)F)cc3n1C(=O)NC2] | 1-amino-5-isopropyl-11-(trifluoromethyl)-6,7-dihydropyrimido[5'',4'':4',5']pyrrolo[2',3':5,6][1,3]diazepino[1,7-a]indol-8(5H)-one | 415.2 (M + H) |
| 83 | 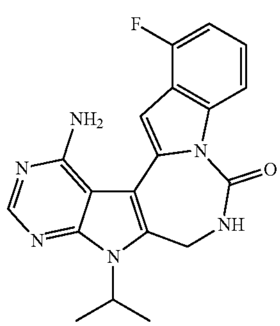 [SMILES: CC(C)n1c2c(c3c(N)ncnc31)-c1cc3c(F)cccc3n1C(=O)NC2] | 1-amino-13-fluoro-5-isopropyl-6,7-dihydropyrimido[5'',4'':4',5']pyrrolo[2',3':5,6][1,3]diazepino[1,7-a]indol-8(5H)-one | 365.2 (M + H) |

TABLE G-continued

| Ex # | Structure | Chemical Name | MS apci (m/z) |
|---|---|---|---|
| 84 | 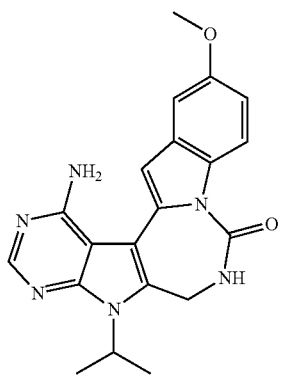 | 1-amino-11-chloro-5-isopropyl-6,7-dihydropyrimido[5",4":4',5']pyrrolo[2',3': 5,6][1,3]diazepino[1,7-a]indol-8(5H)-one | 381.2 (M + H) |

Example 85

1-amino-5-isopropyl-12-methoxy-6,7-dihydropyrimido[5",4":4',5']pyrrolo[2',3':5,6][1,3]diazepino[1,7-a]indol-8(5H)-one Step 1: Preparation of tert-butyl ((4-((2,4-dimethoxybenzyl)amino)-7-isopropyl-5-(5-methoxy-1H-indol-2-yl)-7H-pyrrolo[2,3-d]pyrimidin-6-yl)methyl)carbamate A mixture of tert-butyl ((4-((2,4-dimethoxybenzyl)amino)-5-iodo-7-isopropyl-7H-pyrrolo[2,3-d]pyrimidin-6-yl)methyl)carbamate (Intermediate P32) (48 mg, 0.083 mmol), Pd(PPh$_3$)$_2$Cl$_2$ (12 mg, 0.016 mmol), 5-methoxy-1H-indole-2-boronic acid pinacol ester (68 mg, 0.25 mmol) and Na$_2$CO$_3$ (2 N aq) (83 μL, 0.17 mmol) in dioxane (1.2 mL) was sparged with argon and heated to 80° C. for 20 min. After cooled to rt, the reaction was diluted with water and extracted with DCM (1×) and 4:1 DCM:IPA (3×) through a Phase-Separator frit. The combined organic extracts was concentrated and purified by silica chromatography (0-100% EtOAc in hexanes) to afford the title compound (47 mg, 94%). MS (apci) m/z=601.3 (M+H).

Step 2: Preparation of 6-(aminomethyl)-N-(2,4-dimethoxybenzyl)-7-isopropyl-5-(5-methoxy-1H-indol-2-yl)-7H-pyrrolo[2,3-d]pyrimidin-4-amine To a solution of tert-butyl ((4-((2,4-dimethoxybenzyl)amino)-7-isopropyl-5-(5-methoxy-1H-indol-2-yl)-7H-pyrrolo[2,3-d]pyrimidin-6-yl)methyl)carbamate (20.6 mg, 0.034 mmol) in THF (3.4 mL) was added HCl (4 N dioxane) (857 μL, 3.43 mmol) at rt, and the mixture was stirred overnight. The reaction was neutralized with sat. NaHCO$_3$ (20 mL) and extracted with 25% IPA in DCM (3×20 mL). The combined organic extracts was concentrated and purified by silica chromatography (0-10% MeOH in DCM) to yield the title compound (16 mg, 93%). MS (apci) m/z=501.3 (M+H).

Step 3: Preparation of 1-amino-5-isopropyl-12-methoxy-6,7-dihydropyrimido[5",4":4',5']pyrrolo[2', 3':5,6][1,3]diazepino[1,7-a]indol-8(5H)-one To a solution of 6-(aminomethyl)-N-(2,4-dimethoxybenzyl)-7-isopropyl-5-(5-methoxy-1H-indol-2-yl)-7H-pyrrolo[2,3-d]pyrimidin-4-amine (5.1 mg, 0.010 mmol) in acetonitrile (204 μL) was added bis(4-nitrophenyl) carbonate (3.1 mg, 0.010 mmol) at rt and stirred for 2 h. Triethylamine (10 μL) was then introduced and stirring continued for 10 min. The reaction was diluted with water (10 mL), then extracted with DCM (3×10 mL) through a Phase-Separator frit. The combined organic extracts was concentrated, taken up in DCM then treated with TFA (78 μL, 1.0 mmol) and triethylsilane (65 μL, 0.41 mmol). After stirred at rt for 1 h, the reaction was diluted with sat. NaHCO$_3$ (20 mL) and extracted with DCM (3×20 mL) through a Phase-Separator frit. The combined organic extracts was concentrated and purified by silica chromatography (0-100% DCM in hexanes then 0-10% MeOH in DCM) to afford the title product (1.9 mg, 48%). MS (apci) m/z=377.2 (M+H).

Example 86

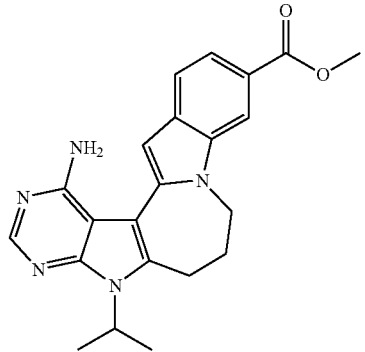 [SMILES: COC(=O)c1ccc2cc3n(c2c1)CCCc1c-3c2c(N)ncnc2n1C(C)C]

Methyl 1-amino-5-isopropyl-5,6,7,8-tetrahydropyrimido[5",4":4',5']pyrrolo[3',2':3,4]azepino[1,2-a]indole-11-carboxylate Step 1: Preparation of methyl 2-(6-(3-((tert-butyldimethylsilyl)oxy)propyl)-4-((2,4-dimethoxybenzyl)amino)-7-isopropyl-7H-pyrrolo[2,3-d]pyrimidin-5-yl)-1H-indole-6-carboxylate A mixture of 6-(3-((tert-butyldimethylsilyl)oxy)propyl)-N-(2,4-dimethoxybenzyl)-5-iodo-7-isopropyl-7H-pyrrolo

[2,3-d]pyrimidin-4-amine (Intermediate P33) (1.0 g, 1.6 mmol), 6-methoxycarbonyl-1H-indole-2-boronic acid pinacol ester (1.45 g, 4.8 mmol), PdCl$_2$PPh$_3$)$_2$ (0.22 g, 0.32 mmol), and Na$_2$CO$_3$ (2 N, aq) (1.6 mL, 3.2 mmol) in dioxane (23 mL) was sparged with argon and heated to 80° C. for 90 min. After cooled to rt, the reaction was diluted with water and extracted with DCM (3×). The combined organic extracts were concentrated and purified by silica chromatography (0-100% EtOAc in hexanes) to afford the title compound (958 mg, 89%). MS (apci) m/z=672.4 (M+H).

Step 2: Preparation of methyl 2-(4-((2,4-dimethoxybenzyl)amino)-6-(3-hydroxypropyl)-7-isopropyl-7H-pyrrolo[2,3-d]pyrimidin-5-yl)-1H-indole-6-carboxylate To a solution of methyl 2-(6-(3-((tert-butyldimethylsilyl)oxy)propyl)-4-((2,4-dimethoxybenzyl)amino)-7-isopropyl-7H-pyrrolo[2,3-d]pyrimidin-5-yl)-1H-indole-6-carboxylate (552 mg, 0.82 mmol) in THF (8.2 mL) cooled to 0° C. was added TBAF (1 M THF) (904 µL, 0.904 mmol). The reaction was then warmed to ambient temperature and stirred overnight. It was subsequently concentrated in vacuo and purified using silica chromatography (0-100% EtOAc in hexanes) to afford the title compound (344 mg, 75%). MS (apci) m/z=558.3 (M+H).

Step 3: Preparation of methyl 1-((2,4-dimethoxybenzyl)amino)-5-isopropyl-5,6,7,8-tetrahydropyrimido[5",4":4',5']pyrrolo[3',2':3,4]azepino[1,2-a]indole-11-carboxylate To a solution of methyl 2-(4-((2,4-dimethoxybenzyl)amino)-6-(3-hydroxypropyl)-7-isopropyl-7H-pyrrolo[2,3-d]pyrimidin-5-yl)-1H-indole-6-carboxylate (344 mg, 0.62 mmol) in DCM (12 mL) were added methanesulfonyl chloride (71 µL, 0.92 mmol) and DIEA (323 µL, 1.85 mmol) at ambient temperature. The reaction mixture was then stirred for 90 min. The reaction was diluted with water (20 mL) and extracted with DCM (3×20 mL) through a Phase-Separator frit. The combined organic extracts was concentrated, dried under high vacuum for 1 h, then dissolved in DMA (12 mL). This solution was treated with Cs$_2$CO$_3$ (402 mg, 1.2 mmol) and was stirred at 45° C. overnight. Upon cooled to ambient temperature, the reaction mixture was partitioned between EtOAc and water (100 mL each), and it was then extracted with EtOAc (3×100 mL). The combined organic extracts was concentrated and purified by silica chromatography (0-100% EtOAc in hexanes) to afford the title compound (236 mg, 71%). MS (apci) m/z=540.3 (M+H).

Step 4: Preparation of methyl 1-amino-5-isopropyl-5,6,7,8-tetrahydropyrimido[5",4":4',5']pyrrolo[3',2':3,4]azepino[1,2-a]indole-11-carboxylate To a solution of methyl 1-((2,4-dimethoxybenzyl)amino)-5-isopropyl-5,6,7,8-tetrahydropyrimido[5",4":4',5']pyrrolo[3',2':3,4]azepino[1,2-a]indole-11-carboxylate (16 mg, 0.030 mmol) in DCM (494 µL) was added TFA (500 µL) and triethylsilane (47.4 µL, 0.30 mmol) at ambient temperature then stirred for 1 h. The reaction was diluted with sat. NaHCO$_3$ (aq) (20 mL) and extracted with DCM (3×20 mL) through a Phase Separator frit. The combined organic extracts was concentrated and purified first by silica chromatography (0-100% EtOAc in hexanes followed by 0-10% MeOH in EtOAc), then by prep-HPLC (5-95% ACN in water with 0.1% TFA). The combined product fractions was diluted with sat. NaHCO$_3$ (aq) (20 mL) and extracted with DCM (3×20 mL) through a Phase Separator frit. The combined organic extracts was concentrated to afford the title product (3.2 mg, 28%). MS (apci) m/z=390.2 (M+H).

Example 87

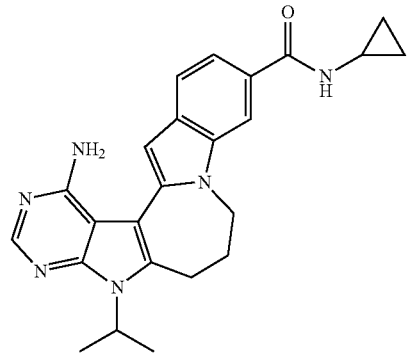 [SMILES: CC(C)n1c2c(c3c(N)ncnc31)-c1cc3ccc(C(=O)NC4CC4)cc3n1CCC2]

1-Amino-N-cyclopropyl-5-isopropyl-5,6,7,8-tetrahydropyrimido[5",4":4',5']pyrrolo[3',2':3,4]azepino[1,2-a]indole-11-carboxamide To a solution of 1-((2,4-dimethoxybenzyl)amino)-5-isopropyl-5,6,7,8-tetrahydropyrimido[5",4":4',5']pyrrolo[3',2':3,4]azepino[1,2-a]indole-11-carboxylic acid (Intermediate P34) (75 mg, 0.14 mmol) in DCM (2.8 mL) was added TEA (60 µL, 0.43 mmol) followed by cyclopropylamine (40 µL, 0.57 mmol) and HATU (60 mg, 0.16 mmol). After stirred at ambient temperature overnight, the reaction was diluted with water (10 mL) and extracted with DCM (3×10 mL) through a Phase-Separator frit. The combined organic extracts were concentrated. The resulting residue was then taken up in DCM (2.8 mL) and treated with TFA (1.1 mL) and triethylsilane (228 µL, 1.43 mmol). After 5 h stirring, the reaction was neutralized with sat. NaHCO$_3$ (100 mL), and then extracted with DCM (4×50 mL) through a Phase Separator frit. The combined organic extracts were concentrated in vacuo and purified twice using silica chromatography (1$^{st}$ time: 0-10% MeOH in DCM with 0.1% NH$_4$OH; 2$^{nd}$ time: 0-100% EtOAc in hexanes followed by 0-10% MeOH in EtOAc) to afford the title product (48.7 mg, 82%). MS (apci) m/z=415.2 (M+H).

The compounds in the following Table were prepared in a similar fashion as described in the synthesis of Example 87, replacing cyclopropylamine with the appropriate amine instead.

TABLE H

| Ex # | Structure | Chemical Name | MS apci (m/z) |
|---|---|---|---|
| 88 | 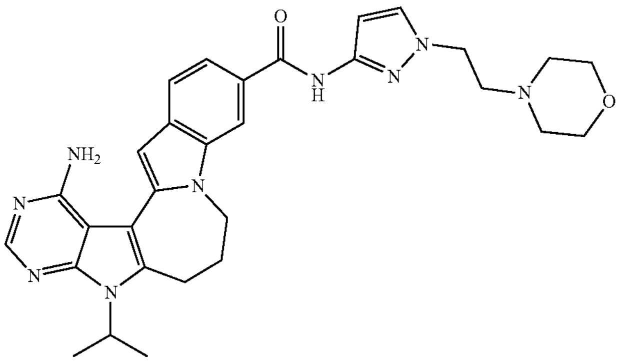 [SMILES: CC(C)n1c2c(c3c(N)ncnc31)-c1cc3ccc(C(=O)Nc4ccn(CCN5CCOCC5)n4)cc3n1CCC2] | 1-amino-5-isopropyl-N-(1-(2-morpholinoethyl)-1H-pyrazol-3-yl)-5,6,7,8-tetrahydropyrimido[5",4":4',5']pyrrolo[3',2':3,4]azepino[1,2-a]indole-11-carboxamide | 554.3 (M + H) |
| 89 | 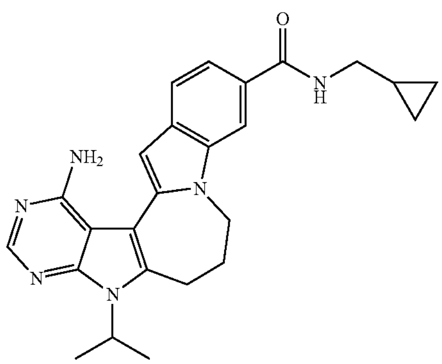 [SMILES: CC(C)n1c2c(c3c(N)ncnc31)-c1cc3ccc(C(=O)NCC4CC4)cc3n1CCC2] | 1-amino-N-(cyclopropylmethyl)-5-isopropyl-5,6,7,8-tetrahydropyrimido[5",4":4',5']pyrrolo[3',2':3,4]azepino[1,2-a]indole-11-carboxamide | 429.2 (M + H) |
| 90 | 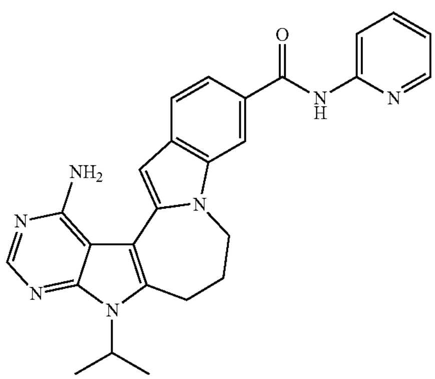 [SMILES: CC(C)n1c2c(c3c(N)ncnc31)-c1cc3ccc(C(=O)Nc4ccccn4)cc3n1CCC2] | 1-amino-5-isopropyl-N-(pyridin-2-yl)-5,6,7,8-tetrahydropyrimido[5",4":4',5']pyrrolo[3',2':3,4]azepino[1,2-a]indole-11-carboxamide | 452.2 (M + H) |
| 91 | 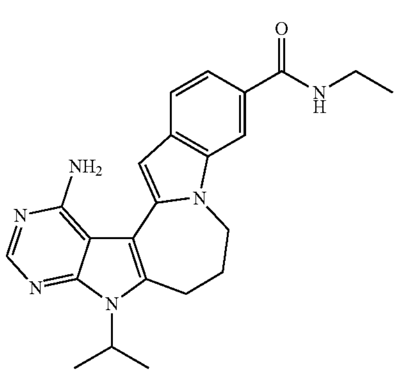 | 1-amino-N-ethyl-5-isopropyl-5,6,7,8-tetrahydropyrimido[5",4":4',5']pyrrolo[3',2':3,4]azepino[1,2-a]indole-11-carboxamide | 403.2 (M + H) |

TABLE H-continued

| Ex # | Structure | Chemical Name | MS apci (m/z) |
|---|---|---|---|
| 92 | 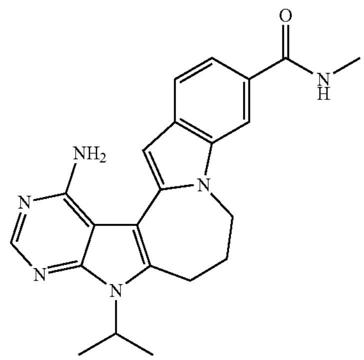 [SMILES: CNC(=O)c1ccc2cc3n(c2c1)CCCc1c-3c2c(N)ncnc2n1C(C)C] | 1-amino-5-isopropyl-N-methyl-5,6,7,8-tetrahydropyrimido[5",4":4',5']pyrrolo[3',2':3,4]azepino[1,2-a]indole-11-carboxamide | 389.2 (M + H) |
| 93 | 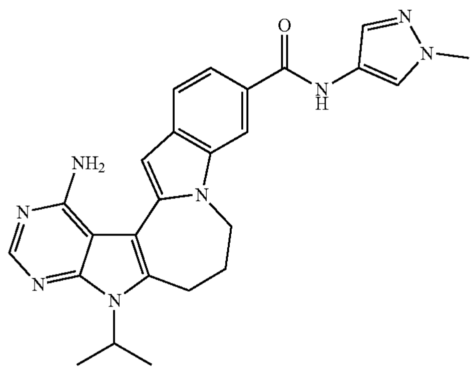 [SMILES: CC(C)n1c2c(c3c(N)ncnc31)-c1cc3ccc(C(=O)Nc4cnn(C)c4)cc3n1CCC2] | 1-amino-5-isopropyl-N-(1-methyl-1H-pyrazol-4-yl)-5,6,7,8-tetrahydropyrimido[5",4":4',5']pyrrolo[3',2':3,4]azepino[1,2-a]indole-11-carboxamide | 455.2 (M + H) |
| 94 | 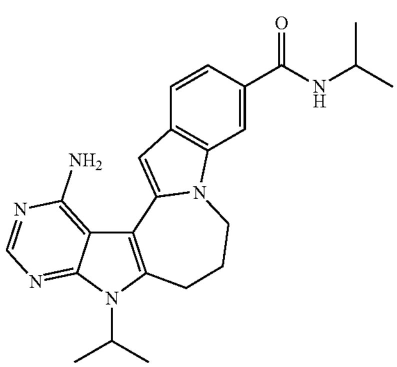 [SMILES: CC(C)NC(=O)c1ccc2cc3n(c2c1)CCCc1c-3c2c(N)ncnc2n1C(C)C] | 1-amino-N,5-diisopropyl-5,6,7,8-tetrahydropyrimido[5",4":4',5']pyrrolo[3',2':3,4]azepino[1,2-a]indole-11-carboxamide | 417.2 (M + H) |
| 95 | 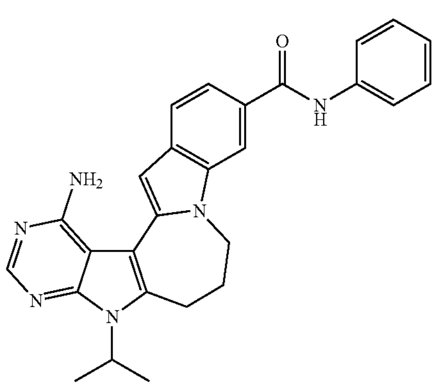 [SMILES: CC(C)n1c2c(c3c(N)ncnc31)-c1cc3ccc(C(=O)Nc4ccccc4)cc3n1CCC2] | 1-amino-5-isopropyl-N-phenyl-5,6,7,8-tetrahydropyrimido[5",4":4',5']pyrrolo[3',2':3,4]azepino[1,2-a]indole-11-carboxamide | 451.2 (M + H) |

TABLE H-continued

| Ex # | Structure | Chemical Name | MS apci (m/z) |
|---|---|---|---|
| 96 | 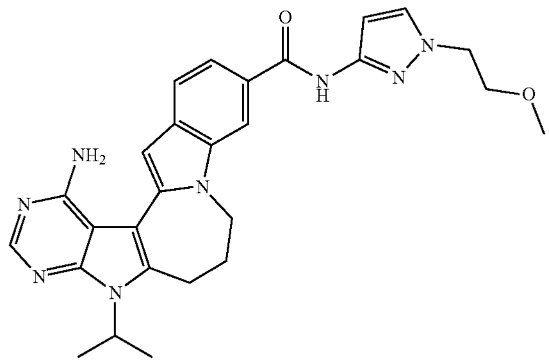 [SMILES: COCCn1ccc(NC(=O)c2ccc3cc4n(c3c2)CCCc2c-4c3c(N)ncnc3n2C(C)C)n1] | 1-amino-5-isopropyl-N-(1-(2-methoxyethyl)-1H-pyrazol-3-yl)-5,6,7,8-tetrahydropyrimido[5",4":4',5']pyrrolo[3',2':3,4]azepino[1,2-a]indole-11-carboxamide | 499.3 (M + H) |
| 97 | 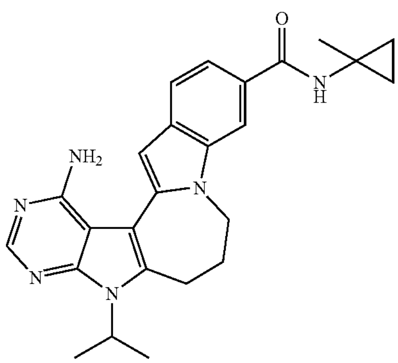 [SMILES: CC(C)n1c2c(c3c(N)ncnc31)-c1cc3ccc(C(=O)NC4(C)CC4)cc3n1CCC2] | 1-amino-5-isopropyl-N-(1-methylcyclopropyl)-5,6,7,8-tetrahydropyrimido[5",4":4',5']pyrrolo[3',2':3,4]azepino[1,2-a]indole-11-carboxamide | 429.2 (M + H) |
| 98 | 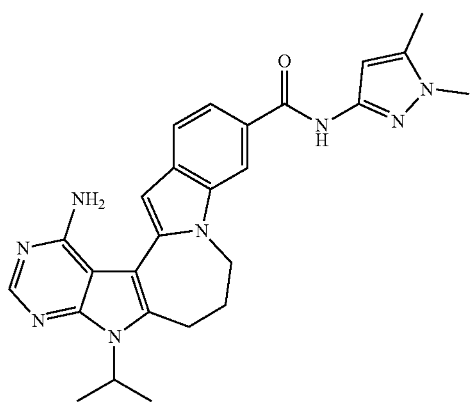 [SMILES: Cc1cc(NC(=O)c2ccc3cc4n(c3c2)CCCc2c-4c3c(N)ncnc3n2C(C)C)nn1C] | 1-amino-N-(1,5-dimethyl-1H-pyrazol-3-yl)-5-isopropyl-5,6,7,8-tetrahydropyrimido[5",4":4',5']pyrrolo[3',2':3,4]azepino[1,2-a]indole-11-carboxamide | 469.2 (M + H) |
| 99 | 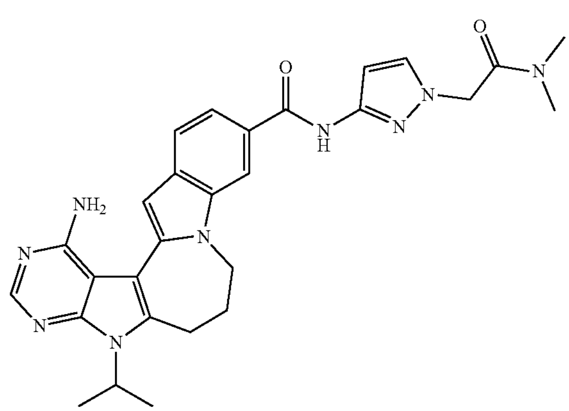 [SMILES: CC(C)n1c2c(c3c(N)ncnc31)-c1cc3ccc(C(=O)Nc4ccn(CC(=O)N(C)C)n4)cc3n1CCC2] | 1-amino-N-(1-(2-(dimethylamino)-2-oxoethyl)-1H-pyrazol-3-yl)-5-isopropyl-5,6,7,8-tetrahydropyrimido[5",4":4',5']pyrrolo[3',2':3,4]azepino[1,2-a]indole-11-carboxamide | 526.2 (M + H) |

TABLE H-continued

| Ex # | Structure | Chemical Name | MS apci (m/z) |
|---|---|---|---|
| 100 | 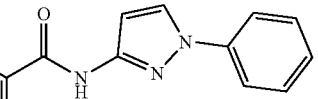 | 1-amino-5-isopropyl-N-(1-phenyl-1H-pyrazol-3-yl)-5,6,7,8-tetrahydropyrimido[5",4":4',5']pyrrolo[3',2':3,4]azepino[1,2-a]indole-11-carboxamide | 517.2 (M + H) |
| 101 | 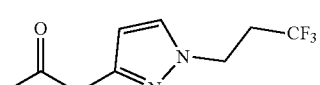 | 1-amino-5-isopropyl-N-(1-(3,3,3-trifluoropropyl)-1H-pyrazol-3-yl)-5,6,7,8-tetrahydropyrimido[5",4":4',5']pyrrolo[3',2':3,4]azepino[1,2-a]indole-11-carboxamide | 537.2 (M + H) |

Example 102

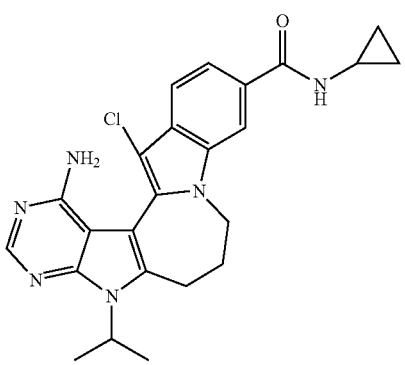 [SMILES: CC(C)n1c2c(c3c(N)ncnc31)-c1c(Cl)c3ccc(C(=O)NC4CC4)cc3n1CCC2]

1-Amino-14-chloro-N-cyclopropyl-5-isopropyl-5,6,7,8-tetrahydropyrimido[5",4":4',5']pyrrolo[3',2':3,4]azepino[1,2-a]indole-11-carboxamide A solution of 1-amino-N-cyclopropyl-5-isopropyl-5,6,7,8-tetrahydropyrimido[5",4":4',5']pyrrolo[3',2':3,4]azepino[1,2-a]indole-11-carboxamide (Example 87) (9.9 mg, 0.024 mmol) in DMF (239 μL) was treated with NCS (3.2 mg, 0.024 mmol) and stirred at 50° C. overnight. Additional NCS (1.6 mg, 0.12 mmol) was added and heating resumed at 50° C. for 8 h, then at 60° C. overnight. The reaction was purified using silica chromatography (0-100% DCM in hexanes then 0-10% MeOH in DCM) to yield the title product (1.3 mg, 12%). MS (apci) m/z=449.2 (M+H).

Example 103

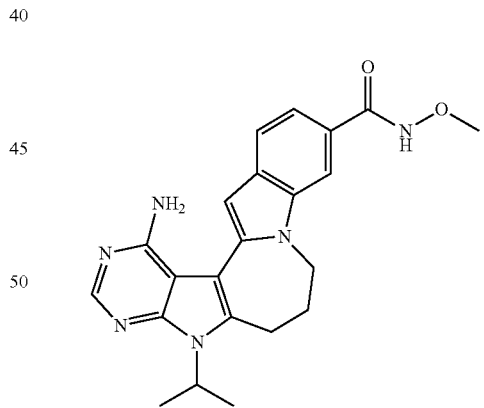

1-Amino-5-isopropyl-N-methoxy-5,6,7,8-tetrahydropyrimido[5",4":4',5']pyrrolo[3',2':3,4]azepino[1,2-a]indole-11-carboxamide Step 1: Preparation of 1-amino-5-isopropyl-5,6,7,8-tetrahydropyrimido[5",4":4',5']pyrrolo[3',2':3,4]azepino[1,2-a]indole-11-carboxylic Acid A solution of 1-((2,4-dimethoxybenzyl)amino)-5-isopropyl-5,6,7,8-tetrahydropyrimido[5",4":4',5']pyrrolo[3',2':3,4]

azepino[1,2-a]indole-11-carboxylic acid (Intermediate P34) (41 mg, 0.079 mmol) in DCM (788 μL) was treated with TFA (364 μL, 4.7 mmol) and triethylsilane (126 μL, 0.79 mmol). The reaction was stirred for 2 d at ambient temperature before it was neutralized with sat. NaHCO₃ (20 mL), and then extracted with DCM (3×10 mL) through a Phase Separator frit. The combined organic extracts were concentrated in vacuo and purified using silica chromatography (0-100% EtOAc in hexanes then 0-10% MeOH in EtOAc) to afford the first batch of the title compound (6.7 mg). The aqueous layer was extracted with 25% IPA in DCM (5×20 mL). The combined organics were dried (Na₂SO₄), filtered, concentrated, and purified using silica chromatography 0-100% EtOAc in hexanes then 0-10% MeOH in EtOAc) to afford the second batch of the title compound (12.2 mg). Both batches were combined as the desired product (18.9 mg, 64%). MS (apci) m/z=376.2 (M+H).

Step 2: Preparation of 1-Amino-5-isopropyl-N-methoxy-5,6,7,8-tetrahydropyrimido[5",4":4',5']pyrrolo[3',2':3,4]azepino[1,2-a]indole-11-carboxamide To a solution of 1-amino-5-isopropyl-5,6,7,8-tetrahydropyrimido[5",4":4',5']pyrrolo[3',2':3,4]azepino[1,2-a]indole-11-carboxylic acid (4 mg, 0.011 mmol) in DCM (213 μL) was added TEA (14.9 μL, 0.11 mmol) followed by methoxylamine hydrochloride (3.6 mg, 0.043 mmol) and HATU (4.5 mg, 0.012 mmol). The reaction was stirred at ambient temperature for 1 h, then concentrated and purified by silica chromatography (0-100% EtOAc in hexanes then 0-10% MeOH in EtOAc) to yield the title product (2.3 mg, 54%). MS (apci) m/z=405.2 (M+H).

Example 104

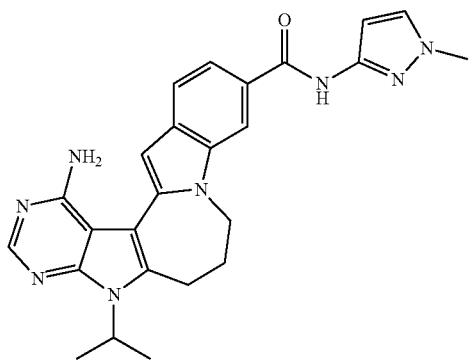 [SMILES: CC(C)n1c2c(c3c(N)ncnc31)-c1cc3ccc(C(=O)Nc4ccn(C)n4)cc3n1CCC2]

1-Amino-5-isopropyl-N-(1-methyl-1H-pyrazol-3-yl)-5,6,7,8-tetrahydropyrimido[5",4":4',5']pyrrolo[3',2':3,4]azepino[1,2-a]indole-11-carboxamide A solution of 1-amino-5-isopropyl-5,6,7,8-tetrahydropyrimido[5",4":4',5']pyrrolo[3',2':3,4]azepino[1,2-a]indole-11-carboxylic acid (Step 1, Example 103) (6.7 mg, 0.018 mmol) in DCM (357 μL) was treated with TEA (7.5 μL, 0.054 mmol) followed by 3-amino-1-methyl-1H-pyrazole (6.2 μL, 0.071 mmol) and HATU (7.5 mg, 0.020 mmol). The reaction was stirred at ambient temperature for 1 h before it was concentrated and purified by silica chromatography (0-100% EtOAc in hexanes followed by 0-10% MeOH in EtOAc) to afford the title product (3.7 mg, 46%). MS (apci) m/z=455.2 (M+H).

Example 105

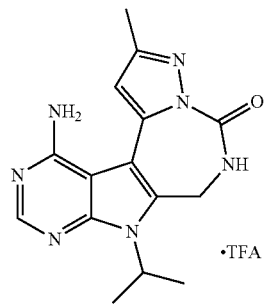 [SMILES: Cc1cc2n(n1)C(=O)NCc1c-2c2c(N)ncnc2n1C(C)C]

12-amino-8-isopropyl-2-methyl-7,8-dihydropyrazolo[1,5-c]pyrimido[5',4':4,5]pyrrolo[3,2-e][1,3]diazepin-5(6H)-one 2,2,2-trifluoroacetate Step 1: Preparation of 6-(((tert-butyldimethylsilyl)oxy)methyl)-N-(2,4-dimethoxybenzyl)-7-isopropyl-5-(3-methyl-1H-pyrazol-5-yl)-7H-pyrrolo[2,3-d]pyrimidin-4-amine A mixture of 6-(((tert-butyldimethylsilyl)oxy)methyl)-N-(2,4-dimethoxybenzyl)-5-iodo-7-isopropyl-7H-pyrrolo[2,3-d]pyrimidin-4-amine (Intermediate P14) (0.60 g, 1.0 mmol), 3-methyl-5-(4,4,5,5-tetramethyl-1,3,2-dioxaborolan-2-yl)-1H-pyrazole (0.27 g, 1.3 mmol), (PPh₃)₂Pd(II)Cl₂ (0.14 g, 0.20 mmol) and Na₂CO₃ (2 M aq) (1.5 mL, 3.0 mmol) in 1,4-dioxane (10 mL) was heated at 90° C. in a sealed pressure vessel for 15 h. The mixture was cooled to rt then concentrated and purified with silica chromatography (0-80% EtOAc in hexanes) to afford the title compound as a brownish oil (0.33 g, 60%). MS (apci) m/z=551.3 (M+H).

Step 2: Preparation of (4-((2,4-dimethoxybenzyl)amino)-7-isopropyl-5-(3-methyl-1H-pyrazol-5-yl)-7H-pyrrolo[2,3-d]pyrimidin-6-yl)methanol To a solution of 6-(((tert-butyldimethylsilyl)oxy)methyl)-N-(2,4-dimethoxybenzyl)-7-isopropyl-5-(3-methyl-1H-pyrazol-5-yl)-7H-pyrrolo[2,3-d]pyrimidin-4-amine (0.33 g, 0.60 mmol) in THF (3.0 mL) was added TBAF (1 M, THF) (0.72 mL, 0.72 mmol) at RT and stirred for 15 min. Another portion of TBAF (0.18 mL, 0.18 mmol) was added. The reaction was stirred for another 15 min, after which it was diluted with EtOAc (10 mL). It was then washed with water (2×10 mL) and brine, dried (Na₂SO₄), filtered and concentrated to a solid residue, which was triturated with hexanes to give the title compound as white solid (0.15 g, 57%). MS (apci) m/z=437.2 (M+H).

Step 3: Preparation of 6-(azidomethyl)-N-(2,4-dimethoxybenzyl)-7-isopropyl-5-(3-methyl-1H-pyrazol-5-yl)-7H-pyrrolo[2,3-d]pyrimidin-4-amine To a suspension of (4-((2,4-dimethoxybenzyl)amino)-7-isopropyl-5-(3-methyl-1H-pyrazol-5-yl)-7H-pyrrolo[2,3-d]pyrimidin-6-yl)methanol (131 mg, 0.30 mmol) in toluene (3.0 mL) was added diphenyl phosphorazidate (97 μL, 0.45 mmol) followed by 2,3,4,6,7,8,9,10-octahydropyrimido[1,2-a]azepine (67 μL, 0.45 mmol). After stirred at RT for 15 h, the reaction mixture was concentrated and purified by silica chromatography (0-100% EtOAc in hexanes) to give the title compound as white solid (80 mg, 58%). MS (apci) m/z=462.2 (M+H).

Step 4: Preparation of 6-(aminomethyl)-N-(2,4-dimethoxybenzyl)-7-isopropyl-5-(3-methyl-1H-pyrazol-5-yl)-7H-pyrrolo[2,3-d]pyrimidin-4-amine A mixture of 6-(azidomethyl)-N-(2,4-dimethoxybenzyl)-7-isopropyl-5-(3-methyl-1H-pyrazol-5-yl)-7H-pyrrolo[2,3-d]pyrimidin-4-amine (75 mg, 0.16 mmol) and Pd/C (10 wt %) (17 mg, 0.016 mmol) in MeOH (3.2 mL) was stirred under a hydrogen-filled balloon at RT for 15 h. The mixture was filtered through a short celite pad and the filtrate was concentrated to give the title compound as white solid (70 mg, 99%). MS (apci) m/z=436.3 (M+H).

Step 5: Preparation of 12-amino-8-isopropyl-2-methyl-7,8-dihydropyrazolo[1,5-c]pyrimido[5',4':4,5]pyrrolo[3,2-e][1,3]diazepin-5(6H)-one 2,2,2-trifluoroacetate To a solution of 6-(aminomethyl)-N-(2,4-dimethoxybenzyl)-7-isopropyl-5-(3-methyl-1H-pyrazol-5-yl)-7H-pyrrolo[2,3-d]pyrimidin-4-amine (35 mg, 0.080 mmol) in DMF (804 μL) was added bis(4-nitrophenyl) carbonate (29 mg, 0.096 mmol) at RT and stirred for 17 h. The reaction was diluted with EtOAc and washed with water. After phase-separation the organic layer was dried (Na₂SO₄), filtered and concentrated. The residue was taken up in TFA (1.6 mL) then stirred at RT for 30 min and 40° C. for 90 min before it was concentrated and purified by reverse-phase chromatography (0-95% MeCN in water with 0.1% TFA), giving the title product as white solid (10 mg, 40%). MS (apci) m/z=312.3 (M+H).

Example 106

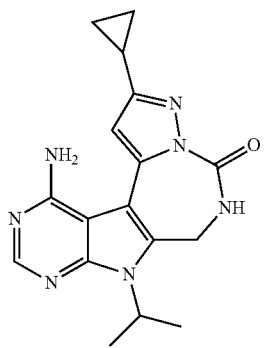 [SMILES: CC(C)n1c2c(c3c(N)ncnc31)-c1cc(C3CC3)nn1C(=O)NC2]

12-Amino-2-cyclopropyl-8-isopropyl-7,8-dihydropyrazolo[1,5-c]pyrimido[5',4':4,5]pyrrolo[3,2-e][1,3]diazepin-5(6H)-one Step 1: Preparation of 6-(((tert-butyldimethylsilyl)oxy)methyl)-5-(3-cyclopropyl-1H-pyrazol-5-yl)-N-(2,4-dimethoxybenzyl)-7-isopropyl-7H-pyrrolo[2,3-d]pyrimidin-4-amine A mixture of 6-(((tert-butyldimethylsilyl)oxy)methyl)-N-(2,4-dimethoxybenzyl)-7-isopropyl-5-(4,4,5,5-tetramethyl-1,3,2-dioxaborolan-2-yl)-7H-pyrrolo[2,3-d]pyrimidin-4-amine (Intermediate P15) (260 mg, 0.44 mmol), 3-cyclopropyl-5-iodo-1H-pyrazole (122 mg, 0.52 mmol) and 1,1'-bis(diphenylphosphino)ferrocenedichloropalladium(II) (31.9 mg, 0.044 mmol) in 1,4-dioxane (4.4 mL) and Na₂CO₃ (2 N, aq) (0.65 mL, 1.3 mmol) was sealed in a pressure vessel under N₂ and stirred at 100° C. for 2 d. After cooled to RT, the reaction mixture was concentrated and purified using silica chromatography (0-50% EtOAc in hexanes) to give the title product as white foamy solid (130 mg, 52%). MS (apci) m/z=577.4 (M+H).

Step 2: Preparation of (4-amino-5-(3-cyclopropyl-1H-pyrazol-5-yl)-7-isopropyl-7H-pyrrolo[2,3-d]pyrimidin-6-yl)methanol 2,2,2-trifluoroacetate A mixture of 6-(((tert-butyldimethylsilyl)oxy)methyl)-5-(3-cyclopropyl-1H-pyrazol-5-yl)-N-(2,4-dimethoxybenzyl)-7-isopropyl-7H-pyrrolo[2,3-d]pyrimidin-4-amine (130 mg, 0.22 mmol) in TFA (4.5 mL) was stirred at RT for 90 min and at 40° C. for 30 min before it was concentrated and purified by reverse-phase chromatography (0-95% MeCN in water with 0.1% TFA) to give the title compound as white solid (55 mg, 78%). MS (apci) m/z=313.3 (M+H).

Step 3: Preparation of 6-(azidomethyl)-5-(3-cyclopropyl-1H-pyrazol-5-yl)-7-isopropyl-7H-pyrrolo[2,3-d]pyrimidin-4-amine 2,2,2-trifluoroacetate To a solution of (4-amino-5-(3-cyclopropyl-1H-pyrazol-5-yl)-7-isopropyl-7H-pyrrolo[2,3-d]pyrimidin-6-yl)methanol 2,2,2-trifluoroacetate (55 mg, 0.13 mmol) in toluene (2.6 mL) and DMF (0.26 mL) was added DPPA (36 μL, 0.17 mmol) followed by DBU (48 μL, 0.32 mmol) at RT. The reaction was stirred for 2.5 h. Additional DPPA (36 μL, 0.17 mmol) and DBU (48 μL, 0.32 mmol) were added, followed by stirring for another 4 h before the reaction was concentrated and subjected to reverse-phase chromatography (0-95% MeCN in water with 0.1% TFA) to give the title compound as white solid (50 mg, 86%). MS (apci) m/z=338.3 (M+H).

Step 4: Preparation of 6-(aminomethyl)-5-(3-cyclopropyl-1H-pyrazol-5-yl)-7-isopropyl-7H-pyrrolo[2,3-d]pyrimidin-4-amine 2,2,2-trifluoroacetate A mixture of 6-(azidomethyl)-5-(3-cyclopropyl-1H-pyrazol-5-yl)-7-isopropyl-7H-pyrrolo[2,3-d]pyrimidin-4-amine 2,2,2-trifluoroacetate (50 mg, 0.11 mmol) and Pd/C (11.8 mg, 0.011 mmol) in MeOH (2.2 mL) was stirred under a hydrogen-filled balloon at RT for 5 h. The reaction was then filtered through a short pad of celite and the filtrate was concentrated to give the title compound (47 mg, 99%). MS (apci) m/z=312.2 (M+H).

Step 5: Preparation of 12-amino-2-cyclopropyl-8-isopropyl-7,8-dihydropyrazolo[1,5-c]pyrimido[5',4':4,5]pyrrolo[3,2-e][1,3]diazepin-5(6H)-one To a solution of 6-(aminomethyl)-5-(3-cyclopropyl-1H-pyrazol-5-yl)-7-isopropyl-7H-pyrrolo[2,3-d]pyrimidin-4-amine 2,2,2-trifluoroacetate (25 mg, 0.058 mmol) in DMF (588 μL) was added triethylamine (12 mg, 0.12 mmol) followed by bis(4-nitrophenyl) carbonate (22 mg, 0.071 mmol). The reaction was stirred at RT for 15 h then directly purified by reverse phase chromatography (0-95% MeCN in water with 0.1% TFA). The combined product-containing fractions were concentrated and triturated with Na₂CO₃ (2

M aq) (3 mL). The resulting suspension was filtered and the solid was further washed with sat. NaHCO$_3$ (3 mL) and water (3 mL), then dried to afford the title product as yellowish solid (6 mg, 30%). MS (apci) m/z=338.1 (M+H).

Example 107

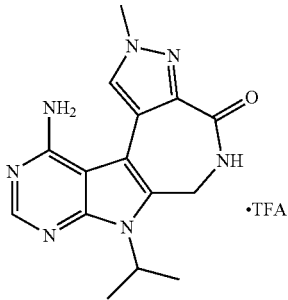 [SMILES: CC(C)n1c2c(c3c(N)ncnc31)-c1cn(C)nc1C(=O)NC2]

11-amino-7-isopropyl-2-methyl-2,5,6,7-tetrahydro-4H-pyrazolo[3,4-c]pyrimido[5',4':4,5]pyrrolo[3,2-e]azepin-4-one 2,2,2-trifluoroacetate Step 1: Preparation of methyl 4-(6-(((tert-butyldimethylsilyl)oxy)methyl)-4-((2,4-dimethoxybenzyl)amino)-7-isopropyl-7H-pyrrolo[2,3-d]pyrimidin-5-yl)-1-methyl-1H-pyrazole-3-carboxylate To a mixture of 6-(((tert-butyldimethylsilyl)oxy)methyl)-N-(2,4-dimethoxybenzyl)-7-isopropyl-5-(4,4,5,5-tetramethyl-1,3,2-dioxaborolan-2-yl)-7H-pyrrolo[2,3-d]pyrimidin-4-amine (Intermediate P15) (120 mg, 0.20 mmol), methyl 4-bromo-1-methyl-1H-pyrazole-3-carboxylate (66.1 mg, 0.30 mmol) and 1,1'-bis(diphenylphosphino)ferrocenedichloropalladium(II) (14.7 mg, 0.020 mmol) in 1,4-dioxane (2.0 mL) was added Na$_2$CO$_3$ (2 N aq) (0.3 mL, 0.6 mmol) under N$_2$. The reaction was sealed in a pressure vessel and heated at 90° C. for 60 h. After cooled to RT the reaction mixture was directly purified by silica chromatography (0-100% EtOAc in hexanes) to afford the title compound as beige solid (32 mg, 26%). MS (apci) m/z=609.3 (M+H).

Step 2: Preparation of methyl 4-(4-((2,4-dimethoxybenzyl)amino)-6-(hydroxymethyl)-7-isopropyl-7H-pyrrolo[2,3-d]pyrimidin-5-yl)-1-methyl-1H-pyrazole-3-carboxylate To a solution of methyl 4-(6-(((tert-butyldimethylsilyl)oxy)methyl)-4-((2,4-dimethoxybenzyl)amino)-7-isopropyl-7H-pyrrolo[2,3-d]pyrimidin-5-yl)-1-methyl-1H-pyrazole-3-carboxylate (30 mg, 0.049 mmol) in THF (0.5 mL) was added TBAF (1 M THF) (59 µL, 0.059 mmol) at RT. The resulting mixture was stirred for 15 min. The reaction was diluted with EtOAc and washed with water, then dried (Na$_2$SO$_4$), filtered and concentrated to give the title compound, which was directly used in the next step assuming quantitative yield. MS (apci) m/z=495.2 (M+H).

Step 3: Preparation of methyl 4-(6-(azidomethyl)-4-((2,4-dimethoxybenzyl)amino)-7-isopropyl-7H-pyrrolo[2,3-d]pyrimidin-5-yl)-1-methyl-1H-pyrazole-3-carboxylate To a suspension of methyl 4-(4-((2,4-dimethoxybenzyl)amino)-6-(hydroxymethyl)-7-isopropyl-7H-pyrrolo[2,3-d]pyrimidin-5-yl)-1-methyl-1H-pyrazole-3-carboxylate (24 mg, 0.048 mmol) in toluene (971 µL) was added DPPA (15.7 µL, 0.073 mmol) followed by DBU (10.9 µL, 0.073 mmol). The resulting mixture was stirred at RT for 15 h, after which it was concentrated and purified by silica chromatography (0-100% EtOAc in hexanes) to give the title compound as white solid (13 mg, 52%). MS (apci) m/z=520.2 (M+H).

Step 4: Preparation of 11-amino-7-isopropyl-2-methyl-2,5,6,7-tetrahydro-4H-pyrazolo[3,4-c]pyrimido[5',4':4,5]pyrrolo[3,2-e]azepin-4-one 2,2,2-trifluoroacetate A mixture of methyl 4-(6-(azidomethyl)-4-((2,4-dimethoxybenzyl)amino)-7-isopropyl-7H-pyrrolo[2,3-d]pyrimidin-5-yl)-1-methyl-1H-pyrazole-3-carboxylate (13 mg, 0.025 mmol) and Pd/C (10 wt %) (13 mg, 0.013 mmol) in MeOH (1.2 mL) was stirred under a balloon of H$_2$ at RT for overnight. It was filtered through a short pad of celite, concentrated then re-dissolved in toluene (1 mL) and heated at 120° C. for 15 h. After cooled to RT, the reaction was concentrated and stirred in TFA (0.5 mL) for 15 min before it was concentrated and purified using reverse phase chromatography (0-95% MeCN in water with 0.1% TFA) to afford the title product (2.4 mg, 31%). MS (apci) m/z=312.1 (M+H).

The compounds in the following Table were prepared in a similar fashion as described in the synthesis of 11-amino-7-isopropyl-2-methyl-2,5,6,7-tetrahydro-4H-pyrazolo[3,4-c]pyrimido[5',4':4,5]pyrrolo[3,2-e]azepin-4-one 2,2,2-trifluoroacetate (Example 107), replacing methyl 4-bromo-1-methyl-1H-pyrazole-3-carboxylate in step 1 with the appropriate halide reagent instead (e.g. methyl 4-bromo-1-methyl-1H-pyrazole-5-carboxylate for Example 108 and ethyl 1-cyclopropyl-4-iodo-1H-pyrazole-5-carboxylate for Example 109).

TABLE I

| Ex # | Structure | Chemical Name | MS apci (m/z) |
|---|---|---|---|
| 108 | 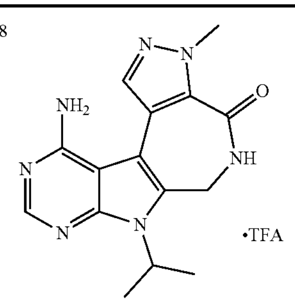 | 11-Amino-7-isopropyl-3-methyl-3,5,6,7-tetrahydro-4H-pyrazolo[3,4-c]pyrimido[5',4':4,5]pyrrolo[3,2-e]azepin-4-one 2,2,2-trifluoroacetate | 312.1 (M + H) |

TABLE I-continued

| Ex # | Structure | Chemical Name | MS apci (m/z) |
|---|---|---|---|
| 109 | 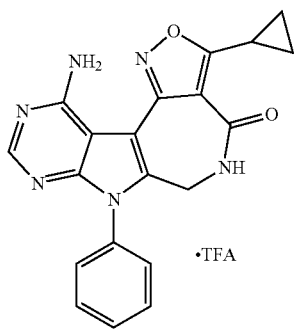 [SMILES: Nc1ncnc2c1c1c(n2-c2ccccc2)CNC(=O)c2c-1noc2C1CC1] | 11-amino-3-cyclopropyl-7-isopropyl-3,5,6,7-tetrahydro-4H-pyrazolo[3,4-c]pyrimido[5',4':4,5]pyrrolo[3,2-e]azepin-4-one 2,2,2-trifluoroacetate | 338.2 (M + H) |

Example 110

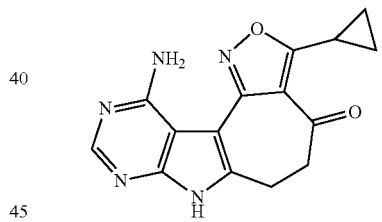

11-amino-3-cyclopropyl-7-phenyl-6,7-dihydroisoxazolo[4,3-c]pyrimido[5',4':4,5]pyrrolo[3,2-e]azepin-4(5H)-one 2,2,2-trifluoroacetate Step 1: Preparation of ethyl 3-(4-chloro-6-methyl-7-phenyl-7H-pyrrolo[2,3-d]pyrimidin-5-yl)-5-cyclopropylisoxazole-4-carboxylate A mixture of ethyl 3-(4-chloro-6-methyl-7H-pyrrolo[2,3-d]pyrimidin-5-yl)-5-cyclopropylisoxazole-4-carboxylate (Intermediate P22) (68 mg, 0.20 mmol), phenylboronic acid (48 mg, 0.39 mmol), alpha,alpha'-bipyridyl (31 mg, 0.20 mmol), Cu(OAc)$_2$ (36 mg, 0.20 mmol), and Na$_2$CO$_3$ (42 mg, 0.39 mmol) in DMA (980 µL) was flushed with N$_2$, then sealed in a pressure vessel and heated at 90° C. for 3 h. After cooled to rt, the mixture was diluted with EtOAc and filtered through a short pad of celite. The filtrate was concentrated and purified by silica chromatography (0-100% EtOAc in hexanes) to afford the title compound as colorless oil (4 mg, 5%). MS (apci) m/z=423.1 (M+H).

Step 2: Preparation of 11-amino-3-cyclopropyl-7-phenyl-6,7-dihydroisoxazolo[4,3-c]pyrimido[5',4':4,5]pyrrolo[3,2-e]azepin-4(5H)-one 2,2,2-trifluoroacetate A mixture of ethyl 3-(4-chloro-6-methyl-7-phenyl-7H-pyrrolo[2,3-d]pyrimidin-5-yl)-5-cyclopropylisoxazole-4-carboxylate (7 mg, 0.017 mmol), NBS (3.5 mg, 0.020 mmol) and AIBN (1.4 mg, 0.0083 mmol) in DCE (331 µL) was flushed with Ar, then sealed and heated at 80° C. for 2 h. Upon cooled to rt, the reaction was concentrated to dryness, the residue thus obtained taken up in dioxane (1 mL), and then concentrated again to dryness. The resulting residue was dissolved in 1,4-dioxane (662 µL) before NH$_4$OH (28% aq) (331 µL) was introduced. The mixture was stirred at rt for 5 min, then sealed and heated at 110° C. for 4 h. Upon cooled to rt, the reaction was concentrated and purified using reverse-phase chromatography (0-95% MeCN in water with 0.1% TFA) to afford the title product as white solid (4 mg, 65%). MS (apci) m/z=373.2 (M+H).

Example 111

11-amino-3-cyclopropyl-6,7-dihydroisoxazolo[4",3":6',7']cyclohepta[1',2':4,5]pyrrolo[2,3-d]pyrimidin-4(5H)-one A solution of 11-chloro-3-cyclopropyl-7-((2-(trimethylsilyl)ethoxy)methyl)-6,7-dihydroisoxazolo[4",3":6',7']cyclohepta[1',2':4,5]pyrrolo[2,3-d]pyrimidin-4(5H)-one (Intermediate P36) (16 mg, 0.036 mmol) in DCM (1 mL) and TFA (1 mL) was stirred at rt for 2.5 h before it was concentrated to near dryness, taken up in dioxane and concentrated again. The resulting residue was treated with NH$_4$OH (28-30% aq) (0.25 mL) and 1,4-dioxane (0.5 ml, 0.036 mmol). The reaction was then sealed and heated at 80° C. for 1 h and at 90° C. for 1.5 h. After cooled to rt, the mixture was concentrated to near dryness, then triturated with water (3 mL) and filtered. The solid thus obtained was rinsed with water and hexanes to afford the title product as beige solid after drying (8.5 mg, 80%). MS (apci) m/z=296.1 (M+H).

Example 112

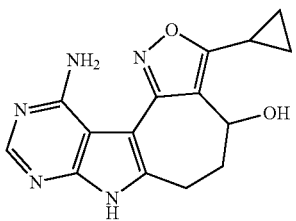 [SMILES: Nc1ncnc2[nH]c3c(c12)-c1noc(C2CC2)c1C(O)CC3]

11-amino-3-cyclopropyl-4,5,6,7-tetrahydroisoxazolo[4",3":6',7']cyclohepta[1',2':4,5]pyrrolo[2,3-d]pyrimidin-4-ol To a suspension of 11-amino-3-cyclopropyl-6,7-dihydroisoxazolo[4",3":6',7']cyclohepta[1',2':4,5]pyrrolo[2,3-d]pyrimidin-4(5H)-one (Example 111) (7 mg, 0.02 mmol) in MeOH (1.2 mL) was added NaBH$_4$ (2 mg, 0.05 mmol) at rt, and the reaction was stirred for 30 min. The reaction was then concentrated to near dryness, triturated with water, filtered and dried to afford the title product as yellowish solid (5 mg, 71%). MS (apci) m/z=298.1 (M+H).

Example 113

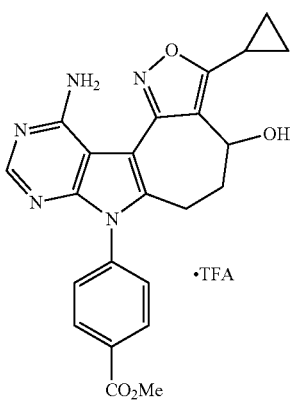 [SMILES: COC(=O)c1ccc(-n2c3c(c4c(N)ncnc42)-c2noc(C4CC4)c2C(O)CC3)cc1]

Methyl 4-(11-amino-3-cyclopropyl-4-hydroxy-5,6-dihydroisoxazolo[4",3":6',7']cyclohepta[1',2':4,5]pyrrolo[2,3-d]pyrimidin-7(4H)-yl)benzoate 2,2,2-trifluoroacetate Step 1: Preparation of methyl 4-(11-amino-3-cyclopropyl-4-oxoisoxazolo[4",3":6',7']cyclohepta[1',2':4,5]pyrrolo[2,3-d]pyrimidin-7(4H)-yl)benzoate A mixture of alpha,alpha'-bipyridyl (32 mg, 0.20 mmol) and Cu(OAc)$_2$ (37 mg, 0.20 mmol) in DMA (1.0 mL) was stirred at rt for 3 min before 4-methoxylcarbonylphenyllboronic acid (55 mg, 0.30 mmol), Na$_2$CO$_3$ (43 mg, 0.41 mmol) and 11-amino-3-cyclopropyl-6,7-dihydroisoxazolo[4",3":6',7']cyclohepta[1',2':4,5]pyrrolo[2,3-d]pyrimidin-4(5H)-one (Example 111) (30 mg, 0.10 mmol) were introduced. The reaction was sealed and stirred at 100° C. overnight. After cooled to rt, the reaction mixture was subjected to reverse phase chromatography (0-95% MeCN in water with 0.1% TFA) to afford the title compound as beige solid (5 mg, 11%). MS (apci) m/z=428.1 (M+H).

Step 2: Preparation of methyl 4-(11-amino-3-cyclopropyl-4-hydroxy-5,6-dihydroisoxazolo[4",3":6',7']cyclohepta[1',2':4,5]pyrrolo[2,3-d]pyrimidin-7(4H)-yl)benzoate 2,2,2-trifluoroacetate To a solution of methyl 4-(11-amino-3-cyclopropyl-4-oxoisoxazolo[4",3":6',7']cyclohepta[1',2':4,5]pyrrolo[2,3-d]pyrimidin-7(4H)-yl)benzoate (5 mg, 0.01 mmol) in MeOH (3 mL) was added NaBH$_4$ (1 mg, 0.04 mmol) at rt, and the reaction was stirred for 30 min. The mixture was concentrated and purified by reverse phase chromatography (0-95% MeCN in water with 0.1% TFA) to afford the title product as beige solid (0.4 mg, 8%). MS (apci) m/z=432.2 (M+H).

Example 114

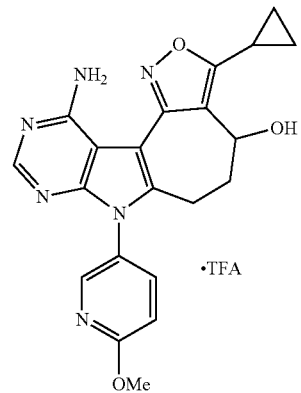 [SMILES: COc1ccc(-n2c3c(c4c(N)ncnc42)-c2noc(C4CC4)c2C(O)CC3)cn1]

11-Amino-3-cyclopropyl-7-(6-methoxypyridin-3-yl)-4,5,6,7-tetrahydroisoxazolo[4",3":6',7']cyclohepta[1',2':4,5]pyrrolo[2,3-d]pyrimidin-4-ol 2,2,2-trifluoroacetate Step 1: Preparation of 11-amino-3-cyclopropyl-7-(6-methoxypyridin-3-yl)-6,7-dihydroisoxazolo[4",3":6',7']cyclohepta[1',2':4,5]pyrrolo[2,3-d]pyrimidin-4(5H)-one 2,2,2-trifluoroacetate A mixture of 11-amino-3-cyclopropyl-6,7-dihydroisoxazolo[4",3":6',7']cyclohepta[1',2':4,5]pyrrolo[2,3-d]pyrimidin-4(5H)-one (Example 111) (30 mg, 0.10 mmol), CuI (2.9 mg, 0.015 mmol) and 5-iodo-2-methoxypyridine (72 mg, 0.30 mmol), K$_2$CO$_3$ (42 mg, 0.30 mmol), and L-proline (5.3 mg, 0.046 mmol) in DMSO (1.0 mL) was flushed with Ar, then sealed and stirred at 100° C. for 30 h. After cooled to rt, the mixture was subjected to reverse phase chromatography (0-95% MeCN in water with 0.1% TFA) to afford the title compound as beige solid (6 mg, 11%). MS (apci) m/z=403.2 (M+H).

Step 2: Preparation of 11-Amino-3-cyclopropyl-7-(6-methoxypyridin-3-yl)-4,5,6,7-tetrahydroisoxazolo[4",3":6',7']cyclohepta[1',2':4,5]pyrrolo[2,3-d]pyrimidin-4-ol 2,2,2-trifluoroacetate To a suspension of 11-amino-3-cyclopropyl-7-(6-methoxypyridin-3-yl)-6,7-dihydroisoxazolo[4",3":6',7']cyclohepta[1',2':4,5]pyrrolo[2,3-d]pyrimidin-4(5H)-one 2,2,2-trifluoroacetate (6 mg, 0.01 mmol) in methanol (1.5 mL) was added NaBH$_4$ (2 mg, 0.04 mmol) at rt and stirred for 15 min. The mixture was concentrated and purified using reverse phase chromatography (0-95% MeCN in water with 0.1% TFA) to afford the title product as beige solid (3 mg, 50%). MS (apci) m/z=405.1 (M+H).

Example 115

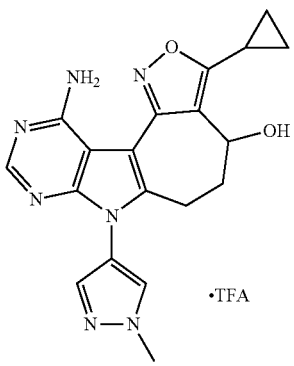 [SMILES: Cn1cc(-n2c3c(c4c(N)ncnc42)-c2noc(C4CC4)c2C(O)CC3)cn1]

11-amino-3-cyclopropyl-7-(1-methyl-1H-pyrazol-4-yl)-4,5,6,7-tetrahydroisoxazolo[4",3":6',7']cyclohepta[1',2':4,5]pyrrolo[2,3-d]pyrimidin-4-ol 2,2,2-trifluoroacetate The title compound was prepared in a similar fashion as described in Example 114, replacing 5-iodo-2-methoxypyridine in Step 1 with 4-iodo-1-methyl-1H-pyrazole instead (5 mg, 55%). MS (apci) m/z=378.3 (M+H).

Example 116

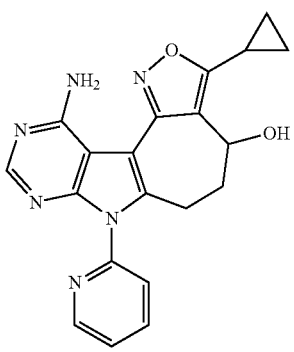 [SMILES: Nc1ncnc2c1c1c(n2-c2ccccn2)CCC(O)c2c-1noc2C1CC1]

11-Amino-3-cyclopropyl-7-(pyridin-2-yl)-4,5,6,7-tetrahydroisoxazolo[4",3":6',7']cyclohepta[1',2':4,5]pyrrolo[2,3-d]pyrimidin-4-ol Step 1: Preparation of 3-cyclopropyl-11-((2,4-dimethoxybenzyl)amino)-7-(pyridin-2-yl)-6,7-dihydroisoxazolo[4",3":6',7']cyclohepta[1',2':4,5]pyrrolo[2,3-d]pyrimidin-4(5H)-one A mixture of 3-cyclopropyl-11-((2,4-dimethoxybenzyl)amino)-6,7-dihydroisoxazolo[4",3":6',7']cyclohepta[1',2':4,5]pyrrolo[2,3-d]pyrimidin-4(5H)-one (Intermediate P37) (35 mg, 0.079 mmol), CuI (7.5 mg, 0.039 mmol), 2-bromopyridine (37 mg, 0.24 mmol), Cs$_2$CO$_3$ (51 mg, 0.16 mmol), and trans-1,2-diaminocyclohexane (9.4 µL, 0.079 mmol) in 1,4-dioxane (786 µL) was flushed with Ar, sealed and stirred at 120° C. for 18 h. After cooled to rt, the reaction was diluted with MeCN and filtered through a short pad of celite. The filtrate was concentrated to afford the crude title compound, which was directly used in the next step without further purifications, assuming quantitative yield. MS (apci) m/z=523.2 (M+H).

Step 2: Preparation of 11-amino-3-cyclopropyl-7-(pyridin-2-yl)-6,7-dihydroisoxazolo[4",3":6',7']cyclohepta[1',2':4,5]pyrrolo[2,3-d]pyrimidin-4(5H)-one 2,2,2-trifluoroacetate A solution of 3-cyclopropyl-11-((2,4-dimethoxybenzyl)amino)-7-(pyridin-2-yl)-6,7-dihydroisoxazolo[4",3":6',7']cyclohepta[1',2':4,5]pyrrolo[2,3-d]pyrimidin-4(5H)-one (41.3 mg, 0.079 mmol) in TFA (1 mL) was stirred at rt for 1 h before it was concentrated and subjected to reverse phase chromatography (0-95% MeCN in water with 0.1% TFA) to afford the title compound as beige solid (24 mg, 62%). MS (apci) m/z=373.2 (M+H).

Step 3: Preparation of 11-amino-3-cyclopropyl-7-(pyridin-2-yl)-4,5,6,7-tetrahydroisoxazolo[4",3":6',7']cyclohepta[1',2':4,5]pyrrolo[2,3-d]pyrimidin-4-ol To a suspension of 11-amino-3-cyclopropyl-7-(pyridin-2-yl)-6,7-dihydroisoxazolo[4",3":6',7']cyclohepta[1',2':4,5]pyrrolo[2,3-d]pyrimidin-4(5H)-one 2,2,2-trifluoroacetate (20 mg, 0.041 mmol) in methanol (1.4 mL) was added NaBH$_4$ (3.1 mg, 0.082 mmol) at rt and stirred for 15 min. The reaction was then concentrated to dryness and triturated with water. The solid was filtered, rinsed with water and dried to give the title product as light yellowish solid (11 mg, 71%). MS (apci) m/z=375.2 (M+H).

Example 117

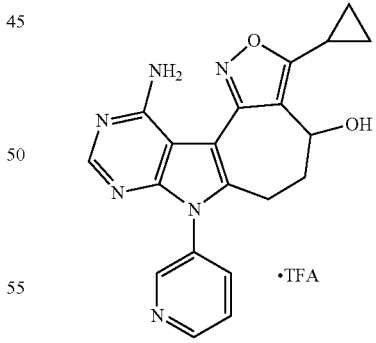

11-amino-3-cyclopropyl-7-(pyridin-3-yl)-4,5,6,7-tetrahydroisoxazolo[4",3":6',7']cyclohepta[1',2':4,5]pyrrolo[2,3-d]pyrimidin-4-ol 2,2,2-trifluoroacetate The title compound was prepared in a similar fashion as described in Example 116, replacing 2-bromopyridine in Step 1 with 3-iodopyridine instead. MS (apci) m/z=375.2 (M+H).

Example 118

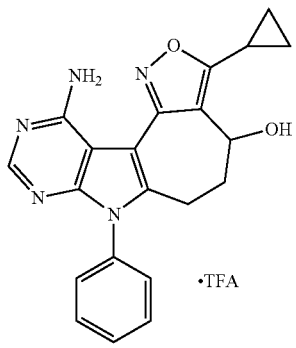 [SMILES: Nc1ncnc2c1c1c(n2-c2ccccc2)CCC(O)c2c-1noc2C1CC1]

11-Amino-3-cyclopropyl-7-phenyl-4,5,6,7-tetrahydroisoxazolo[4",3":6',7']cyclohepta[1',2':4,5]pyrrolo[2,3-d]pyrimidin-4-ol 2,2,2-trifluoroacetate The title compound was prepared in a similar fashion as described in Example 116, replacing 2-bromopyridine in Step 1 with iodobenzene instead (4 mg, 80%). MS (apci) m/z=374.2 (M+H).

Example 119

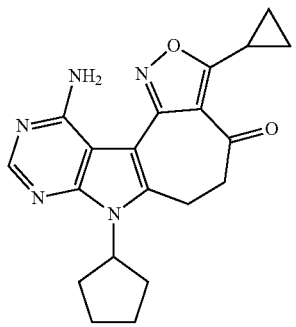 [SMILES: Nc1ncnc2c1c1c(n2C2CCCC2)CCC(=O)c2c-1noc2C1CC1]

11-Amino-7-cyclopentyl-3-cyclopropyl-6,7-dihydroisoxazolo[4",3":6',7']cyclohepta[1',2':4,5]pyrrolo[2,3-d]pyrimidin-4(5H)-one Step 1: Preparation of 11-chloro-7-cyclopentyl-3-cyclopropyl-6,7-dihydroisoxazolo[4",3":6',7']cyclohepta[1',2':4,5]pyrrolo[2,3-d]pyrimidin-4(5H)-one To a suspension of 11-chloro-3-cyclopropyl-6,7-dihydroisoxazolo[4",3":6',7']cyclohepta[1',2':4,5]pyrrolo[2,3-d]pyrimidin-4(5H)-one (Intermediate P36) (31 mg, 0.098 mmol), cyclopentanol (13 µL, 0.15 mmol) and triphenylphosphine (39 mg, 0.15 mmol) in THF (985 µL) was dropwise added DIAD (29 µL, 0.15 mmol) at rt. After addition, the reaction was stirred at rt for 30 min then concentrated and purified by silica chromatography (0-100% EtOAc in hexanes) to afford the title compound as a yellowish solid, which contained some triphenylphosphine oxide but was used directly in the next step without further purifications (43 mg, 114%). MS (apci) m/z=383.2 (M+H).

Step 2: Preparation of 11-amino-7-cyclopentyl-3-cyclopropyl-6,7-dihydroisoxazolo[4",3":6',7']cyclohepta[1',2':4,5]pyrrolo[2,3-d]pyrimidin-4(5H)-one A mixture of 11-chloro-7-cyclopentyl-3-cyclopropyl-6,7-dihydroisoxazolo[4",3":6',7']cyclohepta[1',2':4,5]pyrrolo[2,3-d]pyrimidin-4(5H)-one (38 mg, 0.099 mmol) and NH₄OH (28-30%) (496 µL) in 1,4-dioxane (993 µL) was sealed in a pressure vessel and stirred at 100° C. for 2 h. After cooled to rt, the reaction was diluted with water (10 mL) and filtered. The collected solid was rinsed with water and hexanes and then dried to give the title product as yellowish solid (14 mg, 39%). MS (apci) m/z=364.2 (M+H).

Example 120

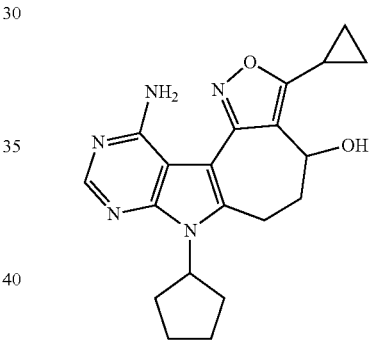

11-Amino-7-cyclopentyl-3-cyclopropyl-4,5,6,7-tetrahydroisoxazolo[4",3":6',7']cyclohepta[1',2':4,5]pyrrolo[2,3-d]pyrimidin-4-ol To a suspension of 11-amino-7-cyclopentyl-3-cyclopropyl-6,7-dihydroisoxazolo[4",3":6',7']cyclohepta[1',2':4,5]pyrrolo[2,3-d]pyrimidin-4(5H)-one (Example 119) (11 mg, 0.030 mmol) in MeOH (1 mL) was added NaBH₄ (2.3 mg, 0.061 mmol) at rt. The reaction was stirred at rt for 30 min. The mixture was then concentrated, treated with water to form a suspension and filtered. The collected solid was rinsed with water and dried to afford the title product as white solid (10 mg, 90%). MS (apci) m/z=366.2 (M+H).

The compounds in the following Table were prepared in a similar fashion as described in the synthesis of Example 120, replacing cyclopentanol in step 1 of the preparation of Example 119 with the appropriate alcohol instead (e.g. 1,3-difluoropropan-2-ol for Example 122).

TABLE J

| Ex # | Structure | Chemical Name | MS apci (m/z) |
|---|---|---|---|
| 121 | 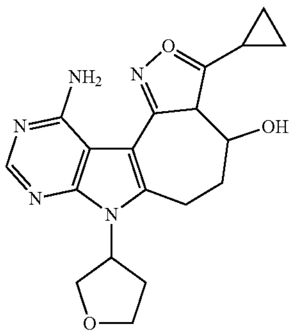 | 11-amino-3-cyclopropyl-7-(tetrahydrofuran-3-yl)-4,5,6,7-tetrahydro-isoxazolo[4'',3'':6',7']cyclohepta[1',2':4,5]pyrrolo[2,3-d]pyrimidin-4-ol | 368.1 (M + H) |
| 122 | 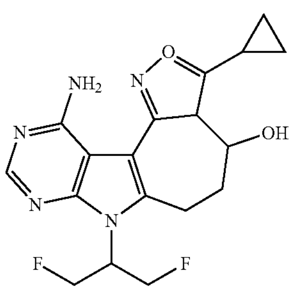 | 11-amino-3-cyclopropyl-7-(1,3-difluoropropan-2-yl)-4,5,6,7-tetrahydro-isoxazolo[4'',3'':6',7']cyclohepta[1',2':4,5]pyrrolo[2,3-d]pyrimidin-4-ol | 376.2 (M + H) |
| 123 | 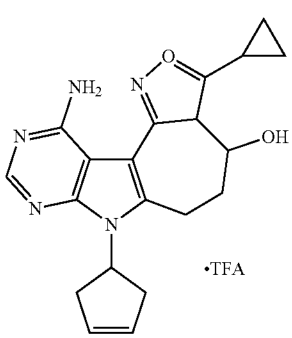 | 11-amino-7-(cyclopent-3-en-1-yl)-3-cyclopropyl-4,5,6,7-tetrahydro-isoxazolo[4'',3'':6',7']cyclohepta[1',2':4,5]pyrrolo[2,3-d]pyrimidin-4-ol 2,2,2-trifluoroacetate | 364.2 (M + H) |

Example 124 Example 125

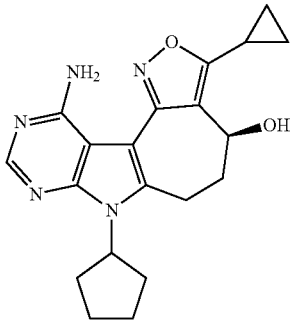

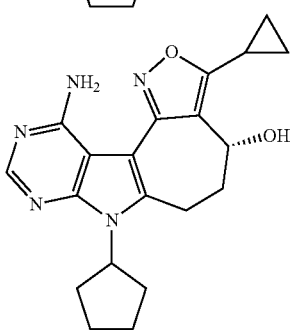

(S)-11-amino-7-cyclopentyl-3-cyclopropyl-4,5,6,7-
tetrahydroisoxazolo[4",3":6',7']cyclohepta[1',2':4,5]
pyrrolo[2,3-d]pyrimidin-4-ol (Example 124)

(R)-11-amino-7-cyclopentyl-3-cyclopropyl-4,5,6,7-
tetrahydroisoxazolo[4",3":6',7']cyclohepta[1',2':4,5]
pyrrolo[2,3-d]pyrimidin-4-ol (Example 125)

The title products were obtained by subjecting 11-amino-7-cyclopentyl-3-cyclopropyl-4,5,6,7-tetrahydroisoxazolo[4",3":6',7']cyclohepta[1',2':4,5]pyrrolo[2,3-d]pyrimidin-4-ol (Example 120) to chiral SFC (ChiralTech IA column, 4.6×250 mm, 4 mL/min, 220 nM, 5-70% over 13 min MeOH:IPA:DEA 80:20:0.1), giving two enantiomerically pure isomer products. The absolute stereochemistry was arbitrarily assigned (first eluent peak as S-isomer and the second, R-isomer). MS (apci) m/z=366.2 (M+H).

Example 126 Example 127

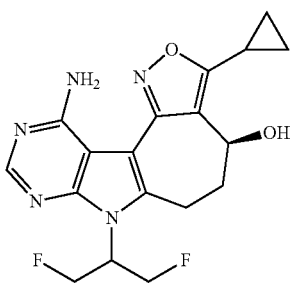

and

-continued

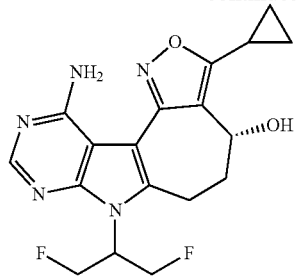

(S)-11-amino-3-cyclopropyl-7-(1,3-difluoropropan-2-yl)-4,5,6,7-tetrahydroisoxazolo[4",3":6',7']cyclohepta[1',2':4,5]pyrrolo[2,3-d]pyrimidin-4-ol (Example 126)

(R)-11-amino-3-cyclopropyl-7-(1,3-difluoropropan-2-yl)-4,5,6,7-tetrahydroisoxazolo[4",3":6',7']cyclohepta[1',2':4,5]pyrrolo[2,3-d]pyrimidin-4-ol (Example 127)

The title products were obtained by subjecting 11-amino-3-cyclopropyl-7-(1,3-difluoropropan-2-yl)-4,5,6,7-tetrahydroisoxazolo[4",3":6',7']cyclohepta[1',2':4,5]pyrrolo[2,3-d]pyrimidin-4-ol (Example 122) to chiral SFC (ChiralTech IA column, 21×250 mm, 19 mL/min, 220 nM, 10-20% MeOH:IPA:DEA 80:20:0.1), giving two enantiomerically pure isomer products. The absolute stereochemistry was first arbitrarily assigned and later confirmed by X-ray crystallography. The first eluent (Peak 1) is the S- and the second eluent (Peak 2), the R-enantiomer. MS (apci) m/z=376.2 (M+H).

Example 128

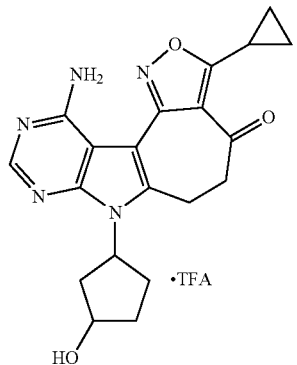 [SMILES: Nc1ncnc2c1c1c(n2C2CCC(O)C2)CCC(=O)c2c-1noc2C1CC1]

11-Amino-3-cyclopropyl-7-(3-hydroxycyclopentyl)-6,7-dihydroisoxazolo[4",3":6',7']cyclohepta[1',2':4,5]pyrrolo[2,3-d]pyrimidin-4(5H)-one 2,2,2-trifluoroacetate Step 1: Preparation of 7-(3-(benzyloxy)cyclopentyl)-11-chloro-3-cyclopropyl-6,7-dihydroisoxazolo[4",3":6',7']cyclohepta[1',2':4,5]pyrrolo[2,3-d]pyrimidin-4(5H)-one To a suspension of 11-chloro-3-cyclopropyl-6,7-dihydroisoxazolo[4",3":6',7']cyclohepta[1',2':4,5]pyrrolo[2,3-d]

pyrimidin-4(5H)-one (Intermediate P36) (62 mg, 0.20 mmol), 1-benzyloxyl-3-hydroxylcyclopentane (49 mg, 0.26 mmol) and triphenylphosphine (78 mg, 0.30 mmol) in THF (2 mL) was dropwise added DIAD (57 μL, 0.30 mmol) at 0° C. then stirred for 1 h. The mixture was concentrated and purified by silica chromatography (0-100% EtOAc in hexanes) to give the title compound as yellowish solid (50 mg, 52%). MS (apci) m/z=489.2 (M+H).

Step 2: Preparation of 11-amino-7-(3-(benzyloxy) cyclopentyl)-3-cyclopropyl-6,7-dihydroisoxazolo[4",3":6',7']cyclohepta[1',2':4,5]pyrrolo[2,3-d]pyrimidin-4(5H)-one A mixture of 7-(3-(benzyloxy)cyclopentyl)-11-chloro-3-cyclopropyl-6,7-dihydroisoxazolo[4",3":6',7']cyclohepta[1',2':4,5]pyrrolo[2,3-d]pyrimidin-4(5H)-one (49 mg, 0.10 mmol) and NH$_4$OH (28-30%) (0.5 mL) in 1,4-dioxane (1 mL) was sealed and stirred at 90° C. for 90 min. After cooled to rt, the mixture was concentrated to dryness and the residue was triturated with water (2×1 mL) then dried to give the crude title compound as orange solid, which was directly used in the next step without further purifications, assuming quantitative yield. MS (apci) m/z=470.2 (M+H).

Step 3: Preparation of 11-amino-3-cyclopropyl-7-(3-hydroxycyclopentyl)-6,7-dihydroisoxazolo[4",3":6',7']cyclohepta[1',2':4,5]pyrrolo[2,3-d]pyrimidin-4(5H)-one 2,2,2-trifluoroacetate A mixture of 11-amino-7-(3-(benzyloxy)cyclopentyl)-3-cyclopropyl-6,7-dihydroisoxazolo[4",3":6',7']cyclohepta[1',2':4,5]pyrrolo[2,3-d]pyrimidin-4(5H)-one (47 mg, 0.1 mmol) and Pd/C (10 wt %) (32 mg, 0.030 mmol) in EtOAc (4 mL) was stirred under an atmosphere of hydrogen-filled balloon at rt for 15 h, then at 50° C. for 11 h. After cooled to rt, the reaction mixture was filtered through a short pad of celite and rinsed with MeCN. The filtrate was concentrated and purified by reverse phase chromatography (0-95% MeCN in water with 0.1% TFA) to afford the title product as a mixture of cis and trans isomers (1:4 ratio, although further study is needed to ascertain which isomer is the major component) (23 mg, 61%). MS (apci) m/z=380.3 (M+H).

Example 129

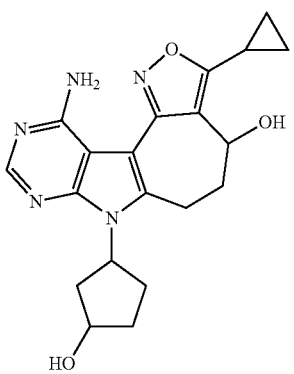 [SMILES: Nc1ncnc2c1c1c(n2C2CCC(O)C2)CCC(O)c2c-1noc2C1CC1]

11-Amino-3-cyclopropyl-7-(3-hydroxycyclopentyl)-4,5,6,7-tetrahydroisoxazolo[4",3":6',7']cyclohepta[1',2':4,5]pyrrolo[2,3-d]pyrimidin-4-ol To a solution of 11-amino-3-cyclopropyl-7-(3-hydroxycyclopentyl)-6,7-dihydroisoxazolo[4",3":6',7']cyclohepta[1',2':4,5]pyrrolo[2,3-d]pyrimidin-4(5H)-one 2,2,2-trifluoroacetate (Example 128) (18 mg, 0.047 mmol) in methanol (237 μL) was added NaBH$_4$ (3.6 mg, 0.095 mmol) at rt. The reaction was stirred at rt for 15 min and concentrated. The crude residue was triturated with water (2 mL) and then filtered. The collected solid was rinsed with water (2 mL) and dried to give the title product as white solid (12 mg, 66%). MS (apci) m/z=382.2 (M+H).

Example 130

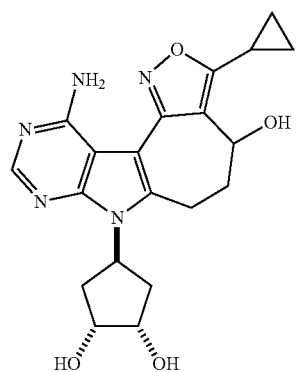 [SMILES: Nc1ncnc2c1c1c(n2[C@@H]2C[C@@H](O)[C@@H](O)C2)CCC(O)c2c-1noc2C1CC1]

(1r,2s,4s)-4-(11-amino-3-cyclopropyl-4-hydroxy-5,6-dihydroisoxazolo[4",3":6',7']cyclohepta[1',2':4,5]pyrrolo[2,3-d]pyrimidin-7(4H)-yl)cyclopentane-1,2-diol To a light suspension of 11-amino-7-(cyclopent-3-en-1-yl)-3-cyclopropyl-4,5,6,7-tetrahydroisoxazolo[4",3":6',7']cyclohepta[1',2':4,5]pyrrolo[2,3-d]pyrimidin-4-ol 2,2,2-trifluoroacetate (Example 123) (7 mg, 0.015 mmol) in acetone (734 μL) and water (73 μL) were added N-methyl morpholine-N-oxide (5.2 mg, 0.044 mmol), OsO$_4$ (9.3 mg, 0.0015 mmol), and sat. NaHCO$_3$ (0.1 mL) at rt. The resulting mixture was then stirred for 2 h. The mixture was concentrated to dryness and the solid was triturated with water (1 mL), then filtered, rinsing the collected solid with water (1 mL) and dried to give the title product as white solid (5 mg, 86%). MS (apci) m/z=398.2 (M+H).

Example 131

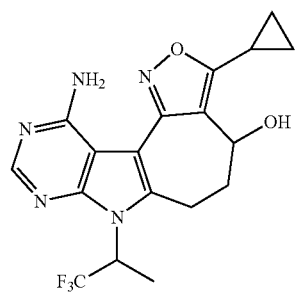 [SMILES: CC(n1c2c(c3c(N)ncnc31)-c1noc(C3CC3)c1C(O)CC2)C(F)(F)F]

11-Amino-3-cyclopropyl-7-(1,1,1-trifluoropropan-2-yl)-4,5,6,7-tetrahydroisoxazolo[4",3":6',7']cyclohepta[1',2':4,5]pyrrolo[2,3-d]pyrimidin-4-ol Step 1: Preparation of 11-chloro-3-cyclopropyl-7-(1,1,1-trifluoropropan-2-yl)-6,7-dihydroisoxazolo[4",3":6',7']cyclohepta[1',2':4,5]pyrrolo[2,3-d]pyrimidin-4(5H)-one A mixture of 11-chloro-3-cyclopropyl-6,7-dihydroisoxazolo[4",3":6',7']cyclohepta[1',2':4,5]pyrrolo[2,3-d]pyrimidin-4(5H)-one (Intermediate P36) (32 mg, 0.10 mmol), 1,1,1-trifluoropropan-2-yl trifluoromethanesulfonate (38 mg, 0.15 mmol), and Cs₂CO₃ (43 mg, 0.13 mmol) in DMF (508 µL) was stirred at rt for 2 h and at 60° C. for 1 h. Additional Cs₂CO₃ (total 90 mg, 0.30 mmol) and 1,1,1-trifluoropropan-2-yl trifluoromethanesulfonate (total 74 mg, 030 mmol) were added over the course of the next 24 h in several portions, while raising the reaction temperature gradually to 80° C. After cooled to rt, the reaction mixture was diluted with water and extracted with EtOAc. The combined organic extracts was dried (Na₂SO₄), filtered, concentrated, and purified by silica chromatography (0-50% EtOAc in hexanes) to afford the title compound as yellowish oil (5 mg, 12%). MS (apci) m/z=411.1 (M+H).

Step 2: Preparation of 11-Amino-3-cyclopropyl-7-(1,1,1-trifluoropropan-2-yl)-4,5,6,7-tetrahydroisoxazolo[4",3":6',7']cyclohepta[1',2':4,5]pyrrolo[2,3-d]pyrimidin-4-ol A mixture of 11-chloro-3-cyclopropyl-7-(1,1,1-trifluoropropan-2-yl)-6,7-dihydroisoxazolo[4",3":6',7']cyclohepta[1',2':4,5]pyrrolo[2,3-d]pyrimidin-4(5H)-one (5 mg, 0.012 mmol) and NH₄OH (28-30% aq) (0.24 mL) in 1,4-dioxane (243 µL) was sealed in a pressure vessel and stirred at 90° C. for 2 h. After cooled to rt, the reaction mixture was concentrated. The residue was taken up in MeOH (609 µL) and treated with NaBH₄ (4.6 mg, 0.12 mmol). The mixture was stirred at rt for 0.5 h then concentrated to dryness. The resulting solid was triturated with water, filtered, rinsed with water and dried to afford the title product as light yellowish solid (3 mg, 63%). MS (apci) m/z=394.2 (M+H).

Example 132 Example 133

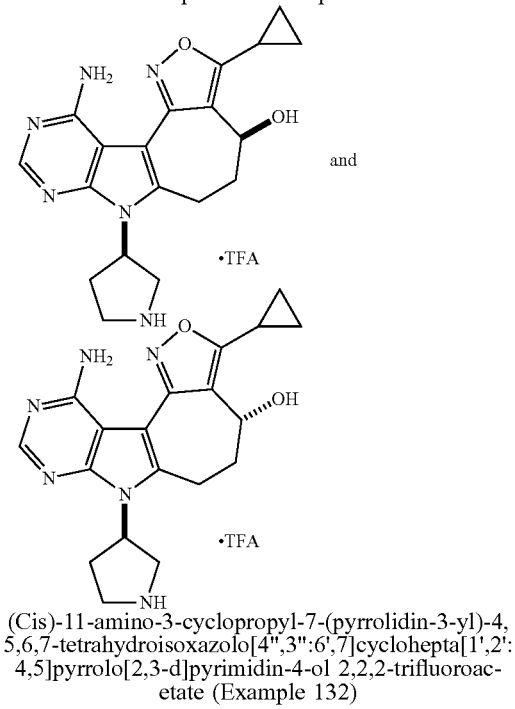

(Cis)-11-amino-3-cyclopropyl-7-(pyrrolidin-3-yl)-4,5,6,7-tetrahydroisoxazolo[4",3":6',7']cyclohepta[1',2':4,5]pyrrolo[2,3-d]pyrimidin-4-ol 2,2,2-trifluoroacetate (Example 132)

(Trans)-11-amino-3-cyclopropyl-7-(pyrrolidin-3-yl)-4,5,6,7-tetrahydroisoxazolo[4",3":6',7']cyclohepta[1',2':4,5]pyrrolo[2,3-d]pyrimidin-4-ol 2,2,2-trifluoroacetate (Example 133)

Step 1: Preparation of tert-butyl 3-(11-chloro-3-cyclopropyl-4-oxo-5,6-dihydroisoxazolo[4",3":6',7']cyclohepta[1',2':4,5]pyrrolo[2,3-d]pyrimidin-7(4H)-yl)pyrrolidine-1-carboxylate To a suspension of 11-chloro-3-cyclopropyl-6,7-dihydroisoxazolo[4",3":6',7']cyclohepta[1',2':4,5]pyrrolo[2,3-d]pyrimidin-4(5H)-one (Intermediate P36) (62 mg, 0.20 mmol), tert-butyl 3-hydroxypyrrolidine-1-carboxylate (48 mg, 0.26 mmol) and triphenylphosphine (78 mg, 0.30 mmol) in THF (2 mL) was dropwise added DIAD (57 µL, 0.30 mmol) at 0° C. The reaction was slowly warmed to rt and stirred for 16 h. It was then concentrated and purified by silica chromatography (0-80% EtOAc in hexanes) to afford the title compound as white foamy solid (65 mg, 68%). MS (apci) m/z=484.3 (M+H).

Step 2: Preparation of 11-amino-3-cyclopropyl-7-(pyrrolidin-3-yl)-6,7-dihydroisoxazolo[4",3":6',7']cyclohepta[1',2':4,5]pyrrolo[2,3-d]pyrimidin-4(5H)-one 2,2,2-trifluoroacetate To a solution of tert-butyl 3-(11-chloro-3-cyclopropyl-4-oxo-5,6-dihydroisoxazolo[4",3":6',7']cyclohepta[1',2':4,5]pyrrolo[2,3-d]pyrimidin-7(4H)-yl)pyrrolidine-1-carboxylate (60 mg, 0.124 mmol) in DMA (1.2 mL) was added 2,4-dimethoxybenzylamine (37.3 µL, 0.248 mmol). The mixture was heated at 70° C. for 2 h. After cooled to rt, the reaction mixture was diluted with EtOAc (15 mL), washed with water and citric acid (10%, 10 mL each), then dried (Na₂SO₄), filtered and concentrated. The resulting yellowish solid was treated with 2,2,2-trifluoroacetic acid (1.2 mL) and stirred at rt for 1 h. It was then concentrated, treated with NaHCO₃ (sat.) and filtered. The collected solid was rinsed with water and dried to give the crude title compound as a light yellowish solid, which was used directly in the next step without further purifications, assuming quantitative yield. MS (apci) m/z=365.2 (M+H).

Step 3: Preparation of 11-amino-3-cyclopropyl-7-(pyrrolidin-3-yl)-4,5,6,7-tetrahydroisoxazolo[4",3":6',7']cyclohepta[1',2':4,5]pyrrolo[2,3-d]pyrimidin-4-ol To a suspension of 11-amino-3-cyclopropyl-7-(pyrrolidin-3-yl)-6,7-dihydroisoxazolo[4",3":6',7']cyclohepta[1',2':4,5]pyrrolo[2,3-d]pyrimidin-4(5H)-one 2,2,2-trifluoroacetate (44 mg, 0.12 mmol) in MeOH (6 mL) was added NaBH₄ (14 mg, 0.36 mmol). The reaction was stirred for 1 h. The mixture was concentrated, triturated with water (5 mL), then filtered, rinsed with water (2 mL) and air-dried to give the crude title compound as white solid. It was used directly in the next step without further purifications, assuming quantitative yield. MS (apci) m/z=367.1 (M+H).

Step 4: Preparation of (Cis)- and (Trans)-11-amino-3-cyclopropyl-7-(pyrrolidin-3-yl)-4,5,6,7-tetrahydroisoxazolo[4",3":6',7']cyclohepta[1',2':4,5]pyrrolo[2,3-d]pyrimidin-4-ol 2,2,2-trifluoroacetate A portion of the crude product obtained from the previous step, 11-amino-3-cyclopropyl-7-(pyrrolidin-3-yl)-4,5,6,7-tetrahydroisoxazolo[4",3":6',7']cyclohepta[1',2':4,5]pyrrolo[2,3-d]pyrimidin-4-ol (8 mg) was subjected to reverse phase chromatography (0-95% MeCN in water with 0.1% TFA) to afford the title products, with the first eluent (2 mg) assigned as the cis- and the second eluent (4 mg), trans-isomer. The stereochemistry was arbitrarily assigned. MS (apci) m/z=367.1 (M+H).

Example 134

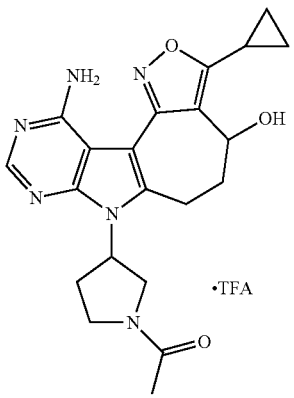 [SMILES: CC(=O)N1CCC(n2c3c(c4c(N)ncnc42)-c2noc(C4CC4)c2C(O)CC3)C1]

1-(3-(11-amino-3-cyclopropyl-4-hydroxy-5,6-dihydroisoxazolo[4",3":6',7']cyclohepta[1',2':4,5]pyrrolo[2,3-d]pyrimidin-7(4H)-yl)pyrrolidin-1-yl)ethan-1-one 2,2,2-trifluoroacetate To a suspension of 11-amino-3-cyclopropyl-7-(pyrrolidin-3-yl)-4,5,6,7-tetrahydroisoxazolo[4",3":6',7']cyclohepta[1',2':4,5]pyrrolo[2,3-d]pyrimidin-4-ol (Step 3 of Example 132) (15 mg, 0.031 mmol) in DCM (0.3 mL) was added TEA (13 μL, 0.094 mmol) followed by acetic anhydride (8.8 μL, 0.094 mmol) at rt. The reaction was then stirred for 15 min. The mixture was quenched with MeOH, concentrated and purified by reverse phase chromatography (0-95% MeCN in water with 0.1% TFA) to afford the title product as white solid (15 mg, 92%). MS (apci) m/z=409.3 (M+H).

Example 135

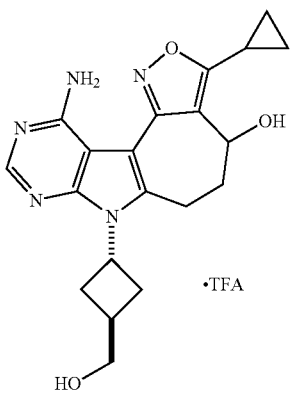 [SMILES: Nc1ncnc2c1c1c(n2[C@H]2C[C@H](CO)C2)CCC(O)c2c-1noc2C1CC1]

11-Amino-3-cyclopropyl-7-((1r,3r)-3-(hydroxymethyl)cyclobutyl)-4,5,6,7-tetrahydroisoxazolo[4",3":6',7']cyclohepta[1',2':4,5]pyrrolo[2,3-d]pyrimidin-4-ol 2,2,2-trifluoroacetate Step 1: Preparation of methyl (1r,3r)-3-(11-chloro-3-cyclopropyl-4-oxo-5,6-dihydroisoxazolo[4",3":6',7']cyclohepta[1',2':4,5]pyrrolo[2,3-d]pyrimidin-7(4H)-yl)cyclobutane-1-carboxylate To a suspension of 11-chloro-3-cyclopropyl-6,7-dihydroisoxazolo[4",3":6',7']cyclohepta[1',2':4,5]pyrrolo[2,3-d]pyrimidin-4(5H)-one (Intermediate P36) (45 mg, 0.14 mmol), methyl (1s,3s)-3-hydroxycyclobutane-1-carboxylate (37 mg, 0.29 mmol) and triphenylphosphine (75 mg, 0.29 mmol) in THF (1.4 mL) was added DIAD (56 μL, 0.29 mmol) dropwise at rt. The reaction was heated at 60° C. for 30 min then cooled to rt. The mixture was concentrated and purified by silica chromatography (0-50% EtOAc in hexanes) to give the title compound as white solid (31 mg, 51%). MS (apci) m/z=427.1 (M+H).

Step 2: Preparation of 11-amino-3-cyclopropyl-7-((1r,3r)-3-(hydroxymethyl)cyclobutyl)-4,5,6,7-tetrahydroisoxazolo[4",3":6',7']cyclohepta[1',2':4,5]pyrrolo[2,3-d]pyrimidin-4-ol 2,2,2-trifluoroacetate To a suspension of methyl (1r,3r)-3-(11-chloro-3-cyclopropyl-4-oxo-5,6-dihydroisoxazolo[4",3":6',7']cyclohepta[1',2':4,5]pyrrolo[2,3-d]pyrimidin-7(4H)-yl)cyclobutane-1-carboxylate (16 mg, 0.037 mmol) in THF (750 μL) was added LiBH₄ (2 M, THF) (94 μL, 0.19 mmol) at rt and stirred for 1 h. Ammonium hydroxide (28-30% aq) (75 μL) was then introduced. The reaction was sealed and heated at 70° C. for 90 min before it was cooled to rt, concentrated and subjected to reverse phase chromatography (0-95% MeCN in water with 0.1% TFA) to afford the title product as white solid (8 mg, 56%). MS (apci) m/z=382.2 (M+H).

Example 136

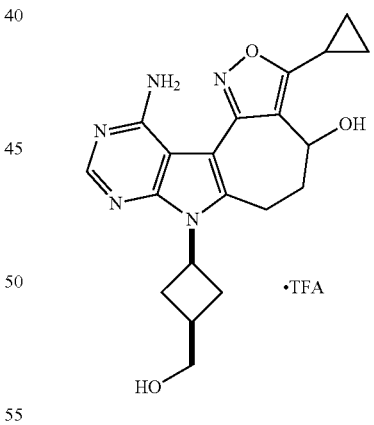

11-Amino-3-cyclopropyl-7-((1s,3s)-3-(hydroxymethyl)cyclobutyl)-4,5,6,7-tetrahydroisoxazolo[4",3":6',7']cyclohepta[1',2':4,5]pyrrolo[2,3-d]pyrimidin-4-ol 2,2,2-trifluoroacetate The title product was prepared in a similar fashion as described in Example 135, replacing methyl (1s,3s)-3-hydroxycyclobutane-1-carboxylate with methyl (1r,3r)-3-hydroxycyclobutane-1-carboxylate in step 1 instead (6 mg, 75%). MS (apci) m/z=382.1 (M+H).

Example 137

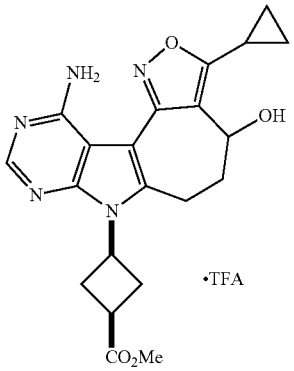 [SMILES: COC(=O)[C@H]1C[C@@H](n2c3c(c4c(N)ncnc42)-c2noc(C4CC4)c2C(O)CC3)C1]

Methyl (1s,3s)-3-(11-amino-3-cyclopropyl-4-hydroxy-5,6-dihydroisoxazolo[4",3":6',7']cyclohepta[1',2':4,5]pyrrolo[2,3-d]pyrimidin-7(4H)-yl)cyclobutane-1-carboxylate 2,2,2-trifluoroacetate Step 1: Preparation of methyl (1s,3s)-3-(11-chloro-3-cyclopropyl-4-oxo-5,6-dihydroisoxazolo[4",3":6',7']cyclohepta[1',2':4,5]pyrrolo[2,3-d]pyrimidin-7(4H)-yl)cyclobutane-1-carboxylate To a suspension of 11-chloro-3-cyclopropyl-6,7-dihydroisoxazolo[4",3":6',7']cyclohepta[1',2':4,5]pyrrolo[2,3-d]pyrimidin-4(5H)-one (Intermediate P36) (31 mg, 0.098 mmol), methyl (1r,3r)-3-hydroxycyclobutane-1-carboxylate (26 mg, 0.20 mmol) and triphenylphosphine (52 mg, 0.20 mmol) in THF (985 μL) was added DIAD (38 μl, 0.20 mmol) dropwise at rt. The reaction was then sealed and stirred at 50° C. for 30 min. After cooled to rt, the reaction was concentrated and purified by silica chromatography (0-50% EtOAc in hexanes) to afford the title compound as yellowish solid (19 mg, 45%). MS (apci) m/z=427.1 (M+H).

Step 2: Preparation of methyl (1s,3s)-3-(11-chloro-3-cyclopropyl-4-hydroxy-5,6-dihydroisoxazolo[4",3":6',7']cyclohepta[1',2':4,5]pyrrolo[2,3-d]pyrimidin-7(4H)-yl)cyclobutane-1-carboxylate To a suspension of methyl (1s,3s)-3-(11-chloro-3-cyclopropyl-4-oxo-5,6-dihydroisoxazolo[4",3":6',7']cyclohepta[1',2':4,5]pyrrolo[2,3-d]pyrimidin-7(4H)-yl)cyclobutane-1-carboxylate (19 mg, 0.045 mmol) in MeOH (2.2 mL) was added NaBH₄ (3.4 mg, 0.089 mmol) at 0° C. and stirred for 20 min. The mixture was quenched with water and NH₄Cl (sat.), then extracted with DCM. The combined DCM extracts was dried (Na₂SO₄), filtered and concentrated to give the crude title compound as yellowish solid, which was directly used in the next step without further purifications, assuming quantitative yield. MS (apci) m/z=429.1 (M+H).

Step 3: Preparation of methyl (1s,3s)-3-(11-amino-3-cyclopropyl-4-hydroxy-5,6-dihydroisoxazolo[4",3":6',7']cyclohepta[1',2':4,5]pyrrolo[2,3-d]pyrimidin-7(4H)-yl)cyclobutane-1-carboxylate 2,2,2-trifluoroacetate A mixture of methyl (1s,3s)-3-(11-chloro-3-cyclopropyl-4-hydroxy-5,6-dihydroisoxazolo[4",3":6',7']cyclohepta[1',2':4,5]pyrrolo[2,3-d]pyrimidin-7(4H)-yl)cyclobutane-1-carboxylate (9 mg, 0.02 mmol), NH₄OH (28-30% aq) (420 μL) and 1,4-dioxane (700 μL) was heated in a sealed vessel at 70° C. for 3 h. After cooled to rt, the reaction was subjected to reverse phase chromatography (0-95% MeCN in water with 0.1% TFA) to yield the title product as white solid (5 mg, 58%). MS (apci) m/z=410.1 (M+H).

Example 138

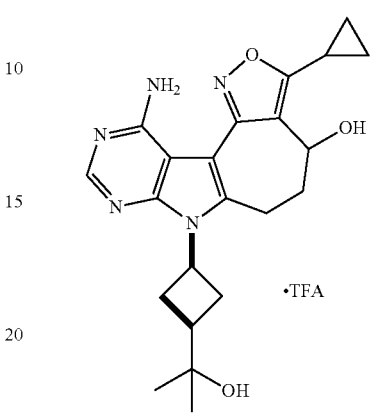

11-Amino-3-cyclopropyl-7-((1s,3s)-3-(2-hydroxypropan-2-yl)cyclobutyl)-4,5,6,7-tetrahydroisoxazolo[4",3":6',7']cyclohepta[1',2':4,5]pyrrolo[2,3-d]pyrimidin-4-ol 2,2,2-trifluoroacetate To a solution of methyl (1s,3s)-3-(11-chloro-3-cyclopropyl-4-hydroxy-5,6-dihydroisoxazolo[4",3":6',7']cyclohepta[1',2':4,5]pyrrolo[2,3-d]pyrimidin-7(4H)-yl)cyclobutane-1-carboxylate (Step 2 of Example 137) (10 mg, 0.023 mmol) in THF (777 μL) was added CH₃MgBr (3 M, THF) (78 μl, 0.23 mmol) at 0° C. and stirred for 1 h. Additional CH₃MgBr (3 M, THF) (78 μl, 0.23 mmol) was introduced, and the reaction was warmed to rt. It was subsequently quenched with NH₄Cl (sat.) and water, after which it was extracted with DCM. The combined DCM extracts were dried (Na₂SO₄), filtered and concentrated. The residue was then taken up in 1,4-dioxane and NH₄OH (28-30% aq) (0.5 mL each), sealed and heated at 90° C. for 2 h. After cooled to rt, the reaction mixture was subjected to reverse phase chromatography (0-95% MeCN in water with 0.1% TFA) to yield the title product as white solid (6 mg, 63%). MS (apci) m/z=410.1 (M+H).

Example 139

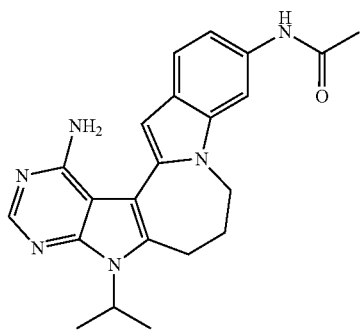 [SMILES: CC(=O)Nc1ccc2cc3n(c2c1)CCCc1c-3c2c(N)ncnc2n1C(C)C]

N-(1-amino-5-isopropyl-5,6,7,8-tetrahydropyrimido[5",4":4',5']pyrrolo[3',2':3,4]azepino[1,2-a]indol-11-yl)acetamide To a solution of 1-((2,4-dimethoxybenzyl)amino)-5-isopropyl-5,6,7,8-tetrahydropyrimido[5",4":4',5]pyrrolo[3',2':

3,4]azepino[1,2-a]indole-11-carboxylic acid (Intermediate P34) (9.5 mg, 0.018 mmol) in toluene (0.18 mL) were added triethylamine (1.8 mg, 0.018 mmol) and diphenylphosphoryl azide (39 μL, 0.18 mmol). The reaction mixture was degassed with argon then sealed and heated to 80° C. for 6 h. After cooled to ambient temperature and stirred for 2 d, the reaction was concentrated in vacuo and dried under high vacuum for 1 h. The resulting residue was then taken up in THF (181 μL) and treated with LiOH (2 M aq) (181 μL, 0.36 mmol). After stirred overnight at ambient temperature, the reaction was neutralized with sat. NH₄Cl (aq) and extracted with DCM. The combined organic extracts were concentrated and purified using silica chromatography (0-100% EtOAc in hexanes then 0-10% MeOH in EtOAc) to yield the intermediate N1-(2,4-dimethoxybenzyl)-5-isopropyl-5,6,7,8-tetrahydropyrimido[5",4":4',5']pyrrolo[3',2':3,4]azepino[1,2-a]indole-1,11-diamine. It was dissolved in toluene (904 μL) and treated with acetic anhydride (2.6 μL, 0.027 mmol). After 30 min stirring, the reaction residue was diluted with water (10 mL) and extracted with DCM (5×20 mL) though a Phase Separator frit. The combined organic extracts were concentrated, taken up in DCM (904 μL) and treated with triethylsilane (21.0 mg, 0.18 mmol) and TFA (139 μL). The reaction was stirred overnight at ambient temperature before it was neutralized with sat. NaHCO₃ (aq) (20 mL) and extracted with DCM (5×20 mL) through a Phase Separator frit. The combined organic extracts were concentrated and purified first by silica chromatography (0-100% EtOAc in hexanes then 0-10% MeOH in EtOAc), then by prep HPLC (5-95% ACN in water with 0.1% TFA). The product-containing fractions were concentrated, re-dissolved in MeOH (2 mL), then neutralized using a NaHCO₃ resin and eluted with MeOH. The filtrate was concentrated in vacuo to yield the title product (0.45 mg, 6%). MS (apci) m/z=389.2 (M+H).

Example 140

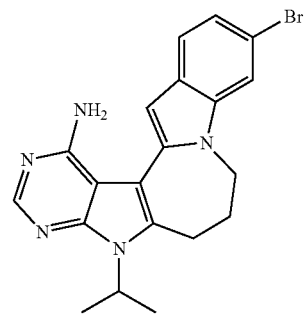 [SMILES: CC(C)n1c2c(c3c(N)ncnc31)-c1cc3ccc(Br)cc3n1CCC2]

11-Bromo-5-isopropyl-5,6,7,8-tetrahydropyrimido [5",4":4',5']pyrrolo[3',2':3,4]azepino[1,2-a]indol-1-amine The title product was prepared in a similar fashion as described in Example 86, replacing methyl 2-(4,4,5,5-tetramethyl-1,3,2-dioxaborolan-2-yl)-1H-indole-6-carboxylate with 6-bromo-2-(4,4,5,5-tetramethyl-1,3,2-dioxaborolan-2-yl)-1H-indole in Step 1 instead (1.1 mg, 23%). MS (apci) m/z=410.1, 412.1 (M+H).

The compounds in the following Table were prepared in a similar fashion as described in the synthesis of Example 119, replacing cyclopentanol in Step 1 with the appropriate alcohol instead.

TABLE K

| Ex # | Structure | Chemical Name | MS apci (m/z) |
|---|---|---|---|
| 141 | 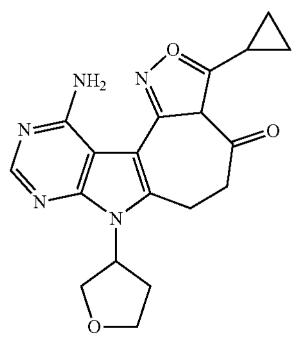 | 11-Amino-3-cyclopropyl-7-(tetrahydrofuran-3-yl)-6,7-dihydroisoxazolo[4",3":6',7']cyclohepta[1',2':4,5]pyrrolo[2,3-d]pyrimidin-4(5H)-one | 366.2 (M + H) |
| 142 | 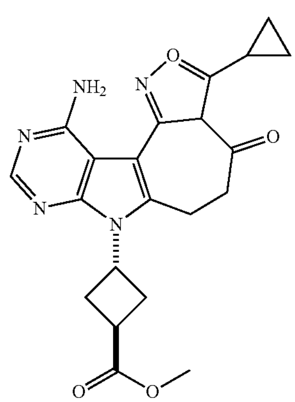 | Methyl (1r,3r)-3-(11-amino-3-cyclopropyl-4-oxo-5,6-dihydroisoxazolo[4",3":6',7']cyclohepta[1',2':4,5]pyrrolo[2,3-d]pyrimidin-7(4H)-yl)cyclobutane-1-carboxylate | 408.2 (M + H) |

TABLE K-continued

| Ex # | Structure | Chemical Name | MS apci (m/z) |
|---|---|---|---|
| 143 | 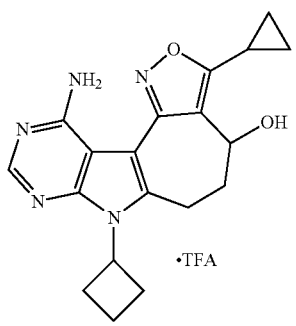 [SMILES: Nc1ncnc2c1c1c(n2C2CCC2)CCC(O)c2c-1noc2C1CC1] | 11-amino-3-cyclopropyl-7-(1,3-difluoropropan-2-yl)-6,7-dihydroisoxazolo[4",3":6',7']cyclohepta[1',2':4,5]pyrrolo[2,3-d]pyrimidin-4(5H)-one | 374.2 (M + H) |

Example 144

11-Amino-7-cyclobutyl-3-cyclopropyl-4,5,6,7-tetrahydroisoxazolo[4",3":6',7']cyclohepta[1',2':4,5]pyrrolo[2,3-d]pyrimidin-4-ol 2,2,2-trifluoroacetate Step 1: Preparation of 7-cyclobutyl-3-cyclopropyl-11-((2,4-dimethoxybenzyl)amino)-6,7-dihydroisoxazolo[4",3":6',7']cyclohepta[1',2':4,5]pyrrolo[2,3-d]pyrimidin-4(5H)-one A mixture of 3-cyclopropyl-11-((2,4-dimethoxybenzyl)amino)-6,7-dihydroisoxazolo[4",3":6',7']cyclohepta[1',2':4,5]pyrrolo[2,3-d]pyrimidin-4(5H)-one (Intermediate P37) (37 mg, 0.083 mmol), bromocyclobutane (34 mg, 0.25 mmol), and $Cs_2CO_3$ (41 mg, 0.12 mmol) in DMF (831 µL) was heated in a closed vessel at 90-100° C. for 6 h. After cooled to rt, the reaction was diluted with EtOAc/IPA (10:1) and washed with water. The organic layer was dried ($Na_2SO_4$), filtered and concentrated to afford the title compound as brownish solid. MS (apci) m/z=500.2 (M+H).

Step 2: Preparation of 11-amino-7-cyclobutyl-3-cyclopropyl-4,5,6,7-tetrahydroisoxazolo[4",3":6',7']cyclohepta[1',2':4,5]pyrrolo[2,3-d]pyrimidin-4-ol 2,2,2-trifluoroacetate A mixture of 7-cyclobutyl-3-cyclopropyl-11-((2,4-dimethoxybenzyl)amino)-6,7-dihydroisoxazolo[4",3":6',7']cyclohepta[1',2':4,5]pyrrolo[2,3-d]pyrimidin-4(5H)-one (20 mg, 0.04 mmol) and TFA (0.4 mL) was stirred at rt for 2 h then concentrated. It was taken up in MeOH (2 mL) and quenched with sat. $NaHCO_3$ (2 mL). To this mixture was added $NaBH_4$ (4.5 mg, 0.12 mmol) at rt and stirred for 30 min. It was then concentrated and purified by reverse-phase chromatography (0-95% MeCN in water with 0.1% TFA) to afford the title product as yellowish solid (7 mg, 38%). MS (apci) m/z=352.2 (M+H).

Example 145 Example 146

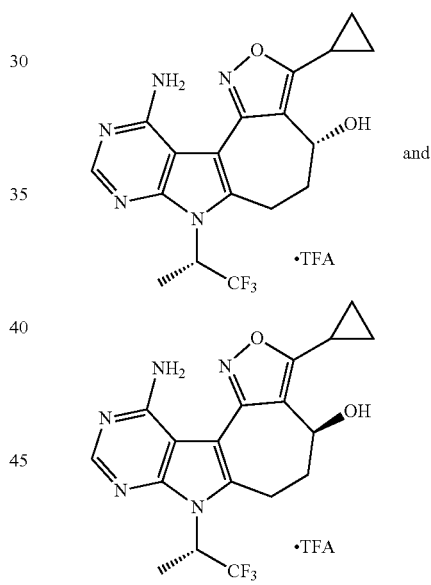

(R)-11-amino-3-cyclopropyl-7-((S)-1,1,1-trifluoropropan-2-yl)-4,5,6,7-tetrahydroisoxazolo[4",3":6',7']cyclohepta[1',2':4,5]pyrrolo[2,3-d]pyrimidin-4-ol 2,2,2-trifluoroacetate (Example 145)

(S)-11-amino-3-cyclopropyl-7-((S)-1,1,1-trifluoropropan-2-yl)-4,5,6,7-tetrahydroisoxazolo[4",3":6',7']cyclohepta[1',2':4,5]pyrrolo[2,3-d]pyrimidin-4-ol 2,2,2-trifluoroacetate (Example 146)

The title products were prepared in a similar fashion as described in Example 131, replacing 1,1,1-trifluoropropan-2-yl trifluoromethanesulfonate in Step 1 with (R)-1,1,1-trifluoropropan-2-yl trifluoromethanesulfonate (Intermediate R4) instead. The diastereomeric product mixture after ketone reduction in Step 2 was purified by reverse-phase chromatography (0-95% MeCN in water with 0.1% TFA) to afford the two title products. The first eluent peak was assigned as the (R,S)-isomer (5 mg, 8.5%) and the second eluent peak, the (S,R)-isomer (2 mg, 3.4%). The absolute stereochemistry of the two title products was arbitrarily assigned. MS (apci) m/z=394.1 (M+H).

Example 147

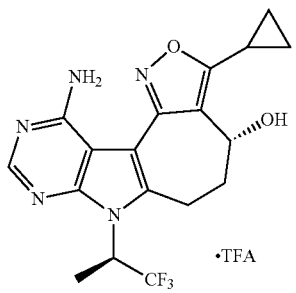 [SMILES: C[C@@H](n1c2c(c3c(N)ncnc31)-c1noc(C3CC3)c1[C@H](O)CC2)C(F)(F)F]

(R)-11-amino-3-cyclopropyl-7-((R)-1,1,1-trifluoropropan-2-yl)-4,5,6,7-tetrahydroisoxazolo[4",3":6',7']cyclohepta[1',2':4,5]pyrrolo[2,3-d]pyrimidin-4-ol 2,2,2-trifluoroacetate The title products were prepared in a similar fashion as described in Example 131, replacing 1,1,1-trifluoropropan-2-yl trifluoromethanesulfonate in Step 1 with (S)-1,1,1-trifluoropropan-2-yl trifluoromethanesulfonate (Intermediate R5) instead. The diastereomeric product mixture after ketone reduction in Step 2 was purified by reverse-phase chromatography (0-95% MeCN in water with 0.1% TFA) to afford the title product, which was the first eluent peak and assigned as the (R,R)-isomer as shown (1 mg, 10%). The second eluent product peak, which would have been assigned as the (S,R)-isomer, (S)-11-amino-3-cyclopropyl-7-((R)-1,1,1-trifluoropropan-2-yl)-4,5,6,7-tetrahydroisoxazolo[4",3":6',7']cyclohepta[1',2':4,5]pyrrolo[2,3-d]pyrimidin-4-ol, was not isolated in sufficient amount to be further characterized. The absolute stereochemistry was arbitrarily assigned. MS (apci) m/z=394.1 (M+H).

Example 148

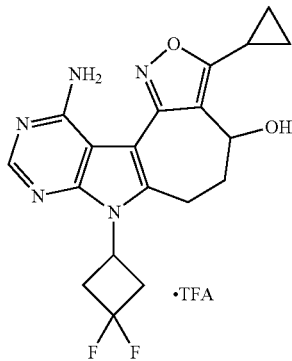 [SMILES: Nc1ncnc2c1c1c(n2C2CC(F)(F)C2)CCC(O)c2c-1noc2C1CC1]

11-amino-3-cyclopropyl-7-(3,3-difluorocyclobutyl)-4,5,6,7-tetrahydroisoxazolo[4",3":6',7']cyclohepta[1',2':4,5]pyrrolo[2,3-d]pyrimidin-4-ol 2,2,2-trifluoroacetate The title products were prepared in a similar fashion as described in Example 131, replacing 1,1,1-trifluoropropan-2-yl trifluoromethanesulfonate in Step 1 with 3,3-difluorocyclobutyl trifluoromethanesulfonate (Intermediate R6) instead (16 mg, 65%). MS (apci) m/z=388.1 (M+H).

Example 149

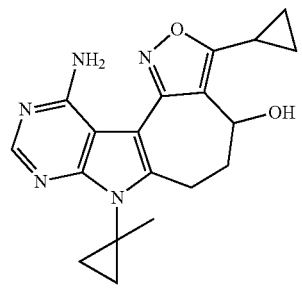 [SMILES: CC1(n2c3c(c4c(N)ncnc42)-c2noc(C4CC4)c2C(O)CC3)CC1]

11-Amino-3-cyclopropyl-7-(1-methylcyclopropyl)-4,5,6,7-tetrahydroisoxazolo[4",3":6',7']cyclohepta[1',2':4,5]pyrrolo[2,3-d]pyrimidin-4-ol Step 1: Preparation of 11-chloro-3-cyclopropyl-7-(1-methylcyclopropyl)-4,5,6,7-tetrahydroisoxazolo[4",3":6',7']cyclohepta[1',2':4,5]pyrrolo[2,3-d]pyrimidin-4-ol To a solution of 11-chloro-3-cyclopropyl-7-(1-methylcyclopropyl)-6,7-dihydroisoxazolo[4",3":6',7']cyclohepta[1',2':4,5]pyrrolo[2,3-d]pyrimidin-4(5H)-one (Intermediate P40) (47 mg, 0.13 mmol) in MeOH (637 µL) cooled to 0° C. was added NaBH$_4$ (14 mg, 0.38 mmol). The reaction was warmed to rt and stirred for 15 min before it was diluted with water and extracted with DCM. The combined organic extracts were concentrated to afford the title compound, which was used in the next step without further purifications, assuming quantitative yield. MS (apci) m/z=371.1 (M+H).

Step 2: Preparation of 11-amino-3-cyclopropyl-7-(1-methylcyclopropyl)-4,5,6,7-tetrahydroisoxazolo[4",3":6',7']cyclohepta[1',2':4,5]pyrrolo[2,3-d]pyrimidin-4-ol A solution of 11-chloro-3-cyclopropyl-7-(1-methylcyclopropyl)-4,5,6,7-tetrahydroisoxazolo[4",3":6',7']cyclohepta[1',2':4,5]pyrrolo[2,3-d]pyrimidin-4-ol (47 mg, 0.13 mmol) in 1,4-dioxane (1.3 mL) and conc. NH$_4$OH (634 µl) was sealed in a pressure vessel and heated to 75° C. for 2 h. After cooled to rt, the reaction mixture was concentrated and purified by reverse-phase chromatography (5-90% MeCN in water) to afford the title product (22 mg, 49%). MS (apci) m/z=352.2 (M+H).

Example 150

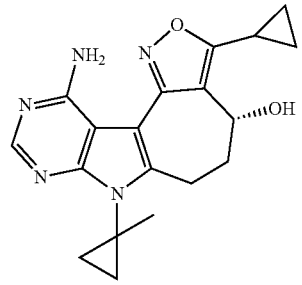 [SMILES: CC1(n2c3c(c4c(N)ncnc42)-c2noc(C4CC4)c2[C@H](O)CC3)CC1]

(R)-11-Amino-3-cyclopropyl-7-(1-methylcyclopropyl)-4,5,6,7-tetrahydroisoxazolo[4",3":6',7']cyclohepta[1',2':4,5]pyrrolo[2,3-d]pyrimidin-4-ol Step 1: Preparation of (R)-11-chloro-3-cyclopropyl-7-(1-methylcyclopropyl)-4,5,6,7-tetrahydroisoxazolo[4",3":6',7']cyclohepta[1',2':4,5]pyrrolo[2,3-d]pyrimidin-4-ol To a solution of (S)—CBS (1 M toluene) (224 µL, 0.224 mmol) in THF (1 mL) cooled to 0° C. was added BH$_3$—

SMe₂ (21.2 μL, 0.224 mmol). After 15 min stirring, a solution of 11-chloro-3-cyclopropyl-7-(1-methylcyclopropyl)-6,7-dihydroisoxazolo[4",3":6',7]cyclohepta[1',2':4,5]pyrrolo[2,3-d]pyrimidin-4(5H)-one (Intermediate P40) (75 mg, 0.203 mmol) in THF (1 mL) was introduced dropwise, and stirring continued at 0° C. for 150 min. The reaction was then diluted with water then extracted with DCM. The combined organic extracts were concentrated to afford the title compound, which was used in the next step without further purifications, assuming quantitative yield. MS (apci) m/z=371.1 (M+H).

Step 2: Preparation of (R)-11-amino-3-cyclopropyl-7-(1-methylcyclopropyl)-4,5,6,7-tetrahydroisoxazolo[4",3":6',7']cyclohepta[1',2':4,5]pyrrolo[2,3-d]pyrimidin-4-ol A solution of (R)-11-chloro-3-cyclopropyl-7-(1-methylcyclopropyl)-4,5,6,7-tetrahydroisoxazolo[4",3":6',7']cyclohepta[1',2':4,5]pyrrolo[2,3-d]pyrimidin-4-ol (70 mg, 0.189 mmol) in 1,4-dioxane (1.8 mL) and conc. NH₄OH (944 μL) was sealed in a pressure vessel and heated to 75° C. for 1 h. After cooled to rt, the reaction mixture was concentrated and purified by reverse-phase chromatography (5-90% MeCN in water) to afford the title product (17.1 mg, 26%), which contained 12% of the opposite enantiomeric isomer product, (S)-11-Amino-3-cyclopropyl-7-(1-methylcyclopropyl)-4,5,6,7-tetrahydroisoxazolo[4",3":6',7']cyclohepta[1',2':4,5]pyrrolo[2,3-d]pyrimidin-4-ol, as determined by chiral HPLC. MS (apci) m/z=352.2 (M+H).

Example 151

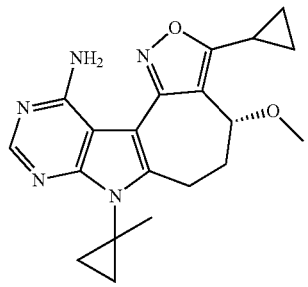 [SMILES: CO[C@@H]1CCc2c(c3c(N)ncnc3n2C2(C)CC2)-c2noc(C3CC3)c21]

(R)-3-Cyclopropyl-4-methoxy-7-(1-methylcyclopropyl)-4,5,6,7-tetrahydroisoxazolo[4",3":6',7]cyclohepta[1',2':4,5]pyrrolo[2,3-d]pyrimidin-11-amine To a solution of (R)-11-amino-3-cyclopropyl-7-(1-methylcyclopropyl)-4,5,6,7-tetrahydroisoxazolo[4",3":6',7']cyclohepta[1',2':4,5]pyrrolo[2,3-d]pyrimidin-4-ol (Example 150) (15 mg, 0.043 mmol) in THF (142 μl) and DMF (85 μl) cooled to 0° C. was added NaH (1.0 mg, 0.043 mmol). After 10 min stirring, iodomethane (2.6 μL, 0.043 mmol) was introduced and the reaction mixture was allowed to slowly warm to rt and stirred for 2.5 h. The reaction was then quenched with sat. NH₄Cl, diluted with sat. NaHCO₃ and extracted with DCM. The combined organic extracts were concentrated and purified by reverse-phase chromatography (5-90% MeCN in water with 0.1% TFA). The combined product fractions was diluted with sat. NaHCO₃ and extracted with DCM. The combined organic extracts were concentrated and purified again by silica chromatography (5-75% acetone in DCM) to afford the title product (8 mg, 51%). MS (apci) m/z=366.2 (M+H).

| Abbreviations: | |
|---|---|
| ACN | Acetonitrile |
| AcOH | Acetic Acid |
| AIBN | Azobisisobutyronitrile |
| aq | Aqueous |
| n-BuLi | n-butyllithium or 1-butyllithium |
| Celite ® | Diatomaceous earth; SiO₂ |
| CuI | Copper (I) Iodide |
| Cu(OAc)₂ | Copper (II) acetate |
| d | day, days |
| DBU | 1,8-Diazabicyclo[5.4.0]undec-7-ene |
| DCE or 1,2-DCE | 1,2-Dichloroethane |
| DCM | Dichloromethane |
| DEA | Diethyl amine |
| DIAD | Diisopropyl azodicarboxylate |
| DIBAL-H | Diisobutylaluminum Hydride |
| DIEA | N,N-Diisopropylethylamine |
| DMA | N,N-Dimethylacetamide |
| DMDS | Dimethyl disulfide |
| DMAP | 4-Dimethylaminopyridine |
| DMF | N,N-Dimethylformamide |
| DMP | Dess-MartinPeriodinane; 1,1,1-Tris(acetyloxy)-1,1-dihydro-1,2-benziodoxol-3-(1H)-one |
| DMSO | Dimethylsulfoxide |
| dioxane | 1,4-dioxane |
| DPPA | Diphenylphosphoryl Azide |
| eq | equivalent |
| Et₂O | Diethyl Ether |
| Et₃SiH | Triethyl Silane |
| EtOAc | Ethyl Acetate |
| EtOH | Ethanol |
| GF/F paper | GF/F glass microfiber filter paper |
| h | hour, hours |

| Abbreviations: | |
|---|---|
| HATU | 1-[Bis(dimethylamino)methylene]-1H-1,2,3-triazolo[4,5-b] pyridinium 3-oxide hexafluorophosphate or 2-(7-Aza-1H-benzotriazole-1-yl)-1,1,3,3-tetramethyluronium hexafluorophosphate |
| HPLC | High-Performance Liquid Chromatography |
| iPrOH or IPA | Isopropanol |
| LCMS | Liquid chromatography-mass spectrometry |
| LiHMDS | Lithium Hexamethyldisilazide; or Lithium bis(trimethylsilyl)amide |
| LiOH | Lithium Hydroxide |
| LDA | Lithium Diisopropylamide |
| MeCN | Acetonitrile |
| MeLi | Methyl Lithium |
| MeMgBr | Methyl Magnesium Bromide |
| MeOH | Methanol |
| mCPBA | meta-Chloroperoxybenzoic acid |
| MeMgBr | Methyl magnesium bromide |
| min | minute, minutes |
| MS | Mass spectrometry |
| MsCl | methanesulfonyl chloride |
| MTBE | Methyl tert-Butyl Ether |
| $NaBH(OAc)_3$ | Sodium Triacetoxyborohydride |
| NaH | Sodium Hydride |
| NaOAc | Sodium Acetate |
| NBS | N-Bromosuccinimide |
| NCS | N-Chlorosuccinimide |
| NIS | N-Iodosuccinimide |
| $NH_2OH \cdot HCl$ | hydroxylamine hydrochloride |
| P1-$HCO_3$ resin | Stratospheres MP-HCO3 |
| 10% Pd/C | Palladium 10 wt. % (dry basis), active carbon, wet, Degussa |
| $Pd(PPh_3)_4$ | Tetrakis(triphenylphosphine)palladium (0) |
| PMB | para-Methoxybenzyl |
| $(PPh_3)_2Pd(II)Cl_2$ or $PdCl_2(PPh_3)_2$ | Palladium(II)bis(triphenylphosphine) dichloride |
| PPA | Polyphosphoric Acid |
| RT | Room temperature |
| SEM-Cl | 2-(Trimethylsilyl)ethoxymethyl Chloride |
| SFC | Supercritical fluid chromatography |
| $SOCl_2$ | Thionyl chloride |
| TBAF | Tetra-n-butylammonium fluoride |
| TBDMS or TBS | Tert-butyldimethyl silyl |
| TEA | Triethylamine |
| TFA | Trifluoroacetic Acid |
| TfOH | Trifluoromethanesulfonic Acid |
| THF | tetrahydrofuran |
| TMSCl | Trimethylsilyl Chloride |
| TMSOTf | Trimethylsilyl trifluoromethanesulfonate |
| Triphosgene | (bis(trichloromethyl) carbonate |
| Xantphos | 4,5-Bis(diphenylphosphino)-9,9-dimethylxanthene |

ADDITIONAL EMBODIMENTS

Embodiment 1

A compound of Formula I

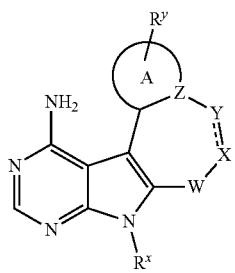

I and tautomers, stereoisomers, and pharmaceutically acceptable salts and solvates thereof, wherein:

W is $CR^3R^4$,

------- represents a single or a double bond, wherein when ------- is a double bond, then X is $CR^5$ and Y is $CR^6$, and when ------- is a single bond, then X is O, $CR^7R^8$ or $NR^9$ and Y is C(=O), $SO_2$, $CR^{10}R^{11}$ or O, and Z is C or N;

$R^3$ is hydrogen;

$R^4$ is hydrogen;

$R^5$ is hydrogen;

$R^6$ is hydrogen;

$R^7$ is hydrogen or C1-C6 alkyl;

$R^8$ is hydrogen;

$R^9$ is hydrogen, C1-C6 alkyl, hydroxyC1-C6 alkyl-, (C1-C6 alkyl)$SO_2$—, (C1-C6 alkoxy)C1-C6 alkyl, C3-C6 cycloalkyl, (C3-C6 cycloalkyl)C1-C6 alkyl-, hetCyc$^1$, (hetCyc$^1$)C1-C6 alkyl-, Ar$^1$, (Ar$^1$)C1-C6 alkyl-, hetAr$^1$, (hetAr$^1$)C1-C6 alkyl-, (C1-C6 alkyl)C(=O)—, (fluoroC1-C6 alkyl)C(=O)—, $H_2$NC(=O)—, Ar$^1$CH$_2$C(=O)— or (C3-C6 cycloalkyl)C(=O)—;

$R^{10}$ is hydrogen, hydroxy, C1-C6 alkoxy, or $R^aR^bN$— where $R^a$ and $R^b$ are independently H or C1-C6 alkyl;

$R^{11}$ is hydrogen, C1-C6 alkyl, or fluoroC1-C6 alkyl;

hetCyc$^1$ is a 5-6 membered saturated heterocyclic ring having 1-2 ring heteroatoms independently selected from N and SO$_2$, wherein said heterocyclic ring is optionally substituted with C1-C6 alkyl or (Ar$^2$)C1-C6 alkyl-;

Ar$^1$ is phenyl optionally substituted with one or more substituents independently selected from halogen and C1-C6 alkoxy;

hetAr$^1$ is a 5-6 membered heteroaryl ring having 1-2 ring nitrogen atoms, wherein said heteroaryl ring is optionally substituted with C1-C6 alkyl;

Ar$^2$ is phenyl optionally substituted with one or more substituents independently selected from halogen and C1-C6 alkoxy;

Ring A, including the atoms at the points of attachment to the ring containing Z, Y, X, and W, is:
(i) a monocyclic aryl ring when Z is C, wherein said ring is optionally substituted with halogen, C3-C6 cycloalkyl, C1-C6 alkoxy, R$^c$NHC(=O)—, R$^c$C(=O)NH—, or R$^c$NHC(=O)NH—,
(ii) a 5-membered monocyclic heteroaryl ring having 2 ring heteroatoms independently selected from N and O when Z is C, or when Z is N, a 5-membered heteroaryl ring having two ring nitrogen atoms, one of which is Z, wherein said rings are optionally substituted with C1-C6 alkyl or C3-C6 cycloalkyl, or
(iii) when Z is N, a bicyclic heteroaryl ring having one ring nitrogen atom which is Z, wherein said ring is optionally substituted with R$^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—;

R$^c$ is C3-C6 cycloalkyl or (C3-C6 cycloalkyl)CH$_2$—;

R$^d$ is C1-C6 alkyl, C1-C6 alkoxy, Cyc$^1$, Cyc$^1$CH$_2$—, phenyl or hetAr$^2$;

Cyc$^1$ is C3-C6 cycloalkyl optionally substituted with C1-C6 alkyl;

hetAr$^2$ is (i) pyrazolyl optionally substituted with 1-2 substituents independently selected from C1-C6 alkyl, fluoroC1-C6 alkyl, (di-C1-C6 alkyl)NC(=O)CH$_2$—, (hetCyc$^2$)CH$_2$CH$_2$—, phenyl, and (C1-C6 alkoxy)C1-C6 alkyl, or (ii) pyridyl;

hetCyc$^2$ is a 6-membered saturated heterocyclic ring having 2 ring heteroatoms independently selected from N and O;

R$^x$ is hydrogen, C1-C6 alkyl, fluoroC1-C6 alkyl, Cyc$^2$, Cyc$^3$, hetCyc$^3$, Ar$^a$ or hetAr$^3$;

Cyc$^2$ is a 3-6 membered saturated carbocyclic ring optionally substituted with 1-2 substituents independently selected from halogen, C1-C6 alkyl, hydroxy, hydroxyC1-C6 alkyl, and (C1-C6 alkoxy)C(=O)—;

Cyc$^3$ is cyclopentenyl;

hetCyc$^3$ is a 5-membered saturated heterocyclic ring having a ring heteroatom selected from N and O and optionally substituted with (C1-C6 alkyl)C(=O)—;

Ar$^3$ is phenyl optionally substituted with (C1-C6 alkoxy)C(=O)—;

hetAr$^3$ is a 5-6 membered heteroaryl ring having 1-2 ring nitrogen atoms and optionally substituted with C1-C6 alkyl or C1-C6 alkoxy; and R$^y$ is hydrogen or halogen.

Embodiment 2

A compound according to embodiment 1, wherein Ring A is a monocyclic aryl ring when Z is C, wherein said ring is optionally substituted with halogen, C3-C6 cycloalkyl, C1-C6 alkoxy, R$^c$NHC(=O)—, R$^c$C(=O)NH—, or R$^c$NHC(=O)NH—.

Embodiment 3

A compound according to embodiment 1, wherein Ring A is a 5-membered monocyclic heteroaryl ring having 2 ring heteroatoms independently selected from N and O when Z is C, or when Z is N, a 5-membered heteroaryl ring having two ring nitrogen atoms, one of which is Z, wherein said rings are optionally substituted with C1-C6 alkyl or C3-C6 cycloalkyl.

Embodiment 4

A compound according to embodiment 1, wherein Ring A is a bicyclic heteroaryl ring having one ring nitrogen atom that results when Z is N, wherein said ring is optionally substituted with R$^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—.

Embodiment 5

A compound according to embodiment 1, wherein W is CR$^3$R$^4$, X is CR$^7$R$^8$, Y is C(=O), Z is N, and ------ is a single bond, wherein Formula I is represented by Formula I-A

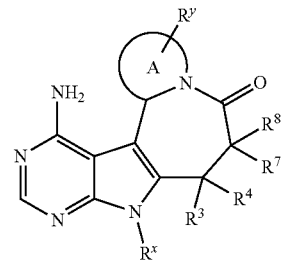

I-A wherein Ring A is (ii) a 5-membered heteroaryl ring having two ring nitrogen atoms, one of which is Z, wherein said ring is optionally substituted with C1-C6 alkyl or C3-C6 cycloalkyl, or (iii) a bicyclic heteroaryl ring having one ring nitrogen atom that results when Z is N, wherein said ring is optionally substituted with R$^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—.

Embodiment 6

A compound according to embodiment 5, wherein Ring A is a bicyclic heteroaryl ring having one ring nitrogen atom that results when Z is N, wherein said ring is optionally substituted with R$^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—.

Embodiment 7

A compound according to embodiment 6, wherein Ring A is 5,6-bicyclic heteroaryl ring optionally substituted with R$^d$NHC(=O)—.

Embodiment 8

A compound according to embodiment 1, wherein W is CR³R⁴, X is NR⁹, Y is C(=O), Z is N, and ------- is a single bond, wherein Formula I is represented by Formula I-B

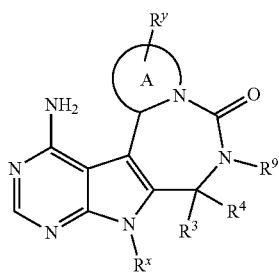

I-B wherein Ring A is (ii) a 5-membered heteroaryl ring having two ring nitrogen atoms, one of which is Z, wherein said ring is optionally substituted with C1-C6 alkyl or C3-C6 cycloalkyl, or (iii) a bicyclic heteroaryl ring having one ring nitrogen atom that results when Z is N, wherein said ring is optionally substituted with $R^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—.

Embodiment 9

A compound according to embodiment 9, wherein Ring A is a 5-membered heteroaryl ring having two ring nitrogen atoms, one of which is Z, wherein said ring is optionally substituted with C1-C6 alkyl or C3-C6 cycloalkyl.

Embodiment 10

A compound according to embodiment 8, wherein Ring A is a bicyclic heteroaryl ring having one ring nitrogen atom that results when Z is N, wherein said ring is optionally substituted with $R^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—.

Embodiment 11

A compound according to any one of embodiments 8-10, wherein R⁹ is hydrogen.

Embodiment 12

A compound according to embodiment 1, wherein W is CR³R⁴, X is NR⁹, Y is C(=O), Z is C, and ------- is a single bond, wherein Formula I is represented by Formula I-C:

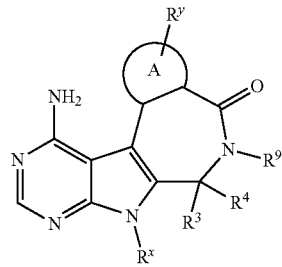

I-C wherein Ring A is (i) a monocyclic aryl ring, wherein said ring is optionally substituted with halogen, C3-C6 cycloalkyl, C1-C6 alkoxy, $R^c$NHC(=O)—, $R^c$C(=O)NH—, or $R^c$NHC(=O)NH— or (ii) a 5-membered monocyclic heteroaryl ring having 2 ring heteroatoms independently selected from N and O, wherein said ring is optionally substituted with C1-C6 alkyl or C3-C6 cycloalkyl.

Embodiment 13

A compound according to embodiment 12, wherein Ring A is a monocyclic aryl ring, wherein said ring is optionally substituted with halogen, C3-C6 cycloalkyl, C1-C6 alkoxy, $R^c$NHC(=O)—, $R^c$C(=O)NH—, or $R^c$NHC(=O)NH—.

Embodiment 14

A compound according to embodiment 12, wherein Ring A is a 5-membered monocyclic heteroaryl ring having 2 ring heteroatoms independently selected from N and O, wherein said ring is optionally substituted with C1-C6 alkyl or C3-C6 cycloalkyl.

Embodiment 15

A compound according to any one of embodiments 12-14, wherein R⁹ is hydrogen, C1-C6 alkyl, (C1-C6 alkoxy)C1-C6 alkyl, (C3-C6 cycloalkyl)C1-C6 alkyl-, hetCyc¹, (hetCyc¹)C1-C6 alkyl-, hetAr¹, (hetAr¹)C1-C6 alkyl-, or (Ar¹)C1-C6 alkyl-.

Embodiment 16

A compound according to embodiment 1, wherein W is CR³R⁴, X is O, Y is C(=O), Z is C, and ------- is a single bond, wherein Formula I is represented by Formula I-D

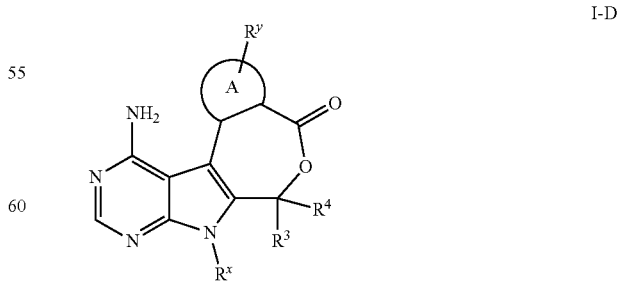

I-D wherein Ring A is (i) a monocyclic aryl ring, wherein said ring is optionally substituted with halogen, C3-C6 cycloalkyl, C1-C6 alkoxy, $R^c$NHC(=O)—, $R^c$C(=O)NH—, or R$^c$NHC(=O)NH— wherein R$^c$ is defined according to embodiment 1 or (ii) a 5-membered monocyclic heteroaryl ring having 2 ring heteroatoms independently selected from N and O, wherein said ring is optionally substituted with C1-C6 alkyl or C3-C6 cycloalkyl.

Embodiment 17

A compound according to embodiment 16, wherein Ring A is a 5-membered monocyclic heteroaryl ring having 1-2 ring heteroatoms independently selected from N and O, wherein said ring is optionally substituted with C1-C6 alkyl or C3-C6 cycloalkyl.

Embodiment 18

A compound according to embodiment 1, wherein W is CR$^3$R$^4$, X is NR$^9$, Y is SO$_2$, Z is C, and ------- is a single bond, wherein Formula I can be represented by Formula I-E

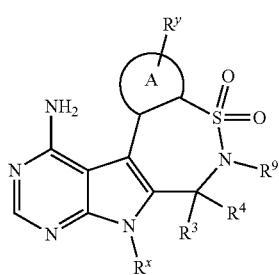

I-E wherein Ring A is (i) a monocyclic aryl ring, wherein said ring is optionally substituted with halogen, C3-C6 cycloalkyl, C1-C6 alkoxy, R$^c$NHC(=O)—, R$^c$C(=O)NH—, or R$^c$NHC(=O)NH— or (ii) a 5-membered monocyclic heteroaryl ring having 2 ring heteroatoms independently selected from N and O, wherein said ring is optionally substituted with C1-C6 alkyl or C3-C6 cycloalkyl.

Embodiment 19

A compound according to embodiment 18, wherein Ring A is a 5-membered monocyclic heteroaryl ring having 2 ring heteroatoms independently selected from N and O, wherein said ring is optionally substituted with C1-C6 alkyl or C3-C6 cycloalkyl.

Embodiment 20

A compound according to any one of embodiments 18-19, wherein R$^9$ is hydrogen or C1-C6 alkyl.

Embodiment 21

A compound according to embodiment 1, wherein W is CR$^3$R$^4$, X is CR$^7$R$^8$, Y is SO$_2$, Z is C, and ------- is a single bond, wherein the compound has the structure of Formula I-F:

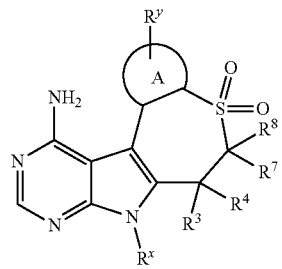

I-F wherein Ring A is (i) a monocyclic aryl ring, wherein said ring is optionally substituted with halogen, C3-C6 cycloalkyl, C1-C6 alkoxy, R$^c$NHC(=O)—, R$^c$C(=O)NH—, or R$^c$NHC(=O)NH— or (ii) a 5-membered monocyclic heteroaryl ring having 2 ring heteroatoms independently selected from N and O, wherein said ring is optionally substituted with C1-C6 alkyl or C3-C6 cycloalkyl.

Embodiment 22

A compound according to embodiment 21, wherein Ring A is a 5-membered heteroaryl ring having 2 ring heteroatoms independently selected from N and O, wherein said ring is optionally substituted C$_1$-C6 alkyl or C3-C6 cycloalkyl.

Embodiment 23

A compound according to embodiment 21 or 22, wherein R$^7$ and R$^8$ are hydrogen.

Embodiment 24

A compound according to embodiment 1, wherein W is CR$^3$R$^4$, X is CR$^7$R$^8$, Y is C(=O), Z is C, and ------- is a single bond, wherein the compound has the structure of Formula I-G

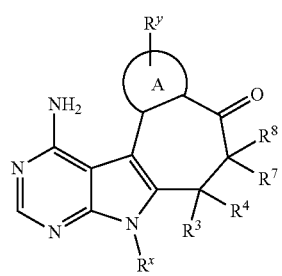

I-G wherein Ring A is (i) a monocyclic aryl ring, wherein said ring is optionally substituted with halogen, C3-C6 cycloalkyl, C1-C6 alkoxy, R$^c$NHC(=O)—, R$^c$C(=O)NH—, or R$^c$NHC(=O)NH— or (ii) a 5-membered monocyclic heteroaryl ring having 2 ring heteroatoms independently selected from N and O, wherein said ring is optionally substituted with C1-C6 alkyl or C3-C6 cycloalkyl.

Embodiment 25

A compound according to embodiment 24, wherein Ring A is a 5-membered heteroaryl ring having 2 ring heteroatoms independently selected from N and O, wherein said ring is optionally substituted with C1-C6 alkyl or C3-C6 cycloalkyl.

Embodiment 26

A compound according to embodiment 24 or 25, wherein $R^7$ and $R^8$ are hydrogen.

Embodiment 27

A compound according to embodiment 1, wherein W is $CR^3R^4$, X is $CR^7R^8$, Y is $CR^{10}R^{11}$, Z is C, and ------- is a single bond, wherein the compound is represented by the structure of Formula I-H:

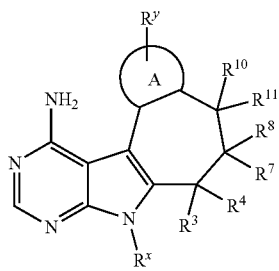

I-H wherein Ring A is (i) a monocyclic aryl ring, wherein said ring is optionally substituted with halogen, C3-C6 cycloalkyl, C1-C6 alkoxy, $R^cNHC(=O)$—, $R^cC(=O)NH$—, or $R^cNHC(=O)NH$— or (ii) a 5-membered monocyclic heteroaryl ring having 2 ring heteroatoms independently selected from N and O, wherein said ring is optionally substituted with C1-C6 alkyl or C3-C6 cycloalkyl.

Embodiment 28

A compound according to embodiment 27, wherein Ring A is a 5-membered heteroaryl ring having 2 ring heteroatoms independently selected from N and O, wherein said ring is optionally substituted with C1-C6 alkyl or C3-C6 cycloalkyl.

Embodiment 29

A compound according to embodiment 27 or 28, wherein $R^7$ and $R^8$ are hydrogen.

Embodiment 30

A compound according to embodiment 1, wherein W is $CR^3R^4$, X is $NR^9$, Y is $CR^{10}R^{11}$, Z is C, and ------- is a single bond, wherein the compound is represented by the structure of Formula I-I:

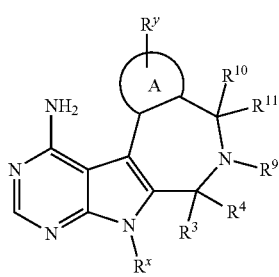

I-I wherein Ring A is (i) a monocyclic aryl ring, wherein said ring is optionally substituted with halogen, C3-C6 cycloalkyl, C1-C6 alkoxy, $R^cNHC(=O)$—, $R^cC(=O)NH$—, or $R^cNHC(=O)NH$— or (ii) a 5-membered monocyclic heteroaryl ring having 2 ring heteroatoms independently selected from N and O, wherein said ring is optionally substituted with C1-C6 alkyl or C3-C6 cycloalkyl.

Embodiment 31

A compound according to embodiment 30, wherein Ring A is a 5-membered heteroaryl ring having 2 ring heteroatoms independently selected from N and O, wherein said ring is optionally substituted with C1-C6 alkyl or C3-C6 cycloalkyl.

Embodiment 32

A compound according to embodiment 31, wherein $R^9$ is hydrogen, C1-C6 alkyl, hydroxyC1-C6 alkyl-, C3-C6 cycloalkyl, $Ar^1$, $hetAr^1$, (C1-C6 alkyl)C(=O)—, (fluoroC1-C6 alkyl)C(=O)—, $H_2NC(=O)$—, $Ar^1CH_2C(=O)$—, (C3-C6 cycloalkylC(=O)— or (C1-C6 alkyl)$SO_2$—.

Embodiment 33

A compound according to any one of embodiments 30-32, wherein $R^{10}$ and $R^{11}$ are hydrogen.

Embodiment 34

A compound according to embodiment 1, wherein W is $CR^3R^4$, X is O, Y is $CR^{10}R^{11}$, Z is C, and ------- is a single bond, wherein the compound is represented by the structure of Formula I-J

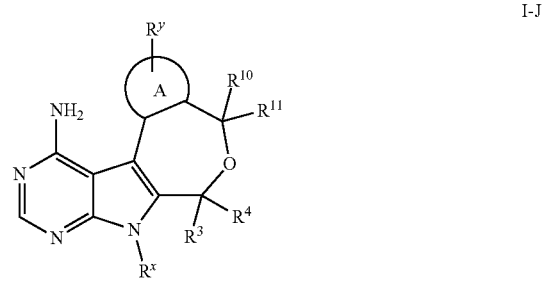

I-J wherein Ring A is (i) a monocyclic aryl ring, wherein said ring is optionally substituted with halogen, C3-C6 cycloalkyl, C1-C6 alkoxy, $R^cNHC(=O)$—, $R^cC(=O)NH$—, or $R^cNHC(=O)NH$— or (ii) a 5-membered monocyclic heteroaryl ring having 2 ring heteroatoms independently selected from N and O, wherein said ring is optionally substituted with C1-C6 alkyl or C3-C6 cycloalkyl.

Embodiment 35

A compound according to embodiment 34, wherein Ring A is a 5-membered heteroaryl ring having 1-2 ring heteroatoms independently selected from N and O, wherein said ring is optionally substituted with C1-C6 alkyl or C3-C6 cycloalkyl.

Embodiment 36

A compound according to embodiment 34 or 35, wherein $R^{10}$ and $R^{11}$ are hydrogen.

Embodiment 37

A compound according to embodiment 1, wherein ------- is a double bond, W is $CR^3R^4$, X is $CR^5$, Y is $CR^6$, $R^5$ and $R^6$ are hydrogen, and Z is C, wherein the compound may be represented by the structure of Formula I-K

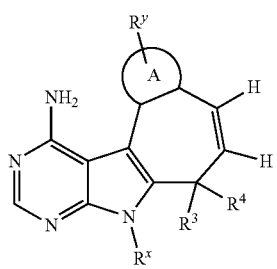

I-K wherein Ring A is (i) a monocyclic aryl ring, wherein said ring is optionally substituted with halogen, C3-C6 cycloalkyl, C1-C6 alkoxy, $R^cNHC(=O)$—, $R^cC(=O)NH$—, or $R^cNHC(=O)NH$— or (ii) a 5-membered monocyclic heteroaryl ring having 2 ring heteroatoms independently selected from N and O, wherein said ring is optionally substituted with C1-C6 alkyl or C3-C6 cycloalkyl.

Embodiment 38

A compound according to embodiment 37, wherein Ring A is a 5-membered heteroaryl ring having 2 ring heteroatoms independently selected from N and O, wherein said ring is optionally substituted with C1-C6 alkyl or C3-C6 cycloalkyl.

Embodiment 39

A compound according to embodiment 1, wherein W is $CR^3R^4$, X is $CR^7R^8$, Y is $CR^{10}R^{11}$, Z is N, and ------- is a single bond, wherein the compound may be represented by the structure of Formula I-L

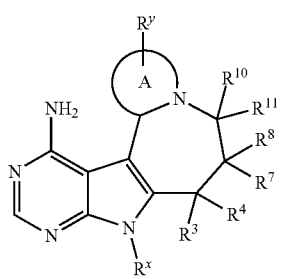

I-L wherein Ring A is (ii) a 5-membered heteroaryl ring having two ring nitrogen atoms, one of which is Z, wherein said ring is optionally substituted with C1-C6 alkyl or C3-C6 cycloalkyl, or (iii) a bicyclic heteroaryl ring having one ring nitrogen atom that results when Z is N, wherein said ring is optionally substituted with $R^dNHC(=O)$—, (C1-C6 alkoxy)$C(=O)$—, C1-C6 alkyl, C1-C6 alkoxy, fluoroC1-C6 alkyl, CN, halogen, or (C1-C6 alkyl)$C(=O)NH$—.

Embodiment 40

A compound according to embodiment 39, wherein Ring A is a bicyclic heteroaryl ring having one ring nitrogen atom that results when Z is N, wherein said ring is optionally substituted with $R^dNHC(=O)$—, (C1-C6 alkoxy)$C(=O)$—, C1-C6 alkyl, C1-C6 alkoxy, fluoroC1-C6 alkyl, CN, halogen, or (C1-C6 alkyl)$C(=O)NH$—.

Embodiment 41

A compound according to embodiment 40, wherein Ring A is a 5,6-bicyclic heteroaryl ring having one ring nitrogen atom that results when Z is N, wherein said ring is optionally substituted with $R^dNHC(=O)$—, (C1-C6 alkoxy)$C(=O)$—, halogen, or (C1-C6 alkyl)$C(=O)NH$—.

Embodiment 42

A compound according to any one of embodiments 39-41, wherein $R^7$ and $R^8$ are hydrogen.

Embodiment 43

A compound according to any one of embodiments 39-42, wherein $R^{10}$ and $R^{11}$ are hydrogen.

Embodiment 44

A compound according to any one of embodiments 1-43, wherein $R^x$ is hydrogen.

Embodiment 45

A compound according to any one of embodiments 1-43, wherein $R^x$ is C1-C6 alkyl.

Embodiment 46

A compound according to any one of embodiments 1-43, wherein $R^x$ is fluoroC1-C6 alkyl.

Embodiment 47

A compound according to any one of embodiments 1-43, wherein $R^x$ is $Cyc^2$.

Embodiment 48

A compound according to any one of embodiments 1-43, wherein $R^x$ is $Cyc^3$.

Embodiment 49

A compound according to any one of embodiments 1-43, wherein $R^x$ is $hetCyc^3$.

Embodiment 50

A compound according to any one of embodiments 1-43, wherein $R^x$ is $Ar^a$.

Embodiment 51

A compound according to any one of embodiments 1-43, wherein $R^x$ is $hetAr^3$.

Embodiment 52

A compound according to any one of embodiments 1-51, wherein $R^y$ is hydrogen.

Embodiment 53

A compound according to embodiment 1, selected from Examples 1-151.

Embodiment 54

A pharmaceutical composition, comprising a compound according to any one of embodiments 1-53 in admixture with a pharmaceutically acceptable diluent or carrier.

Embodiment 55

A process for preparing a compound of Formula I according to embodiment 1, comprising:

(a) for a compound of Formula I, wherein W is $CR^3R^4$; X is $CR^7R^8$; Y is C(=O); Z is N; ------- is a single bond; $R^7$ and $R^8$ are hydrogen; $R^x$ is C1-C6 alkyl, fluoroC1-C6 alkyl, $Cyc^2$, or $Cyc^3$; and Ring A is a monocyclic heteroaryl ring or bicyclic heteroaryl ring defined according to embodiment 1, subjecting a compound of the following formula:

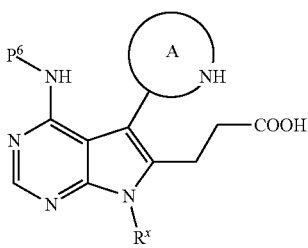

wherein $R^x$ is C1-C6 alkyl, fluoroC1-C6 alkyl, $Cyc^2$, or $Cyc^3$, Ring A is a monocyclic heteroaryl ring or bicyclic heteroaryl ring as defined for Ring A of Formula I in embodiment 1, and $P^6$ is an amino protecting group, to an intramolecular cyclization; and removing the amino protecting group $P^6$ on the resulting intermediate;

(b) for a compound of Formula I, wherein W is $CR^3R^4$; X is $CR^7R^8$; Y is C(=O); Z is N; ------- is a single bond; $R^7$ and $R^8$ are hydrogen; $R^x$ is C1-C6 alkyl, fluoroC1-C6 alkyl, $Cyc^2$, or $Cyc^3$; ring A is a monocyclic heteroaryl ring or bicyclic heteroaryl ring defined according to embodiment 1, wherein ring A is substituted with $NHR^dC(=O)-$, and $R^d$ is C1-C6 alkyl, C1-C6 alkoxy, $Cyc^1$, $Cyc^1CH_2-$, phenyl or $hetAr^2$, coupling a compound of the following formula:

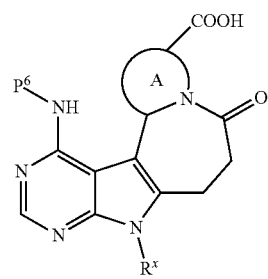

wherein $R^x$ is C1-C6 alkyl, fluoroC1-C6 alkyl, $Cyc^2$, or $Cyc^3$, ring A is a monocyclic heteroaryl ring or bicyclic heteroaryl ring as defined for Ring A of Formula I in embodiment 1, and $P^6$ is an amino protecting group, with a compound of formula $R^dNH_2$ wherein $R^d$ is C1-C6 alkyl, C1-C6 alkoxy, $Cyc^1$, $Cyc^1CH_2-$, phenyl or $hetAr^2$;

and removing the amino protecting group $P^6$;

(c) for a compound of formula I, wherein W is $CR^3R^4$; X is $NR^9$; Y is C(=O); Z is N, and ------- is a single bond; $R^9$ is hydrogen; $R^x$ is C1-C6 alkyl, fluoroC1-C6 alkyl, $Cyc^2$, or $Cyc^3$; and Ring A is a monocyclic heteroaryl ring or a bicyclic heteroaryl ring defined according to embodiment 1, reacting a compound of the following formula:

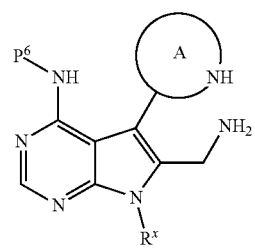

wherein $R^x$ is C1-C6 alkyl, fluoroC1-C6 alkyl, $Cyc^2$, or $Cyc^3$; Ring A is a monocyclic heteroaryl ring or a bicyclic heteroaryl ring as defined for Ring A of Formula I in embodiment 1; and $P^6$ is an amino protecting group, with $Boc_2O$; and removing the amino protecting group $P^6$;

(d) for a compound of Formula I, wherein W is $CR^3R^4$; X is $NR^9$; Y is C(=O); Z is N; ------- is a single bond; $R^9$ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, $hetCyc^1$, $(hetCyc^1)$C1-C6 alkyl-, $(Ar^1)$C1-C6 alkyl-, or $(hetAr^1)$C1-C6 alkyl-; $R^x$ is C1-C6 alkyl, fluoroC1-C6 alkyl, $Cyc^2$, or $Cyc^3$; and Ring A is

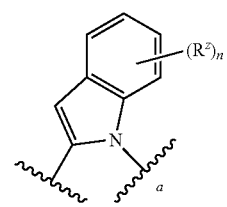

wherein the bond labeled "a" indicates the point of attachment to Y, n is 0, 1, 2, 3 or 4, and each $R^z$ is independently selected from R$^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH— wherein R$^d$ is C1-C6 alkyl, C1-C6 alkoxy, Cyc$^1$, Cyc$^1$CH$_2$—, phenyl or hetAr$^2$, reacting a compound of the following formula:

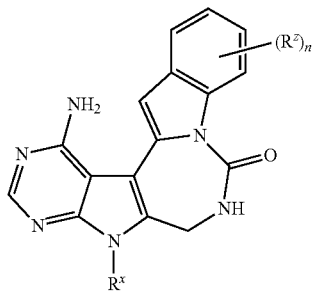

wherein R$^x$ is C1-C6 alkyl, fluoroC1-C6 alkyl, Cyc$^2$, or Cyc$^3$; n is 0, 1, 2, 3 or 4, and each R$^z$ is independently selected from R$^d$NHC(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH— wherein R$^d$ is C1-C6 alkyl, C1-C6 alkoxy, Cyc$^1$, Cyc$^1$CH$_2$—, phenyl or hetAr$^2$, with a compound of formula R$^9$—X, wherein X is a leaving group; and R$^9$ is C1-C6 alkyl, hydroxyC1-C6 alkyl- wherein the hydroxy group is protected with a hydroxy protecting group, (C1-C6 alkoxy)C1-C6 alkyl, C3-C6 cycloalkyl, (C3-C6 cycloalkyl)C1-C6 alkyl-, hetCyc$^1$, (hetCyc$^1$)C1-C6 alkyl-, (Ar$^1$)C1-C6 alkyl-, or (hetAr$^1$)C1-C6 alkyl-; and removing the hydroxy protecting group if present;

(e) for a compound of Formula I, wherein W is CR$^3$R$^4$, X is NR$^9$; Y is C(=O); Z is N; ------ is a single bond); R$^9$ is hydrogen; R$^x$ is C1-C6 alkyl, fluoroC1-C6 alkyl, Cyc$^2$, or Cyc$^3$; and Ring A is

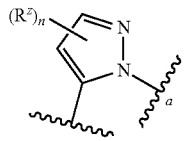

wherein the bond labeled "a" indicates the point of attachment to Y, each R$^z$ is independently selected from C1-C6 alkyl and C3-C6 cycloalkyl, n is 0, 1 or 2, and Ring A is further optionally substituted with one occurrence of halo, reacting a compound of the following formula

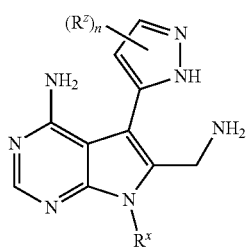

wherein R$^x$ is C1-C6 alkyl, fluoroC1-C6 alkyl, Cyc$^2$, or Cyc$^3$, each R$^z$ is independently selected from C1-C6 alkyl and C3-C6 cycloalkyl, n is 0, 1 or 2, and the pyrazolyl ring is further optionally substituted with one occurrence of halo, with a reagent of formula (p-NO$_2$C$_6$H$_5$O)$_2$CO;

(f) for a compound of Formula I, wherein W is CR$^3$R$^4$; X is NR$^9$; Y is C(=O), Z is C; ------ is a single bond; R$^9$ is hydrogen; R$^x$ is C1-C6 alkyl, fluoroC1-C6 alkyl, Cyc$^2$, or Cyc$^3$; and Ring A is

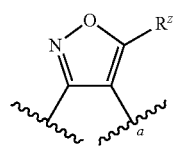

wherein the bond labeled "a" indicates the point of attachment to Y and R$^z$ is C1-C6 alkyl or C3-C6 cycloalkyl, reacting a compound of the following formula:

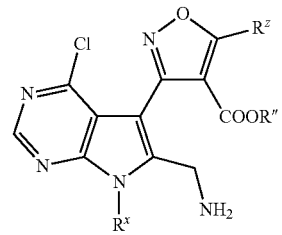

wherein R$^x$ is C1-C6 alkyl, fluoroC1-C6 alkyl, Cyc$^2$, or Cyc$^3$, and R$^z$ is C1-C6 alkyl or C3-C6 cycloalkyl with ammonium hydroxide;

(g) for a compound of Formula I, wherein W is CR$^3$R$^4$; X is NR$^9$; Y is C(=O), Z is C; ------ is a single bond; R$^9$ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, (hetCyc$^1$)C1-C6 alkyl-, (Ar$^1$)C1-C6 alkyl-, or (hetAr$^1$)C1-C6 alkyl-; R$^x$ is C1-C6 alkyl, fluoroC1-C6 alkyl, Cyc$^2$, or Cyc$^3$; and Ring A is

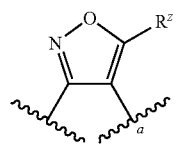

wherein the bond labeled "a" indicates the point of attachment to Y, and R$^z$ is C1-C6 alkyl or C3-C6 cycloalkyl, reacting a compound of the following formula:

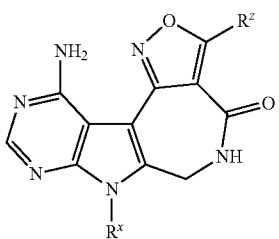

wherein R$^x$ is C1-C6 alkyl, fluoroC1-C6 alkyl, Cyc$^2$, or Cyc$^3$, and R$^z$ is C1-C6 alkyl or C3-C6 cycloalkyl, with a compound of formula R$^9$—X wherein R$^9$ is C1-C6 alkyl, hydroxyC1-C6 alkyl- the hydroxy group is protected with a suitable hydroxy protecting group, (C1-C6 alkoxy)C1-C6 alkyl, C3-C6 cycloalkyl, (C3-C6 cycloalkyl)C1-C6 alkyl-, (hetCyc$^1$)C1-C6 alkyl-, (Ar$^1$)C1-C6 alkyl-, or (hetAr$^1$)C1-C6 alkyl-; and removing the hydroxy protecting group if present;

(h) for a compound of Formula I, wherein W is CR$^3$R$^4$, X is NR$^9$; Y is C(=O); Z is C; and ------- is a single bond; R$^9$ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, (hetCyc$^1$)C1-C6 alkyl-, (Ar$^1$)C1-C6 alkyl-, or (hetAr$^1$)C1-C6 alkyl-; R$^x$ is defined according to embodiment 1; and Ring A is

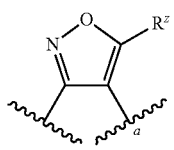

wherein the bond labeled "a" indicates the point of attachment to Y and R$^z$ is C1-C6 alkyl or C3-C6 cycloalkyl, removing the amino protecting group P$^2$ on a compound of the following formula:

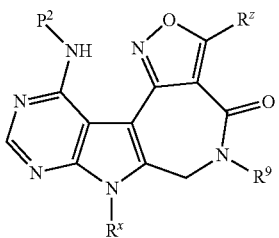

wherein R$^x$ is as defined for R$^x$ in embodiment 1, R$^z$ is C1-C6 alkyl or C3-C6 cycloalkyl, R$^9$ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, (hetCyc$^1$)C1-C6 alkyl-, (Ar$^1$)C1-C6 alkyl-, or (hetAr$^1$)C1-C6 alkyl-, and P$^2$ is an amino protecting group;

(i) for a compound of Formula I, wherein W is CR$^3$R$^4$; X is NR$^9$; Y is C(=O); Z is C; ------- is a single bond; Ring A is a 6-membered aryl ring optionally substituted with one or more substituents independently selected from halogen, C3-C6 cycloalkyl, C1-C6 alkoxy, R$^c$NHC(=O)—, R$^c$C(=O)NH—, or R$^c$NHC(=O)NH— wherein R$^c$ is C3-C6 cycloalkyl or (C3-C6 cycloalkyl)CH$_2$—; and R$^x$ is C1-C6 alkyl, fluoroC1-C6 alkyl, Cyc$^2$, or Cyc$^3$, subjecting a compound of the following formula:

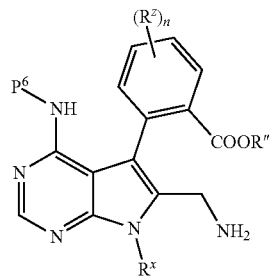

wherein R$^x$ is C1-C6 alkyl, fluoroC1-C6 alkyl, Cyc$^2$, or Cyc$^3$, n is 0, 1, 2, 3, or 4, each R$^z$ is independently selected from halogen, C3-C6 cycloalkyl, C1-C6 alkoxy, R$^c$NHC(=O)—, R$^c$C(=O)NH—, or R$^c$NHC(=O)NH— wherein R$^c$ is C3-C6 cycloalkyl or (C3-C6 cycloalkyl)CH$_2$—, and P$^6$ is an amino protecting group, to an intramolecular cyclization;

and removing the amino protecting group P$^6$;

(j) for a compound of Formula I, wherein W is CR$^3$R$^4$; X is NR$^9$; Y is C(=O); Z is C; ------- is a single bond; Ring A is a 6-membered aryl ring optionally substituted with one or more substituents independently selected from halogen, C3-C6 cycloalkyl, C1-C6 alkoxy, R$^c$NHC(=O)—, R$^c$C(=O)NH—, or R$^c$NHC(=O)NH— wherein R$^c$ is C3-C6 cycloalkyl or (C3-C6 cycloalkyl)CH$_2$—; R$^9$ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, (hetCyc$^1$)C1-C6 alkyl-, (Ar$^1$)C1-C6 alkyl-, or (hetAr$^1$)C1-C6 alkyl-; and R$^x$ is C1-C6 alkyl, fluoroC1-C6 alkyl, Cyc$^2$, or Cyc$^3$, reacting a compound of the following formula:

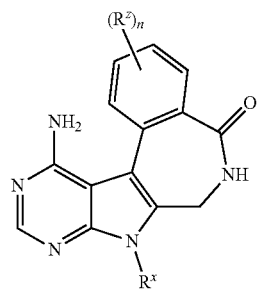

wherein R$^x$ is C1-C6 alkyl, fluoroC1-C6 alkyl, Cyc$^2$, or Cyc$^3$, n is 0, 1, 2, 3, or 4, and each R$^z$ is independently selected from halogen, C3-C6 cycloalkyl, C1-C6 alkoxy, R$^c$NHC(=O)—, R$^c$C(=O)NH—, or R$^c$NHC(=O)NH— wherein R$^c$ is C3-C6 cycloalkyl or (C3-C6 cycloalkyl)CH$_2$—, with a compound of formula R$^9$—X, wherein R$^9$ is C1-C6 alkyl, hydroxyC1-C6 alkyl- wherein the hydroxy group is protected with a suitable hydroxy protecting group, (C1-C6 alkoxy)C1-C6 alkyl, C3-C6 cycloalkyl, (C3-C6 cycloalkyl)C1-C6 alkyl-, (hetCyc$^1$)C1-C6 alkyl-, (Ar$^1$)C1-C6 alkyl-, or (hetAr$^1$)C1-C6 alkyl-, and X is a leaving group; and removing the hydroxy protecting group if present;

(k) for a compound of Formula I wherein W is CR$^3$R$^4$; X is NR$^9$; Y is C(=O); Z is C; ------- is a single bond;

$R^9$ is hydrogen; $R^x$ is hydrogen, C1-C6 alkyl, fluoroC1-C6 alkyl, $Cyc^2$, or $Cyc^3$; and Ring A is

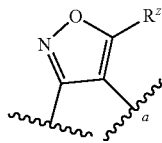

wherein the bond labeled "a" indicates the point of attachment to Y and $R^z$ is C1-C6 alkyl or C3-C6 cycloalkyl, reacting a compound of the following formula:

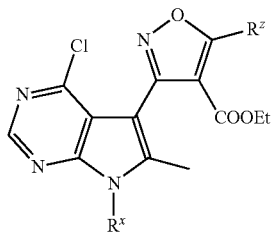

wherein $R^x$ is C1-C6 alkyl, fluoroC1-C6 alkyl, $Cyc^2$, or $Cyc^3$, and $R^z$ is C1-C6 alkyl or C3-C6 cycloalkyl, with N-bromosuccinimide and AIBN; and reacting the resulting intermediate with ammonium hydroxide; or reacting a compound of the following formula:

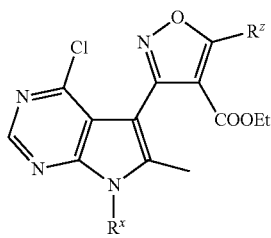

wherein PG is an amino protecting group, and $R^z$ is C1-C6 alkyl or C3-C6 cycloalkyl, with N-bromosuccinimide and AIBN;

reacting the resulting intermediate with ammonium hydroxide; and removing the amino protecting group PG on the resulting intermediate;

(l) for a compound of Formula I wherein W is $CR^3R^4$; X is $NR^9$; Y is C(=O); Z is C; ------- is a single bond; $R^9$ is C1-C6 alkyl, hydroxyC1-C6 alkyl-, (C1-C6 alkyl)SO$_2$—, (C1-C6 alkoxy)C1-C6 alkyl, C3-C6 cycloalkyl, (C3-C6 cycloalkyl)C1-C6 alkyl-, hetCyc$^1$, (hetCyc$^1$)C1-C6 alkyl-, Ar$^1$, (Ar$^1$)C1-C6 alkyl-, hetAr$^1$, (hetAr$^1$)C1-C6 alkyl-, (C1-C6 alkyl)C(=O)—, (fluoroC1-C6 alkyl)C(=O)—, H$_2$NC(=O)—, Ar$^1$CH$_2$C(=O)— or (C3-C6 cycloalkyl)C(=O)—; $R^x$ is C1-C6 alkyl, fluoroC1-C6 alkyl, $Cyc^2$, or $Cyc^3$; and Ring A is

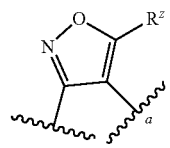

wherein the bond labeled "a" indicates the point of attachment to Y and $R^z$ is C1-C6 alkyl or C3-C6 cycloalkyl, reacting a compound of the following formula:

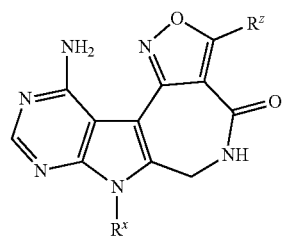

wherein $R^x$ is C1-C6 alkyl, fluoroC1-C6 alkyl, $Cyc^2$, or $Cyc^3$; and $R^z$ is C1-C6 alkyl or C3-C6 cycloalkyl, with a compound of formula $R^9$—X wherein $R^9$ is C1-C6 alkyl, hydroxyC1-C6 alkyl- wherein the hydroxy group is protected with a suitable hydroxy protecting group, (C1-C6 alkyl)SO$_2$—, (C1-C6 alkoxy)C1-C6 alkyl, C3-C6 cycloalkyl, (C3-C6 cycloalkyl)C1-C6 alkyl-, hetCyc$^1$, (hetCyc$^1$)C1-C6 alkyl-, Ar$^1$, (Ar$^1$)C1-C6 alkyl-, hetAr$^1$, (hetAr$^1$)C1-C6 alkyl-, (C1-C6 alkyl)C(=O)—, (fluoroC1-C6 alkyl)C(=O)—, H$_2$NC(=O)—, Ar$^1$CH$_2$C(=O)— or (C3-C6 cycloalkyl)C(=O)—, and X is a leaving group; and removing the hydroxy protecting group if present;

(m) for a compound of Formula I wherein W is $CR^3R^4$; X is $NR^9$; Y is C(=O); Z is C; and ------- is a single bond); $R^9$ is hydrogen; $R^x$ is C1-C6 alkyl, fluoroC1-C6 alkyl, $Cyc^2$, or $Cyc^3$; and Ring A is defined according to embodiment 1, subjecting a compound of the following formula:

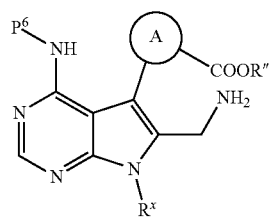

wherein $R^x$ is C1-C6 alkyl, fluoroC1-C6 alkyl, $Cyc^2$, or $Cyc^3$, Ring A is as defined for Ring A of Formula I in embodiment 1, $P^6$ is an amino protecting group, and R" is C1-C6 alkyl, to an intramolecular cyclization; and removing the amino protecting group $P^6$;

(n) for a compound of Formula I wherein W is $CR^3R^4$; X is O; Y is C(=O); Z is C; and ------- is a single bond; $R^x$ is C1-C6 alkyl, fluoroC1-C6 alkyl, $Cyc^2$, or $Cyc^3$, and Ring A is

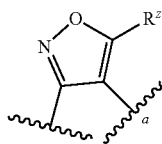

wherein the bond labeled "a" indicates the point of attachment to Y and $R^z$ is C1-C6 alkyl or C3-C6 cycloalkyl, removing the amino protecting group $P^2$ on a compound of the following formula:

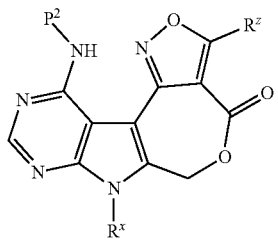

wherein $R^x$ is C1-C6 alkyl, fluoroC1-C6 alkyl, $Cyc^2$, or $Cyc^3$, $R^z$ is C1-C6 alkyl or C3-C6 cycloalkyl, and $P^2$ is an amino protecting group;

(o) for a compound of Formula I wherein W is $CR^3R^4$; X is $NR^9$; Y is $SO_2$; Z is C, and ------- is a single bond; $R^9$ is hydrogen; $R^x$ is C1-C6 alkyl, fluoroC1-C6 alkyl, $Cyc^2$, or $Cyc^3$; and Ring A is

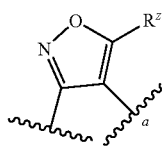

wherein the bond labeled "a" indicates the point of attachment to Y and $R^z$ is C1-C6 alkyl or C3-C6 cycloalkyl, reacting a compound of the following formula

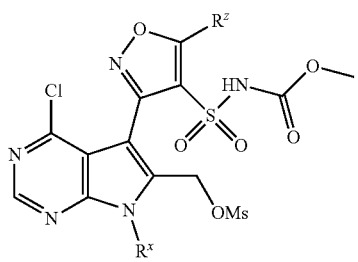

wherein $R^x$ is C1-C6 alkyl, fluoroC1-C6 alkyl, $Cyc^2$, or $Cyc^3$, and $R^z$ is C1-C6 alkyl or C3-C6 cycloalkyl, with ammonium hydroxide;

(p) for a compound of Formula I wherein W is $CR^3R^4$; X is $NR^9$; Y is $SO_2$; Z is C, and ------- is a single bond; $R^9$ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, (hetCyc$^1$)C1-C6 alkyl-, (Ar$^1$) C1-C6 alkyl-, or (hetAr$^1$)C1-C6 alkyl-; $R^x$ is C1-C6 alkyl, fluoroC1-C6 alkyl, $Cyc^2$, or $Cyc^3$; and Ring A is

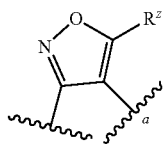

wherein the bond labeled "a" indicates the point of attachment to Y and $R^z$ is C1-C6 alkyl or C3-C6 cycloalkyl, reacting a compound of the following formula

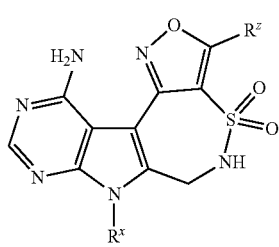

wherein $R^x$ is C1-C6 alkyl, fluoroC1-C6 alkyl, $Cyc^2$, or $Cyc^3$, and $R^z$ is C1-C6 alkyl or C3-C6 cycloalkyl, with a compound of formula $R^9$—X wherein $R^9$ is hydrogen, C1-C6 alkyl, hydroxyC1-C6 alkyl- wherein the hydroxy group is protected with a suitable hydroxy protecting group, (C1-C6 alkoxy)C1-C6 alkyl, C3-C6 cycloalkyl, (C3-C6 cycloalkyl)C1-C6 alkyl-, (hetCyc$^1$) C1-C6 alkyl-, (Ar$^1$)C1-C6 alkyl-, or (hetAr$^1$)C1-C6 alkyl-; and removing the hydroxy protecting group if present;

(q) for a compound of Formula I, wherein W is $CR^3R^4$; X is $CR^7R^8$; Y is $SO_2$; Z is C; and ------- is a single bond; $R^7$ and $R^8$ are hydrogen; $R^x$ is C1-C6 alkyl, fluoroC1-C6 alkyl, $Cyc^2$, or $Cyc^3$; and Ring A is

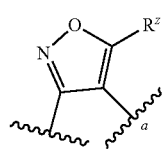

wherein the bond labeled "a" indicates the point of attachment to Y and $R^z$ is C1-C6 alkyl or C3-C6 cycloalkyl, reacting a compound of the following formula:

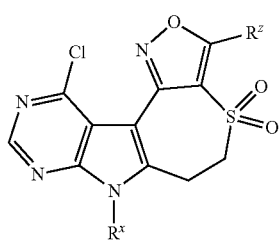

wherein $R^x$ is C1-C6 alkyl, fluoroC1-C6 alkyl, $Cyc^2$, or $Cyc^3$, and $R^z$ is C1-C6 alkyl or C3-C6 cycloalkyl with ammonium hydroxide;

(r) for a compound of Formula I wherein W is CR³R⁴; X is CR⁷R⁸; Y is C(=O); Z is C; ------ is a single bond; R⁷ and R⁸ are hydrogen; Rˣ is C1-C6 alkyl, fluoroC1-C6 alkyl, Cyc², or Cyc³; and Ring A is

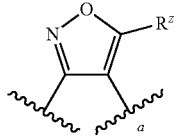

wherein the bond labeled "a" indicates the point of attachment to Y and R^z is C1-C6 alkyl or C3-C6 cycloalkyl, reacting a compound of the following formula:

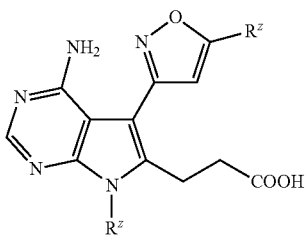

wherein Rˣ is C1-C6 alkyl, fluoroC1-C6 alkyl, Cyc², or Cyc³, and R^z is C1-C6 alkyl or C3-C6 cycloalkyl, with polyphosphoric acid;

(s) for a compound of Formula I wherein W is CR³R⁴; X is CR⁷R⁸; Y is C(=O); Z is C; ------ is a single bond; R⁷ and R⁸ are hydrogen; Rˣ is hydrogen, C1-C6 alkyl, fluoroC1-C6 alkyl, Cyc², Cyc³, hetCyc³, Ar³ or hetAr³; and Ring A is

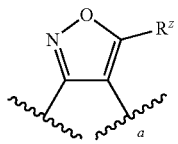

wherein the bond labeled "a" indicates the point of attachment to Y, and R^z is C1-C6 alkyl or C3-C6 cycloalkyl, reacting a compound of the following formula:

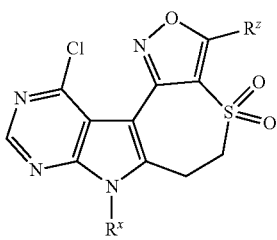

wherein Rˣ is hydrogen, C1-C6 alkyl, fluoroC1-C6 alkyl, Cyc², Cyc³, hetCyc³, Ar³ or hetAr³, and R^z is C1-C6 alkyl or C3-C6 cycloalkyl, with ammonium hydroxide;

(t) for a compound of Formula I wherein W is CR³R⁴; X is CR⁷R⁸; Y is C(=O); Z is C; ------ is a single bond; R⁷ and R⁸ are hydrogen; Rˣ is C1-C6 alkyl, fluoroC1-C6 alkyl, Cyc², Cyc³, hetCyc³, Ar³ or hetAr³; and Ring A is

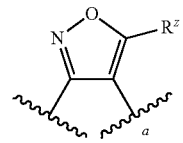

wherein the bond labeled "a" indicates the point of attachment to Y, and R^z is C1-C6 alkyl or C3-C6 cycloalkyl, removing the amino protecting group P⁶ on a compound of the following formula:

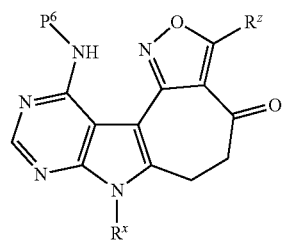

wherein Rˣ is C1-C6 alkyl, fluoroC1-C6 alkyl, Cyc², Cyc³, hetCyc³, Ar³ or hetAr³, R^z is C1-C6 alkyl or C3-C6 cycloalkyl, and P⁶ is an amino protecting group;

(u) for a compound of Formula I wherein W is CR³R⁴; X is CR⁷R⁸; Y is C(=O); Z is C; ------ is a single bond; R⁷ and R⁸ are hydrogen; Rˣ is C1-C6 alkyl, fluoroC1-C6 alkyl, Cyc², Cyc³, hetCyc³, Ar³ or hetAr³; and Ring A is

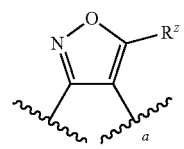

wherein the bond labeled "a" indicates the point of attachment to Y, and R^z is C1-C6 alkyl or C3-C6 cycloalkyl, reacting a compound of the following formula:

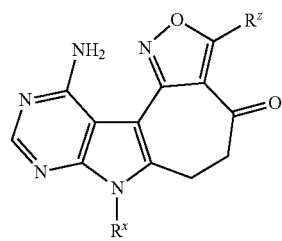

wherein R^z is C1-C6 alkyl or C3-C6 cycloalkyl, with a compound of formula Rˣ—X wherein Rˣ is C1-C6 alkyl, fluoroC1-C6 alkyl, Cyc², Cyc³, hetCyc³, Ar³ or hetAr³, a compound of formula Rˣ—OH wherein Rˣ is C1-C6 alkyl, fluoroC1-C6 alkyl, Cyc², Cyc³, or het- Cyc³, or a compound of formula R$^x$B(OR')$_2$ wherein R$^x$ is C1-C6 alkyl, fluoroC1-C6 alkyl, Cyc², Cyc³, hetCyc³, Ar³ or hetAr³, and each R' is independently H or (1-6C)alkyl, or each R' together with the atoms to which they are connected form a 5-6 membered ring optionally substituted with 1-4 substituents selected from (C1-C3 alkyl);

(v) for a compound of formula I, wherein W is CR³R⁴; X is CR⁷R⁸; Y is CR¹⁰R¹¹; Z is C; ------- is a single bond; R⁷ and R⁸ are hydrogen; R$^x$ is defined according to embodiment 1, R¹⁰ and R¹¹ are defined according to embodiment 1, and Ring A is

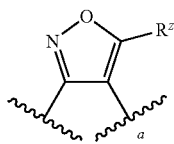

wherein the bond labeled "a" indicates the point of attachment to Y and R$^z$ is C1-C6 alkyl or C3-C6 cycloalkyl, functionalizing a compound of the following formula:

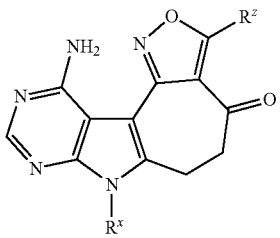

wherein R$^x$ is as defined for R$^x$ in embodiment 1, and R$^z$ is C1-C6 alkyl or C3-C6 cycloalkyl; and optionally subjecting the resulting product to chiral separation;

(w) for a compound of Formula I, wherein W is CR³R⁴; X is CR⁷R⁸; Y is CR¹⁰R¹¹; Z is C; ------- is a single bond; R⁷ and R⁸ are hydrogen; R$^x$ is defined according to embodiment 1, R¹⁰ is hydroxyl, R¹¹ is hydrogen, and Ring A is

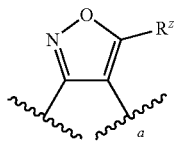

wherein the bond labeled "a" indicates the point of attachment to Y and R$^z$ is C1-C6 alkyl or C3-C6 cycloalkyl, reacting a compound of the following formula:

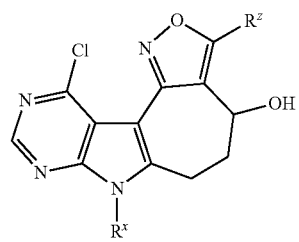

wherein R$^x$ is as defined for R$^x$ in embodiment 1, and R$^z$ is C1-C6 alkyl or C3-C6 cycloalkyl, with ammonium hydroxide; and optionally subjecting the resulting product to chiral separation;

(x) for a compound of Formula I, wherein W is CR³R⁴; X is CR⁷R⁸; Y is CR¹⁰R¹¹; Z is C; ------- is a single bond; R⁷ and R⁸ are hydrogen; R$^x$ is C1-C6 alkyl, fluoroC1-C6 alkyl, Cyc², Cyc³, hetCyc³, Ar$^a$ or hetAr³, R¹⁰ is hydroxyl, and R¹¹ is hydrogen, and Ring A is

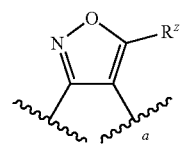

wherein the bond labeled "a" indicates the point of attachment to Y and R$^z$ is C1-C6 alkyl or C3-C6 cycloalkyl, subjecting a compound of the following formula:

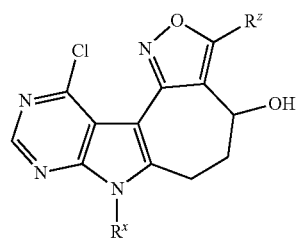

wherein R$^x$ is as defined for R$^x$ in embodiment 1, and R$^z$ is C1-C6 alkyl or C3-C6 cycloalkyl, to chiral separation; and reacting the resulting intermediate with ammonium hydroxide;

(y) for a compound of Formula I, wherein W is CR³R⁴; X is NR⁹; Y is CR¹⁰R¹¹; Z is C; ------- is a single bond; R¹⁰ and R¹¹ are hydrogen; R$^x$ is C1-C6 alkyl, fluoroC1-C6 alkyl, Cyc², or Cyc³; R⁹ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, hetCyc¹, (hetCyc¹)C1-C6 alkyl-, Ar¹, (Ar¹)C1-C6 alkyl-, hetAr¹ or (hetAr¹)C1-C6 alkyl-, and Ring A is

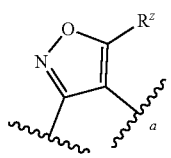

wherein the bond labeled "a" indicates the point of attachment to Y and $R^z$ is C1-C6 alkyl or C3-C6 cycloalkyl, reacting a compound of the following formula:

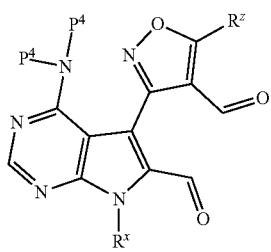

wherein $R^x$ is C1-C6 alkyl, fluoroC1-C6 alkyl, $Cyc^2$, or $Cyc^3$, $R^z$ is C1-C6 alkyl or C3-C6 cycloalkyl, and each $P^4$ is independently an amino protecting group, with a compound of formula $R^9NH_2$, wherein $R^9$ is C1-C6 alkyl, hydroxyC1-C6 alkyl-, (C1-C6 alkoxy)C1-C6 alkyl, C3-C6 cycloalkyl, (C3-C6 cycloalkyl)C1-C6 alkyl-, hetCyc$^1$, (hetCyc$^1$)C1-C6 alkyl-, Ar$^1$, (Ar$^1$)C1-C6 alkyl-, hetAr$^1$ or (hetAr$^1$)C1-C6 alkyl-, in the presence of a reducing agent; and removing the amino protecting groups $P^4$ on the resulting intermediate;

(z) for a compound of Formula I, wherein W is $CR^3R^4$; X is $NR^9$; Y is $CR^{10}R^{11}$; Z is C; ------- is a single bond; $R^{10}$ and $R^{11}$ are hydrogen; $R^x$ is C1-C6 alkyl, fluoroC1-C6 alkyl, $Cyc^2$, or $Cyc^3$; $R^9$ is (C1-C6 alkyl)SO$_2$ or $R^{9'}C(=O)$ wherein $R^{9'}$ is C1-C6 alkyl or fluoroC1-C6 alkyl, and Ring A is

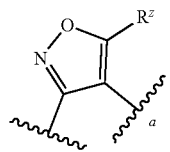

wherein the bond labeled "a" indicates the point of attachment to Y and $R^z$ is C1-C6 alkyl or C3-C6 cycloalkyl, reacting a compound of the following formula:

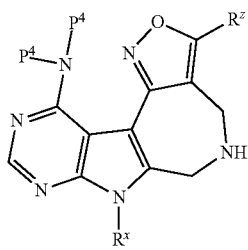

wherein $R^x$ is C1-C6 alkyl, fluoroC1-C6 alkyl, $Cyc^2$, or $Cyc^3$, $R^z$ is C1-C6 alkyl or C3-C6 cycloalkyl, and each $P^4$ is independently an amino protecting group, with a compound of formula (C1-C6 alkyl)SO$_2$Cl or $R^{9'}C(=O)Cl$ wherein $R^{9'}$ is C1-C6 alkyl or fluoroC1-C6 alky; and removing the amino protecting groups $P^4$ on the resulting intermediate;

(aa) for a compound of Formula I, wherein W is $CR^3R^4$; X is O; Y is $CR^{10}R^{11}$; Z is C; ------- is a single bond; $R^{10}$ and $R^{11}$ are hydrogen; $R^x$ is C1-C6 alkyl, fluoroC1-C6 alkyl, $Cyc^2$, or $Cyc^3$; and Ring A is

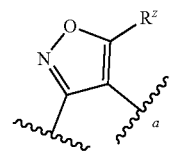

wherein the bond labeled "a" indicates the point of attachment to Y and $R^z$ is C1-C6 alkyl or C3-C6 cycloalkyl, reacting a compound of the following formula:

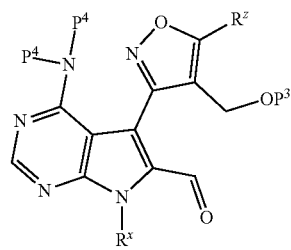

wherein $R^x$ is C1-C6 alkyl, fluoroC1-C6 alkyl, $Cyc^2$, or $Cyc^3$, $R^z$ is C1-C6 alkyl or C3-C6 cycloalkyl, each $P^4$ is independently an amino protecting group, and $P^3$ is a hydroxy protecting group, with CF$_3$SO$_3$TMS and Et$_3$SiH;

(bb) for a compound of Formula I, wherein W is $CR^3R^4$; X is $CR^5$; Y is $CR^6$; Z is C; ------- is a double bond; $R^5$ and $R^6$ are hydrogen; $R^x$ is C1-C6 alkyl, fluoroC1-C6 alkyl, $Cyc^2$, or $Cyc^3$; and Ring A is

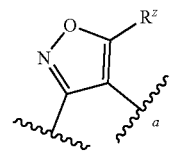

wherein the bond labeled "a" indicates the point of attachment to Y and $R^z$ is C1-C6 alkyl or C3-C6 cycloalkyl, reacting a compound of the following formula:

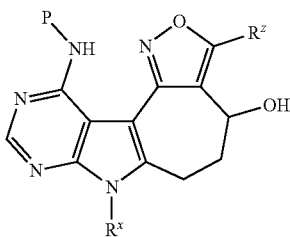

wherein $R^x$ is C1-C6 alkyl, fluoroC1-C6 alkyl, Cyc², or Cyc³, $R^z$ is C1-C6 alkyl or C3-C6 cycloalkyl, and P is an amino protecting group, with iodomethane in the presence of a base; and removing the amino protecting group P on the resulting intermediate; or (cc) for a compound of Formula I, wherein W is $CR^3R^4$; X is $CR^7R^8$; Y is $CR^{10}R^{11}$; Z is N; ------- is a single bond; $R^7$ and $R^8$ are hydrogen; $R^{10}$ and $R^{11}$ are hydrogen; $R^x$ is C1-C6 alkyl, fluoroC1-C6 alkyl, Cyc², or Cyc³; ring A is a monocyclic heteroaryl ring or bicyclic heteroaryl ring defined according to embodiment 1, wherein ring A is substituted with $NHR^dC(=O)$—, and $R^d$ is C1-C6 alkyl, C1-C6 alkoxy, Cyc¹, Cyc¹CH₂—, phenyl or hetAr², removing the amino protecting group $P^6$ on a compound of the following formula:

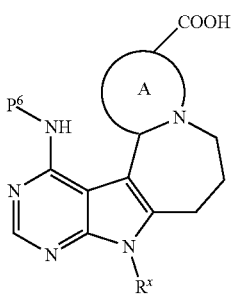

wherein $R^x$ is C1-C6 alkyl, fluoroC1-C6 alkyl, Cyc², or Cyc³, Ring A is a monocyclic heteroaryl ring or bicyclic heteroaryl ring as defined for Ring A of Formula I in embodiment 1, and $P^6$ is an amino protecting group;

and coupling the resulting intermediate with a compound of formula $R^dNH_2$ wherein $R^d$ is C1-C6 alkyl, C1-C6 alkoxy, Cyc¹, Cyc¹CH₂—, phenyl or hetAr²;

(dd) for a compound of Formula I, wherein W is $CR^3R^4$; X is $CR^7R^8$; Y is $CR^{10}R^{11}$; Z is N; ------- is a single bond; $R^7$ and $R^8$ are hydrogen; $R^{10}$ and $R^{11}$ are hydrogen; $R^x$ is C1-C6 alkyl, fluoroC1-C6 alkyl, Cyc², or Cyc³; ring A is a monocyclic heteroaryl ring or bicyclic heteroaryl ring defined according to embodiment 1, wherein ring A is substituted with $NHR^dC(=O)$—, and $R^d$ is C1-C6 alkyl, C1-C6 alkoxy, Cyc¹, Cyc¹CH₂—, phenyl or hetAr², coupling a compound of the following formula:

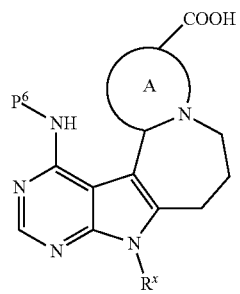

wherein $R^x$ is C1-C6 alkyl, fluoroC1-C6 alkyl, Cyc², or Cyc³, ring A is a monocyclic heteroaryl or bicyclic heteroaryl as defined for Ring A of Formula I in embodiment 1, and $P^6$ is an amino protecting group, with a compound of formula $R^dNH_2$ wherein $R^d$ is C1-C6 alkyl, C1-C6 alkoxy, Cyc¹, Cyc¹CH₂—, phenyl or hetAr²;

and removing the amino protecting group $P^6$;

(ee) for a compound of Formula I, wherein W is $CR^3R^4$; X is $CR^7R^8$; Y is $CR^{10}R^{11}$; Z is N; ------- is a single bond; $R^7$ and $R^8$ are hydrogen; $R^{10}$ and $R^{11}$ are hydrogen; $R^x$ is C1-C6 alkyl, fluoroC1-C6 alkyl, Cyc², or Cyc³; Ring A is a monocyclic heteroaryl ring or bicyclic heteroaryl ring defined according to embodiment 1, wherein ring A is substituted with (C1-C6 alkyl)C(=O)NH—, reacting a compound of the following formula:

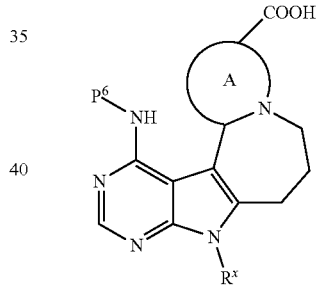

wherein $R^x$ is C1-C6 alkyl, fluoroC1-C6 alkyl, Cyc², or Cyc³, Ring A is a monocyclic heteroaryl ring or bicyclic heteroaryl ring as defined for Ring A of Formula I in embodiment 1, and $P^6$ is an amino protecting group, with diphenylphosphoryl azide (DPPA);

reacting the resulting intermediate with a compound of formula (C1-C6 alkylCO)₂O; and removing the amino protecting group $P^6$ on the resulting intermediate, optionally removing any remaining protecting groups, and optionally forming a pharmaceutically acceptable salt thereof.

Embodiment 56

A method for treating cancer in a subject in need thereof, the method comprising administering a pharmaceutical composition comprising a therapeutically effective amount of a compound according to any one of embodiments 1-53 or a pharmaceutically acceptable salt thereof or a pharmaceutical composition according to embodiment 54.

Embodiment 57

A method for treating cancer in a subject in need thereof, the method comprising:
  (a) determining if the cancer is associated with a dysregulation of a RET gene, a RET kinase, or expression or activity or level of any of the same; and
  (b) if the cancer is determined to be associated with a dysregulation of a RET gene, a RET kinase, or expression or activity or level of any of the same, administering to the subject a therapeutically effective amount of a compound of any one of embodiments 1-53 or a pharmaceutically acceptable salt thereof, or a pharmaceutical composition according to embodiment 54.

Embodiment 58

A method of treating a RET-associated cancer in a subject, the method comprising administering to a subject identified or diagnosed as having a RET-associated cancer a therapeutically effective amount of a compound of any one of embodiments 1-53 or a pharmaceutically acceptable salt thereof, or a pharmaceutical composition according to embodiment 54, to the subject.

Embodiment 59

A method of treating a RET-associated cancer in a subject, the method comprising:
  determining if the cancer in the subject is a RET-associated cancer; and
  administering to a subject determined to have a RET-associated cancer a therapeutically effective amount of a compound of any one of embodiments 1-53 or a pharmaceutically acceptable salt thereof, or a pharmaceutical composition according to embodiment 54.

Embodiment 60

A method of treating a subject, the method comprising administering a therapeutically effective amount of a compound of any one of embodiments 1-53 or a pharmaceutically acceptable salt thereof, or a pharmaceutical composition according to embodiment 54, to a subject having a clinical record that indicates that the subject has dysregulation of a RET gene, a RET kinase, or expression or activity or level of any of the same.

Embodiment 61

A method of selecting a treatment for a subject, the method comprising selecting a treatment comprising administration of a therapeutically effective amount of a compound of any one of embodiments 1-53 or a pharmaceutically acceptable salt thereof, or a pharmaceutical composition according to embodiment 54, for a subject identified or diagnosed as having a RET-associated cancer.

Embodiment 62

A method of selecting a treatment for a subject having a cancer, the method comprising:
  determining if the cancer in the subject is a RET-associated cancer; and
  selecting a treatment including administration of a therapeutically effective amount of a compound of any one of embodiments 1-53 or a pharmaceutically acceptable salt thereof, or a pharmaceutical composition according to embodiment 54, for a subject determined to have a RET-associated cancer.

Embodiment 64

A method of selecting a subject for treatment including administration of a therapeutically effective amount of a compound of any one of embodiments 1-53 or a pharmaceutically acceptable salt thereof, or a pharmaceutical composition according to embodiment 54, the method comprising:
  identifying a subject having a RET-associated cancer; and
  selecting the subject for treatment including administration of a therapeutically effective amount of a compound of any one of embodiments 1-53 or a pharmaceutically acceptable salt thereof, or a pharmaceutical composition according to embodiment 54.

Embodiment 64

A method of selecting a subject having cancer for treatment including administration of a therapeutically effective amount of a compound of any one of embodiments 1-53 or a pharmaceutically acceptable salt thereof, or a pharmaceutical composition according to embodiment 54, the method comprising:
  determining if the cancer in the subject is a RET-associated cancer; and
  selecting a subject determined to have a RET-associated cancer for treatment including administration of a therapeutically effective amount of a compound of any one of embodiments 1-53 or a pharmaceutically acceptable salt thereof, or a pharmaceutical composition according to embodiment 54.

Embodiment 65

The method of any one of embodiments 59, 62, and 64, wherein the step of determining if the cancer in the subject is a RET-associated cancer includes performing an assay to detect dysregulation in a RET gene, a RET kinase protein, or expression or activity or level of any of the same in a sample from the subject.

Embodiment 66

The method of embodiment 65, further comprising obtaining a sample from the subject.

Embodiment 67

The method of embodiment 66, wherein the sample is a biopsy sample.

Embodiment 68

The method of any one of embodiments 65-67, wherein the assay is selected from the group consisting of sequencing, immunohistochemistry, enzyme-linked immunosorbent assay, and fluorescence in situ hybridization (FISH).

Embodiment 69

The method of embodiment 68, wherein the FISH is break apart FISH analysis.

Embodiment 70

The method of embodiment 68, wherein the sequencing is pyrosequencing or next generation sequencing.

Embodiment 71

The method of any one of embodiments 65-70, wherein the dysregulation in a RET gene, a RET kinase protein, or expression or activity or level of any of the same is one or more point mutation in the RET gene.

Embodiment 72

The method of embodiment 71, wherein the one or more point mutations in a RET gene results in the translation of a RET protein having one or more amino acid substitutions at one or more of the following amino acid positions: 2, 3, 4, 5, 6, 7, 8, 11, 12, 13, 20, 32, 34, 40, 56, 64, 67, 114, 136, 145, 180, 200, 292, 294, 321, 330, 338, 360, 373, 393, 423, 432, 446, 505, 506, 510, 511, 513, 515, 525, 531, 532, 533, 550, 591, 593, 595, 600, 602, 603, 606, 609, 611, 616, 618, 619, 620, 623, 624, 630, 631, 632, 633, 634, 635, 636, 640, 641, 648, 649, 664, 665, 666, 675, 686, 689, 691, 694, 700, 706, 713, 732, 736, 748, 750, 765, 766, 768, 769, 770, 771, 777, 778, 781, 788, 790, 791, 802, 804, 805, 806, 810, 818, 819, 823, 826, 833, 836, 841, 843, 844, 848, 852, 865, 870, 873, 876, 881, 882, 883, 884, 886, 891, 897, 898, 900, 901, 904, 905, 907, 908, 911, 912, 918, 919, 921, 922, 930, 961, 972, 981, 982, 1009, 1015, 1017, 1041, 1062, 1064, and 1096.

Embodiment 73

The method of embodiment 72, wherein the one or more point mutations in a RET gene results in the translation of a RET protein having one or more amino acid substitutions at one or more of the following amino acid positions: 32, 34, 40, 56, 64, 67, 114, 145, 292, 321, 330, 338, 360, 393, 423, 446, 510, 511, 513, 515, 525, 531, 532, 533, 550, 591, 593, 595, 600, 602, 603, 606, 609, 611, 616, 618, 619, 620, 623, 624, 630, 631, 632, 634, 635, 636, 640, 641, 648, 649, 664, 665, 666, 675, 686, 689, 691, 694, 700, 706, 713, 732, 736, 748, 750, 765, 766, 768, 769, 770, 771, 777, 778, 781, 788, 790, 791, 804, 805, 806, 810, 818, 819, 823, 826, 833, 836, 841, 843, 844, 848, 852, 865, 870, 873, 876, 881, 883, 884, 886, 891, 897, 898, 900, 901, 904, 905, 907, 908, 911, 912, 918, 919, 921, 922, 930, 961, 972, 981, 982, 1009, 1015, 1017, 1041, 1064, and 1096.

Embodiment 74

The method of embodiment 73, wherein the one or more point mutations in a RET gene results in the translation of a RET protein having one or more of the following amino acid substitutions: S32L, D34S, L40P, L56M, P64L, R67H, R114H, V145G, V292M, G321R, R330Q, T338I, R360W, F393L, G423R, G446R, A510V, E511K, G513D, C515S, C515W, R525W, C531R, G533C, G533S, G550E, V591I, G593E, E595D, E595A, R600Q, I602V, K603Q, K603E, Y606C, C609C, C609Y, C609S, C609G, C609R, C609F, C609W, C611R, C611S, C611G, C611Y, C611F, C611W, E616Q, C618S, C618Y, C618R, C618G, C618F, C618W, F619F, C620S, C620W, C620R, C620G, C620L, C620Y, C620F, E623K, D624N, C630A, C630R, C630S, C630Y, C630F, C630W, D631N, D631Y, D631A, D631G, D631V, D631E, E632K, E632G, C634W, C634Y, C634S, C634R, C634F, C634G, C634L, C634A, C634T, R635G, T636P, T636M, A640G, A641S, A641T, V648I, S649L, A664D, H665Q, K666E, K666M, K666N, K666R, T675T S686N, S689T, G691S, R694Q, M700L, V706M, V706A, E713K, E732K, G736R, G748C, A750P, S765P, P766S, P766M, E768Q, E768D, L769L, R770Q, D771N, N777S, V778I, Q781R, I788I, L790F, Y791F, Y791N, V804L, V804M, V804E, E805K, Y806E, Y806F, Y806S, Y806G, Y806C, Y806H, Y806N, Y806Y, G810R, G810S, G810A, E818K, S819I, G823E, Y826M, Y826S, R833C, S836S, P841L, P841P, E843D, R844W, R844Q, R844L, M848T, I852M, L865V, L870F, R873W, A876V, L881V, A883F, A883S, A883T, E884K, R886W, S891A, S891S, R897Q, D898V, Y900F, E901K, S904F, S904S, S904C, Y905F, K907E, K907M, R908K, G911D, R912P, R912Q, M918T, M918V, M918L, A919V, E921K, S922P, S922Y, T930M, F961L, R972G, Y981F, R982C, M1009V, Y1015F, D1017N, V1041G, M1064T, and Y1096F.

Embodiment 75

The method of embodiment 71, wherein the one or more point mutations in a RET gene occur in one or more of exons 10, 11, 13, 14, 15, and 16 of a human RET gene.

Embodiment 76

The method of any one of embodiments 65-70, wherein the dysregulation in a RET gene, a RET kinase protein, or expression or activity or level of any of the same is a RET gene fusion.

Embodiment 77

The method of embodiment 76, wherein the RET gene fusion is selected from the group consisting of: BCR-RET, CLIP1-RET, KIF5B-RET, CCDC6-RET, NCOA4-RET, TRIM33-RET, ERC1-RET, FGFR1OP-RET, RET-MBD1, RET-RAB6IP2, RET-PRKAR1A, RET-TRIM24, RET-GOLGA5, HOOK3-RET, KTN1-RET, TRIM27-RET, AKAP13-RET, FKBP15-RET, SPECC1L-RET, TBL1XR1/RET, CEP55-RET, CUX1-RET, KIAA1468-RET, RFG8/RET, ACBD5-RET, PTC1ex9-RET, MYH13-RET, PIBF1-RET, KIAA1217-RET, MPRIP-RET, HRH4-RET, Ria-RET, RET-PTC4, FRMD4A-RET, SQSTM1-RET, AFAP1L2-RET, PPFIBP2-RET, EML4-RET, PARD3-RET, MYH10-RET, HTIF1/RET, AFAP1-RET, RASGEF1A-RET, TEL-RET, RUFY1-RET, UEVLD-RET, DLG5-RET, FOXP4-RET, TIF1G-RET, H4L-RET, OFLM4-RET, and RRBP1-RET.

Embodiment 78

The method of any one of embodiments 58, 62, and 63-77, wherein the RET-associated cancer is selected from the group consisting of: lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

Embodiment 79

The method of embodiment 78, wherein the cancer is RET fusion lung cancer or medullary thyroid cancer.

Embodiment 80

The method of embodiment 78, wherein the lung cancer is small cell lung carcinoma, non-small cell lung cancer, bronchioles lung cell carcinoma, or lung adenocarcinoma.

Embodiment 81

The method of any one of embodiments 56-80, wherein the compound of Formula I or a pharmaceutically acceptable salt thereof is orally administered.

Embodiment 82

The method of any one of embodiments 56-80, further comprising administering an additional therapy or therapeutic agent to the subject.

Embodiment 83

The method according to embodiment 88, wherein the additional therapy or therapeutic agent is selected from radiotherapy, cytotoxic chemotherapeutics, kinase targeted-therapeutics, apoptosis modulators, signal transduction inhibitors, immune-targeted therapies and angiogenesis-targeted therapies.

Embodiment 84

The method according to embodiment 83, wherein the additional therapeutic agent is selected from one or more kinase targeted therapeutics.

Embodiment 85

The method according to any one of embodiments 82-84, wherein the compound of any one of embodiments 1-53 or a pharmaceutically acceptable salt or solvate thereof, or a pharmaceutical composition according to embodiment 54, and the additional therapeutic agent are administered simultaneously as separate dosages.

Embodiment 86

The method according to any one of embodiments 82-84, wherein the compound of any one of embodiments 1-53 or a pharmaceutically acceptable salt thereof, or a pharmaceutical composition according to embodiment 54, and the additional therapeutic agent are administered as separate dosages sequentially in any order.

Embodiment 87

Use of a compound of any one of embodiments 1-53 or a pharmaceutically acceptable salt thereof for the manufacture of a medicament for treating a RET-associated cancer in a subject.

Embodiment 88

The use of embodiment 87, wherein the RET-associated cancer is a cancer having a dysregulation in a RET gene, a RET kinase protein, or expression or activity or level of any of the same.

Embodiment 89

The use of embodiment 88, wherein the dysregulation in a RET gene, a RET kinase protein, or expression or activity or level of any of the same is one or more point mutations in the RET gene.

Embodiment 90

The use of embodiment 89, wherein the one or more point mutations in a RET gene results in the translation of a RET protein having one or more amino acid substitutions at one or more of the following amino acid positions: 2, 3, 4, 5, 6, 7, 8, 11, 12, 13, 20, 32, 34, 40, 56, 64, 67, 114, 136, 145, 180, 200, 292, 294, 321, 330, 338, 360, 373, 393, 423, 432, 446, 505, 506, 510, 511, 513, 515, 525, 531, 532, 533, 550, 591, 593, 595, 600, 602, 603, 606, 609, 611, 616, 618, 619, 620, 623, 624, 630, 631, 632, 633, 634, 635, 636, 640, 641, 648, 649, 664, 665, 666, 675, 686, 689, 691, 694, 700, 706, 713, 732, 736, 748, 750, 765, 766, 768, 769, 770, 771, 777, 778, 781, 788, 790, 791, 802, 804, 805, 806, 810, 818, 819, 823, 826, 833, 836, 841, 843, 844, 848, 852, 865, 870, 873, 876, 881, 882, 883, 884, 886, 891, 897, 898, 900, 901, 904, 905, 907, 908, 911, 912, 918, 919, 921, 922, 930, 961, 972, 981, 982, 1009, 1015, 1017, 1041, 1062, 1064, and 1096.

Embodiment 91

The use of embodiment 90, wherein the one or more point mutations in a RET gene results in the translation of a RET protein having one or more amino acid substitutions at one or more of the following amino acid positions: 32, 34, 40, 56, 64, 67, 114, 145, 292, 321, 330, 338, 360, 393, 423, 446, 510, 511, 513, 515, 525, 531, 532, 533, 550, 591, 593, 595, 600, 602, 603, 606, 609, 611, 616, 618, 619, 620, 623, 624, 630, 631, 632, 634, 635, 636, 640, 641, 648, 649, 664, 665, 666, 675, 686, 689, 691, 694, 700, 706, 713, 732, 736, 748, 750, 765, 766, 768, 769, 770, 771, 777, 778, 781, 788, 790, 791, 804, 805, 806, 810, 818, 819, 823, 826, 833, 836, 841, 843, 844, 848, 852, 865, 870, 873, 876, 881, 883, 884, 886, 891, 897, 898, 900, 901, 904, 905, 907, 908, 911, 912, 918, 919, 921, 922, 930, 961, 972, 981, 982, 1009, 1015, 1017, 1041, 1064, and 1096.

Embodiment 92

The use of embodiment 91, wherein the one or more point mutations in a RET gene results in the translation of a RET protein having one or more of the following amino acid substitutions: S32L, D34S, L40P, L56M, P64L, R67H, R114H, V145G, V292M, G321R, R330Q, T338I, R360W, F393L, G423R, G446R, A510V, E511K, G513D, C515S, C515W, R525W, C531R, G533C, G533S, G550E, V591I, G593E, E595D, E595A, R600Q, I602V, K603Q, K603E, Y606C, C609C, C609Y, C609S, C609G, C609R, C609F, C609W, C611R, C611S, C611G, C611Y, C611F, C611W, E616Q, C618S, C618Y, C618R, C618G, C618F, C618W, F619F, C620S, C620W, C620R, C620G, C620L, C620Y, C620F, E623K, D624N, C630A, C630R, C630S, C630Y, C630F, C630W, D631N, D631Y, D631A, D631G, D631V, D631E, E632K, E632G, C634W, C634Y, C634S, C634R, C634F, C634G, C634L, C634A, C634T, R635G, T636P, T636M, A640G, A641S, A641T, V648I, S649L, A664D, H665Q, K666E, K666M, K666N, K666R, T675T S686N, S689T, G691S, R694Q, M700L, V706M, V706A, E713K, E732K, G736R, G748C, A750P, S765P, P766S, P766M, E768Q, E768D, L769L, R770Q, D771N, N777S, V778I, Q781R, I788I, L790F, Y791F, Y791N, V804L, V804M, V804E, E805K, Y806E, Y806F, Y806S, Y806G, Y806C, Y806H, Y806N, Y806Y, G810R, G810S, G810A, E818K, S819I, G823E, Y826M, Y826S, R833C, S836S, P841L, P841P, E843D, R844W, R844Q, R844L, M848T, I852M, L865V, L870F, R873W, A876V, L881V, A883F, A883S, A883T, E884K, R886W, S891A, S891S, R897Q, D898V, Y900F, E901K, S904F, S904S, S904C, Y905F, K907E, K907M, R908K, G911D, R912P, R912Q, M918T, M918V, M918L, A919V, E921K, S922P, S922Y, T930M, F961L, R972G, Y981F, R982C, M1009V, Y1015F, D1017N, V1041G, M1064T, and Y1096F.

Embodiment 93

The use of embodiment 89, wherein the one or more point mutations in a RET gene occur in one or more of exons 10, 11, 13, 14, 15, and 16 of a human RET gene.

Embodiment 94

The use of embodiment 88, wherein the dysregulation in a RET gene, a RET kinase protein, or expression or activity or level of any of the same is a RET gene fusion.

Embodiment 95

The use of embodiment 94, wherein the RET gene fusion is selected from the group consisting of: BCR-RET, CLIP1-RET, KIF5B-RET, CCDC6-RET, NCOA4-RET, TRIM33-RET, ERC1-RET, FGFR1OP-RET, RET-MBD1, RET-RAB6IP2, RET-PRKAR1A, RET-TRIM24, RET-GOLGA5, HOOK3-RET, KTN1-RET, TRIM27-RET, AKAP13-RET, FKBP15-RET, SPECC1L-RET, TBL1XR1/RET, CEP55-RET, CUX1-RET, KIAA1468-RET, RFG8/RET, ACBD5-RET, PTC1ex9-RET, MYH13-RET, PIBF1-RET, KIAA1217-RET, MPRIP-RET, HRH4-RET, Ria-RET, RET-PTC4, FRMD4A-RET, SQSTM1-RET, AFAP1L2-RET, PPFIBP2-RET, EML4-RET, PARD3-RET, MYH10-RET, HTIF1/RET, AFAP1-RET, RASGEF1A-RET, TEL-RET, RUFY1-RET, UEVLD-RET, DLG5-RET, FOXP4-RET, TIF1G-RET, H4L-RET, OFLM4-RET, and RRBP1-RET.

Embodiment 96

The use of any one of embodiments 87-95, wherein the RET-associated cancer is selected from the group consisting of: lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

Embodiment 97

The use of embodiment 96, wherein the cancer is RET fusion lung cancer or medullary thyroid cancer.

Embodiment 98

The use of embodiment 96, wherein the lung cancer is small cell lung carcinoma, non-small cell lung cancer, bronchioles lung cell carcinoma, or lung adenocarcinoma.

Embodiment 99

The use of any one of embodiments 87-98, wherein the medicament is formulated for oral administration.

Embodiment 100

A compound of any one of embodiments 1-53 or a pharmaceutically acceptable salt thereof for use in treating a subject identified or diagnosed as having a RET-associated cancer.

Embodiment 101

The compound of embodiment 100, wherein the RET-associated cancer is a cancer having a dysregulation in a RET gene, a RET kinase protein, or expression or activity or level of any of the same.

Embodiment 102

The compound of embodiment 101, wherein the dysregulation in a RET gene, a RET kinase protein, or expression or activity or level of any of the same is one or more point mutations in the RET gene.

Embodiment 103

The compound of embodiment 102, wherein the one or more point mutations in a RET gene results in the translation of a RET protein having one or more amino acid substitutions at one or more of the following amino acid positions: 2, 3, 4, 5, 6, 7, 8, 11, 12, 13, 20, 32, 34, 40, 56, 64, 67, 114, 136, 145, 180, 200, 292, 294, 321, 330, 338, 360, 373, 393, 423, 432, 446, 505, 506, 510, 511, 513, 515, 525, 531, 532, 533, 550, 591, 593, 595, 600, 602, 603, 606, 609, 611, 616, 618, 619, 620, 623, 624, 630, 631, 632, 633, 634, 635, 636, 640, 641, 648, 649, 664, 665, 666, 675, 686, 689, 691, 694, 700, 706, 713, 732, 736, 748, 750, 765, 766, 768, 769, 770, 771, 777, 778, 781, 788, 790, 791, 802, 804, 805, 806, 810, 818, 819, 823, 826, 833, 836, 841, 843, 844, 848, 852, 865, 870, 873, 876, 881, 882, 883, 884, 886, 891, 897, 898, 900, 901, 904, 905, 907, 908, 911, 912, 918, 919, 921, 922, 930, 961, 972, 981, 982, 1009, 1015, 1017, 1041, 1062, 1064, and 1096.

Embodiment 104

The compound of embodiment 103, wherein the one or more point mutations in a RET gene results in the translation of a RET protein having one or more amino acid substitutions at one or more of the following amino acid positions: 32, 34, 40, 56, 64, 67, 114, 145, 292, 321, 330, 338, 360, 393, 423, 446, 510, 511, 513, 515, 525, 531, 532, 533, 550, 591, 593, 595, 600, 602, 603, 606, 609, 611, 616, 618, 619, 620, 623, 624, 630, 631, 632, 634, 635, 636, 640, 641, 648, 649, 664, 665, 666, 675, 686, 689, 691, 694, 700, 706, 713, 732, 736, 748, 750, 765, 766, 768, 769, 770, 771, 777, 778, 781, 788, 790, 791, 804, 805, 806, 810, 818, 819, 823, 826, 833, 836, 841, 843, 844, 848, 852, 865, 870, 873, 876, 881, 883, 884, 886, 891, 897, 898, 900, 901, 904, 905, 907, 908, 911, 912, 918, 919, 921, 922, 930, 961, 972, 981, 982, 1009, 1015, 1017, 1041, 1064, and 1096.

Embodiment 105

The compound of embodiment 104, wherein the one or more point mutations in a RET gene results in the translation of a RET protein having one or more of the following amino acid substitutions: S32L, D34S, L40P, L56M, P64L, R67H, R114H, V145G, V292M, G321R, R330Q, T338I, R360W, F393L, G423R, G446R, A510V, E511K, G513D, C515S, C515W, R525W, C531R, G533C, G533S, G550E, V591I, G593E, E595D, E595A, R600Q, I602V, K603Q, K603E, Y606C, C609C, C609Y, C609S, C609G, C609R, C609F, C609W, C611R, C611S, C611G, C611Y, C611F, C611W, E616Q, C618S, C618Y, C618R, C618G, C618F, C618W, F619F, C620S, C620W, C620R, C620G, C620L, C620Y, C620F, E623K, D624N, C630A, C630R, C630S, C630Y, C630F, C630W, D631N, D631Y, D631A, D631G, D631V, D631E, E632K, E632G, C634W, C634Y, C634S, C634R, C634F, C634G, C634L, C634A, C634T, R635G, T636P, T636M, A640G, A641S, A641T, V648I, S649L, A664D, H665Q, K666E, K666M, K666N, K666R, T675T S686N, S689T, G691S, R694Q, M700L, V706M, V706A, E713K, E732K, G736R, G748C, A750P, S765P, P766S, P766M, E768Q, E768D, L769L, R770Q, D771N, N777S, V778I, Q781R, I788I, L790F, Y791F, Y791N, V804L, V804M, V804E, E805K, Y806E, Y806F, Y806S, Y806G, Y806C, Y806H, Y806N, Y806Y, G810R, G810S, G810A, E818K, S819I, G823E, Y826M, Y826S, R833C, S836S, P841L, P841P, E843D, R844W, R844Q, R844L, M848T, I852M, L865V, L870F, R873W, A876V, L881V, A883F, A883S, A883T, E884K, R886W, S891A, S891S, R897Q, D898V, Y900F, E901K, S904F, S904S, S904C, Y905F, K907E, K907M, R908K, G911D, R912P, R912Q, M918T, M918V, M918L, A919V, E921K, S922P, S922Y, T930M, F961L, R972G, Y981F, R982C, M1009V, Y1015F, D1017N, V1041G, M1064T, and Y1096F.

Embodiment 106

The compound of embodiment 102, wherein the one or more point mutations in a RET gene occur in one or more of exons 10, 11, 13, 14, 15, and 16 of a human RET gene.

Embodiment 107

The compound of embodiment 101, wherein the dysregulation in a RET gene, a RET kinase protein, or expression or activity or level of any of the same is a RET gene fusion.

Embodiment 108

The compound of embodiment 107, wherein the RET gene fusion is selected from the group consisting of: BCR-RET, CLIP1-RET, KIF5B-RET, CCDC6-RET, NCOA4-RET, TRIM33-RET, ERC1-RET, FGFR1OP-RET, RET-MBD1, RET-RAB61P2, RET-PRKAR1A, RET-TRIM24, RET-GOLGA5, HOOK3-RET, KTN1-RET, TRIM27-RET, AKAP13-RET, FKBP15-RET, SPECC1L-RET, TBL1XR1/RET, CEP55-RET, CUX1-RET, KIAA1468-RET, RFG8/RET, ACBD5-RET, PTC1ex9-RET, MYH13-RET, PIBF1-RET, KIAA1217-RET, MPRIP-RET, HRH4-RET, Ria-RET, RET-PTC4, FRMD4A-RET, SQSTM1-RET, AFAP1L2-RET, PPFIBP2-RET, EML4-RET, PARD3-RET, MYH10-RET, HTIF1/RET, AFAP1-RET, RASGEF1A-RET, TEL-RET, RUFY1-RET, UEVLD-RET, DLG5-RET, FOXP4-RET, TIF1G-RET, H4L-RET, OFLM4-RET, and RRBP1-RET.

Embodiment 109

The compound of any one of embodiments 100-108, wherein the RET-associated cancer is selected from the group consisting of: lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

Embodiment 110

The compound of embodiment 109, wherein the cancer is RET fusion lung cancer or medullary thyroid cancer.

Embodiment 111

The compound of embodiment 109, wherein the lung cancer is small cell lung carcinoma, non-small cell lung cancer, bronciolus lung cell carcinoma, or lung adenocarcinoma.

Embodiment 112

A method for inhibiting RET kinase activity in a mammalian cell, the method comprising contacting the mammalian cell with a compound of any one of embodiments 1-53 or a pharmaceutically acceptable salt thereof.

Embodiment 113

The method of embodiment 112, wherein the contacting occurs in vivo.

Embodiment 114

The method of embodiment 112, wherein the contacting occurs in vitro.

Embodiment 115

The method of any one of embodiments 112-114, wherein the mammalian cell is a mammalian cancer cell.

Embodiment 116

The method of embodiment 115, wherein the mammalian cancer cell is a mammalian RET-associated cancer cell.

Embodiment 117

The method of any one of embodiments 112-116, wherein the cell has dysregulation of a RET gene, a RET kinase protein, or expression or activity or level of any of the same.

Embodiment 118

The method of embodiment 117, wherein the dysregulation in a RET gene, a RET kinase protein, or expression or activity or level of any of the same is one or more point mutations in the RET gene.

Embodiment 119

The method of embodiment 118, wherein the one or more point mutations in a RET gene results in the translation of a RET protein having one or more amino acid substitutions at one or more of the following amino acid positions: 2, 3, 4, 5, 6, 7, 8, 11, 12, 13, 20, 32, 34, 40, 56, 64, 67, 114, 136, 145, 180, 200, 292, 294, 321, 330, 338, 360, 373, 393, 423, 432, 446, 505, 506, 510, 511, 513, 515, 525, 531, 532, 533, 550, 591, 593, 595, 600, 602, 603, 606, 609, 611, 616, 618, 619, 620, 623, 624, 630, 631, 632, 633, 634, 635, 636, 640, 641, 648, 649, 664, 665, 666, 675, 686, 689, 691, 694, 700, 706, 713, 732, 736, 748, 750, 765, 766, 768, 769, 770, 771, 777, 778, 781, 788, 790, 791, 802, 804, 805, 806, 810, 818, 819, 823, 826, 833, 836, 841, 843, 844, 848, 852, 865, 870, 873, 876, 881, 882, 883, 884, 886, 891, 897, 898, 900, 901, 904, 905, 907, 908, 911, 912, 918, 919, 921, 922, 930, 961, 972, 981, 982, 1009, 1015, 1017, 1041, 1062, 1064, and 1096.

Embodiment 120

The method of embodiment 119, wherein the one or more point mutations in a RET gene results in the translation of a RET protein having one or more amino acid substitutions at one or more of the following amino acid positions: 32, 34, 40, 56, 64, 67, 114, 145, 292, 321, 330, 338, 360, 393, 423, 446, 510, 511, 513, 515, 525, 531, 532, 533, 550, 591, 593, 595, 600, 602, 603, 606, 609, 611, 616, 618, 619, 620, 623, 624, 630, 631, 632, 634, 635, 636, 640, 641, 648, 649, 664, 665, 666, 675, 686, 689, 691, 694, 700, 706, 713, 732, 736, 748, 750, 765, 766, 768, 769, 770, 771, 777, 778, 781, 788, 790, 791, 804, 805, 806, 810, 818, 819, 823, 826, 833, 836, 841, 843, 844, 848, 852, 865, 870, 873, 876, 881, 883, 884, 886, 891, 897, 898, 900, 901, 904, 905, 907, 908, 911, 912, 918, 919, 921, 922, 930, 961, 972, 981, 982, 1009, 1015, 1017, 1041, 1064, and 1096.

Embodiment 121

The method of embodiment 120, wherein the one or more point mutations in a RET gene results in the translation of a RET protein having one or more of the following amino acid substitutions: S32L, D34S, L40P, L56M, P64L, R67H, R114H, V145G, V292M, G321R, R330Q, T338I, R360W, F393L, G423R, G446R, A510V, E511K, G513D, C515S, C515W, R525W, C531R, G533C, G533S, G550E, V591I, G593E, E595D, E595A, R600Q, I602V, K603Q, K603E, Y606C, C609C, C609Y, C609S, C609G, C609R, C609F, C609W, C611R, C611S, C611G, C611Y, C611F, C611W, E616Q, C618S, C618Y, C618R, C618G, C618F, C618W, F619F, C620S, C620W, C620R, C620G, C620L, C620Y, C620F, E623K, D624N, C630A, C630R, C630S, C630Y, C630F, C630W, D631N, D631Y, D631A, D631G, D631V, D631E, E632K, E632G, C634W, C634Y, C634S, C634R, C634F, C634G, C634L, C634A, C634T, R635G, T636P, T636M, A640G, A641S, A641T, V648I, S649L, A664D, H665Q, K666E, K666M, K666N, K666R, T675T S686N, S689T, G691S, R694Q, M700L, V706M, V706A, E713K, E732K, G736R, G748C, A750P, S765P, P766S, P766M, E768Q, E768D, L769L, R770Q, D771N, N777S, V778I, Q781R, I788I, L790F, Y791F, Y791N, V804L, V804M, V804E, E805K, Y806E, Y806F, Y806S, Y806G, Y806C, Y806H, Y806N, Y806Y, G810R, G810S, G810A, E818K, S819I, G823E, Y826M, Y826S, R833C, S836S, P841L, P841P, E843D, R844W, R844Q, R844L, M848T, I852M, L865V, L870F, R873W, A876V, L881V, A883F, A883S, A883T, E884K, R886W, S891A, S891S, R897Q, D898V, Y900F, E901K, S904F, S904S, S904C, Y905F, K907E, K907M, R908K, G911D, R912P, R912Q, M918T, M918V, M918L, A919V, E921K, S922P, S922Y, T930M, F961L, R972G, Y981F, R982C, M1009V, Y1015F, D1017N, V1041G, M1064T, and Y1096F.

Embodiment 122

The method of embodiment 118, wherein the one or more point mutations in a RET gene occur in one or more of exons 10, 11, 13, 14, 15, and 16 of a human RET gene.

Embodiment 123

The method of embodiment 117, wherein the dysregulation in a RET gene, a RET kinase protein, or expression or activity or level of any of the same is a RET gene fusion.

Embodiment 124

The method of embodiment 107, wherein the RET gene fusion is selected from the group consisting of: BCR-RET, CLIP1-RET, KIF5B-RET, CCDC6-RET, NCOA4-RET, TRIM33-RET, ERC1-RET, FGFR1OP-RET, RET-MBD1, RET-RAB61P2, RET-PRKAR1A, RET-TRIM24, RET-GOLGA5, HOOK3-RET, KTN1-RET, TRIM27-RET, AKAP13-RET, FKBP15-RET, SPECC1L-RET, TBL1XR1/RET, CEP55-RET, CUX1-RET, KIAA1468-RET, RFG8/RET, ACBD5-RET, PTC1ex9-RET, MYH13-RET, PIBF1-RET, KIAA1217-RET, MPRIP-RET, HRH4-RET, Ria-RET, RET-PTC4, FRMD4A-RET, SQSTM1-RET, AFAP1L2-RET, PPFIBP2-RET, EML4-RET, PARD3-RET, MYH10-RET, HTIF1/RET, AFAP1-RET, RASGEF1A-RET, TEL-RET, RUFY1-RET, UEVLD-RET, DLG5-RET, FOXP4-RET, TIF1G-RET, H4L-RET, OFLM4-RET, and RRBP1-RET.

Embodiment 125

A method of treating irritable bowel syndrome in a subject, the method comprising administering to a subject identified or diagnosed as having irritable bowel syndrome a therapeutically effective amount of a compound of any one of embodiments 1-53 or a pharmaceutically acceptable salt thereof, or a pharmaceutical composition according to embodiment 54 to the subject.

Embodiment 126

A method for reducing pain associated with irritable bowel syndrome in a subject in need thereof, the method comprising administering to a subject identified or diagnosed as having irritable bowel syndrome a therapeutically effective amount of a compound of any one of embodiments 1-53 or a pharmaceutically acceptable salt thereof, or a pharmaceutical composition according to embodiment 54 to the subject.

Embodiment 127

A method for inhibiting metastasis of a cancer in a subject in need thereof, the method comprising administering to the subject a therapeutically effective amount of a compound of any one of embodiments 1-53, or a pharmaceutically acceptable salt thereof or a pharmaceutical composition according to embodiment 54.

Embodiment 128

The method of embodiment 127, wherein the compound of any one of embodiments 1-53 or a pharmaceutically acceptable salt thereof is used in combination with another chemotherapeutic agent.

Embodiment 129

A method of treating a subject having a cancer, wherein the method comprises:
(a) administering one or more doses of a first RET inhibitor to the subject for a period of time;
(b) after (a), determining whether a cancer cell in a sample obtained from the subject has at least one RET inhibitor resistance mutation that confers increased resistance to a cancer cell or tumor to treatment with the first RET inhibitor of step (a); and
(c) administering a compound of any one of embodiments 1-53 or a pharmaceutically acceptable salt thereof as a monotherapy or in conjunction with another anticancer agent to the subject if the subject has a cancer cell that has at least one RET inhibitor resistance mutation that confers increased resistance to a cancer cell or tumor to treatment with the first RET inhibitor of step (a); or
(d) administering additional doses of the first RET inhibitor of step (a) to the subject if the subject has a cancer cell that does not have a RET inhibitor resistance mutation that confers increased resistance to a cancer cell or tumor to treatment with the first RET inhibitor of step (a).

Embodiment 130

The method of embodiment 129, wherein the anticancer agent in step (c) is a second RET inhibitor, an immunotherapy, or a combination thereof.

Embodiment 131

The method of embodiment 129, wherein the anticancer agent in step (c) is the first RET inhibitor administered in step (a).

Embodiment 132

The method of embodiment 129, wherein the subject is administered additional doses of the first RET inhibitor of step (a), and the method further comprises (e) administering another anticancer agent to the subject.

Embodiment 133

The method of embodiment 132, wherein the anticancer agent of step (e) is a second RET inhibitor, an immunotherapy, or a combination thereof.

Embodiment 134

The method of embodiment 132, wherein the anticancer agent of step (e) is a compound of any one of embodiments 1-53 or a pharmaceutically acceptable salt thereof.

Embodiment 135

A method of treating a subject having a cancer, wherein the method comprises:
(a) administering one or more doses of a first RET inhibitor, to the subject for a period of time;
(b) after (a), determining whether a cancer cell in a sample obtained from the subject has at least one RET inhibitor resistance mutation that confers increased resistance to a cancer cell or tumor to treatment with the first RET inhibitor of step (a);
(c) administering a second RET inhibitor as a monotherapy or in conjunction with another anticancer agent to the subject if the subject has a cancer cell that has at least one RET inhibitor resistance mutation that confers increased resistance to a cancer cell or tumor to treatment with the first RET inhibitor of step (a); or
(d) administering additional doses of the first RET inhibitor of step (a) to the subject if the subject has a cancer cell that does not have a RET inhibitor resistance mutation that confers increased resistance to a cancer cell or tumor to treatment with the first RET inhibitor of step (a); wherein the mutation is a substitution at amino acid position 804, e.g., V804M, V804L, or V804E.

Embodiment 136

The method of embodiment 135, wherein the anticancer agent of step (c) is the first RET inhibitor administered in step (a).

Embodiment 137

The method of embodiment 135, wherein the subject is administered additional doses of the first RET inhibitor of step (a), and the method further comprises (e) administering another anticancer agent.

Embodiment 138

The method of embodiment 137, wherein the anticancer agent of step (e) is a second RET inhibitor, an immunotherapy, or a combination thereof.

Embodiment 139

The method of embodiment 137, wherein the anticancer agent of step (e) is a compound of any one of embodiments 1-53 or a pharmaceutically acceptable salt thereof.

Embodiment 140

A method of treating a subject having a cancer, wherein the method comprises:
(a) determining whether a cancer cell in a sample obtained from a subject having a cancer and previously administered one or more doses of a first RET inhibitor has one or more RET inhibitor resistance mutations that confer increased resistance to a cancer cell or tumor to treatment with the first RET inhibitor that was previously administered to the subject; and
(b) administering a compound of any one of embodiments 1-53 or a pharmaceutically acceptable salt thereof as a monotherapy or in conjunction with another anticancer agent to the subject if the subject has a cancer cell that has at least one RET inhibitor resistance mutation that confers increased resistance to a cancer cell or tumor to treatment with the first RET inhibitor that was previously administered to the subject; or
(c) administering additional doses of the first RET inhibitor to the subject if the subject has cancer cell that does not have a RET inhibitor resistance mutation that confers increased resistance to a cancer cell or tumor to treatment with the first RET inhibitor previously administered to the subject.

Embodiment 141

The method of embodiment 140, wherein the anticancer agent of step (b) is a second RET inhibitor, an immunotherapy, or a combination thereof.

Embodiment 142

The method of embodiment 140, wherein the anticancer agent of step (b) is the first RET inhibitor previously administered to the subject.

Embodiment 143

The method of embodiment 142, wherein the subject is administered additional doses of the first RET inhibitor previously administered to the subject, and the method further comprises (d) administering another anticancer agent to the subject.

Embodiment 144

The method of embodiment 143, wherein the anticancer agent of step (d) is a second RET inhibitor, an immunotherapy, or a combination thereof.

Embodiment 145

The method of embodiment 143, wherein the anticancer agent of step (d) is a compound of any one of embodiments 1-53 or a pharmaceutically acceptable salt thereof.

Embodiment 146

A method of treating a subject having a cancer, wherein the method comprises:
(a) determining whether a cancer cell in a sample obtained from a subject having a cancer and previously administered one or more doses of a first RET inhibitor has one or more RET inhibitor resistance mutations that confer increased resistance to a cancer cell or tumor to treatment with the first RET inhibitor previously administered to the subject; and
(b) administering a second RET inhibitor to the subject as a monotherapy or in conjunction with another anticancer agent to the subject if the subject has a cancer cell that has at least one RET inhibitor resistance mutation that confers increased resistance to a cancer cell or tumor to treatment with the first RET inhibitor that was previously administered to the subject; or
(c) administering additional doses of the first RET inhibitor that was previously administered to the subject if the subject has cancer cell that does not have a RET inhibitor resistance mutation that confers increased resistance to a cancer cell or tumor to treatment with the first RET inhibitor that was previously administered to the subject.

Embodiment 147

The method of embodiment 146, wherein the anticancer agent of step (b) is the first RET inhibitor previously administered to the subject.

Embodiment 148

The method of embodiment 146, wherein the subject is administered additional doses of the first RET inhibitor previously administered to the subject, and the method further comprises (d) administering another anticancer agent to the subject.

Embodiment 149

The method of embodiment 148, wherein the anticancer agent of step (d) is a second RET inhibitor, an immunotherapy, or a combination thereof.

Embodiment 150

The method of embodiment 148, wherein the anticancer agent of step (d) is a compound of any one of embodiments 1-53 or a pharmaceutically acceptable salt thereof.

Embodiment 151

A method of treating a subject having a cancer, wherein the method comprises:
(a) administering one or more doses of a compound of any one of embodiments 1-53 or a pharmaceutically acceptable salt thereof for a period of time;
(b) after (a), determining whether a cancer cell in a sample obtained from the subject has one or more RET inhibitor resistance mutations that confer increased resistance to a cancer cell or tumor to treatment with the compound of any one of embodiments 1-53 or a pharmaceutically acceptable salt thereof of step (a); and
(c) administering a second RET inhibitor or a second compound of any one of embodiments 1-53 or a pharmaceutically acceptable salt thereof as a monotherapy or in conjunction with another anticancer agent to a subject having a cancer cell that has one or more RET inhibitor resistance mutations that confer increased resistance to a cancer cell or tumor to treatment with the compound of any one of embodiments 1-53 or a pharmaceutically acceptable salt thereof of step (a); or
(d) administering additional doses of the compound of any one of embodiments 1-53 or a pharmaceutically acceptable salt thereof of step (a) to a subject having a cancer cell that does not have a RET inhibitor resistance mutation that confers increased resistance to a cancer cell or tumor to treatment with the compound of any one of embodiments 1-53 or a pharmaceutically acceptable salt thereof of step (a).

Embodiment 152

The method of embodiment 151, wherein the second RET inhibitor is administered in step (c).

Embodiment 153

The method of embodiment 151, wherein the second compound of the compound of any one of embodiments 1-53 or a pharmaceutically acceptable salt thereof is administered in step (c).

Embodiment 154

The method of embodiment 151, wherein the anticancer agent of step (c) is a first RET inhibitor, an immunotherapy, or a combination thereof.

Embodiment 155

The method of embodiment 151, wherein the anticancer agent of step (c) is a second compound of the compound of any one of embodiments 1-53 or a pharmaceutically acceptable salt thereof that is different from that administered in step (a).

Embodiment 156

The method of embodiment 151, wherein the anticancer agent of step (c) is the compound of any one of embodiments 1-53 or a pharmaceutically acceptable salt thereof administered in step (a).

Embodiment 157

The method of embodiment 151, wherein the subject is administered additional doses of the compound of any one of embodiments 1-53 or a pharmaceutically acceptable salt thereof of step (a), and the method further comprises (e) administering another anticancer agent to the subject.

Embodiment 158

The method of embodiment 157, wherein the anticancer agent of step (e) is a second RET inhibitor, an immunotherapy, or a combination thereof.

Embodiment 159

The method of embodiment 157, wherein the anticancer agent of step (e) is a second compound of any one of embodiments 1-53 or a pharmaceutically acceptable salt thereof that is different from the compound of step (a).

Embodiment 160

A method of treating a subject having a cancer, wherein the method comprises:
(a) determining whether a cancer cell in a sample obtained from a subject having a cancer and previously administered one or more doses of a compound of any one of embodiments 1-53 or a pharmaceutically acceptable salt thereof has one or more RET inhibitor resistance mutations that confer increased resistance to a cancer cell or tumor to treatment with the compound of any one of embodiments 1-53 or a pharmaceutically acceptable salt thereof that was previously administered to the subject;
(b) administering a second RET inhibitor or a second compound of any one of embodiments 1-53 or a pharmaceutically acceptable salt or solvate thereof as a monotherapy or in conjunction with another anticancer agent to a subject having a cancer cell that has one or more RET inhibitor resistance mutations that confer increased resistance to a cancer cell or tumor to treatment the compound of any one of embodiments 1-53 or a pharmaceutically acceptable salt thereof that was previously administered to the subject; or
(c) administering additional doses of the compound of any one of embodiments 1-53 or a pharmaceutically acceptable salt thereof previously administered to a subject having a cancer cell that does not have a RET inhibitor resistance mutation that confers increased resistance to a cancer cell or tumor to treatment with the compound of any one of embodiments 1-53 or a pharmaceutically acceptable salt thereof that was previously administered to the subject.

Embodiment 161

The method of embodiment 160, wherein the second RET inhibitor is administered in step (b).

Embodiment 162

The method of embodiment 160, wherein the second compound of any one of embodiments 1-53 or a pharmaceutically acceptable salt or solvate thereof is administered in step (b).

Embodiment 163

The method of embodiment 160, wherein the anticancer agent of step (b) is a second RET inhibitor, an immunotherapy, or a combination thereof.

Embodiment 164

The method of embodiment 160, wherein the anticancer agent of step (b) is a second compound of any one of embodiments 1-53 or a pharmaceutically acceptable salt thereof.

Embodiment 165

The method of embodiment 160, wherein the anticancer agent of step (b) is the compound of any one of embodiments 1-53 or a pharmaceutically acceptable salt thereof that was previously administered to the subject.

Embodiment 166

The method of embodiment 160, wherein the subject is administered additional doses of the compound of any one of embodiments 1-53 or a pharmaceutically acceptable salt thereof that was previously administered to the subject, and the method further comprises (d) administering another anticancer agent to the subject.

Embodiment 167

The method of embodiment 166, wherein the anticancer agent of step (d) is a second RET inhibitor, an immunotherapy, or a combination thereof.

Embodiment 168

The method of embodiment 166, wherein the anticancer agent of step (d) is a second compound of any one of embodiments 1-53 or a pharmaceutically acceptable salt thereof.

Embodiment 169

A method of treating a RET-associated cancer in a subject, the method comprising:
(a) administering one or more doses of a compound of Formula I, or a pharmaceutically acceptable salt or solvate thereof, as a monotherapy to a subject identified or diagnosed as having a RET-associated cancer;
(b) after step (a), determining a level of circulating tumor DNA in a biological sample obtained from the subject;
(c) administering a therapeutically effective amount of a compound of any one of embodiments 1-53, or a pharmaceutically acceptable salt or solvate thereof, and an additional therapeutic agent or treatment to a subject identified as having about the same or an elevated level of circulating tumor DNA as compared to a reference level of circulating tumor DNA.

Embodiment 170

The method of embodiment 169, wherein the additional therapeutic agent is a second RET kinase inhibitor.

Embodiment 171

The method of embodiment 169, wherein the additional therapeutic agent or treatment comprises one or more of: radiation therapy, a chemotherapeutic agent, a checkpoint inhibitor, surgery, and one or more second kinase inhibitors.

Embodiment 172

The method of embodiment 168, wherein the reference level of circulating tumor DNA is a level of circulating tumor DNA in a biological sample obtained from the subject prior to step (a).

Embodiment 173

A method of treating a RET-associated cancer in a subject, the method comprising:
administering a therapeutically effective amount of a compound of any one of embodiments 1-53, or a pharmaceutically acceptable salt or solvate thereof, and an additional therapeutic agent or treatment to a subject (i) identified or diagnosed as having a RET-associated cancer, (ii) previously administered one or more doses of the compound of any one of embodiments 1-53, or a pharmaceutically acceptable salt or solvate thereof, as a monotherapy, and (iii) after administration of the one or more doses of the compound of any one of embodiments 1-53, or a pharmaceutically acceptable salt or solvate thereof, as a monotherapy, identified as having about the same or an elevated level of circulating tumor DNA as compared to a reference level of circulating tumor DNA.

Embodiment 174

The method of embodiment 173, wherein the reference level of circulating tumor DNA is a level of circulating tumor DNA in a biological sample obtained from the subject prior to administration of the one or more doses of the compound of any one of embodiments 1-53, or a pharmaceutically acceptable salt or solvate thereof, as a monotherapy.

Embodiment 175

The method of embodiment 173, wherein the additional therapeutic agent is a second RET kinase inhibitor.

Embodiment 176

The method of embodiment 173, wherein the additional therapeutic agent or treatment comprises one or more of radiation therapy, a chemotherapeutic agent, a checkpoint inhibitor, surgery, and one or more second kinase inhibitors.

Embodiment 177

A method of selecting a treatment for a subject, the method comprising:
selecting a therapeutically effective amount of a compound of any one of embodiments 1-53, or a pharmaceutically acceptable salt or solvate thereof, for a subject (i) identified or diagnosed as having a RET-associated cancer, (ii) previously administered one or more doses of a second RET kinase inhibitor, and (iii) after administration of the one or more doses of the second RET kinase inhibitor, identified as having about the same or an elevated level of circulating tumor DNA as compared to a reference level of circulating tumor DNA.

Embodiment 178

The method of embodiment 177, wherein the reference level of circulating tumor DNA is a level of circulating tumor DNA in a biological sample obtained from the subject prior to administration of the one or more doses of the second RET kinase inhibitor.

Embodiment 179

A method of selecting a treatment for a subject, the method comprising:
selecting a therapeutically effective amount of a compound of any one of embodiments 1-53, or a pharmaceutically acceptable salt or solvate thereof, and an additional therapeutic treatment for a subject (i) identified or diagnosed as having a RET-associated cancer, (ii) previously administered one or more doses of the compound of any one of embodiments 1-53, or a pharmaceutically acceptable salt or solvate thereof, as a monotherapy, and (iii) after administration of the one or more doses of the compound of any one of embodiments 1-53, or a pharmaceutically acceptable salt or solvate thereof, identified as having about the same or an elevated level of circulating tumor DNA as compared to a reference level of circulating tumor DNA.

Embodiment 180

The method of embodiment 179, wherein the reference level of circulating tumor DNA is a level of circulating tumor DNA in a biological sample obtained from the subject prior to administration of the one or more doses of the compound of any one of embodiments 1-53, or a pharmaceutically acceptable salt or solvate thereof, as a monotherapy.

Embodiment 181

The method of embodiment 179, wherein the additional therapeutic treatment is a second RET kinase inhibitor.

Embodiment 182

The method of embodiment 179, wherein the additional therapeutic treatment comprises one or more of radiation therapy, a chemotherapeutic agent, a checkpoint inhibitor, and one or more second kinase inhibitors.

Embodiment 183

A method of determining efficacy of a treatment in a subject, the method comprising:

(a) determining a first level of circulating tumor DNA in a biological sample obtained from a subject identified or diagnosed as having a RET-associated cancer at a first time point;
(b) administering a treatment comprising one or more doses of a compound of any one of embodiments 1-53, or a pharmaceutically acceptable salt or solvate thereof to the subject, after the first time point and before a second time point;
(c) determining a second level of circulating tumor DNA in a biological sample obtained from the subject at the second time point; and
(d) identifying that the treatment is effective in a subject determined to have a decreased second level of circulating tumor DNA as compared to the first level of circulating tumor DNA; or
identifying the treatment is not effective in a subject determined to have about the same or an elevated second level of circulating tumor DNA as compared to the first level of circulating tumor DNA.

Embodiment 184

The method of embodiment 183, wherein the first time point and the second time point are about 1 week to about 1 year apart.

Embodiment 185

A method of determining whether a subject has developed resistance to a treatment, the method comprising:

(a) determining a first level of circulating tumor DNA in a biological sample obtained from a subject identified or diagnosed as having a RET-associated cancer at a first time point;
(b) administering a treatment comprising one or more doses of a compound of any one of embodiments 1-53, or a pharmaceutically acceptable salt or solvate thereof to the subject, after the first time point and before a second time point;
(c) determining a second level of circulating tumor DNA in a biological sample obtained from the subject at the second time point; and
(d) determining that a subject having a decreased second level of circulating tumor DNA as compared to the first level of circulating tumor DNA has not developed resistance to the treatment; or
determining that a subject having about the same or an elevated second level of circulating tumor DNA as compared to the first level of circulating tumor DNA has developed resistance to the treatment.

Embodiment 186

The method of embodiment 185, wherein the first time point and the second time point are about 1 week to about 1 year apart.

---

What is claimed is:

1. A compound of Formula I

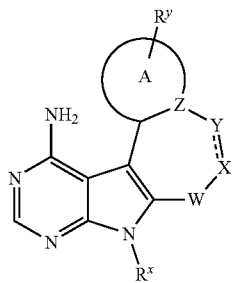

I wherein,

W is $CR^3R^4$,

------- represents a single or a double bond, wherein when ------- is a double bond, then X is $CR^5$ and Y is $CR^6$, and when ------- is a single bond, then X is O, $CR^7R^8$ or $NR^9$ and Y is C(=O), $SO_2$, $CR^{10}R^{11}$ or O, and Z is C or N;

$R^3$ is hydrogen;

$R^4$ is hydrogen;

$R^5$ is hydrogen;

$R^6$ is hydrogen;

$R^7$ is hydrogen or C1-C6 alkyl;

$R^8$ is hydrogen;

$R^9$ is hydrogen, C1-C6 alkyl, hydroxyC1-C6 alkyl-, (C1-C6 alkyl)$SO_2$—, (C1-C6 alkoxy)C1-C6 alkyl, C3-C6 cycloalkyl, (C3-C6 cycloalkyl)C1-C6 alkyl-, hetCyc$^1$, (hetCyc$^1$)C1-C6 alkyl-, Ar$^1$, (Ar$^1$)C1-C6alkyl, hetAr$^1$, (hetAr$^1$)C1-C6 alkyl-, (C1-C6 alkyl)C(=O)—, (fluoroC1-C6 alkyl)C(=O)—, $H_2NC$(=O)—, Ar$^1CH_2C$(=O)— or (C3-C6 cycloalkyl)C(=O)—;

$R^{10}$ is hydrogen, hydroxy, C1-C6 alkoxy, or $R^aR^bN$— where $R^a$ and $R^b$ are independently H or C1-C6 alkyl;

$R^{11}$ is hydrogen, C1-C6 alkyl, or fluoroC1-C6 alkyl;

hetCyc$^1$ is a 5-6 membered saturated heterocyclic ring having 1-2 ring heteroatoms independently selected from N and $SO_2$, wherein said heterocyclic ring is optionally substituted with C1-C6 alkyl or (Ar$^2$)C1-C6 alkyl-;

Ar$^1$ is phenyl optionally substituted with one or more substituents independently selected from halogen and C1-C6 alkoxy;

hetAr$^1$ is a 5-6 membered heteroaryl ring having 1-2 ring nitrogen atoms, wherein said heteroaryl ring is optionally substituted with C1-C6 alkyl;

Ar$^2$ is phenyl optionally substituted with one or more substituents independently selected from halogen and C1-C6 alkoxy;

Ring A, including the atoms at the points of attachment to the ring containing Z, Y, X, and W, is:

(i) a monocyclic aryl ring when Z is C, wherein said ring is optionally substituted with halogen, C3-C6 cycloalkyl, C1-C6 alkoxy, $R^cNHC$(=O)—, $R^cC$(=O)NH—, or $R^cNHC$(=O)NH—, (ii) a 5-membered monocyclic heteroaryl ring having 2 ring heteroatoms independently selected from N and O when Z is C, or when Z is N, a 5-membered heteroaryl ring having two ring nitrogen atoms, one of which is Z, wherein said rings are optionally substituted with C1-C6 alkyl or C3-C6 cycloalkyl, or (iii) when Z is N, a bicyclic heteroaryl ring having one ring nitrogen atom which is Z, wherein said ring is optionally substituted with $R^dNHC$(=O)—, (C1-C6 alkoxy)C(=O)—, C1-C6 alkyl, C1-C6 alkoxy, fluoroC1-C6 alkyl, CN, halogen, or (C1-C6 alkyl)C(=O)NH—;

$R^c$ is C3-C6 cycloalkyl or (C3-C6 cycloalkyl)$CH_2$—;

$R^d$ is C1-C6 alkyl, C1-C6 alkoxy, Cyc$^1$, Cyc$^1CH_2$—, phenyl or hetAr$^2$;

Cyc$^1$ is C3-C6 cycloalkyl optionally substituted with C1-C6 alkyl;

hetAr$^2$ is (i) pyrazolyl optionally substituted with 1-2 substituents independently selected from C1-C6 alkyl, fluoroC1-C6 alkyl, (di-C1-C6 alkyl)NC(=O)$CH_2$—, (hetCyc$^2$)$CH_2CH_2$—, phenyl, and (C1-C6 alkoxy)C1-C6 alkyl, or (ii) pyridyl;

hetCyc$^2$ is a 6-membered saturated heterocyclic ring having 2 ring heteroatoms independently selected from N and O;

$R^x$ is hydrogen, C1-C6 alkyl, fluoroC1-C6 alkyl, Cyc$^2$, Cyc$^3$, hetCyc$^3$, Ar$^3$ or hetAr$^3$;

Cyc² is a 3-6 membered saturated carbocyclic ring optionally substituted with 1-2 substituents independently selected from halogen, C1-C6 alkyl, hydroxy, hydroxyC1-C6 alkyl, and (C1-C6 alkoxy)C(=O)—;
Cyc³ is cyclopentenyl;
hetCyc³ is a 5-membered saturated heterocyclic ring having a ring heteroatom selected from N and O and optionally substituted with (C1-C6 alkyl)C(=O)—;
Ar³ is phenyl optionally substituted with (C1-C6 alkoxy) C(=O)—;
hetAr³ is a 5-6 membered heteroaryl ring having 1-2 ring nitrogen atoms and optionally substituted with C1-C6 alkyl or C1-C6 alkoxy; and
$R^y$ is hydrogen or halogen;
or a pharmaceutically acceptable salt thereof.

2. A compound according to claim 1, wherein Ring A is a monocyclic aryl ring when Z is C, wherein said ring is optionally substituted with halogen, C3-C6 cycloalkyl, C1-C6 alkoxy, $R^cNHC(=O)$—, $R^cC(=O)NH$—, or $R^cNHC(=O)NH$—, or a pharmaceutically acceptable salt thereof.

3. A compound according to claim 1, wherein Ring A is a 5-membered monocyclic heteroaryl ring having 2 ring heteroatoms independently selected from N and O when Z is C, or when Z is N, a 5-membered heteroaryl ring having two ring nitrogen atoms, one of which is Z, wherein said rings are optionally substituted with C1-C6 alkyl or C3-C6 cycloalkyl, or a pharmaceutically acceptable salt thereof.

4. A compound according to claim 1, wherein Ring A is a bicyclic heteroaryl ring having one ring nitrogen atom that results when Z is N, wherein said ring is optionally substituted with $R^dNHC(=O)$—, (C1-C6 alkoxy)C(=O)—, C1-C6 alkyl, C1-C6 alkoxy, fluoroC1-C6 alkyl, CN, halogen, or (C1-C6 alkyl)C(=O)NH—, or a pharmaceutically acceptable salt thereof.

5. A compound according to claim 1, wherein W is $CR^3R^4$, X is $CR^7R^8$, Y is $CR^{10}R^{11}$, Z is C, and ------- is a single bond, wherein the compound is represented by the structure of Formula I-H:

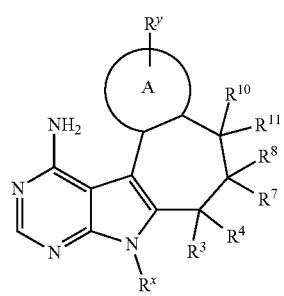

I-H wherein Ring A is (i) a monocyclic aryl ring, wherein said ring is optionally substituted with halogen, C3-C6 cycloalkyl, C1-C6 alkoxy, $R^cNHC(=O)$—, $R^cC(=O)NH$—, or $R^cNHC(=O)NH$— or (ii) a 5-membered monocyclic heteroaryl ring having 2 ring heteroatoms independently selected from N and O, wherein said ring is optionally substituted with C1-C6 alkyl or C3-C6 cycloalkyl, or a pharmaceutically acceptable salt thereof.

6. A compound according to claim 5, wherein Ring A is a 5-membered heteroaryl ring having 2 ring heteroatoms independently selected from N and O, wherein said ring is optionally substituted with C1-C6 alkyl or C3-C6 cycloalkyl, or a pharmaceutically acceptable salt thereof.

7. A compound according to claim 5, wherein $R^7$ and $R^8$ are hydrogen, or a pharmaceutically acceptable salt thereof.

8. A compound according to claim 1, wherein $R^x$ is C1-C6 alkyl, or a pharmaceutically acceptable salt thereof.

9. A compound according to claim 1, selected from:

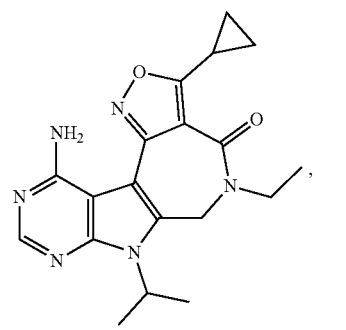

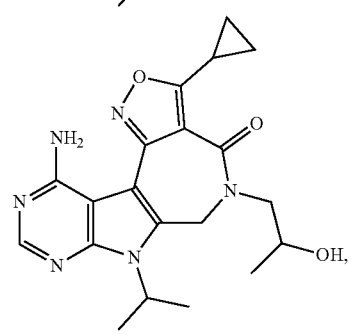

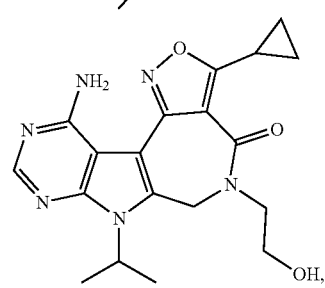

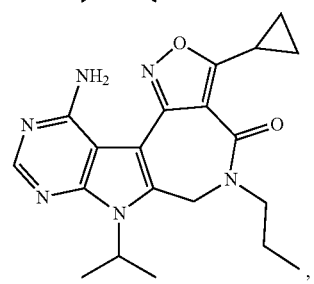

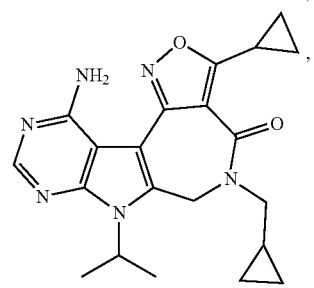

483
-continued
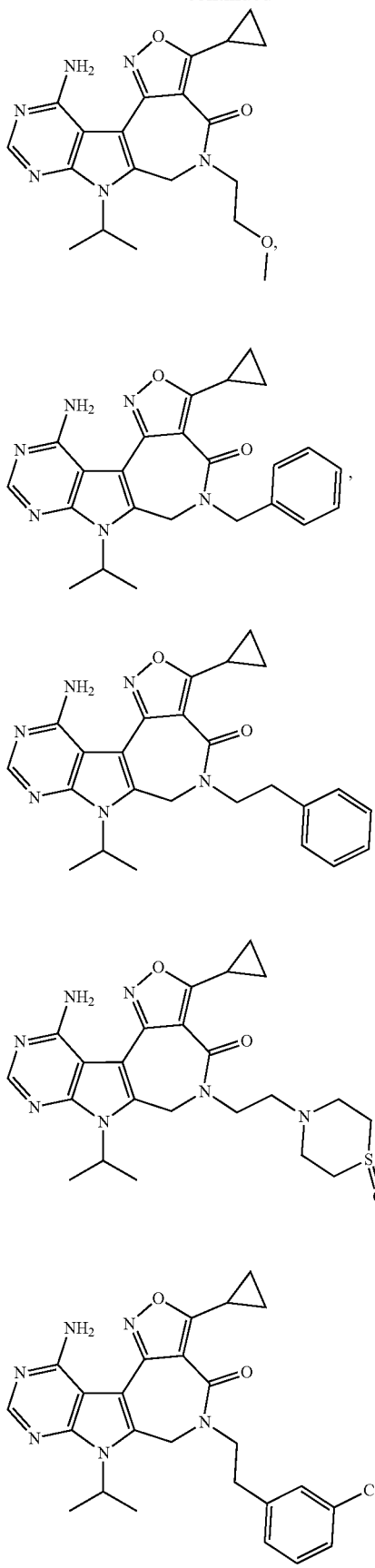
484
-continued
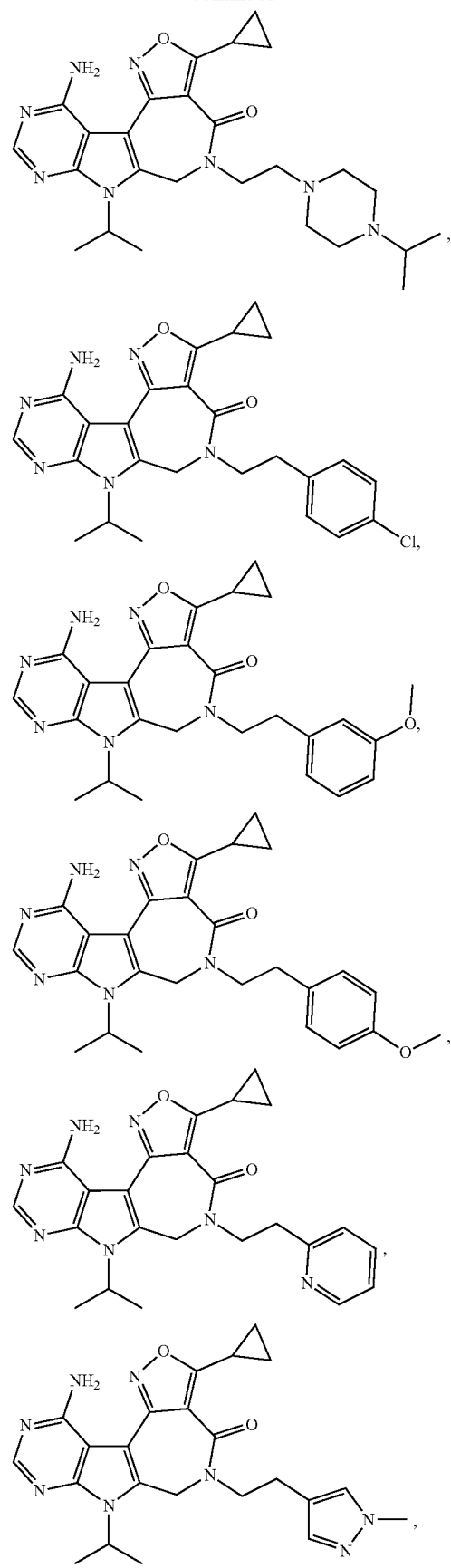

485
-continued
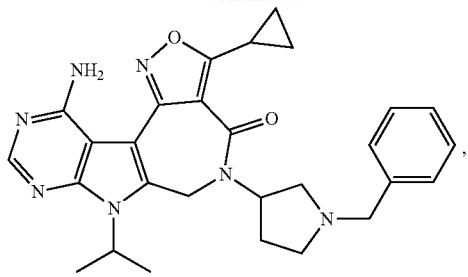
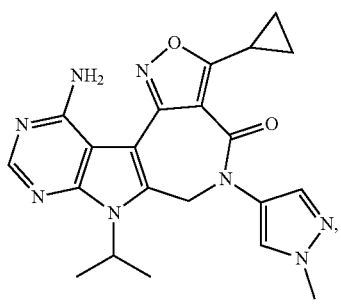
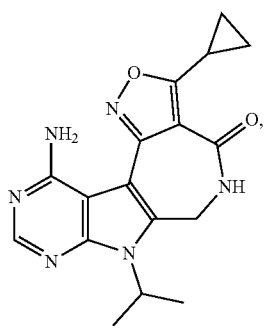
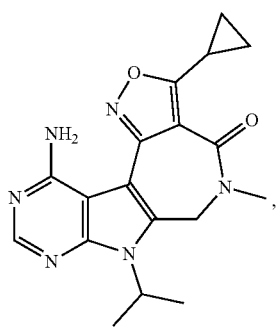
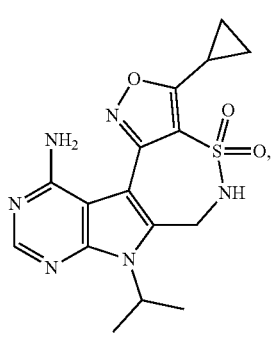
486
-continued
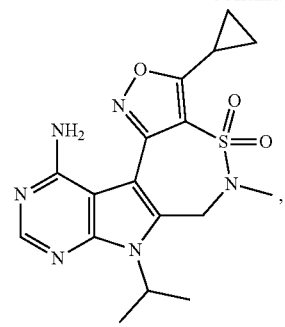
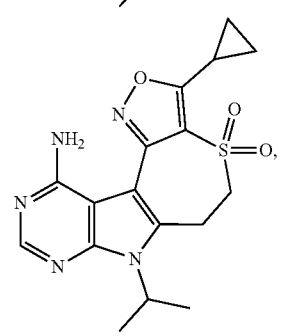
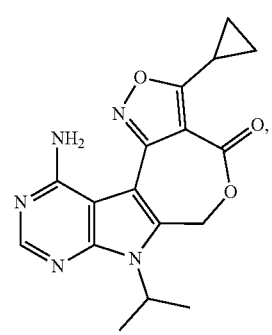
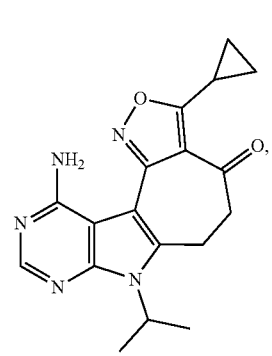
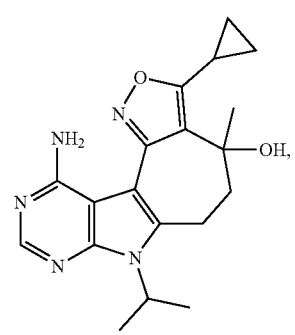

487
-continued
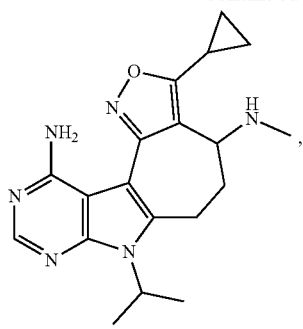
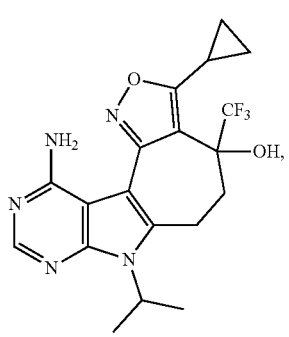
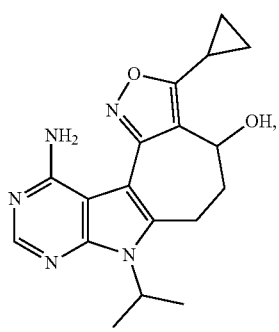
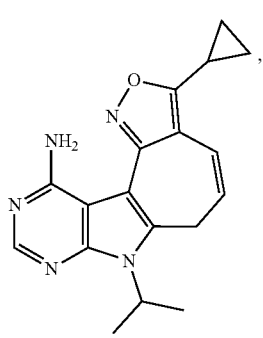
488
-continued
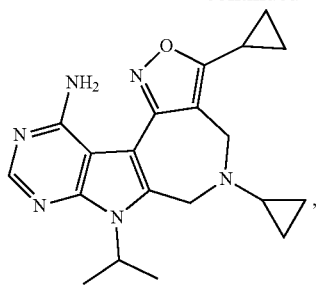
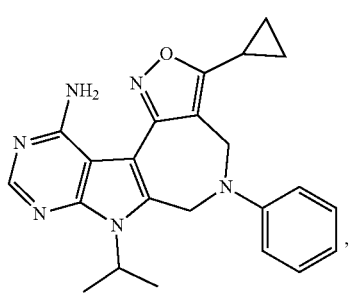

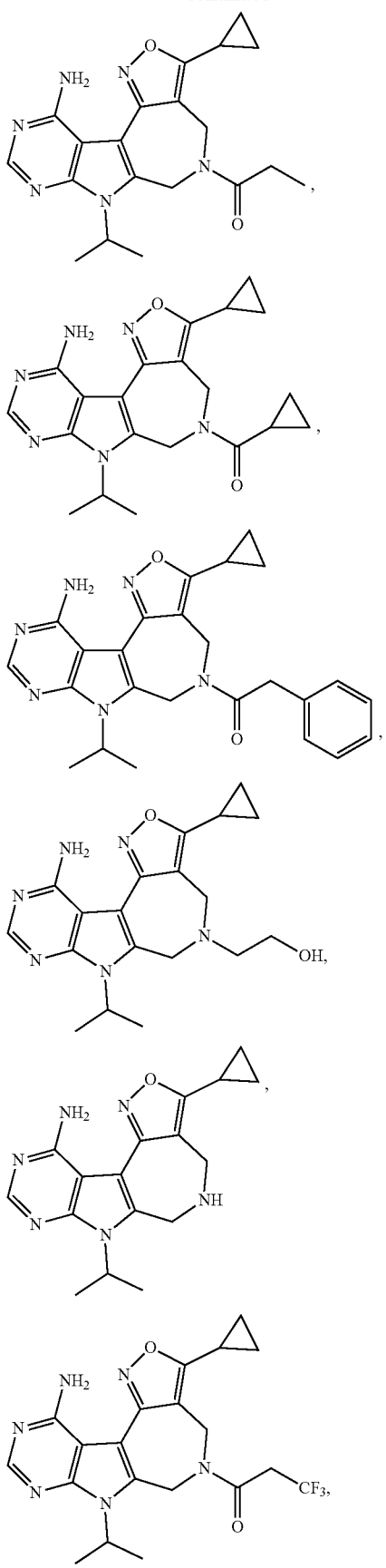
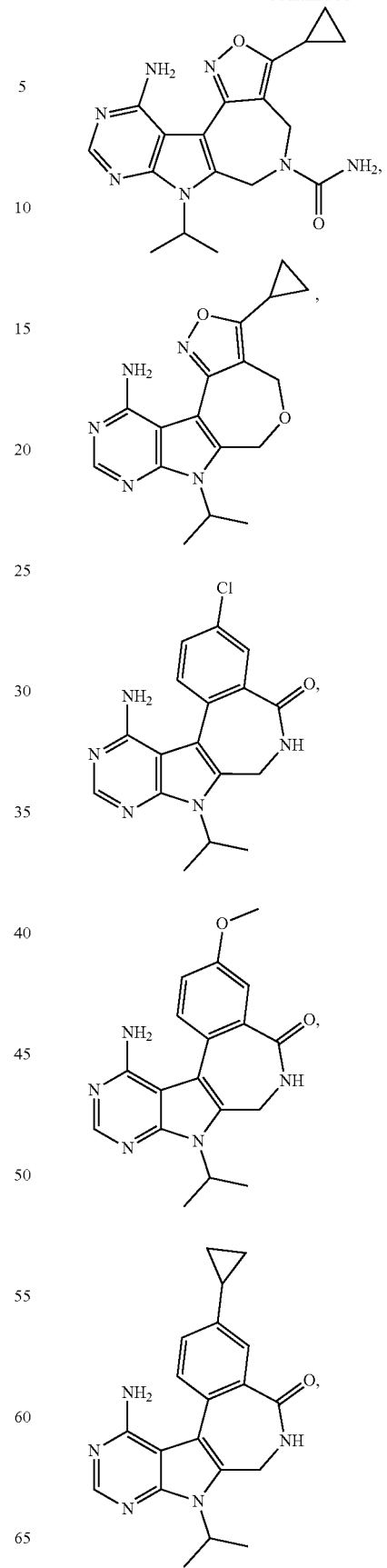

491
-continued
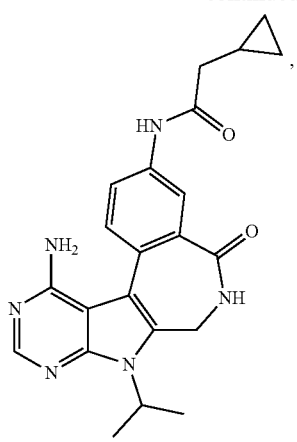
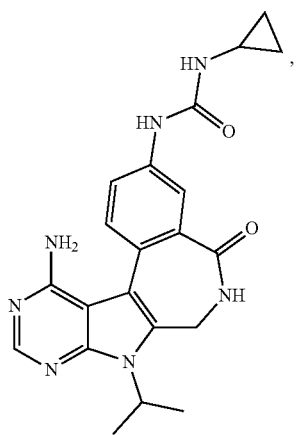
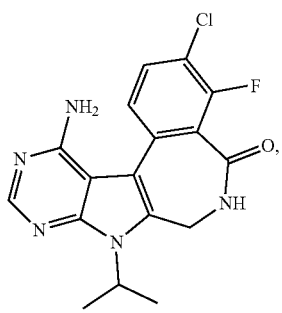
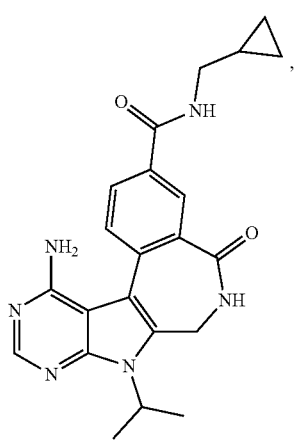
492
-continued
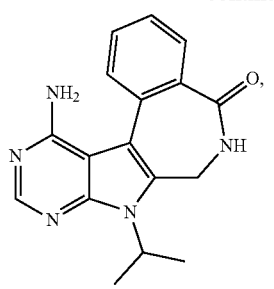
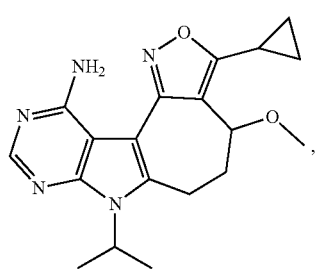
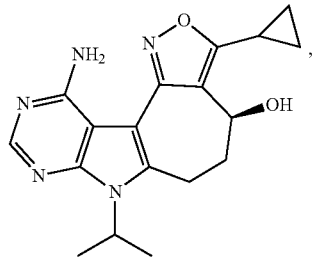
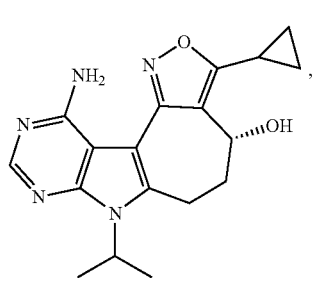
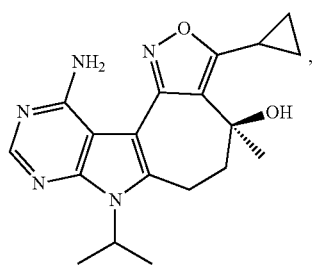
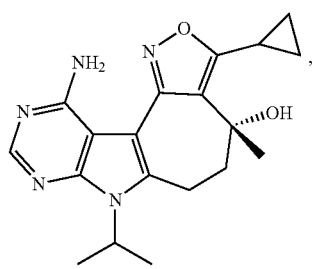

493
-continued
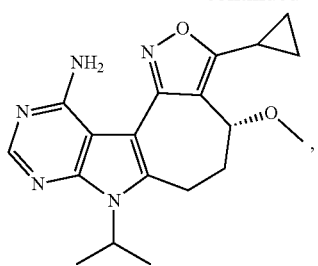,
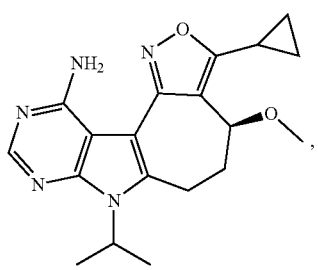,
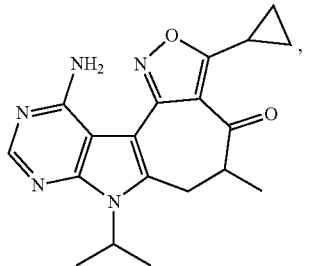,
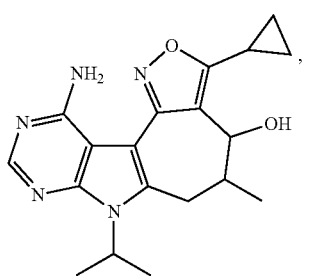,
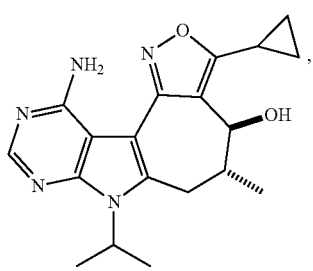,
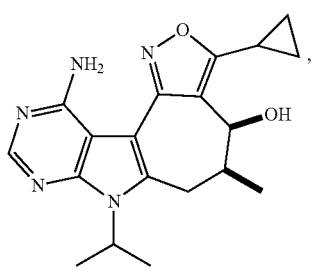,
494
-continued
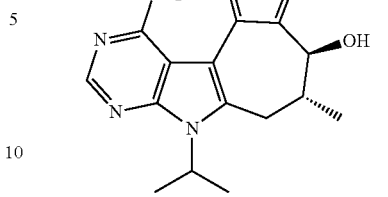,
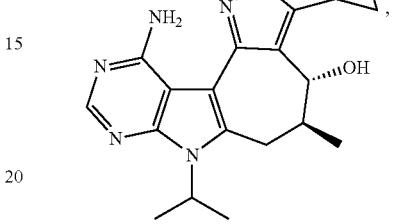,
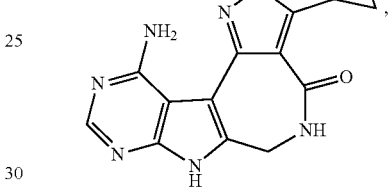,
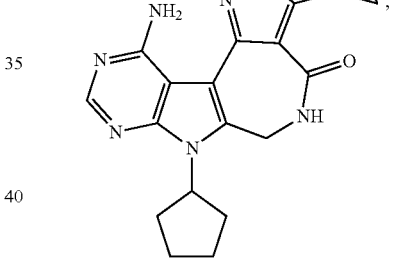,
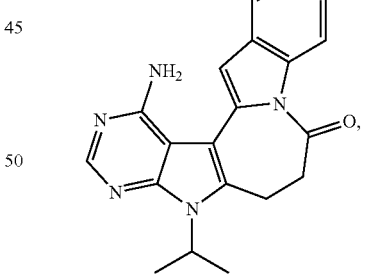,
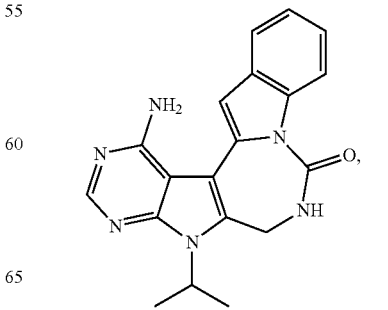, 495
-continued
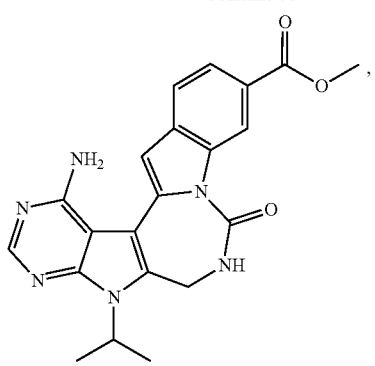
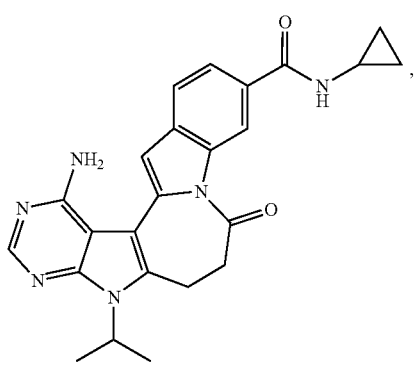
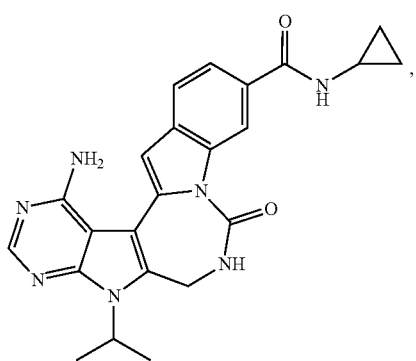
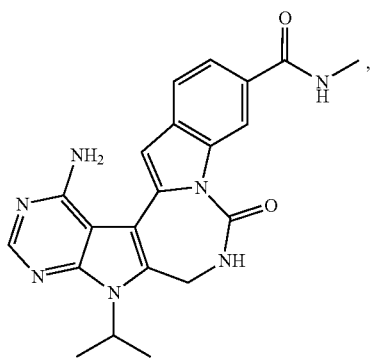
496
-continued
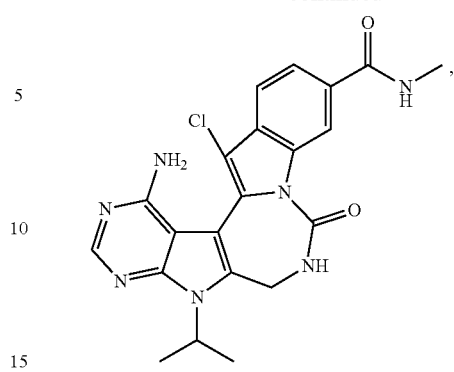
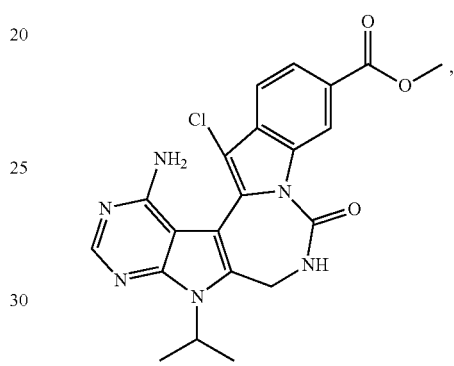
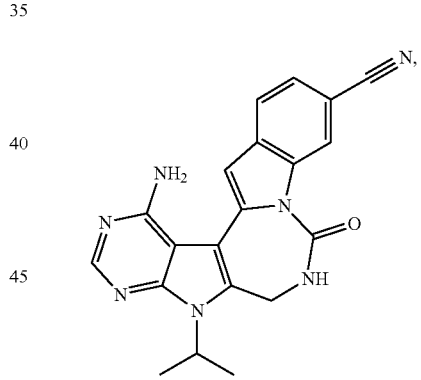
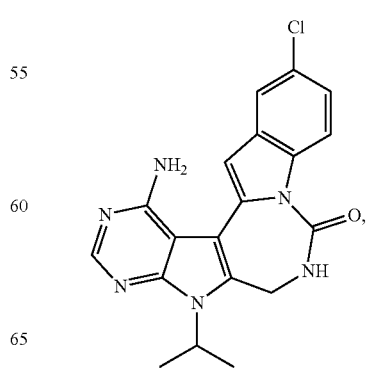

497
-continued
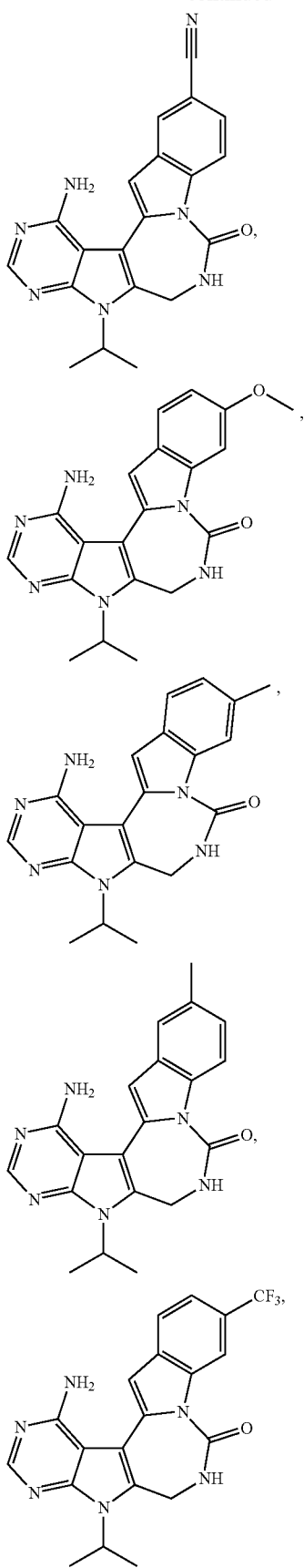
498
-continued
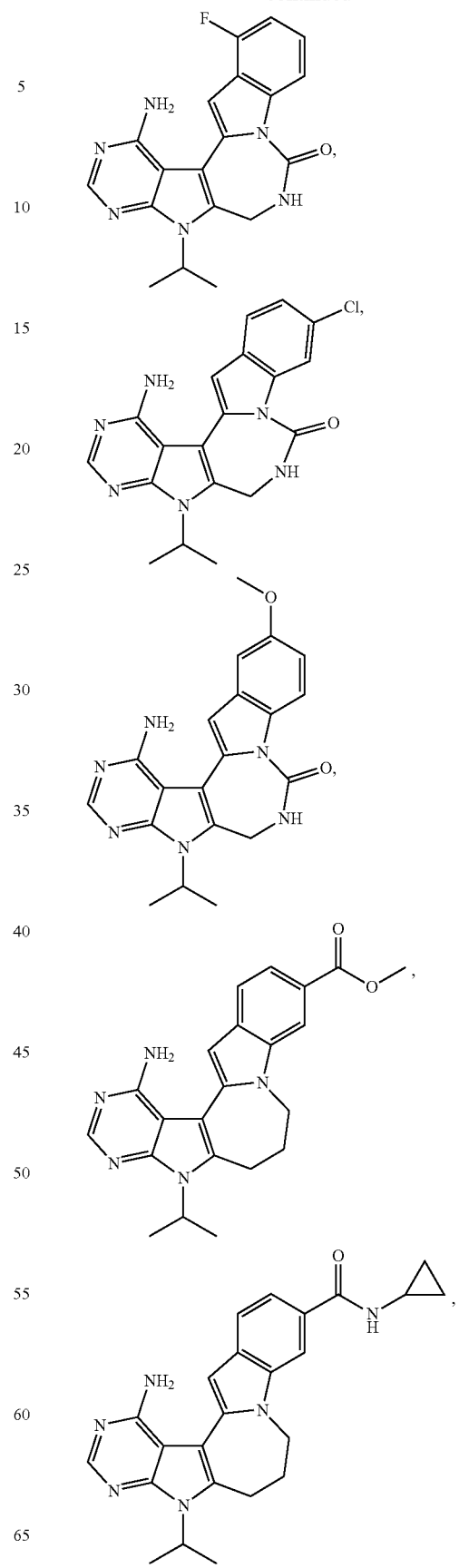

499
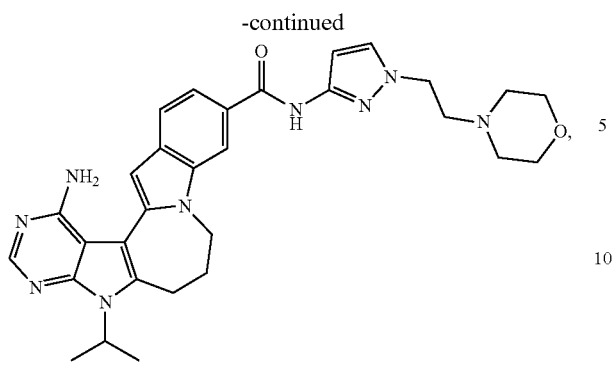
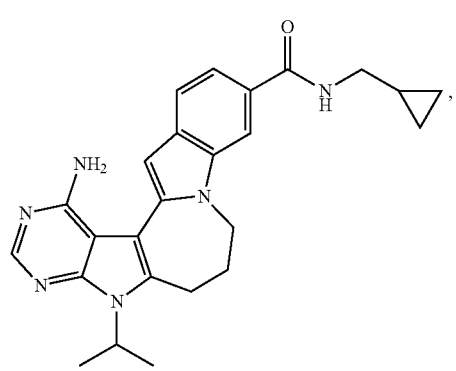
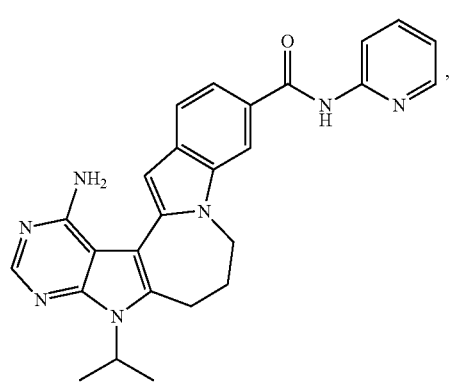
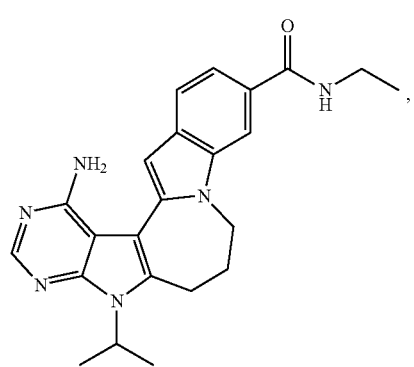
500
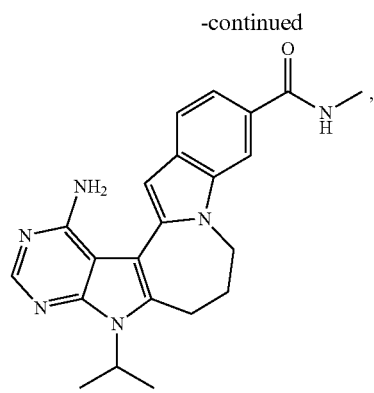
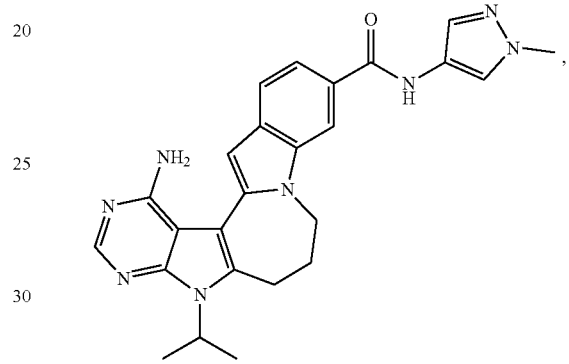
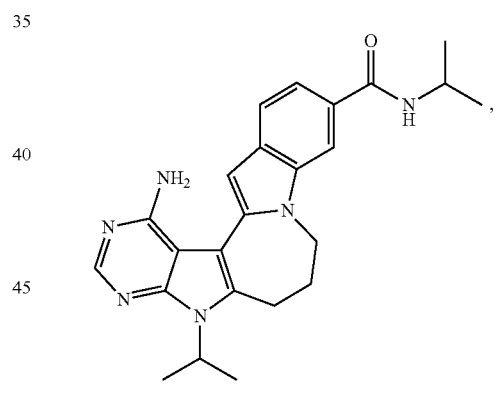
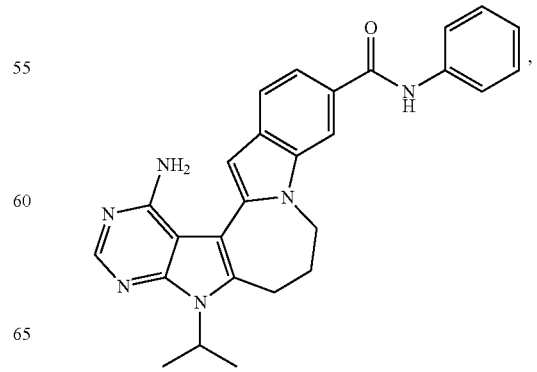

501
-continued
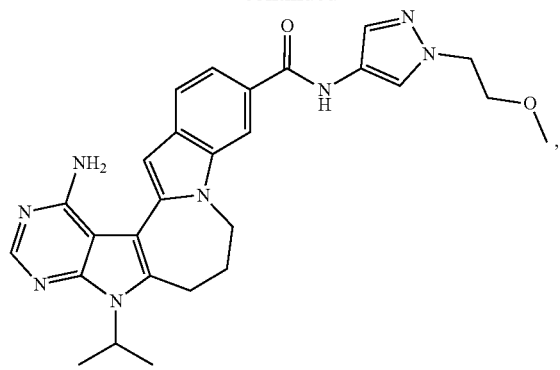
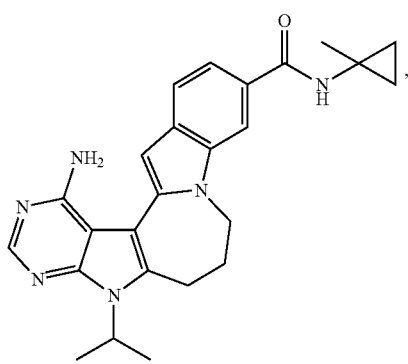
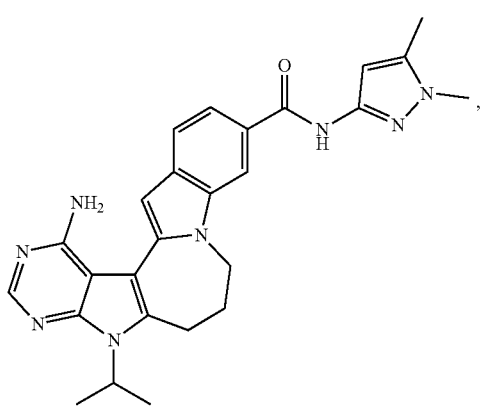
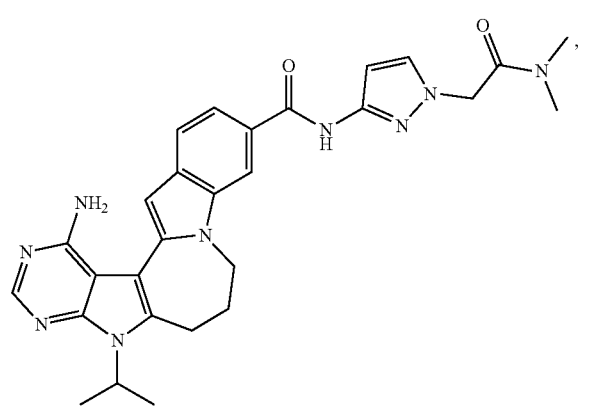
502
-continued
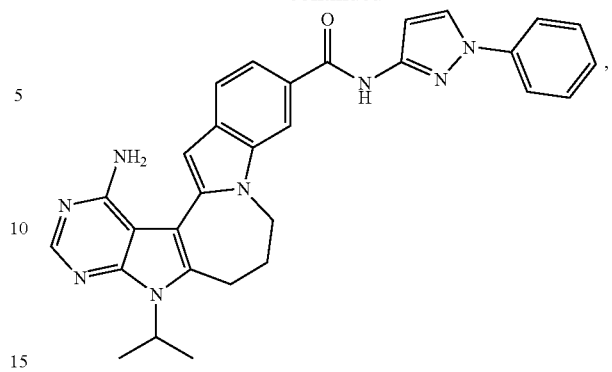
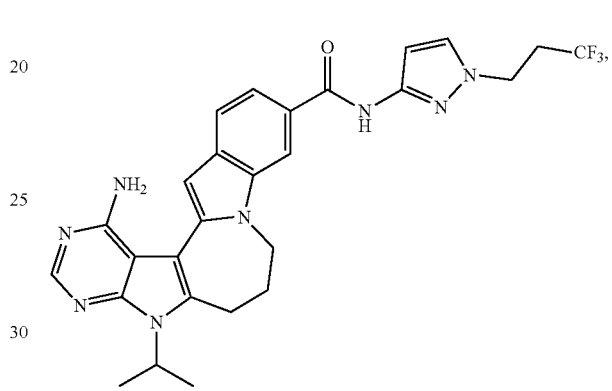
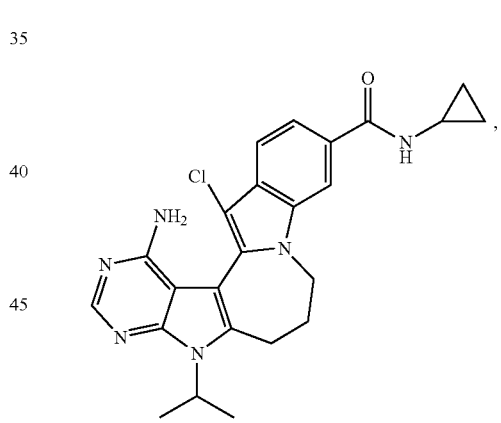
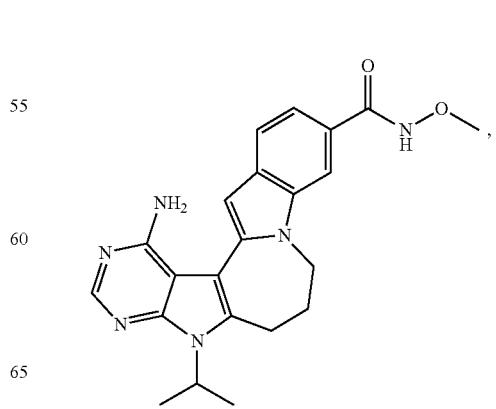

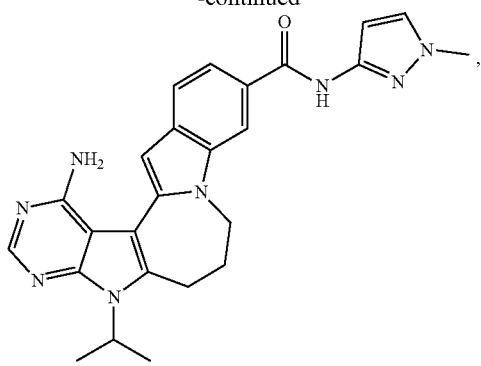

505
-continued
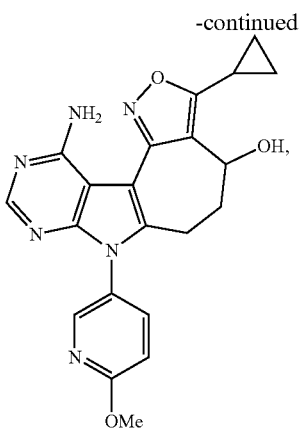
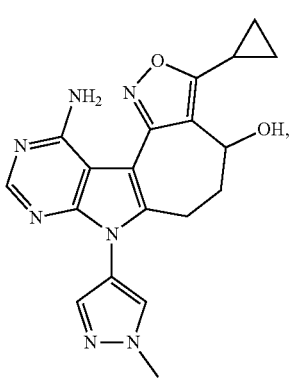
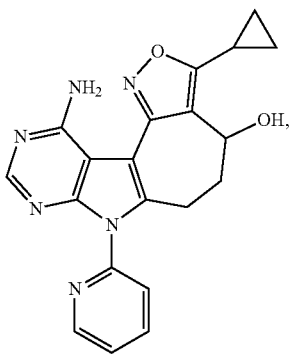
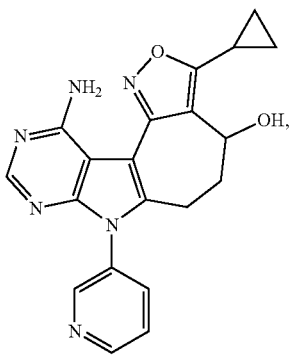
506
-continued
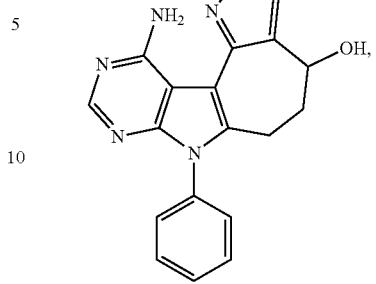
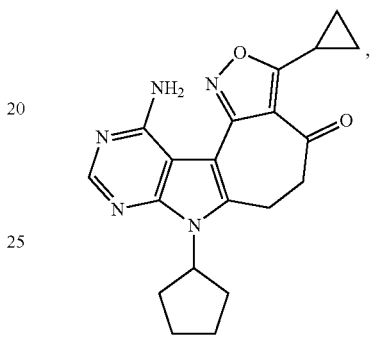
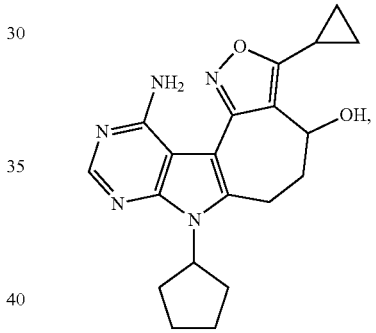
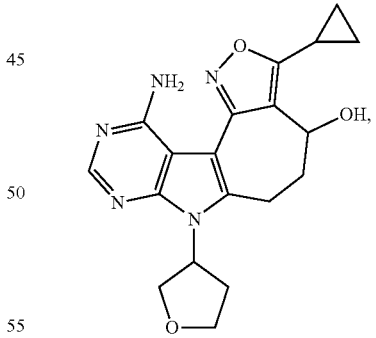
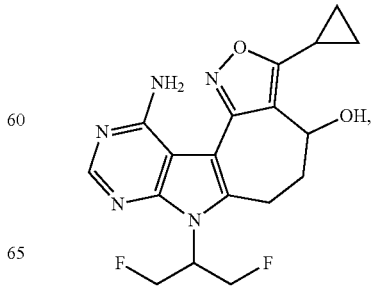

507
-continued
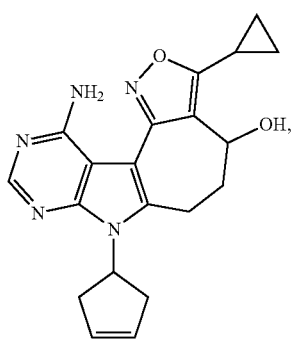
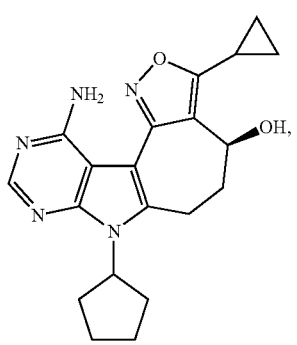
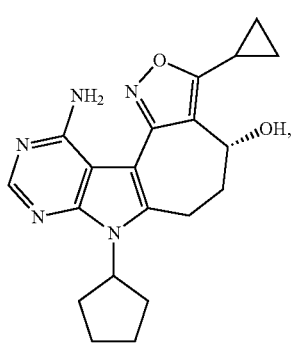
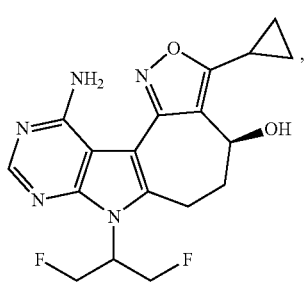
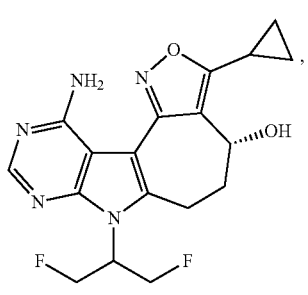
508
-continued
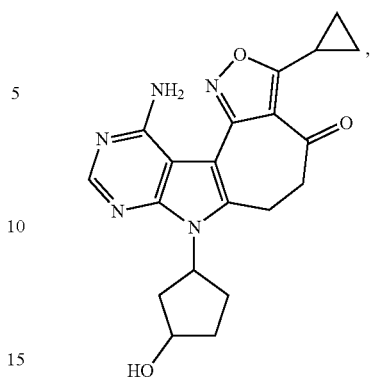
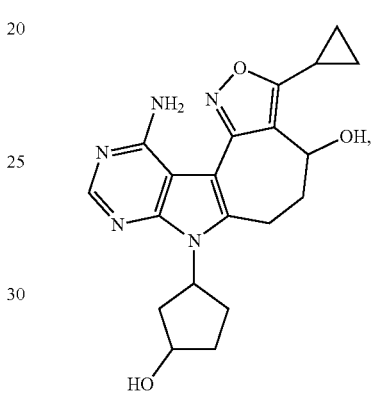
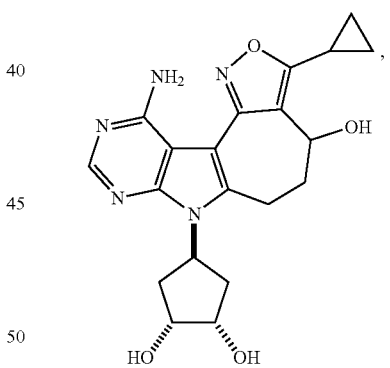
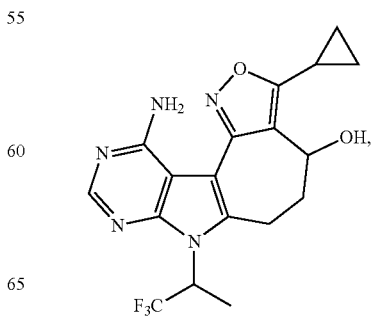

509
-continued
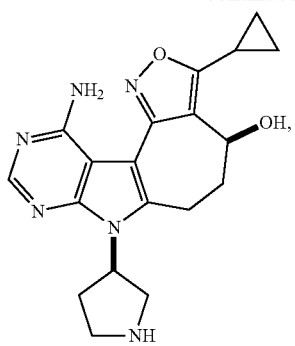
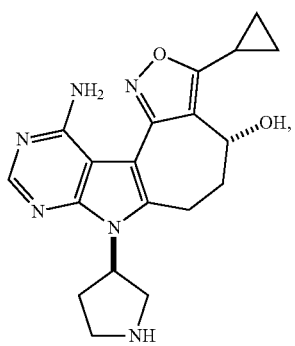
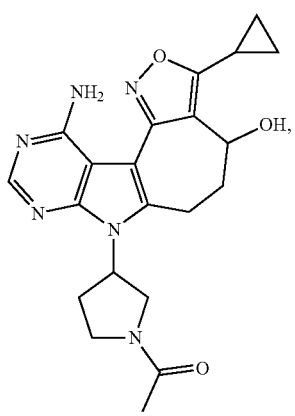
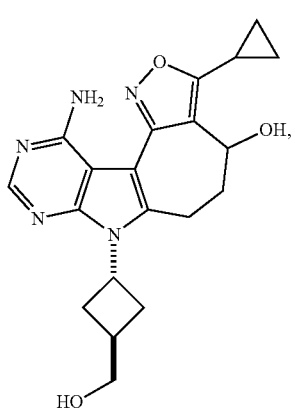
510
-continued
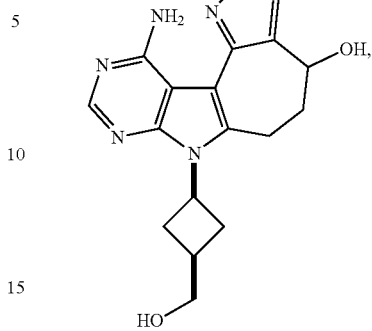
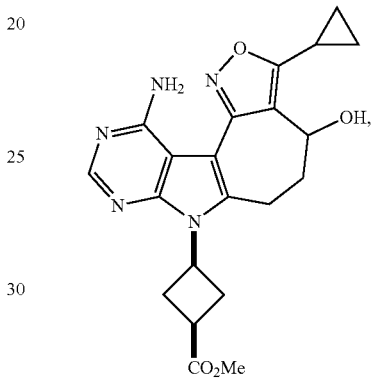
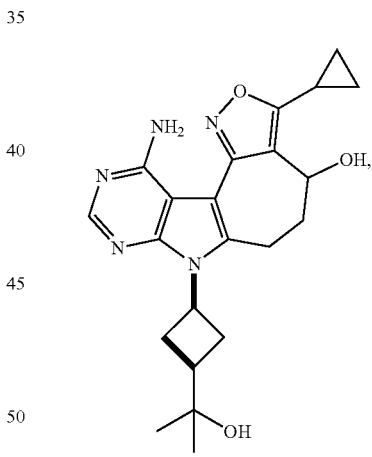
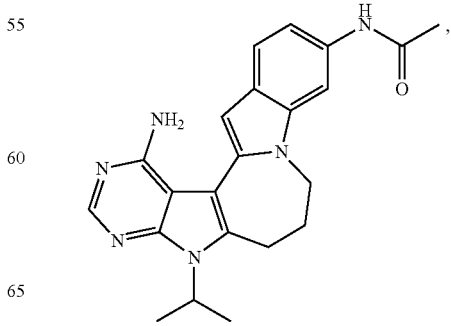

511
-continued
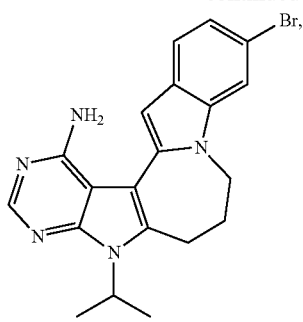
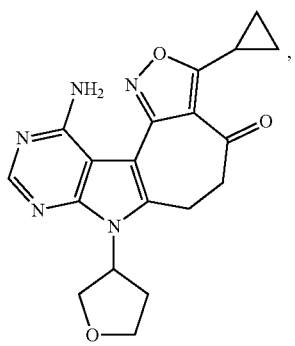
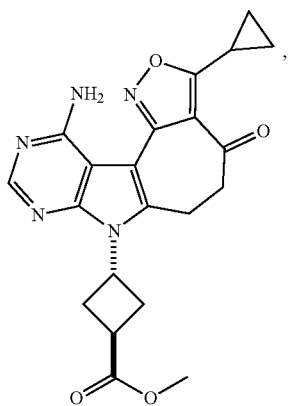
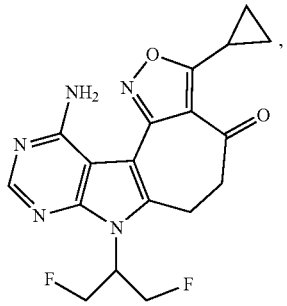
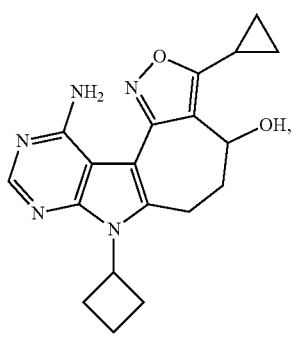
512
-continued
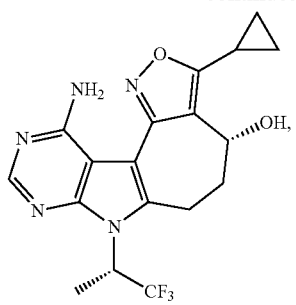
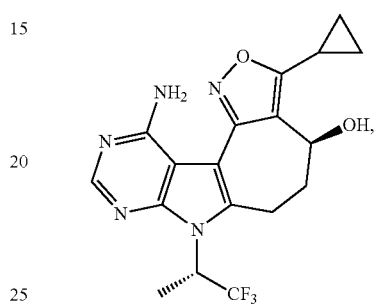
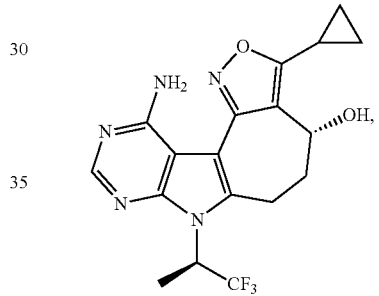
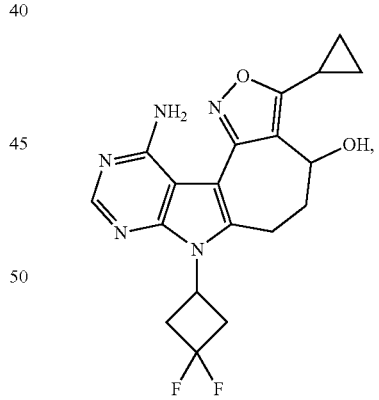
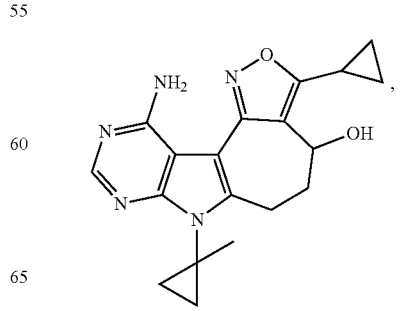

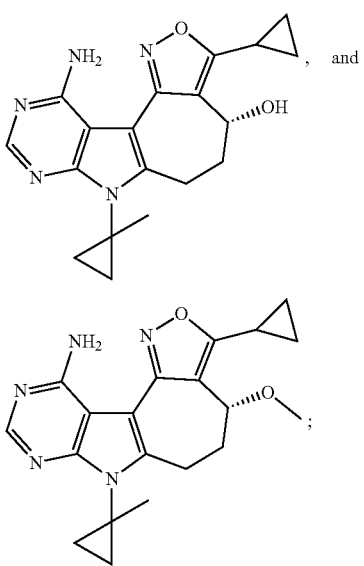

, and

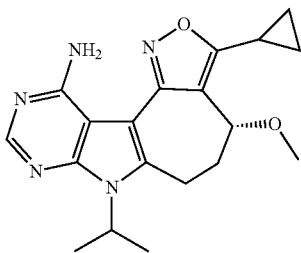 [SMILES: CO[C@@H]1CCc2c(c3c(N)ncnc3n2C(C)C)-c2noc(C3CC3)c21]

or a pharmaceutically acceptable salt thereof.

10. A compound according to claim 1, of the formula:

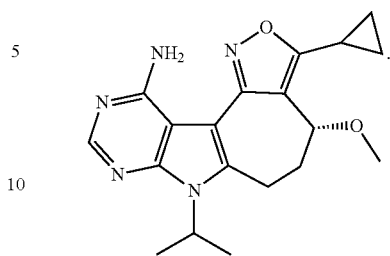

or a pharmaceutically acceptable salt thereof.

11. A compound according to claim 1, of the formula:

or a pharmaceutically acceptable salt thereof.

12. A pharmaceutical composition, comprising a compound according to claim 1 in admixture with a pharmaceutically acceptable diluent or carrier.

13. A method for treating a RET-associated cancer in a subject in need thereof, the method comprising administering a pharmaceutical composition comprising a therapeutically effective amount of a compound according to claim 1.

14. The method of claim 13, wherein the cancer is selected from the group consisting of: lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

15. The method of claim 13, wherein the cancer is medullary thyroid cancer.

16. The method of claim 13, wherein the cancer is lung cancer and the lung cancer is small cell lung carcinoma, non-small cell lung cancer, bronchioles lung cell carcinoma, RET fusion lung cancer, or lung adenocarcinoma.

17. The method of claim 16, wherein the lung cancer is RET fusion lung cancer.

18. The method of claim 13, further comprising administering an additional therapy or therapeutic agent to the subject.

* * * * *

SEQUENCE LISTING

```
<160> NUMBER OF SEQ ID NOS: 1

<210> SEQ ID NO 1
<211> LENGTH: 1114
<212> TYPE: PRT
<213> ORGANISM: Homo sapiens

<400> SEQUENCE: 1

Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
                20                  25                  30

Arg Asp Ala Tyr Trp Glu Lys Leu Tyr Val Asp Gln Ala Ala Gly Thr
            35                  40                  45

Pro Leu Leu Tyr Val His Ala Leu Arg Asp Ala Pro Glu Glu Val Pro
        50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
                100                 105                 110

Asn Arg Gly Phe Pro Leu Leu Thr Val Tyr Leu Lys Val Phe Leu Ser
            115                 120                 125

Pro Thr Ser Leu Arg Glu Gly Glu Cys Gln Trp Pro Gly Cys Ala Arg
        130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175
```

-continued

```
Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Val Val Met Val
                245                 250                 255

Pro Phe Pro Val Thr Val Tyr Asp Glu Asp Ser Ala Pro Thr Phe
            260                 265                 270

Pro Ala Gly Val Asp Thr Ala Ser Ala Val Glu Phe Lys Arg Lys
        275                 280                 285

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
        355                 360                 365

Thr Met Gln Leu Ala Val Leu Val Asn Asp Ser Asp Phe Gln Gly Pro
    370                 375                 380

Gly Ala Gly Val Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
        435                 440                 445

Cys Ser Thr Leu Gly Val Val Thr Ser Ala Glu Asp Thr Ser Gly Ile
    450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
            500                 505                 510

Ala Gly Cys Pro Leu Ser Cys Ala Val Ser Lys Arg Arg Leu Glu Cys
        515                 520                 525

Glu Glu Cys Gly Gly Leu Gly Ser Pro Thr Gly Arg Cys Glu Trp Arg
    530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
            580                 585                 590
```

-continued

```
Gly His Glu Pro Gly Glu Pro Arg Gly Ile Lys Ala Gly Tyr Gly Thr
        595                 600                 605
Cys Asn Cys Phe Pro Glu Glu Lys Cys Phe Cys Glu Pro Glu Asp
    610                 615                 620
Ile Gln Asp Pro Leu Cys Asp Glu Leu Cys Arg Thr Val Ile Ala Ala
625                 630                 635                 640
Ala Val Leu Phe Ser Phe Ile Val Ser Val Leu Ser Ala Phe Cys
                645                 650                 655
Ile His Cys Tyr His Lys Phe Ala His Lys Pro Pro Ile Ser Ser Ala
            660                 665                 670
Glu Met Thr Phe Arg Arg Pro Ala Gln Ala Phe Pro Val Ser Tyr Ser
        675                 680                 685
Ser Ser Gly Ala Arg Arg Pro Ser Leu Asp Ser Met Glu Asn Gln Val
        690                 695                 700
Ser Val Asp Ala Phe Lys Ile Leu Glu Asp Pro Lys Trp Glu Phe Pro
705                 710                 715                 720
Arg Lys Asn Leu Val Leu Gly Lys Thr Leu Gly Glu Gly Glu Phe Gly
                725                 730                 735
Lys Val Val Lys Ala Thr Ala Phe His Leu Lys Gly Arg Ala Gly Tyr
            740                 745                 750
Thr Thr Val Ala Val Lys Met Leu Lys Glu Asn Ala Ser Pro Ser Glu
        755                 760                 765
Leu Arg Asp Leu Leu Ser Glu Phe Asn Val Leu Lys Gln Val Asn His
        770                 775                 780
Pro His Val Ile Lys Leu Tyr Gly Ala Cys Ser Gln Asp Gly Pro Leu
785                 790                 795                 800
Leu Leu Ile Val Glu Tyr Ala Lys Tyr Gly Ser Leu Arg Gly Phe Leu
                805                 810                 815
Arg Glu Ser Arg Lys Val Gly Pro Gly Tyr Leu Gly Ser Gly Gly Ser
            820                 825                 830
Arg Asn Ser Ser Ser Leu Asp His Pro Asp Glu Arg Ala Leu Thr Met
        835                 840                 845
Gly Asp Leu Ile Ser Phe Ala Trp Gln Ile Ser Gln Gly Met Gln Tyr
    850                 855                 860
Leu Ala Glu Met Lys Leu Val His Arg Asp Leu Ala Ala Arg Asn Ile
865                 870                 875                 880
Leu Val Ala Glu Gly Arg Lys Met Lys Ile Ser Asp Phe Gly Leu Ser
                885                 890                 895
Arg Asp Val Tyr Glu Glu Asp Ser Tyr Val Lys Arg Ser Gln Gly Arg
            900                 905                 910
Ile Pro Val Lys Trp Met Ala Ile Glu Ser Leu Phe Asp His Ile Tyr
        915                 920                 925
Thr Thr Gln Ser Asp Val Trp Ser Phe Gly Val Leu Leu Trp Glu Ile
    930                 935                 940
Val Thr Leu Gly Gly Asn Pro Tyr Pro Gly Ile Pro Pro Glu Arg Leu
945                 950                 955                 960
Phe Asn Leu Leu Lys Thr Gly His Arg Met Glu Arg Pro Asp Asn Cys
                965                 970                 975
Ser Glu Glu Met Tyr Arg Leu Met Leu Gln Cys Trp Lys Gln Glu Pro
            980                 985                 990
Asp Lys Arg Pro Val Phe Ala Asp Ile Ser Lys Asp Leu Glu Lys Met
        995                 1000                1005
```

-continued

| Met | Val | Lys | Arg | Arg | Asp | Tyr | Leu | Asp | Leu | Ala | Ala | Ser | Thr | Pro |
| | 1010 | | | | | 1015 | | | | | 1020 | | | |
| Ser | Asp | Ser | Leu | Ile | Tyr | Asp | Asp | Gly | Leu | Ser | Glu | Glu | Glu | Thr |
| | 1025 | | | | | 1030 | | | | | 1035 | | | |
| Pro | Leu | Val | Asp | Cys | Asn | Asn | Ala | Pro | Leu | Pro | Arg | Ala | Leu | Pro |
| | 1040 | | | | | 1045 | | | | | 1050 | | | |
| Ser | Thr | Trp | Ile | Glu | Asn | Lys | Leu | Tyr | Gly | Met | Ser | Asp | Pro | Asn |
| | 1055 | | | | | 1060 | | | | | 1065 | | | |
| Trp | Pro | Gly | Glu | Ser | Pro | Val | Pro | Leu | Thr | Arg | Ala | Asp | Gly | Thr |
| | 1070 | | | | | 1075 | | | | | 1080 | | | |
| Asn | Thr | Gly | Phe | Pro | Arg | Tyr | Pro | Asn | Asp | Ser | Val | Tyr | Ala | Asn |
| | 1085 | | | | | 1090 | | | | | 1095 | | | |
| Trp | Met | Leu | Ser | Pro | Ser | Ala | Ala | Lys | Leu | Met | Asp | Thr | Phe | Asp |
| | 1100 | | | | | 1105 | | | | | 1110 | | | |
| Ser | | | | | | | | | | | | | | |